US009421209B2

(12) United States Patent
Muthuppalaniappan et al.

(10) Patent No.: US 9,421,209 B2
(45) Date of Patent: Aug. 23, 2016

(54) KINASE MODULATORS

(71) Applicant: Rhizen Pharmaceuticals SA, La Chaux-de-Fonds (CH)

(72) Inventors: Meyyappan Muthuppalaniappan, Hyderabad (IN); Srikant Viswanadha, Hyderabad (IN); Govindarajulu Babu, Hyderabad (IN); Swaroop K. Vakkalanka, La Chaux-de-Fonds (CH)

(73) Assignee: RHIZEN PHARMACEUTICALS SA, La Chaux-de-Fonds (CH)

( * ) Notice: Subject to any disclaimer, the term of this patent is extended or adjusted under 35 U.S.C. 154(b) by 0 days.

(21) Appl. No.: 14/642,423

(22) Filed: Mar. 9, 2015

(65) Prior Publication Data

US 2015/0174131 A1 Jun. 25, 2015

Related U.S. Application Data

(63) Continuation of application No. 14/090,517, filed on Nov. 26, 2013, now Pat. No. 9,018,375, which is a continuation of application No. 13/292,746, filed on Nov. 9, 2011, now Pat. No. 8,642,607, which is a continuation of application No. 12/938,609, filed on Nov. 3, 2010.

(60) Provisional application No. 61/364,661, filed on Jul. 15, 2010.

(30) Foreign Application Priority Data

Nov. 5, 2009 (IN) ........................... 2690/CHE/2009
May 24, 2010 (IN) ........................... 1429/CHE/2010

(51) Int. Cl.

| | |
|---|---|
| ***C07D 311/34*** | (2006.01) |
| ***C07D 519/00*** | (2006.01) |
| ***A61K 31/52*** | (2006.01) |
| ***C07D 311/36*** | (2006.01) |
| ***C07D 405/06*** | (2006.01) |
| ***C07D 487/04*** | (2006.01) |
| ***A61K 31/437*** | (2006.01) |
| ***A61K 31/5377*** | (2006.01) |
| ***A61K 45/06*** | (2006.01) |
| ***C07D 413/10*** | (2006.01) |
| ***C07D 413/14*** | (2006.01) |
| ***C07D 471/04*** | (2006.01) |
| ***C07D 473/34*** | (2006.01) |
| ***A61K 31/4178*** | (2006.01) |
| ***A61K 31/4184*** | (2006.01) |
| ***A61K 31/519*** | (2006.01) |
| ***C07D 473/38*** | (2006.01) |

(52) U.S. Cl.

CPC ............. *A61K 31/52* (2013.01); *A61K 31/4178* (2013.01); *A61K 31/4184* (2013.01); *A61K 31/437* (2013.01); *A61K 31/519* (2013.01); *A61K 31/5377* (2013.01); *A61K 45/06* (2013.01); *C07D 311/36* (2013.01); *C07D 405/06* (2013.01); *C07D 413/10* (2013.01); *C07D 413/14* (2013.01); *C07D 471/04* (2013.01); *C07D 473/34* (2013.01); *C07D 473/38* (2013.01); *C07D 487/04* (2013.01)

(58) Field of Classification Search

CPC ............................ C07D 311/34; C07D 519/00
See application file for complete search history.

(56) References Cited

U.S. PATENT DOCUMENTS

| | | | |
|---|---|---|---|
| 4,841,077 | A | 6/1989 | Ito et al. |
| 4,960,908 | A | 10/1990 | Ito et al. |
| 6,403,588 | B1 | 6/2002 | Hayakawa et al. |
| 6,608,053 | B2 | 8/2003 | Hayakawa et al. |
| 6,608,056 | B1 | 8/2003 | Hayakawa et al. |
| 6,653,320 | B2 | 11/2003 | Hayakawa et al. |
| 6,703,414 | B2 | 3/2004 | Powis et al. |
| 6,770,641 | B2 | 8/2004 | Hayakawa et al. |
| 6,838,457 | B2 | 1/2005 | Hayakawa et al. |
| 7,037,915 | B2 | 5/2006 | Hayakawa et al. |
| 7,173,029 | B2 | 2/2007 | Hayakawa et al. |
| 7,589,101 | B2 | 9/2009 | Okram et al. |
| 7,592,342 | B2 | 9/2009 | Feng et al. |
| 7,595,320 | B2 | 9/2009 | Barberis et al. |
| 7,595,330 | B2 | 9/2009 | Cheung et al. |
| 7,598,245 | B2 | 10/2009 | Arnost et al. |
| 7,601,718 | B2 | 10/2009 | Green et al. |
| 7,601,724 | B2 | 10/2009 | Guzi et al. |
| 7,605,155 | B2 | 10/2009 | Guzi et al. |
| 7,605,160 | B2 | 10/2009 | Fink et al. |
| 7,608,622 | B2 | 10/2009 | Liu et al. |

(Continued)

FOREIGN PATENT DOCUMENTS

| | | |
|---|---|---|
| EP | 0245518 A1 | 11/1987 |
| EP | 1417976 A1 | 5/2004 |

(Continued)

OTHER PUBLICATIONS

Williams A C et al., Product Class 4: Benzopyranones and Benzopyranthiones, Jan. 1, 2003, Science of Synthesis, pp. 347-638.

(Continued)

*Primary Examiner* — Brian McDowell

(74) *Attorney, Agent, or Firm* — Blank Rome LLP

(57) ABSTRACT

The present invention provides PI3K protein kinase modulators, methods of preparing them, pharmaceutical compositions containing them and methods of treatment, prevention and/or amelioration of kinase mediated diseases or disorders with them.

13 Claims, No Drawings

(56) References Cited

U.S. PATENT DOCUMENTS

| | | | |
|---|---|---|---|
| 8,642,607 | B2 | 2/2014 | Muthuppalaniappan et al. |
| 2003/0149074 | A1 | 8/2003 | Melese et al. |
| 2003/0158212 | A1 | 8/2003 | Melese et al. |
| 2004/0053946 | A1 | 3/2004 | Lackey et al. |
| 2004/0082638 | A1 | 4/2004 | McDonald et al. |
| 2004/0092561 | A1 | 5/2004 | Ruckle et al. |
| 2006/0270673 | A1 | 11/2006 | Duggan et al. |
| 2008/0039459 | A1 | 2/2008 | Folkes et al. |
| 2008/0076768 | A1 | 3/2008 | Chuckowree et al. |
| 2008/0207611 | A1 | 8/2008 | Shuttleworth et al. |
| 2009/0233926 | A1 | 9/2009 | Butterworth et al. |
| 2009/0233950 | A1 | 9/2009 | Jung et al. |
| 2009/0234132 | A1 | 9/2009 | Budd et al. |
| 2009/0238828 | A1 | 9/2009 | Munzert et al. |
| 2009/0239847 | A1 | 9/2009 | Bruce et al. |
| 2009/0239859 | A1 | 9/2009 | Chua et al. |
| 2009/0239936 | A1 | 9/2009 | Sugimoto et al. |
| 2009/0247538 | A1 | 10/2009 | Berdini et al. |
| 2009/0247554 | A1 | 10/2009 | Dong et al. |
| 2009/0247565 | A1 | 10/2009 | Lim et al. |
| 2009/0247567 | A1 | 10/2009 | Do et al. |
| 2009/0258852 | A1 | 10/2009 | Arrington et al. |
| 2009/0263397 | A1 | 10/2009 | Buck et al. |
| 2009/0263398 | A1 | 10/2009 | Lyons et al. |
| 2009/0270430 | A1 | 10/2009 | Baik et al. |
| 2009/0270445 | A1 | 10/2009 | Zeng et al. |
| 2009/0270621 | A1 | 10/2009 | Wallace et al. |

FOREIGN PATENT DOCUMENTS

| | | | |
|---|---|---|---|
| JP | S5896082 | A | 6/1983 |
| JP | 08175990 | A | 7/1996 |
| JP | 08176070 | A | 7/1996 |
| JP | 2001247477 | A | 1/2003 |
| JP | 2005523312 | A | 8/2005 |
| WO | WO-8702982 | A1 | 5/1987 |
| WO | WO-9715658 | A1 | 5/1997 |
| WO | WO-9829403 | A1 | 7/1998 |
| WO | WO-03034997 | A2 | 5/2003 |
| WO | WO-03035618 | A2 | 5/2003 |
| WO | WO-03037886 | A2 | 5/2003 |
| WO | WO-2004006916 | A1 | 1/2004 |
| WO | WO-2004007491 | A1 | 1/2004 |
| WO | WO-2004017950 | A2 | 3/2004 |
| WO | WO-2005015215 | A1 | 2/2005 |
| WO | WO-2006046031 | A1 | 5/2006 |
| WO | WO-2006046035 | A1 | 5/2006 |
| WO | WO-2006046040 | A1 | 5/2006 |
| WO | WO-2007042806 | A1 | 4/2007 |
| WO | WO-2007042810 | A1 | 4/2007 |
| WO | WO-2008070740 | A1 | 6/2008 |
| WO | WO-2008073785 | A2 | 6/2008 |
| WO | WO-2008118455 | A1 | 10/2008 |
| WO | WO-2009081105 | A2 | 7/2009 |
| WO | WO-2009105712 | A1 | 8/2009 |
| WO | WO-2009109867 | A2 | 9/2009 |
| WO | WO-2009111531 | A1 | 9/2009 |
| WO | WO-2009111547 | A1 | 9/2009 |
| WO | WO-2009112565 | A1 | 9/2009 |
| WO | WO-2009114870 | A2 | 9/2009 |
| WO | WO-2009114874 | A2 | 9/2009 |
| WO | WO-2009117097 | A1 | 9/2009 |
| WO | WO-2009117482 | A1 | 9/2009 |
| WO | WO-2009120094 | A2 | 10/2009 |
| WO | WO-2009126635 | A1 | 10/2009 |
| WO | WO-2009129211 | A1 | 10/2009 |
| WO | WO-2009129259 | A2 | 10/2009 |

OTHER PUBLICATIONS

Daia g e et al., The Directed Lithiation of Some 3-Acylchromone Acetals, Tetrahedron Letters, Elsevier, Amsterdam, NL, vol. 39, No. 10, Mar. 5, 1998, pp. 1215-1218.

Iijima I E et al, Synthesis Utilizing The Beta Carbonyl System 5, a Synthesis Directed Toward the Fungal Xanthone Bikaverin, Journal of the Chemical Society, Perkin Transaction 1, Chemical Society, Letchworth, GB, No. 12, Jan. 1, 1979, pp. 3190-3195.

Ellis G P et al: "Benzopyrones. 14. Synthesis and Antialergic Properties of Some N-Tetrazolylcarboxamides and Related Compounds". Journal of Medicinal Chemistry. American Chemical Society. US. vol. 21. No. 11. Jan. 1, 1978. pp. 1120-1126. XPOOI055197. ISSN: 0022-2623. DOI: DOI:I0.I021/JM00209A006 table 1; compounds 27.28.

Ogawara H et al: "Inhibition of Tyrosine Protein Kinase Activity by Synthetic Isoflavones and Flavones", Journal of Antibiotics, Japan Antibiotics Research Association, Tokyo, JP, vo 1. 42, No. 2, Feb. 1, 1989, pp. 340-343, XP009028517, ISSN: 0021-8820 p. 340; compounds PKI-17, PKI-24 p. 340, left column; p. 341, right column.

Banker, G.S. et al, "Modern Pharmaceutics, 3ed.", Marcel Dekker, New York, 1996, p. 596.

Kawase et al. (Bulletin of the Chemical Society of Japan, 1962, 35, pp. 1366-1369).

Wolff, Manfred E. "Burger's Medicinal Chemistry, 5ed, Part 1", John Wiley & Sons, 1995, pp. 975-977.

Holmberg, et al., The reactions Between Arylmagnesium Bromides and Ethyl 3-Phenyl-Chromone-2-Carboxylate, One or Two Caes of Reduction?, Acta Academiae Aboensis, Ser. B., 1970, 30:14:1-9.

Al-Maharik, et al., Synthesis of C-C-Bridged Bis-Isoflavones, J. Org. Chem., 2000, 65:2305-2308.

Wu, et al., Flavones 3. Synthesis, Biological Activities, and Conformational Analysis of Isolfavone Derivatives and Related Compounds, J. Med. Chem., 1992, 35:3519-3525.

Yoshiyuki, et al., Synthetic Studies on the Benzofuran Derivatives, VIII. Sythnesis of Furo[2,3-f]chromeno[3,4-b]chromone, Bulletin of the Chemical Society of Japan, 1962, 35:1366-1369.

KINASE MODULATORS

This application is a continuation of U.S. patent application Ser. No. 14/090,517, filed on Nov. 26, 2013, which is a continuation of U.S. patent application Ser. No. 13/292,746, filed on Nov. 9, 2011, now U.S. Pat. No. 8,642,607, which is a continuation of U.S. patent application Ser. No. 12/938,609, filed on Nov. 3, 2010, which claims the benefit of Indian Provisional Patent Application Nos. 2690/CHE/2009, filed Nov. 5, 2009, and 1429/CHE/2010, filed May 24, 2010, and U.S. Provisional Patent Application No. 61/364,661, filed Jul. 15, 2010, each of which is hereby incorporated by reference in its entirety.

FIELD OF THE INVENTION

The present invention provides PI3K protein kinase modulators, methods of preparing them, pharmaceutical compositions containing them and methods of treatment, prevention and/or amelioration of kinase mediated diseases or disorders with them.

BACKGROUND OF THE INVENTION

In the recent past immense research has been dedicated to the discovery and understanding of the structure and functions of enzymes and bio-molecules associated with various diseases. One such important class of enzymes that has been the subject of extensive research is Protein Kinase.

In general, protein kinases represent a set of structurally related phosphoryl transferases having conserved structures and catalytic functions. These enzymes modify proteins by chemically adding phosphate groups (phosphorylation). Phosphorylation involves the removal of a phosphate group from ATP and covalently attaching it to amino acids that have a free hydroxyl group such as serine, threonine or tyrosine. Phosphorylation usually results in a functional change of the target protein (substrate) by altering enzyme activity, cellular localization or association with other proteins. Up to 30% of all proteins may be modified by kinase activity.

This class of proteins are classified into subsets depending upon the substrate they act upon such as tyrosine kinase, serine/threonine kinase, histidine kinase and the like. These proteins can also be classified based on their localization into receptor tyrosine kinases (RTKs) or non-receptor tyrosine kinases.

Receptor tyrosine kinases (RTKs) have an extracellular portion, a transmembrane domain, and an intracellular portion, while non-receptor tyrosine kinases are entirely intracellular. Receptor tyrosine kinase mediated signal transduction is typically initiated by an extracellular interaction with a specific growth factor (ligand), followed by receptor dimerization, stimulation of the intrinsic protein tyrosine kinase activity, and phosphorylation of amino acid residues. The ensuing conformational change leads to the formation of complexes with a spectrum of cytoplasmic signalling molecules and facilitates a myriad of responses such as cell division, differentiation, metabolic effects, and changes in the extracellular microenvironment.

Protein kinases are known to control a wide variety of biological processes such as cell growth, survival and differentiation, organ formation and morphogenesis, neovascularisation, tissue repair and regeneration. In addition to their functions in normal tissues/organs, many protein kinases also play specialized roles in a host of human diseases including cancer. A subset of protein kinases (also referred to as oncogenic protein kinases), when dysregulated, can cause tumor formation and growth and contribute to tumor maintenance and progression (Blume-Jensen P et al, Nature 2001, 411 (6835):355-365). Thus far, oncogenic protein kinases represent one of the largest and most attractive groups of protein targets for therapeutic intervention and drug development.

Both receptor and non-receptor protein kinases have been found to be attractive targets for small molecule drug discovery due to their impact on cell physiology and signalling. Dysregulation of protein kinase activity thus leads to altered cellular responses including uncontrolled cell growth associated with cancer. In addition to oncological indications, altered kinase signalling is implicated in numerous other pathological diseases. These include, but are not limited to immunological disorders, cardiovascular diseases, inflammatory diseases, and degenerative diseases.

Modulation (particularly inhibition) of cell proliferation and angiogenesis, the two key cellular processes needed for tumor growth and survival is an attractive goal for development of small-molecule drugs (Matter A. Drug Disc Technol 2001, 6, 1005-1024). Anti-angiogenic therapy represents a potentially important approach for the treatment of solid tumors and other diseases associated with dysregulated vascularisation including ischemic coronary artery disease, diabetic retinopathy, psoriasis and rheumatoid arthritis. Similarly, cell antiproliferative agents are desirable to slow or inhibit the growth of tumors.

Phosphatidylinositol (hereinafter abbreviated as "PI") is one of a number of phospholipids found in cell membranes. In recent years it has become clear that PI plays an important role in intracellular signal transduction. Cell signaling via 3'-phosphorylated phosphoinositides has been implicated in a variety of cellular processes, e.g., malignant transformation, growth factor signaling, inflammation, and immunity (Rameh et al (1999) J. Biol Chem, 274:8347-8350). The enzyme responsible for generating these phosphorylated signaling products, phosphatidylinositol 3-kinase (also referred to as PI 3-kinase or PI3K), was originally identified as an activity associated with viral oncoproteins and growth factor receptor tyrosine kinases that phosphorylate phosphatidylinositol (PI) and its phosphorylated derivatives at the 3'-hydroxyl of the inositol ring (Panayotou et al (1992) Trends Cell Biol 2:358-60).

The phosphoinositide 3-kinases (PI3Ks) are a family of enzymes that regulate diverse biological functions in every cell type by generating phosphoinositide second-messenger molecules. As the activity of these phosphoinositide second messengers is determined by their phosphorylation state, the kinases and phosphatises that act to modify these lipids are central to the correct execution of intracellular signaling events. Phosphoinositide 3-kinases (PI3K) phosphorylate lipids at the 3-hydroxyl residue of an inositol ring (Whitman et al (1988) Nature, 332:664) to generate phosphorylated phospholipids (PIP3s) which act as second messengers recruiting kinases with lipid binding domains (including plekstrin homology (PH) regions), such as Akt and phosphoinositide-dependent kinase-1 (PDK1). Binding of Akt to membrane PIP3s causes the translocation of Akt to the plasma membrane, bringing Akt into contact with PDK1, which is responsible for activating Akt. The tumor-suppressor phosphatase, PTEN, dephosphorylates PIP3 and therefore acts as a negative regulator of Akt activation. The PI3-kinases Akt and PDK1 are important in the regulation of many cellular processes including cell cycle regulation, proliferation, survival, apoptosis and motility and are significant components of the molecular mechanisms of diseases such as cancer, diabetes and immune inflammation (Vivanco et al (2002) Nature Rev. Cancer 2:489; Phillips et al (1998) Cancer 83:41).

The PI3K family is constituted by four different classes: classes I, II and III are lipid kinases while members of class IV are Ser/Thr protein kinases.

The members of the class I family of PI3Ks are dimers of a regulatory and a catalytic subunit. The class I family consists of four isoforms, determined by the catalytic subunits α, β, γ and δ (see Engelman J A, Nat Rev Genet 2006; 7:606-19; Carnero A, Curr Cancer Drug Targets 2008; 8:187-98; Vanhaesebroeck B, Trends Biochem Sci 2005; 30:194-204). Class I can be subdivided into two subclasses: Ia, formed by the combination of p110 α β and δ and a regulatory subunit (p85, p55 or p50) and Ib, formed by p110 γ and p101 regulatory subunits. The regulatory subunit p85 contains Src homology 2 domains, which bind to phosphotyrosines and bring the attached catalytic subunit p110 into the complexes located in the membrane around the receptor. The activation of PI3K is induced by growth factors and insulin targeting the catalytic subunit to the membrane where it is in close proximity with its substrates, mainly PIP2. Alternatively, GTP-bound Ras can bind and activate p110 subunits in a p85-independent manner. Class I phosphoinositide 3-kinases (PI3Ks) are lipid kinases that phosphorylate phosphatidyl-inositide lipids (PI) at the D3 position of the inositol ring producing lipid second messengers (PIPs). The products of PI3K activity, mainly PI(3,4,5)-P3 (PIP3), are present in very low level in quiescent cells but are rapidly produced during cell stimulation and are involved in the regulation of several biological responses including mitogenesis, apoptosis, vesicular trafficking and cytoskeleton rearrangement. The result of rising PIP3 levels is the activation of 3-phosphoinositide-dependent protein kinase-1 and its substrate AKT, which triggers most of the biological activities of the pathway. Phosphatase and tensin homolog in chromosome 10 (PTEN) is a lipidic phosphatase which constitutes the main negative regulator of the route by dephosphorylating PIP3 to PI(4,5)-P2 (PIP2). Class II displays the ability to phosphorylate PI and PI-4 phosphate in vitro. Class III, composed by Vps34 only member, phosphorylates PI at position 3 generating PI 3-phosphate. Vps34 has been implicated in Golgi trafficking of proteins, autophagy and activation of mammalian target of rapamycin (mTOR) by amino acids (see Backer J M. Biochem J 2008; 410:1-17) these classes are generally resistant to class I PI3K inhibitors. Class IV, however, is important because it constitutes the major cross-activity proteins for class I inhibitors. This class includes enzymes involved in signal transduction and DNA damage response such as mTOR, DNA-dependent protein kinase (DNA-PK) or ATM. This fourth class of PI3K-related enzymes contains a catalytic core similar to the PI3K, which can account for the cross-inhibition by class I 'selective' compounds. However, small differences, especially in the hinge region, and the solving of the PI3K-related structures might lead to the fine tuning of different paralog selective PI3K-members. (see *Expert Opin. Investig. Drugs* (2009) 18(9): 1265-1277)

There is now considerable evidence indicating that Class Ia PI3K enzymes contribute to tumourigenesis in a wide variety of human cancers, either directly or indirectly (Vivanco and Sawyers, Nature Reviews Cancer, 2002, 2, 489-501). For example, the pi 10a subunit is amplified in some tumours such as those of the ovary (Shayesteh et al, Nature Genetics. 1999, 21: 99-102) and cervix (Ma et al, Oncogene, 2000, 19: 2739-2744). More recently, activating mutations within the catalytic site of pi 10a have been associated with various other tumours such as those of the colorectal region and of the breast and lung (Samuels et al, Science, 2004, 304, 554). Tumour-related mutations in p85α have also been identified in cancers such as those of the ovary and colon (Philp et al., Cancer Research, 2001, 61, 7426-7429). In addition to direct effects, it is believed that activation of Class Ia PI3K contributes to tumourigenic events that occur upstream in signalling pathways, for example by way of ligand-dependent or ligand-independent activation of receptor tyrosine kinases, GPCR systems or integrins (Vara et al, Cancer Treatment Reviews, 2004, 30, 193-204). Examples of such upstream signalling pathways include over-expression of the receptor tyrosine kinase Erb2 in a variety of tumours leading to activation of PI3K-mediated pathways (Harari et al., Oncogene, 2000, 19, 6102-6114) and over-expression of the oncogene Ras (Kauffmann-Zeh et al., Nature, 1997, 385, 544-548). In addition, Class Ia PBKs may contribute indirectly to tumourigenesis caused by various downstream signalling events. For example, loss of the effect of the PTEN tumour-suppressor phosphatase that catalyses conversion of PI(3,4,5)P3 back to PI(4,5)P2 is associated with a very broad range of tumours via deregulation of PI3K-mediated production of PI(3,4,5)P3 (Simpson and Parsons, Exp. Cell Res. 2001, 264, 29-41). Furthermore, augmentation of the effects of other PI3K-mediated signalling events is believed to contribute to a variety of cancers, for example by activation of Akt (Nicholson and Anderson, Cellular Signalling, 2002, H, 381-395).

In addition to a role in mediating proliferative and survival signalling in tumour cells, there is also good evidence that Class Ia PI3K enzymes will also contribute to tumourigenesis via its function in tumour-associated stromal cells. For example, PI3K signalling is known to play an important role in mediating angiogenic events in endothelial cells in response to pro-angiogenic factors such as VEGF (Abid et al., Arterioscler. Thromb. Vase. Biol., 2004, 24, 294-300). As Class I PI3K enzymes are also involved in motility and migration (Sawyer, Expert Opinion Investig. Drugs, 2004, JJ., 1-19), PI3K inhibitors should provide therapeutic benefit via inhibition of tumour cell invasion and metastasis.

In addition, Class I PI3K enzymes play an important role in the regulation of immune cells with PI3K activity contributing to pro-tumourigenic effects of inflammatory cells (Coussens and Werb, Nature, 2002, 420, 860-867). These findings suggest that pharmacological inhibitors of Class I PI3K enzymes should be of therapeutic value for treatment of the various forms of the disease of cancer comprising solid tumours such as carcinomas and sarcomas and the leukaemias and lymphoid malignancies. In particular, inhibitors of Class I PI3K enzymes should be of therapeutic value for treatment of, for example, cancer of the breast, colorectum, lung (including small cell lung cancer, non-small cell lung cancer and bronchioalveolar cancer) and prostate, and of cancer of the bile duct, bone, bladder, head and neck, kidney, liver, gastrointestinal tissue, esophagus, ovary, pancreas, skin, testes, thyroid, uterus, cervix and vulva, and of leukaemias (including ALL and CML), multiple myeloma and lymphomas.

A recent review by Romina Marone et. al., describes the activation of the PI3K signalling cascade having a positive effect on cell growth, survival and proliferation. Constitutive up-regulation of PI3K signaling can have a deleterious effect on cells leading to uncontrolled proliferation, enhanced migration and adhesion-independent growth. These events favor not only the formation of malignant tumors, but also the development of inflammatory and autoimmune disease indicating the role of PI3K in various diseases including chronic inflammation & allergy, Cardiovascular diseases, cancer and metabolic disorders. (see Biochimica et Biophysica Acta 1784 (2008) 159-185).

Several components of the PI3-kinase/Akt/PTEN pathway are implicated in oncogenesis. In addition to growth factor receptor tyrosine kinases, integrin-dependent cell adhesion and G-protein coupled receptors activate PI3-kinase both directly and indirectly through adaptor molecules. Functional loss of PTEN (the most commonly mutated tumor-suppressor gene in cancer after p53), oncogene mutations in PI3 kinase (Samuels et al (2004) Science 304:554), amplification of PI3-kinase and overexpression of Akt have been established in many malignancies. In addition, persistent signaling through the PI3-kinase/Akt pathway by stimulation of the insulin-like growth factor receptor is a mechanism of resistance to epidermal growth factor receptor inhibitors such as AG1478 and trastuzumab. Oncogenic mutations of p110alpha have been found at a significant frequency in colon, breast, brain, liver, ovarian, gastric, lung, and head and neck solid tumors. PTEN abnormalities are found in glioblastoma, melanoma, prostate, endometrial, ovarian, breast, lung, head and neck, hepatocellular, and thyroid cancers.

The levels of phosphatidylinositol-3,4,5-triphosphate (PIP3), the primary product of PI3-kinase activation, increase upon treatment of cells with a variety of agonists. PI3-kinase activation, therefore, is believed to be involved in a range of cellular responses including cell growth, differentiation, and apoptosis (Parker et al (1995) Current Biology, 5:577-99; Yao et al (1995) Science, 267:2003-05). Though the downstream targets of phosphorylated lipids generated following PI3 kinase activation have not been well characterized, emerging evidence suggests that pleckstrin-homology domain- and FYVE-finger domain-containing proteins are activated when binding to various phosphatidylinositol lipids (Sternmark et al (1999) J Cell Sci, 112:4175-83; Lemmon et al (1997) Trends Cell Biol, 7:237-42). In vitro, some isoforms of protein kinase C (PKC) are directly activated by PIP3, and the PKC-related protein kinase, PKB, has been shown to be activated by PI3 kinase (Burgering et al (1995) Nature, 376:599-602).

PI3 kinase also appears involved in leukocyte activation. A p85-associated PI3 kinase activity has been shown to physically associate with the cytoplasmic domain of CD28, which is an important costimulatory molecule for the activation of T-cells in response to antigen (Pages et al (1994) Nature, 369:327-29; Rudd, (1996) Immunity 4:527-34). Activation of T cells through CD28 lowers the threshold for activation by antigen and increases the magnitude and duration of the proliferative response. These effects are linked to increases in the transcription of a number of genes including interleukin-2 (IL2), an important T cell growth factor (Fraser et al (1991) Science, 251:313-16). Mutation of CD28 such that it can no longer interact with PI3 kinase leads to a failure to initiate IL2 production, suggesting a critical role for PI3 kinase in T cell activation.

Inhibition of class I PI3 kinase induces apoptosis, blocks tumor induced angiogenesis in vivo, and increases the radiosensitivity of certain tumors. At least two compounds, LY294002 and wortmannin, have been widely used as PI3 kinase inhibitors. These compounds, however, are nonspecific PI3K inhibitors, as they do not distinguish among the four members of Class I PI3 kinases. For example, the IC50 values of wortmannin (U.S. Pat. No. 6,703,414) against each of the various Class I PI3 kinases are in the range of 1-10 nanomolar (nM). LY294002 (2-(4-morpholinyl)-8-phenyl-4H-1-benzopyran-4-one) is a well known specific inhibitor of class I PI3 kinases and has anti-cancer properties (Chiosis et al (2001) Bioorganic & Med. Chem. Lett. 11:909-913; Vlahos et al (1994) J. Biol. Chem. 269(7):5241-5248; Walker et al (2000) Mol. Cell 6:909-919; Fruman et al (1998) Ann Rev Biochem, 67:481-507).

Patent literature belonging to various research groups around the world includes several such patents and/or patent applications viz., U.S. Pat. No. 6,608,056; U.S. Pat. No. 6,608,053; U.S. Pat. No. 6,838,457; U.S. Pat. No. 6,770,641; U.S. Pat. No. 6,653,320; U.S. Pat. No. 6,403,588; WO 2004017950; US 2004092561; WO 2004007491; WO 2004006916; WO 2003037886; US 2003149074; WO 2003035618; WO 2003034997; US 2003158212; EP 1417976; US 2004053946; JP 2001247477; JP 08175990; JP 08176070). WO 97/15658, U.S. Pat. No. 7,173,029; U.S. Pat. No. 7,037,915; U.S. Pat. No. 6,703,414; WO 2006/046031; WO 2006/046035; WO 2006/046040; WO 2007/042806; WO 2007/042810; WO 2004/017950; US 2004/092561; WO 2004/007491; WO2004/006916; WO 2003/037886; US 2003/149074; WO 2003/035618; WO 2003/034997; including p110 alpha binding activity US 2008/0207611; US 2008/0039459; US 2008/0076768; WO 2008/073785; WO 2008/070740; US20090270430A1; US2006270673 A1; WO2009129211A1; US2009 0263398A1; US20090263397A1; WO2009129259A2; U.S. Pat. No. 7,605,160; U.S. Pat. No. 7,605,155; U.S. Pat. No. 7,608,622; US20090270621; US20090270445; US20090247567A1; U.S. Pat. No. 7,592,342; US2009 0239847A1; U.S. Pat. No. 7,595,320; US20090247538A1; US20090239936A1; U.S. Pat. No. 7,595,330; US20090239859A1; WO2009117482A1; WO2009117097A1; US20090247565A1; WO2009 120094A2; US20090258852A1; U.S. Pat. No. 7,601,724; WO2009126635A1; U.S. Pat. No. 7,601,718; U.S. Pat. No. 7,598,245; US20090239859A1; US20090247554; US20090238828; WO2009114874A2; WO2009114870A2; US20090234132A1; WO2009112565A1; US20090233950A1; US20090233926A1; U.S. Pat. No. 7,589,101; WO2009111547A1; WO2009111531A1; WO2009109867A2 and WO2009105712A1.

reviews and studies regarding PI3K and related protein kinase pathways have been given by Pixu Liu et. al. (*Nature Reviews Drug Discovery*, 2009, 8, 627-644); Nathan T. et. al. (Mol Cancer Ther., 2009; 8 (1) January, 2009); Romina Marone et, al. (Biochimica et Biophysica Acta 1784 (2008) 159-185) and B. Markman et. al. (Annals of oncology Advance access published August 2009). All of these patents and/or patent applications and literature disclosures are incorporated herein as reference in their entirety for all purposes.

Despite the advances made in the area of kinases and in particular the role that PI3K and related protein kinases play in human diseases, challenges remain in terms of the complexities of the target involved, the protein structure of the kinases, specificity issues for various kinase inhibitors, side effects and desired clinical benefits expected form the PI3K inhibitors. Accordingly, there still remains an unmet and dire need for small molecule kinase modulators in order to regulate and/or modulate transduction of kinases, particularly PI3K and related protein kinase for the treatment of diseases and disorders associated with kinases-mediated events.

SUMMARY OF INVENTION

The present invention is directed to compounds, which are useful as PI3K protein kinase modulators and in particular as PI3K inhibitors. In one embodiment, the compound of the present invention has the formula:

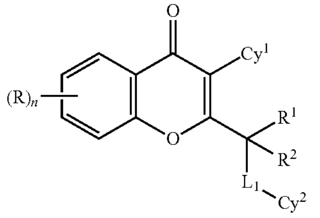

(I)

or a tautomer thereof, N-oxide thereof, pharmaceutically acceptable ester thereof, prodrug thereof, or pharmaceutically acceptable salt thereof, wherein each occurrence of R is independently selected from hydrogen, halogen, —OR$^a$, CN, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-8}$ cycloalkyl, and substituted or unsubstituted heterocyclic group;

$R^1$ and $R^2$ may be the same or different and are independently selected from hydrogen, halogen, and substituted or unsubstituted $C_{1-6}$ alkyl, or both $R^1$ and $R^2$ directly bound to a common atom, may be joined to form an oxo group (═O) or a substituted or unsubstituted saturated or unsaturated 3-10 member ring (including the carbon atom to which $R^1$ and $R^2$ are bound), which may optionally include one or more heteroatoms which may be the same or different and are selected from O, NR$^a$ and S;

$Cy^1$ is a monocyclic group selected from substituted or unsubstituted cycloalkyl, substituted or unsubstituted heterocyclic group, substituted or unsubstituted aryl and substituted or unsubstituted heteroaryl;

$Cy^2$ is selected from a substituted or unsubstituted heterocyclic group, substituted or unsubstituted aryl and substituted or unsubstituted heteroaryl;

$L_1$ is absent or selected from —(CR$^a$R$^b$)$_q$—, —O—, —S(═O)$_q$—, —NR$^a$— or —C(═Y)—.

each occurrence of R$^a$ and R$^b$ may be the same or different and are independently selected from hydrogen, halogen, hydroxy, cyano, substituted or unsubstituted ($C_{1-6}$)alkyl, —NR$^c$R$^d$ (wherein R$^c$ and R$^d$ are independently hydrogen, halogen, hydroxy, cyano, substituted or unsubstituted ($C_{1-6}$) alkyl, and ($C_{1-6}$)alkoxy) and —OR$^c$ (wherein R$^c$ is substituted or unsubstituted ($C_{1-6}$)alkyl) or when R$^a$ and R$^b$ are directly bound to a common atom, they may be joined to form an oxo group (═O) or form a substituted or unsubstituted saturated or unsaturated 3-10 member ring (including the common atom to which R$^a$ and R$^b$ are directly bound), which may optionally include one or more heteroatoms which may be the same or different and are selected from O, NR$^d$ (wherein R$^d$ is hydrogen or substituted or unsubstituted ($C_{1-6}$)alkyl) or S;

Y is selected from O, S, and NR$^a$;

n is an integer from 1 to 4; and q is 0, 1 or 2.

Yet another embodiment is a compound having the formula (I-A) or (I-B)

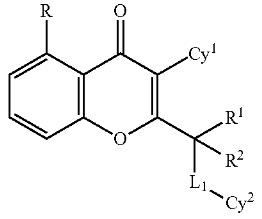

(I-A)

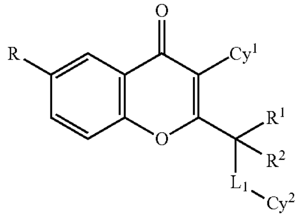

(I-B)

or a tautomer thereof, N-oxide thereof, pharmaceutically acceptable ester thereof, prodrug thereof, or pharmaceutically acceptable salt thereof, wherein R is independently selected from hydrogen, halogen, —OR$^a$, CN, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-8}$ cycloalkyl, and substituted or unsubstituted heterocyclic group;

$R^1$ and $R^2$ may be the same or different and are independently selected from hydrogen, halogen, and substituted or unsubstituted $C_{1-6}$ alkyl or both $R^1$ and $R^2$ directly bound to a common atom, may be joined to form an oxo group (═O) or may be joined to form a substituted or unsubstituted saturated or unsaturated 3-10 member ring (including the common atom to which $R^1$ and $R^2$ are directly bound), which may optionally include one or more heteroatoms which may be the same or different and are selected from O, NR$^a$ and S;

$Cy^1$ is a monocyclic group selected from substituted or unsubstituted cycloalkyl, substituted or unsubstituted heterocyclic group, substituted or unsubstituted aryl and substituted or unsubstituted heteroaryl;

$Cy^2$ is selected from substituted or unsubstituted heterocyclic group and substituted or unsubstituted heteroaryl.

$L_1$ is absent or selected from —(CR$^a$R$^b$)$_q$—, —O—, —S(═O)$_q$—, —NR$^a$— or —C(═Y)—.

each occurrence of R$^a$ and R$^b$ may be the same or different and are independently selected from hydrogen, halogen, hydroxy, cyano, substituted or unsubstituted ($C_{1-6}$)alkyl, —NR$^c$R$^d$ (wherein R$^c$ and R$^d$ are independently hydrogen, halogen, hydroxy, cyano, substituted or unsubstituted ($C_{1-6}$) alkyl, and ($C_{1-6}$)alkoxy) and —OR$^c$ (wherein R$^c$ is substituted or unsubstituted ($C_{1-6}$)alkyl) or when R$^a$ and R$^b$ are directly bound to a common atom, they may be joined to form an oxo group (═O) or form a substituted or unsubstituted saturated or unsaturated 3-10 member ring (including the common atom to which R$^a$ and R$^b$ are directly bound), which may optionally include one or more heteroatoms which may be the same or different and are selected from O, NR$^d$ (wherein R$^d$ is hydrogen or substituted or unsubstituted ($C_{1-6}$)alkyl) or S;

Y is selected from O, S, and NR$^a$; and q is 0, 1 or 2.

Yet another embodiment is a compound having the formula (I), (I-A), or (I-B) wherein R is selected from hydrogen, halogen, substituted or unsubstituted $C_{1-6}$ alkyl or OR$^a$.

Yet another embodiment is a compound having the formula (I), (I-A), or (I-B) wherein R is selected from hydrogen, halogen or $OR^a$.

Further preferred is a compound having the formula (I), (I-A), or (I-B) wherein $Cy^1$ is selected from substituted or unsubstituted aryl and substituted or unsubstituted heteroaryl.

Illustrative examples of optionally substituted $Cy^1$ groups include those shown below:

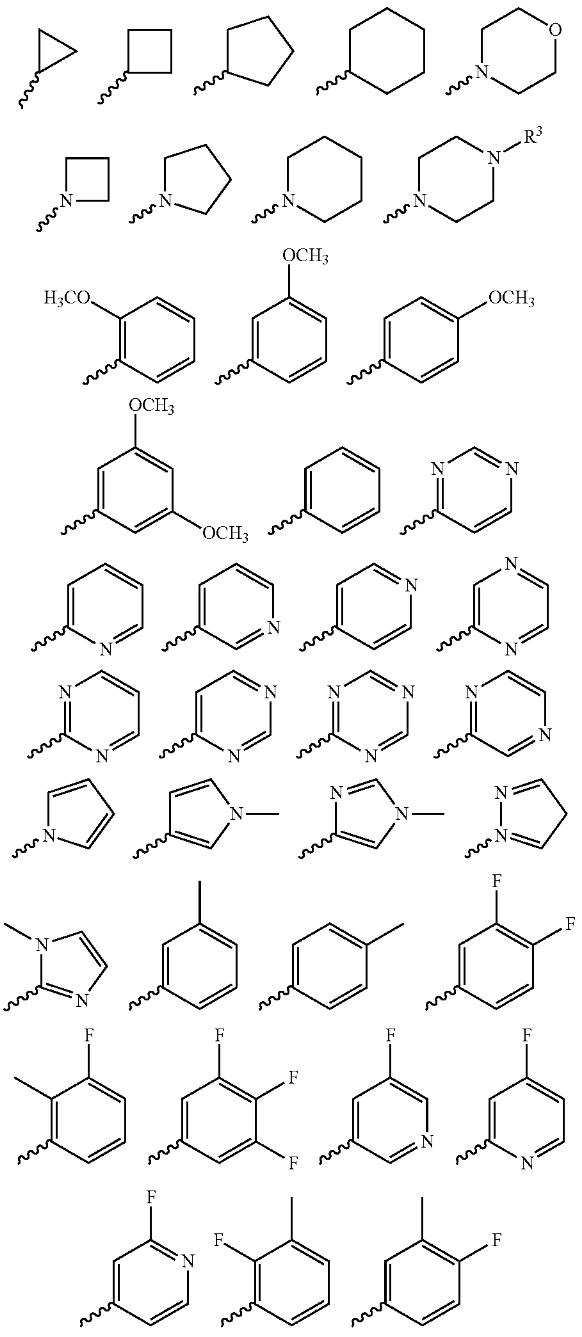

Further preferred is a compound having the formula (I) wherein $Cy^1$ is selected from

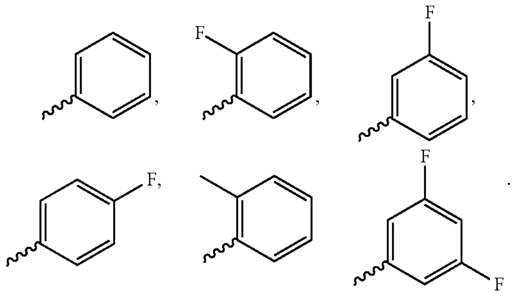

Further preferred is a compound having the formula (I) wherein $Cy^1$ is substituted or unsubstituted phenyl Further preferred is a compound having the formula (I) wherein $Cy^1$ is substituted phenyl.

Further preferred is a compound having the formula (I) wherein $Cy^1$ is 2-methyl phenyl or 3-fluoro phenyl.

Yet another embodiment is a compound having the formula (I) wherein $R^1$ and $R^2$ independently represent hydrogen or substituted or unsubstituted $C_{1-6}$ alkyl.

Yet another embodiment is a compound having the formula (I) wherein $L_1$ is selected from —S(=O)$_q$— or —NR$^a$—.

Yet another embodiment is a compound having the formula (I) wherein q is 0.

Yet another embodiment is a compound having the formula (I) wherein $L_1$ is absent.

Yet another embodiment, is a compound having the formula (I) wherein $Cy^2$ is selected from

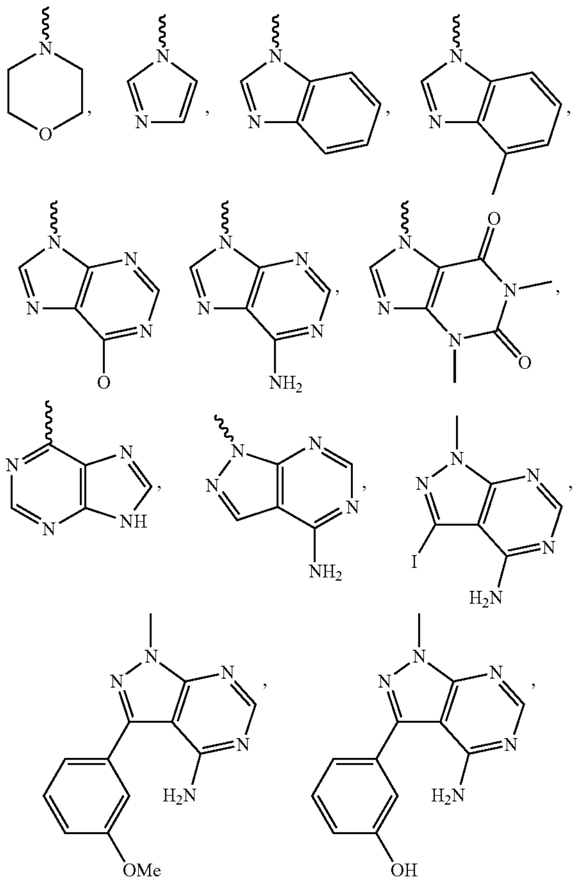

-continued
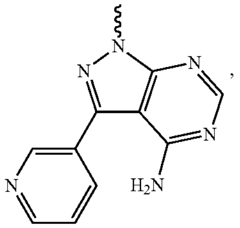,
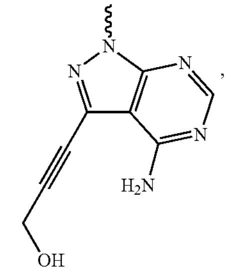,
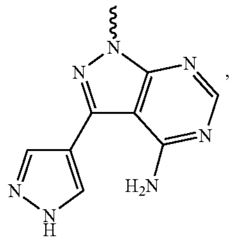,
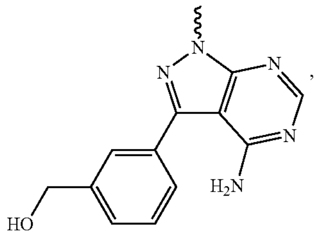,
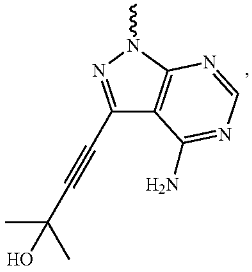,
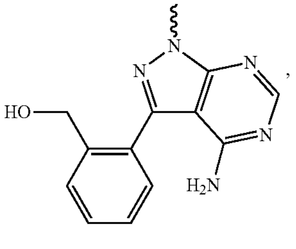,
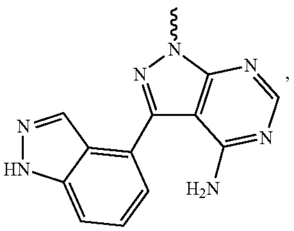,
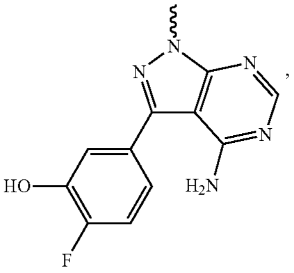,
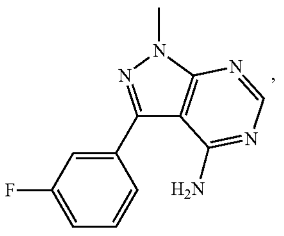,
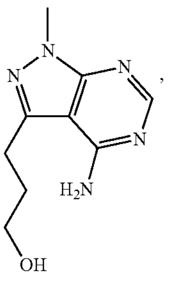,
-continued
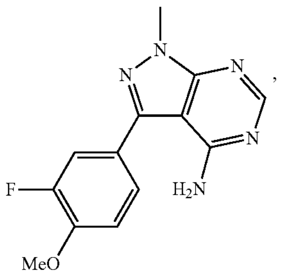,
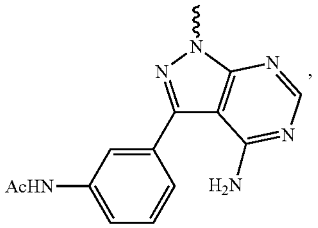,
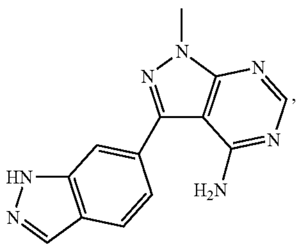,
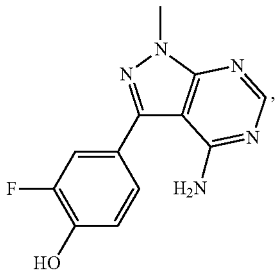,
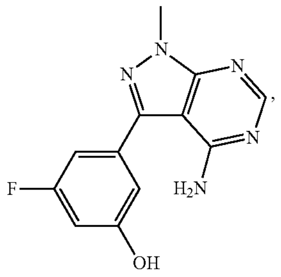,
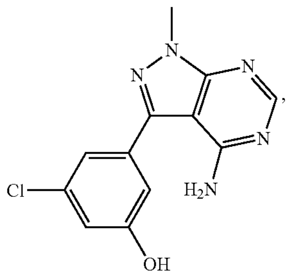,
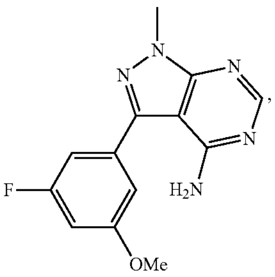,
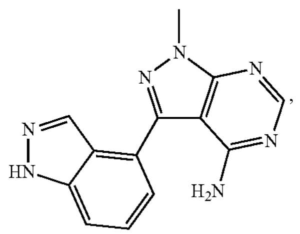, -continued
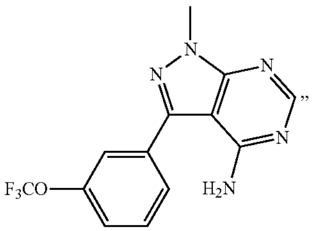
,,
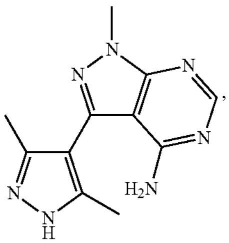
,
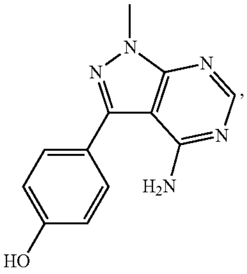
,
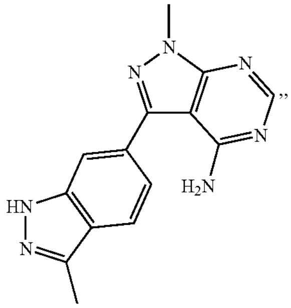
,,
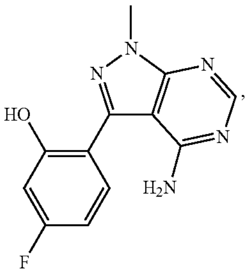
,
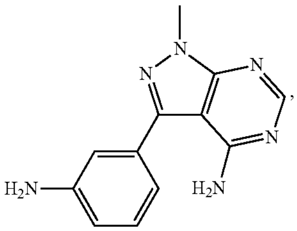
,
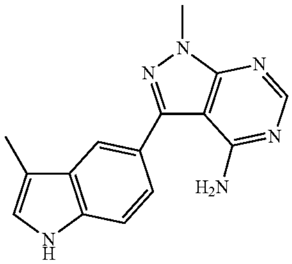
,
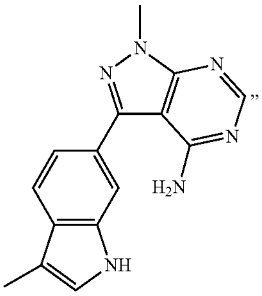
,,
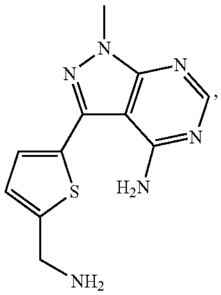
,
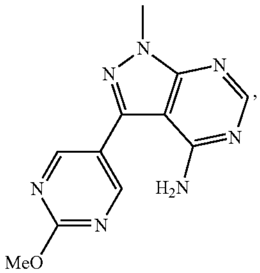
,
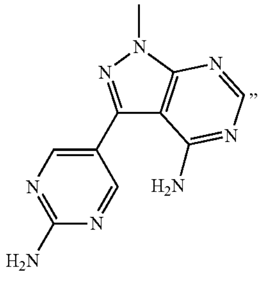
,,
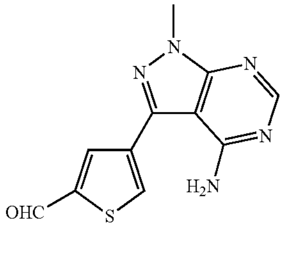
,
-continued
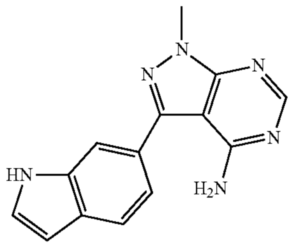
,
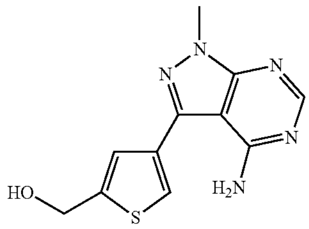
,
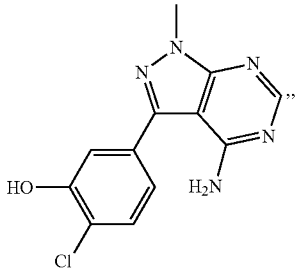
,,
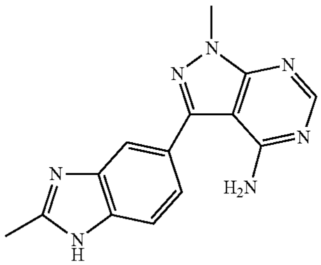
,
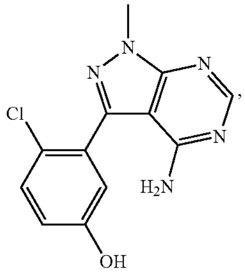
,
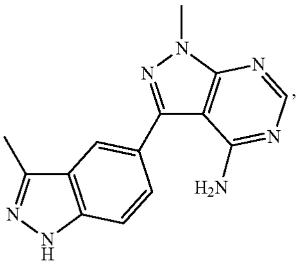
,
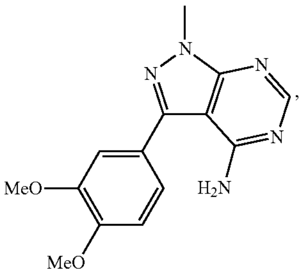
,
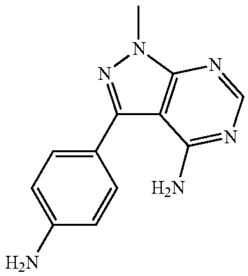
, -continued
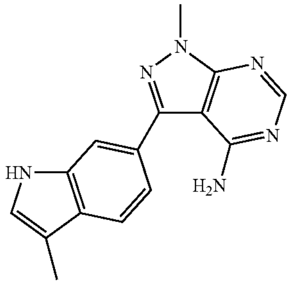,
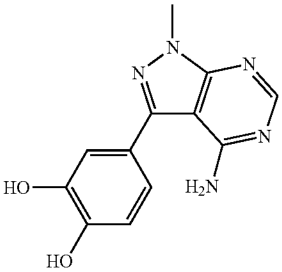,
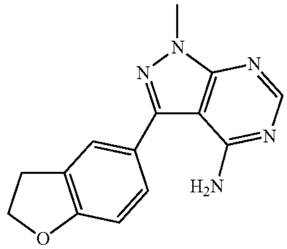,
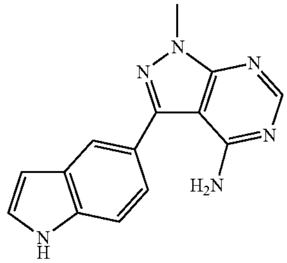,
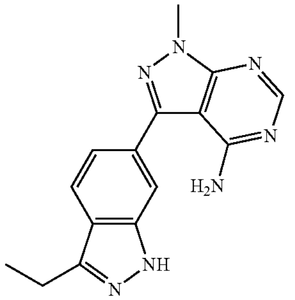
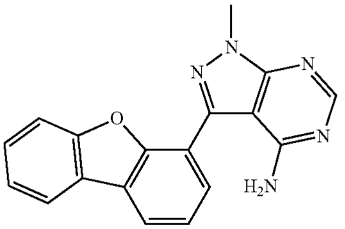
-continued
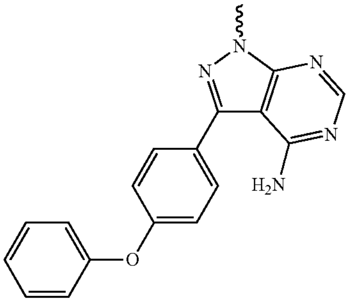
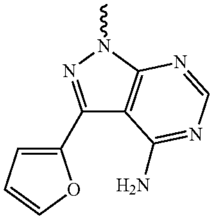
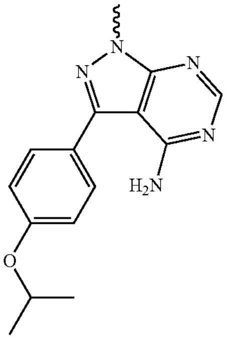
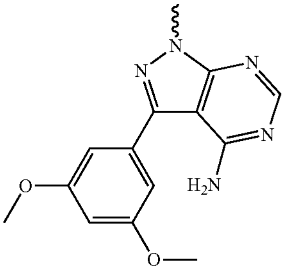
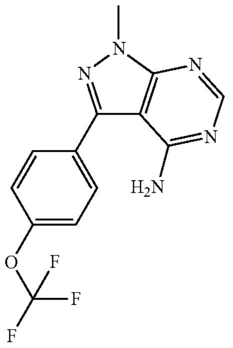
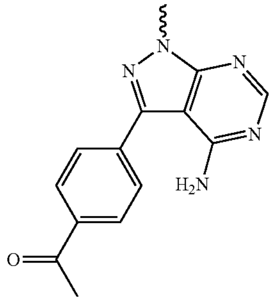
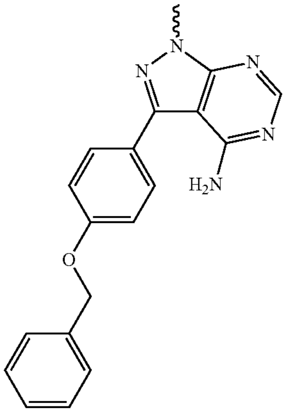
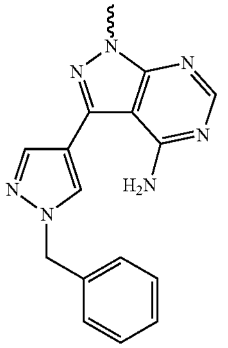

-continued
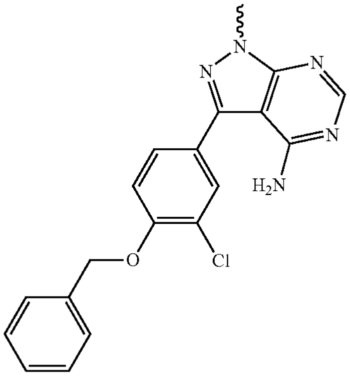
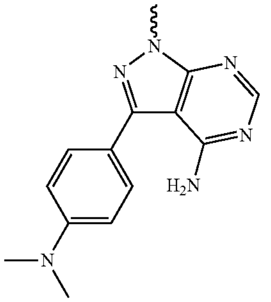
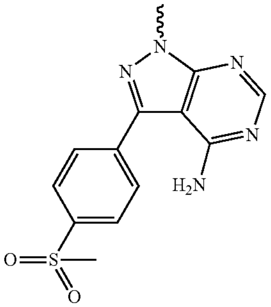
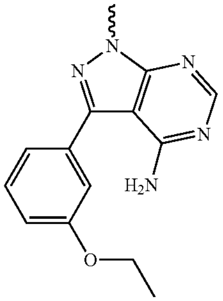
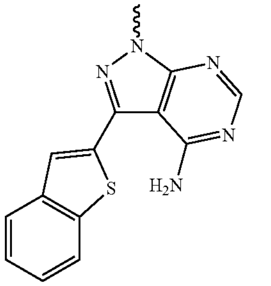
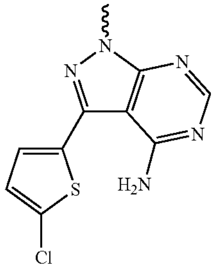
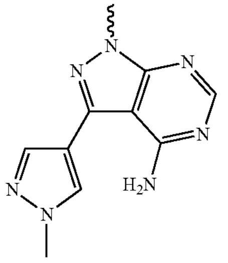
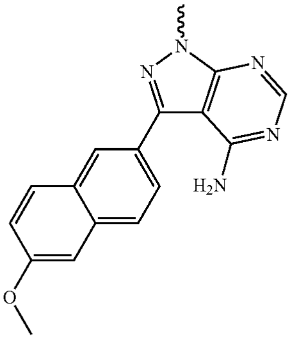
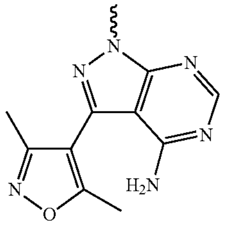
-continued
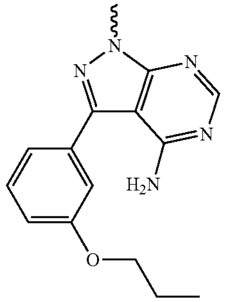
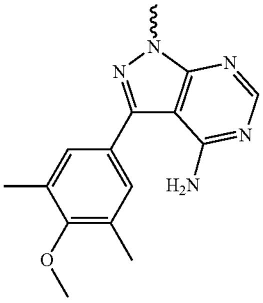
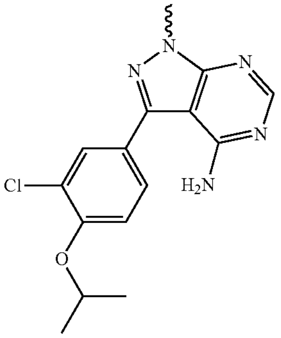
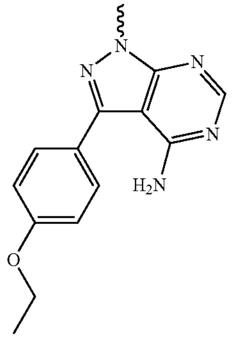
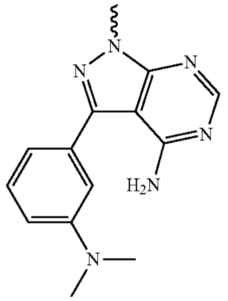
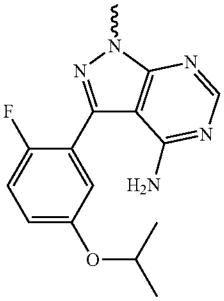
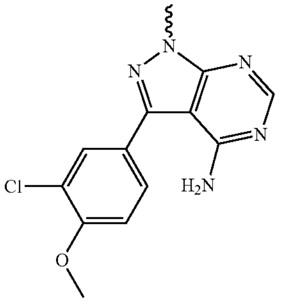
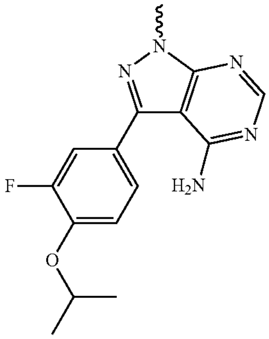
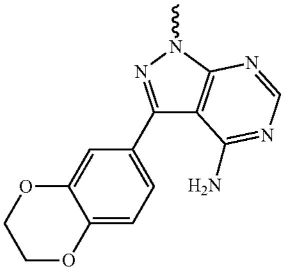
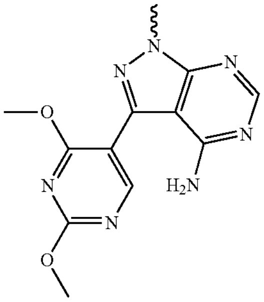

-continued
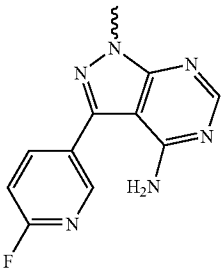
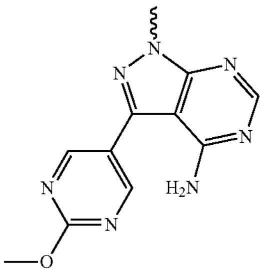
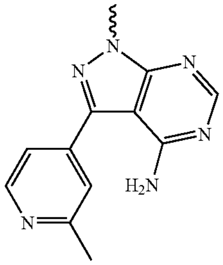
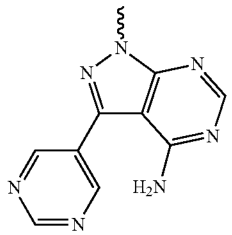
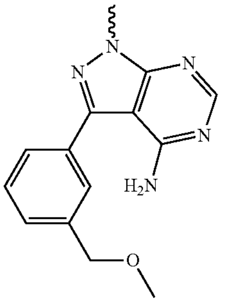
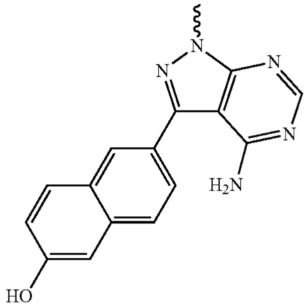
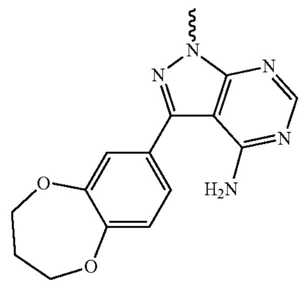
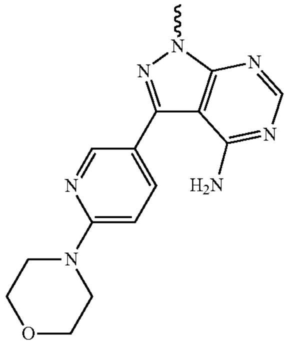
-continued
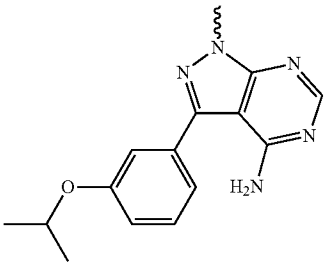
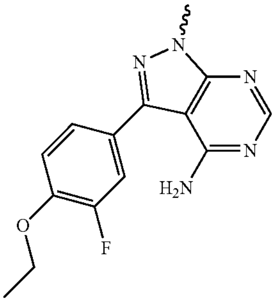
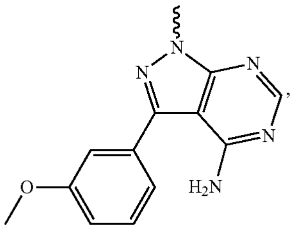
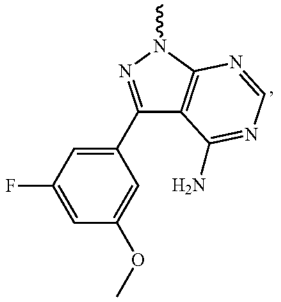
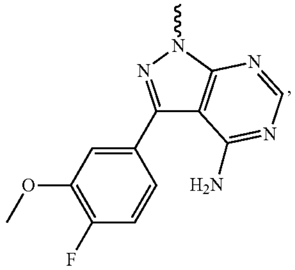
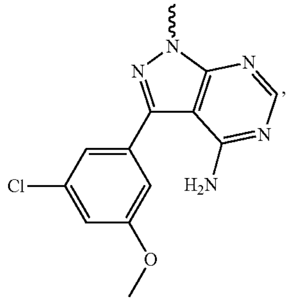
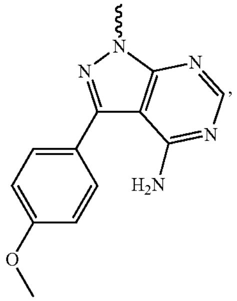
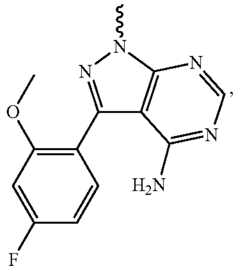
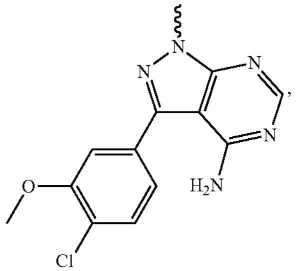

-continued
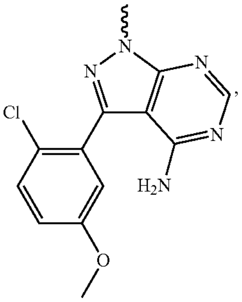
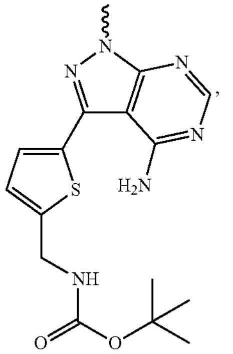
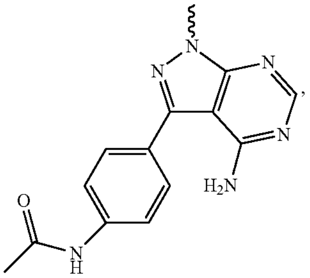
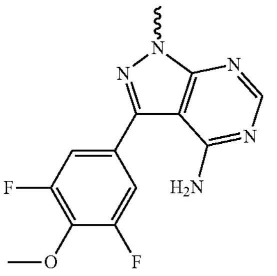
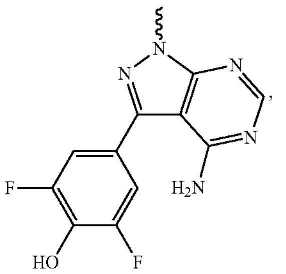
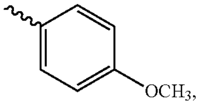
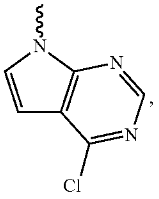
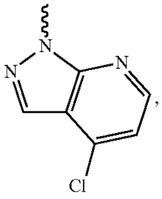
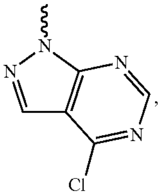
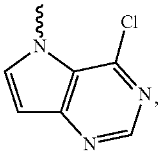
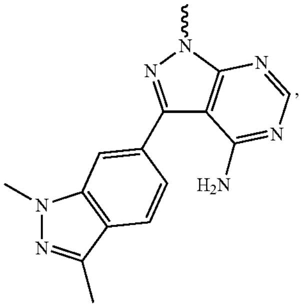
-continued
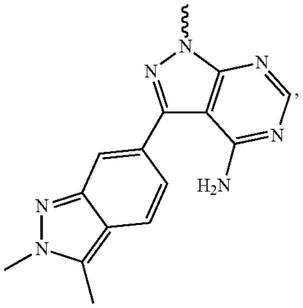
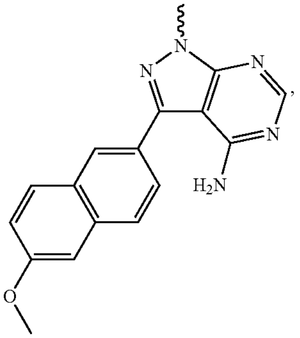
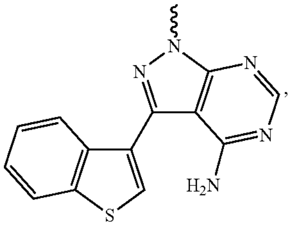
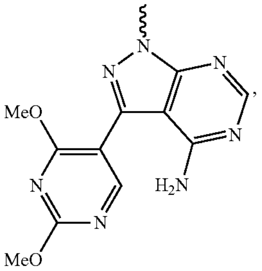
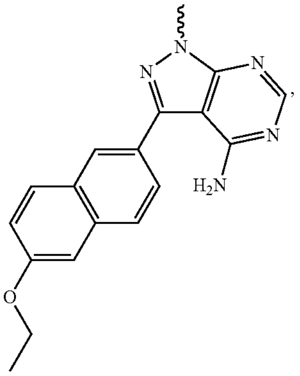
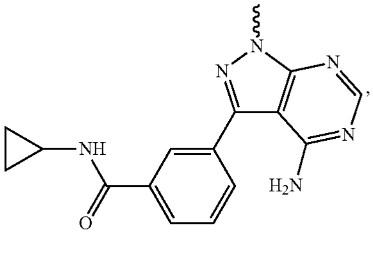

-continued

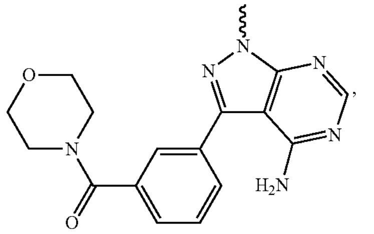

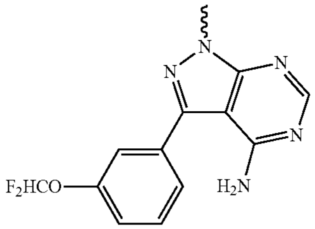

or

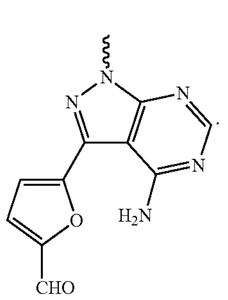

Yet another embodiment, is a compound having the formula (I) wherein $Cy^2$ is selected from a

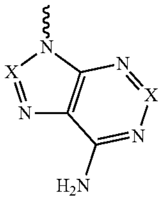

b

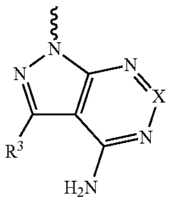

c

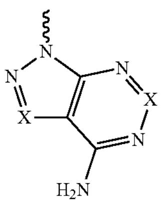

-continued d

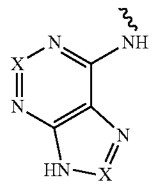

e

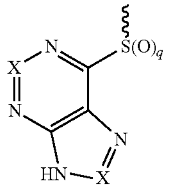

wherein

X is $CR^3$; and $R^3$ is independently selected from hydrogen, hydroxy, halogen, carboxyl, cyano, nitro, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted aryl, substituted or unsubstituted heteroaryl, substituted heterocyclylalkyl ring, substituted or unsubstituted heteroarylalkyl, substituted or unsubstituted heterocyclic ring, substituted or unsubstituted guanidine, $—COOR^x$, $—C(O)R^x$, $—C(S)R^x$, $—C(O)NR^xR^y$, $—C(O)ONR^xR^y$, $—NR^yR^z$, $—NR^xCONR^yR^z$, $—N(R^x)SOR^y$, $—N(R^x)SO_2R^y$, $—(=N—N(R^x)R^y)$, $—NR^xC(O)OR^y$, $—NR^xR^y$, $—NR^xC(O)R^y—$, $—NR^xC(S)R^y—NR^xC(S)NR^yR^z$, $—SONR^xR^y—$, $—SO_2NR^xR^y—$, $—OR^x$, $—OR^xC(O)NR^yR^z$, $—OR^xC(O)OR^y—$, $—OC(O)R^x$, $—OC(O)NR^xR^y$, $—R^xNR^yC(O)R^z$, $—R^xOR^y$, $—R^xC(O)OR^y$, $—R^xC(O)NR^yR^z$, $—R^xC(O)R^x$, $—R^xOC(O)R^y$, $—SR^x$, $—SOR^x$, $—SO_2R^x$, $—ONO_2$, wherein $R^x$, $R^y$ and $R^z$ in each of the above groups can be hydrogen, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted amino, substituted or unsubstituted aryl, substituted or unsubstituted heteroaryl, substituted heterocyclylalkyl ring, substituted or unsubstituted heteroarylalkyl, or substituted or unsubstituted heterocyclic ring, or any two of $R^x$, $R^y$ and $R^z$ may be joined to form a substituted or unsubstituted saturated or unsaturated 3-10 membered ring, which may optionally include heteroatoms which may be the same or different and are selected from O, $NR^X$ or S.

For example, $Cy^2$ represented as formula a, b c, d or e above can be

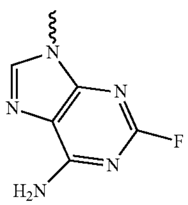

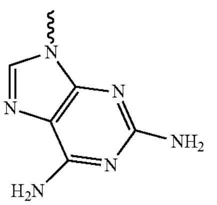

-continued
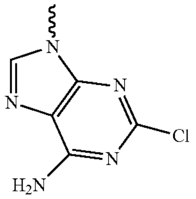
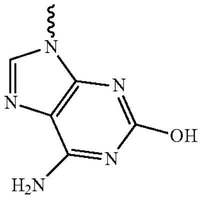
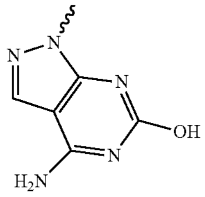
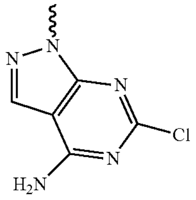
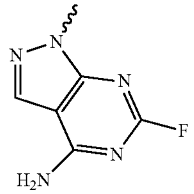
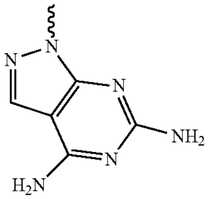
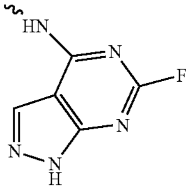
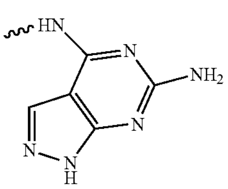
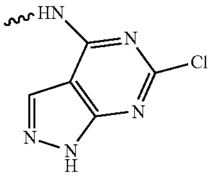
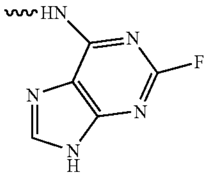
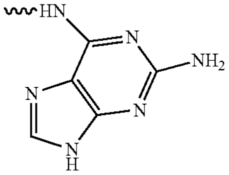
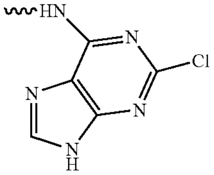
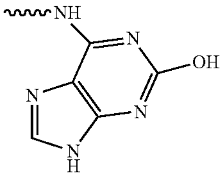
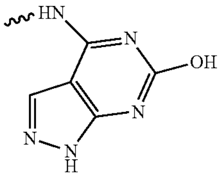
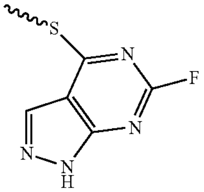
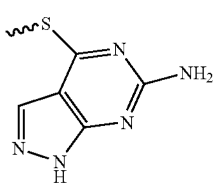
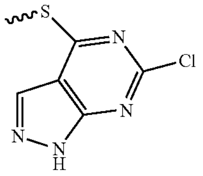
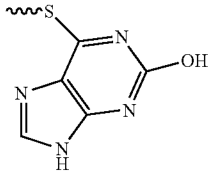
-continued
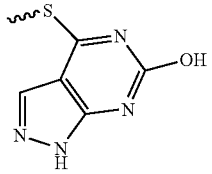
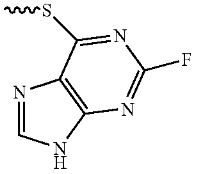
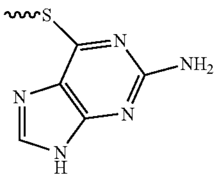
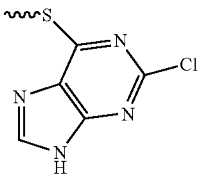
Yet another embodiment is a compound having the formula (IA-I), (IA-II), (IA-III) or (IA-IV)
(IA-I)
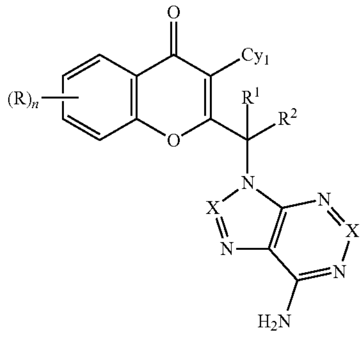
(IA-II)
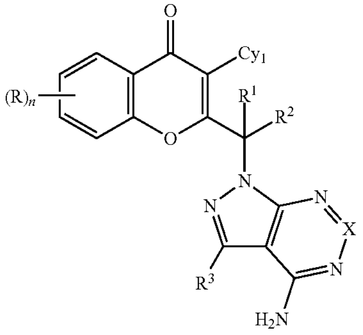
(IA-III)
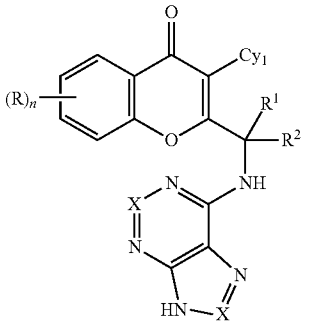

-continued (IA-IV)

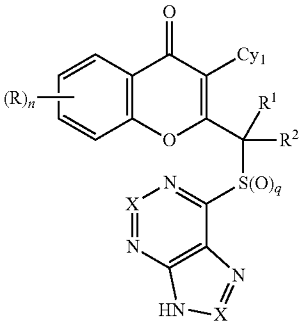

or a tautomer thereof, N-oxide thereof, pharmaceutically acceptable ester thereof, prodrug thereof, or pharmaceutically acceptable salt thereof, wherein:

each occurrence of R is independently selected from hydrogen, halogen, —$OR^a$, CN, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-8}$ cycloalkyl, and substituted or unsubstituted heterocyclic group;

$R^1$ and $R^2$ may be the same or different and are independently selected from hydrogen, halogen, and substituted or unsubstituted $C_{1-6}$ alkyl or both $R^1$ and $R^2$ directly bound to a common atom, may be joined to form an oxo group (═O) or may be joined to form a substituted or unsubstituted saturated or unsaturated 3-10 member ring (including the common atom to which $R^1$ and $R^2$ are directly bound), which may optionally include one or more heteroatoms which may be the same or different and are selected from O, $NR^a$ and S;

$Cy^1$ is a monocyclic group selected from substituted or unsubstituted cycloalkyl, substituted or unsubstituted heterocyclic group, substituted or unsubstituted aryl and substituted or unsubstituted heteroaryl;

each occurrence of X is independently selected from $CR^3$ or N;

each occurrence of $R^3$ is independently selected from hydrogen, hydroxy, halogen, carboxyl, cyano, nitro, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkylalkyl, substituted or unsubstituted cycloalkenylalkyl substituted or unsubstituted cycloalkenyl, substituted or unsubstituted heteroaryl, substituted or unsubstituted heteroarylalkyl, substituted or unsubstituted heterocyclic ring, substituted heterocyclylalkyl ring, substituted or unsubstituted guanidine, —$COOR^x$, —$C(O)R^x$, —$C(S)R^x$, —$C(O)NR^xR^y$, —$C(O)ONR^xR^y$, —$NR^yR^z$, —$NR^xCONR^yR^z$, —$N(R^x)SOR^y$, —$N(R^x)SO_2R^y$, —(═N—$N(R^x)R^y$), —$NR^xC(O)OR^y$, —$NR^xR^y$, —$NR^xC(O)R^y$—, —$NR^xC(S)R^y$—$NR^xC(S)NR^yR^z$, —$SONR^xR^y$—, —$SO_2NR^xR^y$—, —$OR^x$, —$OR^xC(O)NR^yR^z$, —$OR^xC(O)OR^y$—, —$OC(O)R^x$, —$OC(O)NR^xR^y$, —$R^xNR^yC(O)R^z$, —$R^xOR^y$, —$R^xC(O)OR^y$, —$R^xC(O)NR^yR^z$, —$R^xC(O)R^x$, —$R^xOC(O)R^y$, —$SR^x$, —$SOR^x$, —$SO_2R^x$, and —$ONO_2$, wherein $R^x$, $R^y$ and $R^z$ in each of the above groups can be hydrogen, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkylalkyl, substituted or unsubstituted cycloalkenyl, substituted or unsubstituted heteroaryl, substituted or unsubstituted heteroarylalkyl, substituted or unsubstituted heterocyclic ring, substituted or unsubstituted heterocyclylalkyl ring, or substituted or unsubstituted amino, or any two of $R^x$, $R^y$ and $R^z$ may be joined to form a substituted or unsubstituted saturated or unsaturated 3-10 membered ring, which may optionally include heteroatoms which may be the same or different and are selected from O, $NR^x$ (e.g., $R^x$ can be hydrogen or substituted or unsubstituted alkyl) or S.

n is an integer from 1 to 4; and q is 0, 1 or 2.

Yet another embodiment is a compound having the formula (IA-I), (IA-II), (IA-III) or (IA-IV) wherein R is selected from hydrogen, halogen, substituted or unsubstituted $C_{1-6}$ alkyl or $OR^a$.

Yet another embodiment is a compound having the formula (IA-I), (IA-II), (IA-III) or (IA-IV) wherein R is selected from hydrogen, halogen or $OR^a$.

Yet another embodiment is a compound having the formula (IA-I), (IA-II), (IA-III) or (IA-IV) wherein $Cy^1$ is selected from

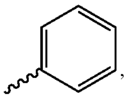, 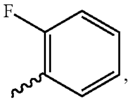, 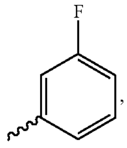, 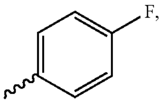, 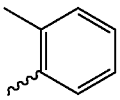 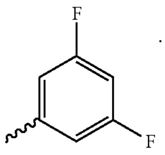.

Yet another embodiment is a compound having the formula (IA-I), (IA-II), (IA-III) or (IA-IV) wherein n is 1.

Yet another embodiment is a compound having the formula (IA-I), (IA-II), (IA-III) or (IA-IV) wherein $R^1$ and $R^2$ independently represent hydrogen or substituted or unsubstituted $C_{1-6}$ alkyl.

Yet another embodiment is a compound having the formula (IA-II) wherein $R^3$ is selected from iodo, cyano, substituted or unsubstituted alkynyl, substituted or unsubstituted aryl, and substituted or unsubstituted heteroaryl.

Yet another embodiment is a compound having the formula (IA-II) wherein $R^3$ is selected from substituted or unsubstituted alkynyl, substituted or unsubstituted aryl, and substituted or unsubstituted heteroaryl.

Yet another embodiment is a compound having the formula (IA-II) wherein $R^3$ is selected from

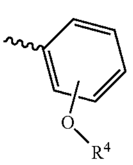 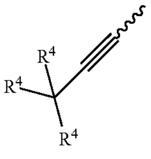 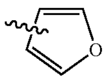 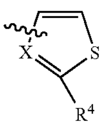

-continued

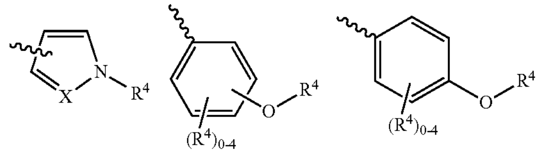
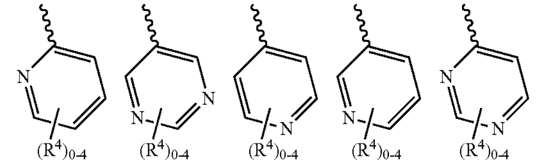
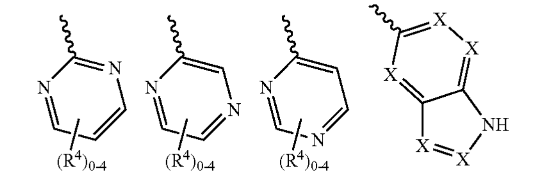
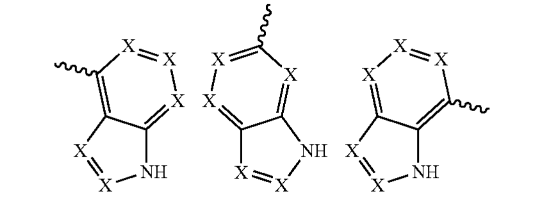
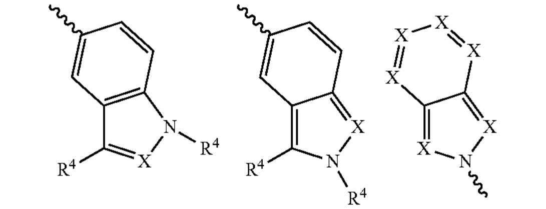
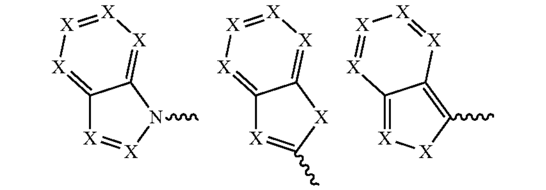
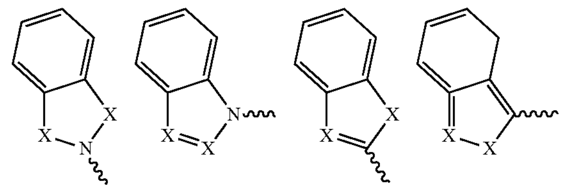
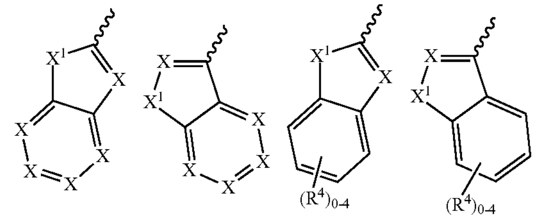
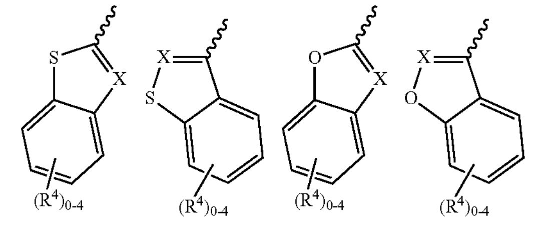

-continued

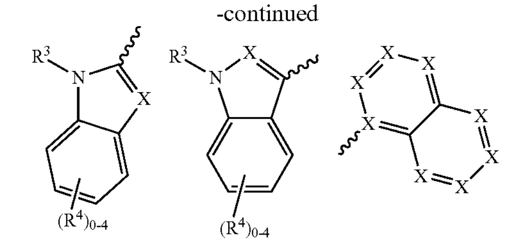
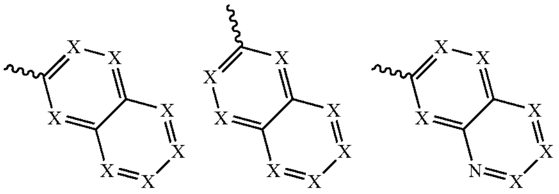
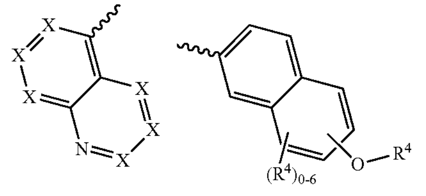

wherein each occurrence of X is independently $CR^4$ or N;

$X^1$ is O, S, or $NR^4$; and each occurrence of $R^4$ is independently selected from hydrogen, hydroxy, halogen, carboxyl, cyano, nitro, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkylalkyl, substituted or unsubstituted cycloalkenylalkyl substituted or unsubstituted cycloalkenyl, substituted or unsubstituted heteroaryl, substituted or unsubstituted heteroarylalkyl, substituted or unsubstituted heterocyclic ring, substituted heterocyclylalkyl ring, substituted or unsubstituted guanidine, $—COOR^x$, $—C(O)R^x$, $—C(S)R^x$, $—C(O)NR^xR^y$, $—C(O)ONR^xR^y$, $—NR^yR^z$, $—NR^xCONR^yR^z$, $—N(R^x)SOR^y$, $—N(R^x)SO_2R^y$, $—(=N—N(R^x)R^y)$, $—NR^xC(O)OR^y$, $—NR^xR^y$, $—NR^xC(O)R^y—$, $—NR^xC(S)R^y—NR^xC(S)NR^yR^z$, $—SONR^xR^y—$, $—SO_2NR^xR^y—$, $—OR^x$, $—OR^xC(O)NR^yR^z$, $—OR^xC(O)OR^y—$, $—OC(O)R^x$, $—OC(O)NR^xR^y$, $—R^xNR^yC(O)R^z$, $—R^xOR^y$, $—R^xC(O)OR^y$, $—R^xC(O)NR^yR^z$, $—R^xC(O)R^x$, $—R^xOC(O)R^y$, $—SR^x$, $—SOR^x$, $—SO_2R^x$, and $—ONO_2$, wherein $R^x$, $R^y$ and $R^z$ in each of the above groups can be hydrogen, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkylalkyl, substituted or unsubstituted cycloalkenyl, substituted or unsubstituted heteroaryl, substituted or unsubstituted heteroarylalkyl, substituted or unsubstituted heterocyclic ring, substituted or unsubstituted heterocyclylalkyl ring, or substituted or unsubstituted amino, or any two of $R^x$, $R^y$ and $R^z$ may be joined to form a substituted or unsubstituted saturated or unsaturated 3-10 membered ring, which may optionally include heteroatoms which may be the same or different and are selected from O, $NR^x$ (e.g., $R^x$ can be hydrogen or substituted or unsubstituted alkyl) or S.

For example, $R^3$ can be any one of the following:
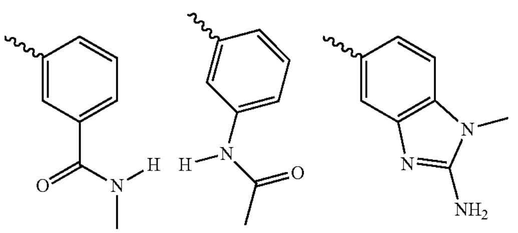
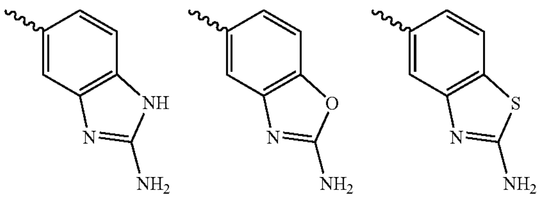
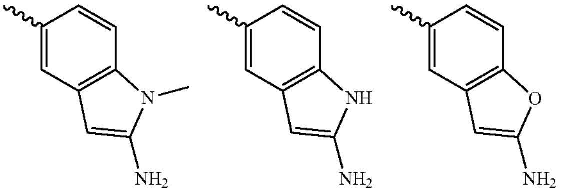
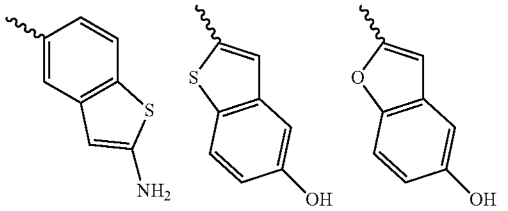
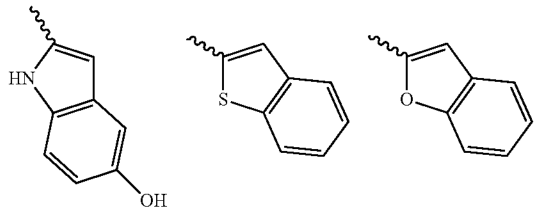
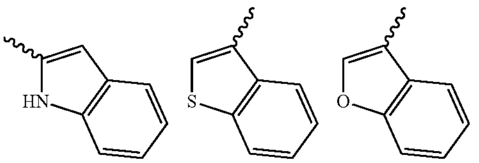
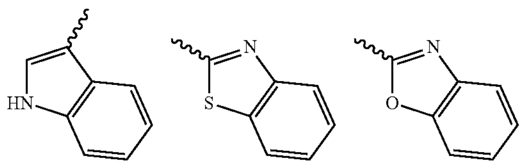
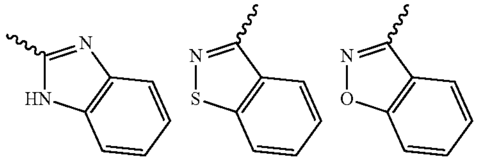
-continued
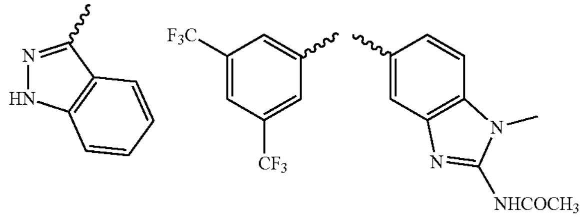
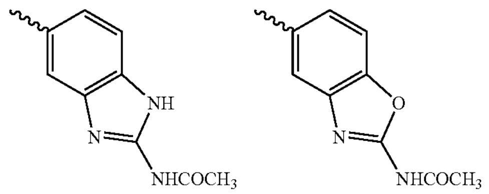
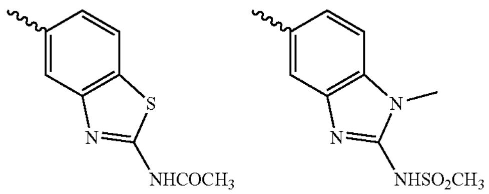
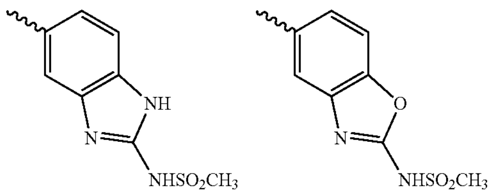
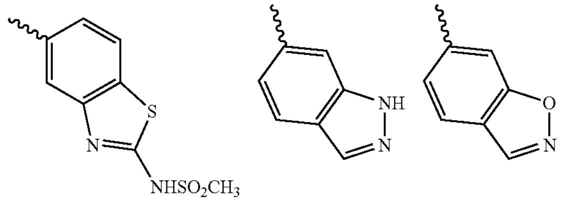
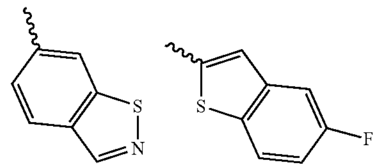
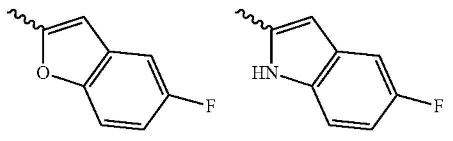
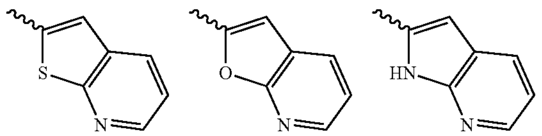
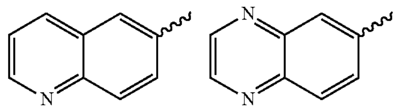
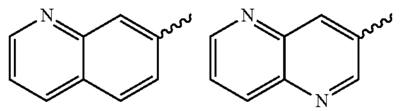

-continued
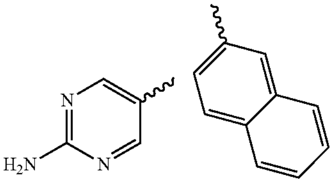
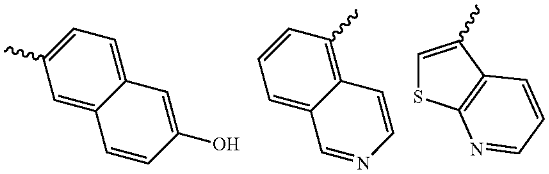
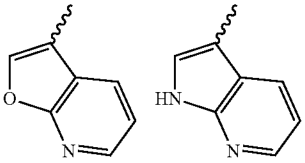
Yet another embodiment is a compound having the formula (IA-II) wherein $R^3$ is selected from
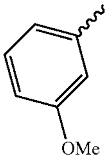 , 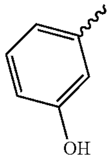 , 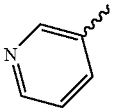 , 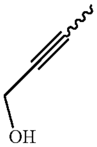 ,
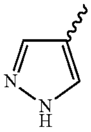 , 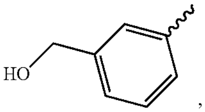 , 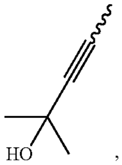 ,
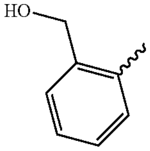 , 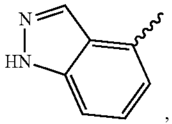 , 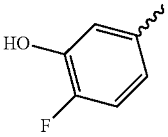 ,
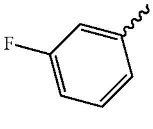 , 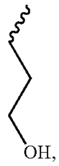 , 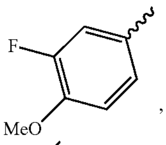 ,
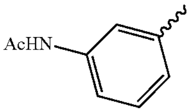 , 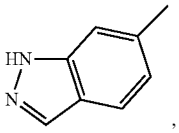 , 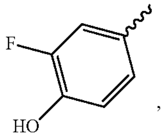 ,
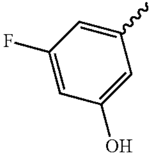 , 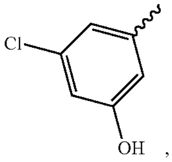 , 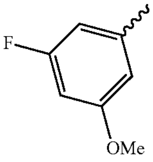 ,
-continued
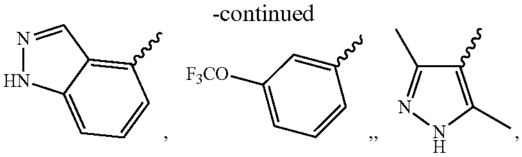 ,
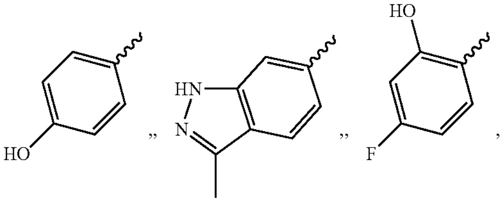 ,
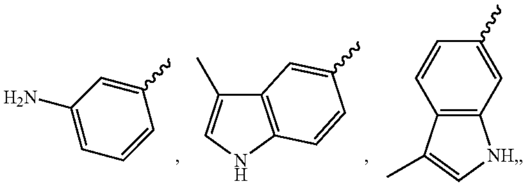 ,
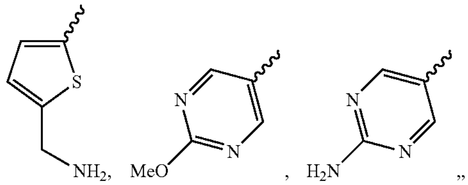 ,
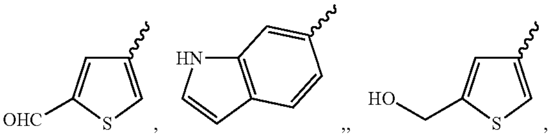 ,
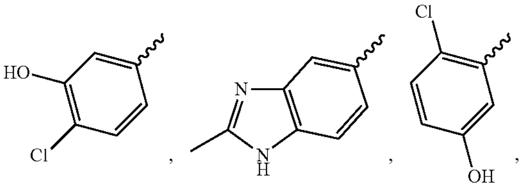 ,
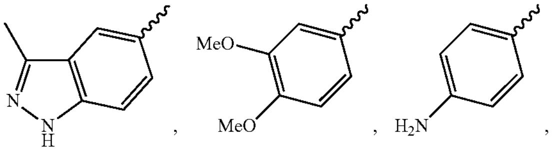 ,
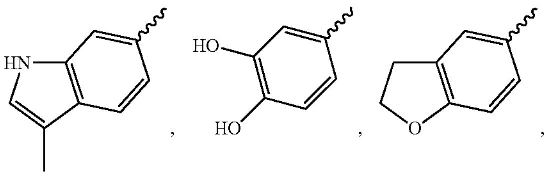 ,
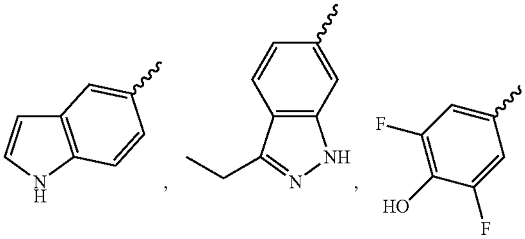

-continued
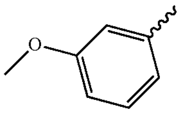 , 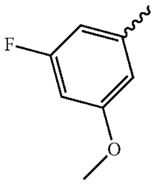 , 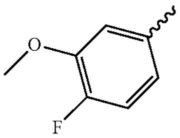 ,
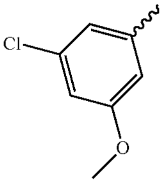 , 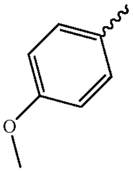 , 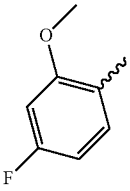 ,
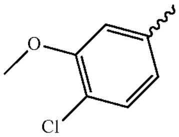 , 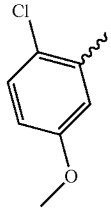 , 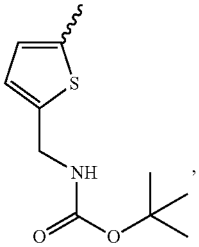 ,
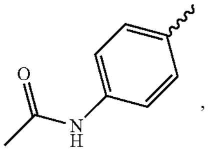 , 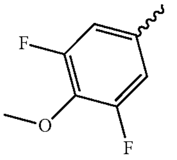 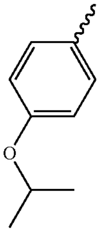
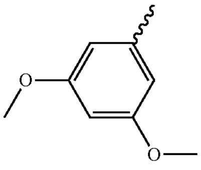 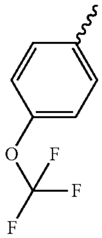 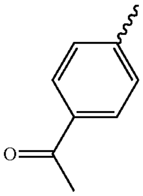
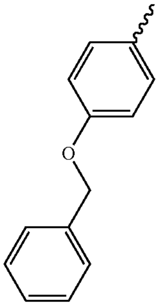 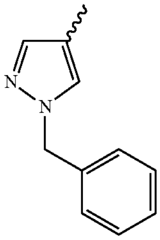 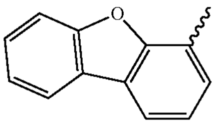
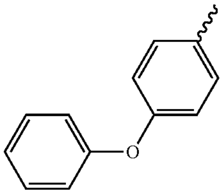 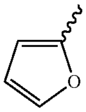 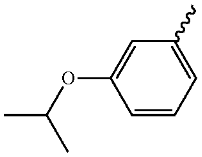
-continued
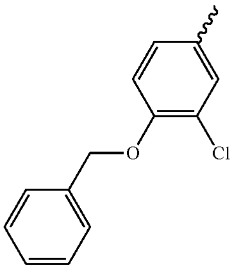 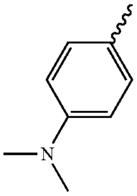 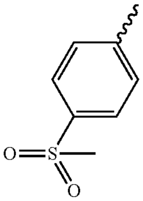
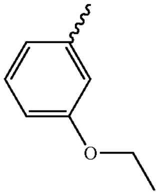 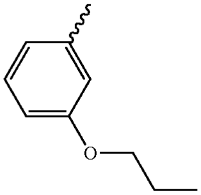 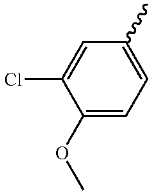
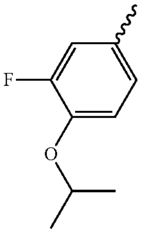 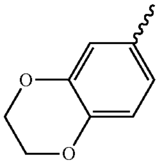 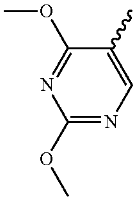
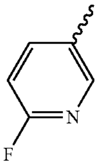 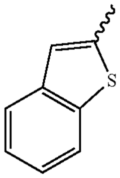 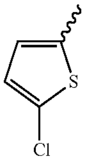 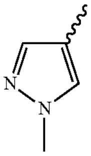
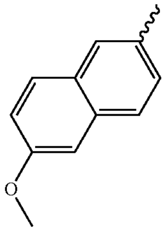 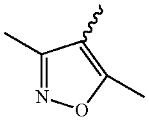 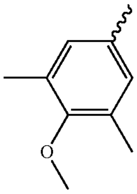
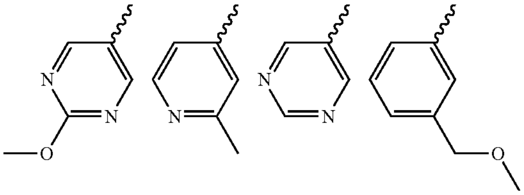
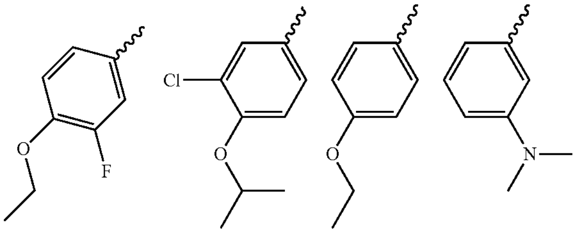

-continued

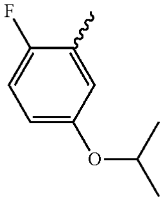
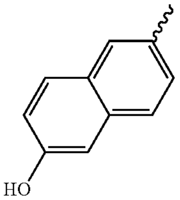
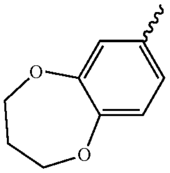

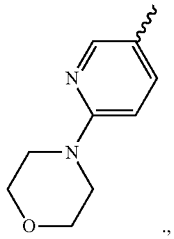.,
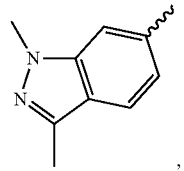,

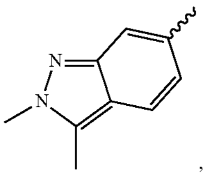,
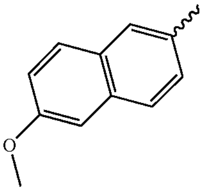,

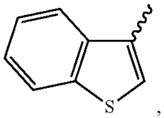,
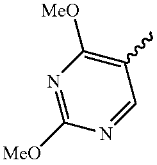,

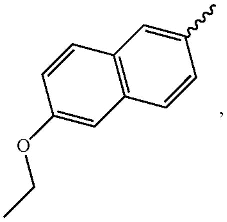,
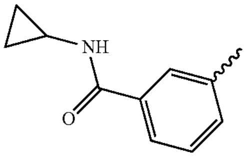,

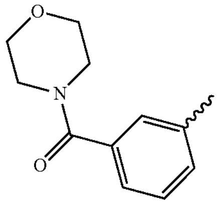,
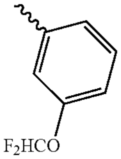 and
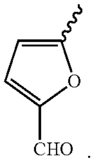.

Yet another embodiment is a compound having the formula (IA-I), (IA-II), (IA-III) and (IA-IV) wherein X is $CR^3$ and each occurrence of $R^3$ is independently hydrogen, halogen, hydroxyl or $NH_2$.

Yet another embodiment is a compound of formula (IA-V)

(IA-V)

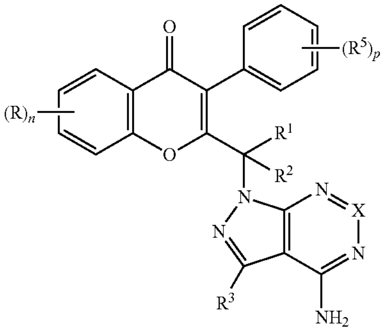

or a pharmaceutically acceptable salt thereof, wherein

R, $R^1$, $R^2$, $R^3$ and X are as defined above with respect to any of formulas (I), (I-A), (I-B), (IA-I) and (IA-II);

each occurrence of $R^5$ is hydrogen, $C_{1-6}$ alkyl or halogen; and p is 0, 1, 2, 3, 4 or 5.

Yet another embodiment is a compound having the formula (IA-V) wherein n is 0.

Yet another embodiment is a compound having the formula (IA-V) wherein n is 1 and R is halogen (such as fluoro).

Yet another embodiment is a compound having the formula (IA-V) wherein p is 0.

Yet another embodiment is a compound having the formula (IA-V) wherein p is 1 and $R^5$ is 3-fluoro or 2-methyl.

Yet another embodiment is a compound having the formula (IA-V) wherein $R^1$ is methyl and $R^2$ is hydrogen.

Yet another embodiment is a compound having the formula (IA-V) wherein $R^1$ is ethyl and $R^2$ is hydrogen.

Yet another embodiment is a compound having the formula (IA-V) wherein $R^1$ and $R^2$ are hydrogen.

Yet another embodiment is a compound having the formula (IA-V) wherein $R^3$ is.

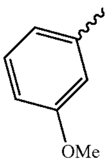,
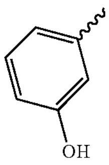,
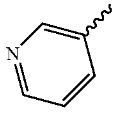,
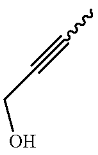,

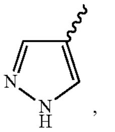,
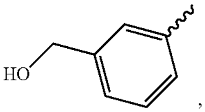,
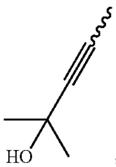,

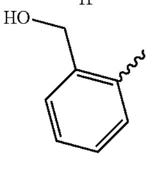,
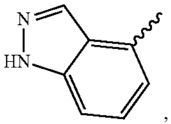,
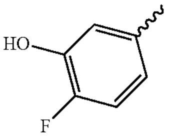,

-continued
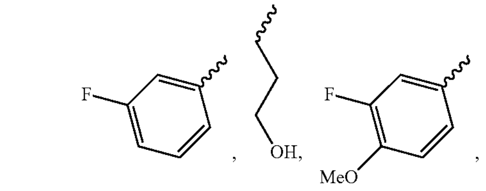
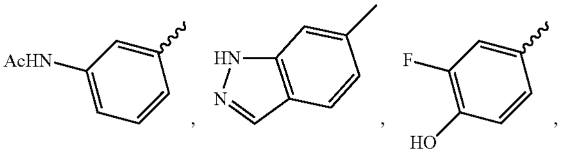
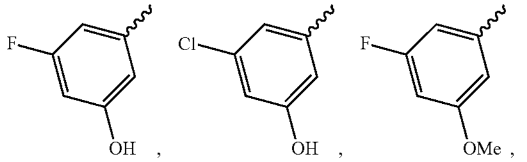
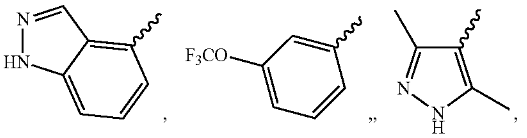
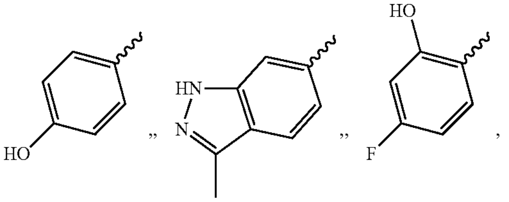
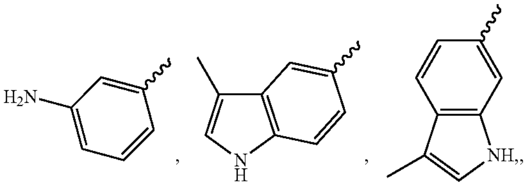
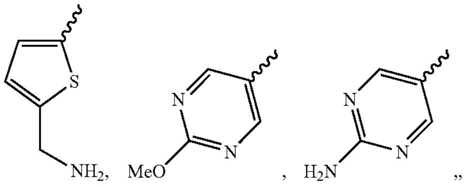
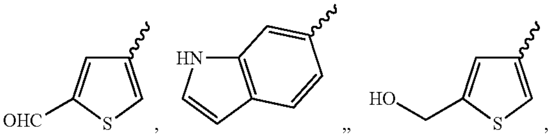
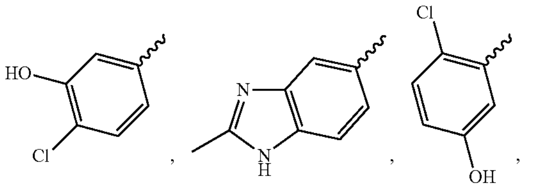
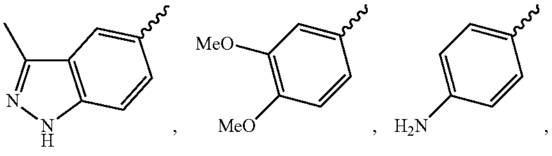
-continued
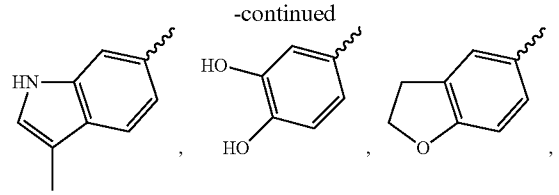
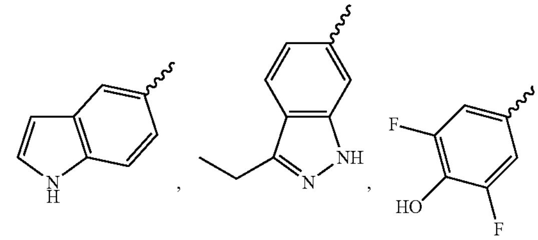
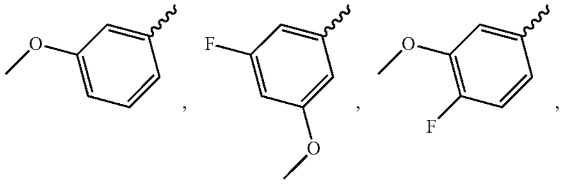
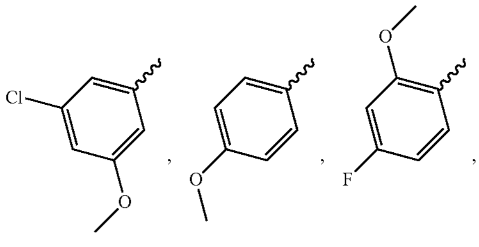
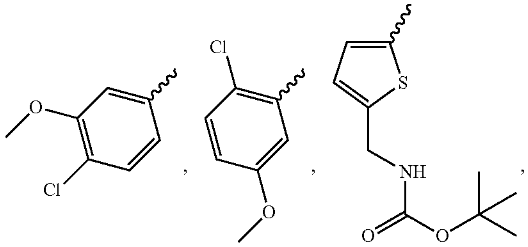
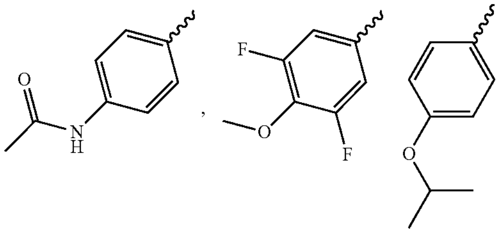
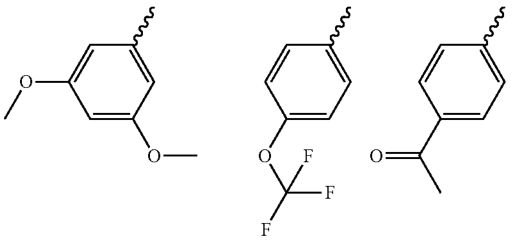

-continued
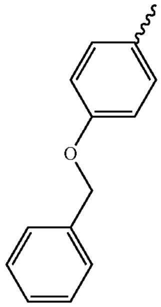 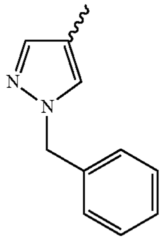 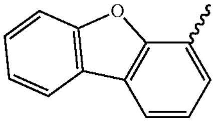
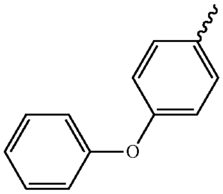 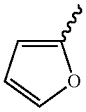 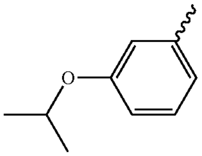
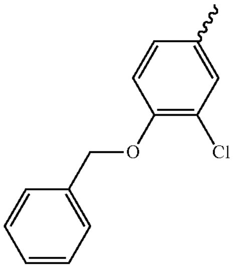 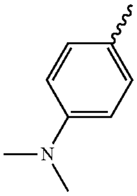 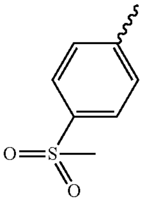
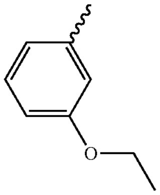 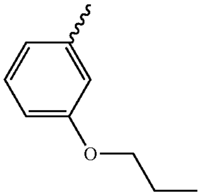 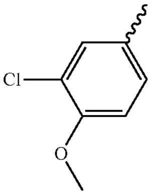
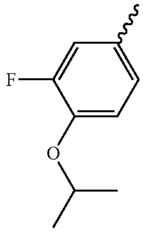 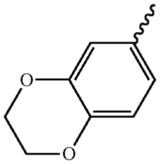 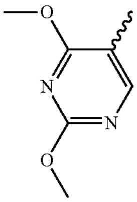
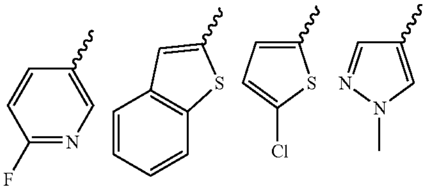
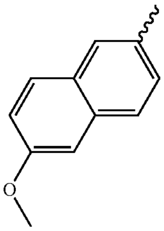 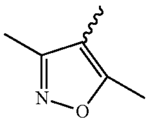 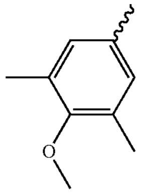
-continued
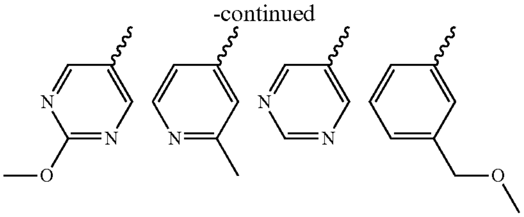
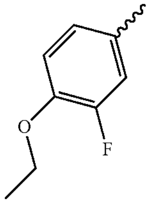 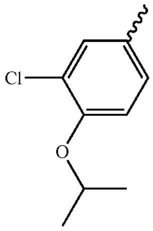 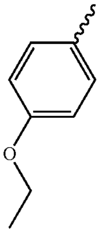 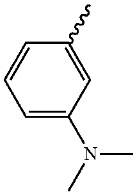
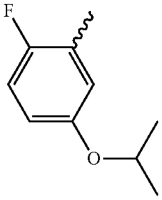 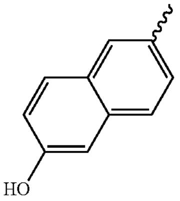 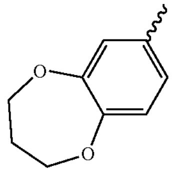
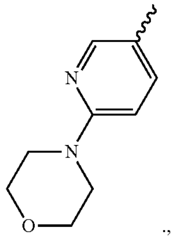 , 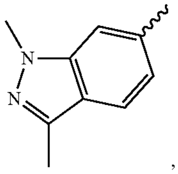 ,
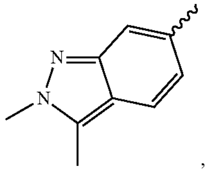 , 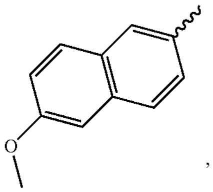 ,
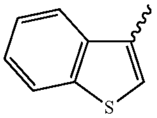 , 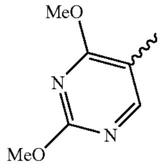 ,
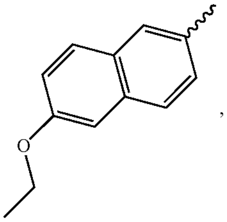 , 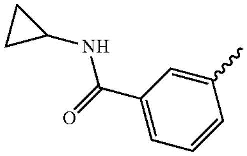 ,
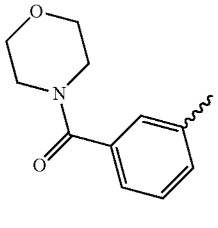 , 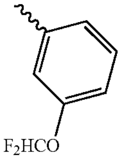 and 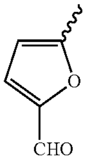 .

Yet another embodiment is a compound having the formula (IA-V) wherein X is C—H, C—F, C—Cl, C—$NH_2$ or C—OH.

Further preferred is a compound having the formula (IA-V) wherein X is C—H.

Yet another embodiment is a compound of formula (IA-VI)

(IA-VI)

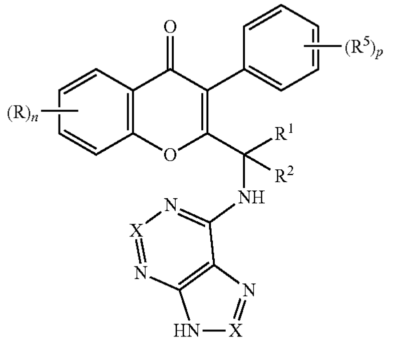

or a pharmaceutically acceptable salt thereof, wherein

R, $R^1$, $R^2$ and X are as defined above with respect to any of formulas (I), (I-A), (I-B) and (IA-III);

each occurrence of $R^5$ is hydrogen, $C_{1-6}$ alkyl or halogen; and p is 0, 1, 2, 3, 4 or 5.

Yet another embodiment is a compound having the formula (IA-VI) wherein n is 0.

Yet another embodiment is a compound having the formula (IA-VI) wherein n is 1 and R is halogen (such as fluoro).

Yet another embodiment is a compound having the formula (IA-VI) wherein p is 0.

Yet another embodiment is a compound having the formula (IA-VI) wherein p is 1 and $R^5$ is 3-fluoro or 2-methyl.

Yet another embodiment is a compound having the formula (IA-VI) wherein $R^1$ is methyl and $R^2$ is hydrogen.

Yet another embodiment is a compound having the formula (IA-VI) wherein $R^1$ is ethyl and $R^2$ is hydrogen.

Yet another embodiment is a compound having the formula (IA-VI) wherein $R^1$ and $R^2$ are hydrogen.

Yet another embodiment is a compound having the formula (IA-VI) wherein each occurrence of X is independently selected from C—H, C—F, C—Cl, C—$NH_2$ or C—OH.

Further preferred is a compound having the formula (IA-VI) wherein X is C—H.

Representative compounds of the present invention include those specified below (including in Table 1) and pharmaceutically acceptable salts thereof. The present invention should not be construed to be limited to them.

2-[(6-Amino-9H-purin-9-yl)methyl]-6-bromo-3-phenyl-4H-chromen-4-one;

6-Bromo-2-(morpholinomethyl)-3-phenyl-4H-chromen-4-one;

6-Bromo-2-(morpholinomethyl)-3-phenyl-4H-chromen-4-one hydrochloride;

2-[(6-Amino-9H-purin-9-yl)methyl]-3-phenyl-4H-chromen-4-one;

2-(Morpholinomethyl)-3-phenyl-4H-chromen-4-one;

2-(Morpholinomethyl)-3-phenyl-4H-chromen-4-one hydrochloride;

2-[(1H-Benzo[d]imidazol-1-yl)methyl]-6-bromo-3-phenyl-4H-chromen-4-one;

6-Bromo-2-[(4-methyl-1H-benzo[d]imidazol-1-yl)methyl]-3-phenyl-4H-chromen-4-one;

2-[(1H-benzo[d]imidazol-1-yl)methyl]-3-phenyl-4H-chromen-4-one;

2-[(4-methyl-1H-benzo[d]imidazol-1-yl)methyl]-3-phenyl-4H-chromen-4-one;

2-[(6-Chloro-9H-purin-9-yl)methyl]-3-phenyl-4H-chromen-4-one;

6-Bromo-2-[(6-chloro-9H-purin-9-yl)methyl]-3-phenyl-4H-chromen-4-one;

2-((9H-Purin-6-ylthio)methyl)-3-phenyl-4H-chromen-4-one;

2-[(1H-Imidazol-1-yl)methyl]-3-phenyl-4H-chromen-4-one;

2-[(9H-Purin-6-ylthio)methyl]-6-bromo-3-phenyl-4H-chromen-4-one;

2-((4-Amino-1H-pyrazolo[3,4-d]pyrimidin-1-yl)methyl)-6-bromo-3-phenyl-4H-chromen-4-one;

2-[(6-Amino-9H-purin-9-yl)methyl]-6-bromo-3-(4-fluorophenyl)-4H-chromen-4-one;

2-[(6-Amino-9H-purin-9-yl)methyl]-3-(4-fluorophenyl)-4H-chromen-4-one;

6-Bromo-3-(4-fluorophenyl)-2-(morpholinomethyl)-4H-chromen-4-one;

6-Bromo-3-(4-fluorophenyl)-2-(morpholinomethyl)-4H-chromen-4-one hydro chloride;

3-(4-fluorophenyl)-2-(morpholinomethyl)-4H-chromen-4-one;

3-(4-fluorophenyl)-2-(morpholinomethyl)-4H-chromen-4-one hydrochloride;

2-[(6-Amino-9H-purin-9-yl)methyl]-6-bromo-3-o-tolyl-4H-chromen-4-one;

7-[(6-Bromo-4-oxo-3-phenyl-4H-chromen-2-yl)methyl]-1,3-dimethyl-1H-purine-2,6(3H,7H)-dione;

2-(1-(6-Amino-9H-purin-9-yl)ethyl)-6-bromo-3-phenyl-4H-chromen-4-one;

2-(1-(9H-Purin-6-ylthio)ethyl)-6-bromo-3-phenyl-4H-chromen-4-one;

2-(1-(6-Amino-9H-purin-9-yl)ethyl)-3-phenyl-4H-chromen-4-one;

(S)-2-(1-(9H-purin-6-ylamino)ethyl)-6-bromo-3-phenyl-4H-chromen-4-one;

2-((9H-purin-6-ylamino)methyl)-6-bromo-3-phenyl-4H-chromen-4-one;

2-(1-(4-amino-1H-pyrazolo[3,4-d]pyrimidin-1-yl)ethyl)-6-bromo-3-phenyl-4H-chromen-4-one;

2-((6-Amino-9H-purin-9-yl)methyl)-6-methoxy-3-phenyl-4H-chromen-4-one;

2-(1-(6-Amino-9H-purin-9-yl)ethyl)-6-bromo-3-(2-fluorophenyl)-4H-chromen-4-one;

2-((6-Amino-9H-purin-9-yl)methyl)-6-bromo-3-(2-fluorophenyl)-4H-chromen-4-one;

2-(1-(4-Amino-1H-pyrazolo[3,4-d]pyrimidin-1-yl)ethyl)-3-phenyl-4H-chromen-4-one;

2-(1-(6-Amino-9H-purin-9-yl) propyl)-3-phenyl-4H-chromen-4-one;

2-(1-(6-Amino-9H-purin-9-yl)ethyl)-3-(3-fluorophenyl)-4H-chromen-4-one;

2-((6-Amino-9H-purin-9-yl)methyl)-3-(2-fluorophenyl)-4H-chromen-4-one;

2-(1-(6-Amino-9H-purin-9-yl)ethyl)-3-(2-fluorophenyl)-4H-chromen-4-one;

2-(1-(6-Amino-9H-purin-9-yl)propyl)-3-(2-fluorophenyl)-4H-chromen-4-one;

2-(1-(6-amino-9H-purin-9-yl)propyl)-3-(3-fluorophenyl)-4H-chromen-4-one;

2-(1-(6-Amino-9H-purin-9-yl)propyl)-3-(4-fluorophenyl)-4H-chromen-4-one;

2-(1-(6-amino-9H-purin-9-yl)propyl)-6-fluoro-3-phenyl-4H-chromen-4-one;

2-(1-(6-Amino-9H-purin-9-yl)ethyl)-3-(4-fluorophenyl)-4H-chromen-4-one;

2-(1-(6-Amino-9H-purin-9-yl)ethyl)-6-fluoro-3-phenyl-4H-chromen-4-one;

2-(1-(4-Amino-3-(3-methoxyphenyl)-1H-pyrazolo[3,4-d]pyrimidin-1-yl)ethyl)-3-phenyl-4H-chromen-4-one;

2-(1-(4-Amino-3-(3-hydroxyphenyl)-1H-pyrazolo[3,4-d]pyrimidin-1-yl)ethyl)-3-phenyl-4H-chromen-4-one;

2-((9H-purin-6-ylamino)methyl)-3-phenyl-4H-chromen-4-one;

2-(1-(6-Amino-9H-purin-9-yl)ethyl)-3-o-tolyl-4H-chromen-4-one;

2-((9H-purin-6-ylamino)methyl)-3-(2-fluorophenyl)-4H-chromen-4-one;

2-((9H-purin-6-ylamino)methyl)-3-(3-fluorophenyl)-4H-chromen-4-one;

(S)-2-(1-(9H-purin-6-ylamino)ethyl)-3-(3-fluorophenyl)-4H-chromen-4-one;

2-(1-(6-amino-9H-purin-9-yl)ethyl)-6-fluoro-3-(2-fluorophenyl)-4H-chromen-4-one;

2-(1-(6-Amino-9H-purin-9-yl)ethyl)-3-(3,5-difluorophenyl)-4H-chromen-4-one;

2-(1-(6-amino-9H-purin-9-yl)ethyl)-6-fluoro-3-(3-fluorophenyl)-4H-chromen-4-one;

2-(1-(4-amino-3-(3-methoxyphenyl)-1H-pyrazolo[3,4-d]pyrimidin-1-yl)ethyl)-3-(3-fluorophenyl)-4H-chromen-4-one;

2-(1-(4-amino-3-(3-hydroxyphenyl)-1H-pyrazolo[3,4-d]pyrimidin-1-yl)ethyl)-3-(3-fluorophenyl)-4H-chromen-4-one;

2-((4-Amino-3-(3-methoxyphenyl)-1H-pyrazolo[3,4-d]pyrimidin-1-yl)methyl)-3-phenyl-4H-chromen-4-one;

2-((4-Amino-3-(3-hydroxyphenyl)-1H-pyrazolo[3,4-d]pyrimidin-1-yl)methyl)-3-phenyl-4H-chromen-4-one;

2-((4-amino-3-(3-methoxyphenyl)-1H-pyrazolo[3,4-d]pyrimidin-1-yl)methyl)-3-(3-fluorophenyl)-4H-chromen-4-one;

2-((4-amino-3-(3-hydroxyphenyl)-1H-pyrazolo[3,4-d]pyrimidin-1-yl)methyl)-3-(3-fluorophenyl)-4H-chromen-4-one;

(R)-2-(1-(9H-purin-6-ylamino)ethyl)-3-(3-fluorophenyl)-4H-chromen-4-one;

(S)-2-(1-(9H-purin-6-ylamino)ethyl)-6-fluoro-3-phenyl-4H-chromen-4-one;

2-((4-Amino-3-iodo-1H-pyrazolo[3,4-d]pyrimidin-1-yl)methyl)-3-phenyl-4H-chromen-4-one;

2-(1-(4-amino-3-iodo-1H-pyrazolo[3,4-d]pyrimidin-1-yl)ethyl)-3-phenyl-4H-chromen-4-one;

2-(1-(4-amino-3-iodo-1H-pyrazolo[3,4-d]pyrimidin-1-yl)ethyl)-3-(3-fluorophenyl)-4H-chromen-4-one;

2-((4-amino-3-iodo-1H-pyrazolo[3,4-d]pyrimidin-1-yl)methyl)-6-fluoro-3-phenyl-4H-chromen-4-one;

2-(1-(4-amino-3-iodo-1H-pyrazolo[3,4-d]pyrimidin-1-yl)ethyl)-6-fluoro-3-phenyl-4H-chromen-4-one;

2-(1-(4-amino-3-iodo-1H-pyrazolo[3,4-d]pyrimidin-1-yl)ethyl)-6-fluoro-3-(3-fluorophenyl)-4H-chromen-4-one;

2-(1-(4-amino-3-iodo-1H-pyrazolo[3,4-d]pyrimidin-1-yl)propyl)-3-(3-fluorophenyl)-4H-chromen-4-one;

2-((4-amino-3-(pyridin-3-yl)-1H-pyrazolo[3,4-d]pyrimidin-1-yl)methyl)-3-phenyl-4H-chromen-4-one;

2-((4-amino-3-(3-hydroxyprop-1-ynyl)-1H-pyrazolo[3,4-d]pyrimidin-1-yl)methyl)-3-phenyl-4H-chromen-4-one;

2-((4-amino-3-(1H-pyrazol-4-yl)-1H-pyrazolo[3,4-d]pyrimidin-1-yl)methyl)-3-phenyl-4H-chromen-4-one;

2-((4-amino-3-(3-(hydroxymethyl)phenyl)-1H-pyrazolo[3,4-d]pyrimidin-1-yl)methyl)-3-phenyl-4H-chromen-4-one;

2-((4-amino-3-(1H-indazol-4-yl)-1H-pyrazolo[3,4-d]pyrimidin-1-yl)methyl)-3-phenyl-4H-chromen-4-one;

2-((4-amino-3-(3-fluorophenyl)-1H-pyrazolo[3,4-d]pyrimidin-1-yl)methyl)-3-phenyl-4H-chromen-4-one 2-((4-amino-3-(3-hydroxypropyl)-1H-pyrazolo[3,4-d]pyrimidin-1-yl)methyl)-3-phenyl-4H-chromen-4-one;

N-(3-(4-amino-1-((4-oxo-3-phenyl-4H-chromen-2-yl)methyl)-1H-pyrazolo[3,4-d]pyrimidin-3-yl)phenyl) acetamide;

2-((4-amino-3-(3-fluoro-5-methoxyphenyl)-1H-pyrazolo[3,4-d]pyrimidin-1-yl)methyl)-3-phenyl-4H-chromen-4-one;

2-((4-amino-3-(3-fluoro-5-hydroxyphenyl)-1H-pyrazolo[3,4-d]pyrimidin-1-yl)methyl)-3-phenyl-4H-chromen-4-one;

2-((4-amino-3-(3-fluoro-5-methoxyphenyl)-1H-pyrazolo[3,4-d]pyrimidin-1-yl)methyl)-3-(3-fluorophenyl)-4H-chromen-4-one;

2-((4-amino-3-(3-fluoro-5-hydroxyphenyl)-1H-pyrazolo[3,4-d]pyrimidin-1-yl)methyl)-3-(3-fluorophenyl)-4H-chromen-4-one;

2-(1-(4-amino-3-(1H-pyrazol-4-yl)-1H-pyrazolo[3,4-d]pyrimidin-1-yl)ethyl)-3-phenyl-4H-chromen-4-one;

2-(1-(4-amino-3-(1H-indazol-6-yl)-1H-pyrazolo[3,4-d]pyrimidin-1-yl)ethyl)-3-phenyl-4H-chromen-4-one;

2-(1-(4-amino-3-(3-hydroxy-3-methylbut-1-ynyl)-1H-pyrazolo[3,4-d]pyrimidin-1-yl)ethyl)-3-phenyl-4H-chromen-4-one;

2-(1-(4-amino-3-(1H-pyrazol-4-yl)-1H-pyrazolo[3,4-d]pyrimidin-1-yl)ethyl)-3-(3-fluorophenyl)-4H-chromen-4-one;

(S)-2-(1-(9H-purin-6-ylamino)ethyl)-3-phenyl-4H-chromen-4-one;

(S)-2-(1-(9H-purin-6-ylamino)ethyl)-6-fluoro-3-(3-fluorophenyl)-4H-chromen-4-one;

2-((4-amino-3-(1H-indazol-6-yl)-1H-pyrazolo[3,4-d]pyrimidin-1-yl)methyl)-3-phenyl-4H-chromen-4-one;

2-(1-(4-amino-3-(3-fluoro-5-methoxyphenyl)-1H-pyrazolo[3,4-d]pyrimidin-1-yl)ethyl)-3-(3-fluorophenyl)-4H-chromen-4-one;

2-(1-(4-amino-3-(3-fluoro-5-hydroxyphenyl)-1H-pyrazolo[3,4-d]pyrimidin-1-yl)ethyl)-3-(3-fluorophenyl)-4H-chromen-4-one;

2-(1-(4-amino-3-(1H-indazol-4-yl)-1H-pyrazolo[3,4-d]pyrimidin-1-yl)ethyl)-3-(3-fluorophenyl)-4H-chromen-4-one;

2-(1-(4-amino-3-(3,5-dimethyl-1H-pyrazol-4-yl)-1H-pyrazolo[3,4-d]pyrimidin-1-yl)ethyl)-3-(3-fluorophenyl)-4H-chromen-4-one;

2-(1-(4-amino-3-(3-methyl-1H-indazol-6-yl)-1H-pyrazolo[3,4-d]pyrimidin-1-yl)ethyl)-3-(3-fluorophenyl)-4H-chromen-4-one;

2-(1-(4-amino-3-(1H-indazol-6-yl)-1H-pyrazolo[3,4-d]pyrimidin-1-yl)ethyl)-3-(3-fluorophenyl)-4H-chromen-4-one;

2-(1-(4-amino-3-(2-(hydroxymethyl)phenyl)-1H-pyrazolo[3,4-d]pyrimidin-1-yl)ethyl)-3-(3-fluorophenyl)-4H-chromen-4-one;

2-(1-(4-amino-3-(4-fluoro-3-methoxyphenyl)-1H-pyrazolo[3,4-d]pyrimidin-1-yl)ethyl)-3-(3-fluorophenyl)-4H-chromen-4-one;

2-(1-(4-amino-3-(4-fluoro-3-hydroxyphenyl)-1H-pyrazolo[3,4-d]pyrimidin-1-yl)ethyl)-3-(3-fluorophenyl)-4H-chromen-4-one;

2-(1-(4-amino-3-(3-hydroxyprop-1-ynyl)-1H-pyrazolo[3,4-d]pyrimidin-1-yl)ethyl)-3-(3-fluorophenyl)-4H-chromen-4-one;
2-(1-(4-amino-3-(3-fluoro-4-methoxyphenyl)-1H-pyrazolo[3,4-d]pyrimidin-1-yl)ethyl)-3-(3-fluorophenyl)-4H-chromen-4-one;
2-(1-(4-amino-3-(3-fluoro-4-hydroxyphenyl)-1H-pyrazolo[3,4-d]pyrimidin-1-yl)ethyl)-3-(3-fluorophenyl)-4H-chromen-4-one;
2-(1-(4-amino-3-(3-chloro-5-methoxyphenyl)-1H-pyrazolo[3,4-d]pyrimidin-1-yl)ethyl)-3-(3-fluorophenyl)-4H-chromen-4-one;
2-(1-(4-amino-3-(3-chloro-5-hydroxyphenyl)-1H-pyrazolo[3,4-d]pyrimidin-1-yl)ethyl)-3-(3-fluorophenyl)-4H-chromen-4-one;
2-(1-(4-amino-3-(3-(trifluoromethoxy)phenyl)-1H-pyrazolo[3,4-d]pyrimidin-1-yl)ethyl)-3-(3-fluorophenyl)-4H-chromen-4-one;
2-(1-(4-amino-3-(4-methoxyphenyl)-1H-pyrazolo[3,4-d]pyrimidin-1-yl)ethyl)-3-(3-fluorophenyl)-4H-chromen-4-one;
2-(1-(4-amino-3-(4-hydroxyphenyl)-1H-pyrazolo[3,4-d]pyrimidin-1-yl)ethyl)-3-(3-fluorophenyl)-4H-chromen-4-one;
2-((6-amino-9H-purin-9-yl)methyl)-3-(3-fluorophenyl)-4H-chromen-4-one;
2-(1-(4-amino-3-(4-fluoro-2-methoxyphenyl)-1H-pyrazolo[3,4-d]pyrimidin-1-yl)ethyl)-3-(3-fluorophenyl)-4H-chromen-4-one;
2-(1-(4-amino-3-(4-fluoro-2-hydroxyphenyl)-1H-pyrazolo[3,4-d]pyrimidin-1-yl)ethyl)-3-(3-fluorophenyl)-4H-chromen-4-one;
2-((4-amino-3-(3-aminophenyl)-1H-pyrazolo[3,4-d]pyrimidin-1-yl)methyl)-3-phenyl-4H-chromen-4-one;
2-((4-amino-3-(3-methyl-1H-indazol-6-yl)-1H-pyrazolo[3,4-d]pyrimidin-1-yl)methyl)-3-phenyl-4H-chromen-4-one;
2-(1-(4-amino-3-(2-aminopyrimidin-5-yl)-1H-pyrazolo[3,4-d]pyrimidin-1-yl)ethyl)-3-(3-fluorophenyl)-4H-chromen-4-one;
2-(1-(4-amino-3-(1H-indol-6-yl)-1H-pyrazolo[3,4-d]pyrimidin-1-yl)ethyl)-3-(3-fluorophenyl)-4H-chromen-4-one;
2-(1-(4-amino-3-(4-chloro-3-methoxyphenyl)-1H-pyrazolo[3,4-d]pyrimidin-1-yl)ethyl)-3-(3-fluorophenyl)-4H-chromen-4-one;
2-(1-(4-amino-3-(4-chloro-3-hydroxyphenyl)-1H-pyrazolo[3,4-d]pyrimidin-1-yl)ethyl)-3-(3-fluorophenyl)-4H-chromen-4-one;
2-(1-(4-amino-3-(2-chloro-5-methoxyphenyl)-1H-pyrazolo[3,4-d]pyrimidin-1-yl)ethyl)-3-(3-fluorophenyl)-4H-chromen-4-one;
2-(1-(4-amino-3-(2-chloro-5-hydroxyphenyl)-1H-pyrazolo[3,4-d]pyrimidin-1-yl)ethyl)-3-(3-fluorophenyl)-4H-chromen-4-one;
2-(1-(4-amino-3-(3,4-dimethoxyphenyl)-1H-pyrazolo[3,4-d]pyrimidin-1-yl)ethyl)-3-(3-fluorophenyl)-4H-chromen-4-one;
2-(1-(4-amino-3-(3,4-dihydroxyphenyl)-1H-pyrazolo[3,4-d]pyrimidin-1-yl)ethyl)-3-(3-fluorophenyl)-4H-chromen-4-one;
2-((4-amino-3-(3-methyl-1H-indazol-6-yl)-1H-pyrazolo[3,4-d]pyrimidin-1-yl)methyl)-3-(3-fluorophenyl)-4H-chromen-4-one;
2-(1-(4-amino-3-(1H-indol-5-yl)-1H-pyrazolo[3,4-d]pyrimidin-1-yl)ethyl)-3-(3-fluorophenyl)-4H-chromen-4-one;
2-(1-(4-Amino-3-(3-methyl-1H-indol-5-yl)-1H-pyrazolo[3,4-d]pyrimidin-1-yl)ethyl)-3-(3-fluorophenyl)-4H-chromen-4-one;
tert-butyl-(5-(4-amino-1-(1-(3-(3-fluorophenyl)-4-oxo-4H-chromen-2-yl)ethyl)-1H-pyrazolo[3,4-d]pyrimidin-3-yl)thiophen-2-yl)methylcarbamate
2-(1-(4-amino-3-(5-(aminomethyl)thiophen-2-yl)-1H-pyrazolo[3,4-d]pyrimidin-1-yl)ethyl)-3-(3-fluorophenyl)-4H-chromen-4-one;
2-((4-amino-3-(3-methyl-1H-indazol-6-yl)-1H-pyrazolo[3,4-d]pyrimidin-1-yl)methyl)-6-fluoro-3-phenyl-4H-chromen-4-one;
2-(1-(4-amino-3-(3-methyl-1H-indazol-6-yl)-1H-pyrazolo[3,4-d]pyrimidin-1-yl)ethyl)-3-phenyl-4H-chromen-4-one;
2-(1-(4-amino-3-(3-methyl-1H-indazol-6-yl)-1H-pyrazolo[3,4-d]pyrimidin-1-yl)ethyl)-6-fluoro-3-phenyl-4H-chromen-4-one;
2-(1-(4-amino-3-(3-methyl-1H-indazol-5-yl)-1H-pyrazolo[3,4-d]pyrimidin-1-yl)ethyl)-3-(3-fluorophenyl)-4H-chromen-4-one;
N-(4-(4-amino-1-(1-(3-(3-fluorophenyl)-4-oxo-4H-chromen-2-yl)ethyl)-1H-pyrazolo[3,4-d]pyrimidin-3-yl)phenyl)acetamide;
2-(1-(4-amino-3-(4-aminophenyl)-1H-pyrazolo[3,4-d]pyrimidin-1-yl)ethyl)-3-(3-fluorophenyl)-4H-chromen-4-one;
2-(1-(4-amino-3-(3-methyl-1H-indazol-6-yl)-1H-pyrazolo[3,4-d]pyrimidin-1-yl)ethyl)-6-fluoro-3-(3-fluorophenyl)-4H-chromen-4-one;
2-(1-(4-amino-3-(2,3-dihydrobenzofuran-5-yl)-1H-pyrazolo[3,4-d]pyrimidin-1-yl)ethyl)-3-(3-fluorophenyl)-4H-chromen-4-one;
2-(1-(4-amino-3-(3-ethyl-1H-indazol-6-yl)-1H-pyrazolo[3,4-d]pyrimidin-1-yl)ethyl)-3-(3-fluorophenyl)-4H-chromen-4-one;
2-(1-(4-amino-3-(3-methyl-1H-indol-6-yl)-1H-pyrazolo[3,4-d]pyrimidin-1-yl)ethyl)-3-(3-fluorophenyl)-4H-chromen-4-one;
2-(1-(4-amino-3-(2-methoxypyrimidin-5-yl)-1H-pyrazolo[3,4-d]pyrimidin-1-yl)ethyl)-3-(3-fluorophenyl)-4H-chromen-4-one;
4-(4-amino-1-(1-(3-(3-fluorophenyl)-4-oxo-4H-chromen-2-yl)ethyl)-1H-pyrazolo[3,4-d]pyrimidin-3-yl)thiophene-2-carbaldehyde;
2-(1-(4-amino-3-(5-(hydroxymethyl)thiophen-3-yl)-1H-pyrazolo[3,4-d]pyrimidin-1-yl)ethyl)-3-(3-fluorophenyl)-4H-chromen-4-one;
2-(1-(4-amino-3-(2-methyl-1H-benzo[d]imidazol-5-yl)-1H-pyrazolo[3,4-d]pyrimidin-1-yl)ethyl)-3-(3-fluorophenyl)-4H-chromen-4-one;
2-(1-(4-amino-3-(3-methyl-1H-indazol-6-yl)-1H-pyrazolo[3,4-d]pyrimidin-1-yl) propyl)-3-(3-fluorophenyl)-4H-chromen-4-one;
2-(1-(4-amino-3-(3-methyl-1H-indol-6-yl)-1H-pyrazolo[3,4-d]pyrimidin-1-yl)ethyl)-3-(3-fluorophenyl)-4H-chromen-4-one;
2-((6-amino-9H-purin-9-yl)methyl)-6-fluoro-3-phenyl-4H-chromen-4-one;
2-((6-amino-9H-purin-9-yl)methyl)-6-fluoro-3-(3-fluorophenyl)-4H-chromen-4-one;
2-((4-amino-3-(3-fluoro-5-methoxyphenyl)-1H-pyrazolo[3,4-d]pyrimidin-1-yl)methyl)-6-fluoro-3-(3-fluorophenyl)-4H-chromen-4-one;
2-((4-amino-3-(3-fluoro-5-hydroxyphenyl)-1H-pyrazolo[3,4-d]pyrimidin-1-yl)methyl)-6-fluoro-3-(3-fluorophenyl)-4H-chromen-4-one;

2-(1-(4-amino-3-(3-methoxyphenyl)-1H-pyrazolo[3,4-d]pyrimidin-1-yl)ethyl)-6-fluoro-3-(3-fluorophenyl)-4H-chromen-4-one;

2-(1-(4-amino-3-(3-hydroxyphenyl)-1H-pyrazolo[3,4-d]pyrimidin-1-yl)ethyl)-6-fluoro-3-(3-fluorophenyl)-4H-chromen-4-one;

2-((9H-purin-6-ylamino)methyl)-6-fluoro-3-(3-fluorophenyl)-4H-chromen-4-one;

2-((9H-purin-6-ylamino)methyl)-6-fluoro-3-phenyl-4H-chromen-4-one;

(R)-2-(1-(9H-purin-6-ylamino)ethyl)-6-fluoro-3-(3-fluorophenyl)-4H-chromen-4-one;

2-((4-amino-3-(1H-pyrazol-4-yl)-1H-pyrazolo[3,4-d]pyrimidin-1-yl)methyl)-6-fluoro-3-phenyl-4H-chromen-4-one;

2-(1-(4-amino-3-(3,5-difluoro-4-methoxyphenyl)-1H-pyrazolo[3,4-d]pyrimidin-1-yl)ethyl)-3-(3-fluorophenyl)-4H-chromen-4-one;

2-(1-(4-amino-3-(3,5-difluoro-4-hydroxyphenyl)-1H-pyrazolo[3,4-d]pyrimidin-1-yl)ethyl)-3-(3-fluorophenyl)-4H-chromen-4-one;

2-((4-amino-3-(3,5-difluoro-4-methoxyphenyl)-1H-pyrazolo[3,4-d]pyrimidin-1-yl)methyl)-6-fluoro-3-(3-fluorophenyl)-4H-chromen-4-one;

2-((4-amino-3-(3,5-difluoro-4-hydroxyphenyl)-1H-pyrazolo[3,4-d]pyrimidin-1-yl)methyl)-6-fluoro-3-(3-fluorophenyl)-4H-chromen-4-one;

(+)-2-(1-(4-amino-3-(3-methyl-1H-indazol-6-yl)-1H-pyrazolo[3,4-d]pyrimidin-1-yl)ethyl)-3-(3-fluorophenyl)-4H-chromen-4-one;

(−)-2-(1-(4-amino-3-(3-methyl-1H-indazol-6-yl)-1H-pyrazolo[3,4-d]pyrimidin-1-yl)ethyl)-3-(3-fluorophenyl)-4H-chromen-4-one;

2-(1-(4-amino-3-(3,5-dimethoxyphenyl)-1H-pyrazolo[3,4-d]pyrimidin-1-yl)ethyl)-3-(3-fluorophenyl)-4H-chromen-4-one;

2-(1-(4-amino-3-(4-methoxy-3,5-dimethylphenyl)-1H-pyrazolo[3,4-d]pyrimidin-1-yl)ethyl)-3-(3-fluorophenyl)-4H-chromen-4-one;

2-(1-(4-amino-3-(2-fluoro-5-isopropoxyphenyl)-1H-pyrazolo[3,4-d]pyrimidin-1-yl)ethyl)-3-(3-fluorophenyl)-4H-chromen-4-one;

2-(1-(4-amino-3-(2,3-dihydrobenzo[b][1,4]dioxin-6-yl)-1H-pyrazolo[3,4-d]pyrimidin-1-yl)ethyl)-3-(3-fluorophenyl)-4H-chromen-4-one;

2-(1-(4-amino-3-(1-benzyl-1H-pyrazol-4-yl)-1H-pyrazolo[3,4-d]pyrimidin-1-yl)ethyl)-3-(3-fluorophenyl)-4H-chromen-4-one;

2-(1-(4-amino-3-(2-methylpyridin-4-yl)-1H-pyrazolo[3,4-d]pyrimidin-1-yl)ethyl)-3-(3-fluorophenyl)-4H-chromen-4-one;

2-(1-(4-amino-3-(3,4-dihydro-2H-benzo[b][1,4]dioxepin-7-yl)-1H-pyrazolo[3,4-d]pyrimidin-1-yl)ethyl)-3-(3-fluorophenyl)-4H-chromen-4-one;

2-(1-(4-amino-3-(6-morpholinopyridin-3-yl)-1H-pyrazolo[3,4-d]pyrimidin-1-yl)ethyl)-3-(3-fluorophenyl)-4H-chromen-4-one;

2-(1-(4-amino-3-(dibenzo[b,d]furan-4-yl)-1H-pyrazolo[3,4-d]pyrimidin-1-yl)ethyl)-3-(3-fluorophenyl)-4H-chromen-4-one;

2-(1-(4-amino-3-(4-phenoxyphenyl)-1H-pyrazolo[3,4-d]pyrimidin-1-yl)ethyl)-3-(3-fluorophenyl)-4H-chromen-4-one;

2-(1-(4-amino-3-(4-(benzyloxy)-3-chlorophenyl)-1H-pyrazolo[3,4-d]pyrimidin-1-yl)ethyl)-3-(3-fluorophenyl)-4H-chromen-4-one;

2-(1-(4-amino-3-(3-chloro-4-isopropoxyphenyl)-1H-pyrazolo[3,4-d]pyrimidin-1-yl)ethyl)-3-(3-fluorophenyl)-4H-chromen-4-one;

2-(1-(4-amino-3-(3-(dimethylamino)phenyl)-1H-pyrazolo[3,4-d]pyrimidin-1-yl)ethyl)-3-(3-fluorophenyl)-4H-chromen-4-one;

2-(1-(4-amino-3-(4-ethoxy-3-fluorophenyl)-1H-pyrazolo[3,4-d]pyrimidin-1-yl)ethyl)-3-(3-fluorophenyl)-4H-chromen-4-one;

2-(1-(4-amino-3-(4-isopropoxyphenyl)-1H-pyrazolo[3,4-d]pyrimidin-1-yl)ethyl)-3-(3-fluorophenyl)-4H-chromen-4-one;

2-(1-(4-amino-3-(4-(trifluoromethoxy)phenyl)-1H-pyrazolo[3,4-d]pyrimidin-1-yl)ethyl)-3-(3-fluorophenyl)-4H-chromen-4-one;

2-(1-(3-(4-acetylphenyl)-4-amino-1H-pyrazolo[3,4-d]pyrimidin-1-yl)ethyl)-3-(3-fluorophenyl)-4H-chromen-4-one;

2-(1-(4-amino-3-(4-(benzyloxy)phenyl)-1H-pyrazolo[3,4-d]pyrimidin-1-yl)ethyl)-3-(3-fluorophenyl)-4H-chromen-4-one;

2-(1-(4-amino-3-(4-(dimethylamino)phenyl)-1H-pyrazolo[3,4-d]pyrimidin-1-yl)ethyl)-3-(3-fluorophenyl)-4H-chromen-4-one;

2-(1-(4-amino-3-(4-(methylsulfonyl)phenyl)-1H-pyrazolo[3,4-d]pyrimidin-1-yl)ethyl)-3-(3-fluorophenyl)-4H-chromen-4-one;

2-(1-(4-amino-3-(3-ethoxyphenyl)-1H-pyrazolo[3,4-d]pyrimidin-1-yl)ethyl)-3-(3-fluorophenyl)-4H-chromen-4-one;

2-(1-(4-amino-3-(benzo[b]thiophen-2-yl)-1H-pyrazolo[3,4-d]pyrimidin-1-yl)ethyl)-3-(3-fluorophenyl)-4H-chromen-4-one;

2-(1-(4-amino-3-(5-chlorothiophen-2-yl)-1H-pyrazolo[3,4-d]pyrimidin-1-yl)ethyl)-3-(3-fluorophenyl)-4H-chromen-4-one;

2-(1-(4-amino-3-(3,5-dimethylisoxazol-4-yl)-1H-pyrazolo[3,4-d]pyrimidin-1-yl)ethyl)-3-(3-fluorophenyl)-4H-chromen-4-one;

2-(1-(4-amino-3-(3-propoxyphenyl)-1H-pyrazolo[3,4-d]pyrimidin-1-yl)ethyl)-3-(3-fluorophenyl)-4H-chromen-4-one;

2-(1-(4-amino-3-(furan-2-yl)-1H-pyrazolo[3,4-d]pyrimidin-1-yl)ethyl)-3-(3-fluorophenyl)-4H-chromen-4-one;

2-(1-(4-amino-3-(4-ethoxyphenyl)-1H-pyrazolo[3,4-d]pyrimidin-1-yl)ethyl)-3-(3-fluorophenyl)-4H-chromen-4-one;

2-(1-(4-amino-3-(3-chloro-4-methoxyphenyl)-1H-pyrazolo[3,4-d]pyrimidin-1-yl)ethyl)-3-(3-fluorophenyl)-4H-chromen-4-one;

2-(1-(4-amino-3-(3-fluoro-4-isopropoxyphenyl)-1H-pyrazolo[3,4-d]pyrimidin-1-yl)ethyl)-3-(3-fluorophenyl)-4H-chromen-4-one;

2-(1-(4-amino-3-(6-fluoropyridin-3-yl)-1H-pyrazolo[3,4-d]pyrimidin-1-yl)ethyl)-3-(3-fluorophenyl)-4H-chromen-4-one;

2-(1-(4-amino-3-(pyrimidin-5-yl)-1H-pyrazolo[3,4-d]pyrimidin-1-yl)ethyl)-3-(3-fluorophenyl)-4H-chromen-4-one;

2-(1-(4-amino-3-(3-(methoxymethyl)phenyl)-1H-pyrazolo[3,4-d]pyrimidin-1-yl)ethyl)-3-(3-fluorophenyl)-4H-chromen-4-one;

2-(1-(4-amino-3-(6-hydroxynaphthalen-2-yl)-1H-pyrazolo[3,4-d]pyrimidin-1-yl)ethyl)-3-(3-fluorophenyl)-4H-chromen-4-one;

2-(1-(4-amino-3-(3-isopropoxyphenyl)-1H-pyrazolo[3,4-d]pyrimidin-1-yl)ethyl)-3-(3-fluorophenyl)-4H-chromen-4-one;

2-(1-(4-amino-3-(1-methyl-1H-pyrazol-4-yl)-1H-pyrazolo[3,4-d]pyrimidin-1-yl)ethyl)-3-(3-fluorophenyl)-4H-chromen-4-one;

6-Fluoro-3-(3-fluorophenyl)-2-(1-(4-methoxyphenylamino)ethyl)-4H-chromen-4-one;

2-(1-(4-Chloro-7H-pyrrolo[2,3-d]pyrimidin-7-yl)ethyl)-3-(3-fluorophenyl)-4H-chromen-4-one;

2-(1-(4-Chloro-1H-pyrazolo[3,4-b]pyridin-1-yl)ethyl)-3-(3-fluorophenyl)-4H-chromen-4-one;

2-(1-(4-Chloro-1H-pyrazolo[3,4-d]pyrimidin-1-yl)ethyl)-3-(3-fluorophenyl)-4H-chromen-4-one;

2-(1-(4-Chloro-5H-pyrrolo[3,2-d]pyrimidin-5-yl)ethyl)-3-(3-fluorophenyl)-4H-chromen-4-one;

2-(1-(4-amino-3-(1,3-dimethyl-1H-indazol-6-yl)-1H-pyrazolo[3,4-d]pyrimidin-1-yl)ethyl)-3-(3-fluorophenyl)-4H-chromen-4-one;

2-(1-(4-amino-3-(2,3-dimethyl-2H-indazol-6-yl)-1H-pyrazolo[3,4-d]pyrimidin-1-yl)ethyl)-3-(3-fluorophenyl)-4H-chromen-4-one;

2-(1-(4-amino-3-(6-methoxynaphthalen-2-yl)-1H-pyrazolo[3,4-d]pyrimidin-1-yl)ethyl)-3-(3-fluorophenyl)-4H-chromen-4-one;

2-(1-(4-amino-3-(benzo[b]thiophen-3-yl)-1H-pyrazolo[3,4-d]pyrimidin-1-yl)ethyl)-3-(3-fluorophenyl)-4H-chromen-4-one;

2-(1-(4-amino-3-(2,4-dimethoxypyrimidin-5-yl)-1H-pyrazolo[3,4-d]pyrimidin-1-yl)ethyl)-3-(3-fluorophenyl)-4H-chromen-4-one;

2-(1-(4-amino-3-(6-ethoxynaphthalen-2-yl)-1H-pyrazolo[3,4-d]pyrimidin-1-yl)ethyl)-3-(3-fluorophenyl)-4H-chromen-4-one;

3-(4-amino-1-(1-(3-(3-fluorophenyl)-4-oxo-4H-chromen-2-yl)ethyl)-1H-pyrazolo[3,4-d]pyrimidin-3-yl)-N-cyclopropylbenzamide;

2-(1-(4-amino-3-(3-(morpholine-4-carbonyl)phenyl)-1H-pyrazolo[3,4-d]pyrimidin-1-yl)ethyl)-3-(3-fluorophenyl)-4H-chromen-4-one;

2-(1-(4-amino-3-(3-(difluoromethoxy)phenyl)-1H-pyrazolo[3,4-d]pyrimidin-1-yl)ethyl)-3-(3-fluorophenyl)-4H-chromen-4-one; and 5-(4-amino-1-(1-(3-(3-fluorophenyl)-4-oxo-4H-chromen-2-yl)ethyl)-1H-pyrazolo[3,4-d]pyrimidin-3-yl)furan-2-carbaldehyde;

and pharmaceutically acceptable salts thereof

TABLE 1

| Ex. | Structure |
|---|---|
| 1 | 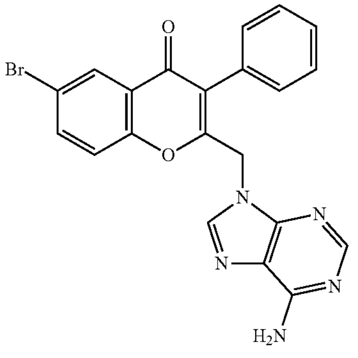 [SMILES: Nc1ncnc2c1ncn2Cc1oc2ccc(Br)cc2c(=O)c1-c1ccccc1] |

TABLE 1-continued

| Ex. | Structure |
|---|---|
| 2 | 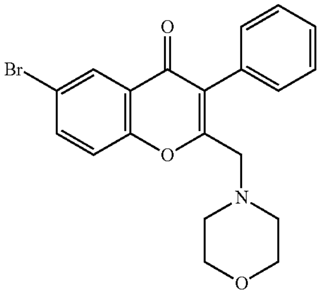 [SMILES: O=c1c(-c2ccccc2)c(CN2CCOCC2)oc2ccc(Br)cc12] |
| 2a | 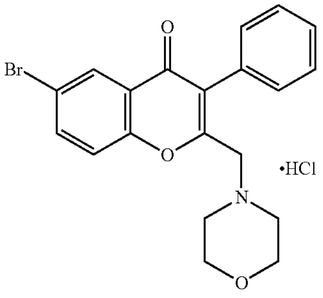 [SMILES: O=c1c(-c2ccccc2)c(CN2CCOCC2)oc2ccc(Br)cc12 ; Cl] •HCl |
| 3 | 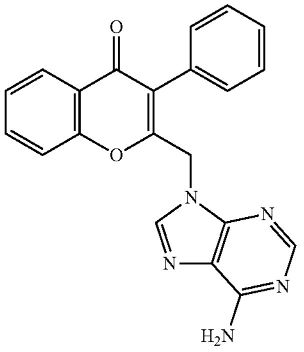 [SMILES: Nc1ncnc2c1ncn2Cc1oc2ccccc2c(=O)c1-c1ccccc1] |
| 4 | 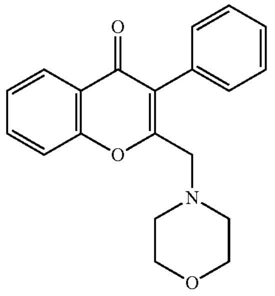 [SMILES: O=c1c(-c2ccccc2)c(CN2CCOCC2)oc2ccccc12] |
| 4a | 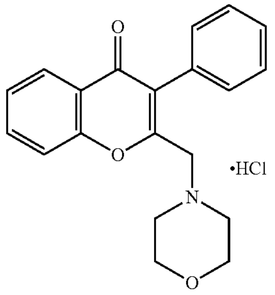 [SMILES: O=c1c(-c2ccccc2)c(CN2CCOCC2)oc2ccccc12 ; Cl] •HCl |

TABLE 1-continued
| Ex. | Structure |
| --- | --- |
| 5 | 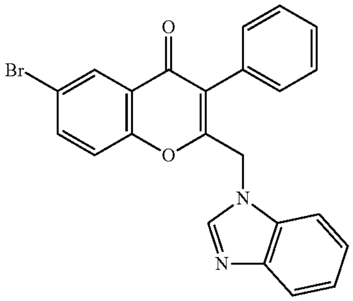 [SMILES: O=c1c(-c2ccccc2)c(Cn2cnc3ccccc32)oc2ccc(Br)cc12] |
| 6 | 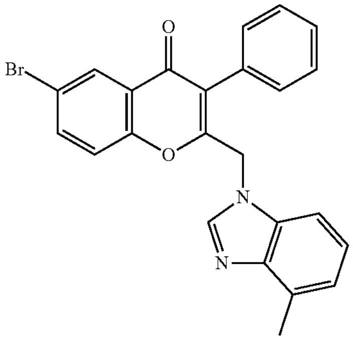 [SMILES: Cc1cccc2c1ncn2Cc1oc2ccc(Br)cc2c(=O)c1-c1ccccc1] |
| 7 | 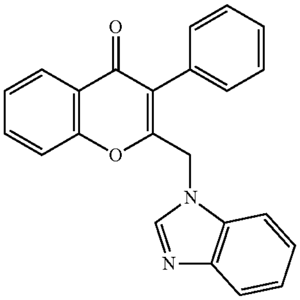 [SMILES: O=c1c(-c2ccccc2)c(Cn2cnc3ccccc32)oc2ccccc12] |
| 8 | 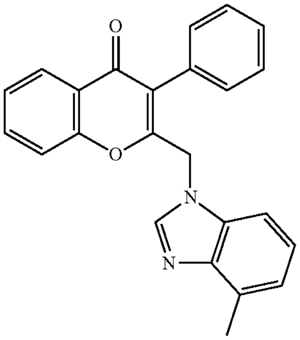 [SMILES: Cc1cccc2c1ncn2Cc1oc2ccccc2c(=O)c1-c1ccccc1] |
TABLE 1-continued
| Ex. | Structure |
| --- | --- |
| 9 | 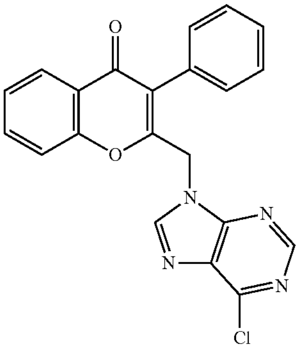 [SMILES: O=c1c(-c2ccccc2)c(Cn2cnc3c(Cl)ncnc32)oc2ccccc12] |
| 10 | 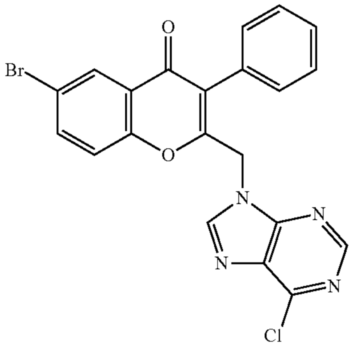 [SMILES: O=c1c(-c2ccccc2)c(Cn2cnc3c(Cl)ncnc32)oc2ccc(Br)cc12] |
| 11 | 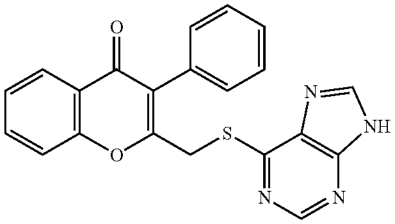 [SMILES: O=c1c(-c2ccccc2)c(CSc2ncnc3[nH]cnc23)oc2ccccc12] |
| 12 | 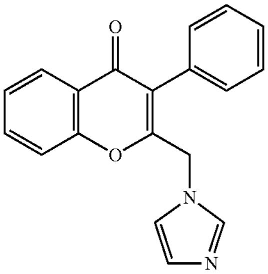 [SMILES: O=c1c(-c2ccccc2)c(Cn2ccnc2)oc2ccccc12] |
| 13 | 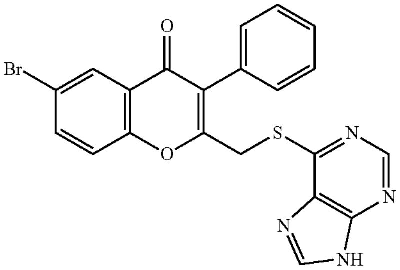 [SMILES: O=c1c(-c2ccccc2)c(CSc2ncnc3[nH]cnc23)oc2ccc(Br)cc12] |

TABLE 1-continued
| Ex. | Structure |
|---|---|
| 14 | 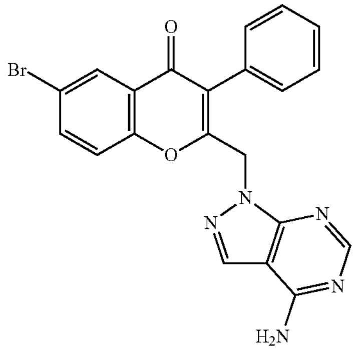 |
| 15 | 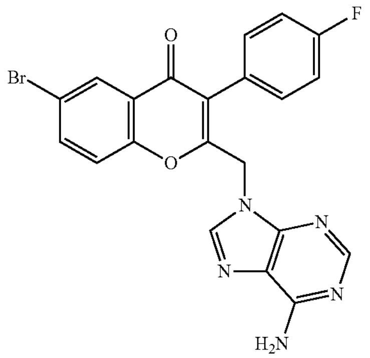 [SMILES: Nc1ncnc2c1ncn2Cc1oc2ccc(Br)cc2c(=O)c1-c1ccc(F)cc1] |
| 16 | 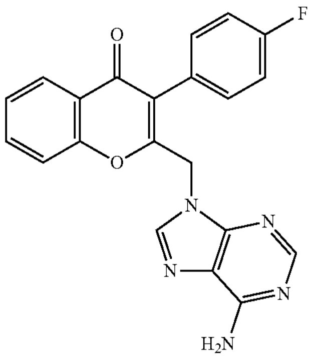 [SMILES: Nc1ncnc2c1ncn2Cc1oc2ccccc2c(=O)c1-c1ccc(F)cc1] |
| 17 | 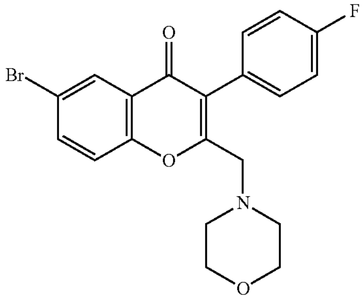 [SMILES: O=c1c(-c2ccc(F)cc2)c(CN2CCOCC2)oc2ccc(Br)cc12] |
TABLE 1-continued
| Ex. | Structure |
|---|---|
| 17a | 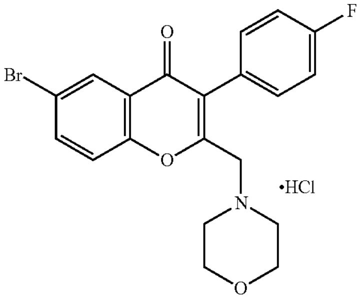 [SMILES: O=c1c(-c2ccc(F)cc2)c(CN2CCOCC2)oc2ccc(Br)cc12 ; Cl] |
| 18 | 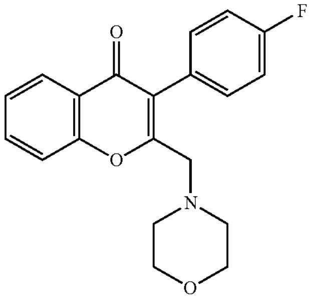 [SMILES: O=c1c(-c2ccc(F)cc2)c(CN2CCOCC2)oc2ccccc12] |
| 18a | 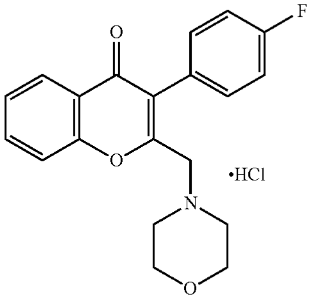 [SMILES: O=c1c(-c2ccc(F)cc2)c(CN2CCOCC2)oc2ccccc12 ; Cl] |
| 19 | 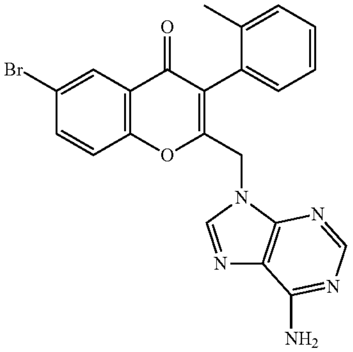 [SMILES: Cc1ccccc1-c1c(Cn2cnc3c(N)ncnc32)oc2ccc(Br)cc2c1=O] |

TABLE 1-continued
| Ex. | Structure |
|---|---|
| 20 | 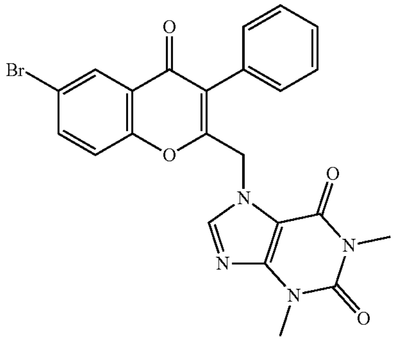 [SMILES: Cn1c(=O)c2c(ncn2Cc2oc3ccc(Br)cc3c(=O)c2-c2ccccc2)n(C)c1=O] |
| 21 | 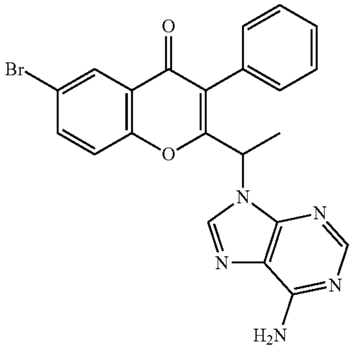 [SMILES: CC(c1oc2ccc(Br)cc2c(=O)c1-c1ccccc1)n1cnc2c(N)ncnc21] |
| 22 | 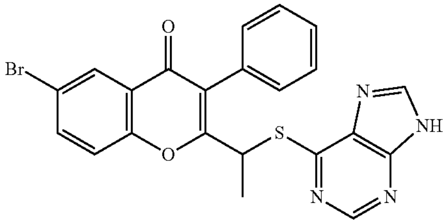 [SMILES: CC(Sc1ncnc2[nH]cnc12)c1oc2ccc(Br)cc2c(=O)c1-c1ccccc1] |
| 23 | 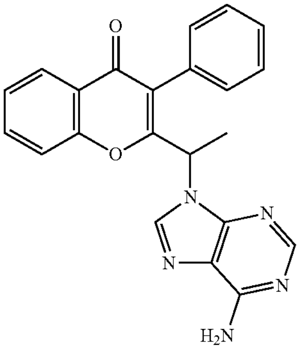 [SMILES: CC(c1oc2ccccc2c(=O)c1-c1ccccc1)n1cnc2c(N)ncnc21] |
| 24 | 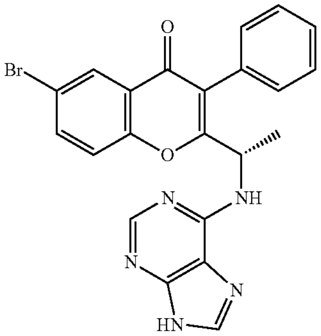 [SMILES: C[C@H](Nc1ncnc2[nH]cnc12)c1oc2ccc(Br)cc2c(=O)c1-c1ccccc1] |
| 25 | 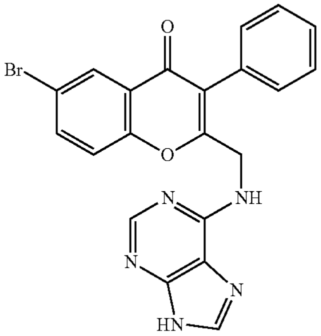 [SMILES: O=c1c(-c2ccccc2)c(CNc2ncnc3[nH]cnc23)oc2ccc(Br)cc12] |
| 26 | 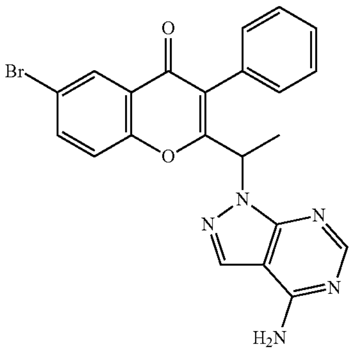 [SMILES: CC(c1oc2ccc(Br)cc2c(=O)c1-c1ccccc1)n1ncc2c(N)ncnc21] |
| 27 | 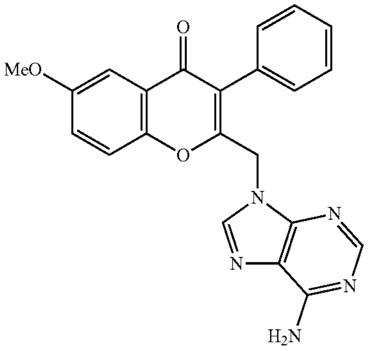 [SMILES: COc1ccc2oc(Cn3cnc4c(N)ncnc43)c(-c3ccccc3)c(=O)c2c1] |

TABLE 1-continued
| Ex. | Structure |
|---|---|
| 28 | 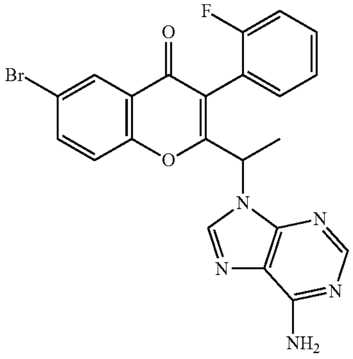 [SMILES: CC(c1oc2ccc(Br)cc2c(=O)c1-c1ccccc1F)n1cnc2c(N)ncnc21] |
| 29 | 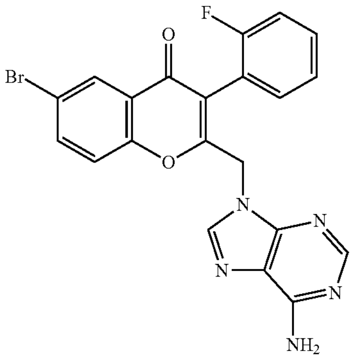 [SMILES: Nc1ncnc2c1ncn2Cc1oc2ccc(Br)cc2c(=O)c1-c1ccccc1F] |
| 30 | 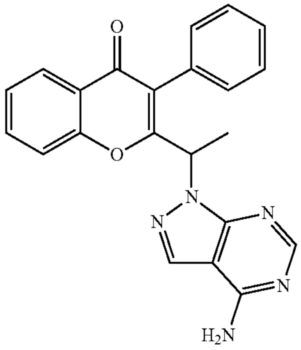 [SMILES: CC(c1oc2ccccc2c(=O)c1-c1ccccc1)n1ncc2c(N)ncnc21] |
| 31 | 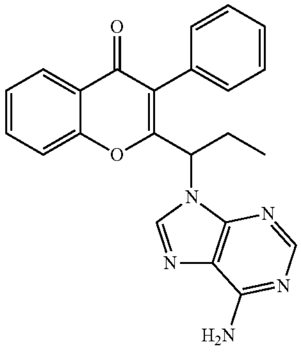 [SMILES: CCC(c1oc2ccccc2c(=O)c1-c1ccccc1)n1cnc2c(N)ncnc21] |
| 32 | 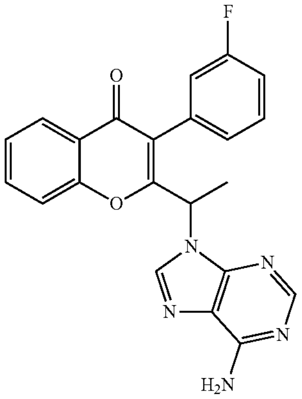 [SMILES: CC(c1oc2ccccc2c(=O)c1-c1cccc(F)c1)n1cnc2c(N)ncnc21] |
| 33 | 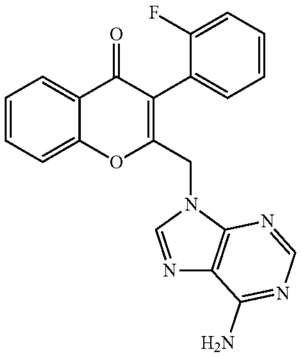 [SMILES: Nc1ncnc2c1ncn2Cc1oc2ccccc2c(=O)c1-c1ccccc1F] |
| 34 | 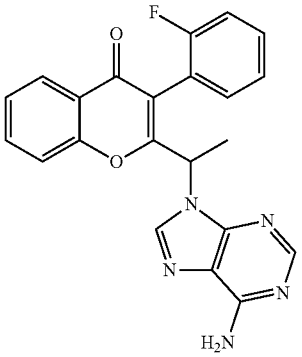 [SMILES: CC(c1oc2ccccc2c(=O)c1-c1ccccc1F)n1cnc2c(N)ncnc21] |
| 35 | 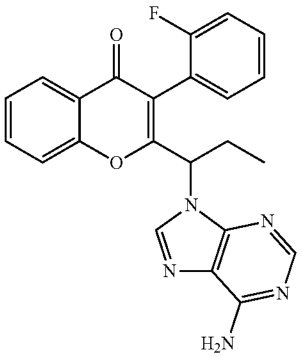 [SMILES: CCC(c1oc2ccccc2c(=O)c1-c1ccccc1F)n1cnc2c(N)ncnc21] |

TABLE 1-continued
| Ex. | Structure |
| --- | --- |
| 36 | 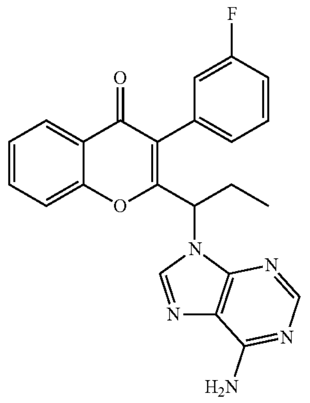 [SMILES: CCC(c1oc2ccccc2c(=O)c1-c1cccc(F)c1)n1cnc2c(N)ncnc21] |
| 37 | 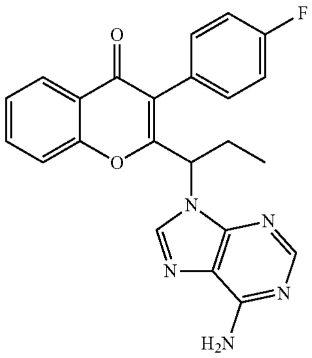 [SMILES: CCC(c1oc2ccccc2c(=O)c1-c1ccc(F)cc1)n1cnc2c(N)ncnc21] |
| 38 | 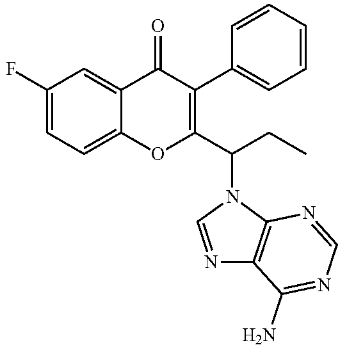 [SMILES: CCC(c1oc2ccc(F)cc2c(=O)c1-c1ccccc1)n1cnc2c(N)ncnc21] |
| 39 | 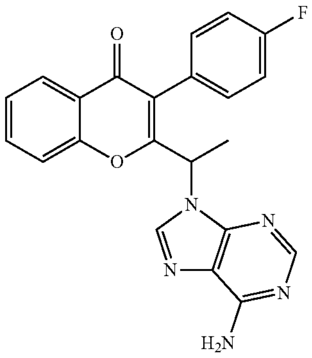 [SMILES: CC(c1oc2ccccc2c(=O)c1-c1ccc(F)cc1)n1cnc2c(N)ncnc21] |
| 40 | 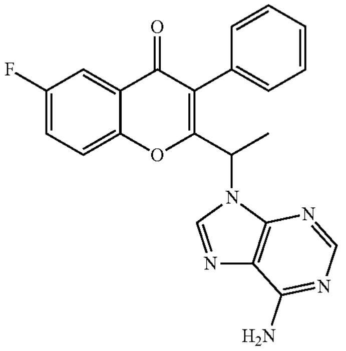 [SMILES: CC(c1oc2ccc(F)cc2c(=O)c1-c1ccccc1)n1cnc2c(N)ncnc21] |
| 41 | 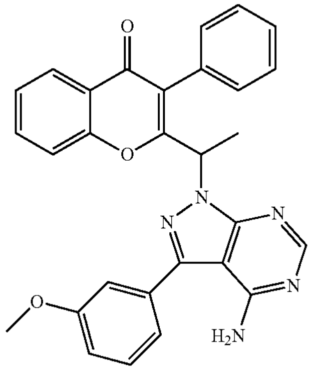 [SMILES: COc1cccc(-c2nn(C(C)c3oc4ccccc4c(=O)c3-c3ccccc3)c3ncnc(N)c23)c1] |
| 42 | 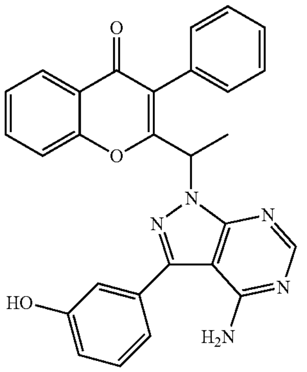 [SMILES: CC(c1oc2ccccc2c(=O)c1-c1ccccc1)n1nc(-c2cccc(O)c2)c2c(N)ncnc21] |
| 43 | 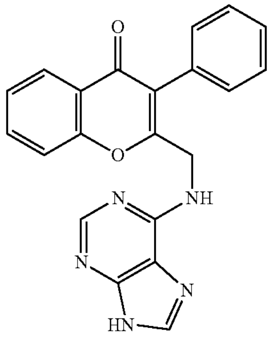 [SMILES: O=c1c(-c2ccccc2)c(CNc2ncnc3[nH]cnc23)oc2ccccc12] |

TABLE 1-continued
| Ex. | Structure |
|---|---|
| 44 | 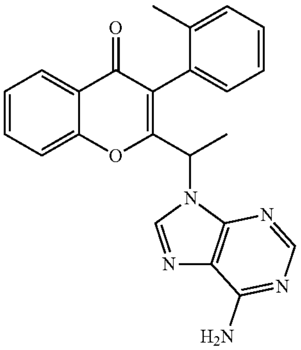 [SMILES: Cc1ccccc1-c1c(C(C)n2cnc3c(N)ncnc32)oc2ccccc2c1=O] |
| 45 | 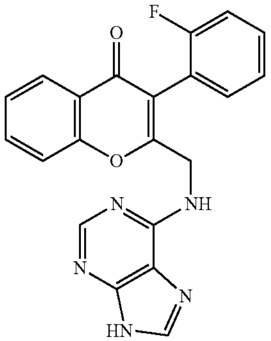 [SMILES: O=c1c(-c2ccccc2F)c(CNc2ncnc3[nH]cnc23)oc2ccccc12] |
| 46 | 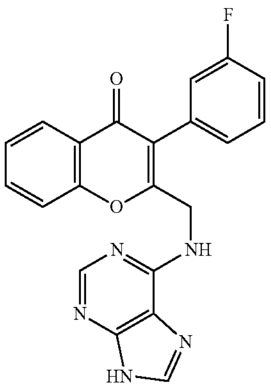 [SMILES: O=c1c(-c2cccc(F)c2)c(CNc2ncnc3[nH]cnc23)oc2ccccc12] |
| 47 | 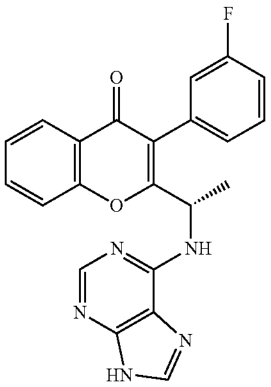 [SMILES: C[C@H](Nc1ncnc2[nH]cnc12)c1oc2ccccc2c(=O)c1-c1cccc(F)c1] |
TABLE 1-continued
| Ex. | Structure |
|---|---|
| 48 | 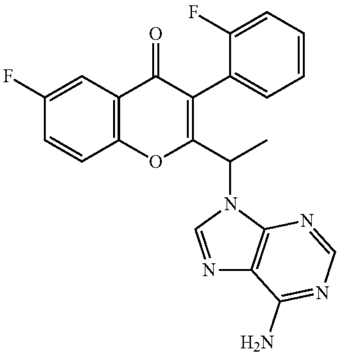 [SMILES: CC(c1oc2ccc(F)cc2c(=O)c1-c1ccccc1F)n1cnc2c(N)ncnc21] |
| 49 | 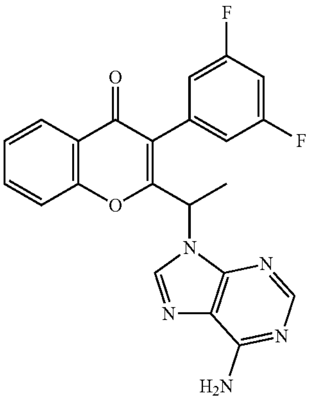 [SMILES: CC(c1oc2ccccc2c(=O)c1-c1cc(F)cc(F)c1)n1cnc2c(N)ncnc21] |
| 50 | 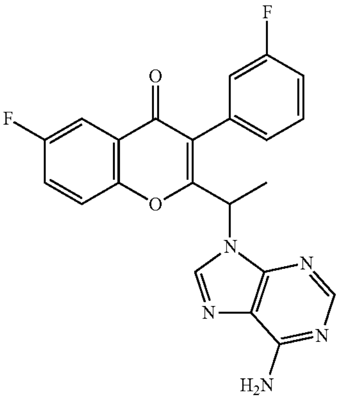 [SMILES: CC(c1oc2ccc(F)cc2c(=O)c1-c1cccc(F)c1)n1cnc2c(N)ncnc21] |
| 51 | 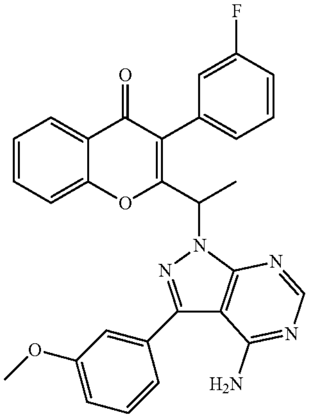 [SMILES: COc1cccc(-c2nn(C(C)c3oc4ccccc4c(=O)c3-c3cccc(F)c3)c3ncnc(N)c23)c1] |

TABLE 1-continued
| Ex. | Structure |
| --- | --- |
| 51a | 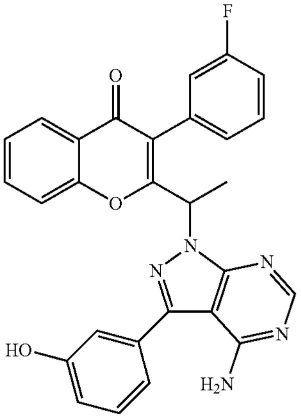 [SMILES: CC(c1oc2ccccc2c(=O)c1-c1cccc(F)c1)n1nc(-c2cccc(O)c2)c2c(N)ncnc21] |
| 52 | 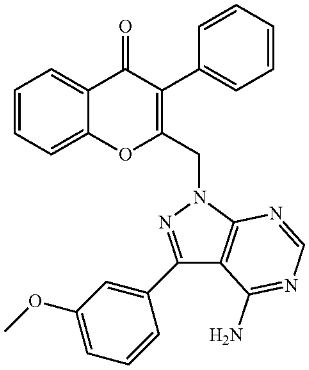 [SMILES: COc1cccc(-c2nn(Cc3oc4ccccc4c(=O)c3-c3ccccc3)c3ncnc(N)c23)c1] |
| 53 | 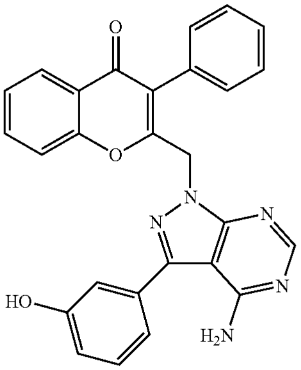 [SMILES: Nc1ncnc2c1c(-c1cccc(O)c1)nn2Cc1oc2ccccc2c(=O)c1-c1ccccc1] |
| 54 | 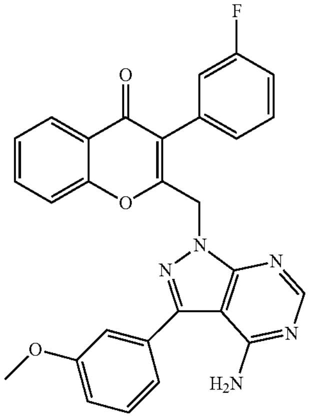 [SMILES: COc1cccc(-c2nn(Cc3oc4ccccc4c(=O)c3-c3cccc(F)c3)c3ncnc(N)c23)c1] |
TABLE 1-continued
| Ex. | Structure |
| --- | --- |
| 55 | 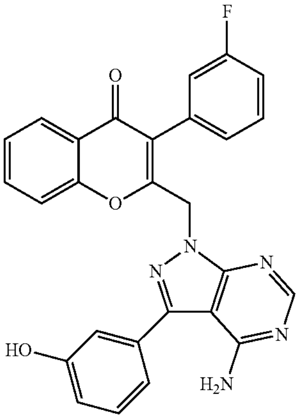 [SMILES: Nc1ncnc2c1c(-c1cccc(O)c1)nn2Cc1oc2ccccc2c(=O)c1-c1cccc(F)c1] |
| 56 | 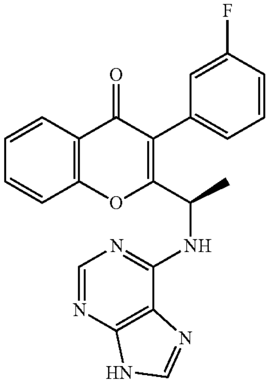 [SMILES: C[C@@H](Nc1ncnc2[nH]cnc12)c1oc2ccccc2c(=O)c1-c1cccc(F)c1] |
| 57 | 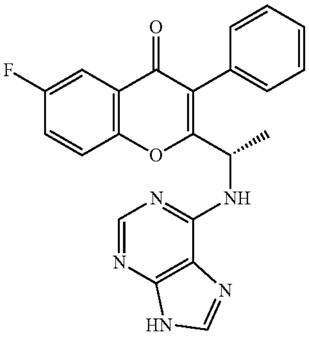 [SMILES: C[C@H](Nc1ncnc2[nH]cnc12)c1oc2ccc(F)cc2c(=O)c1-c1ccccc1] |
| 57a | 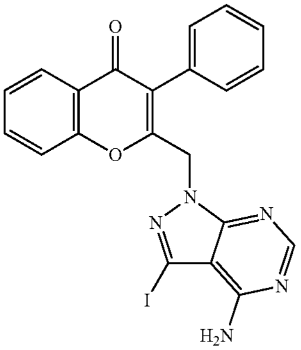 [SMILES: Nc1ncnc2c1c(I)nn2Cc1oc2ccccc2c(=O)c1-c1ccccc1] |

TABLE 1-continued
| Ex. | Structure |
|---|---|
| 57b | 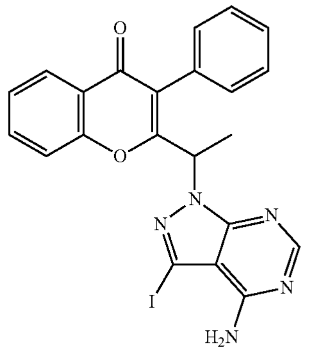 [SMILES: CC(c1oc2ccccc2c(=O)c1-c1ccccc1)n1nc(I)c2c(N)ncnc21] |
| 57c | 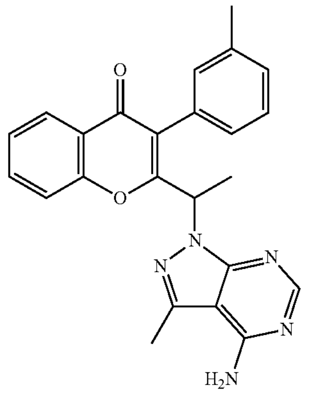 [SMILES: Cc1cccc(-c2c(C(C)n3nc(C)c4c(N)ncnc43)oc3ccccc3c2=O)c1] |
| 57d | 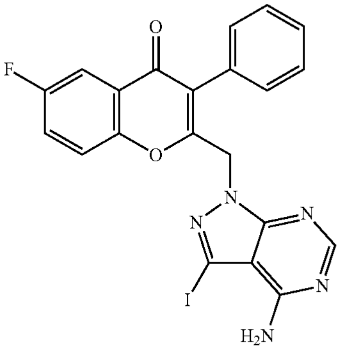 [SMILES: Nc1ncnc2c1c(I)nn2Cc1oc2ccc(F)cc2c(=O)c1-c1ccccc1] |
| 57e | 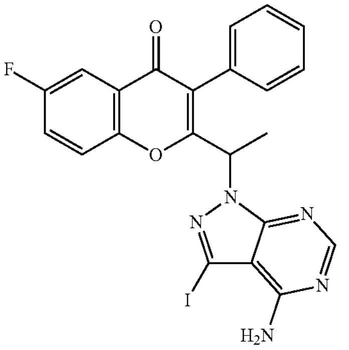 [SMILES: CC(c1oc2ccc(F)cc2c(=O)c1-c1ccccc1)n1nc(I)c2c(N)ncnc21] |
TABLE 1-continued
| Ex. | Structure |
|---|---|
| 57f | 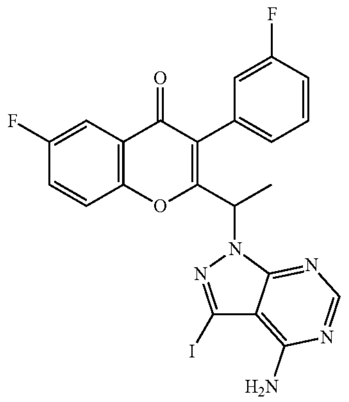 [SMILES: CC(c1oc2ccc(F)cc2c(=O)c1-c1cccc(F)c1)n1nc(I)c2c(N)ncnc21] |
| 57g | 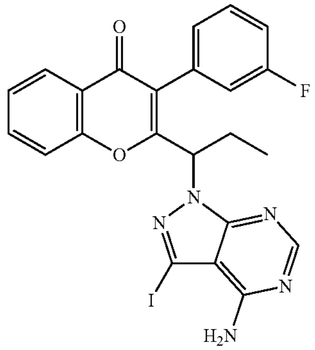 [SMILES: CCC(c1oc2ccccc2c(=O)c1-c1cccc(F)c1)n1nc(I)c2c(N)ncnc21] |
| 58 | 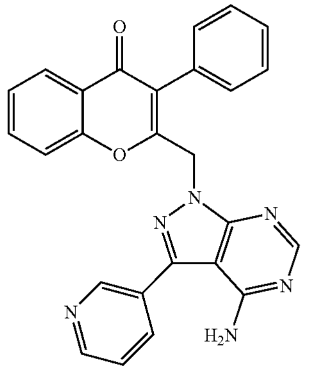 [SMILES: Nc1ncnc2c1c(-c1cccnc1)nn2Cc1oc2ccccc2c(=O)c1-c1ccccc1] |
| 59 | 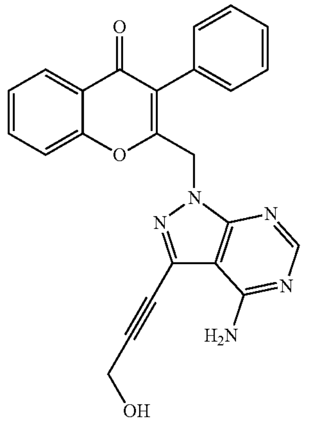 [SMILES: Nc1ncnc2c1c(C#CCO)nn2Cc1oc2ccccc2c(=O)c1-c1ccccc1] |

TABLE 1-continued
| Ex. | Structure |
|---|---|
| 60 | 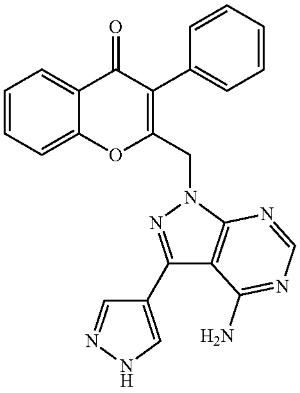 [SMILES: Nc1ncnc2c1c(-c1cn[nH]c1)nn2Cc1oc2ccccc2c(=O)c1-c1ccccc1] |
| 61 | 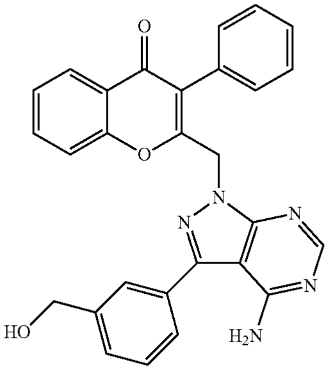 [SMILES: Nc1ncnc2c1c(-c1cccc(CO)c1)nn2Cc1oc2ccccc2c(=O)c1-c1ccccc1] |
| 62 | 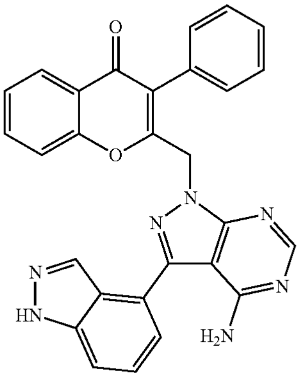 [SMILES: Nc1ncnc2c1c(-c1cccc3[nH]ncc13)nn2Cc1oc2ccccc2c(=O)c1-c1ccccc1] |
| 63 | 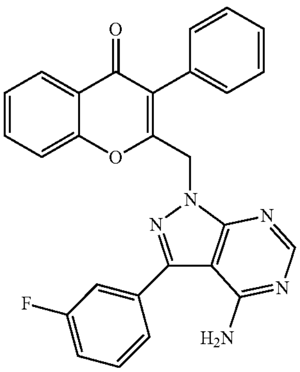 [SMILES: Nc1ncnc2c1c(-c1cccc(F)c1)nn2Cc1oc2ccccc2c(=O)c1-c1ccccc1] |
TABLE 1-continued
| Ex. | Structure |
|---|---|
| 64 | 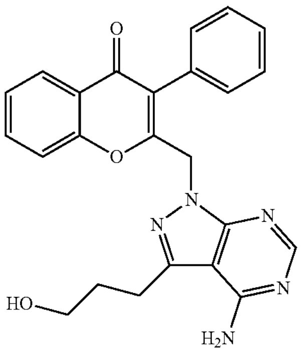 [SMILES: Nc1ncnc2c1c(CCCO)nn2Cc1oc2ccccc2c(=O)c1-c1ccccc1] |
| 65 | 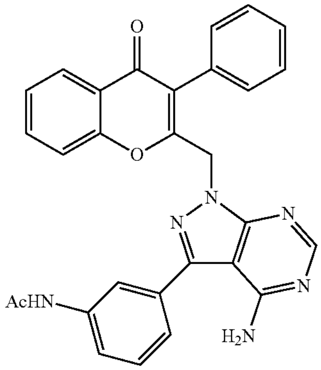 [SMILES: CC(=O)Nc1cccc(-c2nn(Cc3oc4ccccc4c(=O)c3-c3ccccc3)c3ncnc(N)c23)c1] |
| 66 | 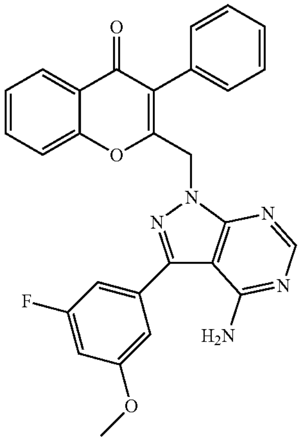 [SMILES: COc1cc(F)cc(-c2nn(Cc3oc4ccccc4c(=O)c3-c3ccccc3)c3ncnc(N)c23)c1] |
| 66a | 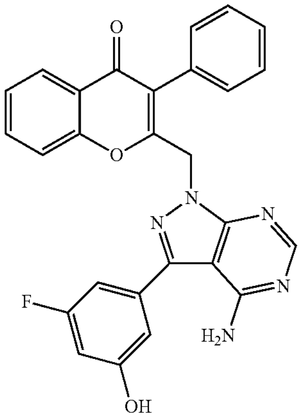 [SMILES: Nc1ncnc2c1c(-c1cc(O)cc(F)c1)nn2Cc1oc2ccccc2c(=O)c1-c1ccccc1] |

TABLE 1-continued
| Ex. | Structure |
|---|---|
| 67 | 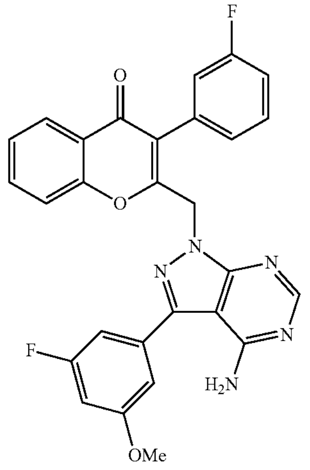 [SMILES: COc1cc(F)cc(-c2nn(Cc3oc4ccccc4c(=O)c3-c3cccc(F)c3)c3ncnc(N)c23)c1] |
| 68 | 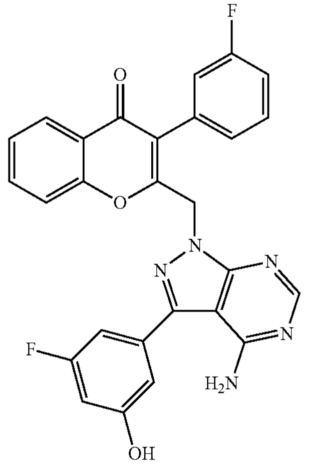 [SMILES: Nc1ncnc2c1c(-c1cc(O)cc(F)c1)nn2Cc1oc2ccccc2c(=O)c1-c1cccc(F)c1] |
| 69 | 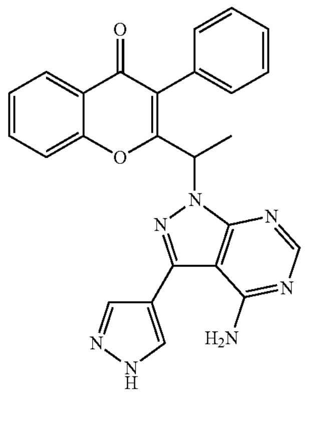 [SMILES: CC(c1oc2ccccc2c(=O)c1-c1ccccc1)n1nc(-c2cn[nH]c2)c2c(N)ncnc21] |
TABLE 1-continued
| Ex. | Structure |
|---|---|
| 70 | 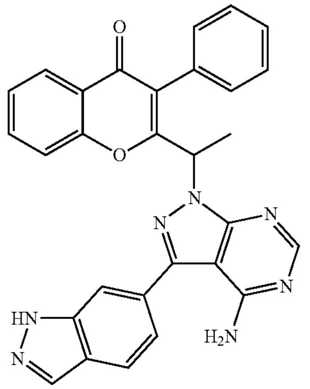 [SMILES: CC(c1oc2ccccc2c(=O)c1-c1ccccc1)n1nc(-c2ccc3cn[nH]c3c2)c2c(N)ncnc21] |
| 71 | 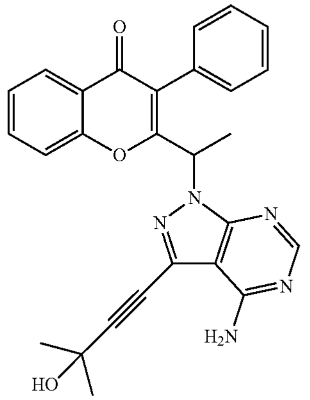 [SMILES: CC(c1oc2ccccc2c(=O)c1-c1ccccc1)n1nc(C#CC(C)(C)O)c2c(N)ncnc21] |
| 72 | 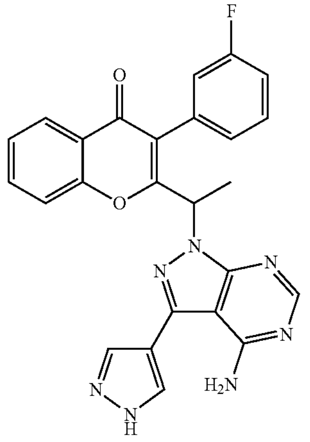 [SMILES: CC(c1oc2ccccc2c(=O)c1-c1cccc(F)c1)n1nc(-c2cn[nH]c2)c2c(N)ncnc21] |
| 73 | 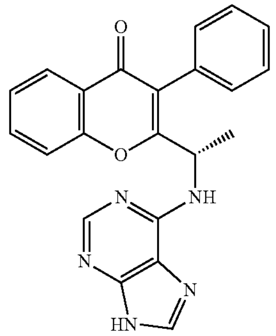 [SMILES: C[C@H](Nc1ncnc2[nH]cnc12)c1oc2ccccc2c(=O)c1-c1ccccc1] |

TABLE 1-continued
| Ex. | Structure |
|---|---|
| 74 | 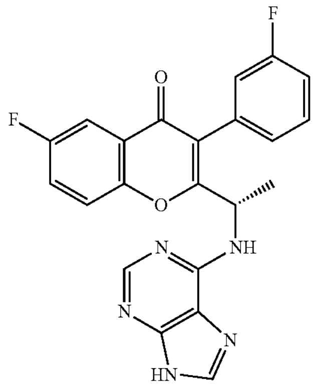 [SMILES: C[C@H](Nc1ncnc2[nH]cnc12)c1oc2ccc(F)cc2c(=O)c1-c1cccc(F)c1] |
| 75 | 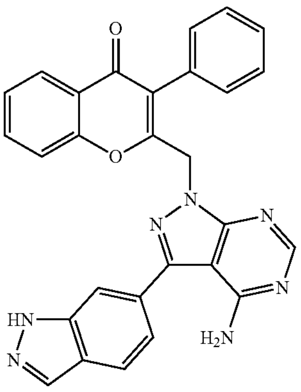 [SMILES: Nc1ncnc2c1c(-c1ccc3cn[nH]c3c1)nn2Cc1oc2ccccc2c(=O)c1-c1ccccc1] |
| 76 | 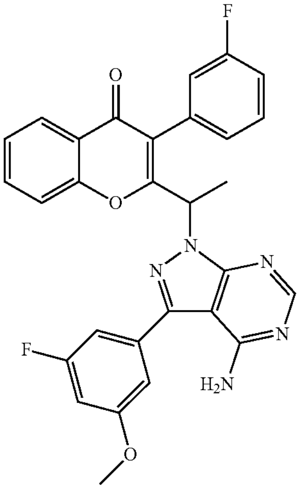 [SMILES: COc1cc(F)cc(-c2nn(C(C)c3oc4ccccc4c(=O)c3-c3cccc(F)c3)c3ncnc(N)c23)c1] |
TABLE 1-continued
| Ex. | Structure |
|---|---|
| 76a | 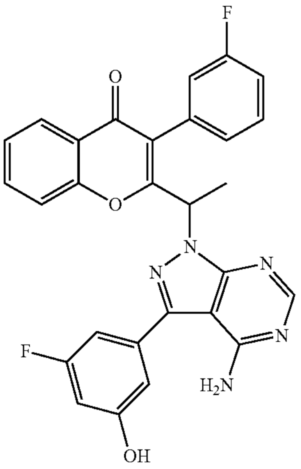 |
| 77 | 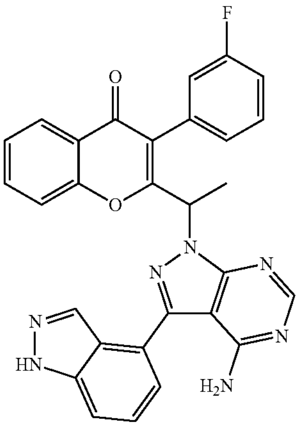 [SMILES: CC(c1oc2ccccc2c(=O)c1-c1cccc(F)c1)n1nc(-c2cccc3[nH]ncc23)c2c(N)ncnc21] |
| 78 | 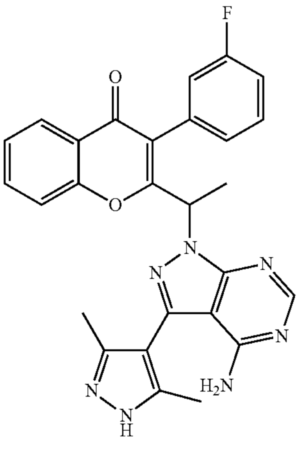 [SMILES: Cc1n[nH]c(C)c1-c1nn(C(C)c2oc3ccccc3c(=O)c2-c2cccc(F)c2)c2ncnc(N)c12] |

TABLE 1-continued
| Ex. | Structure |
| --- | --- |
| 79 | 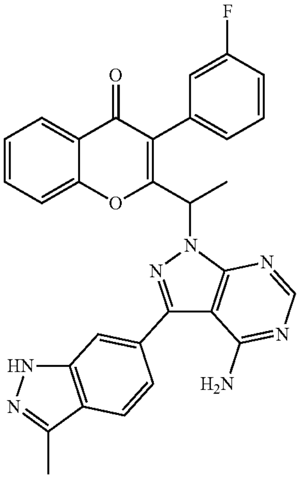 [SMILES: Cc1n[nH]c2cc(-c3nn(C(C)c4oc5ccccc5c(=O)c4-c4cccc(F)c4)c4ncnc(N)c34)ccc12] |
| 80 | 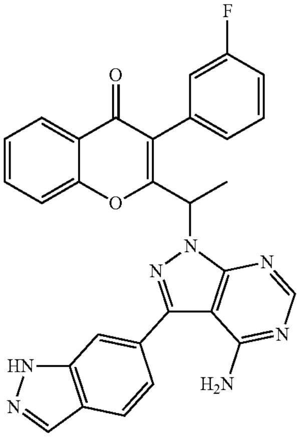 [SMILES: CC(c1oc2ccccc2c(=O)c1-c1cccc(F)c1)n1nc(-c2ccc3cn[nH]c3c2)c2c(N)ncnc21] |
| 81 | 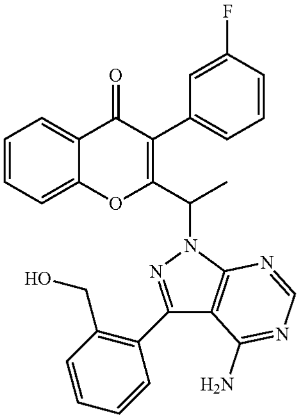 [SMILES: CC(c1oc2ccccc2c(=O)c1-c1cccc(F)c1)n1nc(-c2ccccc2CO)c2c(N)ncnc21] |
TABLE 1-continued
| Ex. | Structure |
| --- | --- |
| 82 | 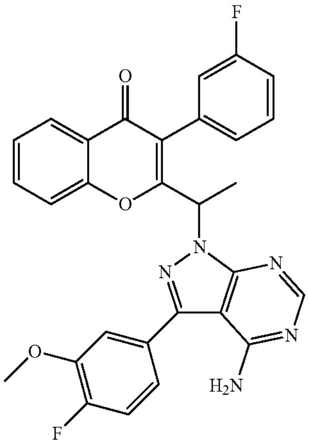 [SMILES: COc1cc(-c2nn(C(C)c3oc4ccccc4c(=O)c3-c3cccc(F)c3)c3ncnc(N)c23)ccc1F] |
| 82a | 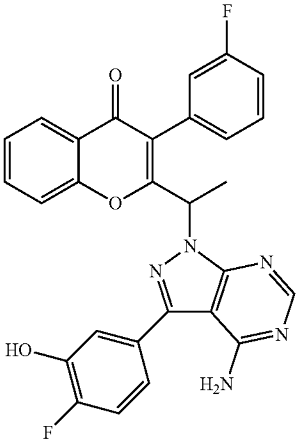 [SMILES: CC(c1oc2ccccc2c(=O)c1-c1cccc(F)c1)n1nc(-c2ccc(F)c(O)c2)c2c(N)ncnc21] |
| 83 | 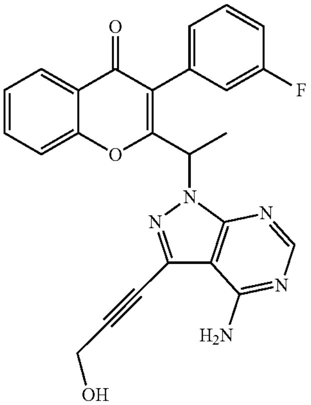 [SMILES: CC(c1oc2ccccc2c(=O)c1-c1cccc(F)c1)n1nc(C#CCO)c2c(N)ncnc21] |

TABLE 1-continued
| Ex. | Structure |
|---|---|
| 84 | 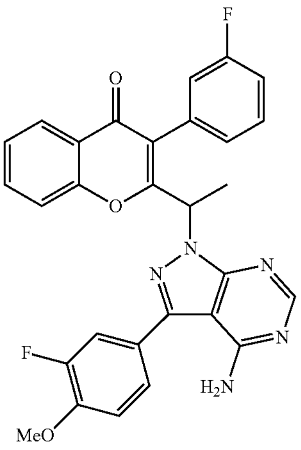 [SMILES: COc1ccc(-c2nn(C(C)c3oc4ccccc4c(=O)c3-c3cccc(F)c3)c3ncnc(N)c23)cc1F] |
| 85 | 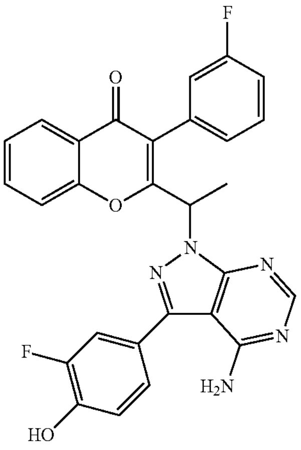 [SMILES: CC(c1oc2ccccc2c(=O)c1-c1cccc(F)c1)n1nc(-c2ccc(O)c(F)c2)c2c(N)ncnc21] |
| 86 | 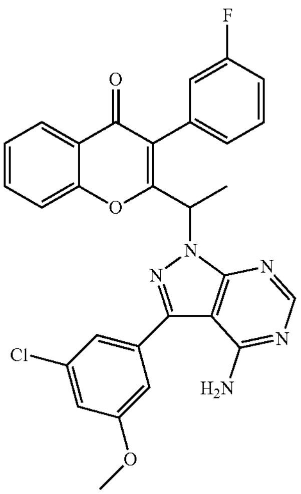 [SMILES: COc1cc(Cl)cc(-c2nn(C(C)c3oc4ccccc4c(=O)c3-c3cccc(F)c3)c3ncnc(N)c23)c1] |
| 86a | 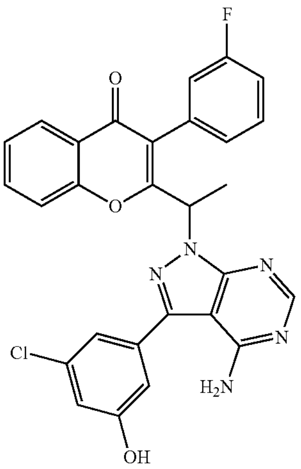 [SMILES: CC(c1oc2ccccc2c(=O)c1-c1cccc(F)c1)n1nc(-c2cc(O)cc(Cl)c2)c2c(N)ncnc21] |
| 87 | 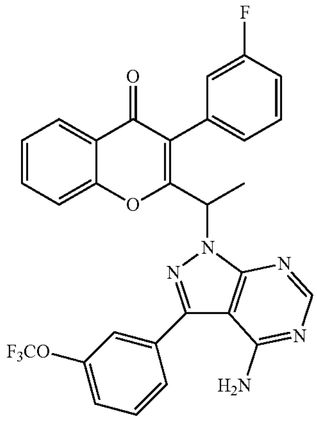 [SMILES: CC(c1oc2ccccc2c(=O)c1-c1cccc(F)c1)n1nc(-c2cccc(OC(F)(F)F)c2)c2c(N)ncnc21] |
| 88 | 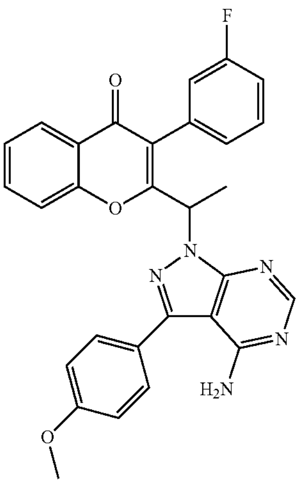 [SMILES: COc1ccc(-c2nn(C(C)c3oc4ccccc4c(=O)c3-c3cccc(F)c3)c3ncnc(N)c23)cc1] |

TABLE 1-continued
| Ex. | Structure |
|---|---|
| 88a | 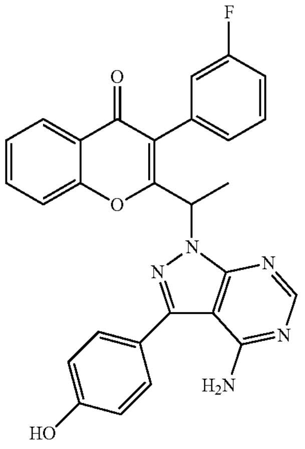 [SMILES: CC(c1oc2ccccc2c(=O)c1-c1cccc(F)c1)n1nc(-c2ccc(O)cc2)c2c(N)ncnc21] |
| 89 | 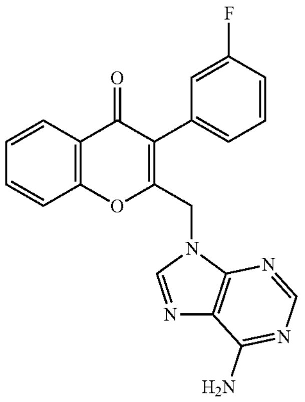 [SMILES: Nc1ncnc2c1ncn2Cc1oc2ccccc2c(=O)c1-c1cccc(F)c1] |
| 90 | 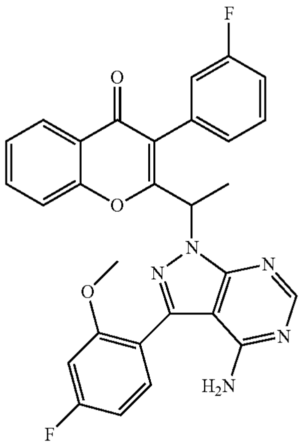 [SMILES: COc1cc(F)ccc1-c1nn(C(C)c2oc3ccccc3c(=O)c2-c2cccc(F)c2)c2ncnc(N)c12] |
TABLE 1-continued
| Ex. | Structure |
|---|---|
| 90a | 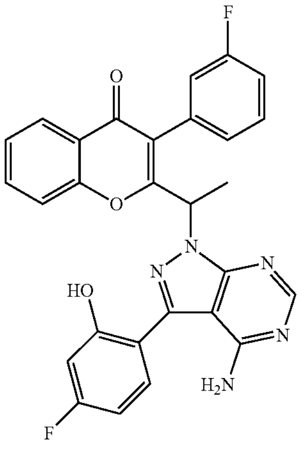 [SMILES: CC(c1oc2ccccc2c(=O)c1-c1cccc(F)c1)n1nc(-c2ccc(F)cc2O)c2c(N)ncnc21] |
| 91 | 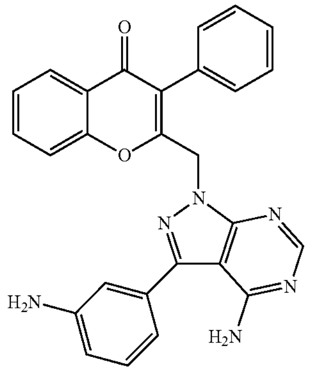 [SMILES: Nc1cccc(-c2nn(Cc3oc4ccccc4c(=O)c3-c3ccccc3)c3ncnc(N)c23)c1] |
| 92 | 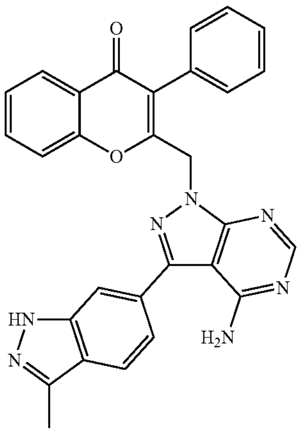 [SMILES: Cc1n[nH]c2cc(-c3nn(Cc4oc5ccccc5c(=O)c4-c4ccccc4)c4ncnc(N)c34)ccc12] |

TABLE 1-continued
| Ex. | Structure |
|---|---|
| 93 | 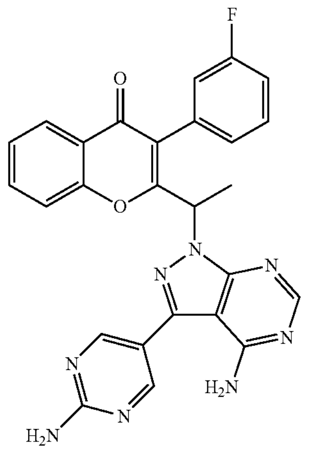 [SMILES: CC(c1oc2ccccc2c(=O)c1-c1cccc(F)c1)n1nc(-c2cnc(N)nc2)c2c(N)ncnc21] |
| 94 | 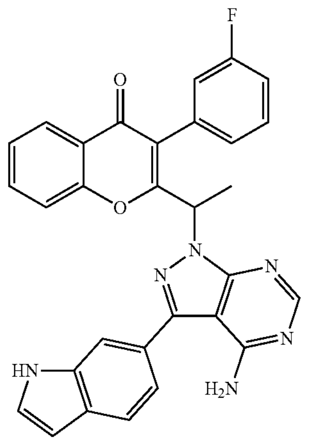 [SMILES: CC(c1oc2ccccc2c(=O)c1-c1cccc(F)c1)n1nc(-c2ccc3cc[nH]c3c2)c2c(N)ncnc21] |
| 95 | 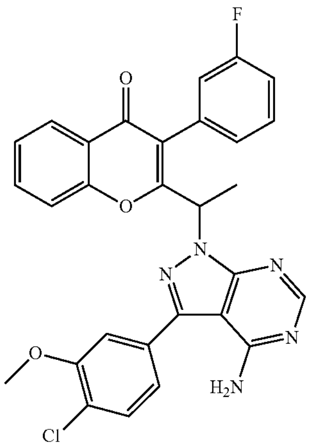 [SMILES: COc1cc(-c2nn(C(C)c3oc4ccccc4c(=O)c3-c3cccc(F)c3)c3ncnc(N)c23)ccc1Cl] |
TABLE 1-continued
| Ex. | Structure |
|---|---|
| 95a | 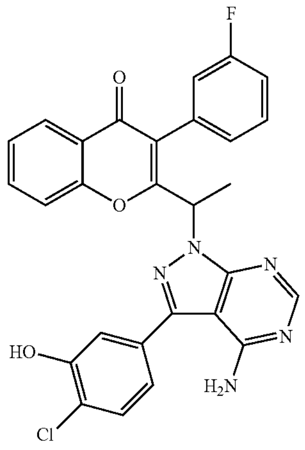 [SMILES: CC(c1oc2ccccc2c(=O)c1-c1cccc(F)c1)n1nc(-c2ccc(Cl)c(O)c2)c2c(N)ncnc21] |
| 96 | 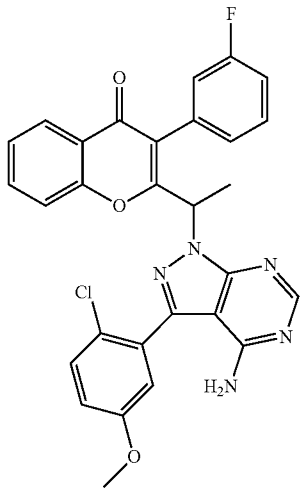 [SMILES: COc1ccc(Cl)c(-c2nn(C(C)c3oc4ccccc4c(=O)c3-c3cccc(F)c3)c3ncnc(N)c23)c1] |
| 96a | 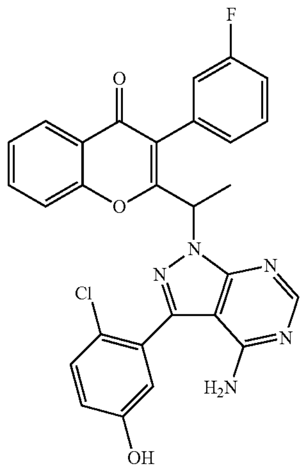 [SMILES: CC(c1oc2ccccc2c(=O)c1-c1cccc(F)c1)n1nc(-c2cc(O)ccc2Cl)c2c(N)ncnc21] |

TABLE 1-continued
| Ex. | Structure |
| --- | --- |
| 97 | 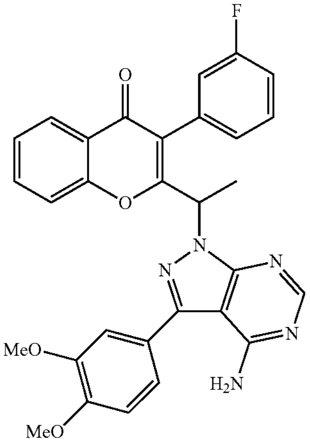 [SMILES: COc1ccc(-c2nn(C(C)c3oc4ccccc4c(=O)c3-c3cccc(F)c3)c3ncnc(N)c23)cc1OC] |
| 98 | 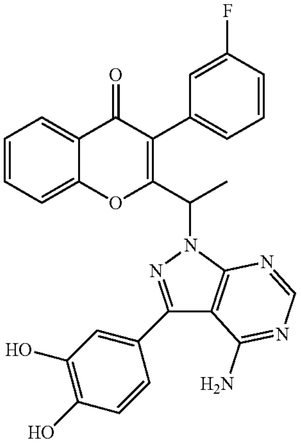 [SMILES: CC(c1oc2ccccc2c(=O)c1-c1cccc(F)c1)n1nc(-c2ccc(O)c(O)c2)c2c(N)ncnc21] |
| 99 | 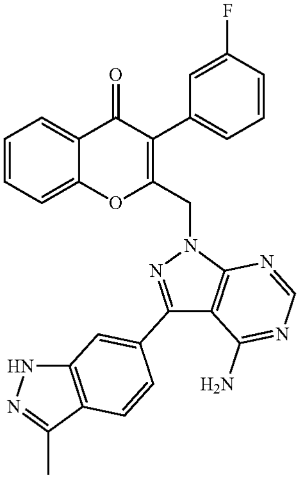 [SMILES: Cc1n[nH]c2cc(-c3nn(Cc4oc5ccccc5c(=O)c4-c4cccc(F)c4)c4ncnc(N)c34)ccc12] |
TABLE 1-continued
| Ex. | Structure |
| --- | --- |
| 100 | 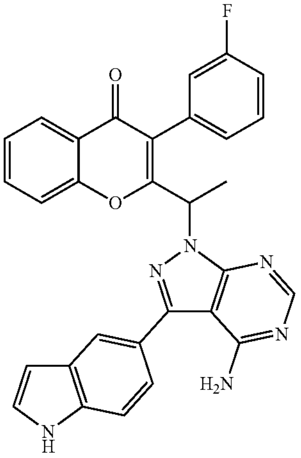 [SMILES: CC(c1oc2ccccc2c(=O)c1-c1cccc(F)c1)n1nc(-c2ccc3[nH]ccc3c2)c2c(N)ncnc21] |
| 101 | 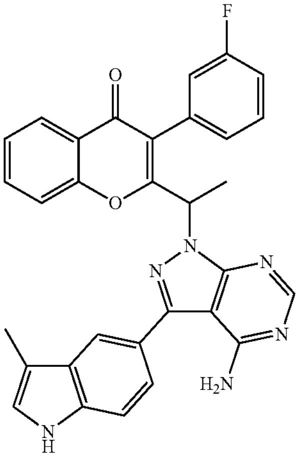 [SMILES: Cc1c[nH]c2ccc(-c3nn(C(C)c4oc5ccccc5c(=O)c4-c4cccc(F)c4)c4ncnc(N)c34)cc12] |
| 102 | 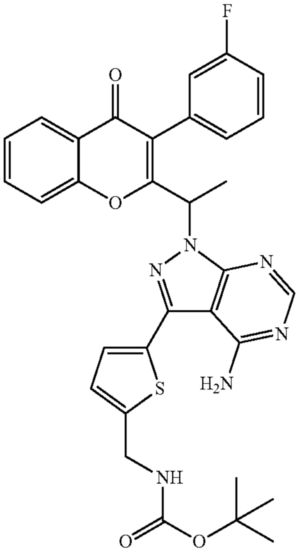 [SMILES: CC(c1oc2ccccc2c(=O)c1-c1cccc(F)c1)n1nc(-c2ccc(CNC(=O)OC(C)(C)C)s2)c2c(N)ncnc21] |

TABLE 1-continued
| Ex. | Structure |
| --- | --- |
| 102a | 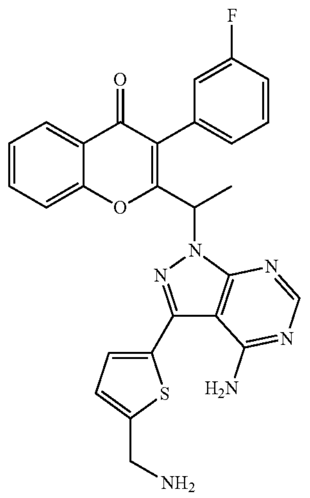 [SMILES: CC(c1oc2ccccc2c(=O)c1-c1cccc(F)c1)n1nc(-c2ccc(CN)s2)c2c(N)ncnc21] |
| 103 | 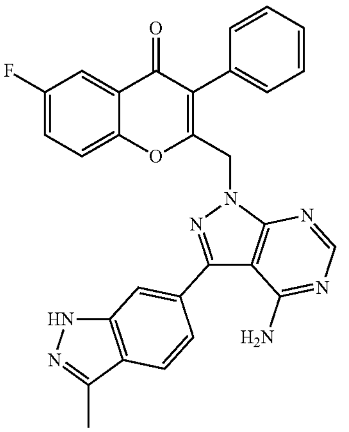 [SMILES: Cc1n[nH]c2cc(-c3nn(Cc4oc5ccc(F)cc5c(=O)c4-c4ccccc4)c4ncnc(N)c34)ccc12] |
| 104 | 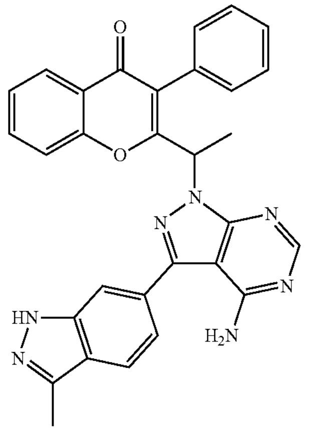 [SMILES: Cc1n[nH]c2cc(-c3nn(C(C)c4oc5ccccc5c(=O)c4-c4ccccc4)c4ncnc(N)c34)ccc12] |
TABLE 1-continued
| Ex. | Structure |
| --- | --- |
| 105 | 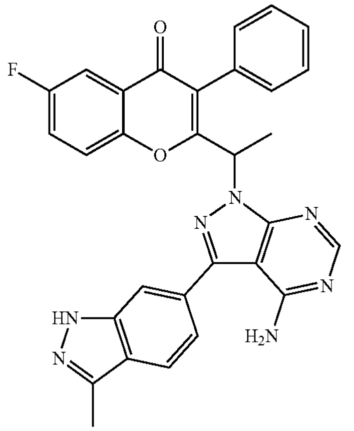 [SMILES: Cc1n[nH]c2cc(-c3nn(C(C)c4oc5ccc(F)cc5c(=O)c4-c4ccccc4)c4ncnc(N)c34)ccc12] |
| 106 | 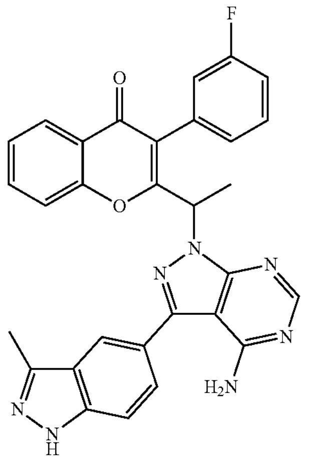 [SMILES: Cc1n[nH]c2ccc(-c3nn(C(C)c4oc5ccccc5c(=O)c4-c4cccc(F)c4)c4ncnc(N)c34)cc12] |
| 107 | 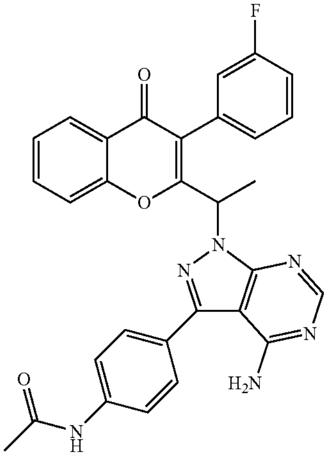 [SMILES: CC(=O)Nc1ccc(-c2nn(C(C)c3oc4ccccc4c(=O)c3-c3cccc(F)c3)c3ncnc(N)c23)cc1] |

TABLE 1-continued
| Ex. | Structure |
| --- | --- |
| 107a | 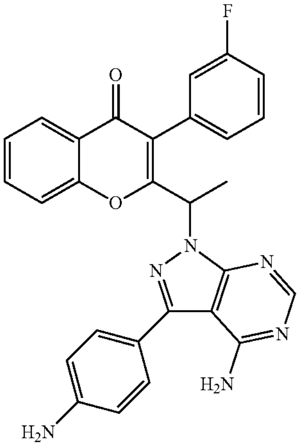 [SMILES: CC(c1oc2ccccc2c(=O)c1-c1cccc(F)c1)n1nc(-c2ccc(N)cc2)c2c(N)ncnc21] |
| 108 | 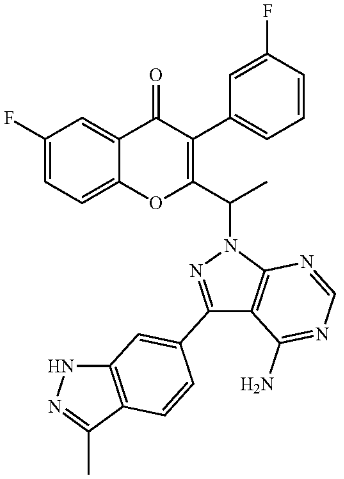 [SMILES: Cc1n[nH]c2cc(-c3nn(C(C)c4oc5ccc(F)cc5c(=O)c4-c4cccc(F)c4)c4ncnc(N)c34)ccc12] |
| 109 | 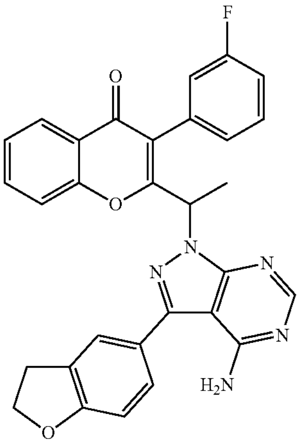 [SMILES: CC(c1oc2ccccc2c(=O)c1-c1cccc(F)c1)n1nc(-c2ccc3c(c2)CCO3)c2c(N)ncnc21] |
TABLE 1-continued
| Ex. | Structure |
| --- | --- |
| 110 | 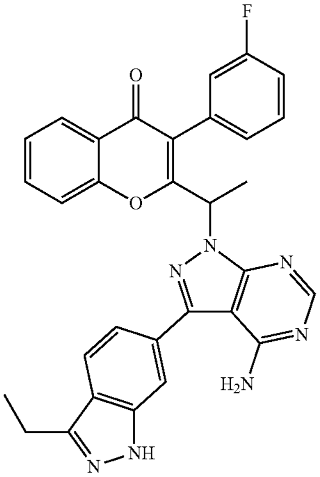 [SMILES: CCc1n[nH]c2cc(-c3nn(C(C)c4oc5ccccc5c(=O)c4-c4cccc(F)c4)c4ncnc(N)c34)ccc12] |
| 111 | 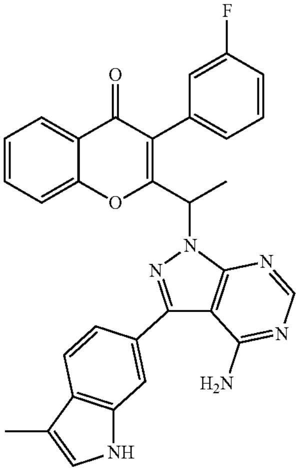 [SMILES: Cc1c[nH]c2cc(-c3nn(C(C)c4oc5ccccc5c(=O)c4-c4cccc(F)c4)c4ncnc(N)c34)ccc12] |
| 112 | 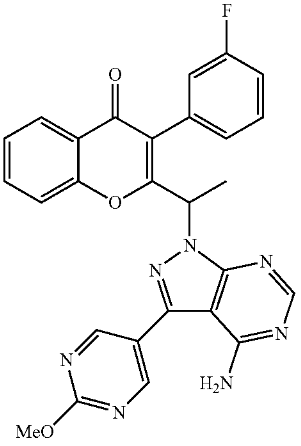 [SMILES: COc1ncc(-c2nn(C(C)c3oc4ccccc4c(=O)c3-c3cccc(F)c3)c3ncnc(N)c23)cn1] |

TABLE 1-continued
| Ex. | Structure |
|---|---|
| 113 | 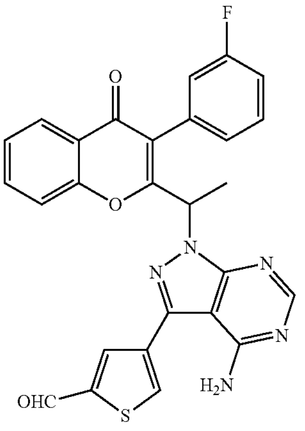 [SMILES: CC(c1oc2ccccc2c(=O)c1-c1cccc(F)c1)n1nc(-c2csc(C=O)c2)c2c(N)ncnc21] |
| 114 | 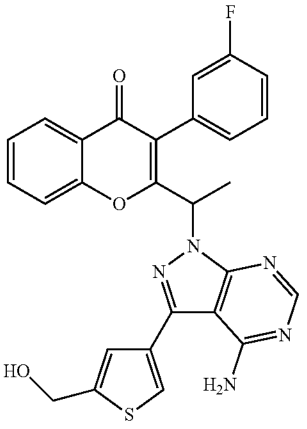 [SMILES: CC(c1oc2ccccc2c(=O)c1-c1cccc(F)c1)n1nc(-c2csc(CO)c2)c2c(N)ncnc21] |
| 115 | 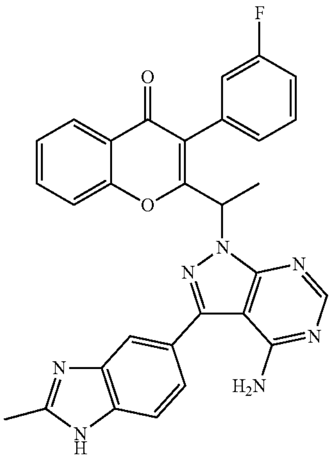 [SMILES: Cc1nc2cc(-c3nn(C(C)c4oc5ccccc5c(=O)c4-c4cccc(F)c4)c4ncnc(N)c34)ccc2[nH]1] |
TABLE 1-continued
| Ex. | Structure |
|---|---|
| 116 | 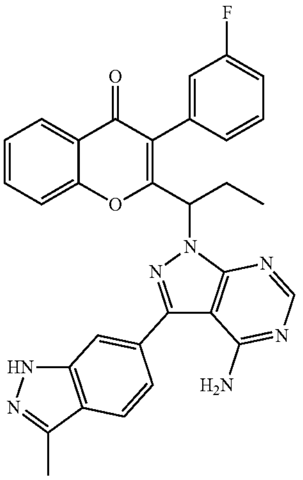 [SMILES: CCC(c1oc2ccccc2c(=O)c1-c1cccc(F)c1)n1nc(-c2ccc3c(C)n[nH]c3c2)c2c(N)ncnc21] |
| 117 | 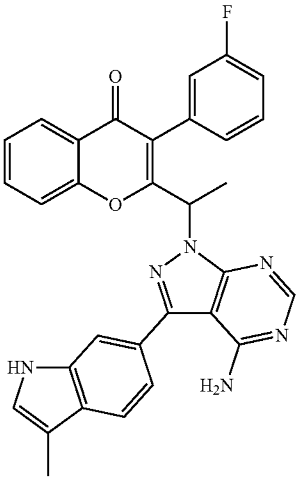 [SMILES: Cc1c[nH]c2cc(-c3nn(C(C)c4oc5ccccc5c(=O)c4-c4cccc(F)c4)c4ncnc(N)c34)ccc12] |
| 118 | 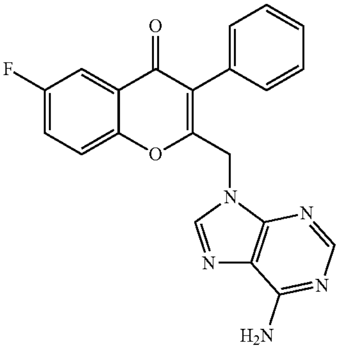 [SMILES: Nc1ncnc2c1ncn2Cc1oc2ccc(F)cc2c(=O)c1-c1ccccc1] |

TABLE 1-continued
| Ex. | Structure |
|---|---|
| 119 | 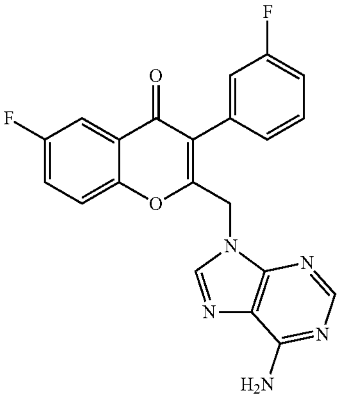 [SMILES: Nc1ncnc2c1ncn2Cc1oc2ccc(F)cc2c(=O)c1-c1cccc(F)c1] |
| 120 | 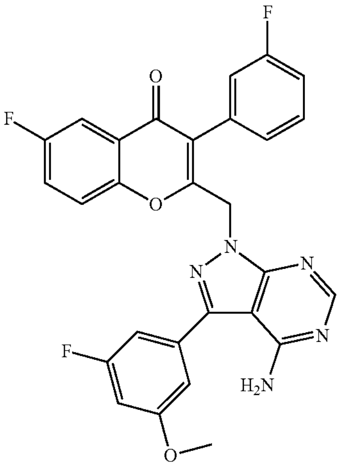 [SMILES: COc1cc(F)cc(-c2nn(Cc3oc4ccc(F)cc4c(=O)c3-c3cccc(F)c3)c3ncnc(N)c23)c1] |
| 120a | 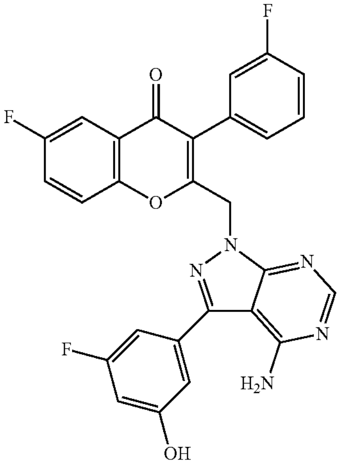 [SMILES: Nc1ncnc2c1c(-c1cc(O)cc(F)c1)nn2Cc1oc2ccc(F)cc2c(=O)c1-c1cccc(F)c1] |
| 121 | 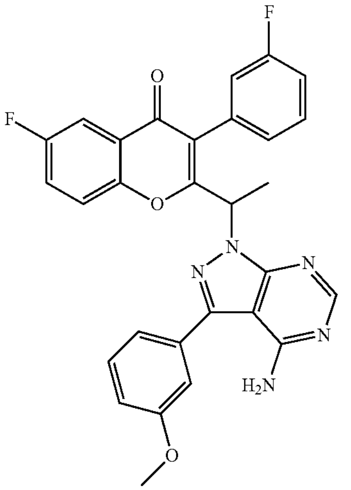 [SMILES: COc1cccc(-c2nn(C(C)c3oc4ccc(F)cc4c(=O)c3-c3cccc(F)c3)c3ncnc(N)c23)c1] |
| 121a | 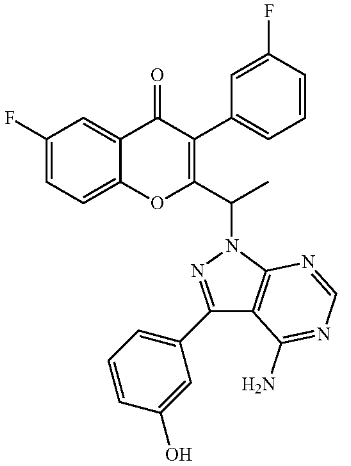 [SMILES: CC(c1oc2ccc(F)cc2c(=O)c1-c1cccc(F)c1)n1nc(-c2cccc(O)c2)c2c(N)ncnc21] |
| 122 | 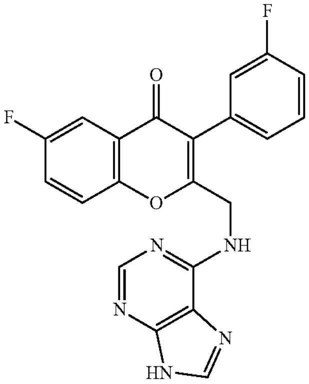 [SMILES: O=c1c(-c2cccc(F)c2)c(CNc2ncnc3[nH]cnc23)oc2ccc(F)cc12] |

TABLE 1-continued
| Ex. | Structure |
| --- | --- |
| 123 | 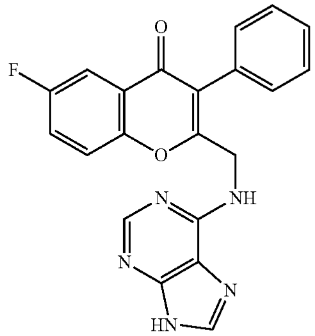 [SMILES: O=c1c(-c2ccccc2)c(CNc2ncnc3[nH]cnc23)oc2ccc(F)cc12] |
| 124 | 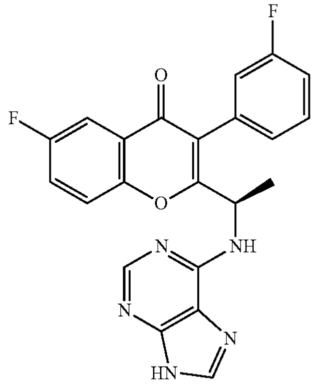 [SMILES: C[C@@H](Nc1ncnc2[nH]cnc12)c1oc2ccc(F)cc2c(=O)c1-c1cccc(F)c1] |
| 125 | 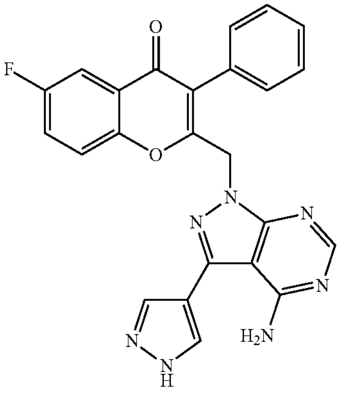 [SMILES: Nc1ncnc2c1c(-c1cn[nH]c1)nn2Cc1oc2ccc(F)cc2c(=O)c1-c1ccccc1] |
| 126 | 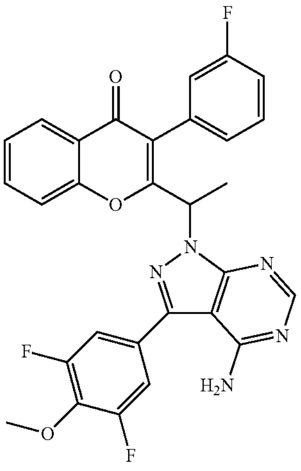 [SMILES: COc1c(F)cc(-c2nn(C(C)c3oc4ccccc4c(=O)c3-c3cccc(F)c3)c3ncnc(N)c23)cc1F] |
| 126a | 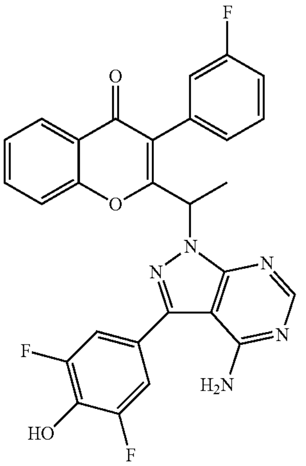 [SMILES: CC(c1oc2ccccc2c(=O)c1-c1cccc(F)c1)n1nc(-c2cc(F)c(O)c(F)c2)c2c(N)ncnc21] |
| 127 | 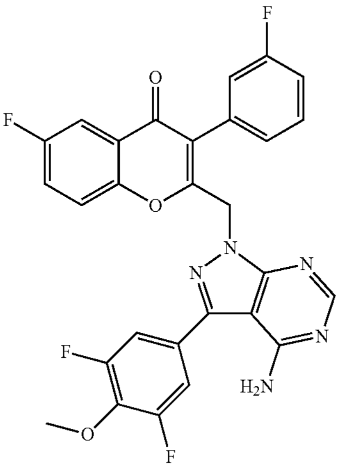 [SMILES: COc1c(F)cc(-c2nn(Cc3oc4ccc(F)cc4c(=O)c3-c3cccc(F)c3)c3ncnc(N)c23)cc1F] |
| 127a | 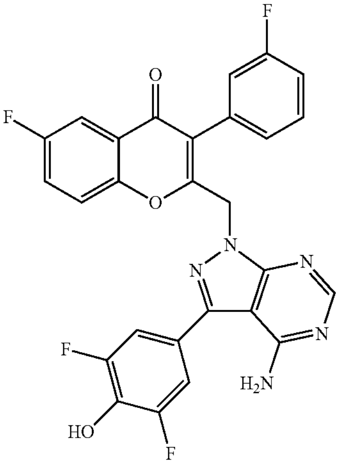 [SMILES: Nc1ncnc2c1c(-c1cc(F)c(O)c(F)c1)nn2Cc1oc2ccc(F)cc2c(=O)c1-c1cccc(F)c1] |

TABLE 1-continued
| Ex. | Structure |
| --- | --- |
| 128 | 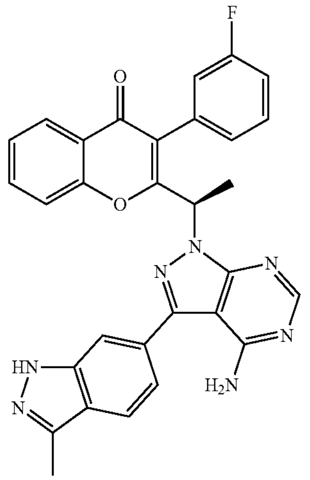 [SMILES: Cc1n[nH]c2cc(-c3nn([C@H](C)c4oc5ccccc5c(=O)c4-c4cccc(F)c4)c4ncnc(N)c34)ccc12] |
| 129 | 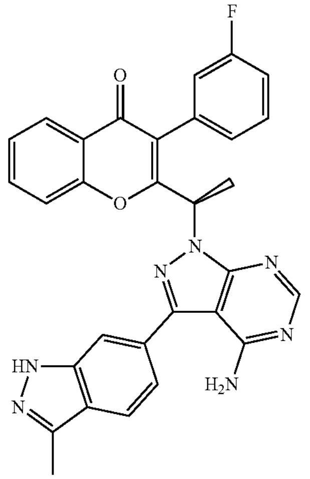 [SMILES: Cc1n[nH]c2cc(-c3nn([C@H](C)c4oc5ccccc5c(=O)c4-c4cccc(F)c4)c4ncnc(N)c34)ccc12] |
| 130 | 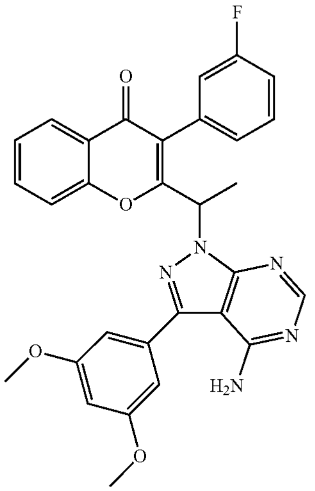 [SMILES: COc1cc(OC)cc(-c2nn(C(C)c3oc4ccccc4c(=O)c3-c3cccc(F)c3)c3ncnc(N)c23)c1] |
TABLE 1-continued
| Ex. | Structure |
| --- | --- |
| 131 | 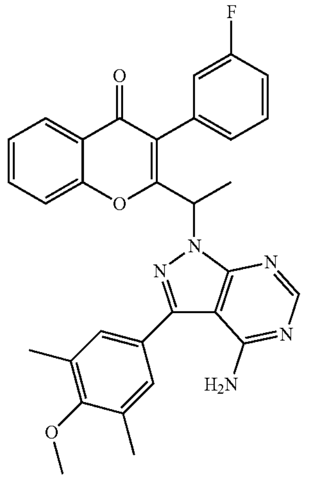 [SMILES: COc1c(C)cc(-c2nn(C(C)c3oc4ccccc4c(=O)c3-c3cccc(F)c3)c3ncnc(N)c23)cc1C] |
| 132 | 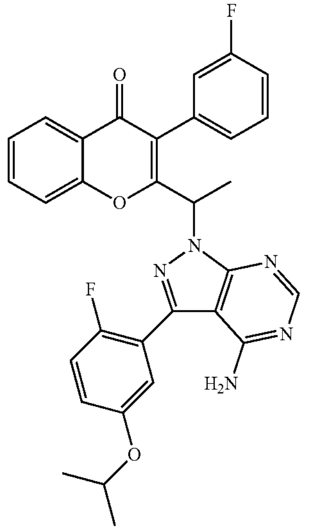 [SMILES: CC(C)Oc1ccc(F)c(-c2nn(C(C)c3oc4ccccc4c(=O)c3-c3cccc(F)c3)c3ncnc(N)c23)c1] |
| 133 | 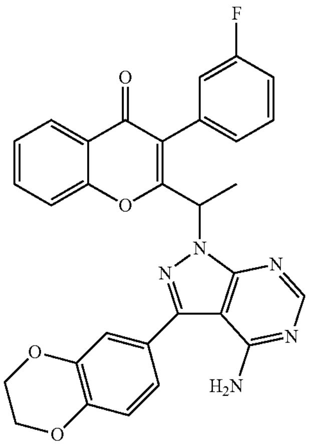 [SMILES: CC(c1oc2ccccc2c(=O)c1-c1cccc(F)c1)n1nc(-c2ccc3c(c2)OCCO3)c2c(N)ncnc21] |

TABLE 1-continued
| Ex. | Structure |
|---|---|
| 134 | 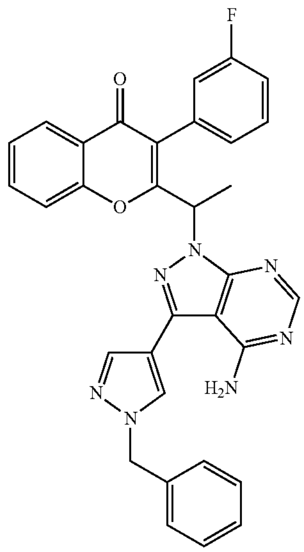 [SMILES: CC(c1oc2ccccc2c(=O)c1-c1cccc(F)c1)n1nc(-c2cnn(Cc3ccccc3)c2)c2c(N)ncnc21] |
| 135 | 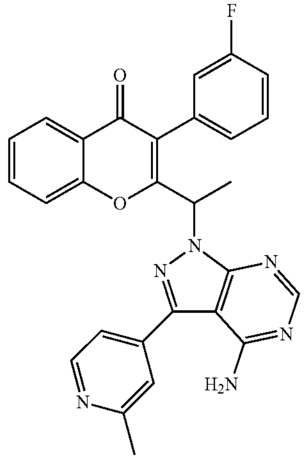 [SMILES: Cc1cc(-c2nn(C(C)c3oc4ccccc4c(=O)c3-c3cccc(F)c3)c3ncnc(N)c23)ccn1] |
| 136 | 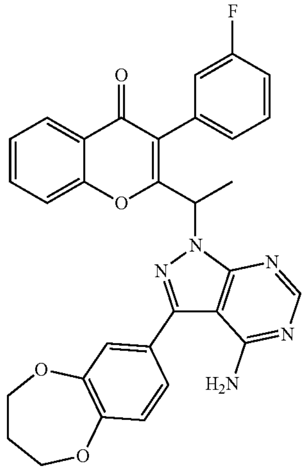 [SMILES: CC(c1oc2ccccc2c(=O)c1-c1cccc(F)c1)n1nc(-c2ccc3c(c2)OCCCO3)c2c(N)ncnc21] |
TABLE 1-continued
| Ex. | Structure |
|---|---|
| 137 | 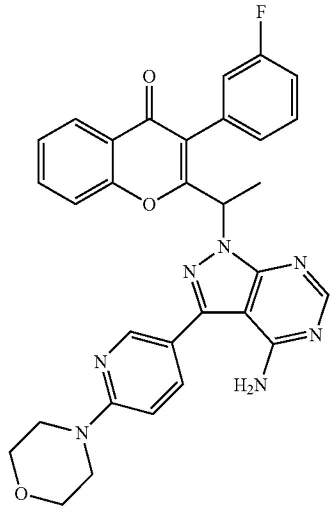 [SMILES: CC(c1oc2ccccc2c(=O)c1-c1cccc(F)c1)n1nc(-c2ccc(N3CCOCC3)nc2)c2c(N)ncnc21] |
| 138 | 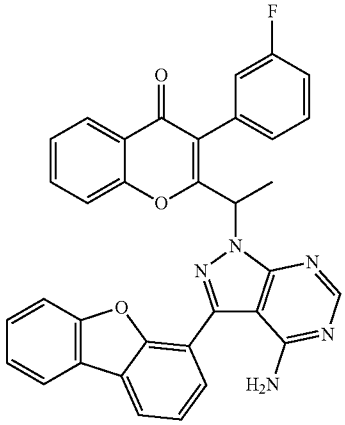 [SMILES: CC(c1oc2ccccc2c(=O)c1-c1cccc(F)c1)n1nc(-c2cccc3c2oc2ccccc23)c2c(N)ncnc21] |
| 139 | 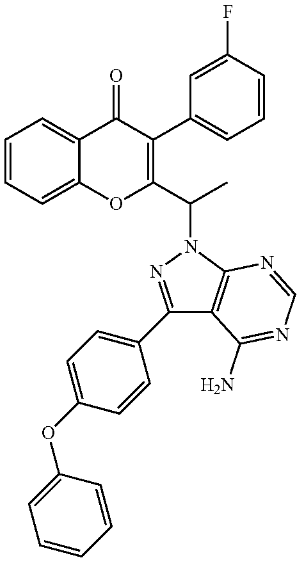 [SMILES: CC(c1oc2ccccc2c(=O)c1-c1cccc(F)c1)n1nc(-c2ccc(Oc3ccccc3)cc2)c2c(N)ncnc21] |

TABLE 1-continued
| Ex. | Structure |
|---|---|
| 140 | 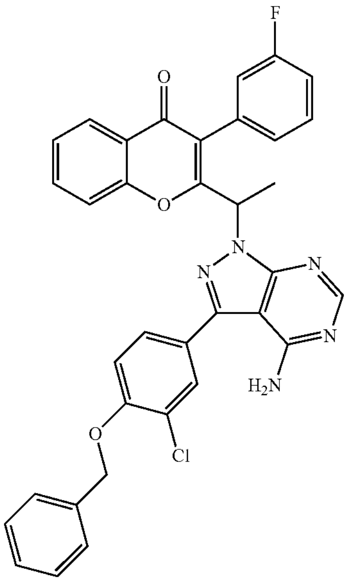 [SMILES: CC(c1oc2ccccc2c(=O)c1-c1cccc(F)c1)n1nc(-c2ccc(OCc3ccccc3)c(Cl)c2)c2c(N)ncnc21] |
| 141 | 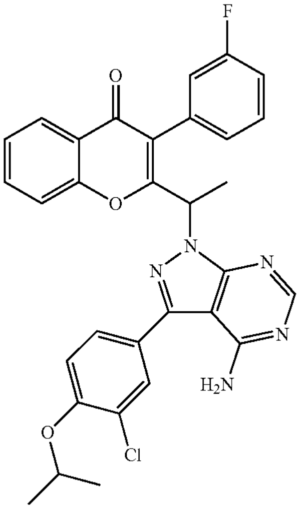 [SMILES: CC(C)Oc1ccc(-c2nn(C(C)c3oc4ccccc4c(=O)c3-c3cccc(F)c3)c3ncnc(N)c23)cc1Cl] |
| 142 | 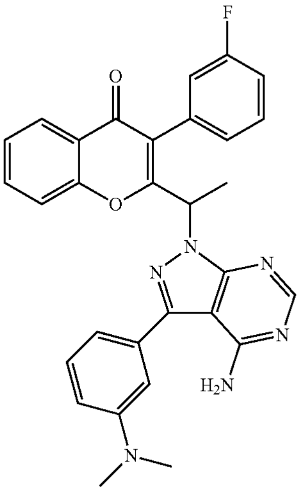 [SMILES: CC(c1oc2ccccc2c(=O)c1-c1cccc(F)c1)n1nc(-c2cccc(N(C)C)c2)c2c(N)ncnc21] |
TABLE 1-continued
| Ex. | Structure |
|---|---|
| 143 | 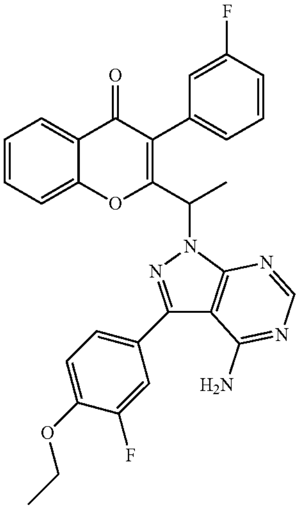 [SMILES: CCOc1ccc(-c2nn(C(C)c3oc4ccccc4c(=O)c3-c3cccc(F)c3)c3ncnc(N)c23)cc1F] |
| 144 | 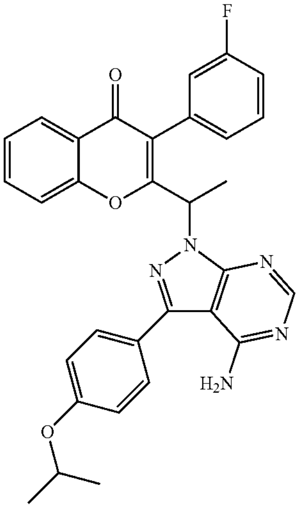 [SMILES: CC(C)Oc1ccc(-c2nn(C(C)c3oc4ccccc4c(=O)c3-c3cccc(F)c3)c3ncnc(N)c23)cc1] |
| 145 | 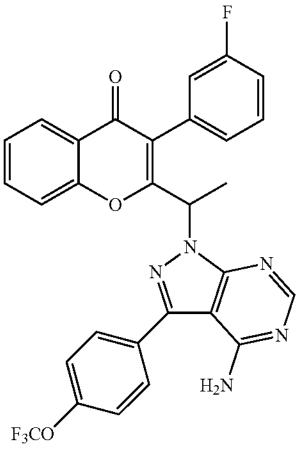 [SMILES: CC(c1oc2ccccc2c(=O)c1-c1cccc(F)c1)n1nc(-c2ccc(OC(F)(F)F)cc2)c2c(N)ncnc21] |

TABLE 1-continued
| Ex. | Structure |
| --- | --- |
| 146 | 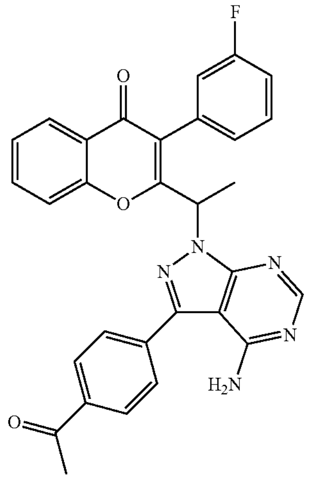 [SMILES: CC(=O)c1ccc(-c2nn(C(C)c3oc4ccccc4c(=O)c3-c3cccc(F)c3)c3ncnc(N)c23)cc1] |
| 147 | 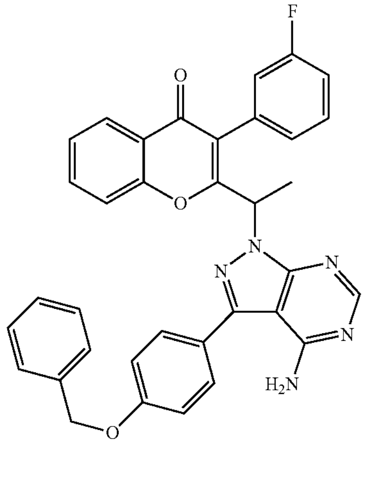 [SMILES: CC(c1oc2ccccc2c(=O)c1-c1cccc(F)c1)n1nc(-c2ccc(OCc3ccccc3)cc2)c2c(N)ncnc21] |
| 148 | 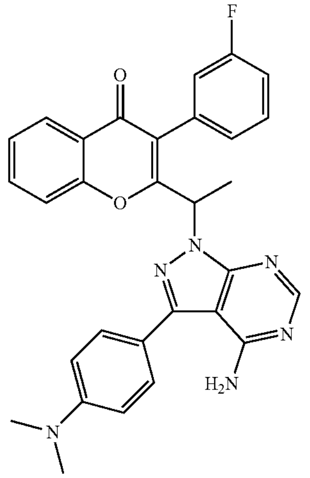 [SMILES: CC(c1oc2ccccc2c(=O)c1-c1cccc(F)c1)n1nc(-c2ccc(N(C)C)cc2)c2c(N)ncnc21] |
TABLE 1-continued
| Ex. | Structure |
| --- | --- |
| 149 | 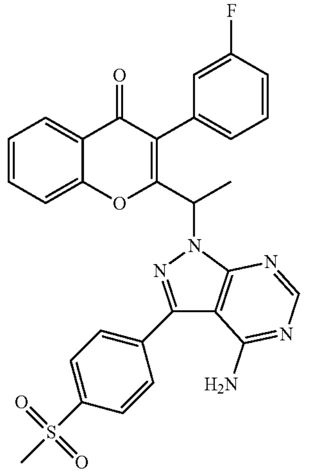 [SMILES: CC(c1oc2ccccc2c(=O)c1-c1cccc(F)c1)n1nc(-c2ccc(S(C)(=O)=O)cc2)c2c(N)ncnc21] |
| 150 | 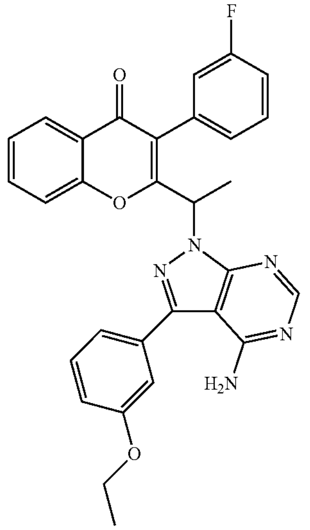 [SMILES: CCOc1cccc(-c2nn(C(C)c3oc4ccccc4c(=O)c3-c3cccc(F)c3)c3ncnc(N)c23)c1] |
| 151 | 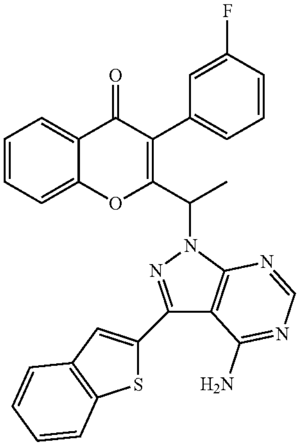 [SMILES: CC(c1oc2ccccc2c(=O)c1-c1cccc(F)c1)n1nc(-c2cc3ccccc3s2)c2c(N)ncnc21] |

| Ex. | Structure |
|---|---|
| 152 | 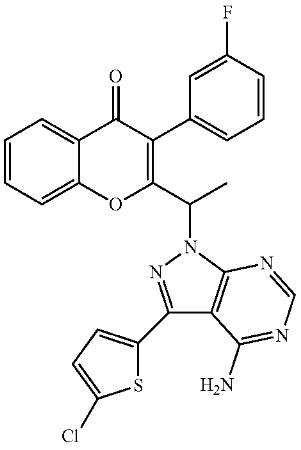 [SMILES: CC(c1oc2ccccc2c(=O)c1-c1cccc(F)c1)n1nc(-c2ccc(Cl)s2)c2c(N)ncnc21] |
| 153 | 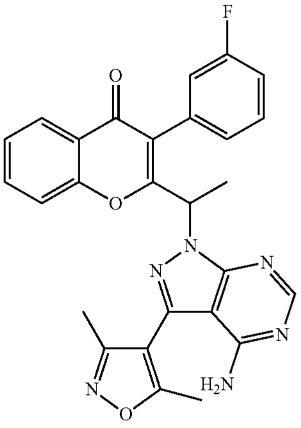 [SMILES: Cc1noc(C)c1-c1nn(C(C)c2oc3ccccc3c(=O)c2-c2cccc(F)c2)c2ncnc(N)c12] |
| 154 | 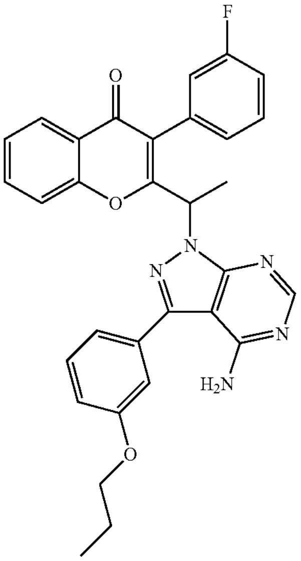 [SMILES: CCCOc1cccc(-c2nn(C(C)c3oc4ccccc4c(=O)c3-c3cccc(F)c3)c3ncnc(N)c23)c1] |
| Ex. | Structure |
|---|---|
| 155 | 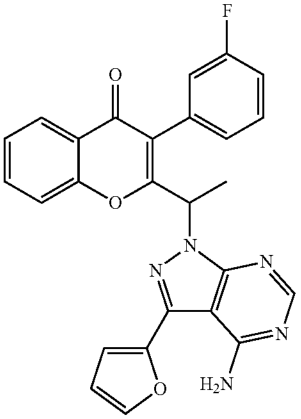 [SMILES: CC(c1oc2ccccc2c(=O)c1-c1cccc(F)c1)n1nc(-c2ccco2)c2c(N)ncnc21] |
| 156 | 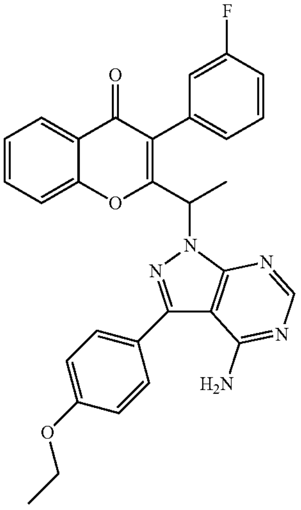 [SMILES: CCOc1ccc(-c2nn(C(C)c3oc4ccccc4c(=O)c3-c3cccc(F)c3)c3ncnc(N)c23)cc1] |
| 157 | 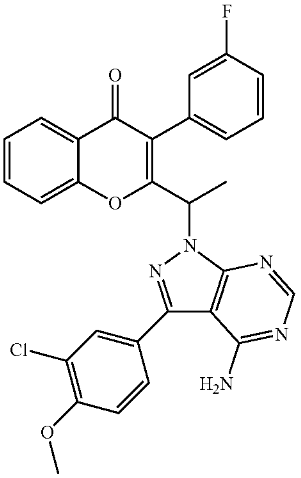 [SMILES: COc1ccc(-c2nn(C(C)c3oc4ccccc4c(=O)c3-c3cccc(F)c3)c3ncnc(N)c23)cc1Cl] |

TABLE 1-continued
| Ex. | Structure |
| --- | --- |
| 158 | 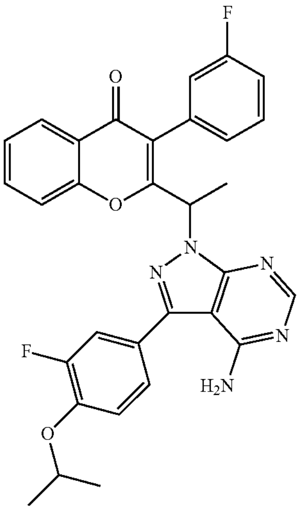 [SMILES: CC(C)Oc1ccc(-c2nn(C(C)c3oc4ccccc4c(=O)c3-c3cccc(F)c3)c3ncnc(N)c23)cc1F] |
| 159 | 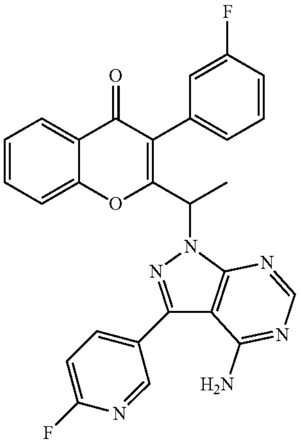 [SMILES: CC(c1oc2ccccc2c(=O)c1-c1cccc(F)c1)n1nc(-c2ccc(F)nc2)c2c(N)ncnc21] |
| 160 | 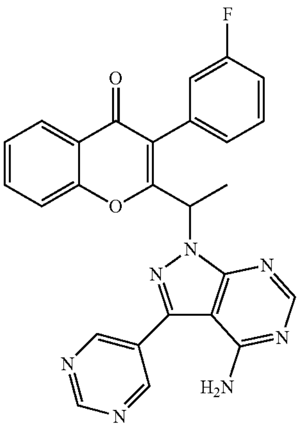 [SMILES: CC(c1oc2ccccc2c(=O)c1-c1cccc(F)c1)n1nc(-c2cncnc2)c2c(N)ncnc21] |
| 161 | 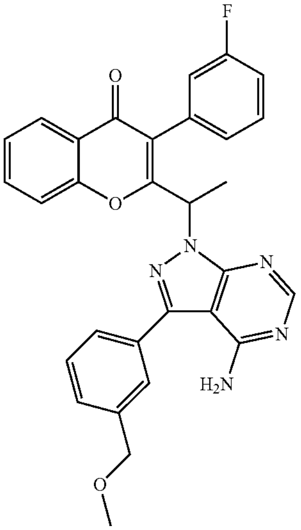 [SMILES: COCc1cccc(-c2nn(C(C)c3oc4ccccc4c(=O)c3-c3cccc(F)c3)c3ncnc(N)c23)c1] |
| 162 | 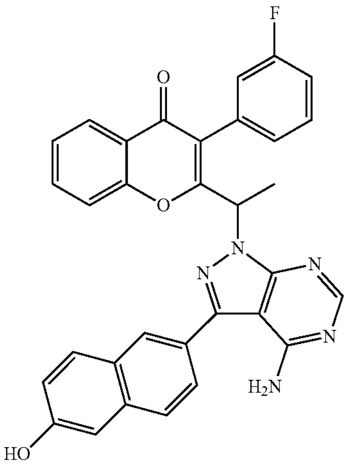 [SMILES: CC(c1oc2ccccc2c(=O)c1-c1cccc(F)c1)n1nc(-c2ccc3cc(O)ccc3c2)c2c(N)ncnc21] |
| 163 | 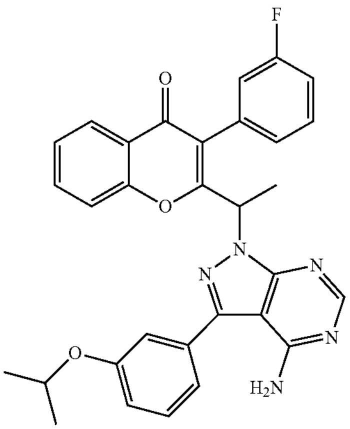 [SMILES: CC(C)Oc1cccc(-c2nn(C(C)c3oc4ccccc4c(=O)c3-c3cccc(F)c3)c3ncnc(N)c23)c1] |

TABLE 1-continued
| Ex. | Structure |
|---|---|
| 164 | 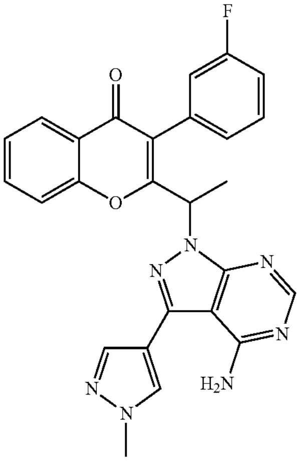 [SMILES: CC(c1oc2ccccc2c(=O)c1-c1cccc(F)c1)n1nc(-c2cnn(C)c2)c2c(N)ncnc21] |
| 165 | 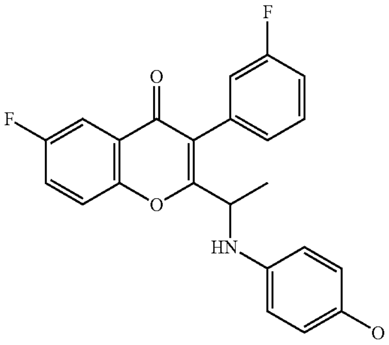 [SMILES: CC(Nc1ccc(O)cc1)c1oc2ccc(F)cc2c(=O)c1-c1cccc(F)c1] |
| 166 | 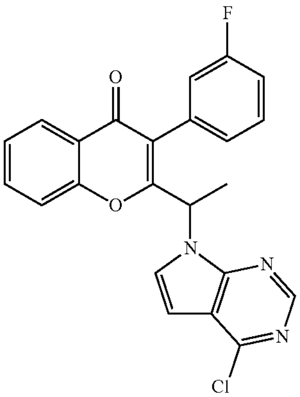 [SMILES: CC(c1oc2ccccc2c(=O)c1-c1cccc(F)c1)n1ccc2c(Cl)ncnc21] |
| 167 | 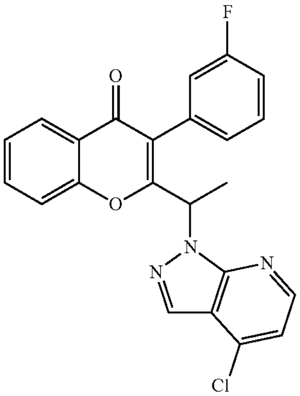 [SMILES: CC(c1oc2ccccc2c(=O)c1-c1cccc(F)c1)n1ncc2c(Cl)ccnc21] |
TABLE 1-continued
| Ex. | Structure |
|---|---|
| 168 | 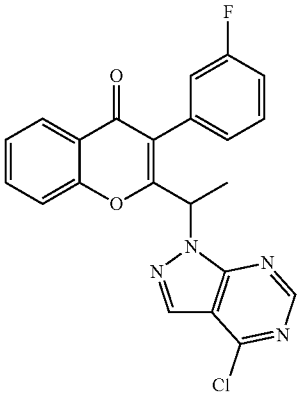 [SMILES: CC(c1oc2ccccc2c(=O)c1-c1cccc(F)c1)n1ncc2c(Cl)ncnc21] |
| 169 | 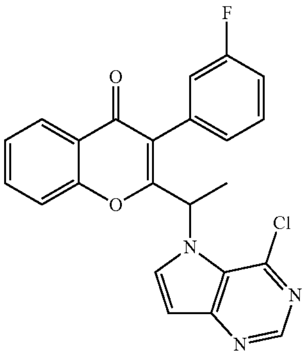 [SMILES: CC(c1oc2ccccc2c(=O)c1-c1cccc(F)c1)n1ccc2ncnc(Cl)c21] |
| 170 | 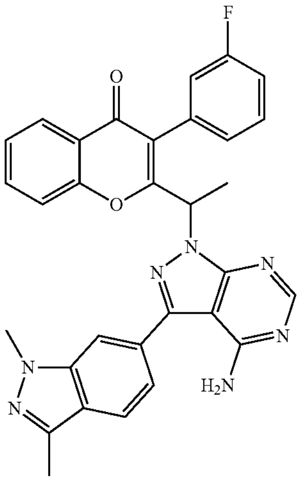 [SMILES: Cc1nn(C)c2cc(-c3nn(C(C)c4oc5ccccc5c(=O)c4-c4cccc(F)c4)c4ncnc(N)c34)ccc12] |

TABLE 1-continued
| Ex. | Structure |
| --- | --- |
| 171 | 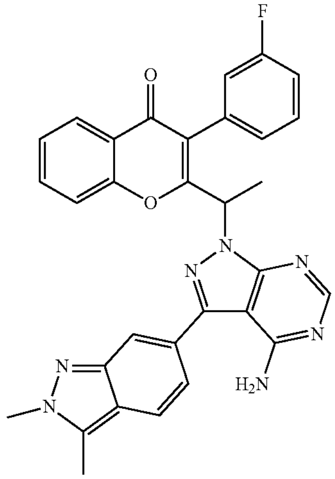 [SMILES: Cc1c2ccc(-c3nn(C(C)c4oc5ccccc5c(=O)c4-c4cccc(F)c4)c4ncnc(N)c34)cc2nn1C] |
| 172 | 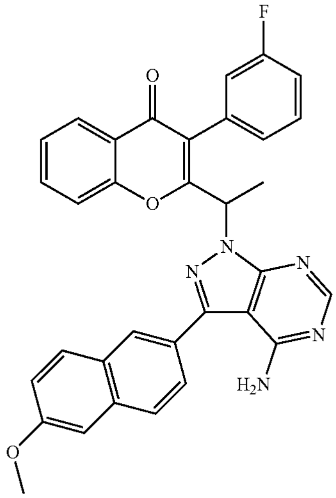 [SMILES: COc1ccc2cc(-c3nn(C(C)c4oc5ccccc5c(=O)c4-c4cccc(F)c4)c4ncnc(N)c34)ccc2c1] |
| 173 | 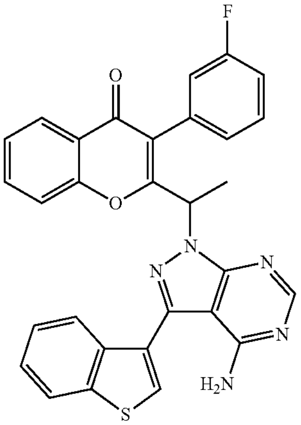 [SMILES: CC(c1oc2ccccc2c(=O)c1-c1cccc(F)c1)n1nc(-c2csc3ccccc23)c2c(N)ncnc21] |
| 174 | 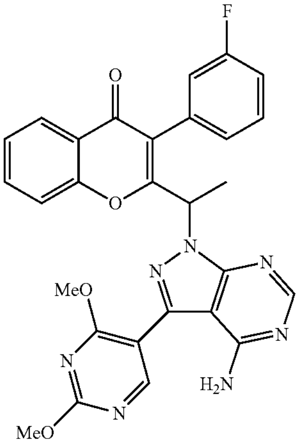 [SMILES: COc1ncc(-c2nn(C(C)c3oc4ccccc4c(=O)c3-c3cccc(F)c3)c3ncnc(N)c23)c(OC)n1] |
| 175 | 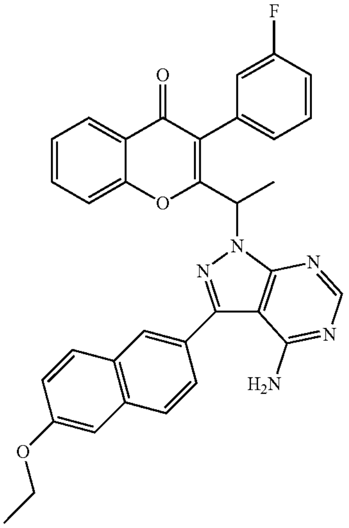 [SMILES: CCOc1ccc2cc(-c3nn(C(C)c4oc5ccccc5c(=O)c4-c4cccc(F)c4)c4ncnc(N)c34)ccc2c1] |
| 176 | 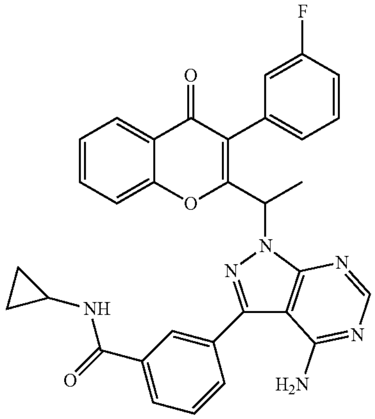 [SMILES: CC(c1oc2ccccc2c(=O)c1-c1cccc(F)c1)n1nc(-c2cccc(C(=O)NC3CC3)c2)c2c(N)ncnc21] |

TABLE 1-continued

| Ex. | Structure |
|---|---|
| 177 | 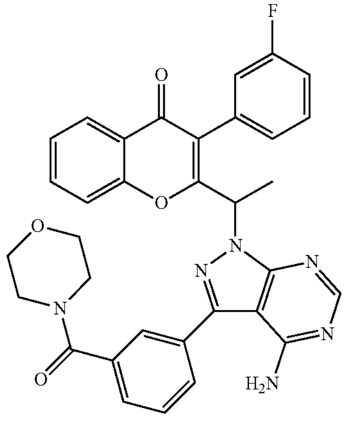 [SMILES: CC(c1oc2ccccc2c(=O)c1-c1cccc(F)c1)n1nc(-c2cccc(C(=O)N3CCOCC3)c2)c2c(N)ncnc21] |
| 178 | 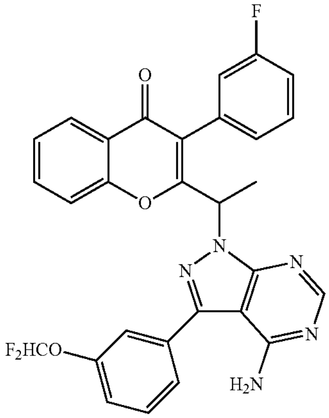 [SMILES: CC(c1oc2ccccc2c(=O)c1-c1cccc(F)c1)n1nc(-c2cccc(OC(F)F)c2)c2c(N)ncnc21] |
| 179 | 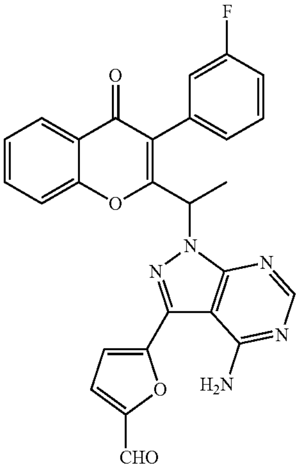 [SMILES: CC(c1oc2ccccc2c(=O)c1-c1cccc(F)c1)n1nc(-c2ccc(C=O)o2)c2c(N)ncnc21] |

Yet another embodiment of the present invention is a method for inhibiting PI3K in a patient by administering to the patient an effective amount of at least one compound of the present invention (for instance, a compound of formula (I), (I-A), (I-B), (IA-I), (IA-II), (IA-III), (IA-IV), (IA-V) or (IA-VI) as defined above.

Yet another embodiment of the present invention is a method for treating a proliferative disease via modulation of a protein kinase (such as PI3K) by administering to a patient in need of such treatment an effective amount of at least one compound of the present invention. In one embodiment, the compound of the present invention inhibits a protein kinase (such as PI3K).

Yet another embodiment of the present invention is a method for treating a proliferative disease via modulation of a protein kinase (such as PI3K) by administering to a patient in need of such treatment an effective amount of at least one compound of the present invention, in combination (simultaneously or sequentially) with at least one other anti-cancer agent. In one embodiment, the compound of formula (I), (I-A), (I-B), (IA-I), (IA-II), (IA-III), (IA-IV), (IA-V) or (IA-VI) inhibits a protein kinase (such as PI3K).

More particularly, the compounds of formula ((I), (I-A), (I-B), (IA-I), (IA-II), (IA-III), (IA-IV), (IA-V) or (IA-VI) and pharmaceutically acceptable esters or salts thereof can be administered for the treatment, prevention and/or amelioration of PI3K and related protein kinase mediated diseases or disorders, including but not limited to, cancer and other proliferative diseases or disorders.

The compounds of the present invention are useful in the treatment of a variety of cancers, including, but not limited to, the following:

- carcinoma, including that of the bladder, breast, colon, kidney, liver, lung, including small cell lung cancer, esophagus, gall bladder, ovary, pancreas, stomach, cervix, thyroid, prostate, and skin, including squamous cell carcinoma;
- hematopoietic tumors of lymphoid lineage, including leukemia, acute lymphocytic leukemia, acute lymphoblastic leukemia, B-cell lymphoma, T-cell lymphoma, Hodgkin's lymphoma, non-Hodgkins lymphoma, hairy cell lymphoma and Burkett's lymphoma;
- hematopoietic tumors of myeloid lineage, including acute and chronic myelogenous leukemias, myelodysplastic syndrome and promyelocytic leukemia;
- tumors of mesenchymal origin, including fibrosarcoma and rhabdomyosarcoma;
- tumors of the central and peripheral nervous system, including astrocytoma, neuroblastoma, glioma and schwannomas; and
- other tumors, including melanoma, seminoma, teratocarcinoma, osteosarcoma, xenoderoma pigmentosum, keratoctanthoma, thyroid follicular cancer and Kaposi's sarcoma.

Due to the key role of protein kinases in the regulation of cellular proliferation in general, the protein kinase inhibitors of the present invention could act as reversible cytostatic agents which may be useful in the treatment of any disease process which features abnormal cellular proliferation, e.g., benign prostatic hyperplasia, familial adenomatosis polyposis, neuro-fibromatosis, atherosclerosis, pulmonary fibrosis, arthritis, psoriasis, glomerulonephritis, restenosis following angioplasty or vascular surgery, hypertrophic scar formation, inflammatory bowel disease, transplantation rejection, endotoxic shock, and fungal infections.

The compounds of the present invention as modulators of apoptosis are useful in the treatment of cancer (including but not limited to those types mentioned herein above), viral infections (including but not limited to herpevirus, poxvirus, Epstein-Barr virus, Sindbis virus and adenovirus), prevention of AIDS development in HIV-infected individuals, autoimmune diseases (including but not limited to systemic lupus, erythematosus, autoimmune mediated glomerulonephritis, rheumatoid arthritis, psoriasis, inflammatory bowel disease, and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases and cancer pain.

The compounds of present invention can modulate the level of cellular RNA and DNA synthesis. These agents are therefore useful in the treatment of viral infections (including but not limited to HIV, human papilloma virus, herpesvirus, poxvirus, Epstein-Barr virus, Sindbis virus and adenovirus).

The compounds of the present invention are useful in the chemoprevention of cancer. Chemoprevention is defined as inhibiting the development of invasive cancer by either blocking the initiating mutagenic event or by blocking the progression of pre-malignant cells that have already suffered an insult or inhibiting tumor relapse. The compounds are also useful in inhibiting tumor angiogenesis and metastasis. One embodiment of the invention is a method of inhibiting tumor angiogenesis or metastasis in a patient in need thereof by administering an effective amount of one or more compounds of the present invention.

Another embodiment of the present invention is a method of treating an immune system-related disease (e.g., an autoimmune disease), a disease or disorder involving inflammation (e.g., asthma, chronic obstructive pulmonary disease, rheumatoid arthritis, inflammatory bowel disease, glomerulonephritis, neuroinflammatory diseases, multiple sclerosis, uveitis and disorders of the immune system), cancer or other proliferative disease, a hepatic disease or disorder, a renal disease or disorder. The method includes administering an effective amount of one or more compounds of the present invention.

Examples of immune disorders include psoriasis, rheumatoid arthritis, vasculitis, inflammatory bowel disease, dermatitis, osteoarthritis, asthma, inflammatory muscle disease, allergic rhinitis, vaginitis, interstitial cystitis, scleroderma, osteoporosis, eczema, allogeneic or xenogeneic transplantation (organ, bone marrow, stem cells and other cells and tissues) graft rejection, graft-versus-host disease, lupus erythematosus, inflammatory disease, type I diabetes, pulmonary fibrosis, dermatomyositis, Sjogren's syndrome, thyroiditis (e.g., Hashimoto's and autoimmune thyroiditis), myasthenia gravis, autoimmune hemolytic anemia, multiple sclerosis, cystic fibrosis, chronic relapsing hepatitis, primary biliary cirrhosis, allergic conjunctivitis and atopic dermatitis.

In one embodiment, the compounds described herein are used as immunosuppressants to prevent transplant graft rejections, allogeneic or xenogeneic transplantation rejection (organ, bone marrow, stem cells, other cells and tissues), and graft-versus-host disease. In other embodiments, transplant graft rejections result from tissue or organ transplants. In further embodiments, graft-versus-host disease results from bone marrow or stem cell transplantation. One embodiment is a method of preventing or decreasing the risk of transplant graft rejection, allogeneic or xenogeneic transplantation rejection (organ, bone marrow, stem cells, other cells and tissues), or graft-versus-host disease by administering an effective amount of one or more compounds of the present invention.

The compounds of the present invention are also useful in combination (administered together or sequentially) with known anti-cancer treatments such as radiation therapy or with cytostatic or cytotoxic or anticancer agents, such as for example, but not limited to, DNA interactive agents, such as cisplatin or doxorubicin; topoisomerase II inhibitors, such as etoposide; topoisomerase I inhibitors such as CPT-11 or topotecan; tubulin interacting agents, such as paclitaxel, docetaxel or the epothilones (for example ixabepilone), either naturally occurring or synthetic; hormonal agents, such as tamoxifen; thymidilate synthase inhibitors, such as 5-fluorouracil; and anti-metabolites, such as methotrexate, other tyrosine kinase inhibitors such as Iressa and OSI-774; angiogenesis inhibitors; EGF inhibitors; VEGF inhibitors; CDK inhibitors; SRC inhibitors; c-Kit inhibitors; Her1/2 inhibitors and monoclonal antibodies directed against growth factor receptors such as erbitux (EGF) and herceptin (Her2) and other protein kinase modulators as well.

The compounds of the present invention are also useful in combination (administered together or sequentially) with one or more steroidal anti-inflammatory drugs, non-steroidal anti-inflammatory drugs (NSAIDs) or Immune Selective Anti-Inflammatory Derivatives (ImSAIDs).

The invention further provides a pharmaceutical composition comprising one or more compounds of the present invention (such as a compound having formula (I), (I-A), (I-B), (IA-I), (IA-II), (IA-III), (IA-IV), (IA-V) or (IA-VI)) together with a pharmaceutically acceptable carrier. The pharmaceutical composition may further comprise one or more of the active ingredients identified above, such as other anti-cancer agents. In one embodiment, the pharmaceutical composition includes a therapeutically effective amount of one or more compounds of formula (I), (I-A), (I-B), (IA-I), (IA-II) (IA-III), (IA-IV), (IA-V) or (IA-VI).

Yet another embodiment is a method of treating leukemia in a patient in need thereof by administering a therapeutically effective amount of a compound of the present invention. For example, the compounds of the present invention are effective for treating chronic lymphocytic leukemia (CLL), non-Hodgkin lymphoma (NHL), acute myeloid leukemia (AML), multiple myeloma (MM), small lymphocytic lymphoma (SLL), and indolent non-Hodgkin's lymphoma (I-NHL).

Yet another embodiment is a method of treating allergic rhinitis in a patient in need thereof by administering a therapeutically effective amount of a compound of the present invention.

DETAILED DESCRIPTION

As used herein the following definitions shall apply unless otherwise indicated. Further many of the groups defined herein can be optionally substituted. The listing of substituents in the definition is exemplary and is not to be construed to limit the substituents defined elsewhere in the specification.

The term "alkyl" refers to a straight or branched hydrocarbon chain radical consisting solely of carbon and hydrogen atoms, containing no unsaturation, having from one to eight carbon atoms, and which is attached to the rest of the molecule by a single bond, e.g., methyl, ethyl, n-propyl, 1-methylethyl(isopropyl), n-butyl, n-pentyl, and 1,1-dimethylethyl (t-butyl). The term "$(C_{1-6})$alkyl" refers to an alkyl group as defined above having up to 6 carbon atoms.

The term "alkenyl" refers to an aliphatic hydrocarbon group containing a carbon-carbon double bond and which may be a straight or branched or branched chain having about 2 to about 10 carbon atoms, e.g., ethenyl, 1-propenyl, 2-propenyl(allyl), iso-propenyl, 2-methyl-1-propenyl, 1-butenyl, and 2-butenyl. The term "($C_{2-6}$)alkenyl" refers to an alkenyl group as defined above having up to 6 carbon atoms.

The term "alkynyl" refers to a straight or branched chain hydrocarbyl radical having at least one carbon-carbon triple bond, and having in the range of 2 to up to 12 carbon atoms (with radicals having in the range of 2 to up to 10 carbon atoms presently being preferred) e.g., ethynyl, propynyl, and butnyl. The term "($C_{2-6}$) alkynyl" refers to an alkynyl group as defined above having up to 6 carbon atoms.

The term "alkoxy" denotes an alkyl, cycloalkyl, or cycloalkylalkyl group as defined above attached via an oxygen linkage to the rest of the molecule. The term "substituted alkoxy" refers to an alkoxy group where the alkyl constituent is substituted (i.e., —O-(substituted alkyl) wherein the term "substituted alkyl" is the same as defined above for "alkyl". For example "alkoxy" refers to the group —O-alkyl, including from 1 to 8 carbon atoms of a straight, branched, cyclic configuration and combinations thereof attached to the parent structure through oxygen. Examples include methoxy, ethoxy, propoxy, isopropoxy, cyclopropyloxy, and cyclohexyloxy.

The term "cycloalkyl" denotes a non-aromatic mono or multicyclic ring system of about 3 to 12 carbon atoms such as cyclopropyl, cyclobutyl, cyclopentyl, and cyclohexyl. Examples of multicyclic cycloalkyl groups include perhydronaphthyl, adamantyl and norbornyl groups, bridged cyclic groups, and sprirobicyclic groups, e.g., sprio(4,4)non-2-yl. The term "($C_{3-8}$) cycloalkyl" refers to a cycloalkyl group as defined above having up to 8 carbon atoms.

The term "cycloalkylalkyl" refers to a cyclic ring-containing radical containing in the range of about 3 up to 8 carbon atoms directly attached to an alkyl group which are then attached to the main structure at any carbon from the alkyl group that results in the creation of a stable structure such as cyclopropylmethyl, cyclobutylethyl, and cyclopentylethyl.

The term "cycloalkenyl" refers to cyclic ring-containing radicals containing in the range of about 3 up to 8 carbon atoms with at least one carbon-carbon double bond such as cyclopropenyl, cyclobutenyl, and cyclopentenyl. The term "cycloalkenylalkyl" refers to a cycloalkenyl group directly attached to an alkyl group which are then attached to the main structure at any carbon from the alkyl group that results in the creation of a stable structure.

The term "aryl" refers to aromatic radicals having in the range of 6 up to 20 carbon atoms such as phenyl, naphthyl, tetrahydronaphthyl, indanyl, and biphenyl.

The term "arylalkyl" refers to an aryl group as defined above directly bonded to an alkyl group as defined above, e.g., $—CH_2C_6H_5$ and $—C_2H_5C_6H_5$.

The term "heterocyclic ring" refers to a non-aromatic 3 to 15 member ring radical which consists of carbon atoms and at least one heteroatom selected from nitrogen, phosphorus, oxygen and sulfur. For purposes of this invention, the heterocyclic ring radical may be a mono-, bi-, tri- or tetracyclic ring system, which may include fused, bridged or spiro ring systems, and the nitrogen, phosphorus, carbon, oxygen or sulfur atoms in the heterocyclic ring radical may be optionally oxidized to various oxidation states. In addition, the nitrogen atom may be optionally quaternized. The heterocyclic ring radical may be attached to the main structure at any heteroatom or carbon atom that results in the creation of a stable structure.

The term "heterocyclyl" refers to a heterocylic ring radical as defined above. The heterocyclyl ring radical may be attached to the main structure at any heteroatom or carbon atom that results in the creation of a stable structure.

The term "heterocyclylalkyl" refers to a heterocylic ring radical as defined above directly bonded to an alkyl group. The heterocyclylalkyl radical may be attached to the main structure at carbon atom in the alkyl group that results in the creation of a stable structure. Examples of such heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl.

The term "heteroaryl" refers to an optionally substituted 5 to 14 member aromatic ring having one or more heteroatoms selected from N, O, and S as ring atoms. The heteroaryl may be a mono-, bi- or tricyclic ring system. Examples of such "heterocyclic ring" or "heteroaryl" radicals include, but are not limited to, oxazolyl, thiazolyl, imidazolyl, pyrrolyl, furanyl, pyridinyl, pyrimidinyl, pyrazinyl, benzofuranyl, indolyl, benzothiazolyl, benzoxazolyl, carbazolyl, quinolyl, isoquinolyl, azetidinyl, acridinyl, benzodioxolyl, benzodioxanyl, benzofuranyl, carbazolyl, cinnolinyl, dioxolanyl, indolizinyl, naphthyridinyl, perhydroazepinyl, phenazinyl, phenothiazinyl, phenoxazinyl, phthalazinyl, pteridinyl, purinyl, quinazolinyl, quinoxalinyl, tetrazoyl, tetrahydroisoquinolyl, piperidinyl, piperazinyl, 2-oxopiperazinyl, 2-oxopiperidinyl, 2-oxopyrrolidinyl, 2-oxoazepinyl, azepinyl, 4-piperidonyl, pyrrolidinyl, pyridazinyl, oxazolinyl, oxazolidinyl, triazolyl, indanyl, isoxazolyl, isoxazolidinyl, morpholinyl, thiazolinyl, thiazolidinyl, isothiazolyl, quinuclidinyl, isothiazolidinyl, isoindolyl, indolinyl, isoindolinyl, octahydroindolyl, octahydroisoindolyl, decahydroisoquinolyl, benzimidazolyl, thiadiazolyl, benzopyranyl, tetrahydrofuryl, tetrahydropyranyl, thienyl, benzothienyl, thiamorpholinyl, thiamorpholinyl sulfoxide, thiamorpholinyl sulfone, dioxaphospholanyl, oxadiazolyl, chromanyl, and isochromanyl. The heteroaryl ring radical may be attached to the main structure at any heteroatom or carbon atom that results in the creation of a stable structure. The term "substituted heteroaryl" also includes ring systems substituted with one or more oxide (—O—) substituents, such as pyridinyl N-oxides.

The term "heteroarylalkyl" refers to a heteroaryl ring radical as defined above directly bonded to an alkyl group. The heteroarylalkyl radical may be attached to the main structure at any carbon atom from alkyl group that results in the creation of a stable structure.

The term "cyclic ring" refers to a cyclic ring containing 3 to 10 carbon atoms.

The term "substituted" unless otherwise specified, refers to substitution with any one or any combination of the following substituents which may be the same or different and are independently selected from hydrogen, hydroxy, halogen, carboxyl, cyano, nitro, oxo (═O), thio (═S), substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkylalkyl, substituted or unsubstituted cycloalkenyl, substituted or unsubstituted cycloalkenylalkyl, substituted or unsubstituted heteroaryl, substituted or unsubstituted heteroarylalkyl, substituted or unsubstituted heterocyclic ring, substituted heterocyclylalkyl ring, substituted or unsubstituted guanidine, $—COOR^x$, $—C(O)R^x$, $—C(S)R^x$, $—C(O)NR^xR^y$, —C(O)ONR$^x$R$^y$, —NR$^y$R$^z$, —NR$^x$CONR$^y$R$^z$, —N(R$^x$)SOR$^y$, —N(R$^x$)SO$_2$R$^y$, —(=N—N(R$^x$)R$^y$), —NR$^x$C(O)OR$^y$, —NR$^x$R$^y$, —NR$^x$C(O)R$^y$—, —NR$^x$C(S)R$^y$—NR$^x$C(S)NR$^y$R$^z$, —SONR$^x$R$^y$—, —SO$_2$NR$^x$R$^y$—, —OR$^x$, —OR$^x$C(O)NR$^y$R$^z$, —OR$^x$C(O)OR$^y$—, —OC(O)R$^x$, —OC(O)NR$^x$R$^y$, —R$^x$NR$^y$C(O)R, —R$^x$OR$^y$, —R$^x$C(O)OR$^y$, —R$^x$C(O)NR$^y$R$^z$, —R$^x$C(O)R$^x$, —R$^x$OC(O)R$^y$, —SR$^x$, —SOR$^x$, —SO$_2$R$^x$, and —ONO$_2$, wherein R$^x$, R$^y$ and R$^z$ in each of the above groups can be hydrogen, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkylalkyl, substituted or unsubstituted cycloalkenyl, substituted or unsubstituted amino, substituted or unsubstituted heteroaryl, substituted or unsubstituted heteroarylalkyl, substituted or unsubstituted heterocyclic ring, or substituted heterocyclylalkyl ring, or any two of R$^x$, R$^y$ and R$^z$ may be joined to form a substituted or unsubstituted saturated or unsaturated 3-10 membered ring, which may optionally include heteroatoms which may be the same or different and are selected from O, NR$^x$ (e.g., Rx can be hydrogen or $C_{1-6}$ alkyl) or S. Substitution or the combinations of substituents envisioned by this invention are preferably those that result in the formation of a stable or chemically feasible compound. The term stable as used herein refers to the compounds or the structure that are not substantially altered when subjected to conditions to allow for their production, detection and preferably their recovery, purification and incorporation into a pharmaceutical composition. The substituents in the aforementioned "substituted" groups cannot be further substituted. For example, when the substituent on "substituted alkyl" is "substituted aryl", the substituent on "substituted aryl" cannot be "substituted alkenyl".

The term "halo", "halide", or, alternatively, "halogen" means fluoro, chloro, bromo or iodo. The terms "haloalkyl," "haloalkenyl," "haloalkynyl" and "haloalkoxy" include alkyl, alkenyl, alkynyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine.

The term "protecting group" or "PG" refers to a substituent that is employed to block or protect a particular functionality. Other functional groups on the compound may remain reactive. For example, an "amino-protecting group" is a substituent attached to an amino group that blocks or protects the amino functionality in the compound. Suitable amino-protecting groups include, but are not limited to, acetyl, trifluoroacetyl, tert-butoxycarbonyl (BOC), benzyloxycarbonyl (CBz) and 9-fluorenylmethylenoxycarbonyl (Fmoc). Similarly, a "hydroxy-protecting group" refers to a substituent of a hydroxy group that blocks or protects the hydroxy functionality. Suitable hydroxy-protecting groups include, but are not limited to, acetyl and silyl. A "carboxy-protecting group" refers to a substituent of the carboxy group that blocks or protects the carboxy functionality. Suitable carboxy-protecting groups include, but are not limited to, —$CH_2CH_2SO_2Ph$, cyanoethyl, 2-(trimethylsilyl)ethyl, 2-(trimethylsilyl)ethoxymethyl, -2-(p-toluenesulfonyl)ethyl, 2-(p-nitrophenylsulfenyl)ethyl, 2-(diphenylphosphino)-ethyl, and nitroethyl. For a general description of protecting groups and their use, see T. W. Greene, Protective Groups in Organic Synthesis, John Wiley & Sons, New York, 1991.

Certain of the compounds described herein contain one or more asymmetric centers and can thus give rise to enantiomers, diastereomers, and other stereoisomeric forms that can be defined, in terms of absolute stereochemistry, as (R)- or (S)-. The present chemical entities, pharmaceutical compositions and methods are meant to include all such possible isomers, including racemic mixtures, optically pure forms and intermediate mixtures. For instance, non-limiting examples of intermediate mixtures include a mixture of isomers in a ratio of 10:90, 13:87, 17:83, 20:80, or 22:78. Optically active (R)- and (S)-isomers can be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers.

The term "tautomers" refers to compounds, which are characterized by relatively easy interconversion of isomeric forms in equilibrium. These isomers are intended to be covered by this invention. "Tautomers" are structurally distinct isomers that interconvert by tautomerization. "Tautomerization" is a form of isomerization and includes prototropic or proton-shift tautomerization, which is considered a subset of acid-base chemistry. "Prototropic tautomerization" or "proton-shift tautomerization" involves the migration of a proton accompanied by changes in bond order, often the interchange of a single bond with an adjacent double bond. Where tautomerization is possible (e.g. in solution), a chemical equilibrium of tautomers can be reached. An example of tautomerization is keto-enol tautomerization. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

A "leaving group or atom" is any group or atom that will, under the reaction conditions, cleave from the starting material, thus promoting reaction at a specified site. Suitable examples of such groups unless otherwise specified are halogen atoms and mesyloxy, p-nitrobenzensulphonyloxy and tosyloxy groups.

The term "prodrug" refers to a compound, which is an inactive precursor of a compound, converted into its active form in the body by normal metabolic processes. Prodrug design is discussed generally in Hardma, et al. (Eds.), Goodman and Gilman's The Pharmacological Basis of Therapeutics, 9th ed., pp. 11-16 (1996). A thorough discussion is provided in Higuchi, et al., Prodrugs as Novel Delivery Systems, Vol. 14, ASCD Symposium Series, and in Roche (ed.), Bioreversible Carriers in Drug Design, American Pharmaceutical Association and Pergamon Press (1987). To illustrate, prodrugs can be converted into a pharmacologically active form through hydrolysis of, for example, an ester or amide linkage, thereby introducing or exposing a functional group on the resultant product. The prodrugs can be designed to react with an endogenous compound to form a water-soluble conjugate that further enhances the pharmacological properties of the compound, for example, increased circulatory half-life. Alternatively, prodrugs can be designed to undergo covalent modification on a functional group with, for example, glucuronic acid, sulfate, glutathione, amino acids, or acetate. The resulting conjugate can be inactivated and excreted in the urine, or rendered more potent than the parent compound. High molecular weight conjugates also can be excreted into the bile, subjected to enzymatic cleavage, and released back into the circulation, thereby effectively increasing the biological half-life of the originally administered compound.

The term "ester" refers to a compound, which is formed by reaction between an acid and an alcohol with elimination of water. An ester can be represented by the general formula RCOOR'.

These prodrugs and esters are intended to be covered within the scope of this invention.

Additionally the instant invention also includes the compounds which differ only in the presence of one or more isotopically enriched atoms for example replacement of hydrogen with deuterium or tritium, or the replacement of a carbon by $^{13}C$- or $^{14}C$-enriched carbon.

The compounds of the present invention may also contain unnatural proportions of atomic isotopes at one or more of atoms that constitute such compounds. For example, the compounds may be radiolabeled with radioactive isotopes, such as for example tritium ($^{3}H$), iodine-125 ($^{125}I$) or carbon-14 ($^{14}C$). All isotopic variations of the compounds of the present invention, whether radioactive or not, are encompassed within the scope of the present invention.

Pharmaceutically acceptable salts forming part of this invention include salts derived from inorganic bases such as Li, Na, K, Ca, Mg, Fe, Cu, Zn, and Mn; salts of organic bases such as N,N'-diacetylethylenediamine, glucamine, triethylamine, choline, hydroxide, dicyclohexylamine, metformin, benzylamine, trialkylamine, and thiamine; chiral bases such as alkylphenylamine, glycinol, and phenyl glycinol; salts of natural amino acids such as glycine, alanine, valine, leucine, isoleucine, norleucine, tyrosine, cystine, cysteine, methionine, proline, hydroxy proline, histidine, omithine, lysine, arginine, and serine; quaternary ammonium salts of the compounds of invention with alkyl halides, alkyl sulphates such as MeI and $(Me)_2SO_4$; non-natural amino acids such as D-isomers or substituted amino acids; guanidine; and substituted guanidine wherein the substituents are selected from nitro, amino, alkyl, alkenyl, alkynyl, ammonium or substituted ammonium salts and aluminum salts. Salts may include acid addition salts where appropriate which are sulphates, nitrates, phosphates, perchlorates, borates, hydrohalides, acetates, tartrates, maleates, citrates, fumarates, succinates, palmoates, methanesulphonates, benzoates, salicylates, benzenesulfonates, ascorbates, glycerophosphates, and ketoglutarates.

When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary from, for example, between 1% and 15% of the stated number or numerical range. The term "comprising" (and related terms such as "comprise" or "comprises" or "having" or "including") includes those embodiments, for example, an embodiment of any composition of matter, composition, method, or process, or the like, that "consist of" or "consist essentially of" the described features.

The following abbreviations and terms have the indicated meanings throughout: PI3-K=Phosphoinositide 3-kinase; PI=phosphatidylinositol; PDK=Phosphoinositide Dependent Kinase; DNA-PK=Deoxyribose Nucleic Acid Dependent Protein Kinase; PTEN=Phosphatase and Tensin homolog deleted on chromosome Ten; PIKK=Phosphoinositide Kinase Like Kinase; AIDS=Acquired Immuno Deficiency Syndrome; HIV=Human Immunodeficiency Virus; MeI=Methyl Iodide; $POCl_3$=Phosphorous Oxychloride; KCNS=Potassium IsoThiocyanate; TLC=Thin Layer Chromatography; MeOH=Methanol; and $CHCl_3$=Chloroform.

Abbreviations used herein have their conventional meaning within the chemical and biological arts.

The term "cell proliferation" refers to a phenomenon by which the cell number has changed as a result of division. This term also encompasses cell growth by which the cell morphology has changed (e.g., increased in size) consistent with a proliferative signal.

The term "co-administration," "administered in combination with," and their grammatical equivalents, as used herein, encompasses administration of two or more agents to an animal so that both agents and/or their metabolites are present in the animal at the same time. Co-administration includes simultaneous administration in separate compositions, administration at different times in separate compositions, or administration in a composition in which both agents are present.

The term "effective amount" or "therapeutically effective amount" refers to that amount of a compound described herein that is sufficient to effect the intended application including but not limited to disease treatment, as defined below. The therapeutically effective amount may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g. reduction of platelet adhesion and/or cell migration. The specific dose will vary depending on the particular compounds chosen, the dosing regimen to be followed, whether it is administered in combination with other compounds, timing of administration, the tissue to which it is administered, and the physical delivery system in which it is carried.

As used herein, "treatment," "treating," or "ameliorating" are used interchangeably. These terms refers to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "subject" or "patient" refers to an animal, such as a mammal, for example a human. The methods described herein can be useful in both human therapeutics and veterinary applications. In some embodiments, the patient is a mammal, and in some embodiments, the patient is human.

"Radiation therapy" means exposing a patient, using routine methods and compositions known to the practitioner, to radiation emitters such as alpha-particle emitting radionuclides (e.g., actinium and thorium radionuclides), low linear energy transfer (LET) radiation emitters (i.e. beta emitters), conversion electron emitters (e.g. strontium-89 and samarium-153-EDTMP, or high-energy radiation, including without limitation x-rays, gamma rays, and neutrons.

"Signal transduction" is a process during which stimulatory or inhibitory signals are transmitted into and within a cell to elicit an intracellular response. A modulator of a signal transduction pathway refers to a compound which modulates the activity of one or more cellular proteins mapped to the same specific signal transduction pathway. A modulator may augment (agonist) or suppress (antagonist) the activity of a signaling molecule.

The term "selective inhibition" or "selectively inhibit" as applied to a biologically active agent refers to the agent's ability to selectively reduce the target signaling activity as compared to off-target signaling activity, via direct or indirect interaction with the target.

The term "pharmaceutically acceptable carrier" or "pharmaceutically acceptable excipient" includes, but is not limited to, any and all solvents, dispersion media, coatings, antibacterial and antifungal agents, isotonic and absorption delaying agents, one or more suitable diluents, fillers, salts, disintegrants, binders, lubricants, glidants, wetting agents, controlled release matrices, colorants/flavoring, carriers, excipients, buffers, stabilizers, solubilizers, and combinations thereof. Except insofar as any conventional media or agent is incompatible with the active ingredient, its use in the therapeutic compositions of the invention is contemplated. Supplementary active ingredients can also be incorporated into the compositions.

In some embodiments, one or more subject compounds bind specifically to a PI3 kinase or a protein kinase selected from the group consisting of mTor, DNA-dependent protein kinase (Pubmed protein accession number (PPAN) AAA79184), Abl tyrosine kinase (CAA52387), Bcr-Abl, hemopoietic cell kinase (PPAN CAI19695), Src (PPAN CAA24495), vascular endothelial growth factor receptor 2 (PPAN ABB82619), epidermal growth factor receptor (PPAN AG43241), EPH receptor B4 (PPAN EAL23820), stem cell factor receptor (PPAN AAF22141), Tyrosine-protein kinase receptor TIE-2 (PPAN Q02858), fms-related tyrosine kinase 3 (PPAN NP_004110), platelet-derived growth factor receptor alpha (PPAN NP_990080), RET (PPAN CAA73131), and any other related protein kinases, as well as any functional mutants thereof.

In some embodiments, the IC50 of a subject compound for pi 10α, pi 10β, pi 10γ, or pi 10δ is less than about 1 uM, less than about 100 nM, less than about 50 nM, less than about 10 nM, less than 1 nM or even less than about 0.5 nM. In some embodiments, the IC50 of a subject compound for mTor is less than about 1 uM, less than about 100 nM, less than about 50 nM, less than about 10 nM, less than 1 nM or even less than about 0.5 nM. In some other embodiments, one or more subject compounds exhibit dual binding specificity and are capable of inhibiting a PI3 kinase (e.g., a class I PI3 kinase) as well as a protein kinase (e.g., mTor) with an IC50 value less than about 1 uM, less than about 100 nM, less than about 50 nM, less than about 10 nM, less than 1 nM or even less than about 0.5 nM.

In some embodiments, the compounds of the present invention exhibit one or more functional characteristics disclosed herein. For example, one or more subject compounds bind specifically to a PI3 kinase. In some embodiments, the IC50 of a subject compound for pi 10α, pi 10β, pi 10γ, or pi 10δ is less than about 1 uM, less than about 100 nM, less than about 50 nM, less than about 10 nM, less than about 1 nM, less than about 0.5 nM, less than about 100 pM, or less than about 50 pM.

In some embodiments, one or more of the subject compounds may selectively inhibit one or more members of type I or class I phosphatidylinositol 3-kinases (PI3-kinase) with an IC50 value of about 100 nM, 50 nM, 10 nM, 5 nM, 100 pM, 10 pM or 1 pM, or less as measured in an in vitro kinase assay.

In some embodiments, one or more of the subject compound may selectively inhibit one or two members of type I or class I phosphatidylinositol 3-kinases (PI3-kinase) consisting of PI3-kinase α, PI3-kinase β, PI3-kinase γ, and PI3-kinase δ. In some aspects, some of the subject compounds selectively inhibit PI3-kinase δ as compared to all other type I PI3-kinases. In other aspects, some of the subject compounds selectively inhibit PI3-kinase δ and PI3-kinase γ as compared to the rest of the type I PI3-kinases. In yet other aspects, some of the subject compounds selectively inhibit PI3-kinase α and PI3-kinase β as compared to the rest of the type I PI3-kinases. In still yet some other aspects, some of the subject compounds selectively inhibit PI3-kinase δ and PI3-kinase α as compared to the rest of the type I PI3-kinases. In still yet some other aspects, some of the subject compounds selectively inhibit PI3-kinase δ and PI3-kinase β as compared to the rest of the type I PI3-kinases, or selectively inhibit PI3-kinase δ and PI3-kinase α as compared to the rest of the type I PI3-kinases, or selectively inhibit PI3-kinase α and PI3-kinase γ as compared to the rest of the type I PI3-kinases, or selectively inhibit PI3-kinase γ and PI3-kinase β as compared to the rest of the type I PI3-kinases.

In yet another aspect, an inhibitor that selectively inhibits one or more members of type I PI3-kinases, or an inhibitor that selectively inhibits one or more type I PI3-kinase mediated signaling pathways, alternatively can be understood to refer to a compound that exhibits a 50% inhibitory concentration (IC50) with respect to a given type I PI3-kinase, that is at least at least 10-fold, at least 20-fold, at least 50-fold, at least 100-fold, at least 1000-fold, or lower, than the inhibitor's IC50 with respect to the rest of the other type I PI3-kinases.

As used herein, the term "PI3-kinase δ selective inhibitor" generally refers to a compound that inhibits the activity of the PI3-kinase δ isozyme more effectively than other isozymes of the PI3K family. A PI3-kinase δ selective inhibitor compound is therefore more selective for PI3-kinase δ than conventional PI3K inhibitors such as wortmannin and LY294002, which are "nonselective PI3K inhibitors."

Inhibition of PI3-kinase δ may be of therapeutic benefit in treatment of various conditions, e.g., conditions characterized by an inflammatory response including but not limited to autoimmune diseases, allergic diseases, and arthritic diseases. Importantly, inhibition of PI3-kinase δ function does not appear to affect biological functions such as viability and fertility.

"Inflammatory response" as used herein is characterized by redness, heat, swelling and pain (i.e., inflammation) and typically involves tissue injury or destruction. An inflammatory response is usually a localized, protective response elicited by injury or destruction of tissues, which serves to destroy, dilute or wall off (sequester) both the injurious agent and the injured tissue. Inflammatory responses are notably associated with the influx of leukocytes and/or leukocyte (e.g., neutrophil) chemotaxis. Inflammatory responses may result from infection with pathogenic organisms and viruses, noninfectious means such as trauma or reperfusion following myocardial infarction or stroke, immune responses to foreign antigens, and autoimmune diseases. Inflammatory responses amenable to treatment with the methods and compounds according to the invention encompass conditions associated with reactions of the specific defense system as well as conditions associated with reactions of the non-specific defense system.

The therapeutic methods of the invention include methods for the amelioration of conditions associated with inflammatory cell activation. "Inflammatory cell activation" refers to the induction by a stimulus (including but not limited to, cytokines, antigens or auto-antibodies) of a proliferative cellular response, the production of soluble mediators (including but not limited to cytokines, oxygen radicals, enzymes, prostanoids, or vasoactive amines), or cell surface expression of new or increased numbers of mediators (including but not limited to, major histocompatibility antigens or cell adhesion molecules) in inflammatory cells (including but not limited to monocytes, macrophages, T lymphocytes, B lymphocytes, granulocytes (polymorphonuclear leukocytes including neutrophils, basophils, and eosinophils) mast cells, dendritic cells, Langerhans cells, and endothelial cells). It will be appreciated by persons skilled in the art that the activation of one or a combination of these phenotypes in these cells can contribute to the initiation, perpetuation, or exacerbation of an inflammatory condition.

"Autoimmune disease" as used herein refers to any group of disorders in which tissue injury is associated with humoral or cell-mediated responses to the body's own constituents. "Transplant rejection" as used herein refers-to any immune response directed against grafted tissue (including organs or cells (e.g., bone marrow), characterized by a loss of function of the grafted and surrounding tissues, pain, swelling, leukocytosis, and thrombocytopenia). "Allergic disease" as used herein refers to any symptoms, tissue damage, or loss of tissue function resulting from allergy. "Arthritic disease" as used herein refers to any disease that is characterized by inflammatory lesions of the joints attributable to a variety of etiologies. "Dermatitis" as used herein refers to any of a large family of diseases of the skin that are characterized by inflammation of the skin attributable to a variety of etiologies.

As previously described, the term "PI3-kinase δ selective inhibitor" generally refers to a compound that inhibits the activity of the PI3-kinase δ isozyme more effectively than other isozymes of the PI3K family. The relative efficacies of compounds as inhibitors of an enzyme activity (or other biological activity) can be established by determining the concentrations at which each compound inhibits the activity to a predefined extent and then comparing the results. Typically, the preferred determination is the concentration that inhibits 50% of the activity in a biochemical assay, i.e., the 50% inhibitory concentration or "IC50". IC50 determinations can be accomplished using conventional techniques known in the art. In general, an IC50 can be determined by measuring the activity of a given enzyme in the presence of a range of concentrations of the inhibitor under study. The experimentally obtained values of enzyme activity then are plotted against the inhibitor concentrations used. The concentration of the inhibitor that shows 50% enzyme activity (as compared to the activity in the absence of any inhibitor) is taken as the IC50 value. Analogously, other inhibitory concentrations can be defined through appropriate determinations of activity. For example, in some settings it can be desirable to establish a 90% inhibitory concentration, i.e., IC90, etc.

Accordingly, a PI3-kinase δ selective inhibitor alternatively can be understood to refer to a compound that exhibits a 50% inhibitory concentration (IC50) with respect to PI3-kinase δ, that is at least 10-fold, in another aspect at least 20-fold, and in another aspect at least 30-fold, lower than the IC50 value with respect to any or all of the other class I PI3K family members. In an alternative embodiment of the invention, the term PI3-kinase δ selective inhibitor can be understood to refer to a compound that exhibits an IC50 with respect to PI3-kinase δ that is at least 50-fold, in another aspect at least 100-fold, in an additional aspect at least 200-fold, and in yet another aspect at least 500-fold, lower than the IC50 with respect to any or all of the other PI3K class I family members. A PI3-kinase δ selective inhibitor is typically administered in an amount such that it selectively inhibits PI3-kinase δ activity, as described above.

The methods of the invention may be applied to cell populations in vivo or ex vivo. "In vivo" means within a living individual, as within an animal or human or in a subject's body. In this context, the methods of the invention may be used therapeutically or prophylactically in an individual. "Ex vivo" or "In vitro" means outside of a living individual. Examples of ex vivo cell populations include in vitro cell cultures and biological samples including but not limited to fluid or tissue samples obtained from individuals. Such samples may be obtained by methods known in the art. Exemplary biological fluid samples include blood, cerebrospinal fluid, urine, and saliva. Exemplary tissue samples include tumors and biopsies thereof. In this context, the invention may be used for a variety of purposes, including therapeutic and experimental purposes. For example, the invention may be used ex vivo or in vitro to determine the optimal schedule and/or dosing of administration of a PI3-kinase δ selective inhibitor for a given indication, cell type, individual, and other parameters. Information gleaned from such use may be used for experimental or diagnostic purposes or in the clinic to set protocols for in vivo treatment. Other ex vivo uses for which the invention may be suited are described below or will become apparent to those skilled in the art.

Pharmaceutical Compositions

The invention provides a pharmaceutical composition comprising one or more compounds of the present invention. The pharmaceutical composition may include one or more additional active ingredients as described herein. The pharmaceutical composition may be administered for any of the disorders described herein In some embodiments, the invention provides pharmaceutical compositions for treating diseases or conditions related to an undesirable, over-active, harmful or deleterious immune response in a mammal. Such undesirable immune response can be associated with or result in, e.g., asthma, emphysema, bronchitis, psoriasis, allergy, anaphylaxsis, auto-immune diseases, rhuematoid arthritis, graft versus host disease, and lupus erythematosus. The pharmaceutical compositions of the present invention can be used to treat other respiratory diseases including but not limited to diseases affecting the lobes of lung, pleural cavity, bronchial tubes, trachea, upper respiratory tract, or the nerves and muscle for breathing.

In some embodiments, the invention provides pharmaceutical compositions for the treatment of disorders such as hyperproliferative disorder including but not limited to cancer such as acute myeloid leukemia, thymus, brain, lung, squamous cell, skin, eye, retinoblastoma, intraocular melanoma, oral cavity and oropharyngeal, bladder, gastric, stomach, pancreatic, bladder, breast, cervical, head, neck, renal, kidney, liver, ovarian, prostate, colorectal, esophageal, testicular, gynecological, thyroid, CNS, PNS, AIDS related (e.g. Lymphoma and Kaposi's Sarcoma) or Viral-Induced cancer. In some embodiments, the pharmaceutical composition is for the treatment of a non-cancerous hyperproliferative disorder such as benign hyperplasia of the skin (e. g., psoriasis), restenosis, or prostate (e. g., benign prostatic hypertrophy (BPH)).

The invention also relates to a composition for treating a disease related to vasculogenesis or angiogenesis in a mammal which can manifest as tumor angiogenesis, chronic inflammatory disease such as rheumatoid arthritis, inflammatory bowel disease, atherosclerosis, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

The invention also provides compositions for the treatment of liver diseases (including diabetes), pancreatitis or kidney disease (including proliferative glomerulonephritis and diabetes-induced renal disease) or pain in a mammal.

The invention further provides a composition for the prevention of blastocyte implantation in a mammal.

The subject pharmaceutical compositions are typically formulated to provide a therapeutically effective amount of a compound of the present invention as the active ingredient, or a pharmaceutically acceptable salt, ester, or prodrug thereof. Where desired, the pharmaceutical compositions contain a compound of the present invention as the active ingredient or a pharmaceutically acceptable salt and/or coordination complex thereof, and one or more pharmaceutically acceptable excipients, carriers, such as inert solid diluents and fillers, diluents, including sterile aqueous solution and various organic solvents, permeation enhancers, solubilizers and adjuvants.

The subject pharmaceutical compositions can be administered alone or in combination with one or more other agents, which are also typically administered in the form of pharmaceutical compositions. Where desired, the subject compounds and other agent(s) may be mixed into a preparation or both components may be formulated into separate preparations to use them in combination separately or at the same time.

Methods include administration of an inhibitor by itself, or in combination as described herein, and in each case optionally including one or more suitable diluents, fillers, salts, disintegrants, binders, lubricants, glidants, wetting agents, controlled release matrices, colorants/flavoring, carriers, excipients, buffers, stabilizers, solubilizers, and combinations thereof.

Preparations of various pharmaceutical compositions are known in the art. See, e.g., Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, N.Y., 1990; Katzung, ed., Basic and Clinical Pharmacology, Ninth Edition, McGraw Hill, 2003; Goodman and Gilman, eds., The Pharmacological Basis of Therapeutics, Tenth Edition, McGraw Hill, 2001; Remingtons Pharmaceutical Sciences, 20th Ed., Lippincott Williams & Wilkins., 2000; Martindale, The Extra Pharmacopoeia, Thirty-Second Edition (The Pharmaceutical Press, London, 1999), all of which are incorporated by reference herein in their entirety.

The compounds or pharmaceutical composition of the present invention can be administered by any route that enables delivery of the compounds to the site of action, such asoral routes, intraduodenal routes, parenteral injection (including intravenous, intraarterial, subcutaneous, intramuscular, intravascular, intraperitoneal or infusion), topical administration (e.g. transdermal application), rectal administration, via local delivery by catheter or stent or through inhalation. The compounds can also be administered intraadiposally or intrathecally.

The compositions can be administered in solid, semi-solid, liquid or gaseous form, or may be in dried powder, such as lyophilized form. The pharmaceutical compositions can be packaged in forms convenient for delivery, including, for example, solid dosage forms such as capsules, sachets, cachets, gelatins, papers, tablets, capsules, suppositories, pellets, pills, troches, and lozenges. The type of packaging will generally depend on the desired route of administration. Implantable sustained release formulations are also contemplated, as are transdermal formulations.

Routes of Administration

In the methods according to the invention, the inhibitor compounds may be administered by various routes. For example, pharmaceutical compositions may be for injection, or for oral, nasal, transdermal or other forms of administration, including, e.g., by intravenous, intradermal, intramuscular, intramammary, intraperitoneal, intrathecal, intraocular, retrobulbar, intrapulmonary (e.g., aerosolized drugs) or subcutaneous injection (including depot administration for long term release e.g., embedded-under the-splenic capsule, brain, or in the cornea); by sublingual, anal, or vaginal administration, or by surgical implantation, e.g., embedded under the splenic capsule, brain, or in the cornea. The treatment may consist of a single dose or a plurality of doses over a period of time. In general, the methods of the invention involve administering effective amounts of a modulator of the invention together with one or more pharmaceutically acceptable diluents, preservatives, solubilizers, emulsifiers, adjuvants and/or carriers, as described above.

The subject pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, and adjuvants.

In one aspect, the invention provides methods for oral administration of a pharmaceutical composition of the invention. Oral solid dosage forms are described generally in Remington's Pharmaceutical Sciences, supra at Chapter 89. Solid dosage forms include tablets, capsules, pills, troches or lozenges, and cachets or pellets. Also, liposomal or proteinoid encapsulation may be used to formulate the compositions (as, for example, proteinoid microspheres reported in U.S. Pat. No. 4,925,673). Liposomal encapsulation may include liposomes that are derivatized with various polymers (e.g., U.S. Pat. No. 5,013,556). The formulation may include a compound of the invention and inert ingredients which protect against degradation in the stomach and which permit release of the biologically active material in the intestine.

Toxicity and therapeutic efficacy of the PI3-kinase δ selective compounds can be determined by standard pharmaceutical procedures in cell cultures or experimental animals, e.g., for determining the LD50 (the dose lethal to 50% of the population) and the ED50 (the dose therapeutically effective in 50% of the population). Additionally, this information can be determined in cell cultures or experimental animals additionally treated with other therapies including but not limited to radiation, chemotherapeutic agents, photodynamic therapies, radiofrequency ablation, anti-angiogenic agents, and combinations thereof.

The amount of the compound administered will be dependent on the mammal being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to 7 g/day, preferably about 0.05 to about 2.5 g/day. In some instances, dosage levels below the lower limit of the aforesaid range may be more than adequate, while in other cases still larger doses may be employed without causing any harmful side effect, e.g. by dividing such larger doses into several small doses for administration throughout the day.

In some embodiments, a compound of the invention is administered in a single dose. Typically, such administration will be by injection, e.g., intravenous injection, in order to introduce the agent quickly. However, other routes may be used as appropriate. A single dose of a compound of the invention may also be used for treatment of an acute condition.

In practice of the methods of the invention, the pharmaceutical compositions are generally provided in doses ranging from 1 pg compound/kg body weight to 1000 mg/kg, 0.1 mg/kg to 100 mg/kg, 0.1 mg/kg to 50 mg/kg, and 1 to 20 mg/kg, given in daily doses or in equivalent doses at longer or shorter intervals, e.g., every other day, twice weekly, weekly, or twice or three times daily. The inhibitor compositions may be administered by an initial bolus followed by a continuous infusion to maintain therapeutic circulating levels of drug product. Those of ordinary skill in the art will readily optimize effective dosages and administration regimens as determined by good medical practice and the clinical condition of the individual to be treated. The frequency of dosing will depend on the pharmacokinetic parameters of the agents and the route of administration. The optimal pharmaceutical formulation will be determined by one skilled in the art depending upon the route of administration and desired dosage [see, for example, Remington's Pharmaceutical Sciences, pp. 1435-1712, the disclosure of which is hereby incorporated by reference]. Such formulations may influence the physical state, stability, rate of in vivo release, and rate of in vivo clearance of the administered agents. Depending on the route of administration, a suitable dose may be calculated according to body weight, body surface area or organ size. Further refinement of the calculations necessary to determine the appropriate dosage for treatment involving each of the above mentioned formulations is routinely made by those of ordinary skill in the art without undue experimentation, especially in light of the dosage information and assays disclosed herein, as well as the pharmacokinetic data observed in human clinical trials. Appropriate dosages may be ascertained by using established assays for determining blood level dosages in conjunction with an appropriate physician considering various factors which modify the action of drugs, e.g., the drug's specific activity, the severity of the indication, and the responsiveness of the individual, the age, condition, body weight, sex and diet of the individual, the time of administration and other clinical factors. As studies are conducted, further information will emerge regarding the appropriate dosage levels and duration of treatment for various diseases and conditions capable of being treated with the methods of the invention.

In some embodiments, a compound of the invention is administered in multiple doses. Dosing may be about once, twice, three times, four times, five times, six times, or more than six times per day. Dosing may be about once a month, once every two weeks, once a week, or once every other day. In another embodiment a compound of the invention and another agent are administered together about once per day to about 6 times per day. In another embodiment the administration of a compound of the invention and an agent continues for less than about 7 days. In yet another embodiment the administration continues for more than about 6, 10, 14, 28 days, two months, six months, or one year. In some cases, continuous dosing is achieved and maintained as long as necessary.

Administration of the agents of the invention may continue as long as necessary. In some embodiments, an agent of the invention is administered for more than 1, 2, 3, 4, 5, 6, 7, 14, or 28 days. In some embodiments, an agent of the invention is administered for less than 28, 14, 7, 6, 5, 4, 3, 2, or 1 day. In some embodiments, an agent of the invention is administered chronically on an ongoing basis, e.g., for the treatment of chronic effects.

An effective amount of a compound of the invention may be administered in either single or multiple doses by any of the accepted modes of administration of agents having similar utilities, including rectal, buccal, intranasal and transdermal routes, by intraarterial injection, intravenously, intraperitoneally, parenterally, intramuscularly, subcutaneously, orally, topically, or as an inhalant.

The compounds of the invention may be administered in dosages. It is known in the art that due to intersubject variability in compound pharmacokinetics, individualization of dosing regimen is necessary for optimal therapy. Dosing for a compound of the invention may be found by routine experimentation in light of the instant disclosure.

When a compound of the invention, is administered in a composition that comprises one or more agents, and the agent has a shorter half-life than the compound of the invention unit dose forms of the agent and the compound of the invention may be adjusted accordingly.

The inhibitors of the invention may be covalently or non-covalently associated with a carrier molecule including but not limited to a linear polymer (e.g., polyethylene glycol, polylysine, dextran, etc.), a branched-chain polymer (see U.S. Pat. Nos. 4,289,872 and 5,229,490; PCT Publication No. WO 93/21259), a lipid, a cholesterol group (such as a steroid), or a carbohydrate or oligosaccharide. Specific examples of carriers for use in the pharmaceutical compositions of the invention include carbohydrate-based polymers such as trehalose, mannitol, xylitol, sucrose, lactose, sorbitol, dextrans such as cyclodextran, cellulose, and cellulose derivatives. Also, the use of liposomes, microcapsules or microspheres, inclusion complexes, or other types of carriers is contemplated.

Other carriers include one or more water soluble polymer attachments such as polyoxyethylene glycol, or polypropylene glycol as described U.S. Pat. Nos. 4,640,835, 4,496,689, 4,301,144, 4,670,417, 4,791,192 and 4,179,337. Still other useful carrier polymers known in the art include monomethoxy-polyethylene glycol, poly-(N-vinyl pyrrolidone)-polyethylene glycol, propylene glycol homopolymers, a polypropylene oxidelethylene oxide co-polymer, polyoxyethylated polyols (e.g., glycerol) and polyvinyl alcohol, as well as mixtures of these polymers.

Derivitization with bifunctional agents is useful for cross-linking a compound of the invention to a support matrix or to a carrier. One such carrier is polyethylene glycol (PEG). The PEG group may be of any convenient molecular weight and may be straight chain or branched. The average molecular weight of the PEG can range from about 2 kDa to about 100 kDa, in another aspect from about 5 kDa to about 50 kDa, and in a further aspect from about 5 kDa to about 10 kDa. The PEG groups will generally be attached to the compounds of the invention via acylation, reductive alkylation, Michael addition, thiol alkylation or other chemoselective conjugation/ligation methods through a reactive group on the PEG moiety (e.g., an aldehyde, amino, ester, thiol, ci-haloacetyl, maleimido or hydrazino group) to a reactive group on the target inhibitor compound (e.g., an aldehyde, amino, ester, thiol, a-haloacetyl, maleimido or hydrazino group). Cross-linking agents can include, e.g., esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithiolpropioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 may be employed for inhibitor immobilization.

Method of Treatment

The invention also provides methods of using the compounds or pharmaceutical compositions of the present invention to treat disease conditions, including but not limited to diseases associated with malfunctioning of one or more types of PI3 kinase. A detailed description of conditions and disorders mediated by pi 10δ kinase activity is set forth in WO 2001/81346 and US 2005/043239, both of which are incorporated herein by reference in their entireties for all purposes.

The treatment methods provided herein comprise administering to the subject a therapeutically effective amount of a compound of the invention. In one embodiment, the present invention provides a method of treating an inflammation disorder, including autoimmune diseases in a mammal. The method comprises administering to said mammal a therapeutically effective amount of a compound of the present invention, or a pharmaceutically acceptable salt, ester, prodrug, solvate, hydrate or derivative thereof.

The disorders, diseases, or conditions treatable with a compound provided herein, include, but are not limited to,

- inflammatory or allergic diseases, including systemic anaphylaxis and hypersensitivity disorders, atopic dermatitis, urticaria, drug allergies, insect sting allergies, food allergies (including celiac disease and the like), anaphylaxis, serum sickness, drug reactions, insect venom allergies, hypersensitivity pneumonitis, angioedema, erythema multiforme, Stevens-Johnson syndrome, atopic keratoconjunctivitis, venereal keratoconjunctivitis, giant papillary conjunctivitis, and mastocytosis;
- inflammatory bowel diseases, including Crohn's disease, ulcerative colitis, ileitis, enteritis, and necrotizing enterocolitis;
- vasculitis, and Behcet's syndrome;
- psoriasis and inflammatory dermatoses, including dermatitis, eczema, allergic contact dermatitis, viral cutaneous pathologies including those derived from human papillomavirus, HIV or RLV infection, bacterial, flugal, and other parasital cutaneous pathologies, and cutaneous lupus erythematosus;
- asthma and respiratory allergic diseases, including allergic asthma, exercise induced asthma, allergic rhinitis, otitis media, hypersensitivity lung diseases, chronic obstructive pulmonary disease and other respiratory problems;
- autoimmune diseases and inflammatory conditions, including but are not limited to acute disseminated encephalomyelitis (ADEM), Addison's disease, antiphospholipid antibody syndrome (APS), aplastic anemia, autoimmune hepatitis, coeliac disease, Crohn's disease, Diabetes mellitus (type 1), Goodpasture's syndrome, Graves' disease, Guillain-Barre syndrome (GBS), Reynaud's syndrome, Hashimoto's disease, lupus erythematosus, systemic lupus erythematosus (SLE), multiple sclerosis, myasthenia gravis, opsoclonus myoclonus syndrome (OMS), optic neuritis, Ord's thyroiditis, oemphigus, polyarthritis, primary biliary cirrhosis, psoriasis, rheumatoid arthritis, psoriatic arthritis, gouty arthritis, spondylitis, reactive arthritis, chronic or acute glomerulonephritis, lupus nephritis, Reiter's syndrome, Takayasu's arteritis, temporal arteritis (also known as "giant cell arteritis"), warn autoimmune hemolytic anemia, Wegener's granulomatosis, alopecia universalis, Chagas' disease, chronic fatigue syndrome, dysautonomia, endometriosis, hidradenitis suppurativa, interstitial cystitis, neuromyotonia, sarcoidosis, scleroderma, ulcerative colitis, connective tissue disease, autoimmune pulmonary inflammation, autoimmune thyroiditis, autoimmune inflammatory eye disease, vitiligo, and vulvodynia. Other disorders include bone-resorption disorders and thrombosis;
- tissue or organ transplant rejection disorders including but not limited to graft rejection (including allograft rejection and graft-v-host disease (GVHD)), e.g., skin graft rejection, solid organ transplant rejection, bone marrow transplant rejection;
- fever;
- cardiovascular disorders, including acute heart failure, hypotension, hypertension, angina pectoris, myocardial infarction, cardiomyopathy, congestive heart failure, atherosclerosis, coronary artery disease, restenosis, and vascular stenosis;
- cerebrovascular disorders, including traumatic brain injury, stroke, ischemic reperfusion injury and aneurysm;
- cancers of the breast, skin, prostate, cervix, uterus, ovary, testes, bladder, lung, liver, larynx, oral cavity, colon and gastrointestinal tract (e.g., esophagus, stomach, pancreas), brain, thyroid, blood, and lymphatic system;
- fibrosis, connective tissue disease, and sarcoidosis;
- genital and reproductive conditions, including erectile dysfunction;
- gastrointestinal disorders, including gastritis, ulcers, nausea, pancreatitis, and vomiting;
- neurologic disorders, including Alzheimer's disease;
- sleep disorders, including insomnia, narcolepsy, sleep apnea syndrome, and Pickwick Syndrome;
- pain, myalgias due to infection;
- renal disorders;
- ocular disorders, including glaucoma;
- infectious diseases, including HIV;
- sepsis; septic shock; endotoxic shock; gram negative sepsis; gram positive sepsis; toxic shock syndrome; multiple organ injury syndrome secondary to septicemia, trauma, or hemorrhage;
- pulmonary or respiratory conditions including but not limited to asthma, chronic bronchitis, allergic rhinitis, adult respiratory distress syndrome (ARDS), severe acute respiratory syndrome (SARS), chronic pulmonary inflammatory diseases (e.g., chronic obstructive pulmonary disease), silicosis, pulmonary sarcoidosis, pleurisy, alveolitis, vasculitis, pneumonia, bronchiectasis, hereditary emphysema, and pulmonary oxygen toxicity;

ischemic-reperfusion injury, e.g., of the myocardium, brain, or extremities;

fibrosis including but not limited to cystic fibrosis; keloid formation or scar tissue formation;

central or peripheral nervous system inflammatory conditions including but not limited to meningitis (e.g., acute purulent meningitis), encephalitis, and brain or spinal cord injury due to minor trauma;

Sjorgren's syndrome; diseases involving leukocyte diapedesis; alcoholic hepatitis; bacterial pneumonia; community acquired pneumonia (CAP); *Pneumocystis carinii* pneumonia (PCP); antigen-antibody complex mediated diseases; hypovolemic shock; acute and delayed hypersensitivity; disease states due to leukocyte dyscrasia and metastasis; thermal injury; granulocyte transfusion associated syndromes; cytokine-induced toxicity; stroke; pancreatitis; myocardial infarction, respiratory syncytial virus (RSV) infection; and spinal cord injury.

In certain embodiments, the cancer or cancers treatable with the methods provided herein includes, but is or are not limited to, leukemias, including, but not limited to, acute leukemia, acute lymphocytic leukemia, acute myelocytic leukemias such as myeloblasts, promyelocyte, myelomonocytic, monocytic, erythroleukemia leukemias and myelodysplastic syndrome or a symptom thereof (such as anemia, thrombocytopenia, neutropenia, bicytopenia or pancytopenia), refractory anemia (RA), RA with ringed sideroblasts (RARS), RA with excess blasts (RAEB), RAEB in transformation (RAEB-T), preleukemia, and chronic myelomonocytic leukemia (CMML);

chronic leukemias, including, but not limited to, chronic myelocytic (granulocytic) leukemia, chronic lymphocytic leukemia, and hairy cell leukemia;

polycythemia vera;

lymphomas, including, but not limited to, Hodgkin's disease and non-Hodgkin's disease;

multiple myelomas, including, but not limited to, smoldering multiple myeloma, nonsecretory myeloma, osteosclerotic myeloma, plasma cell leukemia, solitary plasmacytoma, and extramedullary plasmacytoma;

Waldenstrom's macroglobulinemia;

monoclonal gammopathy of undetermined significance;

benign monoclonal gammopathy;

heavy chain disease;

bone and connective tissue sarcomas, including, but not limited to, bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, metastatic cancers, neurilemmoma, rhabdomyosarcoma, and synovial sarcoma;

brain tumors, including, but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, and primary brain lymphoma;

breast cancer, including, but not limited to, adenocarcinoma, lobular (small cell) carcinoma, intraductal carcinoma, medullary breast cancer, mucinous breast cancer, tubular breast cancer, papillary breast cancer, primary cancers, Paget's disease, and inflammatory breast cancer;

adrenal cancer, including, but not limited to, pheochromocytom and adrenocortical carcinoma;

thyroid cancer, including, but not limited to, papillary or follicular thyroid cancer, medullary thyroid cancer, and anaplastic thyroid cancer;

pancreatic cancer, including, but not limited to, insulinoma, gastrinoma, glucagonoma, vipoma, somatostatin-secreting tumor, and carcinoid or islet cell tumor;

pituitary cancer, including, but limited to, Cushing's disease, prolactin-secreting tumor, acromegaly, and diabetes insipidus;

eye cancer, including, but not limited, to ocular melanoma such as iris melanoma, choroidal melanoma, and cilliary body melanoma, and retinoblastoma;

vaginal cancer, including, but not limited to, squamous cell carcinoma, adenocarcinoma, and melanoma;

vulvar cancer, including, but not limited to, squamous cell carcinoma, melanoma, adenocarcinoma, basal cell carcinoma, sarcoma, and Paget's disease;

cervical cancers, including, but not limited to, squamous cell carcinoma, and adenocarcinoma;

uterine cancer, including, but not limited to, endometrial carcinoma and uterine sarcoma;

ovarian cancer, including, but not limited to, ovarian epithelial carcinoma, borderline tumor, germ cell tumor, and stromal tumor;

esophageal cancer, including, but not limited to, squamous cancer, adenocarcinoma, adenoid cystic carcinoma, mucoepidermoid carcinoma, adenosquamous carcinoma, sarcoma, melanoma, plasmacytoma, verrucous carcinoma, and oat cell (small cell) carcinoma;

stomach cancer, including, but not limited to, adenocarcinoma, fungating (polypoid), ulcerating, superficial spreading, diffusely spreading, malignant lymphoma, liposarcoma, fibrosarcoma, and carcinosarcoma;

colon cancer;

rectal cancer;

liver cancer, including, but not limited to, hepatocellular carcinoma and hepatoblastoma;

gallbladder cancer, including, but not limited to, adenocarcinoma;

cholangiocarcinomas, including, but not limited to, pappillary, nodular, and diffuse;

lung cancer, including, but not limited to, non-small cell lung cancer, squamous cell carcinoma (epidermoid carcinoma), adenocarcinoma, large-cell carcinoma, and small-cell lung cancer;

testicular cancer, including, but not limited to, germinal tumor, seminoma, anaplastic, classic (typical), spermatocytic, nonseminoma, embryonal carcinoma, teratoma carcinoma, and choriocarcinoma (yolk-sac tumor);

prostate cancer, including, but not limited to, adenocarcinoma, leiomyosarcoma, and rhabdomyosarcoma;

penal cancer;

oral cancer, including, but not limited to, squamous cell carcinoma;

basal cancer;

salivary gland cancer, including, but not limited to, adenocarcinoma, mucoepidermoid carcinoma, and adenoidcystic carcinoma;

pharynx cancer, including, but not limited to, squamous cell cancer and verrucous;

skin cancer, including, but not limited to, basal cell carcinoma, squamous cell carcinoma and melanoma, superficial spreading melanoma, nodular melanoma, lentigo malignant melanoma, and acral lentiginous melanoma;

kidney cancer, including, but not limited to, renal cell cancer, adenocarcinoma, hypernephroma, fibrosarcoma, and transitional cell cancer (renal pelvis and/or uterer);

Wilms' tumor;

bladder cancer, including, but not limited to, transitional cell carcinoma, squamous cell cancer, adenocarcinoma, and carcinosarcoma; and other cancer, including, not limited to, myxosarcoma, osteogenic sarcoma, endotheliosarcoma, lymphangio-endotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma, and papillary adenocarcinomas See Fishman et al., 1985, Medicine, 2d Ed., J.B. Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America.

It will be appreciated that the treatment methods of the invention are useful in the fields of human medicine and veterinary medicine. Thus, the individual to be treated may be a mammal, preferably human, or other animals. For veterinary purposes, individuals include but are not limited to farm animals including cows, sheep, pigs, horses, and goats; companion animals such as dogs and cats; exotic and/or zoo animals; laboratory animals including mice, rats, rabbits, guinea pigs, and hamsters; and poultry such as chickens, turkeys, ducks, and geese.

In some embodiments, the method of treating inflammatory or autoimmune diseases comprises administering to a subject (e.g. a mammal) a therapeutically effective amount of one or more compounds of the present invention that selectively inhibit PI3K-δ and/or PI3K-γ as compared to all other type I PI3 kinases. Such selective inhibition of PI3K-δ and/or PI3K-γ may be advantageous for treating any of the diseases or conditions described herein. For example, selective inhibition of PI3K-δ may inhibit inflammatory responses associated with inflammatory diseases, autoimmune disease, or diseases related to an undesirable immune response including but not limited to asthma, emphysema, allergy, dermatitis, rhuematoid arthritis, psoriasis, lupus erythematosus, or graft versus host disease. Selective inhibition of POK-δ may further provide for a reduction in the inflammatory or undesirable immune response without a concomitant reduction in the ability to reduce a bacterial, viral, and/or fungal infection. Selective inhibition of both PI3K-δ and PI3K-γ may be advantageous for inhibiting the inflammatory response in the subject to a greater degree than that would be provided for by inhibitors that selectively inhibit PI3K-δ or PI3K-γ alone. In one aspect, one or more of the subject methods are effective in reducing antigen specific antibody production in vivo by about 2-fold, 3-fold, 4-fold, 5-fold, 7.5-fold, 10-fold, 25-fold, 50-fold, 100-fold, 250-fold, 500-fold, 750-fold, or about 1000-fold or more. In another aspect, one or more of the subject methods are effective in reducing antigen specific IgG3 and/or IgGM production in vivo by about 2-fold, 3-fold, 4-fold, 5-fold, 7.5-fold, 10-fold, 25-fold, 50-fold, 100-fold, 250-fold, 500-fold, 750-fold, or about 1000-fold or more.

In one aspect, one of more of the subject methods are effective in ameliorating symptoms associated with rhuematoid arthritis including but not limited to a reduction in the swelling of joints, a reduction in serum anti-collagen levels, and/or a reduction in joint pathology such as bone resorption, cartilage damage, pannus, and/or inflammation. In another aspect, the subject methods are effective in reducing ankle inflammation by at least about 2%, 5%, 10%, 15%, 20%, 25%, 30%, 50%, 60%, or about 75% to 90%. In another aspect, the subject methods are effective in reducing knee inflammation by at least about 2%, 5%, 10%, 15%, 20%, 25%, 30%, 50%, 60%, or about 75% to 90% or more. In still another aspect, the subject methods are effective in reducing serum anti-type II collagen levels by at least about 10%, 12%, 15%, 20%, 24%, 25%, 30%, 35%, 50%, 60%, 75%, 80%, 86%, 87%, or about 90% or more. In another aspect, the subject methods are effective in reducing ankle histopathology scores by about 5%, 10%, 15%, 20%, 25%, 30%, 40%, 50%, 60%, 75%, 80%, 90% or more. In still another aspect, the subject methods are effective in reducing knee histopathology scores by about 5%, 10%, 15%, 20%, 25%, 30%, 40%, 50%, 60%, 75%, 80%, 90% or more.

In other embodiments, the present invention provides methods of using the compounds or pharmaceutical compositions to treat respiratory diseases including but not limited to diseases affecting the lobes of lung, pleural cavity, bronchial tubes, trachea, upper respiratory tract, or the nerves and muscle for breathing. For example, methods are provided to treat obstructive pulmonary disease. Chronic obstructive pulmonary disease (COPD) is an umbrella term for a group of respiratory tract diseases that are characterized by airflow obstruction or limitation. Conditions included in this umbrella term are: chronic bronchitis, emphysema, and bronchiectasis.

In another embodiment, the compounds described herein are used for the treatment of asthma. Also, the compounds or pharmaceutical compositions described herein may be used for the treatment of endotoxemia and sepsis. In one embodiment, the compounds or pharmaceutical compositions described herein are used to for the treatment of rheumatoid arthritis (RA). In yet another embodiment, the compounds or pharmaceutical compositions described herein is used for the treatment of contact or atopic dermatitis. Contact dermatitis includes irritant dermatitis, phototoxic dermatitis, allergic dermatitis, photoallergic dermatitis, contact urticaria, systemic contact-type dermatitis and the like. Irritant dermatitis can occur when too much of a substance is used on the skin of when the skin is sensitive to certain substance. Atopic dermatitis, sometimes called eczema, is a kind of dermatitis, an atopic skin disease.

The invention also relates to a method of treating a hyperproliferative disorder in a mammal that comprises administering to said mammal a therapeutically effective amount of a compound of the present invention, or a pharmaceutically acceptable salt, ester, prodrug, solvate, hydrate or derivative thereof. In some embodiments, said method relates to the treatment of cancer such as acute myeloid leukemia, thymus, brain, lung, squamous cell, skin, eye, retinoblastoma, intraocular melanoma, oral cavity and oropharyngeal, bladder, gastric, stomach, pancreatic, bladder, breast, cervical, head, neck, renal, kidney, liver, ovarian, prostate, colorectal, esophageal, testicular, gynecological, thyroid, CNS, PNS, AIDS-related (e.g. Lymphoma and Kaposi's Sarcoma) or viral-induced cancer. In some embodiments, said method relates to the treatment of a non-cancerous hyperproliferative disorder such as benign hyperplasia of the skin (e. g., psoriasis), restenosis, or prostate (e.g., benign prostatic hypertrophy (BPH)).

The invention also relates to a method of treating diseases related to vasculogenesis or angiogenesis in a mammal that comprises administering to said mammal a therapeutically effective amount of a compound of the present invention, or a pharmaceutically acceptable salt, ester, prodrug, solvate, hydrate or derivative thereof. In some embodiments, said method is for treating a disease selected from the group consisting of tumor angiogenesis, chronic inflammatory disease such as rheumatoid arthritis, atherosclerosis, inflammatory bowel disease, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

Patients that can be treated with compounds of the present invention, or pharmaceutically acceptable salt, ester, prodrug, solvate, hydrate or derivative of said compounds, according to the methods of this invention include, for example, patients that have been diagnosed as having psoriasis; restenosis; atherosclerosis; BPH; breast cancer such as a ductal carcinoma in duct tissue in a mammary gland, medullary carcinomas, colloid carcinomas, tubular carcinomas, and inflammatory breast cancer; ovarian cancer, including epithelial ovarian tumors such as adenocarcinoma in the ovary and an adenocarcinoma that has migrated from the ovary into the abdominal cavity; uterine cancer; cervical cancer such as adenocarcinoma in the cervix epithelial including squamous cell carcinoma and adenocarcinomas; prostate cancer, such as a prostate cancer selected from the following: an adenocarcinoma or an adenocarinoma that has migrated to the bone; pancreatic cancer such as epitheloid carcinoma in the pancreatic duct tissue and an adenocarcinoma in a pancreatic duct; bladder cancer such as a transitional cell carcinoma in urinary bladder, urothelial carcinomas (transitional cell carcinomas), tumors in the urothelial cells that line the bladder, squamous cell carcinomas, adenocarcinomas, and small cell cancers; leukemia such as acute myeloid leukemia (AML), acute lymphocytic leukemia, chronic lymphocytic leukemia, chronic myeloid leukemia, hairy cell leukemia, myelodysplasia, myeloproliferative disorders, acute myelogenous leukemia (AML), chronic myelogenous leukemia (CML), mastocytosis, chronic lymphocytic leukemia (CLL), multiple myeloma (MM), and myelodysplastic syndrome (MDS); bone cancer; lung cancer such as non-small cell lung cancer (NSCLC), which is divided into squamous cell carcinomas, adenocarcinomas, and large cell undifferentiated carcinomas, and small cell lung cancer; skin cancer such as basal cell carcinoma, melanoma, squamous cell carcinoma and actinic keratosis, which is a skin condition that sometimes develops into squamous cell carcinoma; eye retinoblastoma; cutaneous or intraocular (eye) melanoma; primary liver cancer (cancer that begins in the liver); kidney cancer; thyroid cancer such as papillary, follicular, medullary and anaplastic; AIDS-related lymphoma such as diffuse large B-cell lymphoma, B-cell immunoblastic lymphoma and small non-cleaved cell lymphoma; Kaposi's Sarcoma; viral-induced cancers including hepatitis B virus (HBV), hepatitis C virus (HCV), and hepatocellular carcinoma; human lymphotropic virus-type 1 (HTLV-I) and adult T-cell leukemia/lymphoma; and human papilloma virus (HPV) and cervical cancer; central nervous system cancers (CNS) such as primary brain tumor, which includes gliomas (astrocytoma, anaplastic astrocytoma, or glioblastoma multiforme), Oligodendroglioma, Ependymoma, Meningioma, Lymphoma, Schwannoma, and Medulloblastoma; peripheral nervous system (PNS) cancers such as acoustic neuromas and malignant peripheral nerve sheath tumor (MPNST) including neurofibromas and schwannomas, malignant fibrous cytoma, malignant fibrous histiocytoma, malignant meningioma, malignant mesothelioma, and malignant mixed Müllerian tumor; oral cavity and oropharyngeal cancer such as, hypopharyngeal cancer, laryngeal cancer, nasopharyngeal cancer, and oropharyngeal cancer; stomach cancer such as lymphomas, gastric stromal tumors, and carcinoid tumors; testicular cancer such as germ cell tumors (GCTs), which include seminomas and nonseminomas, and gonadal stromal tumors, which include Leydig cell tumors and Sertoli cell tumors; thymus cancer such as to thymomas, thymic carcinomas, Hodgkin disease, non-Hodgkin lymphomas carcinoids or carcinoid tumors; rectal cancer; and colon cancer.

The invention also relates to a method of treating diabetes in a mammal that comprises administering to said mammal a therapeutically effective amount of a compound of the present invention, or a pharmaceutically acceptable salt, ester, prodrug, solvate, hydrate or derivative thereof.

In addition, the compounds described herein may be used to treat acne.

In addition, the compounds described herein may be used for the treatment of arteriosclerosis, including atherosclerosis. Arteriosclerosis is a general term describing any hardening of medium or large arteries. Atherosclerosis is a hardening of an artery specifically due to an atheromatous plaque.

Further the compounds described herein may be used for the treatment of glomerulonephritis. Glomerulonephritis is a primary or secondary autoimmune renal disease characterized by inflammation of the glomeruli. It may be asymptomatic, or present with hematuria and/or proteinuria. There are many recognized types, divided in acute, subacute or chronic glomerulonephritis. Causes are infectious (bacterial, viral or parasitic pathogens), autoimmune or paraneoplastic.

Additionally, the compounds described herein may be used for the treatment of bursitis, lupus, acute disseminated encephalomyelitis (ADEM), addison's disease, antiphospholipid antibody syndrome (APS), aplastic anemia, autoimmune hepatitis, coeliac disease, Crohn's disease, diabetes mellitus (type 1), goodpasture's syndrome, graves' disease, guillain-barre syndrome (GBS), hashimoto's disease, inflammatory bowel disease, lupus erythematosus, myasthenia gravis, opsoclonus myoclonus syndrome (OMS), optic neuritis, ord's thyroiditiSjOstheoarthritis, uveoretinitis, pemphigus, polyarthritis, primary biliary cirrhosis, reiter's syndrome, takayasu's arteritis, temporal arteritis, warm autoimmune hemolytic anemia, Wegener's granulomatosis, alopecia universalis, chagas[1] disease, chronic fatigue syndrome, dysautonomia, endometriosis, hidradenitis suppurativa, interstitial cystitis, neuromyotonia, sarcoidosis, scleroderma, ulcerative colitis, vitiligo, vulvodynia, appendicitis, arteritis, arthritis, blepharitis, bronchiolitis, bronchitis, cervicitis, cholangitis, cholecystitis, chorioamnionitis, colitis, conjunctivitis, cystitis, dacryoadenitis, dermatomyositis, endocarditis, endometritis, enteritis, enterocolitis, epicondylitis, epididymitis, fasciitis, fibrositis, gastritis, gastroenteritis, gingivitis, hepatitis, hidradenitis, ileitis, iritis, laryngitis, mastitis, meningitis, myelitis, myocarditis, myositis, nephritis, omphalitis, oophoritis, orchitis, osteitis, otitis, pancreatitis, parotitis, pericarditis, peritonitis, pharyngitis, pleuritis, phlebitis, pneumonitis, proctitis, prostatitis, pyelonephritis, rhinitis, salpingitis, sinusitis, stomatitis, synovitis, tendonitis, tonsillitis, uveitis, vaginitis, vasculitis, or vulvitis.

The invention also relates to a method of treating a cardiovascular disease in a mammal that comprises administering to said mammal a therapeutically effective amount of a compound of the present invention, or a pharmaceutically acceptable salt, ester, prodrug, solvate, hydrate or derivative thereof. Examples of cardiovascular conditions include, but are not limited to, atherosclerosis, restenosis, vascular occlusion and carotid obstructive disease.

In another aspect, the present invention provides methods of disrupting the function of a leukocyte or disrupting a function of an osteoclast. The method includes contacting the leukocyte or the osteoclast with a function disrupting amount of a compound of the invention.

In another aspect of the present invention, methods are provided for treating ophthalmic disease by administering one or more of the subject compounds or pharmaceutical compositions to the eye of a subject.

The invention further provides methods of modulating kinase activity by contacting a kinase with an amount of a compound of the invention sufficient to modulate the activity of the kinase. Modulate can be inhibiting or activating kinase activity. In some embodiments, the invention provides methods of inhibiting kinase activity by contacting a kinase with an amount of a compound of the invention sufficient to inhibit the activity of the kinase. In some embodiments, the invention provides methods of inhibiting kinase activity in a solution by contacting said solution with an amount of a compound of the invention sufficient to inhibit the activity of the kinase in said solution. In some embodiments, the invention provides methods of inhibiting kinase activity in a cell by contacting said cell with an amount of a compound of the invention sufficient to inhibit the activity of the kinase in said cell. In some embodiments, the invention provides methods of inhibiting kinase activity in a tissue by contacting said tissue with an amount of a compound of the invention sufficient to inhibit the activity of the kinase in said tissue. In some embodiments, the invention provides methods of inhibiting kinase activity in an organism by contacting said organism with an amount of a compound of the invention sufficient to inhibit the activity of the kinase in said organism. In some embodiments, the invention provides methods of inhibiting kinase activity in an animal by contacting said animal with an amount of a compound of the invention sufficient to inhibit the activity of the kinase in said animal. In some embodiments, the invention provides methods of inhibiting kinase activity in a mammal by contacting said mammal with an amount of a compound of the invention sufficient to inhibit the activity of the kinase in said mammal. In some embodiments, the invention provides methods of inhibiting kinase activity in a human by contacting said human with an amount of a compound of the invention sufficient to inhibit the activity of the kinase in said human. In some embodiments, the % of kinase activity after contacting a kinase with a compound of the invention is less than 1, 5, 10, 20, 30, 40, 50, 60, 70, 80, 90, 95, or 99% of the kinase activity in the absence of said contacting step.

In some embodiments, the kinase is a lipid kinase or a protein kinase. In some embodiments, the kinase is selected from the group consisting of PI3 kinase including different isoforms such as PI3 kinase α, PI3 kinase β, PI3 kinase γ, PI3 kinase δ; DNA-PK; mTor; AbI, VEGFR, Ephrin receptor B4 (EphB4); TEK receptor tyrosine kinase (HE2); FMS-related tyrosine kinase 3 (FLT-3); Platelet derived growth factor receptor (PDGFR); RET; ATM; ATR; hSmg-1; Hck; Src; Epidermal growth factor receptor (EGFR); KIT; Insulin Receptor (IR) and IGFR.

The invention further provides methods of modulating PI3 kinase activity by contacting a PI3 kinase with an amount of a compound of the invention sufficient to modulate the activity of the PI3 kinase. Modulate can be inhibiting or activating PI3 kinase activity. In some embodiments, the invention provides methods of inhibiting PI3 kinase activity by contacting a PI3 kinase with an amount of a compound of the invention sufficient to inhibit the activity of the PI3 kinase. In some embodiments, the invention provides methods of inhibiting PI3 kinase activity. Such inhibition can take place in solution, in a cell expressing one or more PI3 kinases, in a tissue comprising a cell expressing one or more PI3 kinases, or in an organism expressing one or more PI13 kinases. In some embodiments, the invention provides methods of inhibiting PI3 kinase activity in an animal (including mammal such as humans) by contacting said animal with an amount of a compound of the invention sufficient to inhibit the activity of the PI3 kinase in said animal.

The ability of the compounds of the invention to treat arthritis can be demonstrated in a murine collagen-induced arthritis model [Kakimoto, et al., Cell. Immunol., 142:326-337 (1992)], in a rat collagen-induced arthritis model [Knoerzer, et al., Toxicol. Pathol., 25:13-19-(1997)], in a rat adjuvant arthritis model [Halloran, et al., Arthritis Rheum., 39:810-819 (1996)], in a rat streptococcal cell wall-induced arthritis model [Schimmer, et al., J. Immunol., 160:1466-1477 (1998)], or in a SCID-mouse human rheumatoid arthritis model [Oppenheimer-Marks, et al., J. Clin. Invest., 101: 1261-1272(1998)].

The ability of the compounds of the invention to treat Lyme arthritis can be demonstrated according to the method of Gross, et al., Science, 218:703-706, (1998).

The ability of the compounds of the invention to treat asthma can be demonstrated in a murine allergic asthma model according to the method of Wegner, et al., Science, 247:456-459 (1990), or in a murine non-allergic asthma model according to the method of Bloemen, et al, Am. J. Respir. Crit. Care Med., 153:521-529 (1996).

The ability of the compounds of the invention to treat inflammatory lung injury can be demonstrated in a murine oxygen-induced lung injury model according to the method of Wegner, et al., Lung, 170:267-279 (1992), in a murine immune complex-induced lung injury model according to the method of Mulligan, et al., J. Immunol., 154:1350-1363 (1995), or in a murine acid-induced lung injury model according to the method of Nagase, et al., Am. J. Respir. Crit. Care Med., 154:504-510(1996).

The ability of the compounds of the invention to treat inflammatory bowel disease can be demonstrated in a murine chemical-induced colitis model according to the method of Bennett, et al., J. Pharmacol. Exp. Ther., 280:988-1000 (1997).

The ability of the compounds of the invention to treat autoimmune diabetes can be demonstrated in an NOD mouse model according to the method of Hasagawa, et al., Int. Immunol., 6:831-838 (1994), or in a murine streptozotocin-induced diabetes model according to the method of Herrold, et al., Cell Immunol., 157:489-500 (1994).

The ability of the compounds of the invention to treat inflammatory liver injury can be demonstrated in a murine liver injury model according to the method of Tanaka, et al., J. Immunol., 151:5088-5095 (1993).

The ability of the compounds of the invention to treat inflammatory glomerular injury can be demonstrated in a rat nephrotoxic serum nephritis model according to the method of Kawasaki, et al., J. Immunol., 150: 1074-1083 (1993).

The ability of the compounds of the invention to treat radiation-induced enteritis can be demonstrated in a rat abdominal irradiation model according to the method of Panes, et al., Gastroenterology, 108:1761-1769 (1995).

The ability of the PI3K delta selective inhibitors to treat radiation pneumonitis can be demonstrated in a murine pulmonary irradiation model according to the method of Hallahan, et al., Proc. Natl. Acad. Sci (USA), 94:6432-6437 (1997).

The ability of the compounds of the invention to treat reperfusion injury can be demonstrated in the isolated heart according to the method of Tamiya, et al., Immunopharmacology, 29:53-63 (1995), or in the anesthetized dog according to the model of Hartman, et al., Cardiovasc. Res., 30:47-54 (1995).

The ability of the compounds of the invention to treat pulmonary reperfusion injury can be demonstrated in a rat lung allograft reperfusion injury model according to the method of DeMeester, et al., Transplantation, 62:1477-1485 (1996), or in a rabbit pulmonary edema model according to the method of Horgan, et al., Am. J. Physiol., 261:H1578-H1584 (1991).

The ability of the compounds of the invention to treat stroke can be demonstrated in a rabbit cerebral embolism stroke model according to the method of Bowes, et al., Exp. Neurol., 119:215-219 (1993), in a rat middle cerebral artery ischemia-reperfusion model according to the method of Chopp, et al., Stroke, 25:869-875 (1994), or in a rabbit reversible spinal cord ischemia model according to the method of Clark, et al., Neurosurg., 75:623-627 (1991).

The ability of the compounds of the invention to treat cerebral vasospasm can be demonstrated in a rat experimental vasospasm model according to the method of Oshiro, et al., Stroke, 28:2031-2038 (1997).

The ability of the compounds of the invention to treat peripheral artery occlusion can be demonstrated in a rat skeletal muscle ischemia/reperfusion model according to the method of Gute, et al., Mol. Cell Biochem., 179:169-187 (1998).

The ability of the compounds of the invention to treat graft rejection can be demonstrated in a murine cardiac allograft rejection model according to the method of Isobe, et al., Science, 255:1125-1127 (1992), in a murine thyroid gland kidney capsule model according to the method of Talento, et al., Transplantation, 55:418-422 (1993), in a cynomolgus monkey renal allograft model according to the method of Cosimi, et al., J. Immunol., 144:4604-4612 (1990), in a rat nerve allograft model according to the method of Nakao, et al., Muscle Nerve, 18:93-102 (1995), in a murine skin allograft model according to the method of Gorczynski and Wojcik, J. Immunol., 152:2011-2019 (1994), in a murine corneal allograft model according to the method of He, et al., Opthalmol. Vis. Sci., 35:3218-3225 (1994), or in a xenogeneic pancreatic islet cell transplantation model according to the method of Zeng, et al., Transplantation, 58:681-689 (1994).

The ability of the compounds of the invention to treat graft-versus-host disease (GVHD) can be demonstrated in a murine lethal GVHD model according to the method of Harning, et al., Transplantation, 52:842-845 (1991).

The ability of the compounds of the invention to treat cancers can be demonstrated in a human lymphoma metastasis model (in mice) according to the method of Aoudjit, et al., J. Immunol., 161:2333-2338 (1998).

Combination Treatment

The present invention also provides methods for combination therapies in which an agent known to modulate other pathways, or other components of the same pathway, or even overlapping sets of target enzymes are used in combination with a compound of the present invention, or a pharmaceutically acceptable salt, ester, prodrug, solvate, hydrate or derivative thereof. In one aspect, such therapy includes but is not limited to the combination of the subject compound with chemotherapeutic agents, therapeutic antibodies, and radiation treatment, to provide a synergistic or additive therapeutic effect.

In one aspect, the compounds or pharmaceutical compositions of the present invention may present synergistic or additive efficacy when administered in combination with agents that inhibit IgE production or activity. Such combination can reduce the undesired effect of high level of IgE associated with the use of one or more PI3Kδ inhibitors, if such effect occurs. This may be particularly useful in treatment of autoimmune and inflammatory disorders (AIID) such as rheumatoid arthritis. Additionally, the administration of PI3Kδ or PI3Kδ/γ inhibitors of the present invention in combination with inhibitors of mTOR may also exhibit synergy through enhanced inhibition of the PI3K pathway.

In a separate but related aspect, the present invention provides a combination treatment of a disease associated with PI3Kδ comprising administering a PI3Kδ inhibitor and an agent that inhibits IgE production or activity. Other exemplary PI3Kδ inhibitors are applicable for this combination and they are described, e.g., U.S. Pat. No. 6,800,620. Such combination treatment is particularly useful for treating autoimmune and inflammatory diseases (AIID) including but not limited to rheumatoid arthritis.

Agents that inhibit IgE production are known in the art and they include but are not limited to one or more of TEI-9874, 2-(4-(6-cyclohexyloxy-2-naphtyloxy)phenylacetamide)benzoic acid, rapamycin, rapamycin analogs (i.e. rapalogs), TORC1/mTORC1 inhibitors, mTORC2/TORC2 inhibitors, and any other compounds that inhibit TORC1/mTORC1 and mTORC2/TORC2. Agents that inhibit IgE activity include, for example, anti-IgE antibodies such as for example Omalizumab and TNX-901.

For treatment of autoimmune diseases, the subject compounds or pharmaceutical compositions can be used in combination with commonly prescribed drugs including but not limited to Enbrel®, Remicade®, Humira®, Avonex®, and Rebif®. For treatment of respiratory diseaseses, the subject compounds or pharmaceutical compositions can be administered in combination with commonly prescribed drugs including but not limited to Xolair®, Advair®, Singulair®, and Spiriva®.

The compounds of the invention may be formulated or administered in conjunction with other agents that act to relieve the symptoms of inflammatory conditions such as encephalomyelitis, asthma, and the other diseases described herein. These agents include non-steroidal anti-inflammatory drugs (NSAIDs), e.g. acetylsalicylic acid; ibuprofen; naproxen; indomethacin; nabumetone; tolmetin; etc. Corticosteroids are used to reduce inflammation and suppress activity of the immune system. The most commonly prescribed drug of this type is Prednisone. Chloroquine (Aralen) or hydroxychloroquine (Plaquenil) may also be very useful in some individuals with lupus. They are most often prescribed for skin and joint symptoms of lupus. Azathioprine (Imuran) and cyclophosphamide (Cytoxan) suppress inflammation and tend to suppress the immune system. Other agents, e.g. methotrexate and cyclosporin are used to control the symptoms of lupus. Anticoagulants are employed to prevent blood from clotting rapidly. They range from aspirin at very low dose which prevents platelets from sticking, to heparin/coumadin.

In another one aspect, this invention also relates to a pharmaceutical composition for inhibiting abnormal cell growth in a mammal which comprises an amount of a compound of the present invention, or a pharmaceutically acceptable salt, ester, prodrug, solvate, hydrate or derivative thereof, in combination with an amount of an anti-cancer agent (e.g. a chemotherapeutic agent). Many chemotherapeutics are presently known in the art and can be used in combination with the compounds of the invention.

In some embodiments, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens. Non-limiting examples are chemotherapeutic agents, cytotoxic agents, and non-peptide small molecules such as Gleevec (Imatinib Mesylate), Velcade (bortezomib), Iressa (gefitinib), Sprycel (Dasatinib), and Adriamycin as well as a host of chemotherapeutic agents. Non-limiting examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, Casodex™, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, pκ)tfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK.R™-; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside (“Ara-C”); cyclophosphamide; thiotepa; taxanes, e.g. paclitaxel (TAXOL™, Bristol-Myers Squibb Oncology, Princeton, N.J.) and docetaxel (TAXOTERE™, Rhone-Poulenc Rorer, Antony, France); retinoic acid; esperamicins; capecitabine; and pharmaceutically acceptable salts, acids or derivatives of any of the above. Also included as suitable chemotherapeutic cell conditioners are anti-hormonal agents that act to regulate or inhibit hormone action on tumors such as anti-estrogens including for example tamoxifen (Nolvadex™), raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide (Casodex), leuprolide, and goserelin (Zoladex); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; camptothecin-11 (CPT-11); topoisomerase inhibitor RFS 2000; difluoromethylornithine (DMFO), 17α-Ethinylestradiol, Diethylstilbestrol, Testosterone, Prednisone, Fluoxymesterone, Megestrolacetate, Methylprednisolone, Methyl-testosterone, Prednisolone, Triamcinolone, chlorotrianisene, Hydroxyprogesterone, Aminoglutethimide, Medroxyprogesteroneacetate, matrix metalloproteinase inhibitors, EGFR inhibitors, Pan Her inhibitors, VEGF inhibitors, including as anti-VEGF antibodies such as Avastin, and small molecules such as ZD6474 and SU6668, vatalanib, BAY-43-9006, SU11248, CP-547632, and CEP-7055. Anti-Her2 antibodies (such as Herceptin from Genentech) may also be utilized. Suitable EGFR inhibitors include gefitinib, erlotinib, and cetuximab. Pan Her inhibitors include canertinib, EKB-569, and GW-572016. Further suitable anticancer agents include, but are not limited to, Src inhibitors, MEK-1 kinase inhibitors, MAPK kinase inhibitors, PI3 kinase inhibitors, and PDGF inhibitors, such as imatinib. Also included are anti-angiogenic and antivascular agents which, by interrupting blood flow to solid tumors, render cancer cells quiescent by depriving them of nutrition. Castration which also renders androgen dependent carcinomas non-proliferative, may also be utilized. Also included are IGF1R inhibitors, inhibitors of non-receptor and receptor tyrosine kinases, and inhibitors of integrin signalling. Additional anticancer agents include microtubule-stabilizing agents 7-O-methylthiomethylpaclitaxel (disclosed in U.S. Pat. No. 5,646,176), 4-desacetyl-4-methylcarbonatepaclitaxel, 3'-tert-butyl-3'-N-tert-butyloxycarbonyl-4-desacetyl-3'-dephenyl-3'-N-debenzoyl-4-O-methoxycarbonyl-paclitaxel (disclosed in U.S. Ser. No. 09/712,352 filed on Nov. 14, 2000), C-4 methyl carbonate paclitaxel, epothilone A, epothilone B, epothilone C, epothilone D, desoxyepothilone A, desoxyepothilone B, [1S-[1R*,3R*(E),7R*,10S*,11R*,12R*,16S*]]-7-11-dihydroxy-8,8,10,12,16-pentamethyl-3-[1-methyl-2-(2-methyl-4-thiazolyl)ethenyl]-4-aza-17 oxabicyclo[14.1.0]heptadecane-5,9-dione (disclosed in WO 99/02514), [1S-[1R*,3R*(E),7R*,10S*,11R*,12R*,16S*]]-3-[2-[2-(aminomethyl)-4-thiazolyl]-1-methyl ethenyl]-7,11-dihydroxy-8,8,10,12,16-pentamethyl-4-17-dioxabicyclo[14.1.0]-heptadecane-5,-9-dione (as disclosed in U.S. Pat. No. 6,262,094) and derivatives thereof; and microtubule-disruptor agents. Also suitable are CDK inhibitors, an antiproliferative cell cycle inhibitor, epidophyllotoxin; an antineoplastic enzyme; biological response modifiers; growth inhibitors; antihormonal therapeutic agents; leucovorin; tegafur; and haematopoietic growth factors.

Additional cytotoxic agents include, hexamethyl melamine, idatrexate, L-asparaginase, camptothecin, topotecan, pyridobenzoindole derivatives, interferons, and interleukins. Where desired, the compounds or pharmaceutical composition of the present invention can be used in combination with commonly prescribed anti-cancer drugs such as Herceptin®, Avastin®, Erbitux®, Rituxan®, Taxol®, Arimidex®, Taxotere®, and Velcade®

This invention further relates to a method for using the compounds or pharmaceutical composition in combination with radiation therapy in inhibiting abnormal cell growth or treating the hyperproliferative disorder in the mammal. Techniques for administering radiation therapy are known in the art, and these techniques can be used in the combination therapy described herein. The administration of the compound of the invention in this combination therapy can be determined as described herein.

Radiation therapy can be administered through one of several methods, or a combination of methods, including without limitation external-beam therapy, internal radiation therapy, implant radiation, stereotactic radiosurgery, systemic radiation therapy, radiotherapy and permanent or temporary interstitial brachytherapy. The term "brachytherapy," as used herein, refers to radiation therapy delivered by a spatially confined radioactive material inserted into the body at or near a tumor or other proliferative tissue disease site. The term is intended without limitation to include exposure to radioactive isotopes (e.g. At-211, 1-131, 1-125, Y-90, Re-186, Re-188, Sm-153, Bi-212, P-32, and radioactive isotopes of Lu). Suitable radiation sources for use as a cell conditioner of the present invention include both solids and liquids. By way of non-limiting example, the radiation source can be a radionuclide, such as 1-125, 1-131, Yb-169, Ir-192 as a solid source, 1-125 as a solid source, or other radionuclides that emit photons, beta particles, gamma radiation, or other therapeutic rays. The radioactive material can also be a fluid made from any 5 solution of radionuclides), e.g., a solution of 1-125 or 1-131, or a radioactive fluid can be produced using a slurry of a suitable fluid containing small particles of solid radionuclides, such as Au-198, Y-90. Moreover, the radionuclide(s) can be embodied in a gel or radioactive micro spheres.

Without being limited by any theory, the compounds of the present invention can render abnormal cells more sensitive to treatment with radiation for purposes of killing and/or inhibiting the growth of such cells. Accordingly, this invention further relates to a method for sensitizing abnormal cells in a mammal to treatment with radiation which comprises administering to the mammal an amount of a compound of the present invention or pharmaceutically acceptable salt, ester, prodrug, solvate, hydrate or derivative thereof, which amount is effective is sensitizing abnormal cells to treatment with radiation. The amount of the compound, salt, or solvate in this method can be determined according to the means for ascertaining effective amounts of such compounds described herein.

The compounds or pharmaceutical compositions of the present invention can be used in combination with an amount of one or more substances selected from anti-angiogenesis agents, signal transduction inhibitors, and antiproliferative agents.

Anti-angiogenesis agents, such as MMP-2 (matrix-metalloprotienase 2) inhibitors, MMP-9 (matrix-metalloprotienase 9) inhibitors, and COX—H (cyclooxygenase 11) inhibitors, can be used in conjunction with a compound of the present invention and pharmaceutical compositions described herein. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931, 788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain Patent Application No. 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780, 386 (published Jun. 25, 1997), all of which are incorporated herein in their entireties by reference. Preferred MMP-2 and MMP-9 inhibitors are those that have little or no activity inhibiting MMP-I. More preferred, are those that selectively inhibit MMP-2 and/or AMP-9 relative to the other matrix-metalloproteinases (i. e., MAP-1, MMP-3, MMP-4, MMP-5, MMP-6, MMP-7, MMP-8, MMP-10, MMP-11, MMP-12, and MMP-13). Some specific examples of MMP inhibitors useful in the present invention are AG-3340, RO 32-3555, and RS 13-0830.

The invention also relates to a method of and to a pharmaceutical composition of treating a cardiovascular disease in a mammal which comprises an amount of a compound of the present invention, or a pharmaceutically acceptable salt, ester, prodrug, solvate, hydrate or derivative thereof, or an isotopically-labeled derivative thereof, and an amount of one or more therapeutic agents use for the treatment of cardiovascular diseases.

Examples for use in cardiovascular disease applications are anti-thrombotic agents, e.g., prostacyclin and salicylates, thrombolytic agents, e.g., streptokinase, urokinase, tissue plasminogen activator (TPA) and anisoylated plasminogen-streptokinase activator complex (APSAC), anti-platelets agents, e.g., acetyl-salicylic acid (ASA) and clopidrogel, vasodilating agents, e.g., nitrates, calcium channel blocking drugs, antiproliferative agents, e.g., colchicine and alkylating agents, intercalating agents, growth modulating factors such as interleukins, transformation growth factor-beta and congeners of platelet derived growth factor, monoclonal antibodies directed against growth factors, anti-inflammatory agents, both steroidal and non-steroidal, and other agents that can modulate vessel tone, function, arteriosclerosis, and the healing response to vessel or organ injury post intervention. Antibiotics can also be included in combinations or coatings comprised by the invention. Moreover, a coating can be used to effect therapeutic delivery focally within the vessel wall. By incorporation of the active agent in a swellable polymer, the active agent will be released upon swelling of the polymer.

Other exemplary therapeutic agents useful for a combination therapy include but are not limited to agents as described above, radiation therapy, hormone antagonists, hormones and their releasing factors, thyroid and antithyroid drugs, estrogens and progestins, androgens, adrenocorticotropic hormone; adrenocortical steroids and their synthetic analogs; inhibitors of the synthesis and actions of adrenocortical hormones, insulin, oral hypoglycemic agents, and the pharmacology of the endocrine pancreas, agents affecting calcification and bone turnover: calcium, phosphate, parathyroid hormone, vitamin D, calcitonin, vitamins such as water-soluble vitamins, vitamin B complex, ascorbic acid, fat-soluble vitamins, vitamins A, K, and E, growth factors, cytokines, chemokines, muscarinic receptor agonists and antagonists; anticholinesterase agents; agents acting at the neuromuscular junction and/or autonomic ganglia; catecholamines, sympathomimetic drugs, and adrenergic receptor agonists or antagonists; and 5-hydroxytryptamine (5-HT, serotonin) receptor agonists and antagonists.

Therapeutic agents can also include agents for pain and inflammation such as histamine and histamine antagonists, bradykinin and bradykinin antagonists, 5-hydroxytryptamine (serotonin), lipid substances that are generated by biotransformation of the products of the selective hydrolysis of membrane phospholipids, eicosanoids, prostaglandins, thromboxanes, leukotrienes, aspirin, nonsteroidal anti-inflammatory agents, analgesic-antipyretic agents, agents that inhibit the synthesis of prostaglandins and thromboxanes, selective inhibitors of the inducible cyclooxygenase, selective inhibitors of the inducible cyclooxygenase-2, autacoids, paracrine hormones, somatostatin, gastrin, cytokines that mediate interactions involved in humoral and cellular immune responses, lipid-derived autacoids, eicosanoids, β-adrenergic agonists, ipratropium, glucocorticoids, methylxanthines, sodium channel blockers, opioid receptor agonists, calcium channel blockers, membrane stabilizers and leukotriene inhibitors.

Additional therapeutic agents contemplated herein include diuretics, vasopressin, agents affecting the renal conservation of water, rennin, angiotensin, agents useful in the treatment of myocardial ischemia, anti-hypertensive agents, angiotensin converting enzyme inhibitors, β-adrenergic receptor antagonists, agents for the treatment of hypercholesterolemia, and agents for the treatment of dyslipidemia.

Other therapeutic agents contemplated include drugs used for control of gastric acidity, agents for the treatment of peptic ulcers, agents for the treatment of gastroesophageal reflux disease, prokinetic agents, antiemetics, agents used in irritable bowel syndrome, agents used for diarrhea, agents used for constipation, agents used for inflammatory bowel disease, agents used for biliary disease, agents used for pancreatic disease. Therapeutic agents used to treat protozoan infections, drugs used to treat Malaria, Amebiasis, Giardiasis, Trichomoniasis, Trypanosomiasis, and/or Leishmaniasis, and/or drugs used in the chemotherapy of helminthiasis. Other therapeutic agents include antimicrobial agents, sulfonamides, trimethoprim-sulfamethoxazole quinolones, and agents for urinary tract infections, penicillins, cephalosporins, and other, β-Lactam antibiotics, an agent comprising an aminoglycoside, protein synthesis inhibitors, drugs used in the chemotherapy of tuberculosis, *mycobacterium avium* complex disease, and leprosy, antifungal agents, antiviral agents including nonretroviral agents and antiretroviral agents.

Examples of therapeutic antibodies that can be combined with a subject compound include but are not limited to anti-receptor tyrosine kinase antibodies (cetuximab, panitumumab, trastuzumab), anti CD20 antibodies (rituximab, tositumomab), and other antibodies such as alemtuzumab, bevacizumab, and gemtuzumab.

Moreover, therapeutic agents used for immunomodulation, such as immunomodulators, immunosuppressive agents, tolerogens, and immunostimulants are contemplated by the methods herein. In addition, therapeutic agents acting on the blood and the blood-forming organs, hematopoietic agents, growth factors, minerals, and vitamins, anticoagulant, thrombolytic, and antiplatelet drugs.

Further therapeutic agents that can be combined with a subject compound may be found in Goodman and Gilman's "The Pharmacological Basis of Therapeutics" Tenth Edition edited by Hardman, Limbird and Gilman or the Physician's Desk Reference, both of which are incorporated herein by reference in their entirety.

The compounds described herein can be used in combination with the agents disclosed herein or other suitable agents, depending on the condition being treated. Hence, in some embodiments the compounds of the invention will be co-administered with other agents as described above. When used in combination therapy, the compounds described herein may be administered with the second agent simultaneously or separately. This administration in combination can include simultaneous administration of the two agents in the same dosage form, simultaneous administration in separate dosage forms, and separate administration. That is, a compound described herein and any of the agents described above can be formulated together in the same dosage form and administered simultaneously. Alternatively, a compound of the present invention and any of the agents described above can be simultaneously administered, wherein both the agents are present in separate formulations. In another alternative, a compound of the present invention can be administered just followed by and any of the agents described above, or vice versa. In the separate administration protocol, a compound of the present invention and any of the agents described above may be administered a few minutes apart, or a few hours apart, or a few days apart.

The methods in accordance with the invention may include administering a PI3-kinase δ selective inhibitor with one or more other agents that either enhance the activity of the inhibitor or compliment its activity or use in treatment. Such additional factors and/or agents may produce an augmented or even synergistic effect when administered with a PI3-kinase δ selective inhibitor, or minimize side effects.

In one embodiment, the methods of the invention may include administering formulations comprising a PI3-kinase δ selective inhibitor of the invention with a particular cytokine, lymphokine, other hematopoietic factor, thrombolytic or anti-thrombotic factor, or anti-inflammatory agent before, during, or after administration of the PI3-kinase δ selective inhibitor. One of ordinary skill can easily determine if a particular cytokine, lymphokine, hematopoietic factor, thrombolytic of anti-thrombotic factor, and/or anti-inflammatory agent enhances or compliments the activity or use of the PI3-kinase δ selective inhibitors in treatment.

More specifically, and without limitation, the methods of the invention may comprise administering a PI3-kinase δ selective inhibitor with one or more of TNF, IL-1, IL-2, IL-3, IL4, IL-5, IL-6, IL-7, IL-8, IL-9, IL-10, IL-11, IL-12, IL-13, IL-14, IL-15, IL-16, IL-17, IL-18, IFN, G-CSF, Meg-CSF, GM-CSF, thrombopoietin, stem cell factor, and erythropoietin. Compositions in accordance with the invention may also include other known angiopoietins such as Ang-2, Ang4, and Ang-Y, growth factors such as bone morphogenic protein-1, bone morphogenic protein-2, bone morphogenic protein-3, bone morphogenic protein-4, bone morphogenic protein-5, bone morphogenic protein-6, bone morphogenic protein-7, bone morphogenic protein-8, bone morphogenic protein-9, bone morphogenic protein-10, bone morphogenic protein-11, bone morphogenic protein-12, bone morphogenic protein-13, bone morphogenic protein-14, bone morphogenic protein-15, bone morphogenic protein receptor IA, bone morphogenic protein receptor IB, brain derived neurotrophic factor, ciliary neutrophic factor, ciliary neutrophic factor receptor a, cytokine-induced neutrophil chemotactic factor 1, cytokine-induced neutrophil chemotactic factor 2 alpha, cytokine-induced neutrophil chemotactic factor 2 beta, beta endothelial cell growth factor, endothelin 1, epidermal growth factor, epithelial-derived neutrophil attractant, fibroblast growth factor 4, fibroblast growth factor 5, fibroblast growth factor 6, fibroblast growth factor 7, fibroblast growth factor 8, fibroblast growth factor 8b, fibroblast growth factor 8c, fibroblast growth factor 9, fibroblast growth factor 10, fibroblast growth factor acidic, fibroblast growth factor basic, glial cell line-derived neutrophic factor receptor al, glial cell line-derived neutrophic factor receptor a2, growth related protein, growth related protein a, growth related protein .beta., growth related protein .gamma., heparin binding epidermal growth factor, hepatocyte growth factor, hepatocyte growth factor receptor, insulin-like growth factor I, insulin-like growth factor receptor, insulin-like growth factor II, insulin-like growth factor binding protein, keratinocyte growth factor, leukemia inhibitory factor, leukemia inhibitory factor receptor alpha, nerve growth factor, nerve growth factor receptor, neurotrophin-3, neurotrophin-4, placenta growth factor, placenta growth factor 2, platelet derived endothelial cell growth factor, platelet derived growth factor, platelet derived growth factor A chain, platelet derived growth factor AA, platelet derived growth factor AB, platelet derived growth factor B chain, platelet derived growth factor BB, platelet derived growth factor receptor a, platelet derived growth factor receptor beta, pre-B cell growth stimulating factor, stem cell factor, stem cell factor receptor, transforming growth factor alpha, transforming growth factor beta, transforming growth factor beta 1, transforming growth factor beta 1.2, transforming growth factor beta 2, transforming growth factor beta 3, transforming growth factor beta 5, latent transforming growth factor beta 1, transforming growth factor beta binding protein I, transforming growth factor beta binding protein II, transforming growth factor beta binding protein III, tumor necrosis factor receptor type I, tumor necrosis factor receptor type II, urokinase-type plasminogen activator receptor, and chimeric proteins and biologically or immunologically active fragments thereof.

The following general methodology described herein provides the manner and process of making and using the compound of the present invention and are illustrative rather than limiting. Further modification of provided methodology and additionally new methods may also be devised in order to achieve and serve the purpose of the invention. Accordingly, it should be understood that there may be other embodiments which fall within the spirit and scope of the invention as defined by the specification hereto.

Representative compounds of the present invention include those specified above in Table 1 and pharmaceutically acceptable salts thereof. The present invention should not be construed to be limited to them.

General Method of Preparation of Compounds of the Invention

The compounds of the present invention may be prepared by the following processes. Unless otherwise indicated, the variables (e.g., R, $R^1$, $R^2$, $L_1$, $Cy^1$ and $Cy^2$) when used in the below formulae are to be understood to present those groups described above in relation to formula (I). These methods can similarly be applied to other compounds of formula IA, IA-I, IA-II, IA-III and/or IA-IV.

Scheme 1:

This scheme provides a general process for synthesis of a compound of formula (I) wherein all the variables R, $R^1$, $R^2$, $L_1$, $Cy^1$ and $Cy^2$ are as described above in relation to formula (I)

Scheme 1

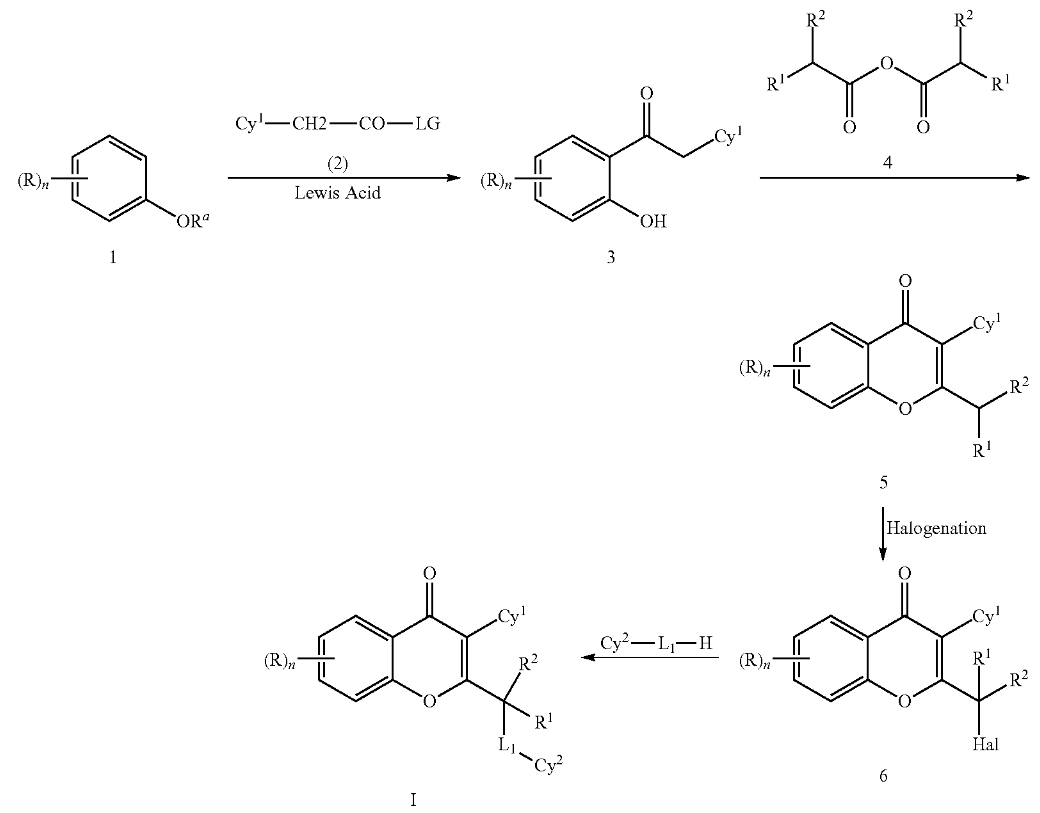

Compound of formula (1) wherein Ra is Hydrogen or alkyl can be converted to compound of formula (3) by reacting with a compound of formula (2) wherein LG is a leaving group such as a halogen or an acyl group in the presence of a lewis acid such as aluminium chloride or boron trifluoride. Compound of formula (3) can be converted to Compound of formula (5) by Kostanecki acylation, i.e., by treating with an anhydride of formula (4), wherein $R^1$ and $R^2$ is hydrogen or substituted or unsubstituted $C_{1-6}$ alkyl in the presence of a base. (See Von Kostanecki, S., Rozycki, A., in Ber. 1901, 34, 102 and by Baker, W. in J. Chem. Soc., 1933, 1381). Compound of formula (5) can then be converted to a compound of formula (6) using a suitable halogenating condition that is known to those skilled in the art. For example, by using bromine in a polar solvent such as acetic acid or N,N-dimethyl formamide or by using a N-halosuccinimide in the presence of a suitable radical initiator such as azabis(isobutyronitrile) or benzoyl peroxide. Compounds of formula (6) can then be reacted with a compound of formula $Cy^2$-$L_1$-H in the presence of a suitable inorganic base such as potassium carbonate or sodium hydride or an organic base such as triethylamine or N,N-diisopropylethylamine to afford the desired compound of formula (I) wherein $R^1$ & $R^2$ are hydrogen or $C_1$-$C_6$ alkyl, $Cy^1$ is monocyclic or bicyclic substituted or unsubstituted aryl and $L_1$, R, and $Cy^2$ are the same as described above in relation to formula (I).

Scheme 1A:

This scheme provides a general process for synthesis of a compound of formula (I) wherein $Cy^1$ is

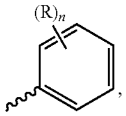

, $Cy^2$ is

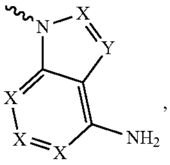

,

X is $CR^a$ or N and all the variables R, $R^1$, $R^2$, $L_1$, and $R^a$ are as described above in relation to formula (I).

Scheme 1A

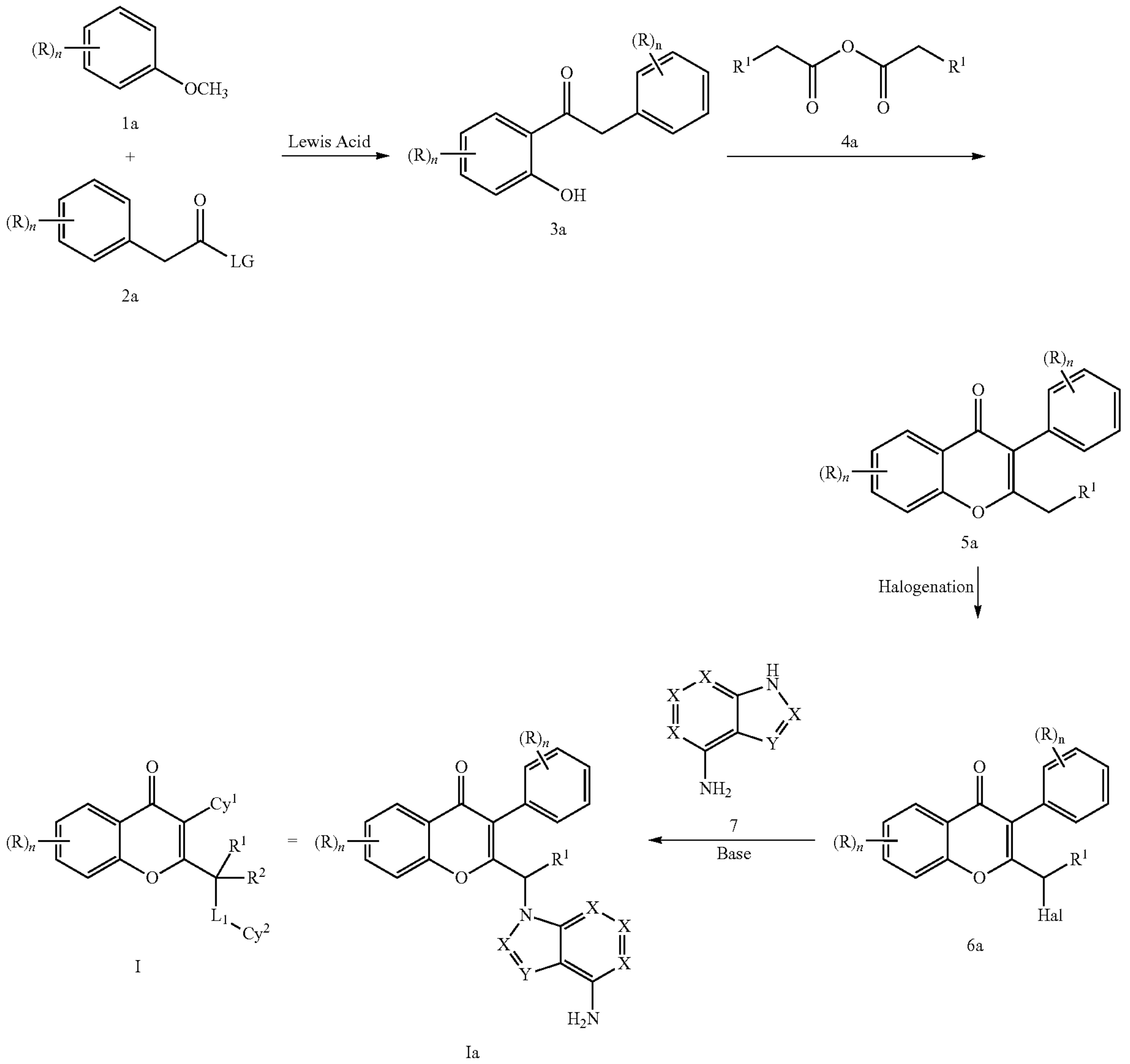

By starting with a suitable anisole derivative (1a) and a phenylacetic acid derivative (2a), compounds of formula (6a) can be synthesised as described in scheme 1 for synthesis of compound of formula (6). Compound of formula (6a) can be reacted with compound of formula (7) wherein X is chosen from CH or N and different occurrence of X can be same or different and Y is chosen from N, CH, C-Hal or C—Ar or C-Het in the presence of a base to afford the desired compound of formula (I) wherein $Cy^1$ is

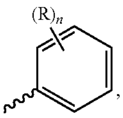

, $Cy^2$ is

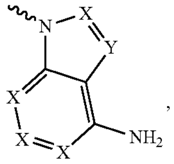

,

X is $CR^a$ or N and all the variables R, $R^1$, $R^2$, $L_1$, and $R^a$ are as described above in relation to formula (I).

Using similar methodologies as described above in Scheme 1 & 1A with certain modifications as known to those skilled in the art can be used to synthesize compounds of formula IA-I and/or IA-II

IA-I

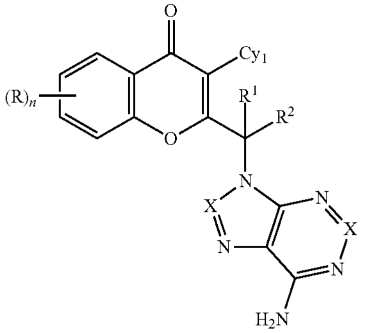

IA-II

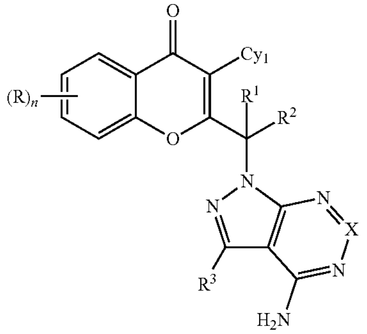

-continued

IA-IV

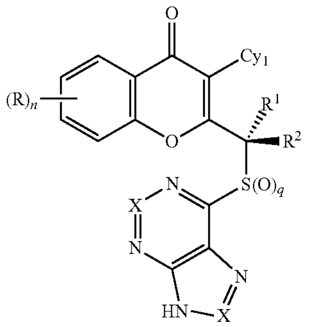

wherein the variables are to be understood to present those groups described above in relation to formula IA-I, IA-II and/or IA-IV using suitable intermediates and reagents For example as illustrated below

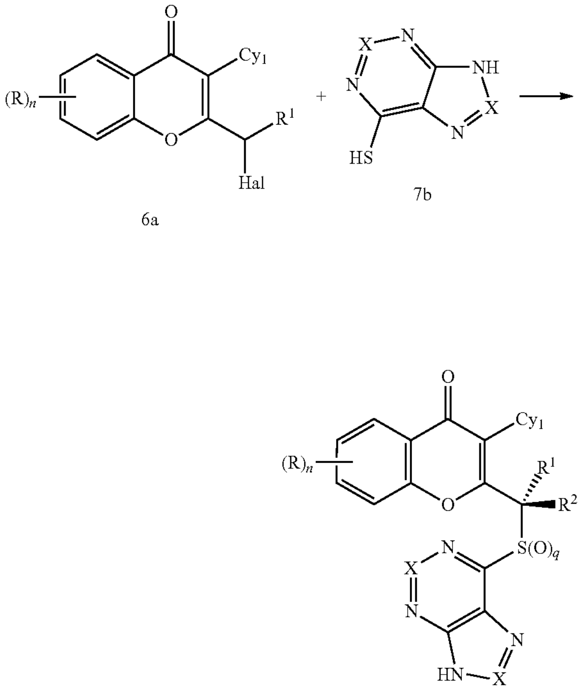

6a 7b

IA-IV

Scheme 1B:

This scheme provides a method for preparation of compound of formula IA-II wherein $R^1$ & $R^2$ are hydrogen or substituted or unsubstituted $C_{1-6}$ alkyl, R3 is substituted or unsubstituted aryl or heteroaryl, $Cy^1$ is monocyclic substituted or unsubstituted aryl and R is the same as described above in relation to formula (I)

Scheme 1B

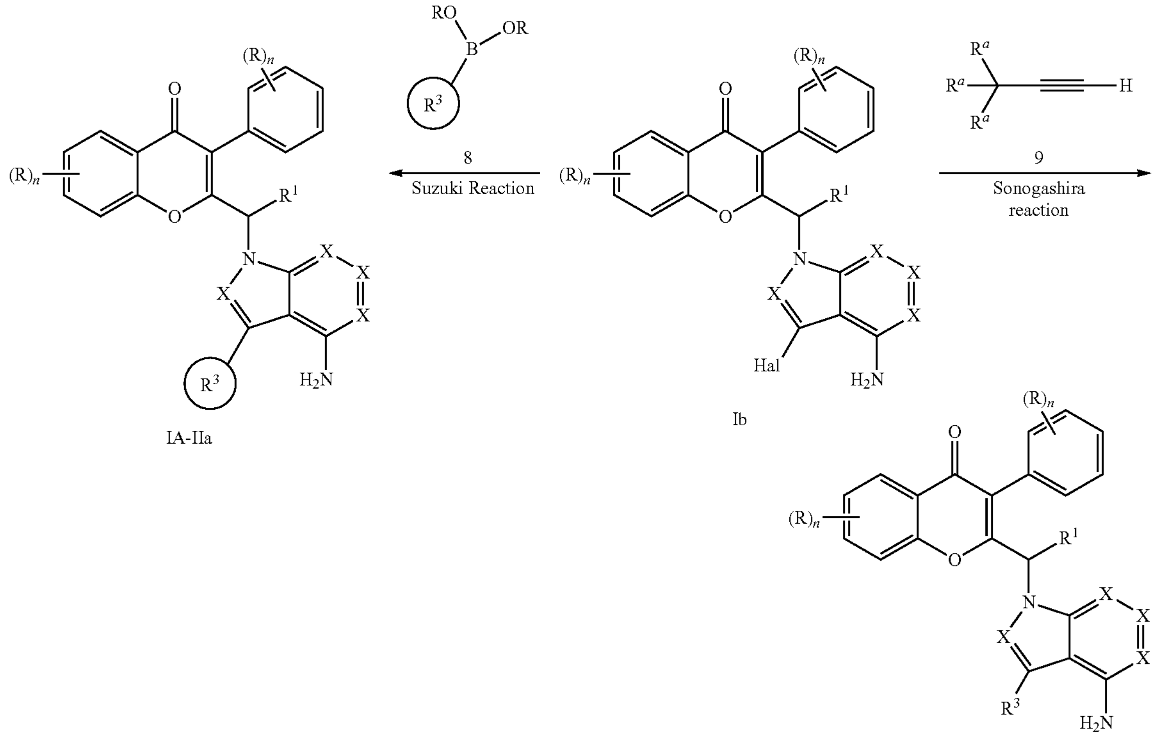

IA-IIa

Ib

IA-IIb

As illustrated in scheme 1B, compound of formula (Ia) wherein Y═C-Hal, i.e., compound of formula (Ib) can be further subjected to a Suzuki reaction to give compound of formula (IA-IIa) wherein $R^3$ is substituted or unsubstituted aryl or heteroaryl. Thus, compound of formula (Ib) can be reacted with a boronic acid or its ester of formula (8), wherein ring $R^3$ is an substituted or unsubstituted aryl or heteroomatic or heteroaromatic ring, in the presence of a suitable palladium catalyst such as tetrakis(triphenylphosphine)palladium (0) or [1,1'-bis(diphenylphosphino)ferrocene]dichloropalladium (II) in the presence of a base such as an alkali metal carbonate to afford compound of formula (IA-IIa). Alternately under Sonogashira reaction conditions, compound of formula (Ib) can be reacted with a compound of formula (9) wherein $R^a$ is the same as described above in relation to formula (I)), in the presence of a palladium catalyst, to give compound of formula (IA-IIb) wherein $R^3$ is substituted or unsubstituted alkynyl. The Suzuki reaction and Sonogashira reaction can be performed under standard thermal conditions or optionally may also be assisted by microwave irradiation.

Scheme 2:

This scheme provides a method for preparation of compound of formula I wherein $R^1$ & $R^2$ are hydrogen or substituted or unsubstituted $C_{1-6}$ alkyl, $Cy^1$ is monocyclic substituted or unsubstituted aryl and $L_1$, R, and $Cy^2$ are the same as described above in relation to formula (I)

Scheme 2

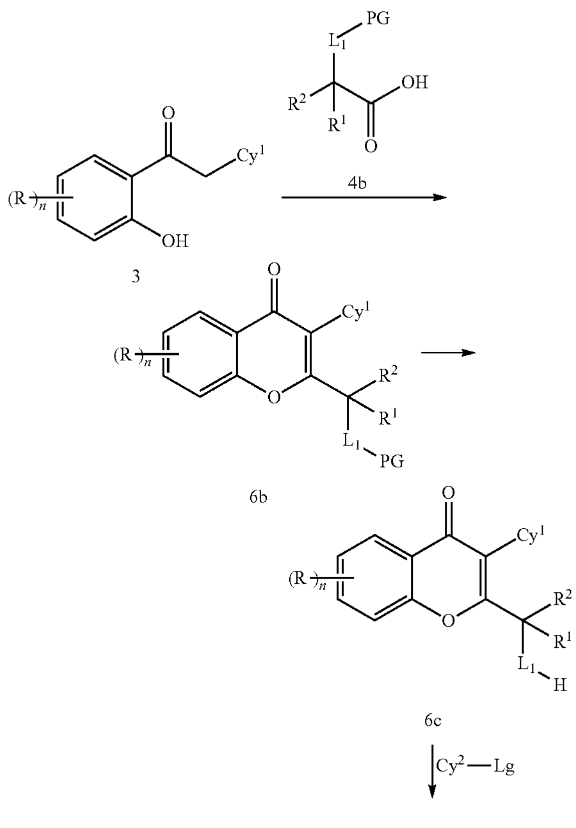

3

6b

6c

-continued

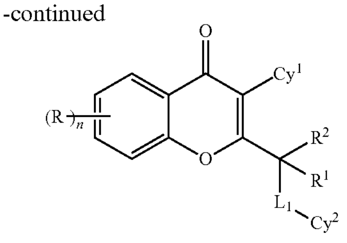

I

Compound of formula (3) can be converted to compound of formula (6b) by reacting with a compound of formula (4b) wherein $L_1$ is a heteroatom containing functional group and PG is a protecting group in the presence of an ester coupling reagent such as 2-(1H-7-azabenzotriazol-1-yl)-1,1,3,3-tetramethyl uronium hexafluorophosphate (HATU) or 2-(1H-benzotriazol-1-yl)-1,1,3,3-tetramethyl uronium hexafluorophosphate (HBTU). Deprotection of compound of formula (6b) can give a compound of formula (6c). Compound of formula (6c) can then be reacted with a compound of formula $Cy^2$-Lg wherein Lg is a good leaving group such as Halogen in the presence of a suitable base such as potassium carbonate or sodium hydride to provide the desired compounds of formula (I) wherein $R^1$ & $R^2$ are hydrogen or substituted or unsubstituted $C_{1-6}$ alkyl, $Cy^1$ is monocyclic substituted or unsubstituted aryl and $L_1$, R, and $Cy^2$ are the same as described above in relation to formula (I)

Scheme 2A:

This scheme provides a method for preparation of compound of formula IA-IIIa wherein $R^1$ & $R^2$ are hydrogen or substituted or unsubstituted $C_{1-6}$ alkyl, $Cy^1$ is substituted or unsubstituted Phenyl, $Cy^2$ is

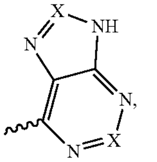

$L_1$ is NH and R, n and $Cy^2$ are the same as described above in relation to formula (IA-III)

Scheme 2A

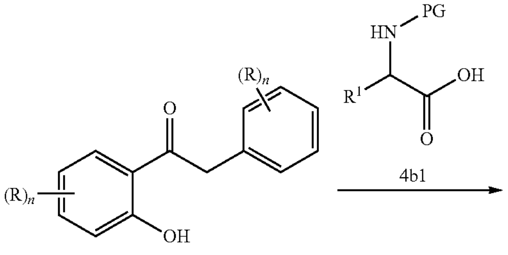

4b1

3a

-continued

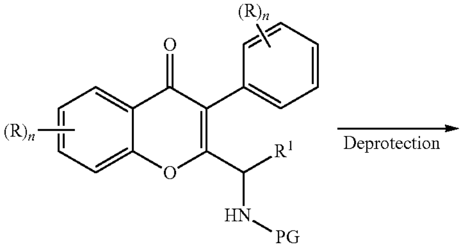

6b1

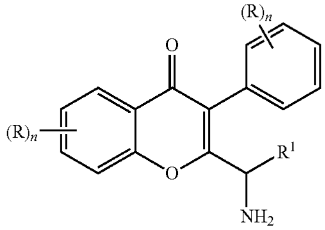

6c1

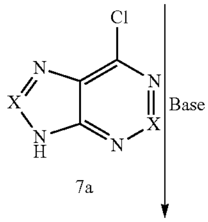

7a

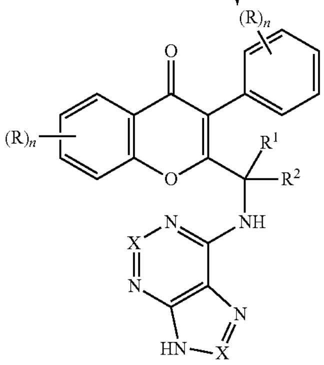

IA-IIIa

The compound of formula (3a) can be reacted with an N-protected amino acid of formula (4b1) in the presence of an ester coupling reagent such as 2-(1H-7-azabenzotriazol-1-yl)-1,1,3,3-tetramethyl uronium hexafluorophosphate (HATU) or 2-(1H-benzotriazol-1-yl)-1,1,3,3-tetramethyl uronium hexafluorophosphate (HBTU) to give compound of formula (6b1). The amine protecting group of (6b1) can be removed to give compound of formula (6c1). Compound of formula (6c1) upon reaction with compound of formula (7a) can give compound of formula (IA-IIIa) wherein $R^1$ & $R^2$ are hydrogen or substituted or unsubstituted $C_{1-6}$ alkyl, $Cy^1$ is substituted or unsubstituted Phenyl, $Cy^2$ is

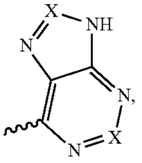

$L_1$ is NH and R, n and $Cy^2$ are the same as described above in relation to formula (IA-III). Optionally the coupling of (6c1) with a compound of formula (7a) may be performed in the absence of a base with the assistance of microwave irradiation.

Using similar methodologies as described above in Scheme 2 & 2A with certain modifications as known to those skilled in the art can be used to synthesize compounds of formula IA-III.

IA-III

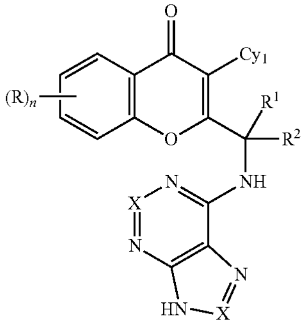

wherein the variables are to be understood to present those groups described above in relation to formula IA-III and/or IA-IV using suitable intermediates and reagents For example as illustrated below

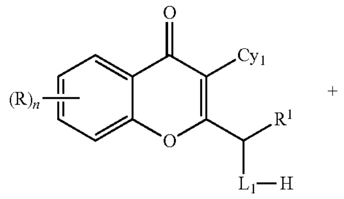

6c
wherein
$L_1$ is NH

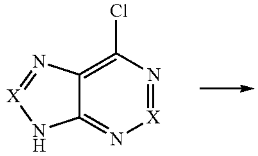

7a

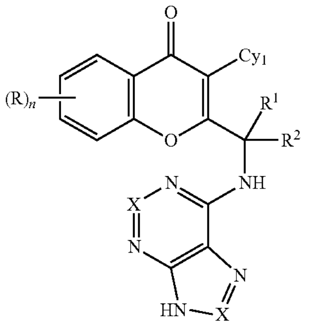

IA-III

EXPERIMENTAL

Unless otherwise mentioned, work-up implies distribution of reaction mixture between the aqueous and organic phases indicated within parenthesis, separation and drying over $Na_2SO_4$ of the organic layer and evaporating the solvent to give a residue. RT implies ambient temperature (25-28° C.).

The terms "solvent," "organic solvent," or "inert solvent" each mean a solvent inert under the conditions of the reaction being described in conjunction therewith including, for example, benzene, toluene, acetonitrile, tetrahydrofuran ("THF"), dimethylformamide ("DMF"), chloroform, methylene chloride (or dichloromethane), diethyl ether, methanol, N-methylpyrrolidone ("NMP"), pyridine and the like. Unless specified to the contrary, the solvents used in the reactions described herein are inert organic solvents. Unless specified to the contrary, for each gram of the limiting reagent, one cc (or ml) of solvent constitutes a volume equivalent.

Isolation and purification of the chemical entities and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples herein below. However, other equivalent separation or isolation procedures can also be used. Unless otherwise stated, purification implies column chromatography using silica gel as the stationary phase and a mixture of petroleum ether (boiling at 60-80° C.) and ethyl acetate or dichloromethane and methanol of suitable polarity as the mobile phases.

When desired, the (R)- and (S)-isomers of the compounds of the present invention, if present, may be resolved by methods known to those skilled in the art, for example by formation of diastereoisomeric salts or complexes which may be separated, for example, by crystallization; via formation of diastereoisomeric derivatives which may be separated, for example, by crystallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. Alternatively, a specific enantiomer may be synthesized by asymmetric synthesis using optically active reagents, substrates, catalysts or solvents, or by converting one enantiomer to the other by asymmetric transformation.

The compounds described herein can be optionally contacted with a pharmaceutically acceptable acid to form the corresponding acid addition salts.

Many of the optionally substituted starting compounds and other reactants are commercially available, e.g., from Sigma Aldrich Chemical Company, Alfa Aesar( ) or can be readily prepared by those skilled in the art using commonly employed synthetic methodology. For instance—various boronic acids which are used can be obtained commercially from various sources.

The compounds of the invention can generally be synthesized by an appropriate combination of generally well known synthetic methods. Techniques useful in synthesizing these chemical entities are both readily apparent and accessible to those of skill in the relevant art, based on the instant disclosure.

The compounds of the invention can be synthesized by an appropriate combination of known synthetic methods in the art. The discussion below is offered to illustrate certain of the diverse methods available for use in making the compounds of the invention and is not intended to limit the scope of reactions or reaction sequences that can be used in preparing the compounds of the present invention.

The examples and preparations provided below further illustrate and exemplify the compounds of the present invention and methods of preparing such compounds. It is to be understood that the scope of the present invention is not limited in any way by the scope of the following examples and preparations. In the following examples molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

Intermediate 1: 1-(5-Bromo-2-hydroxyphenyl)-2-phenylethanone

Phenylacetic acid (1.09 g, 8.0 mmoles) was dissolved in 5 ml dichloromethane. To this mixture, oxalylchloride (1.01 g, 8.0 mmoles) and DMF (3 drops) were added at 0° C. and stirred for 30 min. The solvent was evaporated and dissolved in 5 ml dichloromethane. To this mixture, 4-bromoanisole (1 g, 5.34 mmoles) was added and cooled to 0° C. At 0° C. $AlCl_3$ (1.06 g, 8.0 mmoles) was added and the reaction mixture was warmed to RT and stirred overnight. The reaction mixture was quenched by the addition of 2N HCl and extracted with ethyl acetate, dried over sodium sulphate and concentrated. The crude product was purified by column chromatography to afford the title compound as white solid (1 g, 66% yield). MP: 83-86° C. $^1$H-NMR (δ ppm, $CDCl_3$, 400 MHz): δ 11.56 (s, 1H), 8.01 (d, J=2.2 Hz, 1H), 7.64 (dd, J=8.8, 2.5 Hz, 1H), 7.32 (t, 2H), 7.29 (m, 3H), 6.96 (d, J=8.8 Hz, 1H), 4.43 (s, 2H).

Intermediate 2: 6-Bromo-2-methyl-3-phenyl-4H-chromen-4-one

Intermediate 1 (8.9 g, 30.56 mmoles) was taken in a RB flask and to this acetic anhydride (59 ml) and sodium acetate (17.5 g, 213 mmoles) were added and the mixture was refluxed for 12 h. After cooling to RT, the reaction mixture was quenched by the addition of ice cold water. The solid formed was filtered and washed with water. The product was dried under vacuum to afford the title compound as white solid (9.4 g, 97% yield). MP: 119-121° C. $^1$H-NMR (δ ppm, $CDCl_3$, 400 MHz): δ 8.35 (d, J=2.4 Hz, 1H), 7.75 (dd, J=11.3, 2.4 Hz, 1H), 7.46 (t, 2H), 7.39 (d, J=7.2 Hz, 1H), 7.36 (d, J=8.8 Hz, 1H), 7.28 (m, 2H), 2.32 (s, 3H).

Intermediate 3: 6-Bromo-2-(bromomethyl)-3-phenyl-4H-chromen-4-one

To a solution of Intermediate 2 (4.5 g, 14.27 mmoles) in carbon tetrachloride (60 ml) N-bromosuccinimide (2.5 g, 14.27 mmoles) was added and heated to 80° C. Azobisisobutyronitrile (45 mg) was added to the reaction mixture at 80° C. After 12 h, the reaction mixture was cooled to RT, diluted with dichloromethane and washed with water. The organic layer was dried over sodium sulphate and concentrated under reduced pressure. The crude product was recrystallised from ethyl acetate:petroleum ether (5:95) to afford the title compound as off white solid (3.3 g, 59% yield). MP: 172-175° C. $^1$H-NMR (δ ppm, $CDCl_3$, 400 MHz): δ 8.35 (d, J=2.4 Hz, 1H), 7.80 (dd, J=8.8, 2.4 Hz, 1H), 7.50-7.36 (m, 6H), 4.23 (s, 2H).

Intermediate 4: 2-Methyl-3-phenyl-4H-chromen-4-one

To a solution of intermediate 2 (3 g, 9.51 mmoles) in ethanol (30 ml), ammonium formate (6 g, 95.18 mmoles) and palladium on carbon (10%, 300 mg) were added and the solution was refluxed for 2 h. The solution was filtered through celite, diluted with ethyl acetate, washed with 10% sodium bicarbonate solution (100 ml), dried over sodium sulphate and concentrated to afford the title compound as off-white solid (1.98 g, 86% yield). $^1$H-NMR (δ ppm, $CDCl_3$, 400 MHz): δ 8.17 (dd, J=7.9, 1.4 Hz, 1H), 7.61 (dt, J=8.5, 1.5 Hz, 1H), 7.38-7.28 (m, 5H), 7.25 (m, 2H), 2.25 (s, 3H).

Intermediate 5: 2-(Bromomethyl)-3-phenyl-4H-chromen-4-one

To a solution of intermediate 4 (1.9 g, 8.07 mmoles) in carbon tetrachloride (30 ml) N-bromosuccinimide (1.43 g, 8.07 mmoles) was added and heated to 80° C. Azobisisobutyronitrile (20 mg) was added to the reaction mixture at 80° C. After 12 h, the reaction mixture was cooled to RT, diluted with dichloromethane and washed with water. The organic layer was dried over sodium sulphate and concentrated under reduced pressure to afford the title compound as off white solid (1.62 g, 65% yield). $^1$H-NMR (δ ppm, DMSO-$D_6$, 400 MHz): δ 8.06 (d, J=7.6 Hz, 1H), 7.87 (t, J=7.7 Hz, 1H), 7.71 (d, J=8.5 Hz, 1H), 7.53-7.41 (m, 4H), 7.35 (d, J=6.8 Hz, 2H), 4.37 (s, 2H).

Intermediate 6: 1-(5-Bromo-2-hydroxyphenyl)-2-(4-fluorophenyl)ethanone

4-Fluoro phenylacetic acid (12.3 g, 79.79 mmoles) was dissolved in 30 ml dichloromethane. To this mixture, oxalylchloride (10.17 g, 79.79 mmoles) and DMF (3 drops) were added at 0° C. and stirred for 30 min. The solvent was evaporated and dissolved in 30 ml dichloromethane. To this mixture, 4-bromoanisole (10 g, 53.47 mmoles) was added and cooled to 0° C. At 0° C. $AlCl_3$ (10.6 g, 79.79 mmoles) was added and the reaction mixture was warmed to RT and stirred overnight. The reaction mixture was quenched by the addition of 2N HCl and extracted with ethyl acetate, dried over sodium sulphate and concentrated. The crude product was purified by column chromatography with ethyl acetate:petroleum ether to afford the title compound as white solid (6.1 g, 37% yield. $^1$H-NMR (δ ppm, $CDCl_3$, 400 MHz): δ 12.05 (s, 1H), 7.96 (d, J=2.3 Hz, 1H), 7.58 (dd, J=8.9, 2.4 Hz, 1H), 7.24 (dt, J=5.4, 1.9 Hz, 2H), 7.09 (dt, J=8.6, 2.1 Hz, 2H), 6.79 (d, J=8.7 Hz, 1H), 4.27 (s, 2H).

Intermediate 7: 6-Bromo-3-(4-fluorophenyl)-2-methyl-4H-chromen-4-one

Intermediate 6 (6.1 g, 19.73 mmoles) was taken in a RB flask and to this acetic anhydride (40 ml) and sodium acetate (11.3 g, 137.75 mmoles) were added and the mixture was refluxed for 12 h. After cooling to RT, the reaction mixture was quenched by the addition of ice cold water. The solid formed was filtered and washed with water. The product was dried under vacuum to afford the title compound as white solid (4.1 g, 63% yield). $^1$H-NMR (δ ppm, $CDCl_3$, 400 MHz):

δ 8.35 (d, J=1.9 Hz, 1H), 7.77 (dd, J=8.8, 1.9 Hz, 1H), 7.37 (d, J=8.9 Hz, 1H), 7.27 (t, J=5.7 Hz, 2H), 7.17 (t, J=8.6 Hz, 2H), 2.33 (s, 3H).

Intermediate 8: 6-Bromo-2-(bromomethyl)-3-(4-fluorophenyl)-4H-chromen-4-one

To a solution of intermediate 7 (2 g, 6.00 mmoles) in carbon tetrachloride (20 ml) N-bromo-succinimide (1.06 g, 5.95 mmoles) was added and heated to 80° C. Azobisisobutyronitrile (20 mg) was added to the reaction mixture at 80° C. After 12 h, the reaction mixture was cooled to RT, diluted with dichloromethane and washed with water. The organic layer was dried over sodium sulphate and concentrated under reduced pressure to afford the title compound as off white solid (1.20 g, 50% yield). $^1$H-NMR (δ ppm, DMSO-$D_6$, 400 MHz): δ 8.35 (d, J=2.4 Hz, 1H), 7.81 (dd, J=8.9, 2.4 Hz, 1H), 7.43 (d, J=8.9 Hz, 1H), 7.38 (dt, J=5.4, 2.0 Hz, 2H), 7.20 (t, J=8.6 Hz, 2H), 4.22 (s, 2H).

Intermediate 9: 3-(4-Fluorophenyl)-2-methyl-4H-chromen-4-one

To a solution of intermediate 7 (1.5 g, 4.50 mmoles) in ethanol (15 ml), ammonium formate (2.8 g, 45.02 mmole) and palladium on carbon (10%, 15 mg) were added and the solution was refluxed for 4 h. The solution was filtered through celite, diluted with ethyl acetate, washed with 10% sodium bicarbonate solution (100 ml), dried over sodium sulphate and concentrated. The crude product was purified by column chromatography with ethyl acetate:petroleum ether to afford the title compound as white solid (0.8 g, 72% yield). $^1$H-NMR (δ ppm, $CDCl_3$, 400 MHz): δ 8.71 (d, J=7.8 Hz, 1H), 7.69 (t, J=7.35 Hz, 1H), 7.47 (d, J=8.4 Hz, 1H), 7.42 (t, J=7.4 Hz, 1H), 7.29 (t, J=9.5 Hz, 2H), 7.16 (t, J=8.5 Hz, 2H), 2.33 (s, 3H).

Intermediate 10: 2-(Bromomethyl)-3-(4-fluorophenyl)-4H-chromen-4-one

To a solution of intermediate 9 (0.80 g, 3.146 mmoles) in carbon tetrachloride (10 ml) N-bromosuccinimide (0.560 g, 3.146 mmoles) was added and heated to 80° C. Azobisisobutyronitrile (8 mg) was added to the reaction mixture at 80° C. After 12 h, the reaction mixture was cooled to RT, diluted with dichloromethane and washed with water. The organic layer was dried over sodium sulphate and concentrated under reduced pressure to afford the title compound as off white solid (0.7 g, 67% yield). $^1$H-NMR (δ ppm, DMSO-$D_6$, 400 MHz): δ 8.23 (dd, J=7.9, 1.3 Hz, 1H), 7.74 (dt, J=8.6, 1.5 Hz, 1H), 7.53 (d, J=8.3 Hz, 1H), 7.45 (m, 3H), 7.19 (t, J=8.7 Hz, 2H), 4.24 (s, 2H).

Intermediate 11: 1-(5-bromo-2-hydroxyphenyl)-2-o-tolylethanone

2-Methylphenylacetic acid (9.60 g, 64.15 mmoles) was dissolved in 10 ml dichloromethane. To this mixture, oxalylchloride (7 ml, 80.19 mmoles) and DMF (3 drops) were added at 0° C. and stirred for 30 min. The solvent was evaporated and dissolved in 100 ml dichloromethane. To this mixture, 4-bromoanisole (10 g, 53.47 mmoles) was added and cooled to 0° C. At 0° C. $AlCl_3$ (10.6 g, 80.19 mmoles) was added and the reaction mixture was warmed to RT and stirred for 24 h. The reaction mixture was quenched by the addition of 2N HCl and extracted with ethyl acetate, dried over sodium sulphate and concentrated. The crude product was purified by column chromatography with ethyl acetate:petroleum ether to afford the title compound as white solid (5.5 g, 33% yield. $^1$H-NMR (δ ppm, DMSO-$_{d6}$, 400 MHz): δ 11.52 (s, 1H), 8.02 (d, J=2.4 Hz, 1H), 7.65 (dd, J=8.8, 2.5 Hz, 1H), 7.16 (m, 4H), 6.97 (d, J=8.9 Hz, 1H), 4.47 (s, 2H), 2.14 (s, 3H).

Intermediate 12: 6-bromo-2-methyl-3-o-tolyl-4H-chromen-4-one

Intermediate 11 (5.5 g, 16.38 mmoles) was taken in a RB flask and to this acetic anhydride (50 ml) and sodium acetate (9.40 g, 114.69 mmoles) were added and the mixture was refluxed for 12 h. After cooling to RT, the reaction mixture was quenched by the addition of ice cold water. The solid formed was filtered and washed with water. The product was dried under vacuum to afford the title compound as white solid (1.8 g, 30% yield). $^1$H-NMR (δ ppm, $CDCl_3$, 400 MHz): δ 8.35 (d, J=1.7 Hz, 1H), 7.75 (d, J=6.7 Hz, 1H), 7.37 (d, J=8.8 Hz, 1H), 7.35-7.26 (m, 3H), 7.09 (d, J=6.9 Hz, 1H), 2.20 (s, 3H), 2.15 (s, 3H).

Intermediate 13: 6-Bromo-2-(bromomethyl)-3-o-tolyl-4H-chromen-4-one

To a solution of intermediate 12 (0.20 g, 0.607 mmoles) in acetic acid (3 ml) bromine (0.03 ml, 1.21 mmoles) was added at 0° C. The reaction mixture heated to 60° C. After 3 h, the reaction mixture was cooled to RT, quenched by the addition of water. The precipitate formed was filtered and dried under reduced pressure to afford the title compound as off white solid (0.176 g, 71% yield). $^1$H-NMR (δ ppm, DMSO-$D_6$, 400 MHz): δ 8.35 (d, J=2.2 Hz, 1H), 7.87 (dd, J=8.9, 2.3 Hz, 1H), 7.45 (d, J=8.9 Hz, 1H), 7.39 (m, 3H), 7.17 (d, J=7.3 Hz), 7.12 (d, J=7.5 Hz)(total 1H), 4.20 (d, J=10.8 Hz), 4.08 (d, J=10.7 Hz)(total, 2H), 2.17 (s, 3H).

Intermediate 14: 6-Bromo-2-ethyl-3-phenyl-4H-chromen-4-one

Intermediate 1 (2.0 g, 6.86 mmoles) was taken in a RB flask and to this triethylamine (16 ml) and propionic anhydride (2.80 g, 21.50 mmoles) were added and the mixture was refluxed for 22 h. After cooling to RT, the reaction mixture was acidified by the addition of 1N HCl solution, extracted with ethyl acetate, washed with sodium bicarbonate solution, dried with sodium sulphate and concentrated. The crude product was purified by column chromatography with ethyl acetate:petroleum ether to afford the title compound as off-white solid (0.78 g, 31% yield). $^1$H-NMR (δ ppm, DMSO-$d_6$, 400 MHz): δ 8.10 (d, J=2.4 Hz, 1H), 7.97 (dd, J=8.9, 2.4 Hz, 1H), 7.68 (d, J=8.9 Hz, 1H), 7.46 (m, 3H), 7.27 (d, J=6.9 Hz, 2H), 2.55 (q, J=7.5 Hz, 2H), 1.19 (t, J=7.5 Hz, 3H).

Intermediate 15: 6-Bromo-2-(1-bromoethyl)-3-phenyl-4H-chromen-4-one

To a solution of intermediate 14 (1.0 g, 3.03 mmoles) in carbon tetrachloride (25 ml) N-bromosuccinimide (0.540 g, 3.03 mmoles) was added and heated to 80° C. Azobisisobutyronitrile (5 mg) was added to the reaction mixture at 80° C. After 12 h, the reaction mixture was cooled to RT, diluted with dichloromethane and washed with water. The organic layer was dried over sodium sulphate and concentrated under reduced pressure to afford the title compound as off white solid (0.6 g, 50% yield). $^1$H-NMR (δ ppm, DMSO-$D_6$, 400 MHz): δ 8.11 (d, J=2.5 Hz, 1H), 8.04 (dd, J=8.9, 2.5 Hz, 1H), 7.78 (d, J=9.0 Hz, 1H), 7.51 (m, 3H), 7.32 (dd, J=8.1, 1.7 Hz, 2H), 4.97 (q, J=6.8 Hz, 1H), 1.96 (d, J=6.8 Hz, 3H).

Intermediate 16: (S)-tert-butyl 1-(6-bromo-4-oxo-3-phenyl-4H-chromen-2-yl)ethylcarbamate To a solution of intermediate 1 (5 g, 17.17 mmoles) in dichloromethane (50 ml), triethylamine (5.2 g, 51.52 mmoles) was added followed by L-N-Boc-Alanine (3.5 g, 18.89 mmoles). To this mixture HATU (13 g, 34.34 mmoles) was added and stirred at RT for 12 h. The reaction mixture was quenched by the addition of water and extracted with dichloromethane. The organic layer was dried over sodium sulphate and concentrated under reduced pressure. The crude product was purified by column chromatography with ethyl acetate: petroleum ether to afford the title compound as yellow solid (1.6 g, 21% yield). $^{1}$H-NMR (δ ppm, DMSO-$D_6$, 400 MHz): δ 8.10 (d, J=2.4 Hz, 1H), 7.99 (dd, J=8.9, 2.5 Hz, 1H), 7.62 (d, J=8.9 Hz, 1H), 7.53 (d, J=6.8 Hz, 1H), 7.47 (m, 3H), 7.29 (d, J=7.0 Hz, 2H), 4.49 (q, J=6.9 Hz, 1H), 1.33 (s, 9H), 1.29 (d, J=7.1 Hz, 3H).

Intermediate 17: (S)-2-(1-aminoethyl)-6-bromo-3-phenyl-4H-chromen-4-one

To a solution of intermediate 16 (0.81 g, 1.821 mmoles) in dichloromethane (10 ml), trifluoroacetic acid (1.4 ml, 18.21 mmoles) was added and stirred at RT for 2 h. The reaction mixture was concentrated, basified with sodium bicarbonate solution, extracted with ethyl acetate. The organic layer was dried over sodium sulphate and concentrated under reduced pressure to afford the crude title compound as yellow solid (0.675 g). $^{1}$H-NMR (δ ppm, DMSO-$D_6$, 400 MHz): δ 8.10 (d, J=2.4 Hz, 1H), 8.00 (dd, J=8.9, 2.5 Hz, 1H), 7.69 (d, J=8.9 Hz, 1H), 7.46 (m, 4H), 7.30 (d, J=7.0 Hz, 2H), 7.28 (m, 1H), 3.78 (q, J=6.7 Hz, 1H), 1.29 (d, J=6.7 Hz, 3H).

Intermediate 18: tert-Butyl(6-bromo-4-oxo-3-phenyl-4H-chromen-2-yl)methylcarbamate To a solution of intermediate 1 (2 g, 6.86 mmoles) in dichloromethane (20 ml), triethylamine (2.08 g, 51.52 mmoles) was added followed by N-Boc-Glycine (1.3 g, 7.55 mmoles). To this mixture HATU (5.2 g, 13.67 mmoles) was added and stirred at RT for 12 h. The reaction mixture was quenched by the addition of water and extracted with dichloromethane. The organic layer was dried over sodium sulphate and concentrated under reduced pressure. The crude product was purified by column chromatography with ethyl acetate: petroleum ether to afford the title compound as yellow solid (1.0 g, 33% yield). $^{1}$H-NMR (δ ppm, DMSO-$D_6$, 400 MHz): δ 8.12 (d, J=2.3 Hz, 1H), 7.99 (dd, J=8.9, 2.5 Hz, 1H), 7.59 (d, J=8.9 Hz, 1H), 7.476 (m, 4H), 7.31 (d, J=6.3 Hz, 2H), 4.06 (d, J=5.6 Hz, 2H), 1.37 (s, 9H).

Intermediate 19: 2-(Amino methyl)-6-bromo-3-phenyl-4H-chromen-4-one

To a solution of intermediate 18 (0.440 g, 1.02 mmoles) in dichloromethane (5 ml), trifluoroacetic acid (3 ml) was added and stirred at RT for 2 h. The reaction mixture was concentrated, basified with sodium bicarbonate solution, extracted with ethyl acetate. The organic layer was dried over sodium sulphate and concentrated under reduced pressure to afford the crude title compound as brown liquid (0.400 g). The crude product was taken for next step.

Intermediate 20: 1-(2-Hydroxy-5-methoxyphenyl)-2-phenylethanone

Phenylacetic acid (7.39 g, 54.28 mmoles) was dissolved in 50 ml dichloromethane. To this mixture, oxalylchloride (4.74 ml, 54.28 mmoles) and DMF (3 drops) were added at 0° C. and stirred for 30 min. The solvent was evaporated and dissolved in 30 ml dichloromethane. To this mixture, 4-methoxyanisole (10 g, 53.47 mmoles) was added and cooled to 0° C. At 0° C. $AlCl_3$ (9.63 g, 72.37 mmoles) was added and the reaction mixture was warmed to RT and stirred for 12 h. The reaction mixture was quenched by the addition of 2N HCl and extracted with ethyl acetate, dried over sodium sulphate and concentrated. The crude product was purified by column chromatography with ethyl acetate:petroleum ether to afford the title compound as yellow liquid (4.3 g, 49% yield. $^{1}$H-NMR (δ ppm, DMSO-$d_6$, 400 MHz): δ 11.30 (s, 1H), 7.42 (d, J=3.0 Hz, 1H), 7.33-7.21 (m, 5H), 7.17 (dd, J=9.0, 3.1 Hz, 1H), 6.92 (d, J=9.0 Hz, 1H), 4.43 (s, 2H), 3.74 (s, 3H).

Intermediate 21: 6-Methoxy-2-methyl-3-phenyl-4H-chromen-4-one

Intermediate 20 (4 g, 16.51 mmoles) was taken in a RB flask and to this acetic anhydride (40 ml) and sodium acetate (9.48 g, 115.57 mmoles) were added and the mixture was refluxed for 12 h. After cooling to RT, the reaction mixture was quenched by the addition of ice cold water. The solid formed was filtered and washed with water. The product was dried under vacuum to afford the title compound as yellow solid (3 g, 68% yield). $^{1}$H-NMR (δ ppm, $CDCl_3$, 400 MHz): δ 7.60 (d, J=3.0 Hz, 1H), 7.45 (t, J=7.1 Hz, 2H), 7.37 (m, 2H), 7.29 (m, 3H), 3.89 (s, 3H), 2.31 (s, 3H).

Intermediate 22: 2-(Bromomethyl)-6-methoxy-3-phenyl-4H-chromen-4-one

To a solution of intermediate 21 (2.0 g, 7.501 mmoles) in carbon tetrachloride (25 ml) N-bromosuccinimide (1.30 g, 7.510 mmoles) was added and heated to 80° C. Azobisisobutyronitrile (25 mg) was added to the reaction mixture at 80° C. After 12 h, the reaction mixture was cooled to RT, diluted with dichloromethane and washed with water. The organic layer was dried over sodium sulphate and concentrated under reduced pressure to afford the crude title compound as off white solid (2.6 g). $^{1}$H-NMR (δ ppm, DMSO-$D_6$, 400 MHz): δ 7.68 (d, J=9.1 Hz, 1H), 7.53 (m, 5H), 7.34 (d, J=6.7, 2H), 4.36 (s, 2H), 3.85 (s, 3H).

Intermediate 23: 1-(5-Bromo-2-hydroxyphenyl)-2-(2-fluorophenyl)ethanone

2-Fluorophenylacetic acid (2.96 g, 19.24 mmoles) was dissolved in 50 ml dichloromethane. To this mixture, oxalylchloride (2.1 ml, 24.05 mmoles) and DMF (3 drops) were added at 0° C. and stirred for 30 min. The solvent was evaporated and dissolved in 30 ml dichloromethane. To this mixture, 4-bromoanisole (3.0 g, 16.03 mmoles) was added and cooled to 0° C. At 0° C. $AlCl_3$ (3.21 g, 24.05 mmoles) was added and the reaction mixture was warmed to RT and stirred for 12 h. The reaction mixture was quenched by the addition of 2N HCl and extracted with ethyl acetate, dried over sodium sulphate and concentrated. The crude product was purified by column chromatography with ethyl acetate:petroleum ether to afford the title compound as off-white solid (4.0 g, 81% yield. $^{1}$H-NMR (δ ppm, $CDCl_3$, 400 MHz): δ 11.97 (s, 1H), 8.01 (d, J=1.7 Hz, 1H), 7.58 (dd, J=8.8, 2.3.1 Hz, 1H), 7.35 (m, 1H), 7.23 (d, J=7.3 Hz, 1H), 7.17 (m, 2H), 6.92 (d, J=8.9 Hz, 1H), 4.33 (s, 2H).

Intermediate 24: 6-Bromo-2-ethyl-3-(2-fluorophenyl)-4H-chromen-4-one

Intermediate 23 (1.1 g, 3.55 mmoles) was taken in a RB flask and to this triethylamine (10 ml) and propionic anhydride (1.44 g, 11.13 mmoles) were added and the mixture was refluxed for 22 h. After cooling to RT, the reaction mixture was acidified by the addition of 1N HCl solution, extracted with ethyl acetate, washed with sodium bicarbonate solution, dried with sodium sulphate and concentrated. The crude product was purified by column chromatography with ethyl acetate:petroleum ether to afford the title compound as off-white solid (0.800 g, 65% yield). $^1$H-NMR (δ ppm, DMSO-$d_6$, 400 MHz): δ 8.10 (d, J=2.5 Hz, 1H), 8.00 (dd, J=9.0, 2.5 Hz, 1H), 7.71 (d, J=9.0 Hz, 1H), 7.51 (m, 1H), 7.36 (m, 3H), 2.54 (m, 2H), 1.19 (t, J=7.6 Hz, 3H).

Intermediate 25: 6-Bromo-2-(1-bromoethyl)-3-(2-fluorophenyl)-4H-chromen-4-one

To a solution of intermediate 24 (0.620 g, 1.785 mmoles) in carbon tetrachloride (10 ml) N-bromosuccinimide (0.317 g, 1.785 mmoles) was added and heated to 80° C. Azobisisobutyronitrile (15 mg) was added to the reaction mixture at 80° C. After 12 h, the reaction mixture was cooled to RT, diluted with dichloromethane and washed with water. The organic layer was dried over sodium sulphate and concentrated under reduced pressure to afford the crude title compound as off white solid consisting of two atrop-isomers (0.625 g). $^1$H-NMR (δ ppm, DMSO-$D_6$, 400 MHz): δ 8.13 (t, J=2.3 Hz, 1H), [8.07 (dd, J=2.4, 1.0 Hz), 8.04 (dd, J=2.5, 1.1 Hz), 1H], 7.81 (dd, J=8.8, 1.6 Hz, 1H), 7.57 (m, 1H), 7.39 (m, 3H), [4.99 (q, J=6.8 Hz), 4.93 (q, J=6.8 Hz), 1H], [1.99 (q, J=6.8 Hz), 1.44 (q, J=6.8 Hz), 3H].

Intermediate 26: 6-Bromo-3-(2-fluorophenyl)-2-methyl-4H-chromen-4-one

Intermediate 23 (5 g, 16.17 mmoles) was taken in a RB flask and to this acetic anhydride (40 ml) and sodium acetate (9.2 g, 82.03 mmoles) were added and the mixture was refluxed for 12 h. After cooling to RT, the reaction mixture was quenched by the addition of ice cold water. The solid formed was filtered and washed with water. The product was dried under vacuum to afford the title compound as off-white solid (3.81 g, 71% yield). $^1$H-NMR (δ ppm, $CDCl_3$, 400 MHz): δ 8.34 (d, J=2.3 Hz, 1H), 7.76 (dd, J=8.8, 2.2 Hz, 1H), 7.41 (m, 2H), 7.24 (m, 2H), 7.18 (t, J=8.9 Hz, 1H), 2.30 (s, 3H).

Intermediate 27: 6-Bromo-2-(bromomethyl)-3-(2-fluorophenyl)-4H-chromen-4-one

To a solution of intermediate 26 (2.0 g, 6.00 mmoles) in carbon tetrachloride (20 ml) N-bromosuccinimide (1.0 g, 6.00 mmoles) was added and heated to 80° C. Azobisisobutyronitrile (25 mg) was added to the reaction mixture at 80° C. After 12 h, the reaction mixture was cooled to RT, diluted with dichloromethane and washed with water. The organic layer was dried over sodium sulphate and concentrated under reduced pressure to afford the crude title compound as off white solid (1.86 g). $^1$H-NMR (δ ppm, DMSO-$D_6$, 400 MHz): δ 8.34 (d, J=2.3 Hz, 1H), 7.82 (dd, J=8.9, 2.3 Hz, 1H), 7.44 (d, J=8.8 Hz, 1H), 7.38 (t, J=6.2 Hz, 1H), 7.29 (m, 2H), [4.22 (d, J=11.0 Hz), 4.17 (d, J=11.1 Hz), 2H].

Intermediate 28: 2-Ethyl-3-phenyl-4H-chromen-4-one

To a solution of intermediate 24 (1.0 g, 3.03 mmoles) in ethanol (10 ml), ammonium formate (1.9 g, 30.14 mmoles) and palladium on carbon (10%, 100 mg) were added and the solution was refluxed for 4 h. The solution was filtered through celite, diluted with ethyl acetate, washed with 10% sodium bicarbonate solution (100 ml), dried over sodium sulphate and concentrated. The crude product was purified by column chromatography with ethyl acetate:petroleum ether to afford the title compound as white solid (0.50 g, 66% yield). $^1$H-NMR (δ ppm, $CDCl_3$, 400 MHz): δ 8.24 (dd, J=7.9, 1.4 Hz, 1H), 7.68 (dt, J=8.6, 1.6 Hz, 1H), 7.48-7.35 (m, 5H), 7.28 (dd, J=8.3, 1.4 Hz, 2H), 2.62 (q, J=7.5 Hz, 2H), 1.28 (t, J=7.5 Hz, 3H).

Intermediate 29: 2-(1-Bromoethyl)-3-phenyl-4H-chromen-4-one

To a solution of intermediate 28 (0.550 g, 2.20 mmoles) in carbon tetrachloride (10 ml) N-bromosuccinimide (0.392 g, 2.20 mmoles) was added and heated to 80° C. Azobisisobutyronitrile (5 mg) was added to the reaction mixture at 80° C. After 12 h, the reaction mixture was cooled to RT, diluted with dichloromethane and washed with water. The organic layer was dried over sodium sulphate and concentrated under reduced pressure to afford the crude title compound as yellow solid (0.680 g, 94% yield). $^1$H-NMR (δ ppm, $CDCl_3$, 400 MHz): δ 8.24 (dd, J=8.0, 1.7 Hz, 1H), 7.74 (dt, J=7.2, 1.6 Hz, 1H), 7.57 (d, J=8.0 Hz, 1H), 7.49-7.26 (m, 6H), 4.99 (q, J=6.9 Hz, 1H), 1.99 (d, J=6.9 Hz, 3H).

Intermediate 30: 6-Bromo-3-phenyl-2-propyl-4H-chromen-4-one

Intermediate 1 (3.0 g, 10.30 mmoles) was taken in a RB flask and to this triethylamine (30 ml) and butyric anhydride (5.12 g, 32.37 mmoles) were added and the mixture was refluxed for 22 h. After cooling to RT, the reaction mixture was acidified by the addition of 1N HCl solution, extracted with ethyl acetate, washed with sodium bicarbonate solution, dried with sodium sulphate and concentrated. The crude product was purified by column chromatography with ethyl acetate:petroleum ether to afford the title compound as off-white solid (2.0 g, 56% yield). $^1$H-NMR (δ ppm, DMSO-$d_6$, 400 MHz): δ 8.10 (d, J=2.4 Hz, 1H), 7.97 (dd, J=8.9, 2.5 Hz, 1H), 7.68 (d, J=8.9 Hz, 1H), 7.46 (m, 3H), 7.26 (dd, J=8.2, 1.3 Hz, 2H), 2.49 (t, J=1.6 Hz, 2H), 1.66 (m, 2H), 0.84 (t, J=7.4 Hz, 3H).

Intermediate 31: 3-Phenyl-2-propyl-4H-chromen-4-one

To a solution of intermediate 30 (1.5 g, 4.37 mmoles) in ethanol (15 ml), ammonium formate (2.7 g, 43.70 mmoles) and palladium on carbon (10%, 100 mg) were added and the solution was refluxed for 2 h. The solution was filtered through celite, diluted with ethyl acetate, washed with 10% sodium bicarbonate solution (100 ml), dried over sodium sulphate and concentrated. The crude product was purified by column chromatography with ethyl acetate:petroleum ether to afford the title compound as white solid (0.43 g, % yield). $^1$H-NMR (δ ppm, $CDCl_3$, 400 MHz): δ 8.24 (dd, J=7.9, 1.5

Hz, 1H), 7.68 (dt, J=7.2, 1.6 Hz, 1H), 7.46-7.35 (m, 5H), 7.27 (dd, J=7.2, 1.5 Hz, 2H), 2.57 (t, J=7.6 Hz, 2H), 1.78 (m, 2H0, 0.93 (t, J=7.4 Hz, 3H).

Intermediate 32: 2-(1-Bromopropyl)-3-phenyl-4H-chromen-4-one

To a solution of intermediate 31 (0.900 g, 3.40 mmoles) in carbon tetrachloride (15 ml) N-bromosuccinimide (0.606 g, 3.40 mmoles) was added and heated to 80° C. Azobisisobutyronitrile (9 mg) was added to the reaction mixture at 80° C. After 12 h, the reaction mixture was cooled to RT, diluted with dichloromethane and washed with water. The organic layer was dried over sodium sulphate and concentrated under reduced pressure to afford the title compound as yellow solid (0.880 g, 75% yield). $^1$H-NMR (δ ppm, $CDCl_3$, 400 MHz): δ 8.24 (dd, J=8.0, 1.6 Hz, 1H), 7.74 (dt, J=7.2, 1.7 Hz, 1H), 7.55 (d, J=8.3 Hz, 1H), 7.49-7.20 (m, 6H), 4.71 (t, J=7.6 Hz, 1H), 2.33 (m, 2H), 0.97 (d, J=7.4 Hz, 3H).

Intermediate 33: 1-(5-Bromo-2-hydroxyphenyl)-2-(3-fluorophenyl)ethanone

3-Fluorophenylacetic acid (4.90 g, 32.07 mmoles) was dissolved in 50 ml dichloromethane. To this mixture, oxalylchloride (3.5 ml, 40.08 mmoles) and DMF (3 drops) were added at 0° C. and stirred for 30 min. The solvent was evaporated and dissolved in 50 ml dichloromethane. To this mixture, 4-bromoanisole (5.0 g, 26.72 mmoles) was added and cooled to 0° C. At 0° C. $AlCl_3$ (5.3 g, 40.08 mmoles) was added and the reaction mixture was warmed to RT and stirred for 12 h. The reaction mixture was quenched by the addition of 2N HCl, extracted with ethyl acetate, dried over sodium sulphate and concentrated. The crude product was purified by column chromatography with ethyl acetate:petroleum ether to afford the title compound as off-white solid (6.6 g, 80% yield. $^1$H-NMR (δ ppm, $CDCl_3$, 400 MHz): δ 12.02 (s, 1H), 7.94 (d, J=2.4 Hz, 1H), 7.57 (dd, J=8.9, 2.4.1 Hz, 1H), 7.36 (m, 1H), 7.04 (m, 3H), 6.90 (d, J=8.9 Hz, 1H), 4.28 (s, 2H).

Intermediate 34: 6-Bromo-2-ethyl-3-(3-fluorophenyl)-4H-chromen-4-one

Intermediate 33 (3.0 g, 9.70 mmoles) was taken in a RB flask and to this triethylamine (30 ml) and propionic anhydride (3.94 g, 30.37 mmoles) were added and the mixture was refluxed for 24 h. After cooling to RT, the reaction mixture was acidified by the addition of 1N HCl solution, extracted with ethyl acetate, washed with sodium bicarbonate solution, dried with sodium sulphate and concentrated. The crude product was purified by column chromatography with ethyl acetate:petroleum ether to afford the title compound as off-white solid (1.30 g, 39% yield). $^1$H-NMR (δ ppm, DMSO-$d_6$, 400 MHz): δ 8.10 (d, J=2.3 Hz, 1H), 7.99 (dd, J=8.9, 2.4 Hz, 1H), 7.69 (d, J=8.9 Hz, 1H), 7.51 (q, J=7.9 Hz, 1H), 7.25 (dt, J=10.8, 2.4 Hz, 1H), 7.15 (t, J=12.2 Hz, 2H), 2.57 (q, J=7.6 Hz, 2H), 1.20 (t, J=7.5 Hz, 3H).

Intermediate 35: 2-Ethyl-3-(3-fluorophenyl)-4H-chromen-4-one

To a solution of intermediate 34 (1.0 g, 2.88 mmoles) in ethanol (10 ml), ammonium formate (1.81 g, 28.80 mmoles) and palladium on carbon (10%, 80 mg) were added and the solution was refluxed for 2 h. The solution was filtered through celite, diluted with ethyl acetate, washed with 10% sodium bicarbonate solution (100 ml), dried over sodium sulphate and concentrated to afford the crude title compound as colourless oil (0.792 g). $^1$H-NMR (δ ppm, $CDCl_3$, 400 MHz): δ 8.05 (dd, J=7.9, 1.3 Hz, 1H), 7.83 (dt, J=8.6, 1.6 Hz, 1H), 7.67 (d, J=8.3 Hz, 1H), 7.50 (m, 2H), 7.24 (dt, J=8.8, 2.5 Hz, 1H), 7.15 (t, J=12.3 Hz, 2H), 2.55 (q, J=7.6 Hz, 2H), 1.20 (t, J=7.6 Hz, 3H).

Intermediate 36: 2-(1-Bromoethyl)-3-(3-fluorophenyl)-4H-chromen-4-one

To a solution of intermediate 35 (0.700 g, 2.60 mmoles) in carbon tetrachloride (10 ml) N-bromosuccinimide (0.464 g, 2.60 mmoles) was added and heated to 80° C. Azobisisobutyronitrile (10 mg) was added to the reaction mixture at 80° C. After 12 h, the reaction mixture was cooled to RT, diluted with dichloromethane and washed with water. The organic layer was dried over sodium sulphate and concentrated under reduced pressure to afford the crude title compound as off-white solid (0.820 g, 91% yield). $^1$H-NMR (δ ppm, DMSO-$d_6$, 400 MHz): δ 8.06 (dd, J=7.9, 1.1 Hz, 1H), 7.89 (dt, J=8.4, 1.3 Hz, 1H), 7.77 (d, J=8.3 Hz, 1H), 7.56 (d, J=7.5 Hz, 1H), 7.52 (d, J=7.7 Hz, 1H), 7.31 (dt, J=8.6, 2.1 Hz, 1H), 7.19 (t, J=9.0 Hz, 2H), 5.02 (q, J=6.8 Hz, 1H), 1.97 (d, J=6.8 Hz, 3H).

Intermediate 37: 3-(2-Fluorophenyl)-2-methyl-4H-chromen-4-one

To a solution of intermediate 26 (0.5 g, 1.50 mmoles) in ethanol (5 ml), ammonium formate (0.945 g, 15.0 mmoles) and palladium on carbon (10%, 40 mg) were added and the solution was refluxed for 2 h. The solution was filtered through celite, diluted with ethyl acetate, washed with 10% sodium bicarbonate solution (100 ml), dried over sodium sulphate and concentrated to afford the title compound as white solid (0.302 g, 79% yield). $^1$H-NMR (δ ppm, $CDCl_3$, 400 MHz): δ 8.05 (dd, J=7.9, 1.5 Hz, 1H), 7.84 (m, 1H), 7.67 (d, J=8.3 Hz, 1H), 7.51 (m, 2H), 7.37 (dt, J=7.3, 1.7 Hz, 1H), 7.29 (m, 2H), 2.26 (s, 3H).

Intermediate 38: 2-(Bromomethyl)-3-(2-fluorophenyl)-4H-chromen-4-one

To a solution of intermediate 37 (0.300 g, 1.17 mmoles) in carbon tetrachloride (10 ml) N-bromosuccinimide (0.210 g, 1.17 mmoles) was added and heated to 80° C. Azobisisobutyronitrile (15 mg) was added to the reaction mixture at 80° C. After 12 h, the reaction mixture was cooled to RT, diluted with dichloromethane and washed with water. The organic layer was dried over sodium sulphate and concentrated under reduced pressure to afford the crude title compound as off-white solid (0.281 g, 71% yield).

Intermediate 39: 2-Ethyl-3-(2-fluorophenyl)-4H-chromen-4-one

To a solution of intermediate 24 (0.770 g, 2.21 mmoles) in ethanol (10 ml), ammonium formate (1.39 g, 22.18 mmoles) and palladium on carbon (10%, 60 mg) were added and the solution was refluxed for 2 h. The solution was filtered through celite, diluted with ethyl acetate, washed with 10% sodium bicarbonate solution (100 ml), dried over sodium sulphate and concentrated to afford the title compound as white solid (0.560 g, 94% yield). $^1$H-NMR (δ ppm, $CDCl_3$, 400 MHz): δ 8.05 (dd, J=7.9, 1.5 Hz, 1H), 7.85 (dt, J=7.3, 1.7 Hz, 1H), 7.69 (d, J=8.3 Hz, 1H), 7.52 (m, 2H), 7.36 (m, 2H), 2.52 (m, 2H), 1.19 (t, J=7.5 Hz, 3H).

Intermediate 40: 2-(1-Bromoethyl)-3-(2-fluorophenyl)-4H-chromen-4-one

To a solution of intermediate 39 (0.600 g, 2.27 mmoles) in carbon tetrachloride (10 ml) N-bromosuccinimide (0.404 g, 2.27 mmoles) was added and heated to 80° C. Azobisisobutyronitrile (15 mg) was added to the reaction mixture at 80° C. After 12 h, the reaction mixture was cooled to RT, diluted with dichloromethane and washed with water. The organic layer was dried over sodium sulphate and concentrated under reduced pressure to afford the crude title compound as off-white solid (0.420 g, 53% yield). $^1$H-NMR (δ ppm, DMSO-$d_6$, 400 MHz): δ 8.07 (dd, J=7.9, 1.3 Hz, 1H), 7.92 (dt, J=8.4, 1.3 Hz, 1H), 7.79 (d, J=8.4 Hz, 1H), 7.56 (m, 2H), 7.41 (m, 3H), [4.99 (q, J=6.8 Hz), 4.93 (q, J=6.7 Hz), 1H], [2.00 (d, J=6.8 Hz), 1.95 (d, J=6.8 Hz), 3H].

Intermediate 41: 6-Bromo-3-(2-fluorophenyl)-2-propyl-4H-chromen-4-one

Intermediate 23 (2.0 g, 6.46 mmoles) was taken in a RB flask and to this triethylamine (20 ml) and butyric anhydride (3.19 g, 20.25 mmoles) were added and the mixture was refluxed for 24 h. After cooling to RT, the reaction mixture was acidified by the addition of 1N HCl solution, extracted with ethyl acetate, washed with sodium bicarbonate solution, dried with sodium sulphate and concentrated. The crude product was purified by column chromatography with ethyl acetate:petroleum ether to afford the title compound as colourless liquid (1.60 g, 69% yield).

Intermediate 42: 3-(2-Fluorophenyl)-2-propyl-4H-chromen-4-one

To a solution of intermediate 41 (1.60 g, 4.43 mmoles) in ethanol (15 ml), ammonium formate (2.79 g, 63.03 mmoles) and palladium on carbon (10%, 130 mg) were added and the solution was refluxed for 2 h. The solution was filtered through celite, diluted with ethyl acetate, washed with 10% sodium bicarbonate solution (100 ml), dried over sodium sulphate and concentrated to afford the title compound as brown liquid (1.0 g, 81% yield). $^1$H-NMR (δ ppm, $CDCl_3$, 400 MHz): δ 8.05 (dd, J=7.9, 1.4 Hz, 1H), 7.84 (dt, J=8.5, 1.5 Hz, 1H), 7.68 (d, J=8.4 Hz, 1H), 7.51 (q, J=7.7 Hz, 2H), 7.34 (m, 3H), 2.49 (m, 2H), 1.68 (q, J=7.4 Hz, 2H), 1.17 (t, J=7.4 Hz, 3H)

Intermediate 43: 2-(1-Bromopropyl)-3-(2-fluorophenyl)-4H-chromen-4-one

To a solution of intermediate 42 (1.00 g, 3.59 mmoles) in carbon tetrachloride (20 ml) N-bromosuccinimide (0.639 g, 3.59 mmoles) was added and heated to 80° C. Azobisisobutyronitrile (15 mg) was added to the reaction mixture at 80° C. After 12 h, the reaction mixture was cooled to RT, diluted with dichloromethane and washed with water. The organic layer was dried over sodium sulphate and concentrated under reduced pressure to afford the crude title compound as off-white solid (0.700 g, 54% yield). $^1$H-NMR (δ ppm, DMSO-$d_6$, 400 MHz): δ 8.07 (d, J=7.9 Hz, 1H), 7.91 (t, J=7.9 Hz, 1H), 7.78 (dd, J=8.3, 2.0 Hz, 1H), 7.56 (t, J=7.6 Hz, 2H), 7.36 (m, 3H), [4.69 (t, J=7.6 Hz), 4.64 (t, J=7.5 Hz), 1H], 2.38 (m, 2H), [0.97 (t, J=7.3 Hz), 0.88 (t, J=7.2 Hz), 3H].

Intermediate 44: 6-Bromo-3-(3-fluorophenyl)-2-propyl-4H-chromen-4-one

Intermediate 33 (3.0 g, 9.70 mmoles) was taken in a RB flask and to this triethylamine (3 ml) and butyric anhydride (4.55 g, 30.37 mmoles) were added and the mixture was refluxed for 24 h. After cooling to RT, the reaction mixture was acidified by the addition of 1N HCl solution, extracted with ethyl acetate, washed with sodium bicarbonate solution, dried with sodium sulphate and concentrated. The crude product was purified by column chromatography with ethyl acetate:petroleum ether to afford the title compound as colourless liquid (0.794 g, 23% yield). $^1$H-NMR (δ ppm, DMSO-$d_6$, 400 MHz): δ 8.10 (d, J=2.5 Hz, 1H), 7.98 (dd, J=8.9, 2.5 Hz, 1H), 7.69 (d, J=8.9 Hz, 1H), 7.51 (q, J=8.0 Hz, 1H), 7.26 (dt, J=8.7, 2.5 Hz, 1H), 7.14 (dt, J=9.9, 2.3 Hz, 2H), 2.55 (m, 2H), 1.68 (q, J=7.5 Hz, 2H), 0.85 (t, J=7.5 Hz, 3H).

Intermediate 45: 3-(3-Fluorophenyl)-2-propyl-4H-chromen-4-one

To a solution of intermediate 44 (0.750 g, 2.07 mmoles) in ethanol (10 ml), ammonium formate (1.30 g, 20.76 mmoles) and palladium on carbon (10%, 80 mg) were added and the solution was refluxed for 2 h. The solution was filtered through celite, diluted with ethyl acetate, washed with 10% sodium bicarbonate solution (100 ml), dried over sodium sulphate and concentrated to afford the title compound as colourless liquid (0.51 g, 87% yield). $^1$H-NMR (δ ppm, $CDCl_3$, 400 MHz): δ 8.05 (dd, J=8.0, 1.3 Hz, 1H), 7.83 (dt, J=8.4, 1.3 Hz, 1H), 7.66 (d, J=8.4 Hz, 1H), 7.51 (m, 2H), 7.24 (dt, J=8.9, 2.5 Hz, 1H), 7.14 (t, J=8.1 Hz, 2H), 2.53 (m, 2H), 1.69 (m, 2H), 0.85 (t, J=7.3 Hz, 3H).

Intermediate 46: 2-(1-Bromopropyl)-3-(3-fluorophenyl)-4H-chromen-4-one

To a solution of intermediate 45 (0.48 g, 1.70 mmoles) in carbon tetrachloride (10 ml) N-bromosuccinimide (0.302 g, 1.70 mmoles) was added and heated to 80° C. Azobisisobutyronitrile (10 mg) was added to the reaction mixture at 80° C. After 12 h, the reaction mixture was cooled to RT, diluted with dichloromethane and washed with water. The organic layer was dried over sodium sulphate and concentrated under reduced pressure to afford the crude title compound as off-white solid (0.540 g, 88% yield). $^1$H-NMR (δ ppm, DMSO-$d_6$, 400 MHz): δ 8.07 (dd, J=7.9, 1.5 Hz, 1H), 7.89 (dt, J=8.5, 1.5 Hz, 1H), 7.75 (d, J=8.4 Hz, 1H), 7.57 (q, J=8.0 Hz, 2H), 7.32 (dt, J=8.6, 2.5 Hz, 1H), 7.17 (dt, J=8.4, 2.3 Hz, 2H), 4.70 (t, J=7.5 Hz, 1H), 2.34 (m, 1H), 2.20 (m, 1H), 0.92 (t, J=7.2 Hz, 3H).

Intermediate 47: 6-Bromo-3-(4-fluorophenyl)-2-propyl-4H-chromen-4-one

Intermediate 6 (3.0 g, 9.70 mmoles) was taken in a RB flask and to this triethylamine (30 ml) and butyric anhydride (4.55 g, 30.37 mmoles) were added and the mixture was refluxed for 24 h. After cooling to RT, the reaction mixture was acidified by the addition of 1N HCl solution, extracted with ethyl acetate, washed with sodium bicarbonate solution, dried with sodium sulphate and concentrated. The crude product was purified by column chromatography with ethyl acetate:petroleum ether to afford the title compound as colourless liquid (2.55 g, 71% yield). $^1$H-NMR (δ ppm, $CDCl_3$, 400 MHz): δ 8.33 (d, J=2.3 Hz, 1H), 7.76 (dd, J=8.8, 2.3 Hz, 1H), 7.36 (d, J=8.9 Hz, 1H), 7.23 (dd, J=8.7, 5.6 Hz, 2H), 7.15 (t, J=8.7 Hz, 2H), 2.55 (t, J=7.5 Hz, 2H), 1.77 (m, 2H), 0.93 (t, J=7.4 Hz, 3H).

Intermediate 48: 3-(4-Fuorophenyl)-2-propyl-4H-chromen-4-one

To a solution of intermediate 47 (1.00 g, 2.76 mmoles) in ethanol (10 ml), ammonium formate (1.70 g, 27.60 mmoles)

and palladium on carbon (10%, 80 mg) were added and the solution was refluxed for 1 h. The solution was filtered through celite, diluted with ethyl acetate, washed with 10% sodium bicarbonate solution (100 ml), dried over sodium sulphate and concentrated to afford the title compound as colourless liquid (0.750 g, 96% yield). $^1$H-NMR (δ ppm, $CDCl_3$, 400 MHz): δ 8.23 (dd, J=7.9, 1.4 Hz, 1H), 7.69 (dt, J=8.5, 1.5 Hz, 1H), 7.47 (d, J=8.4 Hz, 1H), 7.41 (t, J=7.8 Hz, 1H), 7.25 (m, 2H), 7.15 (t, J=8.7 Hz, 2H), 2.56 (t, J=7.5 Hz, 2H), 1.78 (m, 2H), 0.94 (t, J=7.3 Hz, 3H).

Intermediate 49: 2-(1-Bromopropyl)-3-(4-fluorophenyl)-4H-chromen-4-one

To a solution of intermediate 48 (0.700 g, 2.47 mmoles) in carbon tetrachloride (10 ml) N-bromosuccinimide (0.441 g, 2.47 mmoles) was added and heated to 80° C. Azobisisobutyronitrile 7 mg) was added to the reaction mixture at 80° C. After 12 h, the reaction mixture was cooled to RT, diluted with dichloromethane and washed with water. The organic layer was dried over sodium sulphate and concentrated under reduced pressure to afford the crude title compound as off-white solid (1.1 g). $^1$H-NMR (δ ppm, $CDCl_3$, 400 MHz): δ 8.23 (dd, J=8.0, 1.2 Hz, 1H), 7.74 (dt, J=8.4, 1.3 Hz, 1H), 7.55 (d, J=8.4 Hz, 1H), 7.45 (t, J=7.4 Hz, 1H), 7.35 (m, 2H), 7.19 (t, J=8.7 Hz, 2H), 4.68 (t, J=7.7 Hz, 1H), 2.31 (m, 2H), 0.97 (t, J=7.3 Hz, 3H).

Intermediate 50: 1-(5-Fluoro-2-hydroxyphenyl)-2-phenylethanone

Phenylacetic acid (8.09 g, 59.46 mmoles) was dissolved in 15 ml dichloromethane. To this mixture, oxalylchloride (5.2 ml, 59.46 mmoles) and DMF (3 drops) were added at 0° C. and stirred for 30 min. The solvent was evaporated and dissolved in 15 ml dichloromethane. To this mixture, 4-fluoroanisole (5.0 g, 39.64 mmoles) was added and cooled to 0° C. At 0° C. $AlCl_3$ (7.92 g, 59.46 mmoles) was added and the reaction mixture was warmed to RT and stirred for 12 h. The reaction mixture was quenched by the addition of 2N HCl, extracted with ethyl acetate, dried over sodium sulphate and concentrated. The crude product was purified by column chromatography with ethyl acetate:petroleum ether to afford the title compound as off-white solid (5.1 g, 56% yield. $^1$H-NMR (δ ppm, DMSO-$d_6$, 400 MHz): δ 11.43 (s, 1H), 7.77 (dd, J=9.5, 3.2 Hz, 1H), 7.42 (dt, J=8.7, 3.2 Hz, 1H), 7.33 (t, J=7.3 Hz, 2H), 7.26 (m, 3H), 7.01 (q, J=4.6 Hz, 1H), 4.42 (s, 2H).

Intermediate 51: 6-Fluoro-3-phenyl-2-propyl-4H-chromen-4-one

Intermediate 50 (1.6 g, 6.94 mmoles) was taken in a RB flask and to this triethylamine (16 ml) and butyric anhydride (3.43 g, 21.72 mmoles) were added and the mixture was refluxed for 24 h. After cooling to RT, the reaction mixture was acidified by the addition of 1N HCl solution, extracted with ethyl acetate, washed with sodium bicarbonate solution, dried with sodium sulphate and concentrated. The crude product was purified by column chromatography with ethyl acetate:petroleum ether to afford the title compound as colourless liquid (1.40 g, 71% yield). $^1$H-NMR (δ ppm, DMSO-$d_6$, 400 MHz): δ 7.79 (dd, J=10.2, 4.3 Hz, 1H), 7.73 (dt, J=6.4, 3.1 Hz, 2H), 7.46 (t, J=6.9 Hz, 2H), 7.42 (m, 1H), 7.26 (dd, J=8.3, 1.5 Hz, 2H), 2.52 (t, J=7.4 Hz, 2H), 1.70 (m, 2H), 0.84 (t, J=7.4 Hz, 3H).

Intermediate 52: 2-(1-Bromopropyl)-6-fluoro-3-phenyl-4H-chromen-4-one

To a solution of intermediate 51 (1.30 g, 4.60 mmoles) in carbon tetrachloride (20 ml) N-bromosuccinimide (0.818 g, 4.60 mmoles) was added and heated to 80° C. Azobisisobutyronitrile (10 mg) was added to the reaction mixture at 80° C. After 12 h, the reaction mixture was cooled to RT, diluted with dichloromethane and washed with water. The organic layer was dried over sodium sulphate and concentrated under reduced pressure to afford the crude title compound as off-white solid (1.40 g, 84% yield). $^1$H-NMR (δ ppm, DMSO-$d_6$, 400 MHz): δ 7.88 (dd, J=9.2, 4.3 Hz, 1H), 7.80-7.71 (m, 2H), 7.52-7.42 (m, 3H), 7.29 (d, J=6.8 Hz, 2H), 4.68 (t, J=7.6 Hz, 1H), 2.34-2.15 (m, 2H), 0.91 (t, J=7.3 Hz, 3H).

Intermediate 53: 6-Bromo-2-ethyl-3-(4-fluorophenyl)-4H-chromen-4-one

Intermediate 6 (3.0 g, 9.70 mmoles) was taken in a RB flask and to this triethylamine (30 ml) and propionic anhydride (3.94 g, 30.37 mmoles) were added and the mixture was refluxed for 24 h. After cooling to RT, the reaction mixture was acidified by the addition of 1N HCl solution, extracted with ethyl acetate, washed with sodium bicarbonate solution, dried with sodium sulphate and concentrated. The crude product was purified by column chromatography with ethyl acetate:petroleum ether to afford the title compound as off-white solid (1.60 g, 47% yield). $^1$H-NMR (δ ppm, $CDCl_3$, 400 MHz): δ 8.33 (d, J=2.4 Hz, 1H), 7.76 (dd, J=8.8, 2.4 Hz, 1H), 7.38 (d, J=8.8 Hz, 1H), 7.24 (dd, J=5.5, 2.0 Hz, 2H), 7.16 (dt, J=11.4, 2.8 Hz, 2H), 2.61 (q, J=7.6 Hz, 2H), 1.27 (t, J=7.5 Hz, 3H).

Intermediate 54: 2-Ethyl-3-(4-fluorophenyl)-4H-chromen-4-one

To a solution of intermediate 53 (1.00 g, 2.88 mmoles) in ethanol (10 ml), ammonium formate (1.70 g, 27.60 mmoles) and palladium on carbon (10%, 80 mg) were added and the solution was refluxed for 1 h. The solution was filtered through celite, diluted with ethyl acetate, washed with 10% sodium bicarbonate solution (100 ml), dried over sodium sulphate and concentrated to afford the title compound as colourless liquid (0.640 g, 83% yield). $^1$H-NMR (δ ppm, $CDCl_3$, 400 MHz): δ 8.24 (dd, J=8.0, 1.5 Hz, 1H), 7.69 (dt, J=8.6, 1.7 Hz, 1H), 7.48 (d, J=8.3 Hz, 1H), 7.41 (t, J=7.9 Hz, 1H), 7.24 (m, 2H), 7.15 (t, J=8.7 Hz, 1H), 2.62 (q, J=7.6 Hz, 2H), 1.28 (t, J=7.6 Hz, 3H).

Intermediate 55: 2-(1-Bromoethyl)-3-(4-fluorophenyl)-4H-chromen-4-one

To a solution of intermediate 54 (0.600 g, 2.23 mmoles) in carbon tetrachloride (15 ml) N-bromosuccinimide (0.398 g, 2.23 mmoles) was added and heated to 80° C. Azobisisobutyronitrile (10 mg) was added to the reaction mixture at 80° C. After 12 h, the reaction mixture was cooled to RT, diluted with dichloromethane and washed with water. The organic layer was dried over sodium sulphate and concentrated under reduced pressure to afford the crude title compound as off-white solid (1.10 g) which is taken as such for next step.

Intermediate 56: 2-Ethyl-6-fluoro-3-phenyl-4H-chromen-4-one

Intermediate 50 (3.0 g, 13.63 mmoles) was taken in a RB flask and to this triethylamine (30 ml) and propionic anhydride (5.30 g, 40.78 mmoles) were added and the mixture was refluxed for 24 h. After cooling to RT, the reaction mixture was acidified by the addition of 1N HCl solution, extracted with ethyl acetate, washed with sodium bicarbonate solution, dried with sodium sulphate and concentrated. The crude product was purified by column chromatography with ethyl acetate:petroleum ether to afford the title compound as off-white solid (2.27 g, 65% yield). $^1$H-NMR (δ ppm, DMSO-$d_6$, 400 MHz): δ 7.79 (dd, J=7.1, 4.4 Hz, 1H), 7.73 (dt, J=7.7, 3.1 Hz, 2H), 7.46 (t, J=8.2 Hz, 2H), 7.40 (m, 1H), 7.27 (dd, J=8.2, 1.4 Hz, 2H), 2.55 (q, J=7.5 Hz, 2H), 1.19 (t, J=7.6 Hz, 3H).

Intermediate 57: 2-(1-Bromoethyl)-6-fluoro-3-phenyl-4H-chromen-4-one

To a solution of intermediate 56 (1.0 g, 3.72 mmoles) in carbon tetrachloride (20 ml) N-bromosuccinimide (0.662 g, 3.72 mmoles) was added and heated to 80° C. Azobisisobutyronitrile (10 mg) was added to the reaction mixture at 80° C. After 12 h, the reaction mixture was cooled to RT, diluted with dichloromethane and washed with water. The organic layer was dried over sodium sulphate and concentrated under reduced pressure to afford the crude title compound as off-white solid (1.37 g). $^1$H-NMR (δ ppm, DMSO-$d_6$, 400 MHz): δ 7.89 (dd, J=9.2, 4.3 Hz, 1H), 7.79 (dt, J=8.3, 3.2 Hz, 2H), 7.73 (dd, J=8.3.3.1 Hz, 2H), 7.51-7.42 (m, 3H), 7.32 (d, J=6.6 Hz, 2H), 4.97 (q, J=6.8 Hz, 1H), 1.96 (d, J=6.8 Hz, 3H).

Intermediate 58: 3-(3-Methoxyphenyl)-1H-pyrazolo[3,4-d]pyrimidin-4-amine

To a solution of 3-Iodo-1H-pyrazolo[3,4-d]pyrimidin-4-amine (0.522 g, 2.0 mmoles) in DMF (10 ml), ethanol (5 ml) and water (5 ml), 3-methoxyphenylboronic acid (0.395 g, 2.59 mmoles) and sodium carbonate (1.05 g, 10 mmoles) were added and the system is degassed for 30 min. Palladium tetrakis triphenylphosphine (0.455 g, 0.39 mmoles) was added under nitrogen atmosphere and heated to 80° C. After 12 h, the reaction mixture neutralised with 1.5N HCl, extracted with ethyl acetate. The organic layer was dried over sodium sulphate and concentrated under reduced pressure. The crude product was purified by column chromatography with methanol:dichloromethane to afford the title compound as off-white solid (0.130 g, 27% yield). $^1$H-NMR (δ ppm, DMSO-$d_6$, 400 MHz): δ 13.57 (s, 1H), 8.20 (s, 1H), 7.46 (t, J=7.8 Hz, 1H), 7.23 (d, J=7.5 Hz, 1H), 7.18 (d, J=2.4 Hz, 1H), 7.04 (dd, J=8.0, 1.8 Hz, 1H), 3.81 (s, 3H).

Intermediate 59: 1-(2-Hydroxyphenyl)-2-phenylethanone

To a solution of intermediate 1 (1.00 g, 3.43 mmoles) in ethanol (10 ml), ammonium formate (2.16 g, 34.34 mmoles) and palladium on carbon (10%, 100 mg) were added and the solution was refluxed for 1 h. The solution was filtered through celite, diluted with ethyl acetate, washed with 10% sodium bicarbonate solution (100 ml), dried over sodium sulphate and concentrated to afford the title compound as colourless liquid (0.560 g, 77% yield). $^1$H-NMR (δ ppm, $CDCl_3$, 400 MHz): δ 11.80 (s, 1H), 8.02 (dd, J=5.7, 1.7 Hz, 1H), 7.54 (dt, J=8.6, 1.7 Hz, 1H), 7.33 (m, 5H), 6.98 (m, 2H), 4.43 (s, 2H).

Intermediate 60: 6-Bromo-2-ethyl-3-o-tolyl-4H-chromen-4-one

Intermediate 11 (3.0 g, 9.83 mmoles) was taken in a RB flask and to this triethylamine (25 ml) and propionic anhydride (4.00 g, 30.76 mmoles) were added and the mixture was refluxed for 24 h. After cooling to RT, the reaction mixture was acidified by the addition of 1N HCl solution, extracted with ethyl acetate, washed with sodium bicarbonate solution, dried with sodium sulphate and concentrated. The crude product was purified by column chromatography with ethyl acetate:petroleum ether to afford the title compound as colourless liquid (0.700 g, 20% yield). $^1$H-NMR (δ ppm, DMSO-$d_6$, 400 MHz): δ 7.73 (d, J=2.5 Hz, 1H), 7.63 (dd, J=8.7, 2.5 Hz, 1H), 7.34 (t, J=4.8 Hz, 1H), 7.22-7.14 (m, 4H), 2.63 (q, J=7.5 Hz, 2H), 0.94 (t, J=7.5 Hz, 3H).

Intermediate 61: 2-Ethyl-3-o-tolyl-4H-chromen-4-one

To a solution of intermediate 60 (0.950 g, 2.76 mmoles) in ethanol (15 ml), ammonium formate (1.73 g, 27.60 mmoles) and palladium on carbon (10%, 80 mg) were added and the solution was refluxed for 1 h. The solution was filtered through celite, diluted with ethyl acetate, washed with 10% sodium bicarbonate solution (100 ml), dried over sodium sulphate and concentrated to afford the title compound as colourless liquid (0.620 g, 85% yield). $^1$H-NMR (δ ppm, DMSO-$d_6$, 400 MHz): δ 8.05 (dd, J=7.9, 1.3 Hz, 1H), 7.83 (dt, J=8.5, 1.5 Hz, 1H), 7.68 (d, J=8.4 Hz, 1H), 7.50 (t, J=7.5 Hz, 1H), 7.30 (d, J=4.3 Hz, 2H), 7.26 (m, 1H), 7.13 (d, J=7.2 Hz, 1H), 2.46 (m, 2H), 1.15 (t, J=7.6 Hz, 3H).

Intermediate 62: 2-(2-Fluorophenyl)-1-(2-hydroxyphenyl)ethanone

To a solution of intermediate 23 (9.0 g, 29.13 mmoles) in ethanol (90 ml), ammonium formate (18.3 g, 291.13 mmoles) and palladium on carbon (10%, 0.50 g) were added and the solution was refluxed for 1 h. The solution was filtered through celite, diluted with ethyl acetate, washed with 10% sodium bicarbonate solution (100 ml), dried over sodium sulphate and concentrated. The crude product was purified by column chromatography with ethyl acetate:petroleum ether to afford the title compound as colourless solid (3.5 g, 52% yield). $^1$H-NMR (δ ppm, $CDCl_3$, 400 MHz): δ 12.08 (s, 1H), 7.90 (d, J=7.0 Hz, 1H), 7.51 (dt, J=7.2, 1.4 Hz, 1H), 7.31-7.23 (m, 2H), 7.15-7.08 (m, 2H), 7.01 (d, J=8.4 Hz, 1H), 6.96 (t, J=8.0 Hz, 1H), 4.36 (s, 2H).

Intermediate 63: tert-butyl(3-(2-fluorophenyl)-4-oxo-4H-chromen-2-yl) methyl carbamate To a solution of intermediate 62 (2 g, 8.68 mmoles) in dichloromethane (20 ml), triethylamine (2.6 g, 26.06 mmoles) was added followed by N-Boc-Glycine (1.8 g, 10.27 mmoles). To this mixture HATU (6.6 g, 17.37 mmoles) was added and stirred at RT for 12 h. The reaction mixture was quenched by the addition of water and extracted with dichloromethane. The organic layer was dried over sodium sulphate and concentrated under reduced pressure. The crude product was purified by column chromatography with ethyl acetate: petroleum ether to afford the title compound as yellow solid (0.72 g, 23% yield). $^1$H-NMR (δ ppm, DMSO-$D_6$, 400 MHz): δ 8.06 (d, J=6.7 Hz, 1H), 7.87 (dt, J=7.0, 1.6 Hz, 1H), 7.62 (d, J=8.5 Hz, 1H), 7.53 (t, J=7.4 Hz, 1H), 7.48-7.35 (m, 3H), 7.30 (m, 2H), 4.04 (d, J=5.9 Hz, 2H), 1.36 (s, 9H).

Intermediate 64: 2-(Amino methyl)-3-(2-fluorophenyl)-4H-chromen-4-one

To a solution of intermediate 63 (0.700 g, 1.89 mmoles) in dichloromethane (10 ml), trifluoroacetic acid (3 ml) was added and stirred at RT for 2 h. The reaction mixture was concentrated, basified with sodium bicarbonate solution, extracted with ethyl acetate. The organic layer was dried over sodium sulphate and concentrated under reduced pressure to afford the title compound as brown liquid (0.440 g, 86%). $^{1}$H-NMR (δ ppm, DMSO-$D_6$, 400 MHz): δ 8.06 (d, J=7.9 Hz, 1H), 7.87 (dt, J=8.5, 1.3 Hz, 1H), 7.70 (d, J=8.4 Hz, 1H), 7.52 (m, 2H), 7.40 (t, J=7.2 Hz, 1H), 7.31 (m, 2H), 3.51 (s, 2H).

Intermediate 65: 2-(3-Fluorophenyl)-1-(2-hydroxyphenyl)ethanone

To a solution of intermediate 33 (11.0 g, 35.58 mmoles) in ethanol (110 ml), ammonium formate (22.4 g, 355.83 mmoles) and palladium on carbon (10%, 0.550 g) were added and the solution was refluxed for 1 h. The solution was filtered through celite, diluted with ethyl acetate, washed with 10% sodium bicarbonate solution (100 ml), dried over sodium sulphate and concentrated. The crude product was purified by column chromatography with ethyl acetate:petroleum ether to afford the title compound as colourless solid (5.6 g, 70% yield). $^{1}$H-NMR (δ ppm, DMSO-$D_6$, 400 MHz): δ 11.68 (s, 1H), 8.00 (dd, J=8.3, 1.6 Hz, 1H), 7.54 (dt, J=8.5, 1.6 Hz, 1H), 7.38 (m, 1H), 7.14-7.04 (m, 3H), 6.99 (m, 2H), 4.48 (s, 2H).

Intermediate 66: 1-(5-Fluoro-2-hydroxyphenyl)-2-(2-fluorophenyl)ethanone

2-Fluorophenylacetic acid (2.0 g, 13.14 mmoles) was dissolved in 20 ml dichloromethane. To this mixture, oxalylchloride (1.66 g, 13.14 mmoles) and DMF (3 drops) were added at 0° C. and stirred for 30 min. The solvent was evaporated and dissolved in 20 ml dichloromethane. To this mixture, 4-fluoroanisole (1.10 g, 8.76 mmoles) was added and cooled to 0° C. At 0° C. $AlCl_3$ (1.75 g, 13.14 mmoles) was added and the reaction mixture was warmed to RT and stirred for 12 h. The reaction mixture was quenched by the addition of 2N HCl, extracted with ethyl acetate, dried over sodium sulphate and concentrated. The crude product was purified by column chromatography with ethyl acetate:petroleum ether to afford the title compound as off-white solid (1.17 g, 54% yield. $^{1}$H-NMR (δ ppm, DMSO-$D_6$, 400 MHz): δ 11.25 (s, 1H), 7.73 (dd, J=9.5, 3.2 Hz, 1H), 7.43 (dt, J=8.8, 3.1 Hz, 1H), 7.35 (d, J=6.2 Hz, 1H), 7.31 (d, J=7.2 Hz, 1H), 7.19 (d, J=8.2 Hz, 1H), 7.03 (dd, J=9.1, 4.6 Hz, 1H), 4.50 (s, 2H).

Intermediate 67: 2-Ethyl-6-fluoro-3-(2-fluorophenyl)-4H-chromen-4-one

Intermediate 66 (1.1 g, 4.43 mmoles) was taken in a RB flask and to this triethylamine (10 ml) and propionic anhydride (1.80 g, 13.86 mmoles) were added and the mixture was refluxed for 24 h. After cooling to RT, the reaction mixture was acidified by the addition of 1N HCl solution, extracted with ethyl acetate, washed with sodium bicarbonate solution, dried with sodium sulphate and concentrated. The crude product was purified by column chromatography with ethyl acetate:petroleum ether to afford the title compound as off-white solid (0.800 g, 63% yield). $^{1}$H-NMR (δ ppm, DMSO-$d_6$, 400 MHz): δ 7.82 (dd, J=9.0, 4.4 Hz, 1H), 7.75 (m, 2H), 7.50 (m, 1H), 7.37-7.28 (m, 3H), 2.56 (m, 2H), 1.19 (t, J=7.6 Hz, 3H).

Intermediate 68: 2-(1-bromoethyl)-6-fluoro-3-(2-fluorophenyl)-4H-chromen-4-one To a solution of intermediate 67 (0.790 g, 2.75 mmoles) in carbon tetrachloride (15 ml) N-bromosuccinimide (0.491 g, 2.75 mmoles) was added and heated to 80° C. Azobisisobutyronitrile (10 mg) was added to the reaction mixture at 80° C. After 12 h, the reaction mixture was cooled to RT, diluted with dichloromethane and washed with water. The organic layer was dried over sodium sulphate and concentrated under reduced pressure to afford the crude title compound as yellow solid (0.824 g). $^{1}$H-NMR (δ ppm, DMSO-$d_6$, 400 MHz): δ [7.93 (d, J=4.3 Hz) 7.91 (d, J=4.2 Hz), 1H], 7.83 (dt, J=8.2, 3.1 Hz, 1H), 7.75 (m, 1H), 7.56 (m, 1H), 7.41 (m, 3H), [5.00 (q, J=6.9 Hz), 4.93 (q, J=6.9 Hz, 1H], [1.99 (d, J=6.9 Hz), 1.95 (d, J=6.8 Hz), 3H).

Intermediate 69: 1-(5-bromo-2-hydroxyphenyl)-2-(3,5-difluorophenyl)ethanone 3,5-Difluorophenylacetic acid (5.0 g, 29.0 mmoles) was dissolved in 50 ml dichloromethane. To this mixture, oxalylchloride (3.8 ml, 43.57 mmoles) and DMF (3 drops) were added at 0° C. and stirred for 30 min. The solvent was evaporated and dissolved in 50 ml dichloromethane. To this mixture, 4-bromooanisole (5.42 g, 29.0 mmoles) was added and cooled to 0° C. At 0° C. $AlCl_3$ (5.80 g, 47.57 mmoles) was added and the reaction mixture was warmed to RT and stirred for 12 h. The reaction mixture was quenched by the addition of 2N HCl, extracted with ethyl acetate, dried over sodium sulphate and concentrated. The crude product was purified by column chromatography with ethyl acetate:petroleum ether to afford the title compound as off-white solid (7.21 g, 77% yield. $^{1}$H-NMR (δ ppm, DMSO-$D_6$, 400 MHz): δ 11.44 (s, 1H), 7.98 (d, J=2.5 Hz, 1H), 7.65 (dd, J=8.9, 2.6 Hz, 1H), 7.13 (tt, J=9.1, 2.4 Hz, 1H), 7.02 (m, 3H), 4.50 (s, 2H).

Intermediate 70: 2-(3,5-Difluorophenyl)-1-(2-hydroxyphenyl)ethanone

To a solution of intermediate 69 (7.20 g, 22.01 mmoles) in ethanol (70 ml), ammonium formate (13.8 g, 220.17 mmoles) and palladium on carbon (10%, 0.250 g) were added and the solution was refluxed for 1 h. The solution was filtered through celite, diluted with ethyl acetate, washed with 10% sodium bicarbonate solution (100 ml), dried over sodium sulphate and concentrated to afford the title compound as yellow solid (4.1 g, 76% yield). $^{1}$H-NMR (δ ppm, DMSO-$D_6$, 400 MHz): δ 11.58 (s, 1H), 7.97 (dd, J=8.3, 1.6 Hz, 1H), 7.55 (dt, J=8.5, 1.5 Hz, 1H), 7.14 (tt, J=7.5, 2.2 Hz, 1H), 7.03-6.96 (m, 4H), 4.52 (s, 2H).

Intermediate 71: 3-(3,5-Difluorophenyl)-2-ethyl-4H-chromen-4-one

Intermediate 70 (2.0 g, 8.08 mmoles) was taken in a RB flask and to this triethylamine (20 ml) and propionic anhydride (3.26 g, 25.2 mmoles) were added and the mixture was refluxed for 24 h. After cooling to RT, the reaction mixture was acidified by the addition of 1N HCl solution, extracted with ethyl acetate, washed with sodium bicarbonate solution, dried with sodium sulphate and concentrated. The crude product was purified by column chromatography with ethyl acetate:petroleum ether to afford the title compound as off-colourless liquid (1.65 g, 72% yield). $^{1}$H-NMR (δ ppm, DMSO-$d_6$, 400 MHz): δ 8.05 (dd, J=7.9, 1.2 Hz, 1H), 7.84 (dt, J=8.5, 1.4 Hz, 1H), 7.68 (d, J=8.4 Hz, 1H), 7.51 (t, J=7.8 Hz, 1H), 7.30 (tt, J=7.2, 2.2 Hz, 1H), 7.07 (d, J=6.1 Hz, 2H), 2.58 (q, J=7.5 Hz, 1H), 1.21 (t, J=7.6 Hz, 3H).

Intermediate 72: 2-(1-Bromoethyl)-3-(3,5-difluorophenyl)-4H-chromen-4-one

To a solution of intermediate 71 (1.60 g, 5.58 mmoles) in carbon tetrachloride (20 ml) N-bromosuccinimide (0.994 g, 5.58 mmoles) was added and heated to 80° C. Azobisisobutyronitrile (30 mg) was added to the reaction mixture at 80° C. After 12 h, the reaction mixture was cooled to RT, diluted with dichloromethane and washed with water. The organic layer was dried over sodium sulphate and concentrated under reduced pressure to afford the crude title compound as brown solid (1.95 g, 96% yield). $^1$H-NMR (δ ppm, DMSO-$d_6$, 400 MHz): δ 8.06 (dd, J=7.9, 1.5 Hz, 1H), 7.90 (dt, J=8.6, 1.6 Hz, 1H), 7.78 (d, J=8.3 Hz, 1H), 7.55 (t, J=7.3 Hz, 1H), 7.38 (tt, J=9.5, 2.3 Hz, 1H), 7.10 (dd, J=8.3, 2.2 Hz, 2H), 5.05 (q, J=6.8 Hz, 1H), 1.97 (d, J=6.8 Hz, 3H).

Intermediate 73: 1-(5-Fluoro-2-hydroxyphenyl)-2-(3-fluorophenyl)ethanone

3-Fluorophenylacetic acid (7.33 g, 47.56 mmoles) was dissolved in 25 ml dichloromethane. To this mixture, oxalylchloride (7.54 g, 59.46 mmoles) and DMF (3 drops) were added at 0° C. and stirred for 30 min. The solvent was evaporated and dissolved in 25 ml dichloromethane. To this mixture, 4-fluoroanisole (5.00 g, 39.64 mmoles) was added and cooled to 0° C. At 0° C. $AlCl_3$ (7.95 g, 59.46 mmoles) was added and the reaction mixture was warmed to RT and stirred for 12 h. The reaction mixture was quenched by the addition of 2N HCl, extracted with ethyl acetate, dried over sodium sulphate and concentrated. The crude product was purified by column chromatography with ethyl acetate:petroleum ether to afford the title compound as colourless solid (4.5 g, 45% yield. $^1$H-NMR (δ ppm, DMSO-$D_6$, 400 MHz): δ 11.34 (s, 1H), 7.75 (dd, J=9.4, 3.1 Hz, 1H), 7.42 (m, 2H), 7.12 (m, 3H), 7.05 (dd, J=9.0, 4.5 Hz, 1H), 4.47 (s, 2H).

Intermediate 74: 2-Ethyl-6-fluoro-3-(3-fluorophenyl)-4H-chromen-4-one

Intermediate 73 (3.00 g, 12.08 mmoles) was taken in a RB flask and to this triethylamine (25 ml) and propionic anhydride (4.92 g, 37.82 mmoles) were added and the mixture was refluxed for 24 h. After cooling to RT, the reaction mixture was acidified by the addition of 1N HCl solution, extracted with ethyl acetate, washed with sodium bicarbonate solution, dried with sodium sulphate and concentrated. The crude product was purified by column chromatography with ethyl acetate:petroleum ether to afford the title compound as off-yellow solid (1.80 g, 52% yield). $^1$H-NMR (δ ppm, DMSO-$d_6$, 400 MHz): δ 7.80 (m, 1H), 7.76 (m, 2H), 7.51 (dd, J=8.0, 6.4 Hz), 7.22 (m, 1H), 7.18 (m, 2H), 2.56 (q, J=7.6 Hz, 2H), 1.20 (t, J=7.6 Hz, 3H).

Intermediate 75: 2-(1-Bromoethyl)-6-fluoro-3-(3-fluorophenyl)-4H-chromen-4-one To a solution of intermediate 74 (1.80 g, 6.28 mmoles) in carbon tetrachloride (20 ml) N-bromosuccinimide (1.11 g, 6.28 mmoles) was added and heated to 80° C. Azobisisobutyronitrile (10 mg) was added to the reaction mixture at 80° C. After 12 h, the reaction mixture was cooled to RT, diluted with dichloromethane and washed with water. The organic layer was dried over sodium sulphate and concentrated under reduced pressure to afford the crude title compound as yellow solid (1.25 g, 55% yield). $^1$H-NMR (δ ppm, DMSO-$d_6$, 400 MHz): δ 7.91 (dd, J=9.2, 4.3 Hz, 1H), 7.81 (dt, J=8.2, 2.8 Hz, 1H), 7.74 (dd, J=8.3, 3.1 Hz, 1H), 7.57 (m, 1H), 7.32 (dt, J=8.5, 2.4 Hz, 1H), 7.19 (m, 2H), 5.00 (q, J=6.8 Hz, 1H), 1.97 (d, J=6.8 Hz, 3H).

Intermediate 76: 3-(3-fluorophenyl)-2-methyl-4H-chromen-4-one

Intermediate 65 (1.50 g, 6.51 mmoles) was taken in a RB flask and to this acetic anhydride (15 ml) and sodium acetate (3.74 g, 45.60 mmoles) were added and the mixture was refluxed for 12 h. After cooling to RT, the reaction mixture was quenched by the addition of ice cold water. The solid formed was filtered and washed with water. The product was dried under vacuum to afford the title compound as colourless solid (1.1 g, 68% yield). $^1$H-NMR (δ ppm, DMSO-$d_6$, 400 MHz): δ 8.05 (dd, J=7.9, 1.6 Hz, 1H), 7.83 (m, 1H), 7.66 (d, J=8.1 Hz, 1H), 7.50 (m, 2H), 7.24-7.13 (m, 3H), 2.29 (s, 3H).

Intermediate 77: 2-(bromomethyl)-3-(3-fluorophenyl)-4H-chromen-4-one

To a solution of intermediate 76 (1.00 g, 3.99 mmoles) in carbon tetrachloride (10 ml) N-bromosuccinimide (0.711 g, 3.99 mmoles) was added and heated to 80° C. Azobisisobutyronitrile (10 mg) was added to the reaction mixture at 80° C. After 12 h, the reaction mixture was cooled to RT, diluted with dichloromethane and washed with water. The organic layer was dried over sodium sulphate and concentrated under reduced pressure to afford the crude title compound as off-white solid (0.990 g, 74% yield). $^1$H-NMR (δ ppm, DMSO-$d_6$, 400 MHz): δ 8.07 (dd, J=8.1, 1.6 Hz, 1H), 7.89 (m, 1H), 7.73 (d, J=8.3 Hz, 1H), 7.56 (m, 2H), 7.32 (dt, J=8.4, 2.3 Hz, 1H), 7.23 (m, 2H), 4.40 (s, 2H).

Intermediate 78: 3-(3-fluorophenyl)-1H-pyrazolo[3,4-d]pyrimidin-4-amine

To a solution of 3-iodo-1H-pyrazolo[3,4-d]pyrimidin-4-amine (1.50 g, 5.74 mmoles) in DMF (12 ml), ethanol (7 ml) and water (7 ml), 3-Fluorophenyl boronic acid (1.6 g, 11.49 mmoles) and sodium carbonate (3.0 g, 28.73 mmoles) were added and the system is degassed for 30 min. Palladium tetrakis triphenylphosphine (1.90 g, 1.72 mmoles) was added under nitrogen atmosphere and heated to 80° C. After 12 h, the reaction mixture neutralised with 1.5N HCl, extracted with ethyl acetate. The organic layer was dried over sodium sulphate and concentrated under reduced pressure. The crude product was purified by column chromatography with methanol:dichloromethane to afford the title compound as yellow solid (0.240 g, 18% yield). $^1$H-NMR (δ ppm, DMSO-$d_6$, 400 MHz): δ 13.66 (s, 1H), 8.21 (s, 1H), 7.59 (m, 1H), 7.50 (d, J=7.6, 1.2 Hz, 1H), 7.45 (m, 1H), 7.31 (m, 1H).

Intermediate 79: 3-(3-fluoro-5-methoxyphenyl)-1H-pyrazolo[3,4-d]pyrimidin-4-amine To a solution of 3-iodo-1H-pyrazolo[3,4-d]pyrimidin-4-amine (0.700 g, 2.68 mmoles) in DMF (10 ml), ethanol (5 ml) and water (5 ml), 3-Fluoro-5-methoxyphenyl boronic acid (0.592 g, 3.48 mmoles) and sodium carbonate (1.42 g, 13.40 mmoles) were added and the system is degassed for 30 min. Palladium tetrakis triphenylphosphine (0.588 g, 0.509 mmoles) was added under nitrogen atmosphere and heated to 80° C. After 12 h, the reaction mixture was celite filtered, concentrated and extracted with ethyl acetate. The organic layer was dried over sodium sulphate and concentrated under reduced pressure. The crude product was purified by column chromatography with methanol:dichloromethane to afford the title compound as yellow solid (0.260 g, 37% yield).

$^1$H-NMR (δ ppm, DMSO-$d_6$, 400 MHz): δ 13.64 (s, 1H), 8.21 (s, 1H), 7.03 (m, 2H), 6.93 (td, J=11.1, 2.3 Hz, 1H), 3.83 (s, 3H).

Intermediate 80: 3-(4-Fluoro-3-methoxyphenyl)-1H-pyrazolo[3,4-d]pyrimidin-4-amine To a solution of 3-iodo-1H-pyrazolo[3,4-d]pyrimidin-4-amine (0.500 g, 1.91 mmoles) in DMF (8 ml), ethanol (4 ml) and water (4 ml), 4-Fluoro-3-methoxyphenyl boronic acid (0.423 g, 2.49 mmoles) and sodium carbonate (1.01 g, 9.57 mmoles) were added and the system is degassed for 30 min. Tetrakis triphenylphosphine Palladium (0.436 g, 0.377 mmoles) was added under nitrogen atmosphere and heated to 80° C. After 12 h, the reaction mixture was celite filtered, concentrated and extracted with ethyl acetate. The organic layer was dried over sodium sulphate and concentrated under reduced pressure. The crude product was purified by column chromatography with methanol:dichloromethane to afford the title compound as yellow solid (0.240 g, 48% yield). $^1$H-NMR (δ ppm, DMSO-$d_6$, 400 MHz): δ 13.64 (s, 1H), 8.20 (s, 1H), 8.08 (s, 1H), 7.54 (d, J=9.3 Hz, 1H), 7.34 (d, J=8.3 Hz, 1H), 3.82 (s, 3H).

Intermediate 81: 3-(3-fluoro-4-methoxyphenyl)-1H-pyrazolo[3,4-d]pyrimidin-4-amine To a solution of 3-iodo-1H-pyrazolo[3,4-d]pyrimidin-4-amine (1.00 g, 3.83 mmoles) in DMF (12 ml), ethanol (7 ml) and water (7 ml), 3-Fluoro-4-methoxyphenyl boronic acid (0.781 g, 4.59 mmoles) and sodium carbonate (2.03 g, 19.15 mmoles) were added and the system is degassed for 30 min. Tetrakis triphenylphosphine Palladium (0.872 g, 0.754 mmoles) was added under nitrogen atmosphere and heated to 80° C. After 12 h, the reaction mixture was celite filtered, concentrated and extracted with ethyl acetate. The organic layer was dried over sodium sulphate and concentrated under reduced pressure. The crude product was purified by column chromatography with methanol:dichloromethane to afford the title compound as brown solid (0.136 g, 14% yield). $^1$H-NMR (δ ppm, DMSO-$d_6$, 400 MHz): δ 13.53 (s, 1H), 8.19 (s, 1H), 7.45 (m, 2H), 7.33 (t, J=8.6 Hz, 1H), 3.89 (s, 3H).

Intermediate 82: 3-(3-chloro-5-methoxyphenyl)-1H-pyrazolo[3,4-d]pyrimidin-4-amine To a solution of 3-iodo-1H-pyrazolo[3,4-d]pyrimidin-4-amine (0.700 g, 2.68 mmoles) in DMF (10 ml), ethanol (6 ml) and water (6 ml), 3-chloro-5-methoxyphenyl boronic acid (0.600 g, 3.21 mmoles) and sodium carbonate (1.40, 13.40 mmoles) were added and the system is degassed for 30 min. Tetrakis triphenylphosphine Palladium (0.610 g, 0.528 mmoles) was added under nitrogen atmosphere and heated to 80° C. After 12 h, the reaction mixture was celite filtered, concentrated and extracted with ethyl acetate. The organic layer was dried over sodium sulphate and concentrated under reduced pressure. The crude product was purified by column chromatography with methanol:dichloromethane to afford the title compound as yellow solid (0.198 g, 27% yield). $^1$H-NMR (δ ppm, DMSO-$d_6$, 400 MHz): δ 13.66 (s, 1H), 8.21 (s, 1H), 7.24 (t, J=1.6 Hz, 1H), 7.13 (d, J=1.2 Hz, 1H), 7.11 (t, J=2.1 Hz, 1H), 3.83 (s, 3H).

Intermediate 83: 3-(3-(trifluoromethoxy)phenyl)-1H-pyrazolo[3,4-d]pyrimidin-4-amine To a solution of 3-iodo-1H-pyrazolo[3,4-d]pyrimidin-4-amine (1.00 g, 3.83 mmoles) in DMF (14 ml), ethanol (7 ml) and water (7 ml), 3-trifluoromethoxyphenyl boronic acid (1.025 g, 4.97 mmoles) and sodium carbonate (2.02 g, 19.15 mmoles) were added and the system is degassed for 30 min. Tetrakis triphenylphosphine Palladium (0.871 g, 0.754 mmoles) was added under nitrogen atmosphere and heated to 80° C. After 12 h, the reaction mixture was celite filtered, concentrated and extracted with ethyl acetate. The organic layer was dried over sodium sulphate and concentrated under reduced pressure. The crude product was purified by column chromatography with methanol:dichloromethane to afford the title compound as yellow solid (0.465 g, 41% yield). $^1$H-NMR (δ ppm, DMSO-$d_6$, 400 MHz): δ 13.71 (s, 1H), 8.22 (s, 1H), 7.70 (m, 2H), 7.59 (s, 1H), 7.46 (td, J=7.9, 1.4 Hz, 1H).

Intermediate 84: 3-(4-methoxyphenyl)-1H-pyrazolo[3,4-d]pyrimidin-4-amine

To a solution of 3-iodo-1H-pyrazolo[3,4-d]pyrimidin-4-amine (1.00 g, 3.83 mmoles) in DMF (14 ml), ethanol (7 ml) and water (7 ml), 4-methoxyphenyl boronic acid (0.873 g, 5.746 mmoles) and sodium carbonate (2.03 g, 19.15 mmoles) were added and the system is degassed for 30 min. Tetrakis triphenylphosphine Palladium (0.871 g, 0.754 mmoles) was added under nitrogen atmosphere and heated to 80° C. After 12 h, the reaction mixture was celite filtered, concentrated and extracted with ethyl acetate. The organic layer was dried over sodium sulphate and concentrated under reduced pressure. The crude product was purified by column chromatography with methanol:dichloromethane to afford the title compound as off-white solid (0.250 g, 27% yield). $^1$H-NMR (δ ppm, DMSO-$d_6$, 400 MHz): δ 13.46 (s, 1H), 8.19 (s, 1H), 7.59 (td, J=9.5, 2.8 Hz, 2H), 7.11 (td, J=11.6, 2.6, 2H), 3.81 (s, 3H).

Intermediate 85: 3-(4-fluoro-2-methoxyphenyl)-1H-pyrazolo[3,4-d]pyrimidin-4-amine To a solution of 3-iodo-1H-pyrazolo[3,4-d]pyrimidin-4-amine (1.00 g, 3.83 mmoles) in DMF (14 ml), ethanol (7 ml) and water (7 ml), 4-fluoro-2-methoxyphenyl boronic acid (0.846 g, 4.979 mmoles) and sodium carbonate (2.06 g, 19.15 mmoles) were added and the system is degassed for 30 min. Tetrakis triphenylphosphine Palladium (0.754 g, 0.652 mmoles) was added under nitrogen atmosphere and heated to 80° C. After 12 h, the reaction mixture was celite filtered, concentrated and extracted with ethyl acetate. The organic layer was dried over sodium sulphate and concentrated under reduced pressure. The crude product was purified by column chromatography with methanol:dichloromethane to afford the title compound as off-white solid (0.350 g, 35% yield). $^1$H-NMR (δ ppm, DMSO-$d_6$, 400 MHz): δ 13.46 (s, 1H), 8.14 (s, 1H), 7.40 (t, J=8.4 Hz, 1H), 7.09 (dd, J=11.5, 2.9 Hz, 1H), 6.91 (dt, J=8.4, 2.4 Hz 1H), 3.78 (s, 3H).

Intermediate 86: 3-(4-chloro-3-methoxyphenyl)-1H-pyrazolo[3,4-d]pyrimidin-4-amine To a solution of 3-iodo-1H-pyrazolo[3,4-d]pyrimidin-4-amine (0.430 g, 1.65 mmoles) in DMF (3.6 ml), ethanol (1.8 ml) and water (1.8 ml), 4-chloro-3-methoxyphenyl boronic acid (0.400 g, 2.145 mmoles) and sodium carbonate (0.873 g, 19.15 mmoles) were added and the system is degassed for 30 min. Tetrakis triphenylphosphine Palladium (0.374 g, 0.313 mmoles) was added under nitrogen atmosphere and heated to 80° C. After 12 h, the reaction mixture was celite filtered, concentrated and extracted with ethyl acetate. The organic layer was dried over sodium sulphate and concentrated under reduced pressure. The crude product was purified by column chromatography with methanol:dichloromethane to afford the title compound as green solid (0.060 g, 10% yield). $^1$H-NMR (δ ppm, DMSO-$d_6$, 400 MHz): δ 13.62 (s, 1H), 8.20 (s, 1H), 7.56 (d, J=8.1 Hz, 1H), 7.34 (s, 1H), 7.23 (d, J=8.1 Hz 1H), 3.91 (s, 3H).

Intermediate 87: 3-(2-chloro-5-methoxyphenyl)-1H-pyrazolo[3,4-d]pyrimidin-4-amine To a solution of 3-iodo-1H-pyrazolo[3,4-d]pyrimidin-4-amine (1.0770 g, 4.12 mmoles) in DMF (10 ml), ethanol (5 ml) and water (5 ml), 2-chloro-5-methoxyphenyl boronic acid (1.00 g, 5.364 mmoles) and sodium carbonate (2.186 g, 20.63 mmoles) were added and the system is degassed for 30 min. Tetrakis triphenylphosphine Palladium (0.905 g, 0.783 mmoles) was added under nitrogen atmosphere and heated to 80° C. After 12 h, the reaction mixture was celite filtered, concentrated and extracted with ethyl acetate. The organic layer was dried over sodium sulphate and concentrated under reduced pressure. The crude product was purified by column chromatography with methanol:dichloromethane to afford the title compound as green solid (0.090 g, 16% yield). $^1$H-NMR (δ ppm, DMSO-$d_6$, 400 MHz): δ 13.61 (s, 1H), 8.19 (s, 1H), 7.51 (d, J=8.9 Hz, 1H), 7.09 (d, J=8.9 Hz 1H), 7.06 (d, J=2.6 Hz 1H), 3.78 (s, 3H).

Intermediate 88: 3-(3,4-dimethoxyphenyl)-1H-pyrazolo[3,4-d]pyrimidin-4-amine To a solution of 3-iodo-1H-pyrazolo[3,4-d]pyrimidin-4-amine (1.00 g, 3.83 mmoles) in DMF (10 ml), ethanol (5 ml) and water (5 ml), 3,4-dimethoxyphenyl boronic acid (1.04 g, 5.746 mmoles) and sodium carbonate (2.03 g, 19.15 mmoles) were added and the system is degassed for 30 min. Tetrakis triphenylphosphine Palladium (0.872 g, 0.754 mmoles) was added under nitrogen atmosphere and heated to 80° C. After 12 h, the reaction mixture was celite filtered, concentrated and extracted with ethyl acetate. The organic layer was dried over sodium sulphate and concentrated under reduced pressure. The crude product was purified by column chromatography with methanol:dichloromethane to afford the title compound as yellow solid (0.220 g, 21% yield). $^1$H-NMR (δ ppm, DMSO-$d_6$, 400 MHz): δ 13.46 (s, 1H), 8.19 (s, 1H), 7.20 (s, 1H), 7.19 (d, J=9.3 Hz, 1H), 7.11 (d, J=8.1 Hz 1H), 3.81 (s, 6H).

Intermediate 89: 6-fluoro-2-methyl-3-phenyl-4H-chromen-4-one

Intermediate 50 (50 g, 0.217 moles) was taken in a RB flask and to this acetic anhydride (424 ml) and sodium acetate (124 g, 1.51 moles) were added and the mixture was refluxed for 12 h. After cooling to RT, the reaction mixture was quenched by the addition of ice cold water. The solid formed was filtered and washed with water. The product was dried under vacuum to afford the title compound as colourless solid (44 g, 80% yield). $^1$H-NMR (δ ppm, $CDCl_3$, 400 MHz): δ 7.87 (dd, J=8.3, 3.0 Hz, 1H), 7.47-7.35 (m, 5H), 7.29 (m, 2H), 2.32 (s, 3H).

Intermediate 90: 2-(bromomethyl)-6-fluoro-3-phenyl-4H-chromen-4-one

To a solution of intermediate 89 (44 gg, 0.16 moles) in carbon tetrachloride (400 ml) N-bromosuccinimide (29.1 g, 0.16 moles) was added and heated to 80° C. Azobisisobutyronitrile (500 mg) was added to the reaction mixture at 80° C. After 12 h, the reaction mixture was cooled to RT, diluted with dichloromethane and washed with water. The organic layer was dried over sodium sulphate and concentrated under reduced pressure to afford the crude title compound as pale yellow solid (40.2 g, 75% yield). $^1$H-NMR (δ ppm, DMSO-$d_6$, 400 MHz): δ 7.87 (dd, J=8.1, 3.0 Hz, 1H), 7.55 (dd, J=9.1, 4.2 Hz, 1H), 7.50-7.37 (m, 6H), 4.24 (s, 2H).

Intermediate 91: 6-fluoro-3-(3-fluorophenyl)-2-methyl-4H-chromen-4-one

Intermediate 73 (24 g, 0.096 moles) was taken in a RB flask and to this acetic anhydride (230 ml) and sodium acetate (55.2 g, 0.673 moles) were added and the mixture was refluxed for 12 h. After cooling to RT, the reaction mixture was quenched by the addition of ice cold water. The solid formed was filtered and washed with water. The product was dried under vacuum to afford the title compound as brown solid (26 g, quant. yield). $^1$H-NMR (δ ppm, $CDCl_3$, 400 MHz): δ 7.87 (dd, J=8.2, 3.0 Hz, 1H), 7.48-7.36 (m, 3H), 7.10-6.99 (m, 3H), 2.33 (s, 3H).

Intermediate 92: 2-(bromomethyl)-6-fluoro-3-(3-fluorophenyl)-4H-chromen-4-one To a solution of intermediate 91 (39 g, 0.143 moles) in carbon tetrachloride (400 ml) N-bromosuccinimide (25.5 g, 0.143 moles) was added and heated to 80° C. Azobisisobutyronitrile (500 mg) was added to the reaction mixture at 80° C. After 12 h, the reaction mixture was cooled to RT, diluted with dichloromethane and washed with water. The organic layer was dried over sodium sulphate and concentrated under reduced pressure to afford the crude title compound as pale brown solid (27 g, 54% yield). $^1$H-NMR (δ ppm, DMSO-$d_6$, 400 MHz): δ 7.87 (dd, J=8.1, 3.0 Hz, 1H), 7.69 (dd, J=9.2, 5.1 Hz, 1H), 7.49 (m, 2H), 7.18-7.10 (m, 3H), 4.23 (s, 2H).

Intermediate 93: 1-(4-bromo-2-fluorophenyl)ethanol

To a ice-cold solution of methyl magnesium iodide prepared from magnesium (1.7 g, 73.88 mmoles) and methyl iodide (4.58 ml, 73.88 mmoles) in diethyl ether (50 ml), 4-bromo-2-fluorobenzaldehyde (5 g, 24.62 mmoles) in diethyl ether (10 ml) was added and warmed to room temperature. After 12 h, the reaction mixture was cooled to 0° C., quenched with dilute HCl and extracted with ethyl acetate. The organic layer was dried over sodium sulphate and concentrated under reduced pressure to afford the title compound as red colour liquid (5 g, 94% yield). $^1$H-NMR (δ ppm, $CDCl_3$, 400 MHz): δ 7.40 (t, J=8.2 Hz, 1H), 7.30 (dd, J=8.3, 1.7 Hz, 1H), 7.21 (dd, J=9.9, 1.9 Hz, 1H), 5.17 (q, J=6.4 Hz, 1H), 1.49 (d, J=6.5 Hz, 3H).

Intermediate 94: 1-(4-bromo-2-fluorophenyl)ethanone

To a solution of intermediate 93 (5.0 g, 22.82 mmoles) in DMF (25 ml), pyridinium dichromate (12.8 g, 34.23 mmoles) was added at room temperature. After 12 h, the reaction mixture was quenched with water, diluted with ethyl acetate. And filtered through celite. The organic layer was washed with brine solution and dried over sodium sulphate and concentrated under reduced pressure to afford the title compound as red colour liquid (4.1 g, 84% yield). $^1$H-NMR (δ ppm, DMSO-$d_6$, 400 MHz): δ 7.76 (t, J=8.3 Hz, 1H), 7.73 (dd, J=10.8, 1.8 Hz, 1H), 7.55 (dd, J=5.2, 1.8 Hz, 1H), 2.55 (s, 3H).

Intermediate 95: 6-bromo-3-methyl-1H-indazole

To a solution of intermediate 94 (3.7 g, 17.04 mmoles) in 1,2-ethanediol (25 ml), hydrazine hydrate (1.65 ml, 34.09 mmoles) was added at room temperature and heated to 165° C. After 12 h, the reaction mixture cooled to room temperature, quenched with water and solid precipitated was filtered and dried under vacuum to afford the title compound as colourless solid (2.5 g, 72% yield). $^1$H-NMR (δ ppm, DMSO-$d_6$, 400 MHz): δ 12.74 (s, 1H), 7.67 (d, J=5.8 Hz, 1H), 7.65 (s, 1H), 7.19 (dd, J=8.6, 1.4 Hz, 1H), 2.46 (s, 3H).

Intermediate 96: tert-butyl 6-bromo-3-methyl-1H-indazole-1-carboxylate

To a solution of intermediate 95 (10.0 g, 47.39 mmoles) in acetonitrile (100 ml) cooled to 20° C., Boc-anhydride (10.3 g, 34.09 mmoles) was added followed by DMAP (0.579 g, 4.73 mmoles) and triethylamine (4.7 g, 47.39 mmoles) and the reaction mixture was stirred at room temperature. After 12 h, the reaction mixture was concentrated and quenched with water and solid precipitated was filtered and dried under vacuum to afford the title compound as colourless solid (10.3 g, 70% yield). $^1$H-NMR (δ ppm, DMSO-$d_6$, 400 MHz): δ 8.19 (d, J=1.2 Hz, 1H), 7.81 (d, J=8.4 Hz, 1H),), 7.54 (dd, J=8.5, 1.7 Hz, 1H), 2.50 (s, 3H), 1.62 (s, 9H).

Intermediate 97: 3-methyl-6-(4,4,5,5-tetramethyl-1,3,2-dioxaborolan-2-yl)-1H-indazole To a solution of intermediate 95 (1.0 g, 4.73 mmoles) in Dioxan 16 ml), bis(pinacaloto)diboron (1.3 g, 5.21 mmoles) and potassium acetate (0.930 g, 9.47 mmoles) were added and the system is degassed for 30 min. Bis(diphenylphosphinoferrocene)dichloro palladium.$CH_2Cl_2$ (0.387 g, 0.473 mmoles) was added under nitrogen atmosphere and heated to 80° C. After 12 h, the reaction mixture filtered through celite and concentrated. The crude product was purified by column chromatography with ethyl acetate:petroleum ether to afford the title compound as off-white solid (1.1 g, 91% yield) which is used as such for the next step.

Intermediate 98: tert-butyl 3-methyl-6-(4,4,5,5-tetramethyl-1,3,2-dioxaborolan-2-yl)-1H-indazole-1-carboxylate To a solution of intermediate 96 (2.70 g, 8.67 mmoles) in Dioxan (44 ml), bis(pinacaloto)diboron (2.4 g, 9.54 mmoles) and potassium acetate (1.70 g, 17.35 mmoles) were added and the system is degassed for 30 min. Bis(diphenylphosphinoferrocene)dichloro palladium.$CH_2Cl_2$ (0.354 g, 0.433 mmoles) was added under nitrogen atmosphere and heated to 80° C. After 12 h, the reaction mixture filtered through celite and concentrated. The crude product was purified by column chromatography with ethyl acetate:petroleum ether to afford the title compound as off-white solid (2.70 g, 87% yield).). $^1$H-NMR (δ ppm, DMSO-$d_6$, 400 MHz): δ 8.46 (s, 1H), 7.82 (d, J=7.9 Hz, 1H), 7.61 (d, J=8.0 Hz, 1H),), 2.51 (s, 3H), 1.62 (s, 9H).

Intermediate 99: 1-(4-bromo-2-fluorophenyl)propan-1-ol

To a ice-cold solution of ethyl magnesium iodide prepared from magnesium (2.39 g, 98.51 mmoles) and ethyl iodide (7.88 ml, 98.51 mmoles) in diethyl ether (50 ml), 4-bromo-2-fluorobenzaldehyde (5 g, 24.62 mmoles) in diethyl ether (10 ml) was added and warmed to room temperature. After 12 h, the reaction mixture was cooled to 0° C., quenched with dilute HCl and extracted with ethyl acetate. The organic layer was dried over sodium sulphate and concentrated under reduced pressure to afford the title compound as red colour liquid (5.8 g, 99% yield) which is used as such for step.

Intermediate 100: 1-(4-bromo-2-fluorophenyl)propan-1-one

To a solution of intermediate 99 (5.8 g, 24.89 mmoles) in DMF (30 ml), pyridinium dichromate (14.04 g, 37.33 mmoles) was added at room temperature. After 12 h, the reaction mixture was quenched with water, diluted with ethyl acetate and filtered through celite. The organic layer was washed with brine solution and dried over sodium sulphate and concentrated under reduced pressure to afford the title compound as colourless liquid (4.4 g, 76% yield). $^1$H-NMR (δ ppm, DMSO-$d_6$, 400 MHz): δ 7.78 (t, J=8.1 Hz, 1H), 7.38 (m, 2H), 2.55 (m, 2H), 1.21 (t, J=7.1 Hz, 3H).

Intermediate 101: 6-bromo-3-ethyl-1H-indazole

To a solution of intermediate 100 (4.3 g, 18.53 mmoles) in DMSO (4.5 ml), hydrazine hydrate 17.3 ml, 357.7 mmoles) was added at room temperature and heated to 130° C. After 22 h, the reaction mixture cooled to room temperature, quenched with water and solid precipitated was filtered and dried under vacuum to afford the title compound as colourless solid (3.8 g, 91% yield). $^1$H-NMR (δ ppm, DMSO-$d_6$, 400 MHz): δ 12.73 (s, 1H), 7.70 (d, J=8.6 Hz, 1H), 7.66 (d, J=1.1 Hz, 1H), 7.18 (dd, J=8.5, 1.5 Hz, 1H), 2.92 (q, J=7.6 Hz, 2H), 1.30 (t, J=7.6 Hz, 3H).

Intermediate 102: tert-butyl 6-bromo-3-ethyl-1H-indazole-1-carboxylate

To a solution of intermediate 101 (3.0 g, 13.32 mmoles) in acetonitrile (30 ml) cooled to 20° C., Boc-anhydride (5.81 g, 26.65 mmoles) was added followed by DMAP (0.162 g, 1.33 mmoles) and triethylamine (1.34 g, 13.32 mmoles) and the reaction mixture was stirred at room temperature. After 12 h, the reaction mixture was concentrated and quenched with water and solid precipitated was filtered and dried under vacuum to afford the title compound as colourless solid (4.04 g, 93% yield). $^1$H-NMR (δ ppm, DMSO-$d_6$, 400 MHz): δ 8.31 (s, 1H), 7.54 (d, J=8.4 Hz, 1H),), 7.42 (dd, J=8.4, 1.3 Hz, 1H), 2.99 (q, J=7.6 Hz, 2H), 1.71 (s, 9H), 1.42 (t, J=7.6 Hz, 3H).

Intermediate 103: tert-butyl 3-ethyl-6-(4,4,5,5-tetramethyl-1,3,2-dioxaborolan-2-yl)-1H-indazole-1-carboxylate To a solution of intermediate 102 (1.50 g, 4.61 mmoles) in Dioxan (24 ml), bis(pinacaloto)diboron (1.40 g, 5.53 mmoles) and potassium acetate (0.9050 g, 9.22 mmoles) were added and the system is degassed for 30 min. Bis(diphenylphosphinoferrocene)dichloro palladium.$CH_2Cl_2$ (0.188 g, 0.230 mmoles) was added under nitrogen atmosphere and heated to 80° C. After 12 h, the reaction mixture filtered through celite and concentrated. The crude product was purified by column chromatography with ethyl acetate:petroleum ether to afford the title compound as off-white solid (1.46 g, 85% yield).). $^1$H-NMR (δ ppm, DMSO-$d_6$, 400 MHz): δ 8.47

(s, 1H), 7.86 (d, J=7.9 Hz, 1H),), 7.60 (d, J=8.0 Hz, 1H), 2.98 (q, J=7.6 Hz, 2H), 1.62 (s, 9H), 1.31 (s, 12H), 1.30 (t, J=7.6 Hz, 3H).

Intermediate 104: 6-bromo-3-hydroxy-3-methylindolin-2-one

To a ice-cold solution of methyl magnesium iodide prepared from magnesium (1.7 g, 70.78 mmoles) and methyl iodide (4.40 ml, 70.78 mmoles) in diethyl ether (60 ml), 6-bromoisatin (4 g, 17.69 mmoles) in THF (120 ml) was added and warmed to room temperature. After 12 h, the reaction mixture was cooled to 0° C., quenched with dilute HCl and extracted with ethyl acetate. The organic layer was dried over sodium sulphate and concentrated under reduced pressure to afford the title compound as brown solid (4.2 g, 93% yield). $^1$H-NMR (δ ppm, $CDCl_3$, 400 MHz): δ 10.34 (s, 1H), 7.23 (t, J=7.9 Hz, 1H), 7.14 (dd, J=7.9, 1.7 Hz, 1H), 6.93 (d, J=1.6 Hz, 1H), 5.92 (s, 1H), 1.33 (s, 3H).

Intermediate 105: 6-bromo-3-methyl-1H-indole

To a solution of intermediate 104 (3.0 g, 12.48 mmoles) in THF (120 ml) cooled to 0° C., boron-dimethylsulfide (2M in THF, 62.44 mmoles) was added and heated to 50° C. After 12 h, the reaction mixture was cooled to 0° C., quenched with methanol and concentrated. The crude product was purified by column chromatography with ethyl acetate:petroleum ether to afford the title compound as off-white solid (1.15 g, 44% yield). $^1$H-NMR (δ ppm, $CDCl_3$, 400 MHz): δ 10.85 (s, 1H), 7.48 (d, J=1.8 Hz, 1H), 7.42 (d, J=8.4 Hz, 1H), 7.12 (t, J=1.1 Hz, 1H), 7.09 (dd, J=8.4, 1.8 Hz, 1H), 2.22 (s, 3H).

Intermediate 106: 3-methyl-6-(4,4,5,5-tetramethyl-1,3,2-dioxaborolan-2-yl)-1H-indole To a solution of intermediate 105 (1.10 g, 5.23 mmoles) in Dioxan (33 ml), bis(pinacaloto)diboron (1.60 g, 6.28 mmoles) and potassium acetate (1.54 g, 15.70 mmoles) were added and the system is degassed for 30 min. Bis(diphenylphosphinoferrocene)dichloro palladium.$CH_2Cl_2$ (0.128 g, 0.157 mmoles) was added under nitrogen atmosphere and heated to 80° C. After 12 h, the reaction mixture filtered through celite and concentrated. The crude product was purified by column chromatography with ethyl acetate:petroleum ether to afford the title compound as off-white solid (0.651 g, 48% yield).). $^1$H-NMR (δ ppm, DMSO-$d_6$, 400 MHz): δ 10.81 (s, 1H), 7.68 (s, 1H), 7.45 (d, J=7.9 Hz, 1H),), 7.28 (d, J=7.9 Hz, 1H), 7.19 (s, 1H), 2.23 (s, 3H), 1.28 (s, 12H).

Intermediate 107: 3-(2,3-dihydrobenzofuran-5-yl)-1H-pyrazolo[3,4-d]pyrimidin-4-amine To a solution of 3-iodo-1H-pyrazolo[3,4-d]pyrimidin-4-amine (0.70 g, 2.68 mmoles) in DMF (10 ml), ethanol (6 ml) and water (6 ml), 2,3-dihydrobenzofuran-5-boronic acid (0.527 g, 3.21 mmoles) and sodium carbonate (0.852 g, 8.04 mmoles) were added and the system is degassed for 30 min. Tetrakistriphenylphosphine Palladium (0.610 g, 0.528 mmoles) was added under nitrogen atmosphere and heated to 80° C. After 12 h, the reaction mixture was celite filtered, concentrated and extracted with ethyl acetate. The organic layer was dried over sodium sulphate and concentrated under reduced pressure. The crude product was purified by column chromatography with methanol:dichloromethane to afford the title compound as brown solid (0.198 g, 29% yield $^1$H-NMR (δ ppm, DMSO-$d_6$, 400 MHz): δ 13.42 (s, 1H), 8.18 (s, 1H), 7.48 (s, 1H), 7.36 (d, J=8.1 Hz, 1H), 6.90 (d, J=8.2 Hz, 1H), 4.61 (d, J=8.7 Hz, 2H), 3.27 (d, J=8.7 Hz, 2H).

Intermediate 108: tert-butyl 6-bromo-2-methyl-1H-benzo[d]imidazole-1-carboxylate To a solution of 6-bromo-2-methylbenzimidazole (1.00 g, 4.737 mmoles) in dichloromethane (20 ml) cooled to 20° C., Boc-anhydride (1.034 g, 4.737 mmoles) was added followed by DMAP (0.057 g, 0.473 mmoles) and triethylamine (0.479 g, 4.73 mmoles) and the reaction mixture was stirred at room temperature. After 12 h, the reaction mixture was concentrated and quenched with water and solid precipitated was filtered and dried under vacuum to afford the title compound as colourless solid as a mixture of two regioisomers (1.22 g, 83% yield). $^1$H-NMR (δ ppm, DMSO-$d_6$, 400 MHz): δ 8.00 (d, J=1.9 Hz, 0.53H), 7.80 (d, J=7.5 Hz, 0.47H), 7.78 (s, 0.47H), 7.55 (d, J=8.5 Hz, 0.53H), 7.47 (m, 1H), 2.69 (s, 1.4H), 2.68 (s, 1.6H), 1.63 (s, 9H).

Intermediate 109: tert-butyl 2-methyl-6-(4,4,5,5-tetramethyl-1,3,2-dioxaborolan-2-yl)-1H-benzo[d]imidazole-1-carboxylate To a solution of intermediate 108 (0.500 g, 1.606 mmoles) in Dioxan (24 ml), bis(pinacaloto)diboron (0.489 g, 1.928 mmoles) and potassium acetate (0.946 g, 9.64 mmoles) were added and the system is degassed for 30 min. Bis(diphenylphosphinoferrocene)dichloro palladium.$CH_2Cl_2$ (0.196 g, 0.241 mmoles) was added under nitrogen atmosphere and heated to 80° C. After 12 h, the reaction mixture filtered through celite and concentrated. The crude product was purified by column chromatography with ethyl acetate:petroleum ether to afford the title compound as brown solid as a mixture of two regioisomers (0.324 g, 56% yield).). $^1$H-NMR (δ ppm, DMSO-$d_6$, 400 MHz): δ 8.42 (s, 0.65H), 8.15 (s, 0.35H), 7.92 (d, J=8.3 Hz, 0.35H), 7.78 (d, J=8.1 Hz, 1H), 7.69 (d, J=7.9 Hz, 0.65H), 2.88 (s, 3H), 1.72 (s, 5.85H), 1.71 (s, 3.15H), 1.35 (s, 12H).

Intermediate 110: 4-bromo-2,6-difluorophenol

To a solution of 2,6-Difluorophenol (10.0 g, 76.86 mmoles) in DMF (60 mll), N-bromosuccinimide (13.68 g, 76.86 mmoles) was added at 0° C. and stirred at RT for 20 h. The reaction mixture was concentrated, diluted with water and extracted with ethyl acetate. The organic layer was dried over sodium sulphate and concentrated under reduced pressure to afford the title compound as light yellow liquid (15.1 g, 93% yield). $^1$H-NMR (δ ppm, DMSO-$D_6$, 400 MHz): δ 10.49 (s, 1H), 7.35 (d, J=6.2 Hz, 2H).

Intermediate 111: 5-bromo-1,3-difluoro-2-methoxybenzene

To a solution of intermediate 110 (15.0 g, 71.73 mmoles) in acetone (60 mll), potassium carbonate (29.75 g, 215.32 mmoles) was added at 0° C. followed by methyl iodide (22 ml, 358.86 mmoles) and stirred at RT for 22 h. The reaction mixture was concentrated, diluted with water and extracted with ethyl acetate. The organic layer was dried over sodium sulphate and concentrated under reduced pressure to afford the title compound as light yellow liquid (1 g, 68% yield). $^1$H-NMR (δ ppm, DMSO-$D_6$, 400 MHz): δ 7.08 (d, J=7.8 Hz, 2H).

Intermediate 112: 2-(3,5-difluoro-4-methoxyphenyl)-4,4,5,5-tetramethyl-1,3,2-dioxa borolane To a solution of intermediate 111 (2.0 g, 8.968 mmoles) in Dioxan (40 ml), bis(pinacaloto)diboron (2.73 g, 10.76 mmoles) and potassium acetate (2.64 g, 26.90 mmoles) were added and the system is degassed for 30 min. Bis(diphenylphosphinoferrocene)dichloro palladium.$CH_2Cl_2$ (0.219 g, 0.269 mmoles) was added under nitrogen atmosphere and heated to 80° C. After 12 h, the reaction mixture filtered through celite and concentrated. The crude product was purified by column chromatography with ethyl acetate:petroleum ether to afford the title compound as yellow liquid (2.2 g, 90% yield).). $^1$H-NMR (δ ppm, DMSO-$d_6$, 400 MHz): δ δ 7.318 (d, J=8.7 Hz, 2H), 4.02 (s, 3H), 1.32 (s, 12H).

Intermediate 113: 3-(3,5-difluoro-4-methoxyphenyl)-1H-pyrazolo[3,4-d]pyrimidin-4-amine To a solution of 3-iodo-1H-pyrazolo[3,4-d]pyrimidin-4-amine (1.0 g, 3.83 mmoles) in DMF (10 ml), ethanol (5 ml) and water (5 ml), intermediate 112 (1.55 g, 5.74 mmoles) and sodium carbonate (1.21 g, 11.49 mmoles) were added and the system is degassed for 30 min. Tetrakistriphenylphosphine Palladium (0.221 g, 0.19 mmoles) was added under nitrogen atmosphere and heated to 80° C. After 12 h, the reaction mixture was celite filtered, concentrated and extracted with ethyl acetate. The organic layer was dried over sodium sulphate and concentrated under reduced pressure. The crude product was purified by column chromatography with methanol:dichloromethane to afford the title compound as yellow solid (0.210 g, 19% yield). $^1$H-NMR (δ ppm, DMSO-$d_6$, 400 MHz): δ 13.66 (s, 1H), 8.20 (s, 1H), 7.36 (d, J=8.9 Hz, 2H), 6.96 (br s, 2H), 3.97 (s, 3H).

Intermediate 114: 6-bromo-1,3-dimethyl-1H-indazole(a) and 6-bromo-2,3-dimethyl-2H-indazole(b)

To a solution of intermediate 95 (2 g, 9.47 mmoles) in THF (30 ml) cooled to 0° C., sodium hydride (0.454 g, 60% in paraffin oil, 11.37 mmoles) was added and stirred for 10 min. Methyl iodide (2.0 gl, 14.21 mmoles) was added warmed to room temperature. After 12 h, the reaction mixture cooled to room temperature, quenched with water, extracted with ethyl acetate and concentrated. The crude product was purified by column chromatography with ethyl acetate:petroleum ether to afford the title compound as colourless solid. Fraction I (114a, 0.90 g, 43% yield). $^1$H-NMR (δ ppm, DMSO-$d_6$, 400 MHz): δ 7.87 (d, J=1.0 Hz, 1H), 7.64 (d, J=9.5 Hz, 1H), 7.20 (dd, J=9.5, 1.5 Hz, 1H), 3.92 (s, 3H), 2.44 (s, 3H). Fraction II (114b, 0.80 g, 38% yield). $^1$H-NMR (δ ppm, DMSO-$d_6$, 400 MHz): δ 7.72 (d, J=1.3 Hz, 1H), 7.65 (d, J=8.8 Hz, 1H), 7.20 (dd, J=8.8, 1.6 Hz, 1H), 4.01 (s, 3H), 2.58 (s, 3H).

Intermediate 115: 1,3-dimethyl-6-(4,4,5,5-tetramethyl-1,3,2-dioxaborolan-2-yl)-1H-indazole To a solution of intermediate 114a (0.90 g, 4.00 mmoles) in Dioxan (14 ml), bis(pinacaloto)diboron (1.1 g, 4.4 mmoles) and potassium acetate (0.785 g, 8.0 mmoles) were added and the system is degassed for 30 min. Bis(diphenylphosphinoferrocene)dichloro palladium.$CH_2Cl_2$ (0.163 g, 0.200 mmoles) was added under nitrogen atmosphere and heated to 80° C. After 12 h, the reaction mixture filtered through celite and concentrated. The crude product was purified by column chromatography with ethyl acetate:petroleum ether to afford the title compound as off-white solid (0.85 g, 78% yield).). $^1$H-NMR (δ ppm, $CDCl_3$, 400 MHz): δ 7.84 (s, 1H), 7.65 (d, J=8.0, 0.7 Hz, 1H), 7.53 (d, J=8.1 Hz, 1H), 4.03 (s, 3H), 2.56 (s, 3H), 1.38 (s, 12H).

Intermediate 116: 2,3-dimethyl-6-(4,4,5,5-tetramethyl-1,3,2-dioxaborolan-2-yl)-2H-indazole To a solution of intermediate 114b (0.80 g, 3.55 mmoles) in Dioxan (14 ml), bis(pinacaloto)diboron (0.992 g, 3.90 mmoles) and potassium acetate (0.697 g, 7.10 mmoles) were added and the system is degassed for 30 min. Bis(diphenylphosphinoferrocene)dichloro palladium.$CH_2Cl_2$ (0.145 g, 0.177 mmoles) was added under nitrogen atmosphere and heated to 80° C. After 12 h, the reaction mixture filtered through celite and concentrated. The crude product was purified by column chromatography with ethyl acetate:petroleum ether to afford the title compound as off-white solid (0.80 g, 83% yield).). $^1$H-NMR (δ ppm, DMSO-$d_6$, 400 MHz): δ 7.85 (s, 1H), 7.62 (dd, J=8.3, 0.8 Hz, 1H), 7.19 (d, J=8.4 Hz, 1H), 4.05 (s, 3H), 2.58 (s, 3H), 1.29 (s, 12H).

Example 1

2-[(6-Amino-9H-purin-9-yl)methyl]-6-bromo-3-phenyl-4H-chromen-4-one

To a solution of Adenine (0.685 g, 5.07 mmoles) in DMF (10 ml), potassium carbonate (0.701 g, 5.07 mmoles) was added and stirred at RT for 10 min. To this mixture intermediate 3 (1 g, 2.53 mmoles) was added and stirred for 12 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as off-white solid (0.496 g, 43% yield). MP: 207-209° C. $^1$H-NMR (δ ppm, DMSO-$D_6$, 400 MHz): δ 8.11 (d, J=2.4 Hz, 1H), 8.09 (d, J=10.4 Hz, 2H), 7.92 (dd, J=9.0, 2.4 Hz, 1H), 7.48-7.39 (m, 6H), 7.21 (s, 2H), 5.33 (s, 2H). Mass: 448.20 (M+).

Example 2

6-Bromo-2-(morpholinomethyl)-3-phenyl-4H-chromen-4-one

To a solution of Intermediate 3 (0.30 g, 0.761 mmoles) in THF (2 ml), was added morpholine (0.066 g, 0.761 mmoles) at RT and refluxed for 12 h. The reaction mixture was cooled, diluted with aqueous bicarbonate solution and extracted with ethyl acetate. The organic layer was dried over sodium sulphate and concentrated under reduced pressure. The crude product was purified by column chromatography with ethyl acetate:petroleum ether to afford the title compound as off-white solid (0.40 g, 79% yield). $^1$H-NMR (δ ppm, DMSO-$D_6$, 400 MHz): δ 8.12 (d, J=2.2 Hz, 1H), 7.98 (dd, J=8.8, 2.3 Hz, 1H), 7.72 (d, J=8.9 Hz, 1H), 7.45-7.39 (m, 3H), 7.29 (d, J=7.0 Hz, 2H), 3.50 (t, J=4.2 Hz, 4H), 3.40 (s, 2H), 2.32 (br S, 4H).

Example 2a

6-Bromo-2-(morpholinomethyl)-3-phenyl-4H-chromen-4-one hydrochloride

To a solution of Example 2 (0.10 g, 0.249 mmoles) in THF (2 ml), was added hydrochloric acid in diethyl ether (2 ml) at 0° C. and stirred for 30 min. The precipitate formed was filtered, washed with pentane and dried to afford the title compound as pale yellow solid (0.110 g, 99% yield. MP: 229-230° C. $^1$H-NMR (δ ppm, DMSO-$D_6$, 400 MHz): δ 8.13 (s, 1H), 8.06 (d, J=8.7 Hz, 1H), 7.77 (d, J=8.8 Hz, 1H), 7.48 (m, 3H), 7.32 (d, J=6.9 Hz, 2H), 4.35 (br s, 2H), 3.80 (br s, 4H), 3.59 (s, 2H), 3.25 (br s, 2H). Mass: 402.04 ($M^+$+1-HCl).

Example 3

2-[(6-Amino-9H-purin-9-yl)methyl]-3-phenyl-4H-chromen-4-one

To a solution of Example 1 (0.1 g, 0.22 mmoles) in methanol (10 ml), palladium on carbon (10 mg) was added and the solution was hydrogenated at RT under 5 kg/cm$^2$ pressure of hydrogen for 3 h. The solution was filtered through celite and concentrated. The crude product was purified by column chromatography with methanol:dichloromethane to afford the title compound as pale yellow solid (0.030 g, 37% yield). MP: 173-175° C. $^1$H-NMR (δ ppm, DMSO-$D_6$, 400 MHz): δ 8.10 (d, J=12.5 Hz, 1H), 8.05 (d, J=8.0 Hz, 1H), 7.77 (t, J=7.7 Hz, 1H), 7.48-7.41 (m, 6H), 7.22 (s, 2H), 5.34 (s, 2H). Mass: 370.05 ($M^+$+1).

Example 4

2-(Morpholinomethyl)-3-phenyl-4H-chromen-4-one

To a solution of Example 2 (0.1 g, 0.249 mmoles) in methanol (10 ml), palladium on carbon 20 mg) was added and the solution was hydrogenated at RT under 5 kg/cm$^2$ pressure of hydrogen for 4 h. The solution was filtered through celite and concentrated. The crude product was purified by column chromatography with ethyl acetate:petroleum ether to afford the title compound as brown solid (0.080 g, 87% yield). $^1$H-NMR (δ ppm, DMSO-$D_6$, 400 MHz): δ 8.08 (d, J=7.8 Hz, 1H), 7.90 (t, J=7.4 Hz, 1H), 7.74 (d, J=8.4 Hz, 1H), 7.55 (t, J=7.4 Hz, 1H), 7.49 (m, 3H), 7.31 (d, J=6.5 Hz, 2H), 3.72 (br s, 4H), 3.42 (br s, 6H).

Example 4a 2-(Morpholinomethyl)-3-phenyl-4H-chromen-4-one hydrochloride

To a solution of Example 4 (0.065 g, 0.202 mmoles) in THF (2 ml), was added hydrochloric acid in diethyl ether (2 ml) at 0° C. and stirred for 30 min. The precipitate formed was filtered, washed with pentane and dried to afford the title compound as off-white solid (0.043 g, 60% yield. MP: 208-209° C. $^1$H-NMR (δ ppm, DMSO-$D_6$, 400 MHz): δ 11.42 (br s, 1H), 8.08 (d, J=7.8 Hz, 1H), 7.90 (t, J=8.1 Hz, 1H), 7.79 (d, J=8.4 Hz, 1H), 7.55 (t, J=7.5 Hz, 1H), 7.49-7.44 (m, 3H), 7.33 (d, J=7.3 Hz, 2H), 4.24 (br s, 2H), 3.81 (br s, 5H), 3.08 (br s, 3H). 322.10 ($M^+$+1-HCl).

Example 5

2-[(1H-Benzo[d]imidazol-1-yl)methyl]-6-bromo-3-phenyl-4H-chromen-4-one

To a solution of intermediate 3 (0.10 g, 0.258 mmoles) in THF (2 ml), was added benzimidazole (0.059 g, 0.507 mmoles) at RT and refluxed for 2 h. The reaction mixture was cooled, diluted with aqueous bicarbonate solution and extracted with ethyl acetate. The organic layer was dried over sodium sulphate and concentrated under reduced pressure. The crude product was purified by column chromatography with ethyl acetate:petroleum ether to afford the title compound as pale yellow solid (0.040 g, 40% yield). MP: 192-197° C. $^1$H-NMR (δ ppm, DMSO-$D_6$, 400 MHz): δ 8.15 (s, 1H), 8.10 (d, J=2.3 Hz, 1H), 7.92 (dd, J=8.9, 2.3 Hz, 1H), 7.63 (m, 1H), 7.54 (m, 4H), 7.41 (d, J=6.8 Hz, 2H), 7.18 (m, 3H), 5.43 (s, 2H). 432.77 ($M^+$+1).

Example 6

6-Bromo-2-[(4-methyl-1H-benzo[d]imidazol-1-yl)methyl]-3-phenyl-4H-chromen-4-one

To a solution of intermediate 3 (0.10 g, 0.258 mmoles) in THF (2 ml), was added 4-methylbenzimidazole (0.066 g, 0.507 mmoles) at RT and refluxed for 2 h. The reaction mixture was cooled, diluted with aqueous bicarbonate solution and extracted with ethyl acetate. The organic layer was dried over sodium sulphate and concentrated under reduced pressure. The crude product was purified by column chromatography with ethyl acetate:petroleum ether to afford the title compound as pale yellow solid (0.040 g, 35% yield). MP: 176-179° C. $^1$H-NMR (δ ppm, DMSO-$D_6$, 400 MHz): δ 8.10 (s, 1H), 8.09 (d, J=2.3 Hz, 1H), 7.92 (dd, J=9.0, 2.5 Hz, 1H), 7.55 (m, 4H), 7.41 (d, J=6.8 Hz, 2H), 7.08 (t, J=7.5 Hz, 1H), 6.98 (m, 2H), 5.43 (s, 2H), 2.49 (s, 3H). Mass: 445.13 (M+).

Example 7

2-[(1H-benzo[d]imidazol-1-yl)methyl]-3-phenyl-4H-chromen-4-one

To a solution of intermediate 5 (0.10 g, 0.317 mmoles) in dioxin (2 ml), was added benzimidazole (0.074 g, 0.634 mmoles) at RT and refluxed for 12 h. The reaction mixture was cooled, diluted with aqueous bicarbonate solution and extracted with ethyl acetate. The organic layer was dried over sodium sulphate and concentrated under reduced pressure. The crude product was purified by column chromatography with methanol:dichloromethane to afford the title compound as yellow solid (0.050 g, 44% yield). MP: 186-191° C. $^1$H-NMR (δ ppm, DMSO-$D_6$, 400 MHz): δ 8.16 (s, 1H), 8.04 (d, J=7.7 Hz, 1H), 7.78 (t, J=8.3 Hz, 1H), 7.64 (d, J=5.5 Hz, 1H), 7.54-7.42 (m, 7H), 7.18 (s, 3H), 5.43 (s, 2H). Mass: 352.83 ($M^+$).

Example 8

2-[(4-methyl-1H-benzo[d]imidazol-1-yl)methyl]-3-phenyl-4H-chromen-4-one

To a solution of intermediate 5 (0.10 g, 0.317 mmoles) in dioxan (2 ml), was added 4-methylbenzimidazole (0.083 g, 0.634 mmoles) at RT and refluxed for 12 h. The reaction mixture was cooled, diluted with aqueous bicarbonate solution and extracted with ethyl acetate. The organic layer was dried over sodium sulphate and concentrated under reduced pressure. The crude product was purified by column chromatography with methanol:dichloromethane to afford the title compound as yellow solid (0.060 g, 51% yield). MP: 204-208° C. $^1$H-NMR (δ ppm, DMSO-$D_6$, 400 MHz): δ 8.11 (s, 1H), 8.04 (d, J=7.6 Hz, 1H), 7.77 (t, J=7.6 Hz, 1H), 7.55 (m, 7H), 7.08 (t, J=8.0 Hz, 1H), 6.99 (d, J=7.6 Hz, 2H), 5.40 (s, 2H), 2.48 (s, 3H). Mass: 367.25 ($M^+$+1).

Example 9

2-[(6-Chloro-9H-purin-9-yl)methyl]-3-phenyl-4H-chromen-4-one

To a solution of 6-Chloropurine (0.146 g, 0.951 mmoles) in DMF (3 ml), potassium carbonate (0.131 g, 0.951 mmoles) was added and stirred at RT for 10 min. To this mixture intermediate 5 (0.150 g, 0.475 mmoles) was added and stirred for 12 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as brownish yellow (0.053 g, 28% yield). MP: 187-190° C. $^1$H-NMR (δ ppm, DMSO-$D_6$, 400 MHz): δ 8.71 (s, 1H), 8.67 (s, 1H), 8.05 (d, J=7.0 Hz, 1H), 7.79 (dt, J=8.1, 1.5 Hz, 1H), 7.50 (t, J=7.9 Hz, 2H), 7.43 (m, 5H), 5.53 (s, 2H). 389.09 ($M^+$+1).

Example 10

6-Bromo-2-[(6-chloro-9H-purin-9-yl)methyl]-3-phenyl-4H-chromen-4-one

To a solution of 6-Chloropurine (0.117 g, 0.761 mmoles) in DMF (3 ml), potassium carbonate (0.105 g, 0.761 mmoles) was added and stirred at RT for 10 min. To this mixture intermediate 3 (0.150 g, 0.380 mmoles) was added and stirred for 12 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as brownish yellow (0.041 g, 22% yield). MP: 234-236° C. $^1$H-NMR (δ ppm, DMSO-$D_6$, 400 MHz): δ 8.71 (s, 1H), 8.67 (s, 1H), 8.11 (d, J=2.4 Hz, 1H), 7.94 (d, J=9.0 Hz, 1H), 7.53 (d, J=8.8 Hz, 1H), 7.41 (m, 5H), 5.52 (s, 2H). Mass: 466.79 ($M^+$−1).

Example 11

2-((9H-Purin-6-ylthio)methyl)-3-phenyl-4H-chromen-4-one

To a solution of 6-Mercaptopurine (0.162 g, 0.951 mmoles) in DMF (3 ml), potassium carbonate (0.131 g, 0.951 mmoles) was added and stirred at RT for 10 min. To this mixture intermediate 5 (0.150 g, 0.475 mmoles) was added and stirred for 12 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as off-white solid (0.061 g, 33% yield). MP: 208-209° C. $^1$H-NMR (δ ppm, DMSO-$D_6$, 400 MHz): δ 13.56 (s, 1H), 8.52 (s, 1H), 8.44 (s, 1H), 8.05 (d, J=7.9 Hz, 1H), 7.81 (t, J=7.2 Hz, 1H), 7.58 (d, J=8.4 Hz, 1H), 7.50 (m 4H), 7.39 (d, J=6.8 Hz, 2H), 4.62 (s, 2H). Mass: 386.78 ($M^+$).

Example 12

2-[(1H-Imidazol-1-yl)methyl]-3-phenyl-4H-chromen-4-one

To a solution of intermediate 5 (0.10 g, 0.317 mmoles) in dioxan (2 ml), was added imidazole (0.043 g, 0.634 mmoles) at RT and refluxed for 12 h. The reaction mixture was cooled, diluted with aqueous bicarbonate solution and extracted with ethyl acetate. The organic layer was dried over sodium sulphate and concentrated under reduced pressure. The crude product was purified by column chromatography with methanol:dichloromethane to afford the title compound as brownish yellow solid (0.040 g, 41% yield). MP: 168-171° C. $^1$H-NMR (δ ppm, DMSO-$D_6$, 400 MHz): δ 8.06 (dd, J=7.9, 1.3 Hz, 1H), 7.83 (dt, J=7.9, 1.5 Hz, 1H), 7.61 (s, 1H), 7.58 (d, J=8.5 Hz, 1H), 7.51 (m, 4H), 7.36 (dd, J=8.0 Hz, 2H), 7.12 (s, 1H), 6.90 (s, 1H), 5.10 (s, 2H). Mass: 303.29 ($M^+$+1).

Example 13

2-[(9H-Purin-6-ylthio)methyl]-6-bromo-3-phenyl-4H-chromen-4-one

To a solution of 6-Mercaptopurine (0.097 g, 0.570 mmoles) in DMF (5 ml), potassium carbonate (0.079 g, 0.570 mmoles) was added and stirred at RT for 10 min. To this mixture intermediate 3 (0.150 g, 0.380 mmoles) was added and stirred for 12 h. The reaction mixture was diluted with water and extracted with ethyl acetate. The organic layer was dried over sodium sulphate and concentrated under reduced pressure. The crude product was purified by column chromatography with ethyl acetate:petroleum ether to afford the title compound as grey solid (0.050 g, 28% yield). MP: 214-218° C. $^1$H-NMR (δ ppm, DMSO-$D_6$, 400 MHz): δ 13.54 (s, 1H), 8.51 (s, 1H), 8.43 (s, 1H), 8.10 (d, J=2.2 Hz, 1H), 7.95 (dd, J=8.9, 2.3 Hz, 1H), 7.59 (d, J=9.0 Hz, 1H), 7.45 (m 3H), 7.34 (d, J=6.5 Hz, 2H), 4.62 (s, 2H). Mass: 465.11 ($M^+$).

Example 14

2-((4-Amino-1H-pyrazolo[3,4-d]pyrimidin-1-yl)methyl)-6-bromo-3-phenyl-4H-chromen-4-one To a solution of 4-Aminopyrazalo[3,4-d]pyramiding (0.102 g, 0.761 mmoles) in DMF (3 ml), potassium carbonate (0.105 g, 0.761 mmoles) was added and stirred at RT for 10 min. To this mixture intermediate 3 (0.150 g, 0.380 mmoles) was added and stirred for 12 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as brownish yellow solid (0.031 g, 18% yield). MP: 236-240° C. $^1$H-NMR (δ ppm, DMSO-$D_6$, 400 MHz): δ 8.16 (s, 1H), 8.11 (s, 1H), 8.10 (s, 1H), 7.89 (dd, J=8.8, 2.2 Hz, 1H), 7.72 (br s, 2H), 7.40 (m 6H), 5.41 (s, 2H). Mass: 449.78 ($M^+$+1).

Example 15

2-[(6-Amino-9H-purin-9-yl)methyl]-6-bromo-3-(4-fluorophenyl)-4H-chromen-4-one

To a solution of Adenine (0.0983 g, 0.727 mmoles) in DMF (5 ml), potassium carbonate (0.125 g, 0.727 mmoles) was added and stirred at RT for 10 min. To this mixture intermediate 8 (0.150 g, 0.364 mmoles) was added and stirred for 12 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as yellow solid (0.030 g, 18% yield). MP: 238-242° C. $^1$H-NMR (δ ppm, DMSO-$D_6$, 400 MHz): δ 8.10 (s, 2H), 8.06 (s, 1H), 7.93 (dd, J=8.9, 2.2 Hz, 1H), 7.50 (d, J=8.9 Hz, 1H), 7.45 (t, J=8.2 Hz, 2H), 7.29 (t, J=8.8 Hz, 2H), 7.22 (s, 2H), 5.34 (s, 2H). Mass: 466.11 (M+).

Example 16

2-[(6-Amino-9H-purin-9-yl)methyl]-3-(4-fluorophenyl)-4H-chromen-4-one

To a solution of Adenine (0.121 g, 0.899 mmoles) in DMF (5 ml), potassium carbonate (0.155 g, 0.899 mmoles) was added and stirred at RT for 10 min. To this mixture intermediate 10 (0.150 g, 0.450 mmoles) was added and stirred for 12 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as yellow solid (0.040 g, 22% yield). MP: 212-216° C. $^1$H-NMR (δ ppm, DMSO-$D_6$, 400 MHz): δ 8.11 (s, 2H), 8.07 (s, 1H), 8.05 (d, J=8.2 Hz, 1H), 7.78 (t, J=8.4 Hz, 1H), 7.50 (m, 4H), 7.29 (m, 4H), 5.34 (s, 2H). Mass: 388.21 (M+1).

Example 17

6-Bromo-3-(4-fluorophenyl)-2-(morpholinomethyl)-4H-chromen-4-one

To a solution of intermediate 8 (0.150 g, 0.364 mmoles) in THF (5 ml), was added morpholine (0.0634 g, 0.728 mmoles) at RT and refluxed for 4 h. The reaction mixture was cooled, diluted with aqueous bicarbonate solution and extracted with ethyl acetate. The organic layer was dried over sodium sulphate and concentrated under reduced pressure. The crude product was purified by column chromatography with ethyl acetate:petroleum ether to afford the title compound as off-white solid (0.50 g, 32% yield). $^1$H-NMR (δ ppm, $CDCl_3$, 400 MHz): δ 8.35 (s, 1H), 7.81 (d, J=7.7 Hz, 1H), 7.39 (m, 3H), 7.18 (t, J=7.7 Hz, 2H), 3.80 (br st, 6H), 2.64 (br s, 4H).

Example 17a

6-Bromo-3-(4-fluorophenyl)-2-(morpholinomethyl)-4H-chromen-4-one hydrochloride To a solution of Example 17 (0.050 g, 0.1192 mmoles) in THF (2 ml), was added hydrochloric acid in diethyl ether (2 ml) at 0° C. and stirred for 30 min. The precipitate formed was filtered, washed with pentane and dried to afford the title compound as yellow solid (0.030 g, 55% yield. MP: 232-236° C. $^1$H-NMR (δ ppm, DMSO-$D_6$, 400 MHz): δ 8.13 (d, J=2.3 Hz, 1H), 8.06 (d, J=8.9 Hz, 1H), 7.80 (d, J=9.0 Hz, 1H), 7.38 (m, 4H), 4.24 (br s, 2H), 3.83 (br s, 4H), 3.62 (br s, 2H), 3.08 (br s, 2H). Mass: 419.75 (M+1-HCl).

Example 18

3-(4-fluorophenyl)-2-(morpholinomethyl)-4H-chromen-4-one

To a solution of intermediate 10 (0.150 g, 0.450 mmoles) in dioxan (5 ml), was added morpholine (0.0784 g, 0.90 mmoles) at RT and refluxed for 12 h. The reaction mixture was cooled, diluted with aqueous bicarbonate solution and extracted with ethyl acetate. The organic layer was dried over sodium sulphate and concentrated under reduced pressure. The crude product was purified by column chromatography with ethyl acetate:petroleum ether to afford the title compound as off-white solid (0.80 g, 52% yield). $^1$H-NMR (δ ppm, DMSO-$d_6$, 400 MHz): δ 8.06 (dd, J=7.9.1.0 Hz, 1H), 7.84 (dt, J=8.3, 1.2 Hz, 1H), 7.70 (d, J=8.4 Hz, 1H), 7.51 (t, J=7.6 Hz, 1H), 7.36 (dt, J=6.0, 2.9 Hz, 2H), 7.28 (t, J=8.9 Hz, 2H), 3.50 (br s, 4H), 3.39 (br s, 2H), 2.49 (br s, 4H).

Example 18a

3-(4-fluorophenyl)-2-(morpholinomethyl)-4H-chromen-4-one hydrochloride

To a solution of Example 18 (0.080 g, 0.235 mmoles) in THF (2 ml), was added hydrochloric acid in diethyl ether (2 ml) at 0° C. and stirred for 30 min. The precipitate formed was filtered, washed with pentane and dried to afford the title compound as yellow solid (0.080 g, 90% yield. MP: 225-229° C. $^1$H-NMR (δ ppm, DMSO-$D_6$, 400 MHz): δ 8.08 (d, J=6.6 Hz, 1H), 7.95 (t, J=7.3 Hz, 1H), 7.78 (d, J=8.2 Hz, 1H), 7.55 (t, J=7.6 Hz, 1H), 7.38 (m, 4H), 4.30 (br s, 2H), 3.88 (br s, 6H), 3.12 (br s, 2H).). Mass: 340.09 (M+1-HCl).

Example 19

2-[(6-Amino-9H-purin-9-yl)methyl]-6-bromo-3-o-tolyl-4H-chromen-4-one

To a solution of Adenine (0.099 g, 0.735 mmoles) in DMF (3 ml), potassium carbonate (0.101 g, 0.735 mmoles) was added and stirred at RT for 10 min. To this mixture intermediate 13 (0.150 g, 0.367 mmoles) was added and stirred for 12 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as brown solid (0.046 g, 27% yield). MP: 252-255° C. $^1$H-NMR (δ ppm, DMSO-$D_6$, 400 MHz): δ 8.11 (d, J=2.3 Hz, 1H), 8.03 (s, 1H), 7.97 (s, 1H), 7.94 (dd, J=8.9, 2.4 Hz, 1H), 7.54 (d, J=8.8 Hz, 1H), 7.31-7.22 (m, 6H), 5.22 (s, 2H), 2.00 (s, 3H).). Mass: 463.85 (M+1).

Example 20

7-[(6-Bromo-4-oxo-3-phenyl-4H-chromen-2-yl)methyl]-1,3-dimethyl-1H-purine-2,6(3H,7H)-dione To a solution of Theophylline (0.137 g, 0.761 mmoles) in DMF (3 ml), potassium carbonate (0.105 g, 0.761 mmoles) was added and stirred at RT for 10 min. To this mixture intermediate 3 (0.150 g, 0.380 mmoles) was added and stirred for 12 h. The reaction mixture was diluted with water and extracted with ethyl acetate. The organic layer was dried over sodium sulphate and concentrated under reduced pressure. The crude product was purified by column chromatography with ethyl acetate:petroleum ether to afford the title compound as brown solid (0.040 g, 21% yield). MP: 253-255° C. $^1$H-NMR (δ ppm, DMSO-$D_6$, 400 MHz): δ 8.11 (d, J=2.4 Hz, 1H), 8.03 (s, 1H), 7.94 (dd, J=8.9, 2.4 Hz, 1H), 7.52 (d, J=9.1 Hz, 1H), 7.42 (m, 3H), 7.31 (d, J=6.6 Hz, 1H), 5.51 (s, 2H), 3.13 (s, 6H).). Mass: 492.69 (M+).

Example 21

2-(1-(6-Amino-9H-purin-9-yl)ethyl)-6-bromo-3-phenyl-4H-chromen-4-one

To a solution of Adenine (0.266 g, 1.969 mmoles) in DMF (10 ml), potassium carbonate (0.272 g, 1.969 mmoles) was added and stirred at RT for 10 min. To this mixture intermediate 15 (0.400 g, 0.984 mmoles) was added and stirred for 12 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as off-white solid (0.200 g, 44% yield). MP: 230-231° C. $^1$H-NMR (δ ppm, DMSO-$D_6$, 400 MHz): δ 8.45 (s, 1H), 8.08 (d, J=2.4 Hz, 1H), 8.02 (s, 1H), 7.99 (dd, J=8.9, 2.4 Hz, 1H), 7.68 (d, J=8.9 Hz, 1H), 7.47 (m, 3H), 7.35 (d, J=6.5 Hz, 1H), 7.20 (s, 2H), 5.69 (q, J=7.2 Hz, 1H), 1.88 (d, J=7.2 Hz, 3H).). Mass: 463.92 (M+1).

Example 22

2-(1-(9H-Purin-6-ylthio)ethyl)-6-bromo-3-phenyl-4H-chromen-4-one

To a solution of 6-Mercaptopurine (0.251 g, 1.477 mmoles) in DMF (10 ml), potassium carbonate (0.255 g, 1.846 mmoles) was added and stirred at RT for 10 min. To this mixture intermediate 15 (0.300 g, 0.738 mmoles) was added and stirred for 12 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as light green solid (0.130 g, 37% yield). MP: 234-237° C. $^1$H-NMR (δ ppm, DMSO-$D_6$, 400 MHz): δ 13.54 (s, 1H), 8.40 (s, 1H), 8.37 (s, 1H), 8.10 (d, J=2.5 Hz, 1H), 7.99 (dd, J=8.8, 2.5 Hz, 1H), 7.77 (d, J=8.9 Hz, 1H), 7.39 (m, 4H), 7.26 (s, 2H), 5.47 (q, J=7.2 Hz, 1H), 1.79 (d, J=7.1 Hz, 3H). Mass: 478.83 ($M^+$).

Example 23

2-(1-(6-Amino-9H-purin-9-yl)ethyl)-3-phenyl-4H-chromen-4-one

To a solution of example 21 (0.080 g, 0.173 mmoles) in methanol (10 ml), palladium on carbon (10% 16 mg) was added and the solution was hydrogenated at RT under 5 kg/cm$^2$ pressure of hydrogen for 24 h. The solution was filtered through celite and concentrated. The crude product was purified by column chromatography with methanol:dichloromethane to afford the title compound as light yellow solid (0.025 g, 38% yield). MP: 254-257° C. $^1$H-NMR (δ ppm, DMSO-$D_6$, 400 MHz): δ 8.46 (s, 1H), 8.03 (s, 1H), 8.01 (d, J=1.6 Hz, 1H), 7.83 (dt, J=7.3, 1.7 Hz, 1H), 7.65 (d, J=8.2 Hz, 1H), 7.50 (m, 4H), 7.37 (dd, J=8.1, 1.7 Hz, 1H), 7.22 (s, 2H), 5.67 (q, J=7.3 Hz, 1H), 1.89 (d, J=7.2 Hz, 3H).). Mass: 384.19 (M+1).

Example 24

(S)-2-(1-(9H-purin-6-ylamino)ethyl)-6-bromo-3-phenyl-4H-chromen-4-one

To a solution of intermediate 17 (0.20 g, 0.581 mmoles) in tert-butanol (6 ml), N,N-diisopropylethyl amine (0.2 ml, 1.162 mmoles) and 6-bromopurine (0.087 g, 0.435 mmoles) were added and refluxed for 24 h. The reaction mixture was concentrated, diluted with water, extracted with ethyl acetate. The organic layer was dried over sodium sulphate and concentrated under reduced pressure. The crude product was purified by column chromatography with methanol:ethyl acetate to afford the title compound as yellow solid (0.065 g, 24% yield). MP: 151-154° C. $^1$H-NMR (δ ppm, DMSO-$D_6$, 400 MHz): δ 12.94 (s, 1H), 8.09 (br s, 3H), 7.94 (d, J=7.9 Hz, 1H), 7.59 (d, J=8.7 Hz, 1H), 7.42 (m, 6H), 5.22 (br t, 1H), 1.82 (d, J=6.4 Hz, 3H). Mass: 463.99 (M+1).

Example 25

2-((9H-purin-6-ylamino)methyl)-6-bromo-3-phenyl-4H-chromen-4-one

To a solution of intermediate 19 (0.20 g, 0.605 mmoles) in tert-butanol (4 ml), N,N-diisopropylethylamine (0.2 ml, 1.211 mmoles) and 6-bromopurine (0.096 g, 0.484 mmoles) were added and refluxed for 24 h. The reaction mixture was concentrated, diluted with water, extracted with ethyl acetate. The organic layer was dried over sodium sulphate and concentrated under reduced pressure. The crude product was purified by column chromatography with methanol:ethyl acetate to afford the title compound as yellow solid (0.065 g, 24% yield). MP: 151-154° C. $^1$H-NMR (δ ppm, DMSO-$D_6$, 400 MHz): δ 12.90 (s, 1H), 8.20 (ms, 4H), 7.91 (dd, J=9.0, 2.5 Hz, 1H), 7.49-7.35 (m, 6H), 4.64 (br s, 2H). Mass: 448.17 (M+).

Example 26

2-(1-(4-amino-1H-pyrazolo[3,4-d]pyrimidin-1-yl)ethyl)-6-bromo-3-phenyl-4H-chromen-4-one To a solution of 4-Aminopyrazalo[3,4-d]pyrimidine (0.299 g, 2.215 mmoles) in DMF (10 ml), potassium carbonate (0.382 g, 2.769 mmoles) was added and stirred at RT for 10 min. To this mixture intermediate 15 (0.450 g, 1.107 mmoles) was added and stirred for 12 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as light yellow solid (0.80 g, 16% yield). MP: 239-240° C. $^1$H-NMR (δ ppm, DMSO-$D_6$, 400 MHz): δ 8.10 (d, J=2.5 Hz, 1H), 8.09 (s, 1H), 8.00 (s, 1H), 7.97 (dd, J=8.9, 2.4 Hz, 1H), 7.69 (br s, 2H), 7.60 (d, J=9.0 Hz, 1H), 7.31 (br s, 3H), 7.12 (br s, 2H), 5.83 (q, J=7.1 Hz, 1H), 1.83 (d, J=7.0 Hz, 3H). Mass: 461.96 (M+).

Example 27

2-((6-Amino-9H-purin-9-yl)methyl)-6-methoxy-3-phenyl-4H-chromen-4-one

To a solution of adenine (0.234 g, 1.738 mmoles) in DMF (6 ml), potassium carbonate (0.240 g, 1.738 mmoles) was added and stirred at RT for 10 min. To this mixture intermediate 22 (0.300 g, 0.869 mmoles) was added and stirred for 12 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as pale yellow solid (0.052 g, 15% yield). MP: 197-198° C. $^1$H-NMR (δ ppm, DMSO-$D_6$, 400 MHz): δ 8.08 (s, 1H), 8.06 (s, 1H), 7.47 (m, 7H), 7.35 (dd, J=9.0, 3.1 Hz, 1H), 7.19 (s, 2H), 5.32 (s, 2H), 3.83 (s, 3H). Mass: 400.03 ($M^+$+1).

Example 28

2-(1-(6-Amino-9H-purin-9-yl)ethyl)-6-bromo-3-(2-fluorophenyl)-4H-chromen-4-one

To a solution of adenine (0.190 g, 1.408 mmoles) in DMF (6 ml), potassium carbonate (0.194 g, 1.408 mmoles) was added and stirred at RT for 10 min. To this mixture intermediate 25 (0.300 g, 0.704 mmoles) was added and stirred for 12 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as light brown solid consisting of a mixture of two atrop-isomers (0.082 g, 24% yield). MP: 256-258° C. $^1$H-NMR (δ ppm, DMSO-$D_6$, 400 MHz): δ [8.47 (s), 8.38 (s), 1H], 8.09 (d, J=2.5 Hz, 1H), [8.05 (dd, J=9.0, 3.0 Hz), 8.00 (dd, J=9.0, 2.5 Hz), 1H], [8.01 (s), 7.91 (s), 1H], [7.81 (d, J=9.0 Hz), 7.69 (d, J=8.9 Hz), 1H], 7.50 (m, 2H), 7.34 (m, 2H), [7.22 (s), 7.16 (s), 2H], [5.71 (q, J=7.0 Hz), 5.64 (q, J=7.2 Hz), 1H], 1.96 (d, J=7.2 Hz), 1.86 (d, J=7.2 Hz), 3H]. Mass: 481.73 (M+1).

Example 29

2-((6-Amino-9H-purin-9-yl)methyl)-6-bromo-3-(2-fluorophenyl)-4H-chromen-4-one

To a solution of adenine (0.131 g, 0.970 mmoles) in DMF (4 ml), potassium carbonate (0.133 g, 0.970 mmoles) was added and stirred at RT for 10 min. To this mixture intermediate 27 (0.200 g, 0.485 mmoles) was added and stirred for 12 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as brown solid (0.031 g, 14% yield). MP: 231-233° C. $^1$H-NMR (δ ppm, DMSO-$D_6$, 400 MHz): δ 8.11 (d, J=2.5 Hz, 1H), 8.08 (s, 1H), 8.04 (s, 1H), 7.96 (dd, J=8.9, 2.5 Hz, 1H), 7.54 (d, J=9.0 Hz, 1H), 7.49 (d, J=3.5 Hz, 1H), 7.30 (m, 4H), [5.42 (d, J=16.5 Hz), 5.30 (d, J=16.5 Hz) 2H]. Mass: 466.23 (M+).

Example 30

2-(1-(4-Amino-1H-pyrazolo[3,4-d]pyrimidin-1-yl)ethyl)-3-phenyl-4H-chromen-4-one

To a solution of 4-Aminopyrazalo[3,4-d]pyrimidine (0.279 g, 2.58 mmoles) in DMF (7 ml), potassium carbonate (0.357 g, 2.58 mmoles) was added and stirred at RT for 10 min. To this mixture intermediate 29 (0.340 g, 1.03 mmoles) was added and stirred for 12 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as light yellow solid (0.80 g, 16% yield). MP: 226-227° C. $^1$H-NMR (δ ppm, DMSO-$D_6$, 400 MHz): δ 8.09 (s, 1H), 8.04 (dd, J=7.9, 1.5 Hz, 1H), 8.01 (s, 1H), 7.82 (dt, J=8.6, 1.6 Hz, 1H), 7.58 (d, J=8.4 Hz, 2H), 7.51

(t, J=7.4 Hz, 2H). 7.31 (br s, 3H), 5.83 (q, J=7.0 Hz, 1H), 1.84 (d, J=7.0 Hz, 3H). Mass: 383.40 (M+).

Example 31

2-(1-(6-Amino-9H-purin-9-yl) propyl)-3-phenyl-4H-chromen-4-one

To a solution of adenine (0.190 g, 1.408 mmoles) in DMF (6 ml), potassium carbonate (0.194 g, 1.408 mmoles) was added and stirred at RT for 10 min. To this mixture intermediate 32 (0.300 g, 0.704 mmoles) was added and stirred for 12 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as light yellow solid (0.082 g, 24% yield). MP: 223-225° C. $^1$H-NMR (δ ppm, DMSO-$D_6$, 400 MHz): δ 8.54 (s, 1H), 8.04 (s, 1H), 8.03 (dd, J=7.9, 1.5 Hz, 1H), 7.86 (dt, J=7.1, 1.6 Hz), 7.78 (d, J=7.9 Hz, 1H), 7.51 (m, 4H), 7.33 (dd, J=7.8, 1.6 Hz, 2H), 7.23 (s, 2H), 5.52 (t, J=7.3 Hz, 1H), 2.49 (m, 2H), 0.74 (t, J=7.3 Hz, 3H). Mass: 398.12 (M+1).

Example 32

2-(1-(6-Amino-9H-purin-9-yl)ethyl)-3-(3-fluorophenyl)-4H-chromen-4-one

To a solution of adenine (0.233 g, 1.728 mmoles) in DMF (6 ml), potassium carbonate (0.238 g, 1.728 mmoles) was added and stirred at RT for 10 min. To this mixture intermediate 36 (0.300 g, 0.864 mmoles) was added and stirred for 12 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as off-white solid (0.200 g, 57% yield). MP: 155-158° C. $^1$H-NMR (δ ppm, DMSO-$D_6$, 400 MHz): δ 8.46 (s, 1H), 8.02 (s, 1H), 8.02 (dd, J=7.7, 1.4 Hz, 1H), 7.84 (dt, J=8.6, 1.5 Hz, 1H), 7.68 (d, J=8.4 Hz, 1H), 7.51 (m, 2H), 7.27-7.19 (m, 5H), 5.70 (q, J=7.2 Hz, 1H), 1.90 (d, J=7.2 Hz, 3H). Mass: 402.25 (M+1).

Example 33

2-((6-Amino-9H-purin-9-yl)methyl)-3-(2-fluorophenyl)-4H-chromen-4-one

To a solution of adenine (0.227 g, 1.68 mmoles) in DMF (5 ml), potassium carbonate (0.232 g, 1.68 mmoles) was added and stirred at RT for 10 min. To this mixture intermediate 38 (0.280 g, 0.840 mmoles) was added and stirred for 12 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as brown solid (0.046 g, 13% yield). MP: 202-205° C. $^1$H-NMR (δ ppm, DMSO-$D_6$, 400 MHz): δ 8.08 (s, 1H), 8.04 (s, 1H), 8.05 (dd, J=5.0, 1.8 Hz, 1H), 7.81 (dt, J=8.5, 1.7 Hz, 1H), 7.53-7.441 (m, 4H), 7.30 (d, J=6.6 Hz, 1H), 7.26 (d, J=6.6 Hz, 1H), 7.22 (s, 2H), [5.43 (d, J=16.4 Hz), 5.30 (d, J=16.4 Hz), 2H]. Mass: 387.83 (M+).

Example 34

2-(1-(6-Amino-9H-purin-9-yl)ethyl)-3-(2-fluorophenyl)-4H-chromen-4-one

To a solution of adenine (0.179 g, 1.32 mmoles) in DMF (5 ml), potassium carbonate (0.183 g, 1.68 mmoles) was added and stirred at RT for 10 min. To this mixture intermediate 40 (0.230 g, 0.662 mmoles) was added and stirred for 12 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as brown solid (0.080 g, 30% yield). MP: 247-250° C. $^1$H-NMR (δ ppm, DMSO-$D_6$, 400 MHz): δ [8.48 (s), 8.39 (s), 1H], [8.05 (s), 7.91 (s), 1H], 8.03 (d, J=7.8 Hz, 1H), 7.86 (m, 2H), 7.53 (m, 3H), 7.36-7.18 (m, 4H), 5.68 (q, J=7.3 Hz, 1H), [1.97 (d, J=7.2 Hz), 1.87 (d, J=7.1 Hz), 3H]. Mass: 402.32 (M+1).

Example 35

2-(1-(6-Amino-9H-purin-9-yl)propyl)-3-(2-fluorophenyl)-4H-chromen-4-one

To a solution of adenine (0.524 g, 3.87 mmoles) in DMF (5 ml), potassium carbonate (0.535 g, 3.87 mmoles) was added and stirred at RT for 10 min. To this mixture intermediate 43 (0.700 g, 1.93 mmoles) was added and stirred for 12 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as brown solid (0.060 g, 7% yield). MP: 160-163° C. $^1$H-NMR (δ ppm, DMSO-$D_6$, 400 MHz): δ [8.57 (s), 8.45 (s), 1H], [8.08 (s), 7.92 (s), 1H], 8.03 (d, J=8.0 Hz, 1H), 7.89 (m, 2H), 7.54 (m, 3H), 7.35-7.17 (m, 4H), [5.48 (t, J=7.9 Hz), 5.46 (t, J=7.0 Hz), 1H], 2.48 (m, 2H), [0.82 (t, J=7.4 Hz), 0.75 (t, J=7.3 Hz), 3H]. Mass: 416.04 (M+1).

Example 36

2-(1-(6-amino-9H-purin-9-yl)propyl)-3-(3-fluorophenyl)-4H-chromen-4-one

To a solution of adenine (0.404 g, 2.99 mmoles) in DMF (12 ml), potassium carbonate (0.413 g, 2.99 mmoles) was added and stirred at RT for 10 min. To this mixture intermediate 46 (0.540 g, 1.49 mmoles) was added and stirred for 12 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as brownish yellow solid (0.115 g, 19% yield). MP: 102-107° C. $^1$H-NMR (δ ppm, DMSO-$D_6$, 400 MHz): δ 8.54 (s, 1H), 8.03 (s, 1H), 8.01 (d, J=10.1 Hz, 1H), 7.87 (t, J=8.4 Hz, 1H), 7.79 (d, J=8.4 Hz, 1H), 7.52 (t, J=7.6 Hz, 2H), 7.28 (m, 3H), 7.18 (d, J=7.4 Hz, 2H), 5.51 (t, J=7.9 Hz, 1H), 2.39 (m, 2H), 0.76 (t, J=7.3 Hz, 3H). Mass: 415.97 (M+).

Example 37

2-(1-(6-Amino-9H-purin-9-yl)propyl)-3-(4-fluorophenyl)-4H-chromen-4-one

To a solution of adenine (0.389 g, 2.87 mmoles) in DMF (12 ml), potassium carbonate (0.497 g, 2.87 mmoles) was added and stirred at RT for 10 min. To this mixture intermediate 49 (0.520 g, 1.43 mmoles) was added and stirred for 12 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as light yellow solid (0.55 g, 9% yield). MP: 223-227° C. $^1$H-NMR (δ ppm, DMSO-$D_6$, 400 MHz): δ 8.54 (s, 1H), 8.05 (s, 1H), 8.03 (dd, J=8.0, 1.6 Hz, 1H), 7.86 (dt, J=7.1, 1.6 Hz, 1H), 7.78 (d, J=7.8 Hz, 1H), 7.51 (dt, J=8.0, 1.1 Hz, 1H), 7.38 (t, J=8.1 Hz, 2H), 7.30 (t, J=8.8 Hz, 2H), 7.23 (s, 2H), 5.50 (t, J=7.7 Hz, 1H), 2.39 (m, 2H), 0.76 (t, J=7.3 Hz, 3H). Mass: 416.11 (M+1).

Example 38

2-(1-(6-amino-9H-purin-9-yl)propyl)-6-fluoro-3-phenyl-4H-chromen-4-one

To a solution of adenine (0.374 g, 2.76 mmoles) in DMF (10 ml), potassium carbonate (0.382 g, 2.76 mmoles) was added and stirred at RT for 10 min. To this mixture intermediate 52 (0.500 g, 1.38 mmoles) was added and stirred for 12 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as light yellow solid (0.110 g, 19% yield). MP: 266-272° C. $^1$H-NMR (δ ppm, DMSO-$D_6$, 400 MHz): δ 8.54 (s, 1H), 8.04 (s, 1H), 7.92 (dd, J=9.3, 4.3 Hz, 1H), 7.78 (dt, J=8.6, 3.2 Hz, 1H), 7.70 (dd, J=8.3, 5.3 Hz, 1H), 7.46 (m, 3H), 7.32 (d, J=6.4 Hz, 2H), 7.21 (s, 2H), 5.53 (t, J=7.7 Hz, 1H), 2.39 (m, 2H), 0.74 (t, J=7.3 Hz, 3H). Mass: 416.11 (M+1).

Example 39

2-(1-(6-Amino-9H-purin-9-yl)ethyl)-3-(4-fluorophenyl)-4H-chromen-4-one

To a solution of adenine (0.412 g, 3.05 mmoles) in DMF (10 ml), potassium carbonate (0.527 g, 3.81 mmoles) was added and stirred at RT for 10 min. To this mixture intermediate 55 (0.530 g, 1.52 mmoles) was added and stirred for 12 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as light yellow solid (0.050 g, 8% yield). MP: 210-212° C. $^1$H-NMR (δ ppm, DMSO-$D_6$, 400 MHz): δ 8.46 (s, 1H), 8.03 (s, 1H), 8.02 (dd, J=8.1, 1.5 Hz, 1H), 7.83 (dt, J=7.1, 1.5 Hz, 1H), 7.67 (d, J=8.3 Hz, 1H), 7.50 (t, J=7.7 Hz, 1H), 7.41 (d, J=8.6 Hz, 1H), 7.39 (d, J=8.4 Hz, 1H), 7.30 (t, J=8.9 Hz, 2H), 7.23 (s, 1H), 5.68 (q, J=6.9 Hz, 1H), 1.90 (d, J=7.2 Hz, 3H). Mass: 402.32 (M+1).

Example 40

2-(1-(6-Amino-9H-purin-9-yl)ethyl)-6-fluoro-3-phenyl-4H-chromen-4-one

To a solution of adenine (0.389 g, 2.88 mmoles) in DMF (12 ml), potassium carbonate (0.398 g, 2.88 mmoles) was added and stirred at RT for 10 min. To this mixture intermediate 57 (0.500 g, 1.44 mmoles) was added and stirred for 12 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as light yellow solid (0.210 g, 36% yield). MP: 264-269° C. $^1$H-NMR (δ ppm, DMSO-$D_6$, 400 MHz): δ 8.46 (s, 1H), 8.02 (s, 1H), 7.80 (dd, J=9.1, 4.4 Hz, 1H), 7.74 (m, 2H), 7.48 (m, 3H), 7.36 (dd, J=8.0, 1.7 Hz, 2H), 7.21 (s, 1H), 5.68 (q, J=7.2 Hz, 1H), 1.88 (d, J=7.2 Hz, 3H). Mass: 402.11 (M+1).

Example 41

2-(1-(4-Amino-3-(3-methoxyphenyl)-1H-pyrazolo[3,4-d]pyrimidin-1-yl)ethyl)-3-phenyl-4H-chromen-4-one To a solution of intermediate 58 (0.498 g, 2.06 mmoles) in DMF (5 ml), potassium carbonate (0.356 g, 2.50 mmoles) was added and stirred at RT for 10 min. To this mixture intermediate 29 (0.340 g, 1.03 mmoles) was added and stirred for 12 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as light yellow solid (0.160 g, 32% yield). MP: 176-178° C. $^1$H-NMR (δ ppm, DMSO-$D_6$, 400 MHz): δ 8.09 (s, 1H), 8.04 (d, J=8.0 Hz, 1H), 7.83 (t, J=7.0 Hz, 1H), 7.63 (d, J=6.5 Hz, 2H), 7.51 (t, J=7.3 Hz, 1H), 7.46 (t, J=8.1 Hz, 1H), 7.33 (m, 3H), 7.12 (m, 4H), 7.06 (dd, J=8.2, 2.3 Hz, 1H), 5.98 (q, J=6.7 Hz, 1H), 3.81 (s, 3H), 1.90 (d, J=7.0 Hz, 3H). Mass: 490.10 (M+1).

Example 42

2-(1-(4-Amino-3-(3-hydroxyphenyl)-1H-pyrazolo[3,4-d]pyrimidin-1-yl)ethyl)-3-phenyl-4H-chromen-4-one To a solution of example 41 (0.130 g, 0.265 mmoles) in dichloromethane (26 ml), $BBr_3$ (1M in dichloromethane, 2.6 ml) was added at 0° C. and the reaction mixture was warmed to RT and then stirred for 12 h. The reaction mixture was quenched with 1.5N HCl solution and extracted with dichloromethane. The organic layer was dried over sodium sulphate and concentrated under reduced pressure to afford the title compound as light yellow solid (0.070 g, 56% yield). MP: 212-216° C. $^1$H-NMR (δ ppm, DMSO-$D_6$, 400 MHz): δ 9.78 (s, 1H), 8.24 (d, J=7.5 Hz, 1H), 8.05 (d, J=7.9 Hz, 1H), 7.85 (t, J=8.4 Hz, 1H), 7.65 (d, J=8.6 Hz, 1H), 7.53 (t, J=7.7 Hz, 1H), 7.36-7.02 (m, 9H), 6.90 (d, J=8.2 Hz, 1H), 6.03 (q, J=6.9 Hz, 1H), 1.91 (d, J=7.3 Hz, 3H). Mass: 476.17 (M+1).

Example 43

2-((9H-purin-6-ylamino)methyl)-3-phenyl-4H-chromen-4-one

To a solution of intermediate 59 (1.50 g, 7.06 mmoles) in dichloromethane (15 ml), triethylamine (2.9 ml, 21.20 mmoles) was added followed by N-Boc-Glycine (1.3 g, 7.77 mmoles). To this mixture HATU (5.3 g, 14.13 mmoles) was added and stirred at RT for 12 h. The reaction mixture was quenched by the addition of water and extracted with dichloromethane. The organic layer was dried over sodium sulphate and concentrated under reduced pressure. The crude product was purified by column chromatography with ethyl acetate: petroleum ether to afford the isoflavone intermediate (1.12 g). To a solution of this intermediate (0.60 g) in dichloromethane (10 ml), trifluoroacetic acid (2.5 ml) was added and stirred at RT for 2 h. The reaction mixture was concentrated, basified with sodium bicarbonate solution, extracted with ethyl acetate. The organic layer was dried over sodium sulphate and concentrated under reduced pressure to afford the amine intermediate (0.38 g). To a solution of this amine intermediate (0.37 g, 1.47 mmoles) in tert-butanol (6 ml), N, N-diisopropylethylamine (0.5 ml, 2.94 mmoles) and 6-chloropurine (0.226 g, 1.47 mmoles) were added and refluxed for 24 h. The reaction mixture was concentrated, diluted with water, extracted with ethyl acetate. The organic layer was dried over sodium sulphate and concentrated under reduced pressure. The crude product was purified by column chromatography with methanol:ethyl acetate to afford the title compound as brown solid (0.131 g, 24% yield). MP: 155-158° C. $^1$H-NMR (δ ppm, DMSO-$D_6$, 400 MHz): δ 12.96 (s, 1H), 8.14-8.040 (m, 4H), 7.77 (t, J=8.2 Hz, 1H), 7.48-7.36 (m, 7H), 4.60 (br s, 2H). Mass: 369.91 ($M^+$).

Example 44

2-(1-(6-Amino-9H-purin-9-yl)ethyl)-3-o-tolyl-4H-chromen-4-one

To a solution of intermediate 61 (0.610 g, 2.30 mmoles) in acetic acid (8 ml) bromine (0.23 ml, 4.61 mmoles) was added at 0° C. The reaction mixture heated to 60° C. After 6 h, the reaction mixture was cooled to RT, quenched by the addition of water. The precipitate formed was filtered and dried under reduced pressure to afford the bromo intermediate (0.700 g). This intermediate (0.650 g, 1.88 mmoles) was added to a solution of adenine (0.510 g, 3.77 mmoles) and potassium carbonate (0.521 g, 3.77 mmoles) in DMF (15 ml). After 12 h, the reaction mixture was diluted with water and extracted with ethyl acetate. The organic layer was dried over sodium sulphate and concentrated under reduced pressure. The crude product was purified by column chromatography with methanol:dichloromethane to afford the title compound as light brown solid as a atrope isomers (0.030 g, 4% yield). MP: 202-205° C. $^1$H-NMR (δ ppm, DMSO-$D_6$, 400 MHz): δ 8.42 (d, J=3.5 Hz, 1H), [8.07 (s), 7.95 (s), 1H], 8.04 (t, J=5.6 Hz, 1H), 7.84 (q, J=7.2 Hz, 1H), [7.70 (d, J=8.2 Hz), 7.68 (d, J=8.1 Hz), 1H], 7.51 (t, J=7.6 Hz, 1H), 7.35-7.20 (m, 6H), 5.56 (m, 1H), [2.09 (s), 1.90 (s), 3H], [1.95 (d, J=7.1 Hz), 1.84 d, J=7.3 Hz), 3H]. Mass: 397.77 ($M^+$).

Example 45

2-((9H-purin-6-ylamino)methyl)-3-(2-fluorophenyl)-4H-chromen-4-one

To a solution of intermediate 64 (0.330 g, 1.22 mmoles) in tert-butanol (4 ml), N,N-diisopropylethylamine (0.42 ml, 2.45 mmoles) and 6-bromopurine (0.195 g, 0.980 mmoles) were added and refluxed for 24 h. The reaction mixture was concentrated, diluted with water, extracted with ethyl acetate. The organic layer was dried over sodium sulphate and concentrated under reduced pressure. The crude product was purified by column chromatography with methanol:ethyl acetate to afford the title compound as yellow solid (0.040 g, 8% yield). MP: 143-147° C. $^1$H-NMR (δ ppm, DMSO-$D_6$, 400 MHz): δ 12.90 (s, 1H), 8.20 (br s, 1H), 8.10 (s, 1H), 8.09

(s, 1H), 8.05 (dd, J=7.9, 1.4 Hz, 1H), 7.79 (dt, J=8.6, 1.5 Hz, 1H), 7.51-7.41 (m, 4H), 7.28 (m, 2H), 4.64 (br s, 2H). Mass: 387.90 ($M^+$).

Example 46

2-((9H-purin-6-ylamino)methyl)-3-(3-fluorophenyl)-4H-chromen-4-one

To a solution of intermediate 65 (1.50 g, 6.51 mmoles) in dichloromethane (15 ml), triethylamine (2.7 ml, 19.54 mmoles) was added followed by N-Boc-Glycine (1.3 g, 7.81 mmoles). To this mixture HATU (4.9 g, 13.03 mmoles) was added and stirred at RT for 12 h. The reaction mixture was quenched by the addition of water and extracted with dichloromethane. The organic layer was dried over sodium sulphate and concentrated under reduced pressure. The crude product was purified by column chromatography with ethyl acetate: petroleum ether to afford the isoflavone intermediate (0.80 g). To a solution of this intermediate (0.80 g) in dichloromethane (10 ml), trifluoroacetic acid (1.5 ml) was added and stirred at RT for 2 h. The reaction mixture was concentrated, basified with sodium bicarbonate solution, extracted with ethyl acetate. The organic layer was dried over sodium sulphate and concentrated under reduced pressure to afford the amine intermediate (0.471 g). To a solution of this amine intermediate (0.30 g, 1.14 mmoles) in tert-butanol (6 ml), N,N-diisopropylethylamine (0.5 ml, 2.94 mmoles) and 6-bromopurine (0.177 g, 0.891 mmoles) were added and refluxed for 24 h. The reaction mixture was concentrated, diluted with water, extracted with ethyl acetate. The organic layer was dried over sodium sulphate and concentrated under reduced pressure. The crude product was purified by column chromatography with methanol:ethyl acetate to afford the title compound as brown solid (0.235 g, 55% yield). MP: 211-214° C. $^1$H-NMR (δ ppm, DMSO-$D_6$, 400 MHz): δ 12.97 (s, 1H), 8.20 (br s, 1H), 8.14 (s, 1H), 8.11 (s, 1H), 8.06 (dd, J=7.9, 1.4 Hz, 1H), 7.78 (dt J=8.4, 1.3 Hz, 1H), 7.49 (m, 3H), 7.27-7.17 (m, 3H), 4.10 (q, J=5.3 Hz, 1H), 3.16 (d, J=5.0 Hz, 2H). Mass: 387.90 ($M^+$).

Example 47

(S)-2-(1-(9H-purin-6-ylamino)ethyl)-3-(3-fluorophenyl)-4H-chromen-4-one

To a solution of intermediate 65 (2.0 g, 8.68 mmoles) in dichloromethane (20 ml), triethylamine (3.6 ml, 26.06 mmoles) was added followed by N-Boc-Alanine (1.97 g, 10.42 mmoles). To this mixture HATU (6.6 g, 17.37 mmoles) was added and stirred at RT for 12 h. The reaction mixture was quenched by the addition of water and extracted with dichloromethane. The organic layer was dried over sodium sulphate and concentrated under reduced pressure. The crude product was purified by column chromatography with ethyl acetate: petroleum ether to afford the isoflavone intermediate (1.70 g). To a solution of this intermediate (1.7 g) in dichloromethane (20 ml), trifluoroacetic acid (3 ml) was added and stirred at RT for 2 h. The reaction mixture was concentrated, basified with sodium bicarbonate solution, extracted with ethyl acetate. The organic layer was dried over sodium sulphate and concentrated under reduced pressure to afford the amine intermediate (0.641 g). To a solution of this amine intermediate (0.30 g, 1.05 mmoles) in tert-butanol (6 ml), N,N-diisopropylethylamine (0.36 ml, 2.17 mmoles) and 6-bromopurine (0.168 g, 0.847 mmoles) were added and refluxed for 24 h. The reaction mixture was concentrated, diluted with water, extracted with ethyl acetate. The organic layer was dried over sodium sulphate and concentrated under reduced pressure. The crude product was purified by column chromatography with methanol:ethyl acetate to afford the title compound as off-white solid (0.041 g, 10% yield). MP: 135-138° C. $^1$H-NMR (δ ppm, DMSO-$D_6$, 400 MHz): δ 12.95 (s, 1H), 8.15 (t, J=6.8 Hz, 1H), 8.11 (s, 1H), 8.08 (s, 1H), 8.03 (d, J=7.8 Hz, 1H), 7.81 (t, J=7.3 Hz, 1H), 7.60 (d, J=8.3 Hz, 1H), 7.49 (t, J=7.3 Hz, 2H), 7.25 (m, 3H), 5.19 (br m, 1H), 1.56 (d, J=6.9 Hz, 3H). Mass: 402.18 ($M^+$+1).

Example 48

2-(1-(6-amino-9H-purin-9-yl)ethyl)-6-fluoro-3-(2-fluorophenyl)-4H-chromen-4-one

To a solution of adenine (0.443 g, 3.28 mmoles) in DMF (10 ml), potassium carbonate (0.453 g, 3.28 mmoles) was added and stirred at RT for 10 min. To this mixture intermediate 68 (0.600 g, 1.64 mmoles) was added and stirred for 12 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as light yellow solid consisting of a mixture of two atrop-isomers (0.082 g, 24% yield). MP: 245-248° C. $^1$H-NMR (δ ppm, DMSO-$D_6$, 400 MHz): δ [8.49 (s), 8.39 (s), 1H], [8.05 (s), 7.91 (s), 1H], 7.92 (m, 1H), 7.81 (m, 2H), 7.52 (m, 2H), 7.36 (m, 4H), [5.69 (q, J=7.2 Hz), 5.64 (q, J=7.2 Hz), 1H], 1.96 (d, J=7.1 Hz), 1.86 (d, J=7.2 Hz), 3H]. Mass: 419.82 ($M^+$).

Example 49

2-(1-(6-Amino-9H-purin-9-yl)ethyl)-3-(3,5-difluorophenyl)-4H-chromen-4-one

To a solution of adenine (0.370 g, 2.73 mmoles) in DMF (8 ml), potassium carbonate (0.378 g, 2.73 mmoles) was added and stirred at RT for 10 min. To this mixture intermediate 72 (0.500 g, 1.36 mmoles) was added and stirred for 12 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as light brown solid (0.121 g, 21% yield). MP: 267-269° C. $^1$H-NMR (δ ppm, DMSO-$D_6$, 400 MHz): δ 8.45 (s, 1H), 8.02 (s, 1H), 8.01 (d, J=5.9 Hz, 1H), 7.85 (t, J=8.5 Hz, 1H), 7.70 (d, J=8.4 Hz, 1H), 7.52 (t, J=7.7 Hz, 1H), 7.30 (t, J=9.4 Hz, 1H), 7.23 (s, 2H), 7.11 (d, J=7.6 Hz, 2H), 5.70 (q, J=7.2 Hz, 1H), 1.91 (d, J=7.1 Hz, 3H). Mass: 419.82 ($M^+$).

Example 50

2-(1-(6-amino-9H-purin-9-yl)ethyl)-6-fluoro-3-(3-fluorophenyl)-4H-chromen-4-one

To a solution of adenine (0.370 g, 2.73 mmoles) in DMF (8 ml), potassium carbonate (0.378 g, 2.73 mmoles) was added and stirred at RT for 10 min. To this mixture intermediate 75 (0.500 g, 1.36 mmoles) was added and stirred for 12 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as light brown solid (0.150 g, 26% yield). MP: 252-255° C. $^1$H-NMR (δ ppm, DMSO-$D_6$, 400 MHz): δ 8.46 (s, 1H), 8.02 (s, 1H), 7.82 (dd, J=9.2, 4.4 Hz, 1H), 7.76 (dd, J=8.0, 3.0 Hz, 1H), 7.72 (td, J=6.8, 3.6 Hz, 1H), 7.51 (q, J=7.8 Hz, 1H), 7.28-7.18 (m, 5H), 5.70 (q, J=7.0 Hz, 1H), 1.89 (d, J=7.2 Hz, 3H). Mass: 420.03 ($M^+$+1).

Example 51

2-(1-(4-amino-3-(3-methoxyphenyl)-1H-pyrazolo[3,4-d]pyrimidin-1-yl)ethyl)-3-(3-fluorophenyl)-4H-chromen-4-one To a solution of intermediate 58 (0.484 g, 2.01 mmoles) in DMF (6 ml), potassium carbonate (0.345 g, 2.50 mmoles) was added and stirred at RT for 10 min. To this mixture intermediate 36 (0.350 g, 1.00 mmoles) was added and stirred for 12 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as light yellow solid (0.302 g, 59% yield). $^1$H-NMR (δ ppm, DMSO-$D_6$, 400 MHz): δ 8.07 (s, 1H), 8.04 (dd, J=7.9, 1.4 Hz, 1H), 8.02 (dt, J=6.9, 1.4 Hz, 1H), 7.67 (d, J=8.4 Hz, 1H), 7.53 (t, J=7.9 Hz, 1H), 7.46 (t, J=7.9 Hz, 1H), 7.31 (br s, 1H), 7.19 (d, J=7.7 Hz, 1H), 7.10 (t, J=2.1 Hz, 1H), 7.07 (dt, J=8.6, 4.0 Hz, 2H), 6.90 (br s, 2H), 6.05 (q, J=6.9 Hz, 1H), 3.80 (s, 3H), 1.90 (d, J=7.1 Hz, 3H).

Example 51a 2-(1-(4-amino-3-(3-hydroxyphenyl)-1H-pyrazolo[3,4-d]pyrimidin-1-yl)ethyl)-3-(3-fluorophenyl)-4H-chromen-4-one To a solution of Example 51 (0.150 g, 0.290 mmoles) in dichloromethane (25 ml), $BBr_3$ (1M in dichloromethane, 1.5 ml) was added at 0° C. and the reaction mixture was warmed to RT and then stirred for 12 h. The reaction mixture was quenched with 1.5N HCl solution and extracted with dichloromethane. The organic layer was dried over sodium sulphate and concentrated. The crude product was purified by column chromatography with methanol:dichloromethane to afford the title compound as grey colour solid (0.110 g, 75% yield). MP: 282-285° C. $^1$H-NMR (δ ppm, DMSO-$D_6$, 400 MHz): δ 9.69 (s, 1H), 8.06 (s, 1H), 8.05 (dd, J=8.0, 1.6 Hz, 1H), 7.86 (dt, J=7.2, 1.6 Hz, 1H), 7.68 (t, J=8.2 Hz, 1H), 7.53 (dt, J=8.0, 0.9 Hz, 1H), 7.34 (t, J=8.0 Hz, 1H), 7.29 (br s, 1H), 7.06-6.84 (m, 6H), 6.03 (q, J=7.1 Hz, 1H), 1.89 (d, J=7.1 Hz, 3H). Mass: 493.95 ($M^+$).

Example 52

2-((4-Amino-3-(3-methoxyphenyl)-1H-pyrazolo[3,4-d]pyrimidin-1-yl)methyl)-3-phenyl-4H-chromen-4-one To a solution of intermediate 58 (0.765 g, 3.17 mmoles) in DMF (7 ml), potassium carbonate (0.548 g, 3.96 mmoles) was added and stirred at RT for 10 min. To this mixture intermediate 5 (0.500 g, 1.58 mmoles) was added and stirred for 12 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as light yellow solid (0.280 g, 37% yield). MP: 111-115° C. $^1$H-NMR (δ ppm, DMSO-$D_6$, 400 MHz): δ 8.23 (s, 1H), 8.05 (dd, J=8.0, 1.4 Hz, 1H), 7.77 (dt, J=8.5, 1.5 Hz, 1H), 7.49-7.31 (m, 8H), 7.20 (d, J=7.6 Hz, 1H), 7.12 (s, 1H), 7.04 (dd, J=8.0, 2.1 Hz, 1H), 5.51 (s, 2H), 3.80 (s, 3H). Mass: 475.89 ($M^+$).

Example 53

2-((4-Amino-3-(3-hydroxyphenyl)-1H-pyrazolo[3,4-d]pyrimidin-1-yl)methyl)-3-phenyl-4H-chromen-4-one To a solution of example 52 (0.150 g, 0.315 mmoles) in dichloromethane (30 ml), $BBr_3$ (1M in dichloromethane, 1.5 ml) was added at 0° C. and the reaction mixture was warmed to RT and then stirred for 12 h. The reaction mixture was quenched with 1.5N HCl solution and extracted with dichloromethane. The organic layer was dried over sodium sulphate and concentrated. The crude product was purified by column chromatography with methanol:dichloromethane to afford the title compound as light yellow solid (0.040 g, 27% yield). MP: 154-158° C. $^1$H-NMR (δ ppm, DMSO-$D_6$, 400 MHz): δ 9.69 (s, 1H), 8.22 (s, 1H), 8.06 (dd, J=7.8, 1.2 Hz, 1H), 7.49 (t, J=7.3 Hz, 1H), 7.44 (d, J=8.5 Hz, 1H), 7.37-7.29 (m, 6H), 7.03 (d, J=7.9 Hz, 2H), 6.86 (dd, J=8.3, 1.6 Hz, 1H), 5.49 (s, 2H). Mass: 462.03 ($M^+$+1).

Example 54

2-((4-amino-3-(3-methoxyphenyl)-1H-pyrazolo[3,4-d]pyrimidin-1-yl)methyl)-3-(3-fluorophenyl)-4H-chromen-4-one To a solution of intermediate 58 (0.278 g, 1.15 mmoles) in DMF (6 ml), potassium carbonate (0.363 g, 2.62 mmoles) was added and stirred at RT for 10 min. To this mixture intermediate 77 (0.350 g, 1.05 mmoles) was added and stirred for 12 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as light brown solid (0.220 g, 40% yield). MP: 175-178° C. $^1$H-NMR (δ ppm, DMSO-$D_6$, 400 MHz): δ 8.21 (s, 1H), 8.05 (dd, J=8.0, 1.7 Hz, 1H), 7.80 (m, 1H), 7.51 (m, 2H), 7.45 (t, J=8.0 Hz, 1H), 7.39 (m, 1H), 7.18-7.08 (m, 5H), 7.04 (dd, J=8.3, 2.0 Hz, 1H), 5.54 (s, 2H), 3.80 (s, 3H). Mass: 493.81 ($M^+$).

Example 55

2-((4-amino-3-(3-hydroxyphenyl)-1H-pyrazolo[3,4-d]pyrimidin-1-yl)methyl)-3-(3-fluorophenyl)-4H-chromen-4-one To a solution of example 54 (0.200 g, 0.383 mmoles) in dichloromethane (30 ml), $BBr_3$ (1M in dichloromethane, 2.0 ml) was added at 0° C. and the reaction mixture was warmed to RT and then stirred for 12 h. The reaction mixture was quenched with 1.5N HCl solution and extracted with dichloromethane. The organic layer was dried over sodium sulphate and concentrated. The crude product was purified by column chromatography with methanol:dichloromethane to afford the title compound as off-white solid (0.070 g, 36% yield). MP: 280-283° C. $^1$H-NMR (δ ppm, DMSO-$D_6$, 400 MHz): δ 9.69 (s, 1H), 8.20 (s, 1H), 8.06 (dd, J=8.2, 1.7 Hz, 1H), 7.80

(m, 1H), 7.51 (m, 2H), 7.39 (m, 2H), 7.17 (m, 2H), 7.11 (dt, J=8.7, 2.2 Hz, 1H), 7.02 (d, J=8.6 Hz, 1H), 7.00 (s, 1H), 6.86 (dd, J=7.7, 1.8 Hz, 1H), 5.53 (s, 2H). Mass: 479.88 ($M^+$).

Example 56

(R)-2-(1-(9H-purin-6-ylamino)ethyl)-3-(3-fluorophenyl)-4H-chromen-4-one

To a solution of intermediate 65 (1.00 g, 4.34 mmoles) in dichloromethane (15 ml), triethylamine (1.8 ml, 13.02 mmoles) was added followed by N-Boc-D-Alanine (0.986 g, 5.21 mmoles). To this mixture HATU (3.3 g, 8.68 mmoles) was added and stirred at RT for 12 h. The reaction mixture was quenched by the addition of water and extracted with dichloromethane. The organic layer was dried over sodium sulphate and concentrated under reduced pressure. The crude product was purified by column chromatography with ethyl acetate: petroleum ether to afford the isoflavone intermediate (1.70 g). To a solution of this intermediate (0.8 g) in dichloromethane (10 ml), trifluoroacetic acid (3 ml) was added and stirred at RT for 2 h. The reaction mixture was concentrated, basified with sodium bicarbonate solution, extracted with ethyl acetate. The organic layer was dried over sodium sulphate and concentrated under reduced pressure to afford the amine intermediate (0.410 g). To a solution of this amine intermediate (0.41 g, 1.52 mmoles) in tert-butanol (7 ml), N,N-diisopropylethylamine (0.53 ml, 3.04 mmoles) and 6-bromopurine (0.242 g, 1.21 mmoles) were added and refluxed for 24 h. The reaction mixture was concentrated, diluted with water, extracted with ethyl acetate. The organic layer was dried over sodium sulphate and concentrated under reduced pressure. The crude product was purified by column chromatography with methanol:ethyl acetate to afford the title compound as off-white solid (0.130 g, 21% yield). MP: 274-276° C. $^1$H-NMR (δ ppm, DMSO-$D_6$, 400 MHz): δ 12.96 (s, 1H), 8.14-8.01 (m, 4H), 8.11 (s, 1H), 7.81 (dt, J=8.5, 1.5 Hz, 1H), 7.60 (d, J=8.4 Hz, 1H), 7.49 (m, 2H), 7.25-7.19 (m, 3H), 5.18 (br m, 1H), 1.56 (d, J=7.0 Hz, 3H). Mass: 402.04 ($M^+$+1).

Example 57

(S)-2-(1-(9H-purin-6-ylamino)ethyl)-6-fluoro-3-phenyl-4H-chromen-4-one

To a solution of intermediate 50 (2.50 g, 10.85 mmoles) in dichloromethane (25 ml), triethylamine (4.5 ml, 32.57 mmoles) was added followed by N-Boc-L-Alanine (2.46 g, 13.03 mmoles). To this mixture HATU (8.25 g, 21.71 mmoles) was added and stirred at RT for 12 h. The reaction mixture was quenched by the addition of water and extracted with dichloromethane. The organic layer was dried over sodium sulphate and concentrated under reduced pressure. The crude product was purified by column chromatography with ethyl acetate:petroleum ether to afford the isoflavone intermediate (1.45 g). To a solution of this intermediate (1.40 g) in dichloromethane (20 ml), trifluoroacetic acid (1.4 ml) was added and stirred at RT for 2 h. The reaction mixture was concentrated, basified with sodium bicarbonate solution, extracted with ethyl acetate. The organic layer was dried over sodium sulphate and concentrated under reduced pressure to afford the amine intermediate (0.850 g). To a solution of this amine intermediate (0.450 g, 1.52 mmoles) in tert-butanol (7 ml), N, N-diisopropylethylamine (0.55 ml, 3.17 mmoles) and 6-chloropurine (0.194 g, 1.27 mmoles) were added and refluxed for 24 h. The reaction mixture was concentrated, diluted with water, extracted with ethyl acetate. The organic layer was dried over sodium sulphate and concentrated under reduced pressure. The crude product was purified by column chromatography with methanol:ethyl acetate to afford the title compound as yellow solid (0.100 g, 15% yield). MP: 196-198° C. $^1$H-NMR (δ ppm, DMSO-$D_6$, 400 MHz): δ 12.95 (s, 1H), 8.11-(m, 3H), 7.69 (m, 3H), 7.42 (m, 5H), 5.20 (br m, 1H), 1.54 (d, J=6.7 Hz, 3H). Mass: 402.18 ($M^+$+1).

Example 57a 2-((4-Amino-3-iodo-1H-pyrazolo[3,4-d]pyrimidin-1-yl)methyl)-3-phenyl-4H-chromen-4-one To a solution of 3-iodo-1H-pyrazolo[3,4-d]pyrimidin-4-amine (1.404 g, 5.36 mmoles) in DMF (28 ml), potassium carbonate (1.85 g, 13.4 mmoles) was added and stirred at RT for 10 min. To this mixture, intermediate 5 (2.11 g, 6.70 mmoles) was added and stirred for 12 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as light yellow solid (1.10 g, 41% yield). $^1$H-NMR (δ ppm, DMSO-$D_6$, 400 MHz): δ 8.18 (s, 1H), 8.06 (dd, J=8.0, 1.6 Hz, 1H), 7.77 (m, 1H), 7.50 (dt, J=8.0, 0.9 Hz, 1H), 7.41-7.30 (m, 6H), 5.44 (s, 2H).

Example 57b 2-(1-(4-amino-3-iodo-1H-pyrazolo[3,4-d]pyrimidin-1-yl)ethyl)-3-phenyl-4H-chromen-4-one To a solution of 3-iodo-1H-pyrazolo[3,4-d]pyrimidin-4-amine (6.0 g, 23 mmoles) in DMF (110 ml), potassium carbonate (7.94 g, 57.2 mmoles) was added and stirred at RT for 10 min. To this mixture, intermediate 29 (9.5 g, 28.76 mmoles) was added and stirred for 12 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as light yellow solid (2.0 g, 17% yield). $^1$H-NMR (δ ppm, DMSO-$D_6$, 400 MHz): δ 8.12 (dd, J=7.9, 1.6 Hz, 1H), 8.10 (s, 1H), 7.91 (m, 1H), 7.68 (d, J=8.2 Hz, 1H), 7.60 (dt, J=7.9, 0.9 Hz, 1H), 7.36 (m, 3H), 7.18 (m, 2H), 5.93 (q, J=7.1 Hz, 1H), 1.91 (d, J=7.1 Hz, 3H).

Example 57c 2-(1-(4-amino-3-iodo-1H-pyrazolo[3,4-d]pyrimidin-1-yl)ethyl)-3-(3-fluorophenyl)-4H-chromen-4-one To a solution of 3-iodo-1H-pyrazolo[3,4-d]pyrimidin-4-amine (1.30 g, 5.299 mmoles) in DMF (23 ml), potassium carbonate (1.80 g, 13.24 mmoles) was added and stirred at RT for 10 min. To this mixture, intermediate 36 (2.3 g, 6.62 mmoles) was added and stirred for 12 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as light yellow solid (0.800 g, 24% yield). $^1$H-NMR (δ ppm, DMSO-$D_6$, 400 MHz): δ 8.04 (d, J=1.6 Hz, 1H), 8.02 (s, 1H), 7.94 (s, 1H), 7.86 (dt, J=8.0, 1.5 Hz, 1H), 7.66 (d, J=8.4 Hz, 1H), 7.53 (t, J=7.5 Hz, 1H), 7.29 (m, 1H), 7.09 (dt, J=7.7, 2.4 Hz, 1H), 6.88 (m, 1H), 5.93 (q, J=7.0 Hz, 1H), 1.83 (d, J=7.1 Hz, 3H).

Example 57d 2-((4-amino-3-iodo-1H-pyrazolo[3,4-d]pyrimidin-1-yl)methyl)-6-fluoro-3-phenyl-4H-chromen-4-one To a solution of 3-iodo-1H-pyrazolo[3,4-d]pyrimidin-4-amine (1.0 g, 3.01 mmoles) in DMF (5 ml), N,N-Diisopropylethylamine (0.5 ml, 6.02 mmoles) was added and stirred at RT for 10 min. To this mixture, intermediate 90 (1.3 g, 5.11 mmoles) was added and stirred for 16 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as light yellow solid (0.351 g, 23% yield). $^1$H-NMR (δ ppm, DMSO-$D_6$, 400 MHz): δ 8.17 (s, 1H), 7.76-7.63 (m, 2H), 7.55 (dd, J=9.1, 4.2 Hz, 1H), 7.39-7.28 (m, 5H), 5.44 (s, 2H).

Example 57e 2-(1-(4-amino-3-iodo-1H-pyrazolo[3,4-d]pyrimidin-1-yl)ethyl)-6-fluoro-3-phenyl-4H-chromen-4-one To a solution of 3-iodo-1H-pyrazolo[3,4-d]pyrimidin-4-amine (12.8 g, 49.03 mmoles) in DMF (50 ml), cesium carbonate (18.7 g, 57.62 mmoles) was added and stirred at RT for 10 min. To this mixture, intermediate 57 (10 g, 28.81 mmoles) was added and stirred for 17 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as light yellow solid (3.8 g, 25% yield). $^1$H-NMR (δ ppm, DMSO-$D_6$, 400 MHz): δ 8.02 (s, 1H), 7.72 (m, 3H), 7.28 (m, 3H), 7.09 (br s, 2H), 5.86 (q, J=7.1 Hz, 1H), 1.82 (d, J=7.0 Hz, 3H).

Example 57f 2-(1-(4-amino-3-iodo-1H-pyrazolo[3,4-d]pyrimidin-1-yl)ethyl)-6-fluoro-3-(3-fluorophenyl)-4H-chromen-4-one To a solution of 3-iodo-1H-pyrazolo[3,4-d]pyrimidin-4-amine (10.9 g, 41.90 mmoles) in DMF (45 ml), cesium carbonate (16.0 g, 49.30 mmoles) was added and stirred at RT for 10 min. To this mixture, intermediate 75 (9.0 g, 24.65 mmoles) was added and stirred for 17 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as light yellow solid (3.2 g, 24% yield). $^1$H-NMR (δ ppm, DMSO-$D_6$, 400 MHz): δ 8.01 (s, 1H), 7.81-7.69 (m, 3H), 7.28 (s, 1H), 7.08 (dt, J=8.5, 1.8 Hz, 1H), 6.88 (br s, 2H), 5.93 (q, J=7.0 Hz, 1H) 1.83 (d, J=7.0 Hz, 3H).

Example 57g 2-(1-(4-amino-3-iodo-1H-pyrazolo[3,4-d]pyrimidin-1-yl) propyl)-3-(3-fluorophenyl)-4H-chromen-4-one To a solution of 3-iodo-1H-pyrazolo[3,4-d]pyrimidin-4-amine (1.44 g, 5.52 mmoles) in DMF (20 ml), potassium carbonate (0.763 g, 5.52 mmoles) was added and stirred at RT for 10 min. To this mixture, intermediate 46 (1.0 g, 2.76 mmoles) was added and stirred for 17 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as light yellow solid (0.440 g, 29% yield). $^1$H-NMR (δ ppm, DMSO-$D_6$, 400 MHz): δ 8.04 (dd, J=7.9, 1.4 Hz, 1H), 8.01 (s, 1H), 7.87 (m, 1H) 7.68 (d, J=8.5 Hz, 1H), 7.53 (t, J=7.2 Hz, 1H), 7.29 (br s, 1H), 7.09 (dt, J=8.9, 1.6 Hz, 1H), 6.88 (m, 2H), 5.72 (J=7.5 Hz, 1H), 2.42 (quintet, J=7.4 Hz, 2H), 0.75 (t, J=7.3 Hz, 3H).

Example 58

2-((4-amino-3-(pyridin-3-yl)-1H-pyrazolo[3,4-d]pyrimidin-1-yl)methyl)-3-phenyl-4H-chromen-4-one To a solution of Example 57a (0.250 g, 0.50 mmoles) in DMF (5 ml), ethanol (2.5 ml) and water (2.5 ml), 3-pyridinylboronic acid (0.080 g, 0.65 mmoles) and sodium carbonate (0.264 g, 2.5 mmoles) were added and the system is degassed for 30 min. Tetrakis triphenylphosphine Palladium (0.109 g, 0.095 mmoles) was added under nitrogen atmosphere and heated to 80° C. After 12 h, the reaction mixture was celite filtered, concentrated and extracted with ethyl acetate. The organic layer was dried over sodium sulphate and concentrated under reduced pressure. The crude product was purified by column chromatography with methanol:dichloromethane to afford the title compound as brown solid (0.030 g, 13% yield). MP: 253-255° C. $^1$H-NMR (δ ppm, DMSO-$d_6$, 400 MHz): δ 8.78 (d, J=1.7 Hz, 1H), 8.65 (dd, J=4.7, 1.3 Hz, 1H), 8.24 (s, 1H), 8.05 (dd, J=7.9, 1.6 Hz, 1H), 8.00 (td, J=7.9, 1.9 Hz, 1H), 7.77 (d, J=7.2, 1.7 Hz, 1H), 7.54-7.43 (m, 3H), 7.37-7.30 (m, 5H), 7.12 (br s, 2H), 5.54 (s, 2H). Mass: 447.19 ($M^+$+1).

Example 59

2-((4-amino-3-(3-hydroxyprop-1-ynyl)-1H-pyrazolo[3,4-d]pyrimidin-1-yl)methyl)-3-phenyl-4H-chromen-4-one To a solution of Example 57a (0.180 g, 0.363 mmoles) in THF (5 ml), propargyl alcohol (0.051 g, 0.436 mmoles) diisopropylamine (0.31 ml, 1.81 mmoles), copper(I) iodide (7 mg, 0.036 mmoles) and) Tetrakis triphenylphosphine Palladium (0.042 g, 0.0363 mmoles) were added and the system is degassed for 30 min. and heated to reflux for 4 h. The reaction mixture filtered through celite pad and washed with ethyl acetate. The filtrate was dried over sodium sulphate and concentrated under reduced pressure. The crude product was purified by column chromatography with methanol:dichloromethane to afford the title compound as brown solid (0.118 g, 77% yield). MP: 171-173° C. $^1$H-NMR (δ ppm, DMSO-$d_6$, 400 MHz): δ 8.21 (s, 1H), 8.06 (dd, J=7.9, 1.6 Hz, 1H), 7.77 (m, 1H), 7.50 (dt, J=8.0, 0.9 Hz, 1H), 7.40-7.33 (m, 6H), 5.43 (s, 2H), 4.33 (d, J=6.1 z, 2H). Mass: 423.88 ($M^+$).

Example 60

2-((4-amino-3-(1H-pyrazol-4-yl)-1H-pyrazolo[3,4-d]pyrimidin-1-yl)methyl)-3-phenyl-4H-chromen-4-one To a solution of Example 57a (0.500 g, 1.00 mmoles) in DMF (7 ml), ethanol (4 ml) and water (4 ml), N-Boc-Pyrazole-4-boronic acid pinacol ester (0.445 g, 1.51 mmoles) and sodium carbonate (0.534 g, 5.04 mmoles) were added and the system is degassed for 30 min. Tetrakis triphenylphosphine Palladium (0.229 g, 0.198 mmoles) was added under nitrogen atmosphere and heated to 80° C. After 12 h, the reaction mixture was celite filtered, concentrated and extracted with ethyl acetate. The organic layer was dried over sodium sulphate and concentrated under reduced pressure. The crude product was purified by column chromatography with methanol:dichloromethane to afford the title compound as yellow solid (0.131 g, 29% yield). MP: 235-237° C. $^1$H-NMR (δ ppm, DMSO-$d_6$, 400 MHz): δ 13.20 (s, 1H), 8.20 (s, 1H), 8.10 (s, 1H), 8.05 (dd, J=8.0, 1.7 Hz, 1H), 7.78 (s, 1H), 7.76 (m, 1H), 7.49 (dt, J=8.0, 0.8 Hz, 1H), 7.39-7.31 (m, 6H), 5.45 (s, 2H). Mass: 436.20 ($M^+$+1).

Example 61

2-((4-amino-3-(3-(hydroxymethyl)phenyl)-1H-pyrazolo[3,4-d]pyrimidin-1-yl)methyl)-3-phenyl-4H-chromen-4-one To a solution of Example 57a (0.250 g, 0.50 mmoles) in DMF (5 ml), ethanol (2.5 ml) and water (2.5 ml), 3-hydroxymethylphenylboronic acid (0.115 g, 0.757 mmoles) and sodium carbonate (0.267 g, 2.53 mmoles) were added and the system is degassed for 30 min. Tetrakis triphenylphosphine Palladium (0.115 g, 0.099 mmoles) was added under nitrogen atmosphere and heated to 80° C. After 12 h, the reaction mixture was celite filtered, concentrated and extracted with ethyl acetate. The organic layer was dried over sodium sulphate and concentrated under reduced pressure. The crude product was purified by column chromatography with methanol:dichloromethane to afford the title compound as brown solid (0.116 g, 44% yield). MP: 219-223° C. $^1$H-NMR (δ ppm, DMSO-$d_6$, 400 MHz): δ 8.23 (s, 1H), 8.05 (dd, J=8.0, 1.6 Hz, 1H), 7.77 (m, 1H), 7.58 (s, 1H), 7.50 (m, 3H), 7.44 (d, J=8.5 Hz, 1H), 7.41-7.31 (m, 6H), 5.52 (s, 2H), 5.27 (t, J=5.8 Hz, 1H), 4.57 (d, J=5.7 Hz, 2H). Mass: 476.31 ($M^+$+1).

Example 62

2-((4-amino-3-(1H-indazol-4-yl)-1H-pyrazolo[3,4-d]pyrimidin-1-yl)methyl)-3-phenyl-4H-chromen-4-one To a solution of Example 57a (0.500 g, 1.00 mmoles) in DMF (5 ml), ethanol (2.5 ml) and water (2.5 ml), 4-Indazole-boronic acid pinacol ester (0.491 g, 2.00 mmoles) and sodium carbonate (0.533 g, 5.02 mmoles) were added and the system is degassed for 30 min. Tetrakis triphenylphosphine Palladium (0.229 g, 0.197 mmoles) was added under nitrogen atmosphere and heated to 80° C. After 12 h, the reaction mixture was celite filtered, concentrated and extracted with ethyl acetate. The organic layer was dried over sodium sulphate and concentrated under reduced pressure. The crude product was purified by column chromatography with methanol:dichloromethane to afford the title compound as brown solid (0.040 g, 8% yield). MP: 248-252° C. $^1$H-NMR (δ ppm, DMSO-$d_6$, 400 MHz): δ 13.24 (s, 1H), 8.27 (s, 1H), 8.07 (dd, J=7.9, 1.6 Hz, 1H), 8.01 (s, 1H), 7.78 (m, 1H), 7.63 (d, J=8.4 Hz, 1H), 7.51-7.32 (m, 10H), 7.14 (br s, 1H), 5.56 (s, 1H). Mass: 486.04 ($M^+$+1).

Example 63

2-((4-amino-3-(3-fluorophenyl)-1H-pyrazolo[3,4-d]pyrimidin-1-yl)methyl)-3-phenyl-4H-chromen-4-one To a solution of intermediate 78 (0.150 g, 0.654 mmoles) in DMF (5 ml), potassium carbonate (0.180 g, 1.30 mmoles) was added and stirred at RT for 10 min. To this mixture, intermediate 5 (0.413 g, 1.30 mmoles) was added and stirred for 12 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as light yellow solid (0.130 g, 43% yield). MP: 244-247° C. $^1$H-NMR (δ ppm, DMSO-$D_6$, 400 MHz): δ 8.23 (s, 1H), 8.05 (dd, J=7.9, 1.6 Hz, 1H), 7.77 (m, 1H), 7.58 (m, 1H), 7.49-7.17 (m, 10H), 5.52 (s, 2H). Mass: 463.92 ($M^+$).

Example 64

2-((4-amino-3-(3-hydroxypropyl)-1H-pyrazolo[3,4-d]pyrimidin-1-yl)methyl)-3-phenyl-4H-chromen-4-one To a solution of example 59 (0.170 g, 0.401 mmoles) in methanol (4 ml), palladium on charcoal 1 (10%, 0.050 g) was added and hydrogenated at 5 kg/$cm^2$ for 48 h. The reaction mixture filtered through celite pad and washed with methanol. The filtrate was dried over sodium sulphate and concentrated under reduced pressure. The crude product was purified by column chromatography with methanol:dichloromethane to afford the title compound as brown solid (0.072 g, 42% yield). MP: 182-184° C. $^1$H-NMR (δ ppm, DMSO-$d_6$, 400 MHz): δ 8.11 (s, 1H), 8.05 (dd, J=8.0, 1.6 Hz, 1H), 7.76 (m, 1H), 7.49 (t, J=7.1 Hz, 1H), 7.39-7.20 (m, 8H), 4.62 (t, J=4.6 Hz, 1H), 3.45 (q, J=6.1 Hz, 2H), 2.92 (t, J=7.4 Hz, 2H), 1.78 (m, 2H). Mass: 427.87 ($M^+$).

Example 65

N-(3-(4-amino-1-((4-oxo-3-phenyl-4H-chromen-2-yl)methyl)-1H-pyrazolo[3,4-d]pyrimidin-3-yl)phenyl)acetamide To a solution of Example 57a (0.250 g, 0.50 mmoles) in DMF (5 ml), ethanol (2.5 ml) and water (2.5 ml), 3-Acetamidophenyl boronic acid (0.116 g, 0.65 mmoles) and sodium carbonate (0.264 g, 2.50 mmoles) were added and the system is degassed for 30 min. Tetrakis triphenylphosphine Palladium (0.109 g, 0.095 mmoles) was added under nitrogen atmosphere and heated to 80° C. After 12 h, the reaction mixture was celite filtered, concentrated and extracted with ethyl acetate. The organic layer was dried over sodium sulphate and concentrated under reduced pressure. The crude product was purified by column chromatography with methanol:dichloromethane to afford the title compound as yellow solid (0.080 g, 23% yield). MP: 122-123° C. $^1$H-NMR (δ ppm, DMSO-$d_6$, 400 MHz): δ 10.13 (s, 1H), 8.06 (dd, J=7.7, 1.4 Hz, 1H), 7.90 (s, 1H), 7.77 (m, 1H), 7.57-7.47 (m, 3H), 7.48 (m, 3H), 7.37-7.29 (m, 6H), 5.52 (s, 2H), 2.05 (s, 3H). Mass: 503.05 ($M^+$+1).

Example 66

2-((4-amino-3-(3-fluoro-5-methoxyphenyl)-1H-pyrazolo[3,4-d]pyrimidin-1-yl)methyl)-3-phenyl-4H-chromen-4-one To a solution of intermediate 79 (0.150 g, 0.58 mmoles) in DMF (5 ml), potassium carbonate (0.160 g, 1.16 mmoles) was added and stirred at RT for 10 min. To this mixture, intermediate 5 (0.366 g, 1.16 mmoles) was added and stirred for 12 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as light yellow solid (0.120 g, 42% yield). $^1$H-NMR (δ ppm, DMSO-$D_6$, 400 MHz): δ 8.23 (s, 1H), 8.05 (dd, J=8.1, 1.5 Hz, 1H), 7.77 (m, 1H), 7.49 (dt, J=8.1, 0.9 Hz, 1H), 7.44 (d, J=8.4 Hz, 1H), 7.38-7.30 (m, 5H), 6.98 (m, 2H), 6.96 (dt, J=7.9, 2.3 Hz, 1H), 5.51 (s, 2H), 3.81 (s, 3H).

Example 66a 2-((4-amino-3-(3-fluoro-5-hydroxyphenyl)-1H-pyrazolo[3,4-d]pyrimidin-1-yl)methyl)-3-phenyl-4H-chromen-4-one To a solution of Example 66 (0.100 g, 0.202 mmoles) in dichloromethane (15 ml), $BBr_3$ (1M in dichloromethane, 1.0 ml) was added at 0° C. and the reaction mixture was warmed to RT and then stirred for 12 h. The reaction mixture was quenched with 1.5N HCl solution and extracted with dichloromethane. The organic layer was dried over sodium sulphate and concentrated. The crude product was purified by column chromatography with methanol:dichloromethane to afford the title compound as yellow solid (0.035 g, 36% yield). MP: 260-262° C. $^1$H-NMR (δ ppm, DMSO-$D_6$, 400 MHz): δ 10.16 (s, 1H), 8.22 (s, 1H), 8.06 (dd, J=7.9, 1.5 Hz, 1H), 7.78 (m, 1H), 7.50 (dt, J=8.0, 1.0 Hz, 1H), 7.44 (d, J=8.5 Hz, 1H), 7.37-7.31 (m, 5H), 6.86 (t, J=1.5 Hz, 1H), 6.82 (dt, J=7.6, 2.3 Hz, 1H), 6.65 (td, J=10.9, 2.3 Hz, 1H), 5.50 (s, 2H). Mass: 480.02 ($M^+$+1).

Example 67

2-((4-amino-3-(3-fluoro-5-methoxyphenyl)-1H-pyrazolo[3,4-d]pyrimidin-1-yl)methyl)-3-(3-fluorophenyl)-4H-chromen-4-one To a solution of intermediate 79 (0.150 g, 0.58 mmoles) in DMF (5 ml), potassium carbonate (0.160 g, 1.16 mmoles) was added and stirred at RT for 10 min. To this mixture, intermediate 77 (0.366 g, 1.16 mmoles) was added and stirred for 12 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as light yellow solid (0.120 g, 42% yield). MP: 115-117° C. $^1$H-NMR (δ ppm, DMSO-$D_6$, 400 MHz): δ 8.21 (s, 1H), 8.06 (dd, J=8.3, 1.7 Hz, 1H), 7.80 (m, 1H), 7.51 (m, 2H), 7.39 (q, J=8.0 Hz, 1H), 7.18 (m, 3H), 6.97 (m, 3H), 5.54 (s, 2H), 3.82 (s, 3H). Mass: 511.80 ($M^+$).

Example 68

2-((4-amino-3-(3-fluoro-5-hydroxyphenyl)-1H-pyrazolo[3,4-d]pyrimidin-1-yl)methyl)-3-(3-fluorophenyl)-4H-chromen-4-one To a solution of example 67 (0.080 g, 0.156 mmoles) in dichloromethane (15 ml), $BBr_3$ (1M in dichloromethane, 0.8 ml) was added at 0° C. and the reaction mixture was warmed to RT and then stirred for 12 h. The reaction mixture was quenched with 1.5N HCl solution and extracted with dichloromethane. The organic layer was dried over sodium sulphate and concentrated. The crude product was purified by column chromatography with methanol:dichloromethane to afford the title compound as off-white solid (0.035 g, 45% yield). MP: 235-237° C. $^1$H-NMR (δ ppm, DMSO-$D_6$, 400 MHz): δ 10.17 (s, 1H), 8.20 (s, 1H), 8.06 (dd, J=8.2, 1.6 Hz, 1H), 7.80 (m, 1H), 7.51 (m, 2H), 7.38 (q, J=7.8 Hz, 1H), 7.17-7.07 (m, 3H), 6.84 (t, J=1.7 Hz, 1H), 6.81 (td, J=79.3, 2.1 Hz, 1H), 6.66 (td, J=10.2, 2.2 Hz, 1H), 5.53 (s, 2H). Mass: 497.87 ($M^+$).

Example 69

2-(1-(4-amino-3-(1H-pyrazol-4-yl)-1H-pyrazolo[3,4-d]pyrimidin-1-yl)ethyl)-3-phenyl-4H-chromen-4-one To a solution of Example 57b (0.400 g, 0.78 mmoles) in DMF (8 ml), ethanol (4 ml) and water (4 ml), N-Boc-pyrazole-4-boronic acid pinacol ester (0.344 g, 1.17 mmoles) and sodium carbonate (0.413 g, 3.9 mmoles) were added and the system is degassed for 30 min Tetrakis triphenylphosphine. Palladium (0.171 g, 0.148 mmoles) was added under nitrogen atmosphere and heated to 80° C. After 12 h, the reaction mixture was celite filtered, concentrated and extracted with ethyl acetate. The organic layer was dried over sodium sulphate and concentrated under reduced pressure. The crude product was purified by column chromatography with methanol:dichloromethane to afford the title compound as yellow solid (0.070 g, 19% yield). MP: 214-217° C. $^1$H-NMR (δ ppm, DMSO-$d_6$, 400 MHz): δ 13.20 (s, 1H), 8.10 (s, 1H), 8.05 (s, 1H), 8.03 (dd, J=8.0, 1.6 Hz, 1H), 7.82 (m, 2H), 7.61 (d, J=8.0 Hz, 1H), 7.51 (dt, J=8.0, 0.9 Hz, 1H), (m, 3H), 7.31-6.87 (m, 5H), 5.92 (q, J=7.1 Hz, 1H), 1.87 (d, J=7.1 Hz, 3H). Mass: 449.852 ($M^+$).

Example 70

2-(1-(4-amino-3-(1H-indazol-6-yl)-1H-pyrazolo[3,4-d]pyrimidin-1-yl)ethyl)-3-phenyl-4H-chromen-4-one To a solution of Example 57b (0.500 g, 0.98 mmoles) in DMF (10 ml), ethanol (4 ml) and water (4 ml), 6-Indazole-boronic acid pinacol ester (0.478 g, 1.96 mmoles) and sodium carbonate (0.519 g, 4.90 mmoles) were added and the system is degassed for 30 min. Tetrakis triphenylphosphine Palladium (0.214 g, 0.185 mmoles) was added under nitrogen atmosphere and heated to 80° C. After 12 h, the reaction mixture was celite filtered, concentrated and extracted with ethyl acetate. The organic layer was dried over sodium sulphate and concentrated under reduced pressure. The crude product was purified by column chromatography with methanol:dichloromethane to afford the title compound as brown solid (0.050 g, 10% yield). MP: 176-178° C. $^1$H-NMR (δ ppm, DMSO-$d_6$, 400 MHz): δ 13.18 (s, 1H), 8.14 (s, 1H), 8.09 (s, 1H), 8.05 (dd, J=8.0, 1.6 Hz, 1H), 7.91 (d, J=8.3 Hz, 1H), 7.83 (m, 1H), 7.73 (s, 1H), 7.63 (d, J=8.3 Hz, 1H), 7.52 (dt, J=7.9, 0.8 Hz, 1H), 7.41 (dd, J=8.3, 1.2 Hz, 1H), 7.31-7.16 (m, 5H), 6.01 (q, J=6.9 Hz, 1H), 1.92 (d, J=7.1 Hz, 3H). Mass: 500.04 ($M^+$+1).

Example 71

2-(1-(4-amino-3-(3-hydroxy-3-methylbut-1-ynyl)-1H-pyrazolo[3,4-d]pyrimidin-1-yl)ethyl)-3-phenyl-4H-chromen-4-one To a solution of Example 57b (0.500 g, 0.981 mmoles) in THF (14 ml), 2-Methyl-3-butyn-2-ol (0.1 ml, 1.178 mmoles) diisopropylamine (0.70 ml, 4.90 mmoles), copper(I) iodide (18.6 mg, 0.098 mmoles) and) Tetrakistriphenylphosphine Palladium (0.113 g, 0.098 mmoles) were added and the system is degassed for 30 min. and heated to reflux for 4 h. The reaction mixture filtered through celite pad and washed with ethyl acetate. The filtrate was dried over sodium sulphate and concentrated under reduced pressure. The crude product was purified by column chromatography with methanol:dichloromethane to afford the title compound as brown solid (0.311 g, 68% yield). MP: 109-113° C. $^{1}$H-NMR (δ ppm, DMSO-$d_6$, 400 MHz): δ 8.05 (m, 3H), 7.83 (dt, J=8.6, 1.5 Hz, 1H), 7.61 (d, J=8.4 Hz, 1H), 7.52 (t, J=7.2 Hz, 1H), 7.30-7.11 (m, 4H), 5.84 (q, J=7.1 z, 1H) 5.74 (s, 1H), 1.82 (d, J=7.0 Hz, 3H), 1.46 (s, 6H). Mass: 466.09 ($M^{+}$+1).

Example 72

2-(1-(4-amino-3-(1H-pyrazol-4-yl)-1H-pyrazolo[3,4-d]pyrimidin-1-yl)ethyl)-3-(3-fluorophenyl)-4H-chromen-4-one To a solution of Example 57c (0.400 g, 0.758 mmoles) in DMF (5.3 ml), ethanol (2.7 ml) and water (2.7 ml), N-Boc-pyrazole-4-boronic acid pinacol ester (0.334 g, 1.137 mmoles) and sodium carbonate (0.401 g, 3.79 mmoles) were added and the system is degassed for 30 min. Tetrakistriphenylphosphine Palladium (0.172 g, 0.149 mmoles) was added under nitrogen atmosphere and heated to 80° C. After 12 h, the reaction mixture was celite filtered, concentrated and extracted with ethyl acetate. The organic layer was dried over sodium sulphate and concentrated under reduced pressure. The crude product was purified by column chromatography with methanol:dichloromethane to afford the title compound as off-white solid (0.040 g, 11% yield). MP: 223-226° C. $^{1}$H-NMR (δ ppm, DMSO-$d_6$, 400 MHz): δ 13.22 (s, 1H), 8.03 (m, 2H), 7.85 (m, 2H), 7.68 (d, J=8.3 Hz, 1H), 7.52 (t, J=7.7 Hz, 1H), 7.25 (m, 1H), 7.07-6.93 (m, 3H), 5.92 (q, J=6.9 Hz, 1H), 1.87 (d, J=7.0 Hz, 3H). Mass: 467.84 ($M^{+}$).

Example 73

(S)-2-(1-(9H-purin-6-ylamino)ethyl)-3-phenyl-4H-chromen-4-one

To a solution of intermediate 59 (2.0 g, 9.42 mmoles) in dichloromethane (20 ml), triethylamine (3.9 ml, 28.26 mmoles) was added followed by N-Boc-Alanine (1.90 g, 10.42 mmoles). To this mixture HATU (6.6 g, 17.37 mmoles) was added and stirred at RT for 12 h. The reaction mixture was quenched by the addition of water and extracted with dichloromethane. The organic layer was dried over sodium sulphate and concentrated under reduced pressure. The crude product was purified by column chromatography with ethyl acetate: petroleum ether to afford the isoflavone intermediate (1.70 g). To a solution of this intermediate (1.7 g) in dichloromethane (20 ml), trifluoroacetic acid (3 ml) was added and stirred at RT for 2 h. The reaction mixture was concentrated, basified with sodium bicarbonate solution, extracted with ethyl acetate. The organic layer was dried over sodium sulphate and concentrated under reduced pressure to afford the amine intermediate (0.641 g). To a solution of this amine intermediate (0.30 g, 1.05 mmoles) in tert-butanol (6 ml), N,N-diisopropylethylamine (0.36 ml, 2.17 mmoles) and 6-bromopurine (0.168 g, 0.847 mmoles) were added and refluxed for 24 h. The reaction mixture was concentrated, diluted with water, extracted with ethyl acetate. The organic layer was dried over sodium sulphate and concentrated under reduced pressure. The crude product was purified by column chromatography with methanol:ethyl acetate to afford the title compound as off-white solid (0.041 g, 10% yield). MP: 135-138° C. $^{1}$H-NMR (δ ppm, DMSO-$D_6$, 400 MHz): δ 12.95 (s, 1H), 8.15 (t, J=6.8 Hz, 1H), 8.11 (s, 1H), 8.08 (s, 1H), 8.03 (d, J=7.8 Hz, 1H), 7.81 (t, J=7.3 Hz, 1H), 7.60 (d, J=8.3 Hz, 1H), 7.49 (t, J=7.3 Hz, 2H), 7.25 (m, 3H), 5.19 (br m, 1H), 1.56 (d, J=6.9 Hz, 3H). Mass: 384.12 ($M^{+}$+1).

Example 74

(S)-2-(1-(9H-purin-6-ylamino)ethyl)-6-fluoro-3-(3-fluorophenyl)-4H-chromen-4-one To a solution of intermediate 73 (2.0 g, 8.05 mmoles) in dichloromethane (20 ml), triethylamine (3.3 ml, 24.17 mmoles) was added followed by N-Boc-L-Alanine (1.82 g, 9.66 mmoles). To this mixture HATU (6.12 g, 16.11 mmoles) was added and stirred at RT for 12 h. The reaction mixture was quenched by the addition of water and extracted with dichloromethane. The organic layer was dried over sodium sulphate and concentrated under reduced pressure. The crude product was purified by column chromatography with ethyl acetate: petroleum ether to afford the isoflavone intermediate (2.15 g). To a solution of this intermediate (2.1 g) in dichloromethane (20 ml), trifluoroacetic acid (4 ml) was added and stirred at RT for 2 h. The reaction mixture was concentrated, basified with sodium bicarbonate solution, extracted with ethyl acetate. The organic layer was dried over sodium sulphate and concentrated under reduced pressure to afford the amine intermediate (0.700 g). To a solution of this amine intermediate (0.450 g, 1.49 mmoles) in tert-butanol (7 ml), N,N-diisopropylethylamine (0.52 ml, 2.98 mmoles) and 6-chloropurine (0.184 g, 1.194 mmoles) were added and refluxed for 24 h. The reaction mixture was concentrated, diluted with water, extracted with ethyl acetate. The organic layer was dried over sodium sulphate and concentrated under reduced pressure. The crude product was purified by column chromatography with methanol:ethyl acetate to afford the title compound as off-white solid (0.060 g, 12% yield). MP: 203-206° C. $^{1}$H-NMR (δ ppm, DMSO-$D_6$, 400 MHz): δ 12.96 (s, 1H), 8.15 (m, 2H), 8.08 (s, 1H), 7.70 (m, 3H), 7.49 (q, J=7.3 Hz, 1H), 7.24 (m, 3H), 5.18 (br m, 1H), 1.55 (d, J=7.1 Hz, 3H). Mass: 420.17 ($M^{+}$+1).

Example 75

2-((4-amino-3-(1H-indazol-6-yl)-1H-pyrazolo[3,4-d]pyrimidin-1-yl)methyl)-3-phenyl-4H-chromen-4-one To a solution of Example 57a (0.700 g, 1.40 mmoles) in DMF (7 ml), ethanol (3.2 ml) and water (3.2 ml), 6-Indazoleboronic acid pinacol ester (0.687 g, 2.81 mmoles) and sodium carbonate (0.745 g, 7.03 mmoles) were added and the system is degassed for 30 min. Tetrakis triphenylphosphine Palladium (0.320 g, 0.277 mmoles) was added under nitrogen atmosphere and heated to 80° C. After 12 h, the reaction mixture was celite filtered, concentrated and extracted with ethyl acetate. The organic layer was dried over sodium sulphate and concentrated under reduced pressure. The crude product was purified by column chromatography with methanol:dichloromethane to afford the title compound as yellow solid (0.020 g, 3% yield). MP: 140-143° C. $^{1}$H-NMR (δ ppm, DMSO-$d_6$, 400 MHz): δ 13.18 (s, 1H), 8.24 (s, 1H), 8.13 (s, 1H), 8.06 (dd, J=7.9, 1.6 Hz, 1H), 7.78 (m, 2H), 7.49-7.30 (m, 7H), 6.89 (q, J=7.7 Hz, 1H), 5.53 (s, 2H). Mass: 485.76 ($M^{+}$+1).

Example 76

2-(1-(4-amino-3-(3-fluoro-5-methoxyphenyl)-1H-pyrazolo[3,4-d]pyrimidin-1-yl)ethyl)-3-(3-fluorophenyl)-4H-chromen-4-one To a solution of intermediate 79 (0.160 g, 0.617 mmoles) in DMF (6 ml), potassium carbonate (0.171 g, 1.16 mmoles) was added and stirred at RT for 10 min. To this mixture, intermediate 36 (0.429 g, 1.23 mmoles) was added and stirred for 12 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as light yellow solid (0.160 g, 49% yield). $^1$H-NMR (δ ppm, DMSO-$D_6$, 400 MHz): δ 8.08 (s, 1H), 8.04 (dd, J=8.0, 1.6 Hz, 1H), 7.85 (m, 1H), 7.68 (d, J=8.2 Hz, 1H), 7.53 (dt, J=7.9, 0.9 Hz, 1H), 7.31 (br s, 1H), 7.07 (dt, J=8.6, 2.1 Hz, 1H), 6.97 (m, 5H), 6.03 (q, J=7.1 Hz, 1H), 3.82 (s, 3H), 1.90 (d, J=7.0 Hz, 3H).

Example 76a 2-(1-(4-amino-3-(3-fluoro-5-hydroxyphenyl)-1H-pyrazolo[3,4-d]pyrimidin-1-yl)ethyl)-3-(3-fluorophenyl)-4H-chromen-4-one To a solution of Example 76 (0.160 g, 0.304 mmoles) in dichloromethane (25 ml), $BBr_3$ (1M in dichloromethane, 1.6 ml) was added at 0° C. and the reaction mixture was warmed to RT and then stirred for 12 h. The reaction mixture was quenched with 1.5N HCl solution and extracted with dichloromethane. The organic layer was dried over sodium sulphate and concentrated. The crude product was purified by column chromatography with methanol:dichloromethane to afford the title compound as off-white solid (0.080 g, 51% yield). MP: 271-273° C. $^1$H-NMR (δ ppm, DMSO-$D_6$, 400 MHz): δ 10.17 (s, 1H), 8.06 (s, 1H), 8.05 (dd, J=7.9, 1.4 Hz, 1H), 7.86 (dt, J=8.5, 1.5 Hz, 1H), 7.68 (d, J=8.3 Hz, 1H), 7.53 (t, J=7.9 Hz, 1H), 7.28 (br s, 1H), 7.05 (dt, J=6.8, 2.0 Hz, 1H), 6.91 (br s, 2H), 6.86 (s, 1H), 6.79 (d, J=9.4 Hz, 1H), 6.66 (td, J=10.3, 2.1 Hz, 1H), 6.05 (q, J=6.7 Hz, 1H), 1.88 (d, J=7.1 Hz, 3H). Mass: 511.80 ($M^+$).

Example 77

2-(1-(4-amino-3-(1H-indazol-4-yl)-1H-pyrazolo[3,4-d]pyrimidin-1-yl)ethyl)-3-(3-fluorophenyl)-4H-chromen-4-one To a solution of Example 57c (0.350 g, 1.00 mmoles) in DMF (8 ml), ethanol (4 ml) and water (4 ml), 4-Indazoleboronic acid pinacol ester (0.322 g, 1.32 mmoles) and sodium carbonate (0.349 g, 3.3 mmoles) were added and the system is degassed for 30 min. Tetrakis triphenylphosphine Palladium (0.150 g, 0.130 mmoles) was added under nitrogen atmosphere and heated to 80° C. After 12 h, the reaction mixture was celite filtered, concentrated and extracted with ethyl acetate. The organic layer was dried over sodium sulphate and concentrated under reduced pressure. The crude product was purified by column chromatography with methanol:dichloromethane to afford the title compound as off-white solid (0.045 g, 13% yield). MP: 231-233° C. $^1$H-NMR (δ ppm, DMSO-$d_6$, 400 MHz): δ 13.25 (s, 1H), 8.10 (s, 1H), 8.06 (m, 2H), 7.86 (m, 1H), 7.66 (t, J=9.0 Hz, 2H), 7.54 (m, 2H), 7.33 (t, J=6.7 Hz, 2H), 7.11-7.06 (m, 3H), 6.07 (q, J=7.1 Hz, 1H), 1.94 (d, J=7.0 Hz, 3H). Mass: 517.96 ($M^+$).

Example 78

2-(1-(4-amino-3-(3,5-dimethyl-1H-pyrazol-4-yl)-1H-pyrazolo[3,4-d]pyrimidin-1-yl)ethyl)-3-(3-fluorophenyl)-4H-chromen-4-one To a solution of Example 57c (0.350 g, 0.661 mmoles) in DMF (6 ml), ethanol (3 ml) and water (3 ml), 3,5-Dimethylpyrazole-4-boronic acid pinacol ester (0.191 g, 0.859 mmoles) and sodium carbonate (0.350 g, 3.30 mmoles) were added and the system is degassed for 30 min. Tetrakistriphenylphosphine Palladium (0.150 g, 0.130 mmoles) was added under nitrogen atmosphere and heated to 80° C. After 12 h, the reaction mixture was celite filtered, concentrated and extracted with ethyl acetate. The organic layer was dried over sodium sulphate and concentrated under reduced pressure. The crude product was purified by column chromatography with methanol:dichloromethane to afford the title compound as brown solid (0.025 g, 7% yield). MP: 240-243° C. $^1$H-NMR (δ ppm, DMSO-$d_6$, 400 MHz): δ 12.44 (s, 1H), 8.04 (dd, J=8.0, 1.6 Hz, 1H), 8.01 (s, 1H), 7.85 (s, 1H), 7.61 (d, J=8.3 Hz, 1H), 7.52 (dt, J=7.9, 0.7 Hz, 1H), 7.33 (br m, 1H), 7.12-6.95 (m, 3H), 5.97 (q, J=7.0 Hz, 1H), 2.09 (s, 6H), 1.86 (d, J=7.0 Hz, 3H). Mass: 495.84 ($M^+$).

Example 79

2-(1-(4-amino-3-(3-methyl-1H-indazol-6-yl)-1H-pyrazolo[3,4-d]pyrimidin-1-yl)ethyl)-3-(3-fluorophenyl)-4H-chromen-4-one To a solution of Example 57c (0.400 g, 0.758 mmoles) in DMF (4 ml), ethanol (2 ml) and water (2 ml), 3-Methylindazole-6-boronic acid pinacol ester 97 (0.391 g, 1.517 mmoles) and sodium carbonate (0.401 g, 3.79 mmoles) were added and the system is degassed for 30 min. Tetrakistriphenylphosphine Palladium (0.172 g, 0.149 mmoles) was added under nitrogen atmosphere and heated to 80° C. After 12 h, the reaction mixture was celite filtered, concentrated and extracted with ethyl acetate. The organic layer was dried over sodium sulphate and concentrated under reduced pressure. The crude product was purified by column chromatography with methanol:dichloromethane to afford the title compound as yellow solid (0.095 g, 23% yield). MP: 214-217° C. $^1$H-NMR (δ ppm, DMSO-$d_6$, 400 MHz): δ 12.75 (s, 1H), 8.08 (s, 1H), 8.05 (dd, J=7.9, 1.4 Hz, 1H), 7.86 (m, 2H), 7.68 (d, J=8.3 Hz, 1H), 7.62 (s, 1H), 7.53 (t, J=7.3 Hz, 1H), 7.33 (d, J=8.5 Hz, 1H), 7.31 (br s, 1H), 7.07 (dt, J=8.9, 2.1 Hz, 1H), 6.93 (m, 2H), 6.07 (q, J=6.7 Hz, 1H), 2.51 (s, 3H), 1.91 (d, J=7.0 Hz, 3H). Mass: 532.03 ($M^+$+1).

Example 80

2-(1-(4-amino-3-(1H-indazol-6-yl)-1H-pyrazolo[3,4-d]pyrimidin-1-yl)ethyl)-3-(3-fluorophenyl)-4H-chromen-4-one To a solution of Example 57c (0.500 g, 0.758 mmoles) in DMF (4.5 ml), ethanol (2.3 ml) and water (2.3 ml), Indazole-6-boronic acid pinacol ester (0.462 g, 1.89 mmoles) and sodium carbonate (0.502 g, 4.74 mmoles) were added and the system is degassed for 30 min. Tetrakistriphenylphosphine Palladium (0.215 g, 0.186 mmoles) was added under nitrogen atmosphere and heated to 80° C. After 12 h, the reaction mixture was celite filtered, concentrated and extracted with ethyl acetate. The organic layer was dried over sodium sulphate and concentrated under reduced pressure. The crude product was purified by column chromatography with methanol:dichloromethane to afford the title compound as brown solid (0.080 g, 16% yield). MP: 206-208° C. $^1$H-NMR (δ ppm, DMSO-d$_6$, 400 MHz): δ 13.19 (s, 1H), 8.14 (s, 1H), 8.08 (s, 1H), 8.05 (dd, J=7.9, 1.5 Hz, 1H), 7.90 (d, J=8.3 Hz, 1H), 7.86 (m, 1H), 7.71 (s, 1H), 7.69 (d, J=8.4 Hz, 1H), 7.53 (t, J=7.1 Hz, 1H), 7.39 (dd, J=8.2, 1.1 Hz, 1H), 7.30 (m, 2H), 7.07 (dt, J=8.7, 2.6 Hz, 1H), 6.92 (br m, 2H), 6.06 (q, J=7.1 Hz, 1H), 1.91 (d, J=7.0 Hz, 3H). Mass: 517.96 (M$^+$).

Example 81

2-(1-(4-amino-3-(2-(hydroxymethyl)phenyl)-1H-pyrazolo[3,4-d]pyrimidin-1-yl)ethyl)-3-(3-fluorophenyl)-4H-chromen-4-one To a solution of Example 57c (0.300 g, 0.568 mmoles) in DMF (3 ml), ethanol (1.5 ml) and water (1.5 ml), 2-Hydroxymethylphenylboronic acid (0.173 g, 1.137 mmoles) and sodium carbonate (0.301 g, 2.844 mmoles) were added and the system is degassed for 30 min. Tetrakistriphenylphosphine Palladium (0.129 g, 0.112 mmoles) was added under nitrogen atmosphere and heated to 80° C. After 12 h, the reaction mixture was celite filtered, concentrated and extracted with ethyl acetate. The organic layer was dried over sodium sulphate and concentrated under reduced pressure. The crude product was purified by column chromatography with methanol:dichloromethane to afford the title compound as off-white solid (0.090 g, 31% yield). MP: 185-189° C. $^1$H-NMR (δ ppm, DMSO-d$_6$, 400 MHz): δ 8.09 (s, 1H), 8.04 (dd, J=7.9, 1.4 Hz, 1H), 7.84 (m, 1H), 7.66-7.35 (m, 10H), 7.17 (dt, J=10.8, 1.4 Hz, 1H), 7.04 (m, 1H), 6.01 (q, J=6.7 Hz, 1H), 5.13 (t, J=5.7 Hz, 1H), 4.54 (m, 2H), 1.87 (d, J=7.1 Hz, 3H). Mass: 508.16 (M$^+$+1).

Example 82

2-(1-(4-amino-3-(4-fluoro-3-methoxyphenyl)-1H-pyrazolo[3,4-d]pyrimidin-1-yl)ethyl)-3-(3-fluorophenyl)-4H-chromen-4-one To a solution of intermediate 80 (0.120 g, 0.617 mmoles) in DMF (6 ml), potassium carbonate (0.128 g, 0.925 mmoles) was added and stirred at RT for 10 min. To this mixture, intermediate 36 (0.323 g, 1.23 mmoles) was added and stirred for 12 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as light yellow solid (0.075 g, 31% yield). $^1$H-NMR (δ ppm, DMSO-D$_6$, 400 MHz): δ 8.07 (s, 1H), 8.04 (d, J=7.0 Hz, 1H), 7.85 (t, J=7.1 Hz, 1H), 7.68 (d, J=8.5 Hz, 1H), 7.61 (m, 1H), 7.53 (t, J=7.1 Hz, 1H), 7.36 (m, 2H), 7.16 (m, 1H), 7.07 (t, J=6.7 Hz, 1H), 6.93 (br s, 2H), 6.03 (q, J=7.0 Hz, 1H), 3.88 (s, 3H), 1.90 (d, J=7.0 Hz, 3H).

Example 82a 2-(1-(4-amino-3-(4-fluoro-3-hydroxyphenyl)-1H-pyrazolo[3,4-d]pyrimidin-1-yl)ethyl)-3-(3-fluorophenyl)-4H-chromen-4-one To a solution of Example 82 (0.075 g, 0.142 mmoles) in dichloromethane (15 ml), $BBr_3$ (1M in dichloromethane, 1 ml) was added at 0° C. and the reaction mixture was warmed to RT and then stirred for 12 h. The reaction mixture was quenched with 1.5N Hal solution and extracted with dichloromethane. The organic layer was dried over sodium sulphate and concentrated. The crude product was purified by column chromatography with methanol:dichloromethane to afford the title compound as pale green solid (0.040 g, 55% yield). MP: 241-244° C. $^1$H-NMR (δ ppm, DMSO-D$_6$, 400 MHz): δ 10.15 (s, 1H), 8.05 (s, 1H), 8.05 (dd, J=8.6, 1.5 Hz, 1H), 7.86 (m, 1H), 7.68 (d, J=8.4 Hz, 1H), 7.53 (t, J=7.4 Hz, 1H), 7.28 (m, 2H), 7.20 (dd, J=8.5, 1.9 Hz, 1H), 7.05 (m, 4H), 6.04 (q, J=7.1 Hz, 1H), 1.88 (d, J=7.1 Hz, 3H). Mass: 511.94 (M$^+$).

Example 83

2-(1-(4-amino-3-(3-hydroxyprop-1-ynyl)-1H-pyrazolo[3,4-d]pyrimidin-1-yl)ethyl)-3-(3-fluorophenyl)-4H-chromen-4-one To a solution of Example-57c (0.400 g, 0.755 mmoles) in THF (10 ml), propargyl alcohol (0.051 g, 0.906 mmoles) diisopropylamine (0.53 ml, 3.77 mmoles), copper (I) iodide (14 mg, 0.075 mmoles) and) Tetrakis triphenylphosphine Palladium (0.087 g, 0.075 mmoles) were added and the system is degassed for 30 min. and heated to reflux for 4 h. The reaction mixture filtered through celite pad and washed with ethyl acetate. The filtrate was dried over sodium sulphate and concentrated under reduced pressure. The crude product was purified by column chromatography with methanol:dichloromethane to afford the title compound as brown solid (0.106 g, 23% yield). MP: 171-173° C. $^1$H-NMR (δ ppm, $CDCl_3$, 400 MHz): δ 11.36 (s, 1H), 8.19 (dd, J=7.9, 1.2 Hz, 1H), 7.70 (dt, J=8.6, 1.5 Hz, 1H), 7.47 (d, J=8.4 Hz, 1H), 7.42 (t, J=7.5 Hz, 1H), 7.38 (m, 2H), 7.07 (t, J=8.2 Hz, 1H), 6.99 (m, 2H), 6.00 (q, J=7.0 Hz, 1H), 4.55 (s, 2H), 1.97 (d, J=7.1 Hz, 1H). Mass: 456.08 (M$^+$+1).

Example 84

2-(1-(4-amino-3-(3-fluoro-4-methoxyphenyl)-1H-pyrazolo[3,4-d]pyrimidin-1-yl)ethyl)-3-(3-fluorophenyl)-4H-chromen-4-one To a solution of intermediate 81 (0.130 g, 0.50 mmoles) in DMF (4 ml), potassium carbonate (0.139 g, 1.00 mmoles) was added and stirred at RT for 10 min. To this mixture, intermediate 36 (0.350 g, 1.00 mmoles) was added and stirred for 12 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as brown solid (0.163 g, 60% yield). MP: 222-224° C. $^1$H-NMR (δ ppm, DMSO-D$_6$, 400 MHz): δ 8.06 (s, 1H), 8.04 (dd, J=7.9, 1.5 Hz, 1H), 7.85 (m, 1H), 7.68 (dd, J=8.4 Hz, 1H), 7.52 (t, J=7.4 Hz, 1H), 7.37-7.28 (m, 4H), 7.07 (dt, J=8.9, 2.4 Hz, 1H), 6.93 (br s, 2H), 6.05 (q, J=7.1 Hz, 1H), 3.89 (s, 3H), 1.89 (d, J=7.0 Hz, 3H). Mass: 525.94 (M$^+$).

Example 85

2-(1-(4-amino-3-(3-fluoro-4-hydroxyphenyl)-1H-pyrazolo[3,4-d]pyrimidin-1-yl)ethyl)-3-(3-fluorophenyl)-4H-chromen-4-one To a solution of example 84 (0.100 g, 0.190 mmoles) in dichloromethane (4 ml), $BBr_3$ (1M in dichloromethane, 1 ml)

was added at 0° C. and the reaction mixture was warmed to RT and then stirred for 12 h. The reaction mixture was quenched with 1.5N HCl solution and extracted with dichloromethane. The organic layer was dried over sodium sulphate and concentrated. The crude product was purified by column chromatography with methanol:dichloromethane to afford the title compound as pale green solid (0.061 g, 63% yield). MP: 244-247° C. $^1$H-NMR (δ ppm, DMSO-$D_6$, 400 MHz): δ 10.19 (s, 1H), 8.04 (s, 1H), 8.04 (dd, J=8.0, 1.4 Hz, 1H), 7.85 (m, 1H), 7.68 (d, J=8.4 Hz, 1H), 7.52 (t, J=7.2 Hz, 1H), 7.33 (m, 2H), 7.24 (dd, J=8.2, 1.4 Hz, 1H), 7.09-6.91 (m, 4H), 6.00 (q, J=7.0 Hz, 1H), 1.88 (d, J=7.0 Hz, 1H). Mass: 511.94 ($M^+$).

Example 86

2-(1-(4-amino-3-(3-chloro-5-methoxyphenyl)-1H-pyrazolo[3,4-d]pyrimidin-1-yl)ethyl)-3-(3-fluorophenyl)-4H-chromen-4-one To a solution of intermediate 82 (0.100 g, 0.362 mmoles) in DMF (4 ml), potassium carbonate (0.100 g, 0.725 mmoles) was added and stirred at RT for 10 min. To this mixture, intermediate 36 (0.252 g, 0.725 mmoles) was added and stirred for 12 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as light yellow solid (0.132 g, 67% yield). $^1$H-NMR (δ ppm, DMSO-$D_6$, 400 MHz): δ 8.08 (s, 1H), 8.04 (d, J=6.8 Hz, 1H), 7.85 (m, 1H), 7.67 (d, J=8.4 Hz, 1H), 7.52 (t, J=7.5 Hz, 1H), 7.28 (br s, 1H), 7.17 (s, 1H), 7.12 (s, 1H), 7.05-6.94 (m, 4H), 6.03 (q, J=7.0 Hz, 1H), 3.82 (s, 3H), 1.90 (d, J=7.0 Hz, 3H).

Example 86a

2-(1-(4-amino-3-(3-chloro-5-hydroxyphenyl)-1H-pyrazolo[3,4-d]pyrimidin-1-yl)ethyl)-3-(3-fluorophenyl)-4H-chromen-4-one To a solution of Example 86 (0.100 g, 0.184 mmoles) in dichloromethane (4 ml), $BBr_3$ (1M in dichloromethane, 1 ml) was added at 0° C. and the reaction mixture was warmed to RT and then stirred for 12 h. The reaction mixture was quenched with 1.5N HCl solution and extracted with dichloromethane. The organic layer was dried over sodium sulphate and concentrated. The crude product was purified by column chromatography with methanol:dichloromethane to afford the title compound as pale green solid (0.032 g, 33% yield). MP: 122-124° C. $^1$H-NMR (δ ppm, DMSO-$D_6$, 400 MHz): δ 10.19 (s, 1H), 8.06 (s, 1H), 8.04 (dd, J=7.9, 1.5 Hz, 1H), 7.86 (m, 1H), 7.67 (d, J=8.3 Hz, 1H), 7.53 (t, J=7.1 Hz, 1H), 7.28 (br s, 1H), 7.06-6.87 (m, 6H), 6.03 (q, J=6.9 Hz, 1H), 1.88 (d, J=7.1 Hz, 1H). Mass: 528.11 ($M^+$+1).

Example 87

2-(1-(4-amino-3-(3-(trifluoromethoxy)phenyl)-1H-pyrazolo[3,4-d]pyrimidin-1-yl)ethyl)-3-(3-fluorophenyl)-4H-chromen-4-one To a solution of intermediate 83 (0.200 g, 0.677 mmoles) in DMF (8 ml), potassium carbonate (0.187 g, 1.354 mmoles) was added and stirred at RT for 10 min. To this mixture, intermediate 36 (0.472 g, 1.354 mmoles) was added and stirred for 12 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as Off-white solid (0.058 g, 15% yield). MP: 155-157° C. $^1$H-NMR (δ ppm, DMSO-$D_6$, 400 MHz): δ 8.09 (s, 1H), 8.04 (dd, J=6.7, 1.3 Hz, 1H), 7.86 (m, 1H), 7.68-7.45 (m, 8H), 7.28 (br s, 1H), 7.03-6.91 (m, 3H), 6.06 (q, J=7.2 Hz, 1H), 1.90 (d, J=7.1 Hz, 3H). Mass: 562.13 ($M^+$+1).

Example 88

2-(1-(4-amino-3-(4-methoxyphenyl)-1H-pyrazolo[3,4-d]pyrimidin-1-yl)ethyl)-3-(3-fluorophenyl)-4H-chromen-4-one To a solution of intermediate 84 (0.200 g, 0.829 mmoles) in DMF (4 ml), potassium carbonate (0.229 g, 1.658 mmoles) was added and stirred at RT for 10 min. To this mixture, intermediate 36 (0.576 g, 1.658 mmoles) was added and stirred for 12 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as light yellow solid (0.180 g, 43% yield). $^1$H-NMR (δ ppm, DMSO-$D_6$, 400 MHz): δ 8.05 (m, 2H), 7.85 (m, 1H), 7.68 (dd, J=8.4, 5.7 Hz, 1H), 7.54 (m, 3H), 7.28 (br s, 1H), 7.09-6.90 (m, 5H), 6.01 (q, J=7.0 Hz, 1H), 3.82 (s, 3H), 1.89 (d, J=7.1 Hz, 3H).

Example 88a

2-(1-(4-amino-3-(4-hydroxyphenyl)-1H-pyrazolo[3,4-d]pyrimidin-1-yl)ethyl)-3-(3-fluorophenyl)-4H-chromen-4-one To a solution of Example 88 (0.150 g, 0.295 mmoles) in dichloromethane (4 ml), $BBr_3$ (1M in dichloromethane, 1.5 ml) was added at 0° C. and the reaction mixture was warmed to RT and then stirred for 12 h. The reaction mixture was quenched with 1.5N HCl solution and extracted with dichloromethane. The organic layer was dried over sodium sulphate and concentrated. The crude product was purified by column chromatography with methanol:dichloromethane to afford the title compound as off-white solid (0.048 g, 33% yield). MP: 244-247° C. $^1$H-NMR (δ ppm, DMSO-$D_6$, 400 MHz): δ 9.79 (s, 1H), 8.04 (s, 1H), 8.04 (dd, J=8.5, 1.4 Hz, 1H), 7.85 (m, 1H), 7.68 (d, J=8.5 Hz, 1H), 7.53 (t, J=7.6 Hz, 1H), 7.42 (d, J=8.5 Hz, 2H), 7.28 (br s, 1H), 7.06 (t, J=8.5 Hz, 1H), 6.91 (d, J=8.5 Hz, 2H), 6.91 (br s, 2H), 6.00 (q, J=7.1 Hz, 1H), 1.88 (d, J=7.0 Hz, 3H). Mass: 492.69 ($M^+$−1).

Example 89

2-((6-amino-9H-purin-9-yl)methyl)-3-(3-fluorophenyl)-4H-chromen-4-one

To a solution of Adenine (0.243 g, 1.80 mmoles) in DMF (5 ml), potassium carbonate (0.248 g, 1.80 mmoles) was added and stirred at RT for 10 min. To this mixture intermediate 77 (0.300 g, 0.900 mmoles) was added and stirred for 12 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as yellow solid (0.080 g, 23% yield). MP: 224-227° C. $^1$H-NMR (δ ppm, DMSO-$D_6$, 400 MHz): δ 8.12 (s, 1H), 8.07 (s, 1H), 8.05 (dd, J=7.7, 1.2 Hz, 1H), 7.79 (m, 1H), 7.55 (m, 3H), 7.28-7.21 (m, 5H), 5.36 (s, 2H). Mass: 388.04 ($M^+$+1).

Example 90

2-(1-(4-amino-3-(4-fluoro-2-methoxyphenyl)-1H-pyrazolo[3,4-d]pyrimidin-1-yl)ethyl)-3-(3-fluorophenyl)-4H-chromen-4-one To a solution of intermediate 85 (0.120 g, 0.462 mmoles) in DMF (6 ml), potassium carbonate (0.127 g, 0.924 mmoles) was added and stirred at RT for 10 min. To this mixture, intermediate 36 (0.321 g, 0.924 mmoles) was added and stirred for 12 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as light yellow solid (0.080 g, 33% yield). $^1$H-NMR (δ ppm, DMSO-$D_6$, 400 MHz): δ 8.04 (d, J=6.6 Hz, 1H), 8.00 (s, 1H), 7.85 (t, J=8.7 Hz, 1H), 7.66-7.49 (m, 4H), 7.38 (t, J=7.3 Hz, 1H), 7.29 (br s, 1H), 7.08-6.85 (m, 5H), 5.99 (q, J=7.0 Hz, 1H), 3.77 (s, 3H), 1.87 (d, J=7.1 Hz, 3H).

Example 90a 2-(1-(4-amino-3-(4-fluoro-2-hydroxyphenyl)-1H-pyrazolo[3,4-d]pyrimidin-1-yl)ethyl)-3-(3-fluorophenyl)-4H-chromen-4-one To a solution of Example 90 (0.080 g, 0.152 mmoles) in dichloromethane (4 ml), $BBr_3$ (1M in dichloromethane, 0.8 ml) was added at 0° C. and the reaction mixture was warmed to RT and then stirred for 12 h. The reaction mixture was quenched with 1.5N HCl solution and extracted with dichloromethane. The organic layer was dried over sodium sulphate and concentrated. The crude product was purified by column chromatography with methanol:dichloromethane to afford the title compound as off-white solid (0.027 g, 35% yield). MP: 235-237° C. $^1$H-NMR (δ ppm, DMSO-$D_6$, 400 MHz): δ 10.66 (s, 1H), 8.04 (d, J=9.8 Hz, 1H), 8.02 (s, 1H), 7.84 (t, J=7.0 Hz, 1H), 7.66 (d, J=8.3 Hz, 1H), 7.52 (t, J=7.9 Hz, 1H), 7.35 (t, J=7.2 Hz, 2H), 7.10 (t, J=8.4 Hz, 1H), 6.96 (br s, 2H), 6.79 (m, 2H), 5.98 (q, J=7.0 Hz, 1H), 1.88 (d, J=7.1 Hz, 3H). Mass: 512.22 ($M^+$+1).

Example 91

2-((4-amino-3-(3-aminophenyl)-1H-pyrazolo[3,4-d]pyrimidin-1-yl)methyl)-3-phenyl-4H-chromen-4-one To a solution of Example 57a (0.400 g, 0.804 mmoles) in DMF (10 ml), ethanol (5 ml) and water (5 ml), 3-Acetamidophenyl boronic acid (0.187 g, 1.045 mmoles) and sodium carbonate (0.426 g, 4.02 mmoles) were added and the system is degassed for 30 min. Palladium tetrakis triphenylphosphine (0.183 g, 0.158 mmoles) was added under nitrogen atmosphere and heated to 80° C. After 12 h, the reaction mixture was celite filtered, concentrated and extracted with ethyl acetate. The organic layer was dried over sodium sulphate and concentrated under reduced pressure. To the concentrate ethanol (5 ml) and Con.HCl (0.5 ml) were added and refluxed for 2 h. The reaction mixture was basified with sodium carbonate solution and extracted with ethyl acetate. The organic layer was dried over sodium sulphate and concentrated under reduced pressure. The crude product was purified by column chromatography with methanol:dichloromethane to afford the title compound as yellow solid (0.140 g, 38% yield). MP: 157-159° C. $^1$H-NMR (δ ppm, DMSO-$d_6$, 400 MHz): δ 8.21 (s, 1H), 8.06 (dd, J=7.8, 1.3 Hz, 1H), 7.77 (dt, J=8.6, 1.5 Hz, 1H), 7.49 (t, J=7.4 Hz, 1H), 7.37-7.29 (m, 5H), 7.17 (t, J=7.7 Hz, 1H), 6.84 (s, 1H), 6.71 (d, J=7.5 Hz, 1H), 6.65 (d, J=7.9 Hz, 1H), 5.51 (s, 2H), 5.34 (s, 2H). Mass: 460.84 ($M^+$).

Example 92

2-((4-amino-3-(3-methyl-1H-indazol-6-yl)-1H-pyrazolo[3,4-d]pyrimidin-1-yl)methyl)-3-phenyl-4H-chromen-4-one To a solution of Example 57a (0.462 g, 0.930 mmoles) in DMF (6 ml), ethanol (3 ml) and water (3 ml), N-Boc-3-methylindazole-6-boronic acid pinacol ester 98 (0.500 g, 1.39 mmoles) and sodium carbonate (0.295 g, 2.79 mmoles) were added and the system is degassed for 30 min. Tetrakistriphenylphosphine Palladium (0.057 g, 0.046 mmoles) was added under nitrogen atmosphere and heated to 80° C. After 12 h, the reaction mixture was celite filtered, concentrated and extracted with ethyl acetate. The organic layer was dried over sodium sulphate and concentrated under reduced pressure. The crude product was purified by column chromatography with methanol:dichloromethane to afford the title compound as off-white solid (0.120 g, 26% yield). MP: 2924-295° C. $^1$H-NMR (δ ppm, DMSO-$d_6$, 400 MHz): δ 12.74 (s, 1H), 8.24 (s, 2H), 8.06 (dd, J=7.9, 1.5 Hz, 1H), 7.84 (d, J=8.3 Hz, 1H), 7.75 (m, 1H), 7.63 (s, 1H), 7.49 (t, J=7.3 Hz, 1H), 7.45 (d, J=8.3 Hz, 1H), 7.38-7.32 (m, 6H), 5.53 (s, 2H), 2.51 (s, 3H). Mass: 499.90 ($M^+$).

Example 93

2-(1-(4-amino-3-(2-aminopyrimidin-5-yl)-1H-pyrazolo[3,4-d]pyrimidin-1-yl)ethyl)-3-(3-fluorophenyl)-4H-chromen-4-one To a solution of Example 57c (0.350 g, 0.663 mmoles) in DMF (4 ml), ethanol (2 ml) and water (2 ml), 2-aminopyrimidine-5-boronic acid (0.184 g, 1.327 mmoles) and sodium carbonate (0.351 g, 3.318 mmoles) were added and the system is degassed for 30 min. Tetrakistriphenylphosphine Palladium (0.151 g, 0.130 mmoles) was added under nitrogen atmosphere and heated to 80° C. After 12 h, the reaction mixture was celite filtered, concentrated and extracted with ethyl acetate. The organic layer was dried over sodium sulphate and concentrated under reduced pressure. The crude product was purified by column chromatography with methanol:dichloromethane to afford the title compound as brown solid (0.045 g, 14% yield). MP: 264-268° C. $^1$H-NMR (δ ppm, DMSO-$d_6$, 400 MHz): δ 8.38 (s, 2H), 8.05 (s, 1H), 8.03 (d, J=7.9, Hz, 1H), 7.85 (m, 1H), 7.68 (d, J=8.3 Hz, 1H), 7.52 (t, J=7.3 Hz, 1H), 7.29 (br s, 1H), 7.07-6.93 (m, 5H), 5.99 (q, J=7.0 Hz, 1H), 1.88 (d, J=7.0 Hz, 3H). Mass: 494.86 ($M^+$).

Example 94

2-(1-(4-amino-3-(1H-indol-6-yl)-1H-pyrazolo[3,4-d]pyrimidin-1-yl)ethyl)-3-(3-fluorophenyl)-4H-chromen-4-one To a solution of Example 57c (0.350 g, 0.663 mmoles) in DMF (4 ml), ethanol (2 ml) and water (2 ml), 6-indoleboronic acid pinacol ester (0.213 g, 1.327 mmoles) and sodium carbonate (0.351 g, 3.318 mmoles) were added and the system is degassed for 30 min. Tetrakistriphenylphosphine Palladium (0.151 g, 0.130 mmoles) was added under nitrogen atmosphere and heated to 80° C. After 12 h, the reaction mixture was celite filtered, concentrated and extracted with ethyl acetate. The organic layer was dried over sodium sulphate and concentrated under reduced pressure. The crude product was purified by column chromatography with methanol:dichloromethane to afford the title compound as brown solid (0.050 g, 15% yield). MP: 222-225° C. $^1$H-NMR (δ ppm, DMSO-$d_6$, 400 MHz): δ 11.27 (s, 1H), 8.06 (s, 1H), 8.05 (dd, J=8.0, 1.6 Hz, 1H), 7.86 (m, 1H), 7.69 (d, J=7.2 Hz, 2H), 7.62 (s, 1H), 7.53 (t, J=8.1 Hz, 1H), 7.45 (t, J=2.8 Hz, 1H), 7.28 (m, 2H), 7.06-6.89 (m, 3H), 6.50 (s, 1H), 6.04 (q, J=7.1 Hz, 1H), 1.91 (d, J=7.1 Hz, 3H). Mass: 516.84 ($M^+$).

Example 95

2-(1-(4-amino-3-(4-chloro-3-methoxyphenyl)-1H-pyrazolo[3,4-d]pyrimidin-1-yl)ethyl)-3-(3-fluorophenyl)-4H-chromen-4-one To a solution of intermediate 86 (0.90 g, 0.3262 mmoles) in DMF (3 ml), potassium carbonate (0.090 g, 0.653 mmoles) was added and stirred at RT for 10 min. To this mixture, intermediate 36 (0.227 g, 0.653 mmoles) was added and stirred for 12 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as green solid (0.055 g, 31% yield). $^1$H-NMR (δ ppm, DMSO-$D_6$, 400 MHz): δ 8.08 (s, 1H), 8.04 (dd, J=8.0, 1.6 Hz, 1H), 7.85 (m, 1H), 7.68 (d, J=8.4 Hz, 1H), 7.55 (m, 2H), 7.29 (br s, 1H), 7.25 (d, J=1.7 Hz, 1H), 7.19 (dd, J=8.1, 1.8 Hz, 1H), 7.08 (dt, J=8.8, 2.4 Hz, 1H), 6.92 (br s, 2H), 6.02 (q, J=7.0 Hz, 1H), 3.90 (s, 3H), 1.90 (d, J=7.1 Hz, 3H).

Example 95a

2-(1-(4-amino-3-(4-chloro-3-hydroxyphenyl)-1H-pyrazolo[3,4-d]pyrimidin-1-yl)ethyl)-3-(3-fluorophenyl)-4H-chromen-4-one To a solution of Example 95 (0.055 g, 0.1012 mmoles) in dichloromethane (4 ml), $BBr_3$ (1M in dichloromethane, 0.5 ml) was added at 0° C. and the reaction mixture was warmed to RT and then stirred for 12 h. The reaction mixture was quenched with 1.5N HCl solution and extracted with dichloromethane. The organic layer was dried over sodium sulphate and concentrated. The crude product was purified by column chromatography with methanol:dichloromethane to afford the title compound as pale green solid (0.025 g, 86% yield). MP: 134-136° C. $^1$H-NMR (δ ppm, DMSO-$D_6$, 400 MHz): δ 10.50 (s, 1H), 8.18 (s, 1H), 8.05 (d, J=8.0 Hz, 1H), 7.87 (t, J=7.0 Hz, 1H), 7.64 (d, J=8.4 Hz, 1H), 7.54 (t, J=7.6 Hz, 1H), 7.50 (d, J=8.0 Hz, 2H), 7.29 (br s, 1H), 7.21 (d, J=1.6 Hz, 1H), 7.07-6.93 (m, 4H), 6.07 (q, J=6.9 Hz, 1H), 1.90 (d, J=7.0 Hz, 3H). Mass: 527.76 ($M^+$).

Example 96

2-(1-(4-amino-3-(2-chloro-5-methoxyphenyl)-1H-pyrazolo[3,4-d]pyrimidin-1-yl)ethyl)-3-(3-fluorophenyl)-4H-chromen-4-one To a solution of intermediate 87 (0.060 g, 0.217 mmoles) in DMF (2 ml), potassium carbonate (0.060 g, 0.435 mmoles) was added and stirred at RT for 10 min. To this mixture, intermediate 36 (0.151 g, 0.435 mmoles) was added and stirred for 12 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as green solid (0.030 g, 30% yield). $^1$H-NMR (δ ppm, DMSO-$D_6$, 400 MHz): δ 8.05 (s, 1H), 8.04 (dd, J=7.9, 1, 3 Hz, 1H), 7.85 (m, 1H), 7.63 (d, J=8.1 Hz, 2H), 7.55 (m, 2H), 7.32 (br s, 1H), 7.18 (m, 2H), 7.00 (d, J=3.0 Hz, 1H), 6.99 (br s, 1H), 6.02 (q, J=7.0 Hz, 1H), 3.90 (s, 3H), 1.90 (d, J=7.1 Hz, 3H).

Example 96a

2-(1-(4-amino-3-(2-chloro-5-hydroxyphenyl)-1H-pyrazolo[3,4-d]pyrimidin-1-yl)ethyl)-3-(3-fluorophenyl)-4H-chromen-4-one To a solution of Example 96 (0.030 g, 0.055 mmoles) in dichloromethane (3 ml), $BBr_3$ (1M in dichloromethane, 0.27 ml) was added at 0° C. and the reaction mixture was warmed to RT and then stirred for 12 h. The reaction mixture was quenched with 1.5N HCl solution and extracted with dichloromethane. The organic layer was dried over sodium sulphate and concentrated to afford the title compound as pale green solid (0.018 g, 62% yield). MP: 192-195° C. $^1$H-NMR (δ ppm, DMSO-$D_6$, 400 MHz): δ 9.95 (s, 1H), 8.15 (s, 1H), 8.05 (dd, J=7.9, 1.2 Hz, 1H), 7.86 (m, 1H), 7.65-7.49 (m, 4H), 7.39 (d, J=8.7 Hz, 1H), 7.35 (br s, 1H), 7.11 (t, J=7.5 Hz, 1H), 6.97 (dd, J=7.6, 3.2 Hz, 1H), 6.86 (d, J=2.8 Hz, 1H), 6.07 (q, J=6.9 Hz, 1H), 1.88 (d, J=7.0 Hz, 3H). Mass: 527.90 ($M^+$).

Example 97

2-(1-(4-amino-3-(3,4-dimethoxyphenyl)-1H-pyrazolo[3,4-d]pyrimidin-1-yl)ethyl)-3-(3-fluorophenyl)-4H-chromen-4-one To a solution of intermediate 88 (0.220 g, 0.808 mmoles) in DMF (8 ml), potassium carbonate (0.223 g, 1.61 mmoles) was added and stirred at RT for 10 min. To this mixture, intermediate 36 (0.562 g, 1.61 mmoles) was added and stirred for 12 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as yellow solid (0.163 g, 60% yield). MP: 232-235° C. $^1$H-NMR (δ ppm, DMSO-$D_6$, 400 MHz): δ 8.05 (s, 1H), 8.04 (dd, J=8.0, 1.5 Hz, 1H), 7.85 (m, 1H), 7.68 (dd, J=8.4 Hz, 1H), 7.52 (t, J=7.2 Hz, 1H), 7.29 (br s, 1H), 7.13-6.93 (m, 6H), 6.01 (q, J=7.1 Hz, 1H), 3.80 (s, 6H), 1.90 (d, J=7.1 Hz, 3H). Mass: 538.05 ($M^+$+1).

Example 98

2-(1-(4-amino-3-(3,4-dihydroxyphenyl)-1H-pyrazolo[3,4-d]pyrimidin-1-yl)ethyl)-3-(3-fluorophenyl)-4H-chromen-4-one To a solution of example 97 (0.180 g, 0.0.335 mmoles) in dichloromethane (10 ml), $BBr_3$ (1M in dichloromethane, 1.8 ml) was added at 0° C. and the reaction mixture was warmed to RT and then stirred for 12 h. The reaction mixture was quenched with 1.5N HCl solution and extracted with dichloromethane. The organic layer was dried over sodium sulphate and concentrated to afford the title compound as off-white pale solid (0.040 g, 24% yield). MP: 193-195° C. $^1$H-NMR (δ ppm, DMSO-$D_6$, 400 MHz): δ 9.27 (s, 1H), 9.22 (s, 1H), 8.05 (dd, J=7.3, 1.4 Hz, 1H), 8.03 (s, 1H), 7.86 (m, 1H), 7.68 (d, J=8.4 Hz, 1H), 7.53 (t, J=7.7 Hz, 1H), 7.35 (s, 1H), 7.27 (br s, 1H), 7.05-6.86 (m, 5H), 6.02 (q, J=7.0 Hz, 1H), 1.87 (d, J=7.0 Hz, 3H). Mass: 509.84 ($M^+$).

Example 99

2-((4-amino-3-(3-methyl-1H-indazol-6-yl)-1H-pyrazolo[3,4-d]pyrimidin-1-yl)methyl)-3-(3-fluorophenyl)-4H-chromen-4-one To a solution of Example 57c (0.477 g, 0.930 mmoles) in DMF (5.3 ml), ethanol (2.6 ml) and water (2.6 ml), N-Boc-3-methyl-6-indazoleboronic acid pinacol ester 98 (0.500 g, 1.395 mmoles) and sodium carbonate (0.295 g, 3.318 mmoles) were added and the system is degassed for 30 min. Tetrakistriphenylphosphine Palladium (0.053 g, 0.046 mmoles) was added under nitrogen atmosphere and heated to 80° C. After 12 h, the reaction mixture was celite filtered, concentrated and extracted with ethyl acetate. The organic layer was dried over sodium sulphate and concentrated under reduced pressure. The crude product was purified by column chromatography with methanol:dichloromethane to afford the title compound as off-white solid (0.100 g, 20% yield). MP: 246-248° C. $^1$H-NMR (δ ppm, DMSO-$d_6$, 400 MHz): δ 12.75 (s, 1H), 8.22 (s, 1H), 8.06 (dd, J=8.5, 1.8 Hz, 1H), 7.84 (d, J=8.3 Hz, 1H), 7.80 (m, 1H), 7.62 (s, 1H), 7.51 (d, J=8.2 Hz, 2H), 7.39-7.31 (m, 2H), 7.18 (m, 2H), 7.12 (dt, J=8.3, 2.6 Hz, 1H), 5.56 (s, 2H), 2.51 (s, 3H). Mass: 517.51 ($M^+$).

Example 100

2-(1-(4-amino-3-(1H-indol-5-yl)-1H-pyrazolo[3,4-d]pyrimidin-1-yl)ethyl)-3-(3-fluorophenyl)-4H-chromen-4-one To a solution of Example 57c (0.350 g, 0.663 mmoles) in DMF (4 ml), ethanol (2 ml) and water (2 ml), 5-indoleboronic acid pinacol ester (0.213 g, 1.327 mmoles) and sodium carbonate (0.351 g, 3.318 mmoles) were added and the system is degassed for 30 min. Tetrakistriphenylphosphine Palladium (0.151 g, 0.130 mmoles) was added under nitrogen atmosphere and heated to 80° C. After 12 h, the reaction mixture was celite filtered, concentrated and extracted with ethyl acetate. The organic layer was dried over sodium sulphate and concentrated under reduced pressure. The crude product was purified by column chromatography with methanol:dichloromethane to afford the title compound as brown solid (0.044 g, 13% yield). MP: 197-199° C. $^1$H-NMR (δ ppm, DMSO-$d_6$, 400 MHz): δ 11.30 (s, 1H), 8.06 (s, 1H), 8.05 (dd, J=7.9, 1.2 Hz, 1H), 7.85 (m, 1H), 7.77 (s, 1H), 7.69 (d, J=8.4 Hz, 1H), 7.55 (m, 2H), 7.44 (t, J=2.8 Hz, 1H), 7.35 (m, 2H), 7.09-6.94 (m, 3H), 6.54 (m, 1H), 6.05 (q, J=7.0 Hz, 1H), 1.91 (d, J=7.0 Hz, 3H). Mass: 516.91 ($M^+$).

Example 101

2-(1-(4-Amino-3-(3-methyl-1H-indol-5-yl)-1H-pyrazolo[3,4-d]pyrimidin-1-yl)ethyl)-3-(3-fluorophenyl)-4H-chromen-4-one To a solution of Example 57c (0.400 g, 0.757 mmoles) in DMF (5 ml), ethanol (2.5 ml) and water (2.5 ml), 3-methyl-5-indoleboronic acid pinacol ester (0.292 g, 1.136 mmoles) and sodium carbonate (0.240 g, 2.272 mmoles) were added and the system is degassed for 30 min. Tetrakistriphenylphosphine Palladium (0.043 g, 0.037 mmoles) was added under nitrogen atmosphere and heated to 80° C. After 12 h, the reaction mixture was celite filtered, concentrated and extracted with ethyl acetate. The organic layer was dried over sodium sulphate and concentrated under reduced pressure. The crude product was purified by column chromatography with methanol:dichloromethane to afford the title compound as brown solid (0.040 g, 13% yield). MP: 171-173° C. $^1$H-NMR (δ ppm, DMSO-$d_6$, 400 MHz): δ 10.96 (s, 1H), 8.06 (s, 1H), 8.04 (dd, J=7.9, 1.4 Hz, 1H), 7.85 (m, 1H), 7.68 (d, J=8.1 Hz, 2H), 7.52 (d, J=7.2 Hz, 1H), 7.49 (d, J=8.3 Hz, 1H), 7.32 (dd, J=8.2, 1.4 Hz, 2H), 7.20 (s, 1H), 7.08 (dt, J=11.2, 2.7 Hz, 1H), 6.93 (br s, 2H), 6.04 (q, J=7.0 Hz, 1H), 2.28 (s, 3H), 1.92 (d, J=7.0 Hz, 3H). Mass: 530.98 ($M^+$).

Example 102 tert-butyl(5-(4-amino-1-(1-(3-(3-fluorophenyl)-4-oxo-4H-chromen-2-yl)ethyl)-1H-pyrazolo[3,4-d]pyrimidin-3-yl)thiophen-2-yl)methylcarbamate To a solution of Example 57c (0.300 g, 0.566 mmoles) in dioxane (4 ml), 2-N-Boc-aminomethylthiophene-5-boronic acid (0.186 g, 0.725 mmoles) and potassium acetate (0.168 g, 1.887 mmoles) were added and the system is degassed for 30 min. Tetrakistriphenylphosphine Palladium (0.052 g, 0.045 mmoles) was added under nitrogen atmosphere and heated to 80° C. After 12 h, the reaction mixture filtered through celite and extracted with ethyl acetate. The organic layer was dried over sodium sulphate and concentrated under reduced pressure. The crude product was purified by column chromatography with methanol:dichloromethane to afford the title compound as brown solid (0.070 g, 20% yield). $^1$H-NMR (δ ppm, DMSO-$d_6$, 400 MHz): δ 8.06 (s, 1H), 8.05 (dd, J=8.0, 1.6 Hz, 1H), 7.85 (m, 1H), 7.65 (d, J=8.5 Hz, 1H), 7.55 (m, 3H), 7.32-7.22 (m, 3H), 7.12 (m, 2H), 6.98 (d, J=3.5 Hz, 1H), 6.92 (br s, 1H), 5.99 (q, J=7.1 Hz, 1H), 4.29 (d, J=6.1 Hz, 2H), 1.87 (d, J=7.0 Hz, 3H).

Example 102a

2-(1-(4-amino-3-(5-(aminomethyl)thiophen-2-yl)-1H-pyrazolo[3,4-d]pyrimidin-1-yl)ethyl)-3-(3-fluorophenyl)-4H-chromen-4-one To a solution of Example 102 (0.070 g, 0.114 mmoles) in dichloromethane (3 ml), TFA (0.1 ml) was added under nitrogen atmosphere stirred at room temperature. After 3 h, the reaction mixture was concentrated, neutralised with sodium bicarbonate solution and extracted with ethyl acetate. The organic layer was dried over sodium sulphate and concentrated under reduced pressure. The crude product was purified by column chromatography with methanol:dichloromethane to afford the title compound as yellow solid (0.030 g, 51% yield). MP: 275-278° C. $^1$H-NMR (δ ppm, DMSO-$d_6$, 400 MHz): δ 8.06 (s, 1H), 8.05 (dd, J=7.9, 1.5 Hz, 1H), 7.85 (m, 1H), 7.66 (d, J=8.3 Hz, 1H), 7.53 (t, J=7.2 Hz, 1H), 7.28 (m, 2H), 7.09 (d, J=3.5 Hz, 1H), 7.05 (dt, J=8.7, 2.4 Hz, 1H), 6.92 (br s, 2H), 6.02 (q, J=7.1 Hz, 1H), 4.03 (s, 2H), 1.87 (d, J=7.1 Hz, 3H). Mass: 513.27 ($M^+$+1).

Example 103

2-((4-amino-3-(3-methyl-1H-indazol-6-yl)-1H-pyrazolo[3,4-d]pyrimidin-1-yl)methyl)-6-fluoro-3-phenyl-4H-chromen-4-one To a solution of Example 57d (0.300 g, 0.584 mmoles) in DMF (3 ml), ethanol (1.5 ml) and water (1.5 ml), N-Boc-3- methyl-6-indazoleboronic acid pinacol ester 98 (0.314 g, 0.877 mmoles) and sodium carbonate (0.185 g, 1.754 mmoles) were added and the system is degassed for 30 min. Tetrakistriphenylphosphine Palladium (0.033 g, 0.029 mmoles) was added under nitrogen atmosphere and heated to 80° C. After 12 h, the reaction mixture was celite filtered, concentrated and extracted with ethyl acetate. The organic layer was dried over sodium sulphate and concentrated under reduced pressure. The crude product was purified by column chromatography with methanol:dichloromethane to afford the title compound as brown solid (0.012 g, 4% yield). MP: 277-279° C. $^1$H-NMR (δ ppm, DMSO-$d_6$, 400 MHz): δ 12.75 (s, 1H), 8.23 (s, 1H), 7.84 (d, J=8.2 Hz, 1H), 7.74 (dd, J=8.2, 3.0 Hz, 1H), 7.66 (m, 2H), 7.59 (dd, J=9.2, 4.2 Hz, 1H), 7.38-7.32 (m, 6H), 6.54 (s, 2H), 2.51 (s, 3H). Mass: 518.17 ($M^+$+1).

Example 104

2-(1-(4-amino-3-(3-methyl-1H-indazol-6-yl)-1H-pyrazolo[3,4-d]pyrimidin-1-yl)ethyl)-3-phenyl-4H-chromen-4-one To a solution of Example 57b (0.350 g, 0.684 mmoles) in DMF (3.5 ml), ethanol (1.7 ml) and water (1.7 ml), 3-methyl-6-indazoleboronic acid pinacol ester 97 (0.353 g, 1.369 mmoles) and sodium carbonate (0.217 g, 2.05 mmoles) were added and the system is degassed for 30 min. Tetrakistriphenylphosphine Palladium (0.040 g, 0.034 mmoles) was added under nitrogen atmosphere and heated to 80° C. After 12 h, the reaction mixture was celite filtered, concentrated and extracted with ethyl acetate. The organic layer was dried over sodium sulphate and concentrated under reduced pressure. The crude product was purified by column chromatography with methanol:dichloromethane to afford the title compound as brown solid (0.073 g, 21% yield). MP: 249-252° C. $^1$H-NMR (δ ppm, DMSO-$d_6$, 400 MHz): δ 12.75 (s, 1H), 8.09 (s, 1H), 8.05 (dd, J=8.0, 1.6 Hz, 1H), 7.85 (d, J=8.2 Hz, 1H), 7.81 (m, 1H), 7.64 (s, 1H), 7.62 (d, J=8.4 Hz, 1H), 7.51 (t, J=7.3 Hz, 1H), 7.36 (dd, J=9.3, 1.0 Hz, 1H), 7.29 (m, 3H), 7.15 (br s, 2H), 6.01 (q, J=7.0 Hz, 1H), 2.52 (s, 3H), 1.92 (d, J=7.0 Hz, 3H). Mass: 514.18 ($M^+$+1).

Example 105

2-(1-(4-amino-3-(3-methyl-1H-indazol-6-yl)-1H-pyrazolo[3,4-d]pyrimidin-1-yl)ethyl)-6-fluoro-3-phenyl-4H-chromen-4-one To a solution of Example 57e (0.400 g, 0.758 mmoles) in DMF (4 ml), ethanol (2 ml) and water (2 ml), 3-methyl-6-indazoleboronic acid pinacol ester 97 (0.391 g, 1.517 mmoles) and sodium carbonate (0.241 g, 2.27 mmoles) were added and the system is degassed for 30 min. Tetrakistriphenylphosphine Palladium (0.044 g, 0.037 mmoles) was added under nitrogen atmosphere and heated to 80° C. After 12 h, the reaction mixture was celite filtered, concentrated and extracted with ethyl acetate. The organic layer was dried over sodium sulphate and concentrated under reduced pressure. The crude product was purified by column chromatography with methanol:dichloromethane to afford the title compound as yellow solid (0.065 g, 15% yield). MP: 253-255° C. $^1$H-NMR (δ ppm, DMSO-$d_6$, 400 MHz): δ 12.75 (s, 1H), 8.08 (s, 1H), 7.85 (d, J=8.3 Hz, 1H), 7.75 (m, 3H), 7.63 (s, 1H), 7.35 (dd, J=8.4, 1.2 Hz, 1H), 7.28 (m, 3H), 7.14 (br s, 2H), 6.00 (q, J=7.1 Hz, 1H), 2.52 (s, 3H), 1.91 (d, J=7.1 Hz, 3H). Mass: 532.03 ($M^+$+1).

Example 106

2-(1-(4-amino-3-(3-methyl-1H-indazol-5-yl)-1H-pyrazolo[3,4-d]pyrimidin-1-yl)ethyl)-3-(3-fluorophenyl)-4H-chromen-4-one To a solution of Example 57c (0.350 g, 0.663 mmoles) in DMF (4 ml), ethanol (2 ml) and water (2 ml), N-Boc-3-methyl, 5-indazoleboronic acid pinacol ester (0.356 g, 0.994 mmoles) and sodium carbonate (0.210 g, 0.98 mmoles) were added and the system is degassed for 30 min. Tetrakistriphenylphosphine Palladium (0.038 g, 0.033 mmoles) was added under nitrogen atmosphere and heated to 80° C. After 12 h, the reaction mixture was celite filtered, concentrated and extracted with ethyl acetate. The organic layer was dried over sodium sulphate and concentrated under reduced pressure. The crude product was purified by column chromatography with methanol:dichloromethane to afford the title compound as pale brown solid (0.050 g, 14% yield). MP: 254-256° C. $^1$H-NMR (δ ppm, DMSO-$d_6$, 400 MHz): δ 12.79 (s, 1H), 8.07 (s, 1H), 8.04 (dd, J=8.0, 1.6 Hz, 1H), 7.87 (s, 1H), 7.85 (m, 1H), 7.69 (d, J=8.3 Hz, 1H), 7.60-7.49 (m, 3H), 7.29 (br s, 1H), 7.07 (dt, J=8.6, 2.3 Hz, 1H), 6.93 (br s, 2H), 6.05 (q, J=7.1 Hz, 1H), 2.51 (s, 3H), 1.91 (d, J=7.0 Hz, 3H). Mass: 532.03 ($M^+$+1).

Example 107

N-(4-(4-amino-1-(1-(3-(3-fluorophenyl)-4-oxo-4H-chromen-2-yl)ethyl)-1H-pyrazolo[3,4-d]pyrimidin-3-yl)phenyl)acetamide To a solution of Example 57c (0.350 g, 0.663 mmoles) in DMF (3.5 ml), ethanol (1.75 ml) and water (1.75 ml), 4-Acetamidophenyl boronic acid (0.237 g, 1.32 mmoles) and sodium carbonate (0.211 g, 1.99 mmoles) were added and the system is degassed for 30 min. Palladium tetrakis triphenylphosphine (0.038 g, 0.033 mmoles) was added under nitrogen atmosphere and heated to 80° C. After 12 h, the reaction mixture was celite filtered, concentrated and extracted with ethyl acetate. The organic layer was dried over sodium sulphate and concentrated under reduced pressure. The crude product was purified by column chromatography with methanol:dichloromethane to afford the title compound as yellow solid (0.080 g, 24% yield). $^1$H-NMR (δ ppm, DMSO-$d_6$, 400 MHz): δ 10.12 (s, 1H), 8.06 (s, 1H), 8.04 (dd, J=8.0, 1.4 Hz, 1H), 7.85 (m, 1H), 7.74 (d, J=8.5 Hz, 2H), 7.68 (d, J=8.2 Hz, 1H), 7.58 (m, 3H), 7.32 (m, 1H), 7.06 (dt, J=8.2, 2.4 Hz, 1H), 6.82 (m, 2H), 6.02 (q, J=7.0 Hz, 1H), 2.06 (s, 3H), 1.89 (d, J=7.1 Hz, 3H).

Example 107a 2-(1-(4-amino-3-(4-aminophenyl)-1H-pyrazolo[3,4-d]pyrimidin-1-yl)ethyl)-3-(3-fluorophenyl)-4H-chromen-4-one To a solution of Example 107 (0.080 g, 0.149 mmoles) in ethanol (5 ml), Con.HCl (0.5 ml) was added and refluxed for 2 h. The reaction mixture was basified with sodium carbonate solution and extracted with ethyl acetate. The organic layer was dried over sodium sulphate and concentrated under reduced pressure. The crude product was purified by column chromatography with methanol:dichloromethane to afford the title compound as brown solid (0.020 g, 27% yield). MP: 91-94° C. $^1$H-NMR (δ ppm, DMSO-$d_6$, 400 MHz): δ 8.04 (dd, J=8.3, 1.5 Hz, 1H), 8.02 (s, 1H), 7.85 (m, 1H), 7.67 (d, J=8.4 Hz, 1H), 7.53 (t, J=7.6 Hz, 2H), 7.29 (m, 3H), 7.06 (dt, J=8.7, 2.3 Hz, 1H), 6.91 (br s, 1H), 6.68 (d, J=8.4 Hz, 2H), 6.00 (q, J=7.0 Hz, 1H), 5.42 (s, 2H), 1.87 (d, J=7.0 Hz, 3H). Mass: 492.83 ($M^+$).

Example 108

2-(1-(4-amino-3-(3-methyl-1H-indazol-6-yl)-1H-pyrazolo[3,4-d]pyrimidin-1-yl)ethyl)-6-fluoro-3-(3-fluorophenyl)-4H-chromen-4-one To a solution of Example 57f (0.400 g, 0.733 mmoles) in DMF (5 ml), ethanol (2.5 ml) and water (2.5 ml), N-Boc-3-methyl-6-indazoleboronic acid pinacol ester 98 (0.393 g, 1.099 mmoles) and sodium carbonate (0.233 g, 2.19 mmoles) were added and the system is degassed for 30 min. Tetrakistriphenylphosphine Palladium (0.043 g, 0.037 mmoles) was added under nitrogen atmosphere and heated to 80° C. After 12 h, the reaction mixture was celite filtered, concentrated and extracted with ethyl acetate. The organic layer was dried over sodium sulphate and concentrated under reduced pressure. The crude product was purified by column chromatography with methanol:dichloromethane to afford the title compound as brown solid (0.045 g, 11% yield). MP: 234-236° C. $^1$H-NMR (δ ppm, DMSO-$d_6$, 400 MHz): δ 12.75 (s, 1H), 8.06 (s, 1H), 7.86-7.70 (m, 4H), 7.61 (s, 1H), 7.33 (m, 2H), 7.06 (dt, J=8.9, 2.5 Hz, 1H), 6.87 (m, 2H), 6.07 (q, J=7.0 Hz, 1H), 2.48 (s, 3H), 1.91 (d, J=7.1 Hz, 3H). Mass: 549.95 ($M^+$).

Example 109

2-(1-(4-amino-3-(2,3-dihydrobenzofuran-5-yl)-1H-pyrazolo[3,4-d]pyrimidin-1-yl)ethyl)-3-(3-fluorophenyl)-4H-chromen-4-one To a solution of intermediate 107 (0.100 g, 0.394 mmoles) in DMF (4 ml), potassium carbonate (0.109 g, 0.789 mmoles) was added and stirred at RT for 10 min. To this mixture intermediate 36 (0.217 g, 0.789 mmoles) was added and stirred for 12 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as off-white solid (0.085 g, 41% yield). MP: 238-241° C. $^1$H-NMR (δ ppm, DMSO-$D_6$, 400 MHz): δ 8.04 (s, 1H), 8.02 (d, J=6.0 Hz, 1H), 7.83 (m, 1H), 7.68 (d, J=8.3 Hz, 1H), 7.53 (t, J=7.7 Hz, 1H), 7.44 (s, 1H), 7.31 (m, 3H), 7.05 (t, J=8.9 Hz, 1H), 6.90 (m, 2H), 6.01 (q, J=7.0 Hz, 1H), 4.60 (t, J=8.7 Hz, 2H), 3.27 (t, J=8.6 Hz, 2H), 1.88 (d, J=7.0 Hz, 3H), Mass: 520.00 ($M^+$).

Example 110

2-(1-(4-amino-3-(3-ethyl-1H-indazol-6-yl)-1H-pyrazolo[3,4-d]pyrimidin-1-yl)ethyl)-3-(3-fluorophenyl)-4H-chromen-4-one To a solution of Example 57c (0.400 g, 0.758 mmoles) in DMF (4 ml), ethanol (2 ml) and water (2 ml), N-Boc-3-ethyl-6-indazoleboronic acid pinacol ester 103 (0.423 g, 1.137 mmoles) and sodium carbonate (0.241 g, 2.27 mmoles) were added and the system is degassed for 30 min. Tetrakistriphenylphosphine Palladium (0.043 g, 0.037 mmoles) was added under nitrogen atmosphere and heated to 80° C. After 12 h, the reaction mixture was celite filtered, concentrated and extracted with ethyl acetate. The organic layer was dried over sodium sulphate and concentrated under reduced pressure. The crude product was purified by column chromatography with methanol:dichloromethane to afford the title compound as off-white solid (0.060 g, 15% yield). MP: 270-273° C. $^1$H-NMR (δ ppm, DMSO-$d_6$, 400 MHz): δ 12.75 (s, 1H), 8.08 (s, 1H), 8.05 (dd, J=7.9, 1.4 Hz, 1H), 7.88 (m, 2H), 7.68 (d, J=8.4 Hz, 1H), 7.63 (s, 1H), 7.53 (d, J=7.2 Hz, 1H), 7.33 (d, J=8.3 Hz, 1H), 7.29 (br s, 1H), 7.07 (dt, J=8.9, 1.4 Hz, 1H), 6.95 (br s, 2H), 6.07 (q, J=6.9 Hz, 1H), 2.98 (q, J=7.5 Hz, 2H), 1.92 (d, J=7.1 Hz, 3H), 1.34 (t, J=7.6 Hz, 3H), Mass: 546.04 ($M^+$).

Example 111

2-(1-(4-amino-3-(3-methyl-1H-indol-6-yl)-1H-pyrazolo[3,4-d]pyrimidin-1-yl)ethyl)-3-(3-fluorophenyl)-4H-chromen-4-one To a solution of Example 57c (0.400 g, 0.758 mmoles) in DMF (4 ml), ethanol (2 ml) and water (2 ml), 3-methyl-6-indoleboronic acid pinacol ester 106 (0.390 g, 1.517 mmoles) and sodium carbonate (0.241 g, 2.27 mmoles) were added and the system is degassed for 30 min. Tetrakistriphenylphosphine Palladium (0.043 g, 0.037 mmoles) was added under nitrogen atmosphere and heated to 80° C. After 12 h, the reaction mixture was celite filtered, concentrated and extracted with ethyl acetate. The organic layer was dried over sodium sulphate and concentrated under reduced pressure. The crude product was purified by column chromatography with methanol:dichloromethane to afford the title compound as off-white solid (0.040 g, 10% yield). MP: 269-272° C. $^1$H-NMR (δ ppm, DMSO-$d_6$, 400 MHz): δ 10.91 (s, 1H), 8.06 (s, 1H), 8.05 (d, J=7.8 Hz, 1H), 7.85 (t, J=7.2 Hz, 1H), 7.68 (d, J=8.4 Hz, 1H), 7.63 (d, J=7.1 Hz, 1H), 7.56 (s, 1H), 7.53 (t, J=7.8 Hz, 1H), 7.25 (d, J=8.1 Hz, 1H), 7.28 (br s, 1H), 7.21 (s, 1H), 7.06 (dt, J=9.0, 2.8 Hz, 1H), 6.98 (br s, 2H), 6.04 (q, J=7.0 Hz, 1H), 2.28 (s, 3H), 1.91 (d, J=7.0 Hz, 3H). Mass: 530.99 ($M^+$).

Example 112

2-(1-(4-amino-3-(2-methoxypyrimidin-5-yl)-1H-pyrazolo[3,4-d]pyrimidin-1-yl)ethyl)-3-(3-fluorophenyl)-4H-chromen-4-one To a solution of Example 57c (0.400 g, 0.758 mmoles) in DMF (4 ml), ethanol (2 ml) and water (2 ml), 2-methoxypyrimidine-5-boronic acid (0.233 g, 1.517 mmoles) and sodium carbonate (0.241 g, 2.27 mmoles) were added and the system is degassed for 30 min. Tetrakistriphenylphosphine Palladium (0.043 g, 0.037 mmoles) was added under nitrogen atmosphere and heated to 80° C. After 12 h, the reaction mixture was celite filtered, concentrated and extracted with ethyl acetate. The organic layer was dried over sodium sulphate and concentrated under reduced pressure. The crude product was purified by column chromatography with methanol:dichloromethane to afford the title compound as off-white solid (0.200 g, 51% yield). MP: 224-227° C. $^1$H-NMR (δ ppm, DMSO-$d_6$, 400 MHz): δ 8.72 (s, 2H), 8.09 (s, 1H), 8.04 (dd, J=7.9, 1.4 Hz, 1H), 7.84 (m, 1H), 7.69 (d, J=8.3 Hz, 1H), 7.52 (t, J=7.8 Hz, 1H), 7.32 (m, 1H), 7.12-6.95 (m, 5H), 6.03 (q, J=7.1 Hz, 1H), 1.90 (d, J=7.0 Hz, 3H). Mass: 509.99 ($M^+$).

Example 113

4-(4-amino-1-(1-(3-(3-fluorophenyl)-4-oxo-4H-chromen-2-yl)ethyl)-1H-pyrazolo[3,4-d]pyrimidin-3-yl)thiophene-2-carbaldehyde To a solution of Example 57c (0.350 g, 0.663 mmoles) in DMF (5 ml), ethanol (2.5 ml) and water (2.5 ml), 2-formyl- 4-thiopheneboronic acid (0.155 g, 0.995 mmoles) and sodium carbonate (0.210 g, 1.98 mmoles) were added and the system is degassed for 30 min. Tetrakistriphenylphosphine Palladium (0.038 g, 0.033 mmoles) was added under nitrogen atmosphere and heated to 80° C. After 12 h, the reaction mixture was celite filtered, concentrated and extracted with ethyl acetate. The organic layer was dried over sodium sulphate and concentrated under reduced pressure. The crude product was purified by column chromatography with methanol:dichloromethane to afford the title compound as light brown solid (0.065 g, 19% yield). MP: 192-195° C. $^1$H-NMR (δ ppm, DMSO-$d_6$, 400 MHz): δ 10.01 (s, 1H), 8.30 (s, 1H), 8.24 (s, 1H), 8.07 (s, 1H), 8.05 (dd, J=7.9, 1.4 Hz, 1H), 7.85 (m, 1H), 7.69 (d, J=8.4 Hz, 1H), 7.53 (t, J=7.8 Hz, 1H), 7.28 (br s, 1H), 7.06 (t, J=8.8 Hz, 1H), 6.93 (br s, 2H), 6.04 (q, J=7.0 Hz, 1H), 1.89 (d, J=7.0 Hz, 3H). Mass: 511.95 ($M^+$).

Example 114

2-(1-(4-amino-3-(5-(hydroxymethyl)thiophen-3-yl)-1H-pyrazolo[3,4-d]pyrimidin-1-yl)ethyl)-3-(3-fluorophenyl)-4H-chromen-4-one To a solution of Example 57c (0.300 g, 0.568 mmoles) in DMF (4 ml), ethanol (2 ml) and water (2 ml), 2-hydroxymethyl-4-thiopheneboronic acid (0.133 g, 0.853 mmoles) and sodium carbonate (0.180 g, 1.70 mmoles) were added and the system is degassed for 30 min. Tetrakistriphenylphosphine Palladium (0.033 g, 0.028 mmoles) was added under nitrogen atmosphere and heated to 80° C. After 12 h, the reaction mixture was celite filtered, concentrated and extracted with ethyl acetate. The organic layer was dried over sodium sulphate and concentrated under reduced pressure. The crude product was purified by column chromatography with methanol:dichloromethane to afford the title compound as light brown solid (0.042 g, 14% yield). MP: 154-156° C. $^1$H-NMR (δ ppm, DMSO-$d_6$, 400 MHz): δ 8.05 (s, 1H), 8.04 (dd, J=7.9, 1.4 Hz, 1H), 7.85 (m, 1H), 7.67 (d, J=6.4 Hz, 1H), 7.66 (s, 1H), 7.53 (t, J=7.2 Hz, 1H), 7.29 (br s, 1H), 7.20 (s, 1H), 7.06 (dt, J=8.8, 2.1 Hz, 1H), 6.98 (br s, 2H), 6.02 (q, J=6.9 Hz, 1H), 5.54 (t, J=5.8 Hz, 1H), 4.68 (d, J=5.7 Hz, 2H), 1.88 (d, J=7.0 Hz, 3H). Mass: 514.19 ($M^+$+1).

Example 115

2-(1-(4-amino-3-(2-methyl-1H-benzo[d]imidazol-5-yl)-1H-pyrazolo[3,4-d]pyrimidin-1-yl)ethyl)-3-(3-fluorophenyl)-4H-chromen-4-one To a solution of Example 57c (0.400 g, 0.758 mmoles) in DMF (5 ml), ethanol (2.5 ml) and water (2.5 ml), intermediate 109 (0.407 g, 1.137 mmoles) and sodium carbonate (0.241 g, 2.274 mmoles) were added and the system is degassed for 30 min. Tetrakistriphenylphosphine Palladium (0.043 g, 0.037 mmoles) was added under nitrogen atmosphere and heated to 80° C. After 12 h, the reaction mixture was celite filtered, concentrated and extracted with ethyl acetate. The organic layer was dried over sodium sulphate and concentrated under reduced pressure. The crude product was purified by column chromatography with methanol:dichloromethane to afford the title compound as light brown solid (0.025 g, 6% yield). MP: 154-156° C. $^1$H-NMR (δ ppm, DMSO-$d_6$, 400 MHz): δ 12.34 (s, 1H), 8.07 (s, 1H), 8.05 (dd, J=7.9, 1.3 Hz, 1H), 7.83 (m, 1H), 7.68 (d, J=8.4 Hz, 1H), 7.62 (m, 2H), 7.53 (t, J=7.3 Hz, 1H), 7.38-7.30 (m, 3H), 7.05 (dt, J=8.5, 1.9 Hz, 1H), 6.93 (br s, 1H), 6.05 (q, J=6.9 Hz, 1H), 2.50 (s, 3H), 1.91 (d, J=7.0 Hz, 3H). Mass: 531.97 ($M^+$).

Example 116

2-(1-(4-amino-3-(3-methyl-1H-indazol-6-yl)-1H-pyrazolo[3,4-d]pyrimidin-1-yl) propyl)-3-(3-fluorophenyl)-4H-chromen-4-one To a solution of Example 57 g (0.400 g, 0.738 mmoles) in DMF (4 ml), ethanol (2 ml) and water (2 ml), N-Boc-3-methyl-6-indazoleboronic acid pinacol ester 98 (0.397 g, 1.108 mmoles) and sodium carbonate (0.157 g, 1.47 mmoles) were added and the system is degassed for 30 min. Tetrakistriphenylphosphine Palladium (0.043 g, 0.037 mmoles) was added under nitrogen atmosphere and heated to 80° C. After 12 h, the reaction mixture was celite filtered, concentrated and extracted with ethyl acetate. The organic layer was dried over sodium sulphate and concentrated under reduced pressure. The crude product was purified by column chromatography with methanol:dichloromethane to afford the title compound as off-white solid (0.023 g, 6% yield). MP: 268-270° C. $^1$H-NMR (δ ppm, DMSO-$d_6$, 400 MHz): δ 12.75 (s, 1H), 8.07 (s, 1H), 8.04 (dd, J=7.9, 1.5 Hz, 1H), 7.86 (m, 2H), 7.69 (d, J=8.2 Hz, 1H), 7.64 (s, 1H), 7.53 (t, J=7.9 Hz, 1H), 7.35 (dd, J=8.2, 1.4 Hz, 1H), 7.33 (br s, 1H), 7.09 (dt, J=8.9, 2.2 Hz, 1H), 6.90 (br s, 2H), 5.85 (t, J=6.1 Hz, 1H), 2.51 (s, 3H), 2.50 (m, 2H), 0.82 (t, J=7.3 Hz, 3H). Mass: 545.96 ($M^+$).

Example 117

2-(1-(4-amino-3-(3-methyl-1H-indol-6-yl)-1H-pyrazolo[3,4-d]pyrimidin-1-yl)ethyl)-3-(3-fluorophenyl)-4H-chromen-4-one To a solution of Example 57b (0.290 g, 0.583 mmoles) in DMF (4 ml), ethanol (2 ml) and water (2 ml), 3-methyl-6-indoleboronic acid pinacol ester 106 (0.299 g, 1.163 mmoles) and sodium carbonate (0.185 g, 1.749 mmoles) were added and the system is degassed for 30 min. Tetrakistriphenylphosphine Palladium (0.033 g, 0.029 mmoles) was added under nitrogen atmosphere and heated to 80° C. After 12 h, the reaction mixture was celite filtered, concentrated and extracted with ethyl acetate. The organic layer was dried over sodium sulphate and concentrated under reduced pressure. The crude product was purified by column chromatography with methanol:dichloromethane to afford the title compound as pale brown solid (0.014 g, 5% yield). MP: 262-265° C. $^1$H-NMR (δ ppm, DMSO-$d_6$, 400 MHz): δ 10.92 (s, 1H), 8.07 (s, 1H), 8.04 (d, J=7.9 Hz, 1H), 7.81 (m, 1H), 7.64 (d, J=7.3 Hz, 1H), 7.57 (s, 1H), 7.51 (t, J=7.6 Hz, 1H), 7.35-7.10 (m, 7H), 5.97 (q, J=7.0 Hz, 1H), 2.28 (s, 3H), 1.91 (d, J=7.0 Hz, 3H). Mass: 512.99 ($M^+$).

Example 118

2-((6-amino-9H-purin-9-yl)methyl)-6-fluoro-3-phenyl-4H-chromen-4-one

To a solution of Adenine (0.162 g, 1.20 mmoles) in DMF (3.5 ml), potassium carbonate (0.165 g, 1.20 mmoles) was added and stirred at RT for 10 min. To this mixture intermediate 90 (0.200 g, 0.600 mmoles) was added and stirred for 12 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as brown solid (0.040 g, 17% yield). MP: 207-209° C. $^1$H-NMR (δ ppm, DMSO-$D_6$, 400 MHz): δ 8.09 (s, 1H), 8.07 (s, 1H), 7.73

(dd, J=8.4, 3.1 Hz, 1H), 7.66 (dt, J=8.1, 3.1 Hz, 1H), 7.59 (dd, J=9.1, 4.3 Hz, 1H), 7.45-7.40 (m, 5H), 7.22 (s, 2H), 5.34 (s, 2H). Mass: 388.18 ($M^+$+1).

Example 119

2-((6-amino-9H-purin-9-yl)methyl)-6-fluoro-3-(3-fluorophenyl)-4H-chromen-4-one

To a solution of Adenine (0.153 g, 1.13 mmoles) in DMF (3.5 ml), potassium carbonate (0.156 g, 1.13 mmoles) was added and stirred at RT for 10 min. To this mixture intermediate 92 (0.200 g, 0.567 mmoles) was added and stirred for 12 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as green solid (0.020 g, 9% yield). MP: 180-183° C. $^1$H-NMR (δ ppm, DMSO-$D_6$, 400 MHz): δ 8.11 (s, 1H), 8.07 (s, 1H), 7.73-7.65 (m, 2H), 7.62 (dd, J=9.2, 4.4 Hz, 1H), 7.50 (q, J=7.9 Hz, 1H), 7.26 (m, 5H), 5.36 (s, 2H). Mass: 406.10 ($M^+$+1).

Example 120

2-((4-amino-3-(3-fluoro-5-methoxyphenyl)-1H-pyrazolo[3,4-d]pyrimidin-1-yl)methyl)-6-fluoro-3-(3-fluorophenyl)-4H-chromen-4-one To a solution of intermediate 79 (0.110 g, 0.424 mmoles) in DMF (3 ml), N, N-diisopropylethylamine (0.109 g, 0.848 mmoles) was added and stirred at RT for 10 min. To this mixture, intermediate 92 (0.298 g, 0.848 mmoles) was added and stirred for 12 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as light yellow solid (0.075 g, 33% yield). $^1$H-NMR (δ ppm, DMSO-$D_6$, 400 MHz): δ 8.20 (s, 1H), 7.73-7.61 (m, 3H), 7.38 (q, J=7.6 Hz, 1H), 7.17 (m, 3H), 6.95 (m, 3H), 5.55 (s, 2H), 3.82 (s, 3H). Mass: 515.93 ($M^+$).

Example 120a 2-((4-amino-3-(3-fluoro-5-hydroxyphenyl)-1H-pyrazolo[3,4-d]pyrimidin-1-yl)methyl)-6-fluoro-3-(3-fluorophenyl)-4H-chromen-4-one To a solution of Example 120 (0.075 g, 0.140 mmoles) in dichloromethane (10 ml), $BBr_3$ (1M in dichloromethane, 1.0 ml) was added at 0° C. and the reaction mixture was warmed to RT and then stirred for 12 h. The reaction mixture was quenched with 1.5N HCl solution and extracted with dichloromethane. The organic layer was dried over sodium sulphate and concentrated. The crude product was purified by column chromatography with methanol:dichloromethane to afford the title compound as light brown solid (0.023 g, 31% yield). MP: 127-129° C. $^1$H-NMR (δ ppm, DMSO-$D_6$, 400 MHz): δ 10.18 (s, 1H), 8.19 (s, 1H), 7.74-7.61 (m, 3H), 7.38 (q, J=7.8 Hz, 1H), 7.15 (m, 3H), 6.84 (s, 1H), 6.81 (d, J=8.8 Hz, 1H), 6.65 (d, J=10.8 Hz, 1H), 5.54 (s, 2H). Mass: 515.54 ($M^+$).

Example 121

2-(1-(4-amino-3-(3-methoxyphenyl)-1H-pyrazolo[3,4-d]pyrimidin-1-yl)ethyl)-6-fluoro-3-(3-fluorophenyl)-4H-chromen-4-one To a solution of intermediate 58 (0.254 g, 1.054 mmoles) in DMF (6 ml), potassium carbonate (0.331 g, 2.39 mmoles) was added and stirred at RT for 10 min. To this mixture, intermediate 75 (0.350 g, 0.958 mmoles) was added and stirred for 12 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as light yellow solid (0.210 g, 42% yield). $^1$H-NMR (δ ppm, DMSO-$D_6$, 400 MHz): δ 8.07 (s, 1H), 7.82 (dd, J=9.2, 4.4 Hz, 1H), 7.76 (dd, J=8.0, 3.1 Hz, 1H), 7.72 (dd, J=8.2, 2.7 Hz, 1H), 7.46 (t, J=7.9 Hz, 1H), 7.28 (br s, 1H), 7.18 (d, J=7.7 Hz, 1H), 7.10 (t, J=2.4 Hz, 1H), 7.07 (m, 2H), 6.92 (m, 2H), 6.04 (q, J=7.0 Hz, 1H), 3.80 (s, 3H) 1.89 (d, J=7.1 Hz, 3H).

Example 121a 2-(1-(4-amino-3-(3-hydroxyphenyl)-1H-pyrazolo[3,4-d]pyrimidin-1-yl)ethyl)-6-fluoro-3-(3-fluorophenyl)-4H-chromen-4-one To a solution of Example 121 (0.180 g, 0.324 mmoles) in dichloromethane (15 ml), $BBr_3$ (1M in dichloromethane, 1.6 ml) was added at 0° C. and the reaction mixture was warmed to RT and then stirred for 12 h. The reaction mixture was quenched with 1.5N HCl solution and extracted with dichloromethane. The organic layer was dried over sodium sulphate and concentrated. The crude product was purified by column chromatography with methanol:dichloromethane to afford the title compound as grey solid (0.045 g, 27% yield). MP: 193-196° C. $^1$H-NMR (δ ppm, DMSO-$D_6$, 400 MHz): δ 9.74 (s, 1H), 8.17 (s, 1H), 7.83-7.70 (m, 4H), 7.63 (m, 1H), 7.35 (t, J=8.2 Hz, 1H), 7.31 (m, 1H), 7.12 (m, 4H), 6.99 (m, 2H), 6.08 (q, J=6.8 Hz, 1H), 1.90 (d, J=7.0 Hz, 3H). Mass: 511.87 ($M^+$).

Example 122

2-((9H-purin-6-ylamino)methyl)-6-fluoro-3-(3-fluorophenyl)-4H-chromen-4-one

To a solution of intermediate 73 (3.0 g, 12.03 mmoles) in dichloromethane (30 ml), triethylamine (5.0 ml, 36.11 mmoles) was added followed by N-Boc-Glycine (2.53 g, 14.44 mmoles). To this mixture HATU (9.15 g, 24.07 mmoles) was added and stirred at RT for 12 h. The reaction mixture was quenched by the addition of water and extracted with dichloromethane. The organic layer was dried over sodium sulphate and concentrated under reduced pressure. The crude product was purified by column chromatography with ethyl acetate:petroleum ether to afford the isoflavone intermediate (4 g). To a solution of this intermediate (4.0 g), trifluoroacetic acid (4 ml) was added and stirred at RT for 2 h. The reaction mixture was concentrated, basified with sodium bicarbonate solution, extracted with ethyl acetate. The organic layer was dried over sodium sulphate and concentrated under reduced pressure to afford the amine intermediate (2.5 g). To a solution of this amine intermediate (0.500 g, 1.74 mmoles) in tert-butanol (8 ml), N, N-diisopropylethylamine (0.6 ml, 2.94 mmoles) and 6-chloropurine (0.268 g, 1.74 mmoles) were added and refluxed for 24 h. The reaction mixture was concentrated, diluted with water, extracted with ethyl acetate. The organic layer was dried over sodium sulphate and concentrated under reduced pressure. The crude product was purified by column chromatography with methanol:ethyl acetate to afford the title compound as pale brown solid (0.090 g, 13% yield). MP: 229-232° C. $^1$H-NMR (δ ppm, DMSO-$D_6$, 400 MHz): δ 12.97 (s, 1H), 8.15 (m, 1H), 8.13 (s, 1H), 8.11 (s, 1H), 7.73 (dd, J=8.4, 3.1 Hz, 1H), 7.68 (m, 2H), 7.46 (q, J=6.4 Hz), 7.26-7.20 (m, 3H), 4.60 (br s, 2H). Mass: 406.17 ($M^+$+1).

Example 123

2-((9H-purin-6-ylamino)methyl)-6-fluoro-3-phenyl-4H-chromen-4-one

To a solution of intermediate 50 (3.0 g, 13.03 mmoles) in dichloromethane (30 ml), triethylamine (5.4 ml, 39.09 mmoles) was added followed by N-Boc-Glycine (2.73 g, 15.63 mmoles). To this mixture HATU (9.90 g, 26.08 mmoles) was added and stirred at RT for 12 h. The reaction mixture was quenched by the addition of water and extracted with dichloromethane. The organic layer was dried over sodium sulphate and concentrated under reduced pressure. The crude product was purified by column chromatography with ethyl acetate:petroleum ether to afford the isoflavone intermediate (2.5 g). To a solution of this intermediate (2.5 g), trifluoroacetic acid (3 ml) was added and stirred at RT for 2 h. The reaction mixture was concentrated, basified with sodium bicarbonate solution, extracted with ethyl acetate. The organic layer was dried over sodium sulphate and concentrated under reduced pressure to afford the amine intermediate (1.7 g). To a solution of this amine intermediate (0.500 g, 1.85 mmoles) in tert-butanol (8 ml), N, N-diisopropylethylamine (0.64 ml, 3.71 mmoles) and 6-chloropurine (0.286 g, 1.85 mmoles) were added and refluxed for 24 h. The reaction mixture was concentrated, diluted with water, extracted with ethyl acetate. The organic layer was dried over sodium sulphate and concentrated under reduced pressure. The crude product was purified by column chromatography with methanol:ethyl acetate to afford the title compound as pale brown solid (0.070 g, 10% yield). MP: 183-186° C. $^1$H-NMR (δ ppm, DMSO-$D_6$, 400 MHz): δ 12.96 (s, 1H), 8.16 (m, 1H), 8.14 (s, 1H), 8.11 (s, 1H), 7.73 (dd, J=8.4, 3.1 Hz, 1H), 7.67 (m, 2H), 7.45-7.35 (m, 5H), 4.59 (br s, 2H). Mass: 388.25 ($M^+$+1).

Example 124

(R)-2-(1-(9H-purin-6-ylamino)ethyl)-6-fluoro-3-(3-fluorophenyl)-4H-chromen-4-one To a solution of intermediate 73 (3.0 g, 12.03 mmoles) in dichloromethane (30 ml), triethylamine (5.0 ml, 36.11 mmoles) was added followed by N-Boc-D-Alanine (2.70 g, 14.44 mmoles). To this mixture HATU (9.15 g, 24.07 mmoles) was added and stirred at RT for 12 h. The reaction mixture was quenched by the addition of water and extracted with dichloromethane. The organic layer was dried over sodium sulphate and concentrated under reduced pressure. The crude product was purified by column chromatography with ethyl acetate:petroleum ether to afford the isoflavone intermediate (1.8 g). To a solution of this intermediate (1.8 g), trifluoroacetic acid (1.8 ml) was added and stirred at RT for 2 h. The reaction mixture was concentrated, basified with sodium bicarbonate solution, extracted with ethyl acetate. The organic layer was dried over sodium sulphate and concentrated under reduced pressure to afford the amine intermediate (1.1 g). To a solution of this amine intermediate (1.0 g, 3.31 mmoles) in tert-butanol (20 ml), N, N-diisopropylethylamine (1.15 ml, 6.63 mmoles) and 6-chloropurine (0.384 g, 2.48 mmoles) were added and refluxed for 24 h. The reaction mixture was concentrated, diluted with water, extracted with ethyl acetate. The organic layer was dried over sodium sulphate and concentrated under reduced pressure. The crude product was purified by column chromatography with methanol:ethyl acetate to afford the title compound as pale brown solid (0.100 g, 7% yield). MP: 194-197° C. $^1$H-NMR (δ ppm, DMSO-$D_6$, 400 MHz): δ 12.96 (s, 1H), 8.14 (m, 3H), 7.70 (m, 3H), 7.49 (q, J=7.3 Hz, 1H), 7.25 (m, 3H), 5.20 (br s, 1H), 1.55 (d, J=6.9 Hz, 3H). Mass: 419.96 ($M^+$).

Example 125

2-((4-amino-3-(1H-pyrazol-4-yl)-1H-pyrazolo[3,4-d]pyrimidin-1-yl)methyl)-6-fluoro-3-phenyl-4H-chromen-4-one To a solution of intermediate 57d (0.400 g, 0.77 mmoles) in DMF (5 ml), ethanol (2.5 ml) and water (2.5 ml), N-Boc-pyrazole-4-boronic acid pinacol ester (0.344 g, 1.16 mmoles) and sodium carbonate (0.165 g, 1.16 mmoles) were added and the system is degassed for 30 min Tetrakis triphenylphosphine. Palladium (0.027 g, 0.023 mmoles) was added under nitrogen atmosphere and heated to 80° C. After 12 h, the reaction mixture was celite filtered, concentrated and extracted with ethyl acetate. The organic layer was dried over sodium sulphate and concentrated under reduced pressure. The crude product was purified by column chromatography with methanol:dichloromethane to afford the title compound as yellow solid (0.120 g, 34% yield). MP: 211-214° C. $^1$H-NMR (δ ppm, DMSO-$d_6$, 400 MHz): δ 13.19 (s, 1H), 8.19 (s, 1H), 8.10 (s, 1H), 7.79 (s, 1H), 7.73 (dd, J=8.3, 3.1 Hz, 1H), 7.71 (dt, J=8.7.5, 3.1 Hz, 1H), 7.54 (dd, J=9.3, 4.3 Hz, 1H), 7.40-7.20 (m, 5H), 6.92 (br s, 2H), 5.46 (s, 2H). Mass: 454.26 ($M^+$).

Example 126

2-(1-(4-amino-3-(3,5-difluoro-4-methoxyphenyl)-1H-pyrazolo[3,4-d]pyrimidin-1-yl)ethyl)-3-(3-fluorophenyl)-4H-chromen-4-one To a solution of intermediate 113 (0.110 g, 0.396 mmoles) in DMF (10 ml), cesium carbonate (0.258 g, 0.792 mmoles) was added and stirred at RT for 10 min. To this mixture, intermediate 36 (0.275 g, 0.792 mmoles) was added and stirred for 12 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as yellow solid (0.122 g, 56% yield). $^1$H-NMR (δ ppm, DMSO-$D_6$, 400 MHz): δ 8.07 (s, 1H), 8.04 (dd, J=7.9, 1.5 Hz, 1H), 7.85 (m, 1H), 7.68 (dd, J=8.3 Hz, 1H), 7.63 (m, 1H), 7.56 (m, 2H), 7.35 (s, 1H), 7.30 (d, J=8.7 Hz, 2H), 7.07 (dt, J=8.7, 2.3 Hz, 1H), 6.93 (br s, 2H), 6.04 (q, J=6.9 Hz, 1H), 3.97 (s, 3H), 1.88 (d, J=7.0 Hz, 3H).

Example 126a 2-(1-(4-amino-3-(3,5-difluoro-4-hydroxyphenyl)-1H-pyrazolo[3,4-d]pyrimidin-1-yl)ethyl)-3-(3-fluorophenyl)-4H-chromen-4-one To a solution of example 126 (0.122 g, 0.224 mmoles) in dichloromethane (10 ml), $BBr_3$ (1M in dichloromethane, 1.2 ml) was added at 0° C. and the reaction mixture was warmed to RT and then stirred for 12 h. The reaction mixture was quenched with 1.5N HCl solution and extracted with dichloromethane. The organic layer was dried over sodium sulphate and concentrated to afford the title compound as brown solid (0.086 g, 72% yield). MP: 253-257° C. $^1$H-NMR (δ ppm, DMSO-$D_6$, 400 MHz): δ 9.64 (s, 1H), 8.05 (s, 1H), 8.04 (dd, J=8.0, 1.4 Hz, 1H), 7.83 (m, 1H), 7.68 (d, J=8.4 Hz, 1H), 7.52 (t, J=5.3 Hz, 1H), 7.30 (m, 1H), 7.20 (d, J=8.7 Hz, 2H), 7.06 (dt, J=8.7, 2.2 Hz, 1H), 6.98 (br s, 2H), 6.00 (q, J=7.0 Hz, 1H), 1.88 (d, J=7.0 Hz, 3H). Mass: 5530.14 ($M^+$+1).

Example 127

2-((4-amino-3-(3,5-difluoro-4-methoxyphenyl)-1H-pyrazolo[3,4-d]pyrimidin-1-yl)methyl)-6-fluoro-3-(3-fluorophenyl)-4H-chromen-4-one To a solution of intermediate 113 (0.080 g, 0.288 mmoles) in DMF (3 ml), N, N-diisopropylethylamine (0.074 g, 0.577 mmoles) was added and stirred at RT for 10 min. To this mixture, intermediate 92 (0.203 g, 0.577 mmoles) was added and stirred for 12 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as brown solid (0.109 g, 68% yield). $^1$H-NMR (δ ppm, DMSO-$D_6$, 400 MHz): δ 8.20 (s, 1H), 7.73-7.52 (m, 4H), 7.38 (m, 1H), 7.30 (d, J=8.8 Hz, 2H), 7.16-7.07 (m, 4H), 5.53 (s, 2H), 3.96 (s, 3H).

Example 127a 2-((4-amino-3-(3,5-difluoro-4-hydroxyphenyl)-1H-pyrazolo[3,4-d]pyrimidin-1-yl)methyl)-6-fluoro-3-(3-fluorophenyl)-4H-chromen-4-one To a solution of example 127 (0.099 g, 0.180 mmoles) in dichloromethane (10 ml), $BBr_3$ (1M in dichloromethane, 0.99 ml) was added at 0° C. and the reaction mixture was warmed to RT and then stirred for 12 h. The reaction mixture was quenched with 1.5N HCl solution and extracted with dichloromethane. The organic layer was dried over sodium sulphate and concentrated to afford the title compound as brown solid (0.022 g, 23% yield). MP: 274-278° C. $^1$H-NMR (δ ppm, DMSO-$D_6$, 400 MHz): δ 10.20 (s, 1H), δ 8.18 (s, 1H), 7.72-7.60 (m, 4H), 7.38 (m, 1H), 7.20 (d, J=8.7 Hz, 2H), 7.17-7.10 (m, 4H), 5.51 (s, 2H). Mass: 534.06 ($M^+$+1).

Example 128

(+)-2-(1-(4-amino-3-(3-methyl-1H-indazol-6-yl)-1H-pyrazolo[3,4-d]pyrimidin-1-yl)ethyl)-3-(3-fluorophenyl)-4H-chromen-4-one Example 129

(−)-2-(1-(4-amino-3-(3-methyl-1H-indazol-6-yl)-1H-pyrazolo[3,4-d]pyrimidin-1-yl)ethyl)-3-(3-fluorophenyl)-4H-chromen-4-one The two enantiomerically pure isomers were obtained by preparative chiral hplc separation from example 79 on a CHIRALPAK IA column (250×20 mm; 5μ) using dichloromethane:acetonitrile:methanol (90:08:02, v/v/v) as the mobile phase.

(+)-Isomer: Off-white solid, e.e. 99.68%. Rt: 5.55 min (CHIRALPAK IA, conditions as above). MP: 158-161° C. $[\alpha]^{25}_D$ 196.56 (c=0.40, $CH_2Cl_2$). $^1$H-NMR (δ ppm, DMSO-$d_6$, 400 MHz): δ 12.74 (s, 1H), 8.08 (s, 1H), 8.05 (dd, J=7.9, 1.4 Hz, 1H), 7.86 (m, 2H), 7.68 (d, J=8.4 Hz, 1H), 7.62 (s, 1H), 7.53 (t, J=7.8 Hz, 1H), 7.34 (d, J=8.3 Hz, 1H), 7.31 (m, 1H), 7.07 (dt, J=8.8, 2.3 Hz, 1H), 6.93 (br s, 2H), 6.07 (q, J=7.0 Hz, 1H), 2.51 (s, 3H), 1.92 (d, J=7.1 Hz, 3H). Mass: 532.39 ($M^+$+1).

(−)-Isomer: Off-white solid, e.e. 98.33%. Rt: 7.39 min (CHIRALPAK IA, conditions as above). MP: 157-160° C. $[\alpha]^{25}_D$ −191.54 (c=0.40, $CH_2Cl_2$). $^1$H-NMR (δ ppm, DMSO-$d_6$, 400 MHz): δ 12.75 (s, 1H), 8.08 (s, 1H), 8.05 (dd, J=7.9, 1.4 Hz, 1H), 7.85 (m, 2H), 7.68 (d, J=8.4 Hz, 1H), 7.62 (s, 1H), 7.53 (t, J=7.9 Hz, 1H), 7.34 (dd, J=8.3, 1.1 Hz, 1H), 7.31 (m, 1H), 7.07 (dt, J=8.6, 2.1 Hz, 1H), 6.94 (br s, 2H), 6.07 (q, J=6.9 Hz, 1H), 2.51 (s, 3H), 1.92 (d, J=7.1 Hz, 3H). Mass: 532.39 ($M^+$+1).

Example 130

2-(1-(4-amino-3-(3,5-dimethoxyphenyl)-1H-pyrazolo[3,4-d]pyrimidin-1-yl)ethyl)-3-(3-fluorophenyl)-4H-chromen-4-one To a solution of example 57c (100 mg, 0.190 mmol) in DME (1 ml), and water (0.5 ml), 3,5-dimethoxy phenyl boronic acid (0.209 mmol) and sodium carbonate (40 mg, 0.380 mmol) were added and the system was degassed for 5 min. 1,1'-Bis(diphenylphosphino)ferrocene]dichloropalladium(II) (27.8 mg, 0.038 mmol) was added under nitrogen atmosphere and the mixture was heated to 90° C. at a microwave reactor for 15 min. LC-MS analysis indicated the total consumption of example 57c, then ethyl acetate (2 ml) and water (0.5 ml) was added. The two phases were separated and the aqueous layer was extracted by ethyl acetate (1 ml). The combined organic layer was dried over $Na_2SO_4$, filtered and evaporated to dryness. The residue was purified by preparative TLC using mixture of ethyl acetate:petroleum ether in 2:1 ratio as an eluent to afford the desired compound. Brown solid (23.4 mg, 23%). MP: 224-227° C. $^1$H-NMR (δ ppm, $CDCl_3$, 300 MHz): δ 8.24 (s, 1H), 8.21 (dd, J=8.0, 1.5 Hz, 1H), 7.69 (m, 1H), 7.48 (d, J=8.4 Hz, 1H), 7.42 (t, J=8.0 Hz, 1H), 7.32 (m, 1H), 7.04 (m, 3H), 6.79 (d, J=2.3 Hz, 2H), 6.56 (t, J=2.1 Hz, 1H), 6.11 (q, J=7.2 Hz, 1H), 5.58 (s, 2H), 3.85 (s, 6H), 2.02 (d, J=7.1 Hz, 3H). Mass: 537.8 (M+).

Example 131

2-(1-(4-amino-3-(4-methoxy-3,5-dimethylphenyl)-1H-pyrazolo[3,4-d]pyrimidin-1-yl)ethyl)-3-(3-fluorophenyl)-4H-chromen-4-one The compound was prepared as per the procedure provided above for Example 130 wherein the 3,5-dimethoxy phenyl boronic acid was replaced by 3,5-dimethyl-4-methoxyphenyl boronic acid (0.209 mmol). Brown solid (20 mg, 20%). MP: 234-236° C. $^1$H-NMR (δ ppm, $CDCl_3$, 300 MHz): δ 8.22 (s, 1H), 8.21 (dd, J=8.0, 1.5 Hz, 1H), 7.69 (m, 1H), 7.48 (d, J=8.4 Hz, 1H), 7.42 (t, J=8.0 Hz, 1H), 7.30 (s, 2H), 7.29 (m, 1H), 7.02-6.95 (m, 3H), 6.10 (q, J=7.1 Hz, 1H), 5.43 (s, 2H), 3.77 (s, 3H), 2.36 (s, 6H), 2.01 (d, J=7.1 Hz, 3H). Mass: 535.9 (M+).

Example 132

2-(1-(4-amino-3-(2-fluoro-5-isopropoxyphenyl)-1H-pyrazolo[3,4-d]pyrimidin-1-yl)ethyl)-3-(3-fluorophenyl)-4H-chromen-4-one The compound was prepared as per the procedure provided above for Example 130 wherein the 3,5-dimethoxy phenyl boronic acid was replaced by 2-Fluoro-5-isopropoxyphenyl boronic acid (0.209 mmol). Brown solid (50.6 mg, 48%). MP: 198-201° C. $^{1}$H-NMR (δ ppm, $CDCl_3$, 300 MHz): δ 8.24 (s, 1H), 8.21 (dd, J=7.9, 1.5 Hz, 1H), 7.68 (m, 1H), 7.47 (d, J=8.0 Hz, 1H), 7.41 (dd, J=8.0, 0.9 Hz, 1H), 7.34 (m, 1H), 7.18 (t, J=9.9 Hz, 1H), 7.07-6.96 (m, 5H), 6.13 (q, J=7.1 Hz, 1H), 5.32 (s, 2H), 4.53 (quintet, J=6.0 Hz, 1H), 2.01 (d, J=7.1 Hz, 3H), 1.35 (d, J=6.0 Hz, 6H). Mass: 553.8 (M+).

Example 133

2-(1-(4-amino-3-(2,3-dihydrobenzo[b][1,4]dioxin-6-yl)-1H-pyrazolo[3,4-d]pyrimidin-1-yl)ethyl)-3-(3-fluorophenyl)-4H-chromen-4-one The compound was prepared as per the procedure provided above for Example 130 wherein the 3,5-dimethoxy phenyl boronic acid (or boronic acid pinacol ester) was replaced by -2,3-dihydrobenzo[b][1,4]dioxin-6-ylboronic acid (0.209 mmol) Off-white solid (22 mg, 22%). MP: 225-226° C. $^{1}$H-NMR (δ ppm, $CDCl_3$, 300 MHz): δ 8.21 (s, 1H), 8.19 (dd, J=8.1, 1.2 Hz, 1H), 7.69 (m, 1H), 7.48 (d, J=8.4 Hz, 1H), 7.42 (dt, J=8.1, 1.2 Hz, 1H), 7.31 (m, 1H), 7.19 (d, J=2.1 Hz, 1H), 7.15 (dd, J=8.4, 2.1 Hz, 1H), 7.03-6.95 (m, 4H), 6.09 (q, J=7.2 Hz, 1H), 5.58 (s, 2H), 4.31 (s, 4H), 2.00 (d, J=7.2 Hz, 3H). Mass: 535.8 (M+).

Example 134

2-(1-(4-amino-3-(1-benzyl-1H-pyrazol-4-yl)-1H-pyrazolo[3,4-d]pyrimidin-1-yl)ethyl)-3-(3-fluorophenyl)-4H-chromen-4-one The compound was prepared as per the procedure provided above for Example 130 wherein the 3,5-dimethoxy phenyl boronic acid (or boronic acid pinacol ester) was replaced by -1-benzylpyrazole-4-boronic acid pinacol ester (0.209 mmol) Brown solid (35 mg, 33%). MP: 140-142° C. $^{1}$H-NMR (δ ppm, $CDCl_3$, 300 MHz): δ 8.21 (s, 1H), 8.21 (dd, J=8.2, 1.5 Hz, 1H), 7.84 (s, 1H), 7.73 (s, 1H), 7.67 (m, 1H), 7.47 (d, J=8.2 Hz, 1H), 7.40-7.32 (m, 7H), 6.98 (m, 3H), 6.05 (q, J=7.2 Hz, 1H), 5.41 (s, 2H), 5.38 (s, 2H), 1.98 (d, J=7.1 Hz, 3H). Mass: 557.8 (M+).

Example 135

2-(1-(4-amino-3-(2-methylpyridin-4-yl)-1H-pyrazolo[3,4-d]pyrimidin-1-yl)ethyl)-3-(3-fluorophenyl)-4H-chromen-4-one The compound was prepared as per the procedure provided above for Example 130 wherein the 3,5-dimethoxy phenyl boronic acid was replaced by 2-methylpyridine-4-boronic acid (0.209 mmol) Off-white solid (30 mg, 32%). MP: 266-268° C. $^{1}$H-NMR (δ ppm, $CDCl_3$, 300 MHz): δ), 8.68 (d, J=5.4 Hz, 1H), 8.27 (s, 1H), 8.22 (dd, J=7.9, 1.5 Hz, 1H), 7.70 (m, 1H), 7.49-7.32 (m, 5H), 7.04-6.92 (m, 3H), 6.13 (q, J=7.2 Hz, 1H), 5.47 (s, 2H), 2.67 (s, 3H), 2.02 (d, J=7.2 Hz, 3H). Mass: 492.8 (M+).

Example 136

2-(1-(4-amino-3-(3,4-dihydro-2H-benzo[b][1,4]dioxepin-7-yl)-1H-pyrazolo[3,4-d]pyrimidin-1-yl)ethyl)-3-(3-fluorophenyl)-4H-chromen-4-one The compound was prepared as per the procedure provided above for Example 130 wherein the 3,5-dimethoxy phenyl boronic acid was replaced by 3,4-dihydro-2H-benzo[b][1,4]dioxepin-7-ylboronic acid (0.209 mmol) Brown solid (15 mg, 14%). MP: 234-237° C. $^{1}$H-NMR (δ ppm, $CDCl_3$, 300 MHz): δ 8.22 (s, 1H), 8.19 (dd, J=7.5, 1.8 Hz, 1H), 7.69 (m, 1H), 7.48 (d, J=8.4 Hz, 1H), 7.43 (dt, J=7.8, 0.9 Hz, 1H), 7.30 (d, J=2.1 Hz, 1H), 7.28 (m, 2H), 7.23 (d, J=2.1 Hz, 1H), 7.20 (m, 3H), 6.10 (q, J=7.2 Hz, 1H), 5.62 (s, 2H), 4.31 (d, J=5.7 Hz, 4H), 2.27 (t, J=5.7 Hz, 2H), 2.01 (d, J=7.2 Hz, 3H). Mass: 549.5 (M+).

Example 137

2-(1-(4-amino-3-(6-morpholinopyridin-3-yl)-1H-pyrazolo[3,4-d]pyrimidin-1-yl)ethyl)-3-(3-fluorophenyl)-4H-chromen-4-one The compound was prepared as per the procedure provided above for Example 130 wherein the 3,5-dimethoxy phenyl boronic acid was replaced by 6-morpholinopyridin-3-ylboronic acid (0.209 mmol) Brown solid (36 mg, 34%). MP: 269-271° C. $^{1}$H-NMR (δ ppm, $CDCl_3$, 300 MHz): δ 8.49 (d, J=2.1 Hz, 1H), 8.24 (s, 1H), 8.21 (dd, J=8.0, 1.5 Hz, 1H), 7.82 (dd, J=8.8, 2.4 Hz, 1H), 7.69 (m, 1H), 7.48 (d, J=8.4 Hz, 1H), 7.42 (t, J=8.0 Hz, 1H), 7.30 (m, 1H), 7.02-6.91 (m, 3H), 6.77 (d, J=8.8 Hz, 1H), 6.12 (q, J=7.2 Hz, 1H), 5.41 (s, 2H), 3.86 (t, J=4.6 Hz, 4H), 3.61 (t, J=5.0 Hz, 4H), 2.01 (d, J=7.1 Hz, 3H). Mass: 563.8 (M+).

Example 138

2-(1-(4-amino-3-(dibenzo[b,d]furan-4-yl)-1H-pyrazolo[3,4-d]pyrimidin-1-yl)ethyl)-3-(3-fluorophenyl)-4H-chromen-4-one The compound was prepared as per the procedure provided above for Example 130 wherein the 3,5-dimethoxy phenyl boronic acid was replaced by -dibenzo[b,d]furan-4-ylboronic acid (0.209 mmol) Brown solid (52.6 mg, 49%). MP: 238-240° C. $^{1}$H-NMR (δ ppm, $CDCl_3$, 300 MHz): δ 8.28 (s, 1H), 8.23 (d, J=6.7 Hz, 1H), 8.10 (d, J=7.1 Hz, 1H), 8.03 (d, J=7.6 Hz, 1H), 7.71 (m, 2H), 7.54-7.49 (m, 4H), 7.46 (t, J=7.6 Hz, 2H), 7.34 (m, 1H), 7.11 (d, J=7.6 Hz, 1H), 7.06 (m, 2H), 6.20 (q, J=7.1 Hz, 1H), 5.29 (s, 2H), 2.07 (d, J=7.1 Hz, 3H). Mass: 567.8 (M+).

Example 139

2-(1-(4-amino-3-(4-phenoxyphenyl)-1H-pyrazolo[3,4-d]pyrimidin-1-yl)ethyl)-3-(3-fluorophenyl)-4H-chromen-4-one The compound was prepared as per the procedure provided above for Example 130 wherein the 3,5-dimethoxy phenyl boronic acid was replaced by 4-phenoxyphenylboronic acid (0.209 mmol) Brown solid (61.9 mg, 57%). MP: 218-220° C. $^{1}$H-NMR (δ ppm, $CDCl_3$, 300 MHz): δ 8.24 (s, 1H), 8.22 (dd, J=7.9, 1.5 Hz, 1H), 7.69 (m, 3H), 7.42 (d, J=8.2 Hz, 1H), 7.41

(m, 3H), 7.32 (m, 1H), 7.19-7.13 (m, 3H), 7.08-6.92 (m, 5H), 6.11 (q, J=7.1 Hz, 1H), 5.39 (s, 2H), 2.02 (d, J=7.2 Hz, 3H). Mass: 569.8 (M+).

Example 140

2-(1-(4-amino-3-(4-(benzyloxy)-3-chlorophenyl)-1H-pyrazolo[3,4-d]pyrimidin-1-yl)ethyl)-3-(3-fluorophenyl)-4H-chromen-4-one The compound was prepared as per the procedure provided above for Example 130 wherein the 3,5-dimethoxy phenyl boronic acid was replaced by 4-(benzyloxy)-3-chlorophenylboronic acid (0.209 mmol) Brown solid (58 mg, 49%). MP: 214-216° C. $^1$H-NMR (δ ppm, $CDCl_3$, 300 MHz): δ 8.24 (s, 1H), 8.22 (dd, J=7.9, 1.5 Hz, 1H), 7.74 (d, J=2.1 Hz, 1H), 7.69 (m, 1H), 7.49-7.31 (m, 9H), 7.12 (d, J=8.5 Hz, 1H), 7.03 (m, 2H), 6.94 (d, J=9.3 Hz, 1H), 6.10 (q, J=7.2 Hz, 1H), 5.38 (s, 2H), 5.24 (s, 2H), 2.00 (d, J=7.1 Hz, 3H). Mass: 618.8 (M+).

Example 141

2-(1-(4-amino-3-(3-chloro-4-isopropoxyphenyl)-1H-pyrazolo[3,4-d]pyrimidin-1-yl)ethyl)-3-(3-fluorophenyl)-4H-chromen-4-one The compound was prepared as per the procedure provided above for Example 130 wherein the 3,5-dimethoxy phenyl boronic acid was replaced by -3-chloro-4-isopropoxyphenylboronic acid (0.209 mmol) Brown solid (52.8 mg, 49%). MP: 198-200° C. $^1$H-NMR (δ ppm, $CDCl_3$, 300 MHz): δ 8.24 (s, 1H), 8.22 (dd, J=8.0, 1.5 Hz, 1H), 7.70 (m, 2H), 7.51-7.47 (m, 2H), 7.42 (dt, J=8.0, 0.9 Hz, 1H), 7.30 (m, 1H), 7.09 (d, J=7.5 Hz, 1H), 7.03-6.91 (m, 3H), 6.12 (q, J=7.1 Hz, 1H), 5.41 (s, 2H), 4.67 (quintet, J=6.2 Hz, 1H), 2.01 (d, J=7.1 Hz, 3H), 1.44 (d, J=6.0 Hz, 6H). Mass: 570.8 (M+).

Example 142

2-(1-(4-amino-3-(3-(dimethylamino)phenyl)-1H-pyrazolo[3,4-d]pyrimidin-1-yl)ethyl)-3-(3-fluorophenyl)-4H-chromen-4-one The compound was prepared as per the procedure provided above for Example 130 wherein the 3,5-dimethoxy phenyl boronic acid was replaced by -3-(dimethylamino)phenylboronic acid (0.209 mmol) Brown solid (60 mg, 60%). MP: 218-220° C. $^1$H-NMR (δ ppm, $CDCl_3$, 300 MHz): δ 8.23 (s, 1H), 8.21 (dd, J=8.0, 1.5 Hz, 1H), 7.68 (m, 1H), 7.48 (d, J=8.2 Hz, 1H), 7.41 (m, 2H), 7.35 (m, 1H), 7.05 (d, J=7.6 Hz, 1H), 7.01-6.95 (m, 4H), 6.83 (dd, J=8.7, 2.1 Hz, 1H), 6.11 (q, J=7.1 Hz, 1H), 5.52 (s, 2H), 3.01 (s, 6H), 2.02 (d, J=7.1 Hz, 3H). Mass: 520.8 (M+).

Example 143

2-(1-(4-amino-3-(4-ethoxy-3-fluorophenyl)-1H-pyrazolo[3,4-d]pyrimidin-1-yl)ethyl)-3-(3-fluorophenyl)-4H-chromen-4-one The compound was prepared as per the procedure provided above for Example 130 wherein the 3,5-dimethoxy phenyl boronic was replaced by 4-ethoxy-3-fluorophenylboronic acid (0.209 mmol) Brown solid (47.5 mg, 46%). MP: 216-218° C. $^1$H-NMR (δ ppm, $CDCl_3$, 300 MHz): δ 8.24 (s, 1H), 8.22 (dd, J=8.1, 1.5 Hz, 1H), 7.68 (m, 1H), 7.49-7.35 (m, 5H), 7.13 (t, J=8.4 Hz, 1H), 7.07 (m, 3H), 6.10 (q, J=7.2 Hz, 1H), 5.50 (s, 2H), 4.19 (q, J=7.2 Hz, 2H), 2.01 (d, J=7.2 Hz, 3H), 1.52 (t, J=7.2 Hz, 3H). Mass: 539.8 (M+). MS DATA

Example 144

2-(1-(4-amino-3-(4-isopropoxyphenyl)-1H-pyrazolo[3,4-d]pyrimidin-1-yl)ethyl)-3-(3-fluorophenyl)-4H-chromen-4-one The compound was prepared as per the procedure provided above for Example 130 wherein the 3,5-dimethoxy phenyl boronic acid was replaced by -4-isopropoxyphenylboronic acid (0.209 mmol) Brown solid (23.2 mg, 23%). MP: 224-226° C. $^1$H-NMR (δ ppm, $CDCl_3$, 300 MHz): δ 8.22 (s, 1H), 8.22 (dd, J=8.0, 1.5 Hz, 1H), 7.67 (m, 1H), 7.58 (dd, J=6.7, 1.9 Hz, 2H), 7.49 (d, J=8.3 Hz, 1H), 7.42 (dt, J=8.0, 1.0 Hz, 1H), 7.30 (m, 1H), 7.04-6.98 (m, 5H), 6.12 (q, J=7.1 Hz, 1H), 5.41 (s, 2H), 4.65 (quintet, J=6.1 Hz, 1H), 2.01 (d, J=7.1 Hz, 3H), 1.38 (d, J=6.0 Hz, 6H). Mass: 535.8 (M+).

Example 145

2-(1-(4-amino-3-(4-(trifluoromethoxy)phenyl)-1H-pyrazolo[3,4-d]pyrimidin-1-yl)ethyl)-3-(3-fluorophenyl)-4H-chromen-4-one The compound was prepared as per the procedure provided above for Example 130 wherein the 3,5-dimethoxy phenyl boronic acid was replaced by 4-(trifluoromethoxy)phenylboronic acid (0.209 mmol) Brown solid (46.6 mg, 48%). MP: 224-226° C. $^1$H-NMR (δ ppm, $CDCl_3$, 300 MHz): δ 8.26 (s, 1H), 8.22 (dd, J=7.9, 1.5 Hz, 1H), 7.74 (d, J=7.6 Hz, 2H), 7.70 (m, 1H), 7.48 (d, J=8.3 Hz, 1H), 7.42 (m, 1H), 7.40 (d, J=8.1 Hz, 2H), 7.33 (m, 1H), 7.04 (m, 2H), 6.93 (d, J=7.9 Hz, 2H), 6.12 (q, J=7.2 Hz, 1H), 5.39 (s, 2H), 2.02 (d, J=7.2 Hz, 3H). Mass: 561.8 (M+).

Example 146

2-(1-(3-(4-acetylphenyl)-4-amino-1H-pyrazolo[3,4-d]pyrimidin-1-yl)ethyl)-3-(3-fluorophenyl)-4H-chromen-4-one The compound was prepared as per the procedure provided above for Example 130 wherein the 3,5-dimethoxy phenyl boronic acid was replaced by 4-acetylphenylboronic acid (0.209 mmol) Off-white solid (20 mg, 20%). MP: 218-221° C. $^1$H-NMR (δ ppm, $CDCl_3$, 300 MHz): δ 8.26 (s, 1H), 8.22 (dd, J=7.9, 1.5 Hz, 1H), 8.13 (d, J=8.3 Hz, 2H), 7.82 (d, J=8.4 Hz, 2H), 7.70 (m, 1H), 7.48 (d, J=8.2 Hz, 1H), 7.43 (dt, J=8.0, 0.9 Hz, 1H), 7.31 (m, 1H), 7.04-6.92 (m, 3H), 6.13 (q, J=7.1 Hz, 1H), 5.47 (s, 2H), 2.67 (s, 3H), 2.03 (d, J=7.2 Hz, 3H). Mass: 519.8 (M+).

Example 147

2-(1-(4-amino-3-(4-(benzyloxy)phenyl)-1H-pyrazolo[3,4-d]pyrimidin-1-yl)ethyl)-3-(3-fluorophenyl)-4H-chromen-4-one The compound was prepared as per the procedure provided above for Example 130 wherein the 3,5-dimethoxy phenyl boronic acid was replaced by 4-(benzyloxy)phenylboronic acid (0.209 mmol) Off-white solid (68.2 mg, 61%). MP: 176-178° C. $^1$H-NMR (δ ppm, $CDCl_3$, 300 MHz): δ 8.22 (s, 1H), 8.22 (dd, J=9.0, 1.6 Hz, 1H), 7.69 (m, 1H), 7.48-7.23 (m, 11H), 7.12-6.92 (m, 4H), 6.12 (q, J=7.1 Hz, 1H), 5.37 (s, 2H), 5.16 (s, 2H), 2.01 (d, J=7.1 Hz, 3H). Mass: 583.9 (M+).

Example 148

2-(1-(4-amino-3-(4-(dimethylamino)phenyl)-1H-pyrazolo[3,4-d]pyrimidin-1-yl)ethyl)-3-(3-fluorophenyl)-4H-chromen-4-one The compound was prepared as per the procedure provided above for Example 130 wherein the 3,5-dimethoxy phenyl boronic acid was replaced by 4-(dimethylamino)phenylboronic acid (0.209 mmol) Brown solid (12.6 mg, 13%). MP: 214-217° C. $^1$H-NMR (δ ppm, $CDCl_3$, 300 MHz): δ 8.21 (dd, J=7.8, 1.6 Hz, 1H), 8.21 (s, 1H), 7.69 (m, 1H), 7.54-7.48 (m, 3H), 7.41 (dt, J=8.0, 0.9 Hz, 1H), 7.31 (m, 1H), 7.02-6.95 (m, 3H), 6.84 (d, J=8.8 Hz, 2H), 6.09 (q, J=7.1 Hz, 1H), 5.47 (s, 2H), 3.02 (s, 6H), 2.01 (d, J=7.2 Hz, 3H). Mass: 520.89 (M+).

Example 149

2-(1-(4-amino-3-(4-(methylsulfonyl)phenyl)-1H-pyrazolo[3,4-d]pyrimidin-1-yl)ethyl)-3-(3-fluorophenyl)-4H-chromen-4-one The compound was prepared as per the procedure provided above for Example 130 wherein the 3,5-dimethoxy phenyl boronic acid was replaced by 4-(methylsulfonyl)phenylboronic acid (0.209 mmol). Off-white solid (48.9 mg, 46%). MP: 259-262° C. $^1$H-NMR (δ ppm, $CDCl_3$, 300 MHz): δ 8.27 (s, 1H), 8.22 (dd, J=8.0, 1.5 Hz, 1H), 8.14 (d, J=8.5 Hz, 2H), 7.93 (d, J=8.5 Hz, 2H), 7.69 (m, 1H), 7.47 (d, J=8.2 Hz, 1H), 7.43 (dt, J=8.0, 1.0 Hz, 1H), 7.32 (m, 1H), 7.03-6.90 (m, 3H), 6.16 (q, J=7.1 Hz, 1H), 5.56 (s, 2H), 3.12 (s, 3H), 2.02 (d, J=7.1 Hz, 3H). Mass: 555.8 (M+).

Example 150

2-(1-(4-amino-3-(3-ethoxyphenyl)-1H-pyrazolo[3,4-d]pyrimidin-1-yl)ethyl)-3-(3-fluorophenyl)-4H-chromen-4-one The compound was prepared as per the procedure provided above for Example 130 wherein the 3,5-dimethoxy phenyl boronic acid was replaced by 3-ethoxyphenylboronic acid (0.209 mmol) Off-white solid (42.6 mg, 43%). MP: 162-165° C. $^1$H-NMR (δ ppm, $CDCl_3$, 300 MHz): δ 8.15 (m, 2H), 7.38 (t, J=7.5 Hz, 1H), 7.18 (m, 3H), 7.11 (m, 3H), 6.95 (m, 4H), 6.04 (q, J=7.0 Hz, 1H), 5.63 (s, 2H), 4.03 (q, J=7.2 Hz, 2H), 1.95 (d, J=6.9 Hz, 3H), 1.39 (t, J=7.2 Hz, 3H). Mass 521.8 (M+).

Example 151

2-(1-(4-amino-3-(benzo[b]thiophen-2-yl)-1H-pyrazolo[3,4-d]pyrimidin-1-yl)ethyl)-3-(3-fluorophenyl)-4H-chromen-4-one The compound was prepared as per the procedure provided above for Example 130 wherein the 3,5-dimethoxy phenyl boronic acid was replaced by -benzo[b]thiophen-2-ylboronic acid (0.209 mmol) Brown solid (25 mg, 24%). MP: 242-245° C. $^1$H-NMR (δ ppm, $CDCl_3$, 300 MHz): δ 8.30-8.20 (m, 2H), 7.91 (m, 2H), 7.69 (m, 2H), 7.50-7.25 (m, 5H), 7.07 (m, 3H), 6.12 (q, J=7.1 Hz, 1H), 5.77 (s, 2H), 2.04 (d, J=7.2 Hz, 3H). Mass 533.8 (M+).

Example 152

2-(1-(4-amino-3-(5-chlorothiophen-2-yl)-1H-pyrazolo[3,4-d]pyrimidin-1-yl)ethyl)-3-(3-fluorophenyl)-4H-chromen-4-one The compound was prepared as per the procedure provided above for Example 130 wherein the 3,5-dimethoxy phenyl boronic acid was replaced by 5-chlorothiophen-2-ylboronic acid (0.209 mmol) Brown solid (14.5 mg, 15%). MP: 226-229° C. $^1$H-NMR (δ ppm, $CDCl_3$, 300 MHz): δ 8.25 (s, 1H), 8.21 (dd, J=8.0, 1.5 Hz, 1H), 7.70 (m, 1H), 7.48 (d, J=8.2 z, 1H), 7.42 (dt, J=8.0, 1.1 Hz, 1H), 7.34 (m, 1H), 7.16 (dt, J=3.8 Hz, 1H), 7.04 (m, 3H), 6.96 (d, J=9.3 Hz, 1H), 6.08 (q, J=7.1 Hz, 1H), 5.62 (s, 2H), 2.00 (d, J=7.1 Hz, 3H). Mass: 517.88 (M+)

Example 153

2-(1-(4-amino-3-(3,5-dimethylisoxazol-4-yl)-1H-pyrazolo[3,4-d]pyrimidin-1-yl)ethyl)-3-(3-fluorophenyl)-4H-chromen-4-one The compound was prepared as per the procedure provided above for Example 130 wherein the 3,5-dimethoxy phenyl boronic acid was replaced by 3,5-dimethylisoxazol-4-ylboronic acid (0.209 mmol) Brown solid (23.1 mg, 24%). MP: 218-222° C. $^1$H-NMR (δ ppm, $CDCl_3$, 300 MHz): δ 8.27 (s, 1H), 8.22 (dd, J=8.5, 1.6 Hz, 1H), 7.69 (m, 1H), 7.42 (m, 3H), 7.11-6.99 (m, 3H), 6.12 (q, J=7.2 Hz, 1H), 5.21 (s, 2H), 2.44 (s, 3H), 2.29 (s, 3H), 1.99 (d, J=7.2 Hz, 3H). Mass: 496.9 (M+).

Example 154

2-(1-(4-amino-3-(3-propoxyphenyl)-1H-pyrazolo[3,4-d]pyrimidin-1-yl)ethyl)-3-(3-fluorophenyl)-4H-chromen-4-one The compound was prepared as per the procedure provided above for Example 130 wherein the 3,5-dimethoxy phenyl boronic was replaced by 3-propoxyphenylboronic acid (0.209 mmol) Brown solid (65.4 mg, 64%). MP: 178-182° C. $^1$H-NMR (δ ppm, $CDCl_3$, 300 MHz): δ 8.24 (s, 1H), 8.22 (dd, J=8.0, 1.6 Hz, 1H), 7.69 (m, 1H), 7.48-7.38 (m, 3H), 7.31 (m, 1H), 7.23 (m, 2H), 7.04-6.93 (m, 4H), 6.13 (q, J=7.2 Hz, 1H), 5.47 (s, 2H), 4.00 (t, J=6.6 Hz, 2H), 2.02 (d, J=7.1 Hz, 3H), 1.86 (m, 2H), 1.07 (t, J=7.4 Hz, 3H). Mass: 535.8 (M+).

Example 155

2-(1-(4-amino-3-(furan-2-yl)-1H-pyrazolo[3,4-d]pyrimidin-1-yl)ethyl)-3-(3-fluorophenyl)-4H-chromen-4-one The compound was prepared as per the procedure provided above for Example 130 wherein the 3,5-dimethoxy phenyl boronic acid was replaced by -furan-2-ylboronic acid (0.209 mmol) Brown solid (24.6 mg, 28%). MP: 234-236° C. $^1$H-NMR (δ ppm, $CDCl_3$, 300 MHz): δ 8.22 (s, 1H), 8.19 (dd, J=8.3, 1.7 Hz, 1H), 7.68 (m, 1H), 7.59 (d, J=1.5 Hz, 1H), 7.49 (t, J=6.8 Hz, 1H), 7.40 (t, J=7.4 Hz, 1H), 7.31 (m, 1H), 6.99-6.96 (m, 4H), 6.61 (q, J=1.7 Hz, 1H), 6.07 (q, J=7.2 Hz, 1H), 1.99 (d, J=7.2 Hz, 3H. Mass: 467.9 (M+).

Example 156

2-(1-(4-amino-3-(4-ethoxyphenyl)-1H-pyrazolo[3,4-d]pyrimidin-1-yl)ethyl)-3-(3-fluorophenyl)-4H-chromen-4-one The compound was prepared as per the procedure provided above for Example 130 wherein the 3,5-dimethoxy phenyl boronic was replaced by 4-ethoxyphenylboronic acid (0.209 mmol). Brown solid (53.4 mg, 54%). MP: 229-232° C. $^1$H-NMR (δ ppm, $CDCl_3$, 300 MHz): δ 8.22 (s, 1H), 8.22 (d, J=7.8 Hz, 1H), 7.68 (m, 1H), 7.59 (d, J=8.7 Hz, 2H), 7.49 (d, J=8.4 Hz, 1H), 7.40 (m, 2H), 7.06 (m, 5H), 6.11 (q, J=7.2 Hz, 1H), 5.62 (s, 2H), 4.11 (q, J=7.2 Hz, 2H), 2.02 (d, J=7.2 Hz, 3H), 1.48 (t, J=7.2 Hz, 3H). Mass: 521.9 (M+).

Example 157

2-(1-(4-amino-3-(3-chloro-4-methoxyphenyl)-1H-pyrazolo[3,4-d]pyrimidin-1-yl)ethyl)-3-(3-fluorophenyl)-4H-chromen-4-one The compound was prepared as per the procedure provided above for Example 130 wherein the 3,5-dimethoxy phenyl boronic acid (or boronic acid pinacol ester) was replaced by 3-chloro-4-methoxyphenylboronic acid (0.209 mmol) Brown solid (30 mg, 29%). MP: 246-249° C. $^1$H-NMR (δ ppm, $CDCl_3$, 300 MHz): δ 8.24 (s, 1H), 8.22 (dd, J=8.0, 1.5 Hz, 1H), 7.72-7.65 (m, 2H), 7.55 (dd, J=8.4, 2.1 Hz, 1H), 7.49 (d, J=8.3 Hz, 1H), 7.42 (dt, J=8.0, 0.9 Hz, 1H), 7.32 (m, 1H), 7.09 (d, J=8.5 Hz, 1H), 7.04 (m, 2H), 6.93 (d, J=8.1 Hz, 1H), 6.12 (q, J=7.3 Hz, 1H), 5.38 (s, 2H), 3.98 (s, 3H), 2.01 (d, J=7.1 Hz, 3H). Mass: 541.8M+).

Example 158

2-(1-(4-amino-3-(3-fluoro-4-isopropoxyphenyl)-1H-pyrazolo[3,4-d]pyrimidin-1-yl)ethyl)-3-(3-fluorophenyl)-4H-chromen-4-one The compound was prepared as per the procedure provided above for Example 130 wherein the 3,5-dimethoxy phenyl boronic acid was replaced by 3-fluoro-4-isopropoxyphenylboronic acid (0.209 mmol) Brown solid (23 mg, 22%). MP: 218-221° C. $^1$H-NMR (δ ppm, $CDCl_3$, 300 MHz): δ 8.24 (s, 1H), 8.22 (dd, J=8.0, 1.5 Hz, 1H), 7.70 (m, 1H), 7.49 (d, J=8.2 Hz, 1H), 7.44-7.30 (m, 4H), 7.14 (d, J=8.4 Hz, 1H), 7.03-6.91 (m, 3H), 6.12 (q, J=7.0 Hz, 1H), 5.43 (s, 2H), 4.66 (quintet, J=6.2 Hz, 1H), 2.00 (d, J=7.1 Hz, 3H) 1.42 (d, J=6.1 Hz, 6H). Mass: 553.8 (M+).

Example 159

2-(1-(4-amino-3-(6-fluoropyridin-3-yl)-1H-pyrazolo[3,4-d]pyrimidin-1-yl)ethyl)-3-(3-fluorophenyl)-4H-chromen-4-one The compound was prepared as per the procedure provided above for Example 130 wherein the 3,5-dimethoxy phenyl boronic acid was replaced by 6-fluoropyridin-3-ylboronic acid (0.209 mmol) Brown solid (56.6 mg, 60%). MP: 203-206° C. $^1$H-NMR (δ ppm, $CDCl_3$, 300 MHz): δ 8.57 (d, J=1.9 Hz, 1H), 8.28 (s, 1H), 8.22 (dd, J=7.9, 1.4 Hz, 1H), 8.16 (dt, J=7.9, 2.4 Hz, 1H), 7.70 (m, 1H), 7.47 (d, J=8.3 Hz, 1H), 7.43 (t, J=7.9 Hz, 1H), 7.34 (m, 1H), 7.15 (dd, J=8.4, 2.8 Hz, 1H), 7.04 (m, 2H), 6.93 (d, J=7.8 Hz, 1H), 6.13 (q, J=7.1 Hz, 1H), 5.38 (s, 2H), 2.02 (d, J=7.1 Hz, 3H). –Mass: 496.9 (M+).

Example 160

2-(1-(4-amino-3-(pyrimidin-5-yl)-1H-pyrazolo[3,4-d]pyrimidin-1-yl)ethyl)-3-(3-fluorophenyl)-4H-chromen-4-one The compound was prepared as per the procedure provided above for Example 130 wherein the 3,5-dimethoxy phenyl boronic was replaced by pyrimidin-5-ylboronic acid (0.209 mmol) Brown solid (34 mg, 37%). MP: 207-211° C. $^1$H-NMR (δ ppm, $CDCl_3$, 300 MHz): δ 9.35 (s, 1H), 9.11 (s, 2H), 8.32 (s, 1H), 8.22 (dd, J=8.0, 1.5 Hz, 1H), 7.69 (m, 1H), 7.48 (d, J=8.4 Hz, 1H), 7.43 (t, J=8.0 Hz, 1H), 7.35 (m, 1H), 7.06 (m, 2H), 6.95 (d, J=9.9 Hz, 1H), 6.15 (q, J=7.1 Hz, 1H), 5.31 (s, 2H), 2.03 (d, J=7.1 Hz, 3H). Mass: 479.9 (M+).

Example 161

2-(1-(4-amino-3-(3-(methoxymethyl)phenyl)-1H-pyrazolo[3,4-d]pyrimidin-1-yl)ethyl)-3-(3-fluorophenyl)-4H-chromen-4-one The compound was prepared as per the procedure provided above for Example 130 wherein the 3,5-dimethoxy phenyl boronic acid was replaced by 3-(methoxymethyl)phenylboronic acid (0.209 mmol) Brown solid (60.5 mg, 61%). MP: 167-170° C. $^1$H-NMR (δ ppm, $CDCl_3$, 300 MHz): δ 8.27 (m, 2H), 7.69-7.23 (m, 8H), 7.04-6.94 (m, 3H), 6.12 (q, J=7.0 Hz, 1H), 5.41 (s, 2H), 3.48 (s, 3H), 2.02 (d, J=7.2 Hz, 3H). Mass: 521.9 (M+).

Example 162

2-(1-(4-amino-3-(6-hydroxynaphthalen-2-yl)-1H-pyrazolo[3,4-d]pyrimidin-1-yl)ethyl)-3-(3-fluorophenyl)-4H-chromen-4-one The compound was prepared as per the procedure provided above for Example 130 wherein the 3,5-dimethoxy phenyl boronic acid was replaced by 6-hydroxynaphthalen-2-ylboronic acid (0.209 mmol) Brown solid (32 mg, 31%). MP: 281-285° C. $^1$H-NMR (δ ppm, $CDCl_3$, 300 MHz): δ 8.26 (s, 1H), 8.22 (dd, J=9.1, 1.4 Hz, 1H), 8.04 (s, 1H), 7.81 (d, J=8.5 Hz, 2H), 7.72-7.65 (m, 2H), 7.51 (d, J=8.4 Hz, 1H), 7.42 (dt, J=8.0, 0.9 Hz, 1H), 7.32 (m, 1H), 7.19 (m, 2H), 7.05 (d, J=7.5 Hz, 1H), 6.16 (q, J=7.1 Hz, 1H), 5.46 (s, 2H), 2.05 (d, J=7.1 Hz, 3H). Mass: 543.8 (M+).

Example 163

2-(1-(4-amino-3-(3-isopropoxyphenyl)-1H-pyrazolo[3,4-d]pyrimidin-1-yl)ethyl)-3-(3-fluorophenyl)-4H-chromen-4-one The compound was prepared as per the procedure provided above for Example 130 wherein the 3,5-dimethoxy phenyl boronic acid was replaced by 3-isopropoxyphenylboronic acid (0.209 mmol) Off-white solid (65 mg, 64%). MP: 153-157° C. $^1$H-NMR (δ ppm, $CDCl_3$, 300 MHz): δ 8.24 (s, 1H), 8.22 (dd, J=8.0, 1.5 Hz, 1H), 7.69 (m, 1H), 7.48 (d, J=8.2 Hz, 1H), 7.44 (m, 2H), 7.30 (m, 1H), 7.21 (m, 2H), 7.04-6.93 (m, 4H), 6.11 (q, J=7.1 Hz, 1H), 5.46 (s, 2H), 4.63 (quintet, J=6.1 Hz, 1H), 2.02 (d, J=7.1 Hz, 3H), 1.37 (d, J=6.1 Hz, 6H). Mass: 535.9 (M+).

Example 164

2-(1-(4-amino-3-(1-methyl-1H-pyrazol-4-yl)-1H-pyrazolo[3,4-d]pyrimidin-1-yl)ethyl)-3-(3-fluorophenyl)-4H-chromen-4-one The compound was prepared as per the procedure provided above for Example 130 wherein the 3,5-dimethoxy phenyl boronic acid (or boronic acid pinacol ester) was replaced by -1-methyl-1H-pyrazol-4-ylboronic acid pinacol ester (0.209 mmol) Yellow semi solid (30 mg, 33%). $^1$H-NMR (δ ppm, $CDCl_3$, 300 MHz): δ 8.21 (dd, J=8.0, 1.4 Hz, 1H), 8.18 (s, 1H), 7.78 (s, 1H), 7.73 (s, 1H), 7.69 (m, 1H), 7.48 (d, J=8.1 Hz, 1H), 7.42 (dt, J=7.1, 1.8 Hz, 1H), 7.32 (m, 1H), 7.00-6.93 (m, 3H), 6.06 (q, J=7.1 Hz, 1H), 5.54 (d, J=1.3 Hz, 2H), 4.00 (s, 3H), 2.01 (d, J=7.2 Hz, 3H). Mass: 481.9 (M+).

Example 165

6-Fluoro-3-(3-fluorophenyl)-2-(1-(4-methoxyphenylamino)ethyl)-4H-chromen-4-one To a solution of 4-methoxyaniline (0.201 g, 1.637 mmoles) in DMF (5 ml), N,N-diisopropylethylamine (0.158 g, 1.22 mmoles) was added and stirred at RT for 10 min. To this mixture intermediate 75 (0.300 g, 0.818 mmoles) was added and stirred for 12 h. The reaction mixture was diluted with water and extracted with ethyl acetate. The organic layer was dried over sodium sulphate and concentrated under reduced pressure. The crude product was purified by column chromatography with ethyl acetate 1: petroleum ether to afford the title compound as brown solid (0.105 g, 31% yield). MP: 152-156° C. $^1$H-NMR (δ ppm, DMSO-$D_6$, 400 MHz): δ 7.73-7.66 (m, 3H), 7.58 (q, J=7.7 Hz, 1H), 7.35 (m, 1H), 7.13 (d, J=7.6 Hz, 2H), 6.61 (d, J=8.9 Hz, 2H), 6.34 (d, J=8.9 Hz, 2H), 5.72 (d, J=9.0 Hz, 1H), 4.22 (q, J=6.9 Hz, 1H), 3.56 (s, 3H), 1.55 (d, J=6.8 Hz, 3H). Mass: 408.27 ($M^+$+1).

Example 166

2-(1-(4-Chloro-7H-pyrrolo[2,3-d]pyrimidin-7-yl)ethyl)-3-(3-fluorophenyl)-4H-chromen-4-one To a solution of 6-chloro-7-deazapurine (0.100 g, 0.651 mmoles) in DMF (4 ml), cesium carbonate (0.424 g, 1.302 mmoles) was added and stirred at RT for 10 min. To this mixture intermediate 36 (0.452 g, 1.302 mmoles) was added and stirred for 12 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as light yellow solid (0.105 g, 38% yield). MP: 71-75° C. $^1$H-NMR (δ ppm, $CDCl_3$, 400 MHz): δ 8.53 (s, 1H), 8.21 (dd, J=7.9, 1.4 Hz, 1H), 7.71 (m, 1H), 7.61 (d, J=3.7 Hz, 1H), 7.44-7.36 (m, 3H), 7.17-7.06 (m, 3H), 6.69 (d, J=3.7 Hz, 1H), 6.14 (q, J=7.2 Hz, 1H), 1.90 (d, J=7.2 Hz, 3H). Mass: 420.10 (M+).

Example 167

2-(1-(4-Chloro-1H-pyrazolo[3,4-b]pyridin-1-yl)ethyl)-3-(3-fluorophenyl)-4H-chromen-4-one To a solution of 4-chloro-1H-pyrazolo[3,4-b]pyridine (0.100 g, 0.711 mmoles) in DMF (3 ml), cesium carbonate (0.463 g, 1.422 mmoles) was added and stirred at RT for 10 min. To this mixture intermediate 36 (0.495 g, 1.422 mmoles) was added and stirred for 12 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as pale yellow solid (0.080 g, 27% yield). MP: 173-176° C. $^1$H-NMR (δ ppm, $CDCl_3$ 400 MHz): δ 8.29 (d, J=5.0 Hz, 1H), 8.20 (dd, J=8.0, 1.5 Hz, 1H), 8.11 (s, 1H), 7.68 (m, 1H), 7.47 (d, J=8.5 Hz, 1H), 7.41-7.32 (m, 2H), 7.12 (d, J=5.0 Hz, 1H), 7.03-6.95 (m, 3H), 6.20 (q, J=7.2 Hz, 1H), 2.02 (d, J=7.2 Hz, 3H). Mass: 419.96 ($M^+$+1).

Example 168

2-(1-(4-Chloro-1H-pyrazolo[3,4-d]pyrimidin-1-yl)ethyl)-3-(3-fluorophenyl)-4H-chromen-4-one To a solution of 4-chloro-1H-pyrazolo[3,4-d]pyrimidine (0.100 g, 0.745 mmoles) in DMF (3 ml), cesium carbonate (0.485 g, 1.49 mmoles) was added and stirred at RT for 10 min. To this mixture intermediate 36 (0.517 g, 1.49 mmoles) was added and stirred for 12 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as brown solid (0.040 g, 13% yield). MP: 197-201° C. $^1$H-NMR (δ ppm, $CDCl_3$, 400 MHz): δ 8.21 (s, 1H), 8.19 (d, J=1.4 Hz, 1H), 7.96 (s, 1H), 7.66 (m, 1H), 7.50 (d, J=8.4 Hz, 1H), 7.41 (t, J=7.2 Hz, 1H), 7.327 m, 1H), 7.03 (m, 2H), 6.90 (m, 1H), 6.05 (q, J=7.1 Hz, 1H), 1.95 (d, J=7.1 Hz, 3H). Mass: 419.87 ($M^+$+1).

Example 169

2-(1-(4-Chloro-5H-pyrrolo[3,2-d]pyrimidin-5-yl)ethyl)-3-(3-fluorophenyl)-4H-chromen-4-one To a solution of 4-chloro-5H-pyrrolo[3,2-d]pyrimidine (0.100 g, 0.653 mmoles) in DMF (4 ml), cesium carbonate (0.425 g, 1.30 mmoles) was added and stirred at RT for 10 min. To this mixture intermediate 36 (0.455 g, 1.30 mmoles) was added and stirred for 12 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as light yellow solid (0.080 g, 29% yield). MP: 166-168° C. $^1$H-NMR (δ ppm, $CDCl_3$, 400 MHz): δ 8.66 (s, 1H), 8.24 (dd, J=7.9, 1.4 Hz, 1H), 7.86 (d, J=3.4 Hz, 1H), 7.78 (m, 1H), 7.56 (d, J=8.4 Hz, 1H), 7.48 (t, J=7.7 Hz, 1H), 7.30 (m, 2H), 7.09 (dt, J=8.5, 2.0 Hz, 1H), 6.80 (d, J=3.4 Hz, 1H), 6.74 (m, 1H), 6.50 (q, J=7.1 Hz, 1H), 1.99 (d, J=7.1 Hz, 3H). Mass: 419.89 (M+).

Example 170

2-(1-(4-amino-3-(1,3-dimethyl-1H-indazol-6-yl)-1H-pyrazolo[3,4-d]pyrimidin-1-yl)ethyl)-3-(3-fluorophenyl)-4H-chromen-4-one To a solution of Example 57c (0.400 g, 0.758 mmoles) in DMF (4 ml), ethanol (2 ml) and water (2 ml), intermediate 115 (0.309 g, 1.137 mmoles) and sodium carbonate (0.241 g, 2.27 mmoles) were added and the system is degassed for 30 min. Tetrakistriphenylphosphine Palladium (0.043 g, 0.037 mmoles) was added under nitrogen atmosphere and heated to 80° C. After 12 h, the reaction mixture was celite filtered, concentrated and extracted with ethyl acetate. The organic layer was dried over sodium sulphate and concentrated under reduced pressure. The crude product was purified by column chromatography with methanol:dichloromethane to afford the title compound as off-white solid (0.071 g, 17% yield). MP: 270-272° C. $^1$H-NMR (δ ppm, DMSO-$d_6$, 400 MHz): δ 8.08 (s, 1H), 8.04 (d, J=6.8 Hz, 1H), 7.84 (m, 2H), 7.69 (s, 1H), 7.69 (d, J=10.8 Hz, 1H), 7.53 (t, J=7.5 Hz, 1H), 7.33 (d, J=8.3 Hz, 2H), 7.03-6.95 (m, 3H), 6.06 (q, J=7.1 Hz, 1H), 3.99 (s, 3H), 2.48 (s, 3H), 1.92 (d, J=7.0 Hz, 3H). Mass: 546.24 ($M^+$+1).

Example 171

2-(1-(4-amino-3-(2,3-dimethyl-2H-indazol-6-yl)-1H-pyrazolo[3,4-d]pyrimidin-1-yl)ethyl)-3-(3-fluorophenyl)-4H-chromen-4-one To a solution of Example 57c (0.400 g, 0.758 mmoles) in DMF (4 ml), ethanol (2 ml) and water (2 ml), intermediate 116 (0.309 g, 1.137 mmoles) and sodium carbonate (0.241 g, 2.27 mmoles) were added and the system is degassed for 30 min. Tetrakistriphenylphosphine Palladium (0.043 g, 0.037 mmoles) was added under nitrogen atmosphere and heated to 80° C. After 12 h, the reaction mixture was celite filtered, concentrated and extracted with ethyl acetate. The organic layer was dried over sodium sulphate and concentrated under reduced pressure. The crude product was purified by column chromatography with methanol:dichloromethane to afford the title compound as off-white solid (0.100 g, 24% yield). MP: 269-274° C. $^1$H-NMR (δ ppm, DMSO-$d_6$, 400 MHz): δ 8.08 (s, 1H), 8.04 (d, J=8.0, 1.5 Hz, 1H), 7.86 (m, 2H), 7.68 (d, J=4.2 Hz, 2H), 7.53 (t, J=8.8 Hz, 1H), 7.35 (m, 1H), 7.24 (m, 1H), 7.07-6.84 (m, 3H), 6.06 (q, J=6.9 Hz, 1H), 4.07 (s, 3H), 2.64 (s, 3H), 1.92 (d, J=7.1 Hz, 3H). Mass: 546.03 ($M^+$+1).

Example 172

2-(1-(4-amino-3-(6-methoxynaphthalen-2-yl)-1H-pyrazolo[3,4-d]pyrimidin-1-yl)ethyl)-3-(3-fluorophenyl)-4H-chromen-4-one The compound was prepared as per the procedure provided above for Example 130 wherein the 3,5-dimethoxy phenyl boronic acid was replaced by 6-methoxynaphthalen-2-ylboronic acid (0.209 mmol). Brown solid (44.2 mg, 42%). MP: 285-287° C. $^1$H-NMR (δ ppm, $CDCl_3$, 300 MHz): δ 8.26 (s, 1H), 8.22 (dd, J=7.9, 1.5 Hz, 1H), 8.06 (s, 1H), 7.91 (d, J=8.5 Hz, 1H), 7.84 (d, J=7.9 Hz, 1H), 7.76 (dd, J=8.4, 1.7 Hz, 1H), 7.69 (m, 1H), 7.50 (d, J=8.2 Hz, 1H), 7.42 (dt, J=8.0, 0.9 Hz, 1H), 7.31 (m, 1H), 7.24 (m, 2H), 7.06-6.95 (m, 3H), 6.16 (q, J=7.1 Hz, 1H), 5.44 (s, 2H), 3.96 (s, 3H), 2.05 (d, J=7.1 Hz, 3H). Mass: 558.3 ($M^+$+1).

Example 173

2-(1-(4-amino-3-(benzo[b]thiophen-3-yl)-1H-pyrazolo[3,4-d]pyrimidin-1-yl)ethyl)-3-(3-fluorophenyl)-4H-chromen-4-one The compound was prepared as per the procedure provided above for Example 130 wherein the 3,5-dimethoxy phenyl boronic acid was replaced by benzo[b]thiophen-3-ylboronic acid (0.209 mmol). Brown solid (22.4 mg, 22%). MP: 226-229° C. $^1$H-NMR (δ ppm, $CDCl_3$, 300 MHz): δ 8.28 (s, 1H), 8.23 (dd, J=7.9, 1.4 Hz, 1H), 8.01 (d, J=7.6 Hz, 1H), 7.99 (d, J=9.1 Hz, 1H), 7.74 (s, 1H), 7.70 (m, 1H), 7.48-7.37 (m, 6H), 7.11-6.99 (m, 2H), 6.19 (q, J=7.1 Hz, 1H), 5.35 (s, 2H), 2.05 (d, J=7.1 Hz, 3H). Mass 534.3 ($M^+$+1).

Example 174

2-(1-(4-amino-3-(2,4-dimethoxypyrimidin-5-yl)-1H-pyrazolo[3,4-d]pyrimidin-1-yl)ethyl)-3-(3-fluorophenyl)-4H-chromen-4-one The compound was prepared as per the procedure provided above for Example 130 wherein the 3,5-dimethoxy phenyl boronic acid was replaced by 2,4-dimethoxypyrimidin-5-ylboronic acid (0.209 mmol). Brown solid (28.2 mg, 26%). MP: 286-290° C. $^1$H-NMR (δ ppm, $CDCl_3$, 300 MHz): δ 8.25 (s, 1H), 8.22 (dd, J=8.0, 1.5 Hz, 1H), 8.05 (s, 1H), 7.87 (d, J=8.5 Hz, 1H), 7.83 (d, J=8.9 Hz, 1H), 7.75-7.65 (m, 2H), 7.50 (d, J=8.2 Hz, 1H), 7.42 (dt, J=8.1, 1.0 Hz, 1H), 7.35 (m, 1H), 7.24 (m, 1H), 7.05-6.75 (m, 4H), 6.14 (q, J=7.2 Hz, 1H), 5.46 (s, 2H), 4.21 (q, J=6.9 Hz, 2H), 2.04 (d, J=7.1 Hz, 3H), 1.52 (t, J+6.9 Hz, 3H). Mass: 572.3 ($M^+$+1).

Example 175

2-(1-(4-amino-3-(6-ethoxynaphthalen-2-yl)-1H-pyrazolo[3,4-d]pyrimidin-1-yl)ethyl)-3-(3-fluorophenyl)-4H-chromen-4-one The compound was prepared as per the procedure provided above for Example 130 wherein the 3,5-dimethoxy phenyl boronic acid was replaced by 6-ethoxynaphthalen-2-ylboronic acid (0.209 mmol). Brown solid (28.2 mg, 26%). MP: 286-290° C. $^1$H-NMR (δ ppm, $CDCl_3$, 300 MHz): δ 8.25 (s, 1H), 8.22 (dd, J=8.0, 1.5 Hz, 1H), 8.05 (s, 1H), 7.87 (d, J=8.5 Hz, 1H), 7.83 (d, J=8.9 Hz, 1H), 7.75-7.65 (m, 2H), 7.50 (d, J=8.2 Hz, 1H), 7.42 (dt, J=8.1, 1.0 Hz, 1H), 7.35 (m, 1H), 7.24 (m, 1H), 7.05-6.75 (m, 4H), 6.14 (q, J=7.2 Hz, 1H), 5.46 (s, 2H), 4.21 (q, J=6.9 Hz, 2H), 2.04 (d, J=7.1 Hz, 3H), 1.52 (t, J+6.9 Hz, 3H). Mass: 572.3 ($M^+$+1).

Example 176

3-(4-amino-1-(1-(3-(3-fluorophenyl)-4-oxo-4H-chromen-2-yl)ethyl)-1H-pyrazolo[3,4-d]pyrimidin-3-yl)-N-cyclopropylbenzamide The compound was prepared as per the procedure provided above for Example 130 wherein the 3,5-dimethoxy phenyl boronic acid was replaced by 3-(cyclopropylcarbamoyl)phenylboronic acid (0.209 mmol). Reddish brown solid (47 mg, 44%). MP: 127-132° C. $^1$H-NMR (δ ppm, $CDCl_3$, 300 MHz): δ 8.26 (s, 1H), 8.21 (dd, J=7.9, 1.4 Hz, 1H), 8.05 (s, 1H), 7.84 (d, J=7.9 Hz, 1H), 7.69-7.47 (m, 4H), 7.42 (t, J=7.1 Hz, 1H), 7.32 (m, 1H), 7.03-6.93 (m, 3H), 6.32 (s, 1H), 6.13 (q, J=7.1 Hz, 1H), 5.37 (s, 2H), 2.95 (m, 1H), 2.02 (d, J=7.1 Hz, 3H), 0.89 (m, 2H), 0.66 (m, 2H). Mass: 561.3 ($M^+$+1).

Example 177

2-(1-(4-amino-3-(3-(morpholine-4-carbonyl)phenyl)-1H-pyrazolo[3,4-d]pyrimidin-1-yl)ethyl)-3-(3-fluorophenyl)-4H-chromen-4-one The compound was prepared as per the procedure provided above for Example 130 wherein the 3,5-dimethoxy phenyl boronic acid was replaced by 3-(morpholine-4-carbonyl)phenylboronic acid (0.209 mmol). Brown solid (30 mg, 26%). MP: 104-106° C. $^1$H-NMR (δ ppm, $CDCl_3$, 300 MHz): δ 8.25 (s, 1H), 8.22 (dd, J=7.9, 1.5 Hz, 1H), 7.77-7.32 (m, 9H), 7.01 (m, 2H), 6.12 (q, J=7.2 Hz, 1H), 5.44 (s, 2H), 3.78-3.55 (m, 8H), 2.01 (d, J=7.1 Hz, 3H). Mass: 591.3 ($M^+$+1).

Example 178

2-(1-(4-amino-3-(3-(difluoromethoxy)phenyl)-1H-pyrazolo[3,4-d]pyrimidin-1-yl)ethyl)-3-(3-fluorophenyl)-4H-chromen-4-one The compound was prepared as per the procedure provided above for Example 130 wherein the 3,5-dimethoxy phenyl boronic acid was replaced by 3-(difluoromethoxy)phenylboronic acid (0.209 mmol). Brown solid (56 mg, 54%). MP: 176-179° C. $^1$H-NMR (δ ppm, $CDCl_3$, 300 MHz): δ 8.26 (s, 1H), 8.22 (dd, J=8.0, 1.4 Hz, 1H), 7.70 (m, 1H), 7.55-7.32 (m, 7H), 7.05-6.93 (m, 3H), 6.12 (q, J=7.2 Hz, 1H), 5.42 (s, 2H), 2.02 (d, J=7.1 Hz, 3H). Mass: 544.3 ($M^+$+1).

Example 179

5-(4-amino-1-(1-(3-(3-fluorophenyl)-4-oxo-4H-chromen-2-yl)ethyl)-1H-pyrazolo[3,4-d]pyrimidin-3-yl)furan-2-carbaldehyde The compound was prepared as per the procedure provided above for Example 130 wherein the 3,5-dimethoxy phenyl boronic acid was replaced by 5-formylfuran-2-ylboronic acid (0.209 mmol). Yellow solid (25 mg, 27%). MP: 215-217° C. $^1$H-NMR (δ ppm, $CDCl_3$, 300 MHz): δ 9.65 (s, 1H), 8.24 (s, 1H), 8.21 (dd, J=7.8 Hz, 1H), 7.69 (m, 1H), 7.45 (m, 3H), 7.32 (m, 1H), 7.17 (d, J=3.7 Hz, 1H), 7.04 (m, 3H), 6.10 (q, J=7.2 Hz, 1H), 1.99 (d, J=7.1 Hz, 3H). Mass: 496.3 ($M^+$+1).

Biological Assay

The pharmacological properties of the compounds of this invention may be confirmed by a number of pharmacological assays. The pharmacological assays which can be been carried out with the compounds according to the invention and/or their pharmaceutically acceptable salts is exemplified below.

Assay 1: Fluorescent determination of PI3Kinase Kinase enzyme activity

Phosphoinositide 3 kinases (PI3K) belong to a class of lipid kinases that play a critical role in the regulation of several key cellular processes. The PI3K are capable of phosphorylating the 3-hydroxy position of phosphoinositols thereby generating second messengers involved in downstream signalling events. The homogenous time resolved fluorescence (HTRF) assay allows detection of 3,4,5-triphosphate (PIP3) formed as a result of phosphorylation of phosphotidylinositol 4,5-biphosphate (PIP2) by PI3K isoforms such as α, β, γ or δ.

PI3K isoform activity for α, β, γ or δ was determined using a PI3K human HTRF™ Assay Kit (Millipore, Billerica, Mass.) with modifications. All incubations were carried out at room temperature. Briefly, 0.5 μl of 40× inhibitor (in 100% DMSO) or 100% DMSO were added to each well of a 384-well black plate (Greiner Bio-One, Monroe, N.C.) containing 14.5 μl 1× reaction buffer/PIP2 (10 mM $MgCl_2$, 5 mM DTT, 1.38 μM PIP2) mix with or without enzyme and incubated for 10 min. After the initial incubation, 5 μl/well of 400 μM ATP was added and incubated for an additional 30 minutes. Reaction was terminated by adding 5 μl/well stop solution (Millipore, Billerica, Mass.). Five microliters of detection mix (Millipore, Billerica, Mass.) were then added to each well and was incubated for 6-18 h in the dark. HRTF ratio was measured on a microplate reader (BMG Labtech., Germany) at an excitation wavelength of 337 nm and emission wavelengths of 665 and 620 nm with an integration time of 400 sec. Data were analyzed using Graphpad Prism (Graphpad software; San Diego Calif.) for $IC_{50}$ determination. Percent inhibition was calculated based on the values for the blank and enzyme controls. The results are provided below in Table 2 & 3.

Assay 2: Selectivity for PI3Kδ in isoform specific cell-based assays

Specificity of test compounds towards PI3Kδ can be confirmed using isoform-specific cell based assays as outlined below:

PI3Kα: NIH-3T3 cells were seeded at a concentration of $0.5\times10^6$ cells per well in a 6-well tissue culture plate and incubated overnight. Complete medium was replaced with serum-free media the following day and compounds at the desired concentrations are to be added. After 15 min, 20 ng/ml PDGF was added and incubated for an additional 10 min. Cells were then lysed and AKT phosphorylation was determined by Western Blotting. Intensity of pAKT bands were normalized based on Actin and Data were analysed using Graphpad Prism (Graphpad software; San Diego Calif.) and % inhibition due to the test compound compared to the control was calculated accordingly.

PI3Kβ: NIH-3T3 cells were seeded at a concentration of $0.5\times10^6$ cells per well in a 6-well tissue culture plate and incubated overnight. Complete medium was replaced with serum-free media the following day and compounds at the desired concentrations were added. After 15 min 5 μM LPA was added and incubated for an additional 5 min. Cells were lysed and AKT phosphorylation was determined by Western Blotting. Intensity of pAKT bands were normalized based on Actin and Data were analysed using Graphpad Prism (Graphpad software; San Diego Calif.) and % inhibition due to the test compound compared to the control was calculated accordingly.

PI3Kγ: RAW cells were seeded at a concentration of $1\times10^6$ cells per well in a 6-well tissue culture plate and incubated overnight. Complete medium was replaced with serum-free media the following day and compounds at the desired concentrations were added. After 15 min, 50 ng/ml c5a was added and incubated for an additional 10 min. Cells were lysed and AKT phosphorylation was determined by Western Blotting. Intensity of pAKT bands were normalized based on Actin and data were analysed using Graphpad Prism (Graphpad software; San Diego Calif.) and % inhibition due to the test compound compared to the control was calculated accordingly.

PI3Kδ: Compound specificity towards PI3Kδ was determined in an IgM-induced B cell proliferation assay. Briefly, T-cells were rosetted from human whole blood using sheep RBC and B-cells were separated on a Ficoll-Hypaque gradient. Purified B-cells were seeded at a concentration of $0.1\times10^6$ cells per well in a 96-well tissue culture plate and incubated with desired concentrations of the test compound for 30 min. Cells were stimulated with 5 μg/ml purified goat anti-human IgM. Growth was assessed using the 3-[4,5-dimethylthiazol-2-yl]-2,5-diphenyltetrazolium bromide (MTT) dye reduction test at 0 h (prior to the addition of the test compound) and 48 h after the addition of test compound. Absorbance was read on a Fluostar Optima (BMG Labtech, Germany) at a wave length of 450 nm. Data were analysed using Graphpad Prism (Graphpad software; San Diego Calif.) and % inhibition due to the test compound compared to the control was calculated accordingly.

Compounds of the present invention when tested at 1 μM did not show any significant inhibition of Pi3kα isoform.

TABLE 2

| P110 δ/Pi3K δ | | |
|---|---|---|
| Compound | % inhibition (1 μM) | IC 50 nM |
| Example 1 | + | A |
| Example 2a | – | – |
| Example 3 | + | – |
| Example 4a | + | – |
| Example 5 | – | – |
| Example 6 | + | – |
| Example 7 | + | – |
| Example 8 | – | – |
| Example 9 | + | – |
| Example 10 | – | – |
| Example 11 | + | – |
| Example 12 | + | – |
| Example 13 | + | – |
| Example 14 | + | – |
| Example 15 | + | – |
| Example 16 | + | – |
| Example 17a | – | – |
| Example 18a | + | – |
| Example 19 | – | – |
| Example 20 | + | – |
| Example 21 | + | – |
| Example 22 | + | – |
| Example 23 | ++ | A |
| Example 24 | + | – |
| Example 25 | + | – |
| Example 26 | + | – |
| Example 27 | + | – |
| Example 28 | + | – |
| Example 29 | + | – |
| Example 30 | + | – |
| Example 31 | ++ | B |
| Example 32 | ++ | A |
| Example 33 | + | – |
| Example 34 | ++ | – |
| Example 35 | + | – |
| Example 36 | + | – |
| Example 37 | + | – |
| Example 38 | + | – |
| Example 39 | + | – |
| Example 40 | ++ | – |
| Example 41 | ++ | – |
| Example 42 | ++ | A |
| Example 43 | + | – |
| Example 44 | ++ | – |
| Example 45 | + | – |
| Example 46 | + | – |
| Example 47 | ++ | A |
| Example 48 | + | – |
| Example 49 | + | – |
| Example 50 | ++ | – |
| Example 51a | ++ | A |
| Example 52 | + | |
| Example 53 | ++ | A |
| Example 54 | + | – |
| Example 55 | ++ | A |
| Example 56 | + | – |
| Example 57 | ++ | A |
| Example 58 | + | – |
| Example 59 | ++ | B |
| Example 60 | ++ | A |
| Example 61 | + | – |
| Example 62 | + | – |
| Example 63 | + | – |
| Example 64 | + | – |
| Example 65 | + | – |
| Example 66a | ++ | A |
| Example 67 | + | – |
| Example 68 | ++ | A |
| Example 69 | ++ | – |
| Example 70 | ++ | – |
| Example 71 | + | – |
| Example 72 | ++ | A |

TABLE 2-continued

| P110 δ/Pi3K δ | | |
|---|---|---|
| Compound | % inhibition (1 μM) | IC 50 nM |
| Example 73 | ++ | – |
| Example 74 | ++ | A |
| Example 75 | ++ | – |
| Example 76a | ++ | – |
| Example 77 | ++ | – |

+ is less than equal to 50% inhibition at 1 μM;
++ is less than equal to 100% inhibition but more than equal to 50% at 1 μM;
A represents an IC 50 value of less than equal to 250 nM;
B represents an IC50 value of 250-500 nM;
C represents an IC50 value of greater than 500 nM.

TABLE 2

| P110 δ/ Pi3K δ | | |
|---|---|---|
| Compound | % inhibition* | IC 50 nM |
| Example 78 | + | – |
| Example 79 | ++ | A |
| Example 80 | + | – |
| Example 81 | + | – |
| Example 82 | ++ | – |
| Example 83 | ++ | – |
| Example 84 | ++ | A |
| Example 85 | ++ | – |
| Example 86a | ++ | – |
| Example 87 | ++ | |
| Example 88a | ++ | A |
| Example 89 | + | |
| Example 90 | + | |
| Example 91 | + | |
| Example 92 | ++ | |
| Example 93 | ++ | |
| Example 94 | ++ | |
| Example 95a | ++ | A |
| Example 96a | ++ | |
| Example 97 | ++ | |
| Example 98 | ++ | A |
| Example 99 | ++ | A |
| Example 100 | ++ | |
| Example 101 | + | |
| Example 102a | + | |
| Example 103 | ++ | A |
| Example 104 | ++ | A |
| Example 105 | ++ | A |
| Example 106 | + | |
| Example 107a | + | |
| Example 108 | ++ | A |
| Example 109 | ++ | |
| Example 110 | ++ | |
| Example 111 | ++ | |
| Example 112 | + | |
| Example 113 | ++ | |
| Example 114 | ++ | |
| Example 115 | ++ | A |
| Example 116 | ++ | – |
| Example 117 | ++ | |
| Example 118 | + | |
| Example 119 | + | |
| Example 120a | ++ | |
| Example 121a | ++ | |
| Example 122 | + | |
| Example 123 | + | |
| Example 124 | + | |
| Example 125 | + | |
| Example 126a | + | |
| Example 127a | + | |
| Example 128 | – | A |
| Example 129 | – | C |
| Example 130 | + | |
| Example 131 | + | |
| Example 132 | + | |
| Example 133 | + | |

TABLE 2-continued

| P110 δ/ Pi3K δ | | |
|---|---|---|
| Compound | % inhibition* | IC 50 nM |
| Example 134 | + | |
| Example 135 | + | |
| Example 136 | + | |
| Example 137 | + | |
| Example 138 | – | |
| Example 139 | + | |
| Example 140 | + | |
| Example 141 | ++ | A |
| Example 142 | + | |
| Example 143 | + | |
| Example 144 | ++ | A |
| Example 145 | + | |
| Example 146 | ++ | |
| Example 147 | + | |
| Example 148 | ++ | |
| Example 149 | + | |
| Example 150 | + | |
| Example 151 | ++ | A |
| Example 152 | + | |
| Example 153 | + | |
| Example 154 | + | |
| Example 155 | ++ | |
| Example 156 | + | |
| Example 157 | + | |
| Example 158 | ++ | A |
| Example 159 | + | |
| Example 160 | + | |

TABLE 2-continued

| P110 δ/ Pi3K δ | | |
|---|---|---|
| Compound | % inhibition* | IC 50 nM |
| Example 161 | + | |
| Example 162 | ++ | |
| Example 163 | + | |
| Example 164 | + | |
| Example 165 | + | |
| Example 166 | + | |
| Example 167 | + | |
| Example 168 | + | |
| Example 169 | + | |
| Example 170 | ++ | |
| Example 171 | + | |
| Example 172 | + | |
| Example 173 | ++ | |
| Example 174 | – | |
| Example 175 | – | |
| Example 176 | + | |
| Example 177 | + | |
| Example 178 | ++ | |
| Example 179 | ++ | |

+ is less than equal to 50% inhibition at 1 μM;
++ is less than equal to 100% inhibition but more than equal to 50% at 1 μM;
A represents an IC 50 value of less than equal to 250 nM;
B represents an IC50 value of 250-500 nM;
C represents an IC50 value of greater than 500nM;
*@ 0.3 uM.

TABLE 3

| | % inhibition (1 μM) | | | | % inhibition (1 μM) | | |
|---|---|---|---|---|---|---|---|
| Compound | P110α | P110β | P110γ | Compound | P110α | P110β | P110γ |
| Example 1 | + | + | – | Example 46 | – | – | – |
| Example 2 | – | – | – | Example 47 | + | ++ | ++ |
| Example 3 | – | – | – | Example 48 | – | – | – |
| Example 4 | – | – | – | Example 49 | – | – | – |
| Example 5 | – | – | – | Example 50 | – | – | – |
| Example 6 | – | – | – | Example 51 | + | +++ | + |
| Example 7 | – | – | – | Example 52 | – | – | – |
| Example 8 | – | – | – | Example 53 | + | +++ | + |
| Example 9 | – | – | – | Example 54 | – | – | – |
| Example 10 | + | + | – | Example 55 | + | + | +++ |
| Example 11 | – | – | – | Example 56 | – | – | – |
| Example 12 | – | – | – | Example 57 | + | ++ | – |
| Example 13 | – | – | – | Example 58 | – | – | – |
| Example 14 | – | – | – | Example 59 | – | – | – |
| Example 15 | – | – | | Example 60 | – | – | – |
| Example 16 | – | – | – | Example 61 | – | – | – |
| Example 17 | – | + | – | Example 62 | – | – | – |
| Example 18 | – | – | – | Example 63 | – | – | – |
| Example 19 | – | – | – | Example 64 | – | – | – |
| Example 20 | – | – | – | Example 65 | – | – | – |
| Example 21 | – | – | – | Example 66 | – | – | – |
| Example 22 | – | – | – | Example 67 | – | – | – |
| Example 23 | + | + | – | Example 68 | + | ++ | + |
| Example 24 | – | – | – | Example 69 | – | – | – |
| Example 25 | – | – | – | Example 70 | – | – | – |
| Example 26 | – | – | – | Example 71 | – | – | – |
| Example 27 | – | – | – | Example 72 | – | – | – |
| Example 28 | – | – | – | Example 73 | – | – | – |
| Example 29 | – | – | – | Example 74 | – | ++ | ++ |
| Example 30 | – | – | – | Example 75 | – | – | – |
| Example 31 | – | – | – | Example 76 | – | – | – |
| Example 32 | + | + | + | Example 77 | – | – | – |
| Example 33 | – | – | – | Example 78 | – | – | – |
| Example 34 | – | – | – | Example 79 | + | ++ | ++ |
| Example 35 | – | – | – | Example 80 | – | – | – |
| Example 36 | – | – | – | Example 81 | – | – | – |
| Example 37 | – | – | – | Example 82 | – | – | – |
| Example 38 | – | – | – | Example 83 | – | – | – |
| Example 39 | – | – | – | Example 84 | + | + | – |
| Example 40 | – | – | – | Example 85 | ++ | ++ | – |

TABLE 3-continued

| | % inhibition (1 μM) | | | | % inhibition (1 μM) | | |
|---|---|---|---|---|---|---|---|
| Compound | P110α | P110β | P110γ | Compound | P110α | P110β | P110γ |
| Example 41 | − | − | − | Example 86 | | | |
| Example 42 | + | ++ | + | Example 87 | | | |
| Example 43 | − | − | − | Example 88 | | | |
| Example 44 | − | − | − | Example 89 | | | |
| Example 45 | − | − | − | Example 90 | | | |
| Example 91 | | | | Example 128 | + | + | ++ |
| Example 92 | | | | Example 129 | − | ++ | − |
| Example 93 | | | | Example 130 | + | + | − |
| Example 94 | | | | Example 131 | ++ | + | − |
| Example 95 | | | | Example 132 | | | |
| Example 96 | | | | Example 133 | + | +++ | − |
| Example 97 | | | | Example 134 | − | ++ | − |
| Example 98 | | | | Example 135 | − | ++ | − |
| Example 99 | | | | Example 136 | − | ++ | − |
| Example 100 | | | | Example 137 | − | ++ | − |
| Example 101 | | | | Example 138 | − | ++ | − |
| Example 102 | | | | Example 139 | − | ++ | ++ |
| Example 103 | | | | Example 140 | − | ++ | ++ |
| Example 104 | | | | Example 141 | − | ++ | +++ |
| Example 105 | − | +++ | +++ | Example 142 | − | ++ | + |
| Example 106 | − | + | ++ | Example 143 | − | ++ | + |
| Example 107 | | | | Example 144 | − | +++ | − |
| Example 108 | − | ++ | +++ | Example 145 | − | ++ | − |
| Example 109 | + | + | ++ | Example 146 | | + | − |
| Example 110 | − | + | +++ | Example 147 | | ++ | − |
| Example 111 | + | + | +++ | Example 148 | | +++ | − |
| Example 112 | + | + | − | Example 149 | | ++ | − |
| Example 113 | − | + | − | Example 150 | | ++ | |
| Example 114 | − | + | − | Example 151 | | ++ | |
| Example 115 | + | + | − | Example 152 | | + | |
| Example 116 | + | + | − | Example 153 | | + | |
| Example 117 | − | + | − | Example 154 | | + | |
| Example 118 | + | ++ | − | Example 155 | | + | |
| Example 119 | + | + | − | Example 156 | | ++ | |
| Example 120 | + | + | − | Example 157 | | − | |
| Example 121 | | | | Example 158 | | | |
| Example 122 | − | +++ | − | Example 159 | | | |
| Example 123 | − | + | − | Example 160 | | | |
| Example 124 | + | + | − | Example 161 | | | |
| Example 125 | + | + | − | Example 162 | | | |
| Example 126 | − | + | − | Example 163 | | | |
| Example 127 | − | +++ | − | Example 164 | | | |
| Example 165 | | | | Example 166 | | | |
| Example 167 | | | | Example 168 | | | |
| Example 169 | | | | Example 170 | | | |
| Example 171 | | | | Example 172 | | | |
| Example 173 | | | | Example 174 | | | |
| Example 175 | | | | Example 176 | | | |
| Example 177 | | | | Example 178 | | | |
| Example 179 | | | | | | | |

+ is less than equal to 25% inhibition at 1 μM;
++ is less than equal to 50% inhibition but more than equal to 25% at 1 μM;
+++ is less than equal to 100% inhibition but more than equal to 50% at 1 μM;

Assay 3: In Vitro Cell Proliferation Assay in Leukemic Cell Lines

Growth inhibition assays were carried out using 10% FBS supplemented media. Cells were seeded at a concentration of 5000-20,000 cells/well in a 96-well plate. Test compound at a concentration range from 0.01 to 10000 nM were added after 24 h. Growth was assessed using the 3-[4,5-dimethylthiazol-2-yl]-2,5-diphenyltetrazolium bromide (MTT) dye reduction test at 0 h (prior to the addition of the test compound) and 48 h after the addition of test compound. Absorbance was read on a Fluostar Optima (BMG Labtech, Germany) at a wave length of 450 nm. Data were analysed using GraphPad Prism and % inhibition due to the test compound compared to the control was calculated accordingly. Exemplary compounds of the present invention when tested @1 uM in THP-1; DLBCL; HL-60; MDA-MB-468; RPMI8226 and TOLEDO cell lines showed a 20 to 80% inhibition.

Assay 4: Determination of Cytotoxicity in Leukemic Cell Lines

Cytotoxicity of test compounds was determined using a lactate dehydrogenase assay kit (Cayman Chemicals, MI) as per the manufacturer's instructions with some minor modifications. Briefly, 20,000 cells/well in complete RPMI-1640 media were seeded in a 96-well tissue culture plate and incubated overnight at 37° C. and 5% $CO_2$. Inhibitors were added to the wells in triplicate at the desired concentrations. Doxorubicin and/or 1% Triton-X were used as a positive control. After 48 h, media was removed and assayed for lactate dehydrogenase in a colorimetric assay. Optical density was measured on a microplate reader (BMG Labtech., Germany) at 490 nM. Data were analyzed using Graphpad Prism (Graphpad software; San Diego Calif.).

Results: Exemplary compounds of the present invention were found to be non-toxic when tested @10 uM.

Assay 5: Inhibition of PI3Kδ Signalling in Basophils from Human Whole Blood

PI3Kδ signalling in basophils manifested by an alteration of anti-FcεR1 induced CD63 expression is a useful pharmacodynamic marker determined using the Flow2CAST® kit (Buhlmann Laboratories, Switzerland). Briefly, it involves the following steps:

Mix the anti-coagulated blood sample by inverting the venipuncture tube several times Prepare fresh and pyrogen-free 3.5 ml polypropylene or polystyrene tubes suitable for Flow Cytometry measurements Add 49 μl of patient's whole blood to each tube.

Add 1 μl of 10% DMSO (background) or compound (10% DMSO) to the assigned tubes and mix gently. Incubate at room temperature for 15 min Pipet 50 μl of the Stimulation buffer (background) or anti-FcεRI Ab to each tube Add 100 μl of Stimulation Buffer to each tube Mix gently. Add 20 μl Staining Reagent (1:1 mix of FITC-CD63 and PE-CCR3) to each tube Mix gently, cover the tubes and incubate for 15 minutes at 37° C. in a water bath. (using an incubator will take about 10 minutes longer incubation time due to less efficient heat transfer)

Add 2 ml pre-warmed (18-28° C.) Lysing Reagent to each tube, mix gently

Incubate for 5-10 minutes at 18-28° C.

Centrifuge the tubes for 5 minutes at 500×g

Decant the supernatant by using blotting paper

Resuspend the cell pellet with 300-800 μl of Wash Buffer

Vortex gently and acquire the data on the flow cytometer within the same day.

Percent CD63 positive cells within the gated basophil population are to be determined in different treatment groups and normalized to vehicle control.

Assay 6: Inhibition of Apoptosis in Leukemic Cell Lines

Apoptosis in leukemic cells was determined using an in-situ Caspase 3 kit (Millipore, US) as outlined below:

Seed leukemic cells—at a density of $1\times10^6$ cells/well in a 6 well plate

Add test compound/DMSO at desired concentrations

Incubate the plate for 24 hrs at 37° C. in 5% $CO_2$ incubator

Collect cells in a 2 ml centrifuge tube

Add 1.6 μL of freshly prepared 5×FLICA reagent and mix cells by slightly flicking the tubes Incubate tubes for 1 hour at 37° C. under 5% $CO_2$ Add 2 ml of 1× wash buffer to each tube and mix Centrifuge cells at <400×g for 5 minutes at room temperature.

Carefully remove and discard supernatant, and gently vortex cell pellet to disrupt any cell-to-cell clumping.

Resuspend cell pellet in 300 ul of 1× wash buffer

Place 100 μL of each cell suspension into each of two wells of a black microtiter plate. Avoid creation of bubbles.

Read absorbance of each microwell using an excitation wavelength of 490 nm and an emission wavelength of 520 nm Percent increase in caspase-3 activity manifested by an increase in fluorescence compared to the control blank is to be calculated.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as described above. It is intended that the appended claims define the scope of the invention and that methods and structures within the scope of these claims and their equivalents be covered thereby.

All publications and patent and/or patent applications cited in this application are herein incorporated by reference to the same extent as if each individual publication or patent application was specifically and individually indicated to be incorporated herein by reference.

We claim:

1. A method of inhibiting a catalytic activity of a PI3 kinase present in a cell, comprising contacting the cell with an effective amount of a compound of the formula (I)

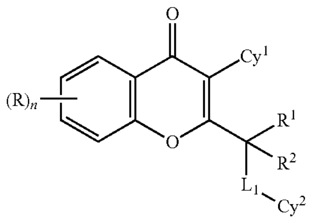

or a tautomer thereof, N-oxide thereof, pharmaceutically acceptable ester thereof, prodrug thereof, or pharmaceutically acceptable salt thereof, wherein each occurrence of R is independently selected from hydrogen, halogen, —$OR^a$, CN, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-8}$ cycloalkyl, and substituted or unsubstituted heterocyclic group;

$R^1$ and $R^2$ may be the same or different and are independently selected from hydrogen, halogen, and substituted or unsubstituted $C_{1-6}$ alkyl, or both $R^1$ and $R^2$ directly bound to a common atom, may be joined to form an oxo group (═O) or a substituted or unsubstituted saturated or unsaturated 3-10 member ring (including the carbon atom to which $R^1$ and $R^2$ are bound), which may optionally include one or more heteroatoms which may be the same or different and are selected from O, $NR^a$ and S;

$Cy^1$ is a monocyclic group selected from substituted or unsubstituted cycloalkyl, substituted or unsubstituted heterocyclic group, substituted or unsubstituted aryl and substituted or unsubstituted heteroaryl;

$Cy^2$ is selected from a substituted or unsubstituted heterocyclic group, substituted or unsubstituted aryl and substituted or unsubstituted heteroaryl;

$L_1$ is selected from —S(═O)$_q$— and —$NR^a$—;

each occurrence of $R^a$ is selected from hydrogen, halogen, hydroxy, cyano, substituted or unsubstituted ($C_{1-6}$)alkyl, —$NR^cR^d$ (wherein $R^c$ and $R^d$ are independently hydrogen, halogen, hydroxy, cyano, substituted or unsubstituted ($C_{1-6}$)alkyl, and ($C_{1-6}$)alkoxy) and —$OR^c$ (wherein $R^c$ is substituted or unsubstituted ($C_{1-6}$)alkyl);

n is 1, 2, 3 or 4; and q is 0, 1 or 2.

2. The method of claim 1, wherein the inhibition takes place in a subject suffering from lymphocytic leukemia (CLL), non-Hodgkin's lymphoma (NHL), acute myeloid leukemia (AML), multiple myeloma (MM), small lymphocytic lymphoma (SLL) or indolent non-Hodgkin's lymphoma (I-NHL).

3. The method of claim 1, further comprising the step of administering simultaneously or sequentially to a subject in need thereof at least one other anti-cancer agent, anti-inflammatory agent, immunosuppressive agent, steroid, non-steroidal anti-inflammatory agent, antihistamine, analgesic, or a mixture thereof.

4. The method of claim 1, where the compound of formula (I) is selected from the group consisting of:

2-((9H-Purin-6-ylthio)methyl)-3-phenyl-4H-chromen-4-one;

2-[(9H-Purin-6-ylthio)methyl]-6-bromo-3-phenyl-4H-chromen-4-one;

2-(1-(9H-Purin-6-ylthio)ethyl)-6-bromo-3-phenyl-4H-chromen-4-one;

(S)-2-(1-(9H-purin-6-ylamino)ethyl)-6-bromo-3-phenyl-4H-chromen-4-one;

2-((9H-purin-6-ylamino)methyl)-6-bromo-3-phenyl-4H-chromen-4-one;

2-((9H-purin-6-ylamino)methyl)-3-phenyl-4H-chromen-4-one;

2-((9H-purin-6-ylamino)methyl)-3-(2-fluorophenyl)-4H-chromen-4-one;

2-((9H-purin-6-ylamino)methyl)-3-(3-fluorophenyl)-4H-chromen-4-one;

(S)-2-(1-(9H-purin-6-ylamino)ethyl)-3-(3-fluorophenyl)-4H-chromen-4-one;

(R)-2-(1-(9H-purin-6-ylamino)ethyl)-3-(3-fluorophenyl)-4H-chromen-4-one;

(S)-2-(1-(9H-purin-6-ylamino)ethyl)-6-fluoro-3-phenyl-4H-chromen-4-one;

(S)-2-(1-(9H-purin-6-ylamino)ethyl)-3-phenyl-4H-chromen-4-one;

(S)-2-(1-(9H-purin-6-ylamino)ethyl)-6-fluoro-3-(3-fluorophenyl)-4H-chromen-4-one;

2-((9H-purin-6-ylamino)methyl)-6-fluoro-3-(3-fluorophenyl)-4H-chromen-4-one;

2-((9H-purin-6-ylamino)methyl)-6-fluoro-3-phenyl-4H-chromen-4-one;

(R)-2-(1-(9H-purin-6-ylamino)ethyl)-6-fluoro-3-(3-fluorophenyl)-4H-chromen-4-one;

6-Fluoro-3-(3-fluorophenyl)-2-(1-(4-methoxyphenylamino)ethyl)-4H-chromen-4-one, and pharmaceutically acceptable salts thereof.

5. The method of claim 1, wherein the compound has the formula:

(I-A)

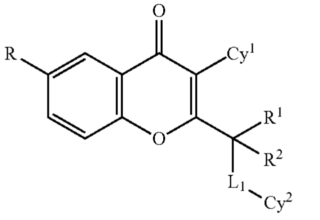

or a tautomer thereof, N-oxide thereof, pharmaceutically acceptable ester thereof, prodrug thereof, or pharmaceutically acceptable salt thereof, wherein $Cy^2$ is selected from substituted or unsubstituted heterocyclic group and substituted or unsubstituted heteroaryl.

6. The method of claim 1, wherein the compound has the formula (IA-III), or (IA-IV):

(IA-III)

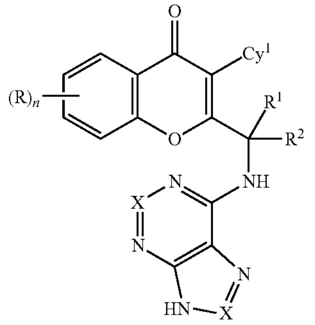

(IA-IV)

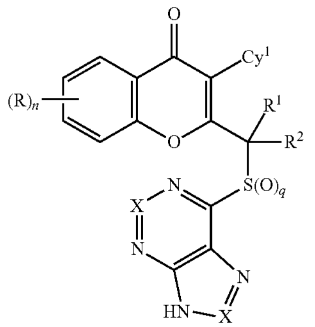

or a tautomer thereof, N-oxide thereof, pharmaceutically acceptable ester thereof, prodrug thereof, or pharmaceutically acceptable salt thereof, wherein each occurrence of X is independently selected from $CR^3$ or N; and each occurrence of $R^3$ is independently selected from hydrogen, hydroxy, halogen, carboxyl, cyano, nitro, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkylalkyl, substituted or unsubstituted cycloalkenylalkyl substituted or unsubstituted cycloalkenyl, substituted or unsubstituted heteroaryl, substituted or unsubstituted heteroarylalkyl, substituted or unsubstituted heterocyclic ring, substituted heterocyclylalkyl ring, substituted or unsubstituted guanidine, $-COOR^x$, $-C(O)R^x$, $-C(S)R^x$, $-C(O)NR^xR^y$, $-C(O)ONR^xR^y$, $-NR^xCONR^yR^z$, $-N(R^x)SOR^y$, $-N(R^x)SO_2R^y$, $-(=N-N(R^x)R^y)$, $-NR^xC(O)OR^y$, $-NR^xR^y$, $-NR^xC(O)R^y-$, $-NR^xC(S)R^y-NR^xC(S)NR^yR^z$, $-SONR^xR^y-$, $-SO_2NR^xR^y-$, $-OR^x$, $-OR^xC(O)NR^yR^z$, $-OR^xC(O)OR^y-$, $-OC(O)R^x$, $-OC(O)NR^xR^y$, $-R^xNR^yC(O)R^z$, $-R^xOR^y$, $-R^xC(O)OR^y$, $-R^xC(O)NR^yR^z$, $-R^xC(O)R^x$, $-R^xOC(O)R^y$, $-SR^x$, $-SOR^x$, $-SO_2R^x$, and $-ONO_2$, wherein $R^x$, $R^y$ and $R^z$ in each of the above groups can be hydrogen, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkylalkyl, substituted or unsubstituted cycloalkenyl, substituted or unsubstituted heteroaryl, substituted or unsubstituted heteroarylalkyl, substituted or unsubstituted heterocyclic ring, substituted or unsubstituted heterocyclylalkyl ring, or substituted or unsubstituted amino, or any two of $R^x$, $R^y$ and $R^z$ may be joined to form a substituted or unsubstituted saturated or unsaturated 3-10 membered ring, which may optionally include heteroatoms which may be the same or different and are selected from 0, $NR^W$ (wherein $R^W$ is hydrogen or substituted or unsubstituted alkyl) or S.

7. The method of claim 1, wherein $Cy^1$ is substituted or unsubstituted aryl and substituted or unsubstituted heteroaryl;

$Cy^2$ is

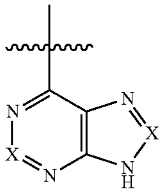

wherein X is $CR^3$;

$R^3$ is independently selected from hydrogen, hydroxy, halogen, carboxyl, cyano, nitro, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted heteroaryl, substituted heterocyclylalkyl ring, substituted or unsubstituted heteroarylalkyl, substituted or unsubstituted heterocyclic ring, substituted or unsubstituted guanidine, $—COOR^x$, $—C(O)R^x$, $—C(S)R^x$, $—C(O)NR^xR^y$, $—C(O)ONR^xR^y$, $—NR^xCONR^yR^z$, $—N(R^x)SOR^y$, $—N(R^x)SO_2R^y$, $—(=N—N(R^x)R^y)$, $— NR^xC(O)OR^y$, $—NR^xR^y$, $—NR^xC(O)R^y—$, $—NR^xC(S)R^y—NR^xC(S)NR^yR^z$, $—SONR^xR^y—$, $—SO_2NR^xR^y—$, $—OR^x$, $—OR^xC(O)NR^yR^z$, $—OR^xC(O)OR^y—$, $—OC(O)R^x$, $—OC(O)NR^xR^y$, $—R^xNR^yC(O)R^z$, $—R^xOR^y$, $—R^xC(O)OR^y$, $—R^xC(O)NR^yR^z$, $—R^xC(O)R^x$, $—R^xOC(O)R^y$, $—SR^x$, $—SOR^x$, $—SO_2R^x$, and $—ONO_2$, wherein $R^x$, $R^y$ and $R^z$ in each of the above groups can be hydrogen, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted amino, substituted or unsubstituted heteroaryl, substituted heterocyclylalkyl ring, substituted or unsubstituted heteroarylalkyl, or substituted or unsubstituted heterocyclic ring, or any two of $R^x$, $R^y$ and $R^z$ may be joined to form a substituted or unsubstituted saturated or unsaturated 3-10 membered ring, which may optionally include heteroatoms which may be the same or different and are selected from O, $NR^W$ (wherein $R^W$ is hydrogen or substituted or unsubstituted alkyl) or S; and Li is $—NR^a$.

8. The method of claim 7, wherein $Cy^1$ is

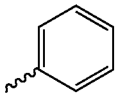 , 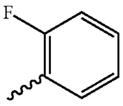 , or 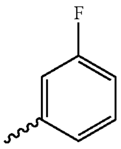 ;

$Cy^2$ is

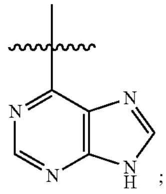 [SMILES: *c1ncnc2[nH]cnc12] ;

and $L_1$ is NH.

9. The method of claim 1, wherein $R^1$ and $R^2$ represent hydrogen or substituted or unsubstituted $C_{1-6}$ alkyl; and $L_1$ is $—NR^a—$.

10. The method of claim 1 wherein both $R^1$ and $R^2$ are directly bound to a common atom to form an oxo group (=O); and $Cy^2$ is selected from substituted or unsubstituted aryl and substituted or unsubstituted heteroaryl.

11. The method of claim 10, wherein $Cy^1$ is substituted or unsubstituted aryl and substituted or unsubstituted heteroaryl;

$Cy^2$ is

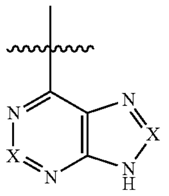

wherein X is $CR^3$;

$R^3$ is independently selected from hydrogen, hydroxy, halogen, carboxyl, cyano, nitro, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted heteroaryl, substituted heterocyclylalkyl ring, substituted or unsubstituted heteroarylalkyl, substituted or unsubstituted heterocyclic ring, substituted or unsubstituted guanidine, —COOR$^x$, —C(O)R$^x$, —C(S)R$^x$, —C(O)NR$^x$R$^y$, —C(O)ONR$^x$R$^y$, —NR$^x$CONR$^y$R$^z$, —N(R$^x$)SOR$^y$, —N(R$^x$)SO$_2$R$^y$, —(=N—N(R$^x$)R$^y$), —NR$^x$C(O)OR$^y$, —NR$^x$R$^y$, —NR$^x$C(O)R$^y$—, —NR$^x$C(S)R$^y$—NR$^x$C(S)NR$^y$R$^z$, —SONR$^x$R$^y$—, —SO$_2$NR$^x$R$^y$—, —OR$^x$, —OR$^x$C(O)NR$^y$R$^z$, —OR$^x$C(O)OR$^y$—, —OC(O)R$^x$, —OC(O)NR$^x$R$^y$, —R$^x$NR$^y$C(O)R$^z$, —R$^x$OR$^y$, —R$^x$C(O)OR$^y$, —R$^x$C(O)NR$^y$R$^z$, —R$^x$C(O)R$^x$, —R$^x$OC(O)R$^y$, —SR$^x$, —SOR$^x$, —SO$_2$R$^x$, and —ONO$_2$, wherein R$^x$, R$^y$ and R$^z$ in each of the above groups can be hydrogen, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted amino, substituted or unsubstituted heteroaryl, substituted heterocyclylalkyl ring, substituted or unsubstituted heteroarylalkyl, or substituted or unsubstituted heterocyclic ring, or any two of R$^x$, R$^y$ and R$^z$ may be joined to form a substituted or unsubstituted saturated or unsaturated 3-10 membered ring, which may optionally include heteroatoms which may be the same or different and are selected from 0, NR$^W$ (wherein R$^W$ is hydrogen or substituted or unsubstituted alkyl) or S; and L$_1$ is —NR$^a$—.

12. The method of claim 10, wherein

Cy$^1$ is

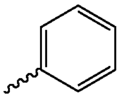, 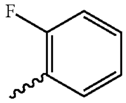, or 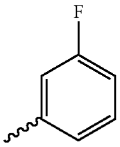;

Cy$^2$ is

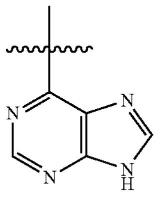 [SMILES: *c1ncnc2[nH]cnc12]

and L$_1$ is —NH—.

13. The method of claim 1, where the compound of formula (I) is selected from (S)-2-(1-(9H-purin-6-ylamino)ethyl)-6-fluoro-3-(3-fluorophenyl)-4H-chromen-4-one and pharmaceutically acceptable salts thereof.

* * * * *